(12) United States Patent
Wakamatsu et al.

(10) Patent No.: US 8,153,764 B2
(45) Date of Patent: Apr. 10, 2012

(54) BIOMARKER SPECIFIC TO BRAIN/NERVE OR SPECIFIC TO NEURONAL DIFFERENTIATION

(75) Inventors: Ai Wakamatsu, Tokyo (JP); Junichi Yamamoto, Sakura (JP); Takao Isogai, Inashiki-gun (JP)

(73) Assignee: Reverse Proteomics Research Institute Co., Ltd., Tokyo (JP)

( * ) Notice: Subject to any disclaimer, the term of this patent is extended or adjusted under 35 U.S.C. 154(b) by 28 days.

(21) Appl. No.: 12/531,430

(22) PCT Filed: Mar. 13, 2008

(86) PCT No.: PCT/JP2008/054575
§ 371 (c)(1),
(2), (4) Date: Sep. 15, 2009

(87) PCT Pub. No.: WO2008/111634
PCT Pub. Date: Sep. 18, 2008

(65) Prior Publication Data
US 2010/0098695 A1    Apr. 22, 2010

(30) Foreign Application Priority Data
Mar. 15, 2007  (JP) .............................. 2007-066430

(51) Int. Cl.
*C07K 14/705* (2006.01)
*C12N 15/63* (2006.01)

(52) U.S. Cl. ..... 530/350; 536/23.4; 536/23.5; 435/69.1; 435/69.7

(58) Field of Classification Search .................. None
See application file for complete search history.

(56) References Cited

U.S. PATENT DOCUMENTS
2006/0263774 A1 * 11/2006 Clark et al. ............... 435/6

FOREIGN PATENT DOCUMENTS
JP       2003-116575 A     4/2003
WO    WO 2005/039635 A2   5/2005

OTHER PUBLICATIONS

Bach et al., *Proc. Natl. Acad. Sci. U.S.A.*, 85(13): 4934-4938 (Jul. 1988).
Bach et al., *Nature Genetics*, 22(4): 394-399 (1999).
Byrne et al., *Genomics*, 35(3): 523-532 (1996).
Chen et al., *Oncogene*, 12(4): 741-751 (1996).
Hogenboom et al., *J. Cell. Sci.*, 117(Pt. 4): 631-639 (2004).
Kato et al., *Biochemical and Biophysical Research Communications*, 302(4): 767-772 (2003).
Katoh et al., *International Journal of Molecular Medicine*, 13(4): 607-613 (2004).
Kochersperger et al., *Journal of Neuroscience Research*, 16(4): 601-616 (1986).
Koga et al., *Biochemical and Biophysical Research Communications*, 324(1): 321-325 (2004).
Kopito et al., *Proc. Natl. Acad. Sci. U.S.A.*, 77(10): 5738-5740 (Oct. 1980).
Kouroku et al., *Biochemical and Biophysical Research Communications*, 252(3): 738-742 (1998).
Lingrel et al., *Progress in Nucleic Acid Res. Mol. Biol.*, 38: 37-89 (1990).
Malik et al., *Journal of Biological Chemistry*, 271(37): 22754-22758 (1996).
Marie-Cardine et al., *FEBS Letters*, 435(1): 55-60 (1998).
Meyer et al., *Neuropharmacology*, 47(5): 724-733 (2004).
Mirza et al., *Mol. Cell. Biol.*, 24(24): 10868-10881 (2004).
Nobuhisa et al., *J. Exp. Med.*, 199(5): 737-742 (2004).
Ota et al., *Nature Genetics*, 36(1): 40-55 (2004).
Schafer et al., *Journal of Biological Chemistry*, 267(19): 13229-13238 (1992).
Sproat et al., *Nucleic Acids Research*, 19(4): 733-738 (1991).
Staal et al., *Genomics*, 2(1): 96-98 (1988).
Staal et al., *Proc. Natl. Acad. Sci. U.S.A.*, 84(14): 5034-5037 (1987).
Strausberg et al., *Proc. Natl. Acad. Sci. U.S.A.*, 99(26): 16899-16903 (2002).
Takahashi et al., *Journal of Biological Chemistry*, 278(43): 42225-42233 (2003).
Tiacci et al., *Blood*, 105(7): 2812-2820 (2005).
Tuerk et al., *Science*, 249(4968): 505-510 (1990).
Wakioka et al., *Nature*, 412(6847): 647-651 (2001).
Wu et al., *Genomics*, 80(6): 553-557 (2002).
Bundschu et al., *J. Biol. Chem.*, 280: 28572-28580 (2005).
Inoue et al., *J. Exp. Med.*, 201: 73-82 (2005).
King et al., *Biochem. J.*, 388: 445-454 (2005).
Wakamatsu et al., *DNA Research*, 16: 371-383 (2009) with Supplementary Data.
Yoshida et al., *Oncogene*, 25: 6056-6066 (2006).

* cited by examiner

*Primary Examiner* — John Ulm
(74) *Attorney, Agent, or Firm* — Leydig, Voit & Mayer, Ltd.

(57) ABSTRACT

The invention provides a polypeptide and a specific partial peptide thereof, as well as a polynucleotide and a specific partial nucleotide thereof, that can be used as a biomarker specific for the brain/nerves or specific for nerve differentiation; an expression vector for such a polynucleotide and a specific partial peptide thereof; a transformant incorporating such an expression vector; an antisense molecule, RNAi-inducing nucleic acid (e.g., siRNA), aptamer, or antibody for such a biomarker, and a composition comprising the same; a mammalian cell or non-human mammal wherein the expression or a function of such a biomarker is regulated; a measuring means (e.g., primer set, nucleic acid probe, antibody, aptamer) for such a biomarker, and a reagent comprising the same and the like.

6 Claims, No Drawings

BIOMARKER SPECIFIC TO BRAIN/NERVE OR SPECIFIC TO NEURONAL DIFFERENTIATION

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 378,772 bytes ASCII (Text) file named "705455 SequenceListing.txt," created Sep. 14, 2009.

TECHNICAL FIELD

The present invention provides a polypeptide and a partial peptide thereof, as well as a polynucleotide and a partial nucleotide thereof, that can be used as biomarkers specific for the brain/nerves or specific for nerve differentiation; an expression vector; a transformant; an antisense molecule, an RNAi-inducing nucleic acid (e.g., siRNA), an aptamer, an antibody, and a composition comprising them; a mammalian cell or a non-human mammal; a measuring means for a biomarker specific for the brain/nerves or specific for nerve differentiation (e.g., primer set, nucleic acid probe, antibody, aptamer), a measuring method and the like.

BACKGROUND ART

Although there have been remarkable advances in the analysis of human chromosome sequences thanks to the progress in human genome research, this does not mean that all the human genetic functions have been clarified. In humans, gene diversity is significantly associated with changes in gene functions. In fact, it is known that in humans, a plurality of mRNAs are transcribed from a particular region of a chromosome to produce different variants.

For the series of genes that have been discovered by the present inventors, and that can be used as biomarkers specific for the brain/nerves or specific for nerve differentiation (abbreviated as "brain/nerve-specific genes" or "brain/nerve-specific genes 1 to 10" as required), known variants have been reported. Examples of such known variants include known variants of brain/nerve-specific gene 1 (Genbank accession number: NM_133460.1; non-patent documents 1 and 2), brain/nerve-specific gene 2 (Genbank accession number: NM_005163.1; non-patent documents 3 and 4), brain/nerve-specific gene 3 (Genbank accession number: NM_181784.1; non-patent documents 5 and 6), brain/nerve-specific gene 4 (Genbank accession number: NM_003930.3; non-patent documents 7 and 8), brain/nerve-specific gene 5 (Genbank accession number: NM_000898.3; non-patent documents 9 and 10), brain/nerve-specific gene 6 (Genbank accession number: NM_005079.1; non-patent documents 11 and 12), brain/nerve-specific gene 7 (Genbank accession number: NM_001679.2; non-patent document 13 and 14), brain/nerve-specific gene 8 (Genbank accession number: NM_000431.1; non-patent documents 15 and 16), brain/nerve-specific gene 9 (Genbank accession number: NM_153449.2; non-patent document 17), and brain/nerve-specific gene 10 (Genbank accession number: NM_015009.1; non-patent documents 18 and 19).

However, it is not known that the brain/nerve-specific genes 1 to 10 can be useful as biomarkers specific for the brain/nerves or specific for nerve cell differentiation, and that the particular variants discovered by the present inventors exist in the brain/nerve-specific genes 1 to 10.

[Non-patent document 1] Ota, T. et al., Nat. Genet. 36 (1), 40-45 (2004)
[Non-patent document 2] Strausberg, R. L. et al., Proc. Natl. Acad. Sci. U.S.A. 99 (26), 16899-16903 (2002)
[Non-patent document 3] Staal, S. P., Proc. Natl. Acad. Sci. U.S.A. 84 (14), 5034-5037 (1987)
[Non-patent document 4] Staal, S. P. et al., Genomics 2 (1), 96-98 (1988)
[Non-patent document 5] Wakioka, T. et al., Nature 412 (6847), 647-651 (2001)
[Non-patent document 6] Kato, R. et al., Biochem. Biophys. Res. Commun. 302 (4), 767-772 (2003)
[Non-patent document 7] Marie-Cardine, A. et al., FEES Lett. 435 (1), 55-60 (1998)
[Non-patent document 8] Kouroku, Y. et al., Biochem. Biophys. Res. Commun. 252 (3), 738-742 (1998)
[Non-patent document 9] Kochersperger, L. M. et al., J. Neurosci. Res. 16 (4), 601-616 (1986)
[Non-patent document 10] Bach, A. W. et al., Proc. Natl. Acad. Sci. U.S.A. 85 (13), 4934-4938 (1988)
[Non-patent document 11] Chen, S. L. et al., Oncogene 12 (4), 741-751 (1996)
[Non-patent document 12] Byrne, J. A. et al., Genomics 35 (3), 523-532 (1996)
[Non-patent document 13] Lingrel, J. B. et al., Prog. Nucleic Acid Res. Mol. Biol. 38, 37-89 (1990)
[Non-patent document 14] Malik, N. et al., J. Biol. Chem. 271 (37), 22754-22758 (1996)
[Non-patent document 15] Kopito, R. R. et al., Proc. Natl. Acad. Sci. U.S.A. 77 (10), 5738-5740 (1980)
[Non-patent document 16] Schafer, B. L. et al., J. Biol. Chem. 267 (19), 13229-13238 (1992)
[Non-patent document 17] Wu, X. et al., Genomics 80 (6), 553-557 (2002)
[Non-patent document 18] Bach, I. et al., Nat. Genet. 22 (4), 394-399 (1999)
[Non-patent document 19] Katoh, M. et al., Int. J. Mol. Med. 13 (4), 607-613 (2004)

DISCLOSURE OF THE INVENTION

Problems to be Solved by the Invention

Analyzing a biomarker specific for the brain/nerve cells or specific for nerve cell differentiation leads to the development of, for example, a reagent for nerve cell identification or nerve cell differentiation state determination, a diagnostic reagent for a disease based on a nerve cell disorder, a pharmaceutical for a disease based on a nerve cell disorder, having a new mechanism of action, and the like. Based on the findings obtained by expression profile analysis of specified genes, the present invention is directed to providing such reagents, pharmaceuticals and the like, and providing a means useful in developing such reagents, pharmaceuticals and the like.

Means of Solving the Problems

The present inventors conducted extensive investigations and discovered brain/nerve-specific genes 1 to 10 as biomarkers specific for the brain/nerves or specific for nerve cell differentiation. The present inventors also discovered novel variants of the brain/nerve-specific genes 1 to 10 that can be used as biomarkers specific for the brain/nerves or specific for nerve cell differentiation. Therefore, it is thought that by utilizing the brain/nerve-specific genes 1 to 10 and/or novel variants thereof, it will become possible to identify nerve cells, to determine nerve cell differentiation states, to diagnose a disease based on a nerve cell disorder, and the like. In particular, because the brain/nerve-specific genes 1 to 10 and/or novel variants thereof are expressed specifically in particular differentiation stages of nerve cells, the accuracy of the determination of nerve cells in the particular differentiation stages can be increased. It is also thought that by utilizing the brain/nerve-specific genes 1 to 10 and/or novel variants thereof, it will become possible to develop a novel pharmaceutical for a specified disease such as a disease based on a nerve cell disorder, and the like.

Based on the findings shown above, the present inventors developed the present invention.

Accordingly, the present invention relates to the following aspects and the like.

[1] A polypeptide of any one of 1) to 10) below or a specific partial peptide thereof:
1) a polypeptide having an amino acid sequence shown by SEQ ID NO:18 or SEQ ID NO:10 or substantially the same amino acid sequence thereas;
2) a polypeptide having the amino acid sequence shown by SEQ ID NO:43 or substantially the same amino acid sequence thereas;
3) a polypeptide having the amino acid sequence shown by SEQ ID NO:58 or substantially the same amino acid sequence thereas;
4) a polypeptide having the amino acid sequence shown by SEQ ID NO:74 or substantially the same amino acid sequence thereas;
5) a polypeptide having an amino acid sequence shown by SEQ ID NO:89 or SEQ ID NO:99 or substantially the same amino acid sequence thereas;
6) a polypeptide having the amino acid sequence shown by SEQ ID NO:118 or substantially the same amino acid sequence thereas;
7) a polypeptide having the amino acid sequence shown by SEQ ID NO:133 or substantially the same amino acid sequence thereas;
8) a polypeptide having an amino acid sequence shown by SEQ ID NO:152 or SEQ ID NO:159 or substantially the same amino acid sequence thereas;
9) a polypeptide having an amino acid sequence shown by SEQ ID NO:184 or SEQ ID NO:190 or substantially the same amino acid sequence thereas; and
10) a polypeptide having an amino acid sequence shown by SEQ ID NO:207, SEQ ID NO:213, SEQ ID NO:219, SEQ ID NO:225, SEQ ID NO:231 or SEQ ID NO:236 or substantially the same amino acid sequence thereas.

[2] The polypeptide or specific partial peptide thereof according to [1] above, wherein the polypeptide is any of the polypeptides 1) to 10) below:
1) a polypeptide consisting of an amino acid sequence shown by SEQ ID NO:18 or SEQ ID NO:10;
2) a polypeptide consisting of the amino acid sequence shown by SEQ ID NO:43;
3) a polypeptide consisting of the amino acid sequence shown by SEQ ID NO:58;
4) a polypeptide consisting of the amino acid sequence shown by SEQ ID NO:74;
5) a polypeptide consisting of an amino acid sequence shown by SEQ ID NO:89 or SEQ ID NO:99;
6) a polypeptide consisting of the amino acid sequence shown by SEQ ID NO:118;
7) a polypeptide consisting of the amino acid sequence shown by SEQ ID NO:133;
8) a polypeptide consisting of an amino acid sequence shown by SEQ ID NO:152 or SEQ ID NO:159;
9) a polypeptide consisting of an amino acid sequence shown by SEQ ID NO:184 or SEQ ID NO:190; and
10) a polypeptide consisting of an amino acid sequence shown by SEQ ID NO:207, SEQ ID NO:213, SEQ ID NO:219, SEQ ID NO:225, SEQ ID NO:231 or SEQ ID NO:236.

[3] The polypeptide or specific partial peptide thereof according to [1] or [2] above, which is fused with a polypeptide consisting of a heterologous amino acid sequence.

[4] A partial peptide specific for a polypeptide encoded by one of the brain/nerve-specific genes 1 to 10, being any one of the partial peptides 1) to 10) below:
1) a partial peptide consisting of an amino acid sequence shown by SEQ ID NO:12, SEQ ID NO:15, SEQ ID NO:20 or SEQ ID NO:22 or a partial amino acid sequence thereof;
2) a partial peptide consisting of the amino acid sequence shown by SEQ ID NO:264 or a partial amino acid sequence thereof;
3) a partial peptide having the amino acid sequence shown by SEQ ID NO:60;
4) a partial peptide consisting of the amino acid sequence shown by SEQ ID NO:265 or a partial amino acid sequence thereof;
5) a partial peptide consisting of an amino acid sequence shown by SEQ ID NO:93, SEQ ID NO:94, SEQ ID NO:96, or SEQ ID NO:266 or a partial amino acid sequence thereof;
6) a partial peptide consisting of the amino acid sequence shown by SEQ ID NO:120 or a partial amino acid sequence thereof;
7) a partial peptide consisting of an amino acid sequence shown by SEQ ID NO:135, SEQ ID NO:138 or SEQ ID NO:139 or a partial amino acid sequence thereof;
8) a partial peptide consisting of an amino acid sequence shown by SEQ ID NO:156, SEQ ID NO:161 or SEQ ID NO:163 or a partial amino acid sequence thereof;
9) a partial peptide consisting of an amino acid sequence shown by SEQ ID NO:186 or SEQ ID NO:192 or a partial amino acid sequence thereof; and
10) a partial peptide consisting of an amino acid sequence shown by SEQ ID NO:209, SEQ ID NO:215, SEQ ID NO:221 or SEQ ID NO:227 or a partial amino acid sequence thereof, or a partial peptide having the amino acid sequence shown by SEQ ID NO:238.

[5] A polynucleotide that encodes any one of the polypeptides [1] to [3] above, or any one of the specific partial peptides [1] to [4] above.

[6] A polynucleotide of any one of 1) to 10) below or a specific partial nucleotide thereof:
1) a polynucleotide having a nucleic acid sequence shown by SEQ ID NO:16 or SEQ ID NO:8, or a nucleic acid sequence corresponding to the ORF thereof, or substantially the same nucleic acid sequence thereas;
2) a polynucleotide having the nucleic acid sequence shown by SEQ ID NO:41, or a nucleic acid sequence corresponding to the ORF thereof, or substantially the same nucleic acid sequence thereas;
3) a polynucleotide having the nucleic acid sequence shown by SEQ ID NO:56, or a nucleic acid sequence corresponding to the ORF thereof, or substantially the same nucleic acid sequence thereas;
4) a polynucleotide having the nucleic acid sequence shown by SEQ ID NO:72, or a nucleic acid sequence corresponding to the ORF thereof, or substantially the same nucleic acid sequence thereas;
5) a polynucleotide having a nucleic acid sequence shown by SEQ ID NO:87 or SEQ ID NO:97, or a nucleic acid sequence corresponding to the ORF thereof, or substantially the same nucleic acid sequence thereas;
6) a polynucleotide having the nucleic acid sequence shown by SEQ ID NO:116, or a nucleic acid sequence corresponding to the ORF thereof, or substantially the same nucleic acid sequence thereas;
7) a polynucleotide having the nucleic acid sequence shown by SEQ ID NO:131, or a nucleic acid sequence corresponding to the ORF thereof, or substantially the same nucleic acid sequence thereas;
8) a polynucleotide having a nucleic acid sequence shown by SEQ ID NO:150 or SEQ ID NO:157, or a nucleic acid sequence corresponding to the ORF thereof, or substantially the same nucleic acid sequence thereas;
9) a polynucleotide having a nucleic acid sequence shown by SEQ ID NO:182 or SEQ ID NO:188, or a nucleic acid sequence corresponding to the ORF thereof, or substantially the same nucleic acid sequence thereas; and
10) a polynucleotide having a nucleic acid sequence shown by SEQ ID NO:205, SEQ ID NO:211, SEQ ID NO:217, SEQ ID NO:223, SEQ ID NO:229 or SEQ ID NO:234, or a nucleic acid sequence corresponding to the ORF thereof, or substantially the same nucleic acid sequence thereas.

[7] The polynucleotide or specific partial nucleotide thereof according to [6] above, wherein the any one of the polynucleotides 1) to 10) is any one of the polynucleotides 1) to 10) below:
1) a polynucleotide consisting of a nucleic acid sequence shown by SEQ ID NO:16 or SEQ ID NO:8 or a nucleic acid sequence corresponding to the ORF thereof;
2) a polynucleotide consisting of the nucleic acid sequence shown by SEQ ID NO:41 or a nucleic acid sequence corresponding to the ORF thereof;
3) a polynucleotide consisting of the nucleic acid sequence shown by SEQ ID NO:56 or a nucleic acid sequence corresponding to the ORF thereof;
4) a polynucleotide consisting of the nucleic acid sequence shown by SEQ ID NO:72 or a nucleic acid sequence corresponding to the ORF thereof;
5) a polynucleotide consisting of a nucleic acid sequence shown by SEQ ID NO:87 or SEQ ID NO:97 or a nucleic acid sequence corresponding to the ORF thereof;
6) a polynucleotide consisting of the nucleic acid sequence shown by SEQ ID NO:116 or a nucleic acid sequence corresponding to the ORF thereof;
7) a polynucleotide consisting of the nucleic acid sequence shown by SEQ ID NO:131 or a nucleic acid sequence corresponding to the ORF thereof;
8) a polynucleotide consisting of a nucleic acid sequence shown by SEQ ID NO:150 or SEQ ID NO:157 or a nucleic acid sequence corresponding to the ORF thereof;
9) a polynucleotide consisting of a nucleic acid sequence shown by SEQ ID NO:182 or SEQ ID NO:188 or a nucleic acid sequence corresponding to the ORF thereof; and
10) a polynucleotide consisting of a nucleic acid sequence shown by SEQ ID NO:205, SEQ ID NO:211, SEQ ID NO:217, SEQ ID NO:223, SEQ ID NO:229 or SEQ ID NO:234 or a nucleic acid sequence corresponding to the ORF thereof.

[8] A partial nucleotide specific for any one of the polynucleotides encoded by the brain/nerve-specific genes 1 to 10, being any one of the partial nucleotides 1) to 10) below:
1) a partial nucleotide consisting of a nucleic acid sequence shown by SEQ ID NO:11, SEQ ID NO:13, SEQ ID NO:19, SEQ ID NO:21, SEQ ID NO:25, SEQ ID NO:29, SEQ ID NO:33, SEQ ID NO:39 or SEQ ID NO:40 or a partial nucleic acid sequence thereof;
2) a partial nucleotide consisting of a nucleic acid sequence shown by SEQ ID NO:44, SEQ ID NO:45, SEQ ID NO:48, SEQ ID NO:51 or SEQ ID NO:55 or a partial nucleic acid sequence thereof;
3) a partial nucleotide consisting of a nucleic acid sequence shown by SEQ ID NO:59, SEQ ID NO:61, SEQ ID NO:64, SEQ ID NO:67 or SEQ ID NO:71 or a partial nucleic acid sequence thereof;
4) a partial nucleotide consisting of a nucleic acid sequence shown by SEQ ID NO:75, SEQ ID NO:76, SEQ ID NO:79, SEQ ID NO:82 or SEQ ID NO:86 or a partial nucleic acid sequence thereof;
5) a partial nucleotide consisting of a nucleic acid sequence shown by SEQ ID NO:90, SEQ ID NO:91, SEQ ID NO:92, SEQ ID NO:95, SEQ ID NO:100, SEQ ID NO:101, SEQ ID NO:104, SEQ ID NO:107, SEQ ID NO:110, SEQ ID NO:114 or SEQ ID NO:115 or a partial nucleic acid sequence thereof;
6) a partial nucleotide consisting of a nucleic acid sequence shown by SEQ ID NO:119, SEQ ID NO:123, SEQ ID NO:126 or SEQ ID NO:130 or a partial nucleic acid sequence thereof;
7) a partial nucleotide consisting of a nucleic acid sequence shown by SEQ ID NO:134, SEQ ID NO:136, SEQ ID NO:137, SEQ ID NO:142, SEQ ID NO:145 or SEQ ID NO:149 or a partial nucleic acid sequence thereof;
8) a partial nucleotide consisting of a nucleic acid sequence shown by SEQ ID NO:153, SEQ ID NO:154, SEQ ID NO:155, SEQ ID NO:160, SEQ ID NO:162, SEQ ID NO:166, SEQ ID NO:170, SEQ ID NO:174, SEQ ID NO:180 or SEQ ID NO:181 or a partial nucleic acid sequence thereof;
9) a partial nucleotide consisting of a nucleic acid sequence shown by SEQ ID NO:185, SEQ ID NO:187, SEQ ID NO:191, SEQ ID NO:193, SEQ ID NO:199, SEQ ID NO:203 or SEQ ID NO:204 or a partial nucleic acid sequence thereof; and
10) a partial nucleotide consisting of a nucleic acid sequence shown by SEQ ID NO:208, SEQ ID NO:210, SEQ ID NO:214, SEQ ID NO:216, SEQ ID NO:220, SEQ ID NO:222, SEQ ID NO:226, SEQ ID NO:228, SEQ ID NO:232, SEQ ID NO:233, SEQ ID NO:237, SEQ ID NO:239, SEQ ID NO:242, SEQ ID NO:245, SEQ ID NO:248, SEQ ID NO:251, SEQ ID NO:254, SEQ ID NO:258, SEQ ID NO:259, SEQ ID NO:260, SEQ ID NO:261, SEQ ID NO:262 or SEQ ID NO:263 or a partial nucleic acid sequence thereof.

[9] An expression vector for the polypeptide according to any one of [1] to [3] above or the specific partial peptide according to any one of [1] to [4] above, comprising the polynucleotide according to any one of [5] to [7] above or the specific partial nucleotide according to any one of [6] to [8] above, and a promoter operably linked thereto.

[10] A transformant incorporating the expression vector according to [9] above.

[11] An antisense molecule comprising a nucleic acid sequence complementary to the nucleic acid sequence of the specific partial nucleotide according to [7] or [8] above, and capable of suppressing the expression of any one of the polypeptides encoded by the brain/nerve-specific genes 1 to 10.

[12] An RNAi-inducing nucleic acid capable of suppressing the expression of any one of the polypeptides encoded by the brain/nerve-specific genes 1 to 10, that is configured by a sense strand consisting of the nucleic acid sequence of the specific partial nucleotide according to [7] or [8] above, and an antisense strand consisting of a nucleic acid sequence complementary thereto, and that may have an overhang at the 5' terminus and/or 3' terminus of one or both of the sense strand and the antisense strand.

[13] The RNAi-inducing nucleic acid according to [12] above, wherein the RNAi-inducing nucleic acid is an siRNA.

[14] An aptamer capable of binding to any one of the polypeptides encoded by the brain/nerve-specific genes 1 to 10 via a region corresponding to the specific partial peptide according to any one of [2] to [4] above.

[15] An antibody capable of binding to any one of the polypeptides encoded by the brain/nerve-specific genes 1 to 10 via a region corresponding to the specific partial peptide according to any one of [2] to [4] above.

[16] The antibody according to [15] above, wherein the antibody is any one of the i) to iii) below:
i) a polyclonal antibody;
ii) a monoclonal antibody or a portion thereof;
iii) a chimeric antibody, a humanized antibody or a human antibody.

[17] A cell that produces the antibody according to [15] or [16] above.

[18] The cell according to [17] above, wherein the cell is a hybridoma.

[19] A composition comprising the polypeptide according to any one of [1] to [3] above, the antisense molecule according to [11] above, the RNAi-inducing nucleic acid according to [12] or [13] above, the aptamer according to [14] above, the antibody according to [15] or [16] above, or an expression vector therefor, and a pharmaceutically acceptable carrier.

[20] A mammalian cell or non-human mammal wherein the expression or a function of the polypeptide according to any one of [1] to [3] above is regulated.

[21] A primer set specific for any one of the polynucleotides encoded by the brain/nerve-specific genes 1 to 10 or a specific partial nucleotide thereof, comprising the following (a) or (b):
(a) a sense primer corresponding to a first nucleic acid sequence of the polynucleotide according to [7] above or the specific partial nucleotide according to [7] or [8] above; and
(b) an antisense primer corresponding to a nucleic acid sequence complementary to a second nucleic acid sequence of the polynucleotide according to [7] above or the specific partial nucleotide according to [7] or [8] above.

[22] A nucleic acid probe specific for any one of the polynucleotides encoded by the brain/nerve-specific genes 1 to 10 or a specific partial nucleotide thereof, being any one of the following (a) or (b):
(a) a single-stranded polynucleotide comprising a nucleic acid sequence complementary to the nucleic acid sequence of the specific partial nucleotide according to [7] or [8] above; or
(b) a double-stranded polynucleotide configured by a sense strand comprising the nucleic acid sequence of the specific partial nucleotide according to [7] or [8] above, and an antisense strand comprising a nucleic acid sequence complementary thereto.

[23] A reagent or kit for detection or quantification of any one of the polypeptides or polynucleotides encoded by the brain/nerve-specific genes 1 to 10, comprising one or more substances or sets selected from among the aptamer according to [14] above, the antibody according to [15] or [16] above, the primer set according to [21] above and the nucleic acid probe according to [22] above.

[24] The reagent or kit according to [23] above, being a reagent or kit for determination of nerve cell differentiation.

[25] A method of detecting or quantifying any one of the polypeptides or polynucleotides encoded by the brain/nerve-specific genes 1 to 10, comprising measuring the expression of the polypeptide or polynucleotide in a biological sample or cell or tissue culture obtained from a mammal, wherein the biological sample or the culture contains a nerve cell or a tissue in the brain.

[26] A method of detecting or quantifying the polypeptide according to [2] or [3] above or the polynucleotide according to [7] above, comprising measuring the expression of the polypeptide or the polynucleotide in a biological sample or cell or tissue culture obtained from a mammal.

[27] The method of detection or quantification according to [26] above, wherein the biological sample or the culture contains a nerve cell or a tissue in the brain.

EFFECT OF THE INVENTION

A polypeptide of the present invention and a partial peptide of the present invention can be useful, for example, as a biomarker specific for the brain/nerves or specific for nerve cell differentiation, and in developing a substance capable of specifically recognizing a polypeptide of the present invention or a known polypeptide, or a substance capable of comprehensively recognizing both a polypeptide of the present invention and a known polypeptide, and a substance capable of specifically regulating a function of a polypeptide of the present invention or a known polypeptide, or a substance capable of comprehensively regulating functions of both a polypeptide of the present invention and a known polypeptide.

A polynucleotide of the present invention and a partial nucleotide of the present invention can be useful, for example, as a biomarker specific for the brain/nerves or specific for nerve cell differentiation, and in developing a substance capable of specifically recognizing a polynucleotide of the present invention or a known polynucleotide, or a substance capable of comprehensively recognizing both a polynucleotide of the present invention and a known polynucleotide, and a substance capable of specifically regulating the expression of a polypeptide of the present invention or a known polypeptide, or a substance capable of comprehensively regulating the expression of both a polypeptide of the present invention and a known polypeptide.

Related substances of the present invention (e.g., antisense molecules, RNAi-inducing nucleic acids such as siRNAs, aptamers and antibodies, and expression vectors therefor) can be useful as, for example, pharmaceuticals or reagents.

A cell of the present invention can be useful in, for example, producing a polypeptide of the present invention and a partial peptide of the present invention, and an antibody of the present invention. A cell of the present invention can also be useful in developing a pharmaceutical (e.g., a prophylactic or therapeutic drug for a disease based on a nerve cell disorder), identifying a further marker gene specific for the brain/nerves or specific for nerve cell differentiation, and analyzing a mechanism associated with nerve cell differentiation.

An animal of the present invention can be useful in, for example, developing a pharmaceutical, identifying a further marker gene specific for the brain/nerves or specific for nerve cell differentiation, and analyzing a mechanism associated with nerve cell differentiation.

Measuring means (e.g., primer set, nucleic acid probe, antibody, aptamer) and measuring methods of the present invention can be useful in, for example, specific detection and quantitation of a polynucleotide of the present invention or a known polynucleotide, or a polypeptide of the present invention or a known polypeptide, or comprehensive detection and quantitation of both a polynucleotide of the present invention and a known polynucleotide, or both a polypeptide of the present invention and a known polypeptide. These means and methods can also be utilized for determining nerve cell differentiation states and screening for pharmaceuticals, reagents or foods.

BEST MODE FOR CARRYING OUT THE INVENTION

1. Brain/Nerve-specific Genes

A gene of the present invention can be a gene derived from an optionally chosen mammal. As examples of the mammal, primates and rodents, as well as laboratory animals, domestic animals, working animals, companion animals and the like can be mentioned. In detail, as examples of the mammal, humans, monkeys, rats, mice, rabbits, horses, cattle, goat, sheep, dogs, cats and the like can be mentioned. Preferably, the mammal is a human.

A gene of the present invention is capable or incapable of being expressed specifically in a tissue in the brain. A gene of the present invention is also capable of being expressed at a higher or lower level in a tissue in the brain, compared with a known polynucleotide and/or a known polypeptide. As examples of such tissues in the brain, the cerebrum, cerebral cortex, cerebellum, caudate nucleus, corpus callosum, hippocampus, substantia nigra, thalamus, hypothalamus, subthalamic nucleus, hypophysis, amygdala and the like can be mentioned.

A gene of the present invention is capable or incapable of being expressed specifically in nerve cells. A gene of the present invention is also capable of being expressed at a higher or lower level in nerve cells, compared with a known polynucleotide and/or a known polypeptide. As examples of such nerve cells, nerve cells in the aforementioned tissues can be mentioned.

Hereinafter, the polypeptides and partial peptides thereof, and polynucleotides and partial nucleotides thereof, provided by the present invention, are described.

1.1. Polypeptides and Partial Peptides Thereof

The present invention provides a polypeptide having an amino acid sequence shown by SEQ ID NO:X or substantially the same amino acid sequence thereas (abbreviated as "amino acid sequence shown by SEQ ID NO:X and the like" as required).

"SEQ ID NO:X" denotes the SEQ ID NO of an optionally chosen amino acid sequence disclosed herein. A polypeptide "having" an amino acid sequence shown by SEQ ID NO:X and the like means a polypeptide "consisting of" an amino acid sequence shown by SEQ ID NO:X and the like, and a polypeptide "comprising" the amino acid sequence and the like.

In one embodiment, substantially the same amino acid sequence as an amino acid sequence shown by SEQ ID NO:X can be an amino acid sequence having a specified amino acid sequence identity to the amino acid sequence shown by SEQ ID NO:X. The degree of amino acid sequence identity can be about 90% or more, preferably about 92% or more, more preferably about 95% or more, still more preferably about 96% or more, and most preferably about 97% or more, about 98% or more or about 99% or more. Amino acid sequence identity can be determined by a method known per se. Unless otherwise specified, amino acid sequence identity (%) is calculated by, for example, executing the commands for the maximum matching method, using the DNASIS sequence analytical software (Hitachi Software Engineering). The parameters for the calculation should be used in default settings. Amino acid sequence identity (%) can also be determined, without following the above procedures, using a program in common use in the art (for example, BLAST, FASTA and the like) in the default settings thereof. In another aspect, the identity (%) can be determined using an optionally chosen algorithm publicly known in the art, for example, the algorithms of Needleman et al. (1970) (J. Mol. Biol. 48: 444-453) and Myers and Miller (CABIOS, 1988, 4: 11-17) and the like. The algorithm of Needleman et al. is incorporated in the GAP program in the GCG software package, and the identity (%) can be determined by, for example, using BLOSUM 62 matrix or PAM250 matrix, with a gap weight of 16, 14, 12, 10, 8, 6 or 4, and a length weight of 1, 2, 3, 4, 5 or 6. The algorithm of Myers and Miller is incorporated in the ALIGN program, which is a portion of the GCG sequence alignment software package. When the ALIGN program is utilized to compare amino acid sequences, for example, PAM120 weight residue table, gap length penalty 12, gap penalty 4, can be used. For calculating amino acid sequence identity, the method that produces the least value among the above-mentioned methods may be employed.

In another embodiment, substantially the same amino acid sequence as an amino acid sequence shown by SEQ ID NO:X can be an amino acid sequence shown by SEQ ID NO:X wherein one or more amino acids have one or more modifications selected from among substitutions, additions, deletions and insertions. The number of amino acids modified is not particularly limited, as far as it is one or more; the number can be, for example, 1 to about 50, preferably 1 to about 30, more preferably 1 to about 20, still more preferably 1 to about 10, and most preferably 1 to about 5 (e.g., 1 or 2).

Substantially the same amino acid sequence as an amino acid sequence shown by SEQ ID NO:X may completely retain a characteristic portion thereof (e.g., a portion corresponding to a specific partial polypeptide described below), and may have another portion (e.g., a portion present in a known polypeptide) being substantially the same as the corresponding portion of the amino acid sequence shown by SEQ ID NO:X. Alternatively, substantially the same amino acid sequence as an amino acid sequence shown by SEQ ID NO:X may have a non-characteristic portion thereof being identical to the corresponding portion of the amino acid sequence shown by SEQ ID NO:X, and a characteristic portion thereof being substantially identical to the corresponding portion of the amino acid sequence shown by SEQ ID NO:X.

A polypeptide of the present invention can have a function that is homogenous or heterogeneous to that of a known polypeptide (e.g., known variant). A polypeptide of the present invention can also have an enhanced or reduced function compared with a known polypeptide (e.g., known variant).

In detail, the novel polypeptides of the brain/nerve-specific genes 1 to 10 are as follows.
1) Brain/Nerve-specific Gene 1
  D-BRACE3000012.1 (SEQ ID NO:18)
  D-UTERU2026184.1 (SEQ ID NO:10)
  As a known variant of the brain/nerve-specific gene 1, for example, a variant disclosed in an Example (human zinc finger protein 418 (ZNF418); total number of nucleotides in the ORF nucleic acid sequence: 2031; total number of amino acids in the protein: 676; see GenBank accession number:

NM_133460.1) has been reported. A known variant of the brain/nerve-specific gene 1 can have a specified function (e.g., transcription regulatory capacity) (see, e.g., Ota, T. et al., Nat. Genet. 36 (1), 40-45 (2004)). Generally, it is known that a plurality of variants resulting from a single locus (splicing variants) have similar functions, although the degree can vary. Therefore, novel variants of the brain/nerve-specific gene 1 can also have these functions.

2) Brain/Nerve-specific Gene 2
   D-NT2RP8004156.1 (SEQ ID NO:43)

As a known variant of the brain/nerve-specific gene 2, for example, a variant disclosed in an Example (human v-akt mouse thymoma virus oncogene homologue 1 (AKT1); total number of nucleotides in the ORF nucleic acid sequence: 1443; total number of amino acids in the protein: 480; see GenBank accession number: NM_005163.1) has been reported. It has been reported that known variants of the brain/nerve-specific gene 2 have a specified function (e.g., kinase activity, anti-apoptotic activity, or cell cycle regulatory capacity) (see, e.g., Mirza, A. M. et al., Mol. Cell. Biol. 24 (24), 10868-10881 (2004); Koga, M. et al., Biochem. Biophys. Res. Commun. 324 (1), 321-325 (2004)). Generally, it is known that a plurality of variants resulting from a single locus (splicing variants) have similar functions, although the degree can vary. Therefore, novel variants of the brain/nerve-specific gene 2 can also have these functions.

3) Brain/Nerve-specific Gene 3
   D-NT2RI3005525.1 (SEQ ID NO:58)

As a known variant of the brain/nerve-specific gene 3, for example, a variant disclosed in an Example (human budding-related, EVH1 domain-containing 2 (SPRED2); total number of nucleotides in the ORF nucleic acid sequence: 1257; total number of amino acids in the protein: 418; see GenBank accession number: NM_181784.1) has been reported. It has been reported that known variants of the brain/nerve-specific gene 3 have a specified function (e.g., MAP kinase activation inhibitory capacity, tyrosine kinase-mediated Erk activation inhibitory capacity) (see, e.g., Nobuhisa, I. et al., J. Exp. Med. 199 (5), 737-742 (2004); Kato, R. et al., Biochem. Biophys. Res. Commun. 302 (4), 767-772 (2003)). Generally, it is known that a plurality of variants resulting from a single locus (splicing variants) have similar functions, although the degree can vary. Therefore, novel variants of the brain/nerve-specific gene 3 can also have these functions.

4) Brain/Nerve-specific Gene 4
   D-NT2RP8004592.1 (SEQ ID NO:74)

As a known variant of the brain/nerve-specific gene 4, for example, a variant disclosed in an Example (human src kinase related phosphoprotein 2 (SKAP2); total number of nucleotides in the ORF nucleic acid sequence: 1080; total number of amino acids in the protein: 359; see GenBank accession number: NM_003930.3) has been reported. It has been reported that known variants of the brain/nerve-specific gene 4 have a specified function (e.g., α-synuclein phosphorylation inhibitory capacity) (see, e.g., Takahashi, T. et al., J. Biol. Chem. 278 (43), 42225-42233 (2003)). Generally, it is known that a plurality of variants resulting from a single locus (splicing variants) have similar functions, although the degree can vary. Therefore, novel variants of the brain/nerve-specific gene 4 can also have these functions.

5) Brain/Nerve-specific Gene 5
   D-NT2RI2014164.1 (SEQ ID NO:89)
   D-BRAMY2029564.1 (SEQ ID NO:99)

As a known variant of the brain/nerve-specific gene 5, for example, a variant disclosed in an Example (human monoamine oxidase B (MAOB); total number of nucleotides in the ORF nucleic acid sequence: 1563; total number of amino acids in the protein: 520; see GenBank accession number: NM_000898.3) has been reported. It has been reported that known variants of the brain/nerve-specific gene 5 have a specified function (e.g., monoamine oxidase activity) (see, e.g., Bach, A. W. et al., Proc. Natl. Acad. Sci. U.S.A. 85 (13), 4934-4938 (1988)). Generally, it is known that a plurality of variants resulting from a single locus (splicing variants) have similar functions, although the degree can vary. Therefore, novel variants of the brain/nerve-specific gene 5 can also have these functions.

6) Brain/Nerve-specific Gene 6
   D-BRHIP2003515.1 (SEQ ID NO:118)

As a known variant of the brain/nerve-specific gene 6, for example, a variant disclosed in an Example (human tumor protein D52 (TPD52); total number of nucleotides in the ORF nucleic acid sequence: 555; total number of amino acids in the protein: 184; see GenBank accession number: NM_005079.1) has been reported. It has been reported that known variants of the brain/nerve-specific gene 6 have a specified function (e.g., capability of $Ca^{2+}$ dependent interaction with annexin VI) (see, e.g., Tiacci, E. et al., Blood 105 (7), 2812-2820 (2005)). Generally, it is known that a plurality of variants resulting from a single locus (splicing variants) have similar functions, although the degree can vary. Therefore, novel variants of the brain/nerve-specific gene 6 can also have these functions.

7) Brain/Nerve-Specific Gene 7
   D-BRACE2044661.1 (SEQ ID NO:133)

As a known variant of the brain/nerve-specific gene 7, for example, a variant disclosed in an Example (human ATPase, $Na^+/K^+$ transport property, β3 polypeptide (ATP1B3); total number of nucleotides in the ORF nucleic acid sequence: 840; total number of amino acids in the protein: 279; see GenBank accession number: NM_001679.2) has been reported. It has been reported that known variants of the brain/nerve-specific gene 7 have a specified function (e.g., ATP hydrolysis activity in the presence of an ion such as $Na^+$ or $K^+$) (see, e.g., Malik, N. et al., J. Biol. Chem. 271 (37), 22754-22758 (1996)). Generally, it is known that a plurality of variants resulting from a single locus (splicing variants) have similar functions, although the degree can vary. Therefore, novel variants of the brain/nerve-specific gene 7 can also have these functions.

8) Brain/Nerve-Specific Gene 8
   D-3NB692002462.1 (SEQ ID NO:152)
   D-BRCAN2027778.1 (SEQ ID NO:159)

As a known variant of the brain/nerve-specific gene 8, for example, a variant disclosed in an Example (human mevalonic acid kinase (MVK); total number of nucleotides in the ORF nucleic acid sequence: 1191; total number of amino acids in the protein: 396; see GenBank accession number: NM_000431.1) has been reported. It has been reported that known variants brain/nerve-specific gene 8 have a specified function (e.g., mevalonic acid kinase activity) (see, e.g., Hogenboom, S. et al., J. Cell. Sci. 117 (PT 4), 631-639 (2004)). Generally, it is known that a plurality of variants resulting from a single locus (splicing variants) have similar functions, although the degree can vary. Therefore, novel variants of the brain/nerve-specific gene 8 can also have these functions.

9) Brain/Nerve-Specific Gene 9
   D-NT2RI3001005.1 (SEQ ID NO:184)
   D-NT2RI3005261.1 (SEQ ID NO:190)

As a known variant of the brain/nerve-specific gene 9, for example, a variant disclosed in an Example (human solute carrier family 2 (promoting glucose transporter), member 14 (SLC2A14); total number of nucleotides in the ORF nucleic acid sequence: 1563; total number of amino acids in the protein: 520; see GenBank accession number: NM__153449.2) has been reported. Known variants of the brain/nerve-specific gene 9 can have a specified function (e.g., glucose transportation capacity) (see, e.g., Wu, X. et al., Genomics 80 (6), 553-557 (2002)). Generally, it is known that a plurality of variants resulting from a single locus (splicing variants) have similar functions, although the degree can vary. Therefore, novel variants of the brain/nerve-specific gene 9 can also have these functions.

10) Brain/Nerve-Specific Gene 10

D-OCBBF2010718.1 (SEQ ID NO:207)
D-OCBBF3004194.1 (SEQ ID NO:213)
D-NT2RP8000826.1 (SEQ ID NO:219)
D-NT2RP7007268.1 (SEQ ID NO:225)
D-BRAWH3008172.1 (SEQ ID NO:331)
D-BRAWH3011965.1 (SEQ ID NO:236)

As a known variant of the brain/nerve-specific gene 10, for example, a variant disclosed in an Example (human PDZ domain-containing RING finger 3 (PDZRN3); total number of nucleotides in the ORF nucleic acid sequence: 3201; total number of amino acids in the protein: 1066; see GenBank accession number: NM__015009.1) has been reported. Known variants of the brain/nerve-specific gene 10 can have a specified function (e.g., capability of binding to a cell surface protein such as neuroligin via the PDZ domain thereof) (see, e.g., Meyer, G. et al., Neuropharmacology 47 (5), 724-733 (2004)). Generally, it is known that a plurality of variants resulting from a single locus (splicing variants) have similar functions, although the degree can vary. Therefore, novel variants of the brain/nerve-specific gene 10 can also have these functions.

A polypeptide of the present invention can be useful in, for example, developing a substance capable of specifically recognizing a polypeptide of the present invention, a substance incapable of specifically recognizing a polypeptide of the present invention, or a substance capable of comprehensively recognizing both a polypeptide of the present invention and a known polypeptide, and in developing a substance capable of specifically regulating a function of a polypeptide of the present invention, a substance incapable of specifically regulating a function of a polypeptide of the present invention, or a substance capable of comprehensively recognizing functions of both a polypeptide of the present invention and a known polypeptide.

The present invention also provides a partial peptide.

"A partial peptide" consists of at least 6, preferably at least 8, more preferably at least 10, still more preferably at least 12, and most preferably at least 15, consecutive amino acid residues selected from among subject polypeptides, that can have a specified utility (e.g., use as an immunogenic or antigenic peptide, a functional peptide having a particular domain and the like).

"An insert amino acid sequence of a polypeptide of the present invention" refers to an amino acid sequence that is incorporated in a polypeptide of the present invention (e.g., novel variant), but lacked in a known polypeptide (e.g., known variant). Meanwhile, "an insert amino acid sequence of a known polypeptide" refers to an amino acid sequence that is incorporated in a known polypeptide (e.g., known variant), but lacked in a polypeptide of the present invention (e.g., novel variant). These insert amino acid sequences are obvious from the disclosure herein.

"A deleted amino acid sequence of a polypeptide of the present invention" refers to an amino acid sequence that is lacked in a polypeptide of the present invention (e.g., novel variant), but incorporated in a known polypeptide (e.g., known variant). Meanwhile, "a deleted amino acid sequence of a known polypeptide" refers to an amino acid sequence that is lacked in a known polypeptide (e.g., known variant), but incorporated in a polypeptide of the present invention (e.g., novel variant). These deleted amino acid sequences are obvious from the disclosure herein. "A deleted amino acid sequence of a polypeptide of the present invention" can have the same definition as that for "an insert amino acid sequence of a known polypeptide"; "a deleted amino acid sequence of a known polypeptide" can have the same definition as that for "an insert amino acid sequence of a polypeptide of the present invention".

A partial peptide of the present invention can be a) a specific partial peptide of a polypeptide of the present invention, capable of distinguishing a polypeptide of the present invention from a known polypeptide (abbreviated as "specific partial peptide A" as required), b) a specific partial peptide of a known polypeptide, capable of distinguishing a known polypeptide from a polypeptide of the present invention (abbreviated as "specific partial peptide B" as required), or c) a partial peptide common to both a polypeptide of the present invention and a known polypeptide (abbreviated as "shared partial peptide" as required). For these particular partial peptides, there appears a motivation for preparing them or utilizing them as markers on the basis of the present inventors' findings; however, without these findings, there is no motivation for preparing them or utilizing them as markers. Being partial peptides specific for the polypeptides encoded by the brain/nerve-specific genes 1 to 10, the specific partial peptides A and B are abbreviated as "specific partial peptides of the present invention" or "specific partial peptides" as required.

The specific partial peptide A of the present invention is a partial peptide that is present only in a polypeptide having an amino acid sequence shown by SEQ ID NO:X and the like, and that is not present in any known polypeptide. As examples of the specific partial peptide A, i) a partial peptide consisting of an insert amino acid sequence of a polypeptide of the present invention or a partial amino acid sequence thereof, ii) a partial peptide consisting of an insert amino acid sequence of a polypeptide of the present invention or a terminal partial amino acid sequence thereof and an adjacent amino acid sequence thereof, and iii) a partial peptide consisting of an amino acid sequence wherein both amino acid sequences present on the N-terminal side and C-terminal side relative to an insert amino acid sequence of a known polypeptide are linked together, formed as a result of exon deletion, can be mentioned.

The specific partial peptide A of i) above consists of an insert amino acid sequence of a polypeptide of the present invention or a partial amino acid sequence thereof. Such partial amino acid sequences are obvious from the disclosure herein.

The specific partial peptide A of ii) above consists of an insert amino acid sequence of a polypeptide of the present invention or a terminal partial amino acid sequence thereof and an adjacent amino acid sequence thereof. As such terminal partial amino acid sequences, an amino acid sequence corresponding to an N-terminal portion of an insert amino acid sequence of a polypeptide of the present invention (abbreviated as "N-terminal partial amino acid sequence A" as required), and an amino acid sequence corresponding to a C-terminal portion of an insert amino acid sequence of a polypeptide of the present invention (abbreviated as "C-terminal partial amino acid sequence A" as required) can be mentioned. As such adjacent amino acid sequences, an amino acid sequence present on the N-terminal side relative to an insert amino acid sequence of a polypeptide of the present invention (abbreviated as "N-terminal adjacent amino acid sequence A" as required), and an amino acid sequence present on the C-terminal side relative to an insert amino acid sequence of a polypeptide of the present invention (abbreviated as "C-terminal adjacent amino acid sequence A" as required) can be mentioned. Therefore, the specific partial peptide A of ii) above can be a partial peptide consisting of an amino acid sequence spanning from a specified position of the N-terminal adjacent amino acid sequence A to a specified position of an insert amino acid sequence of a polypeptide of the present invention, a partial peptide consisting of an amino acid sequence spanning from a specified position of an insert amino acid sequence of a polypeptide of the present invention to a specified position of the C-terminal adjacent amino acid sequence A, or a partial peptide consisting of an amino acid sequence comprising the whole insert amino acid sequence of a polypeptide of the present invention, spanning from a specified position of the N-terminal adjacent amino acid sequence A to a specified position of the C-terminal adjacent amino acid sequence A. The number of amino acid residues in the insert amino acid sequence (or N-terminal or C-terminal partial amino acid sequence A) or adjacent amino acid sequence (or N-terminal or C-terminal adjacent amino acid sequence A), contained in the specific partial peptide A of ii) above, is not particularly limited, as far as it is a number that ensures the specificity of the specific partial peptide A of ii) above; the number can be, for example, at least 3, preferably at least 4, more preferably at least 5, still more preferably at least 6, and most preferably at least 7, 8, 9 or 10. Such terminal partial amino acid sequences and such adjacent amino acid sequences are obvious from the disclosure herein.

The specific partial peptide A of iii) above is a partial peptide not present in a known polypeptide, consisting of an amino acid sequence wherein both amino acid sequences present on the N-terminal side and C-terminal side relative to an insert amino acid sequence of a known polypeptide are linked together (in a polypeptide of the present invention, these amino acid sequences are linked together as a result of exon deletion). The number of amino acid residues in each amino acid sequence present on the N-terminal side and C-terminal side relative to an insert amino acid sequence of a known polypeptide, contained in the specific partial peptide A of iii) above, is not particularly limited, as far as it is a number that ensures the specificity of the specific partial peptide A of iii) above; the number can be, for example, at least 3, preferably at least 4, more preferably at least 5, still more preferably at least 6, and most preferably at least 7, 8, 9 or 10.

The specific partial peptide A of the present invention can be useful as, for example, a target for specifically detecting a polypeptide of the present invention, and as a marker specific for the brain/nerves or specific for nerve differentiation. The specific partial peptide A of the present invention can also be useful in developing a substance capable of specifically recognizing a polypeptide of the present invention, or a substance incapable of specifically recognizing a polypeptide of the present invention, or developing a substance capable of specifically regulating a function of a polypeptide of the present invention, or a substance incapable of specifically regulating a function of a polypeptide of the present invention.

The specific partial peptide B of the present invention is a partial peptide that is present only in a known polypeptide, and that is not present in a polypeptide having an amino acid sequence shown by SEQ ID NO:X and the like. As examples of the specific partial peptide B, i) a partial peptide consisting of an insert amino acid sequence of a known polypeptide or a partial amino acid sequence thereof, ii) a partial peptide consisting of an insert amino acid sequence of a known polypeptide or a terminal partial amino acid sequence thereof and an adjacent amino acid sequence thereof, and iii) a partial peptide consisting of an amino acid sequence wherein both amino acid sequences present on the N-terminal side and C-terminal side relative to an insert amino acid sequence of a polypeptide of the present invention are linked together, formed as a result of exon deletion, can be mentioned.

The specific partial peptide B of i) above consists of an insert amino acid sequence of a known polypeptide or a partial amino acid sequence thereof. Such partial amino acid sequences are obvious from the disclosure herein.

The specific partial peptide B of ii) above consists of an insert amino acid sequence of a known polypeptide or a terminal partial amino acid sequence thereof and an adjacent amino acid sequence thereof. As such terminal partial amino acid sequences, an amino acid sequence corresponding to an N-terminal portion of an insert amino acid sequence of a known polypeptide (abbreviated as "N-terminal partial amino acid sequence B" as required), and an amino acid sequence corresponding to a C-terminal portion of an insert amino acid sequence of a known polypeptide (abbreviated as "C-terminal partial amino acid sequence B" as required) can be mentioned. As such adjacent amino acid sequences, an amino acid sequence present on the N-terminal side relative to an insert amino acid sequence of a known polypeptide (abbreviated as "N-terminal adjacent amino acid sequence B" as required), and an amino acid sequence present on the C-terminal side relative to an insert amino acid sequence of a known polypeptide (abbreviated as "C-terminal adjacent amino acid sequence B" as required) can be mentioned. Therefore, the specific partial peptide B of ii) above can be a partial peptide consisting of an amino acid sequence spanning from a specified position of the N-terminal adjacent amino acid sequence B to a specified position of an insert amino acid sequence of a known polypeptide, a partial peptide consisting of an amino acid sequence spanning from a specified position of an insert amino acid sequence of a known polypeptide to a specified position of the C-terminal adjacent amino acid sequence B, or a partial peptide consisting of an amino acid sequence comprising the whole insert amino acid sequence of a known polypeptide, spanning from a specified position of the N-terminal adjacent amino acid sequence B to a specified position of the C-terminal adjacent amino acid sequence B. The number of amino acid residues in the insert amino acid sequence (or N-terminal or C-terminal partial amino acid sequence B) or adjacent amino acid sequence (or N-terminal or C-terminal adjacent amino acid sequence B), contained in the specific partial peptide B of ii) above, is not particularly limited, as far as it is a number that ensures the specificity of the specific partial peptide B of ii) above; the number can be, for example, at least 3, preferably at least 4, more preferably at least 5, still more preferably at least 6, and most preferably at least 7, 8, 9 or 10. Such terminal partial amino acid sequences and such adjacent amino acid sequences are obvious from the disclosure herein.

The specific partial peptide B of iii) above is a partial peptide that is not present in a polypeptide of the present invention, consisting of an amino acid sequence wherein both amino acid sequences present on the N-terminal side and C-terminal side relative to an insert amino acid sequence of a polypeptide of the present invention are linked together (in a known polypeptide, these amino acid sequences are linked together as a result of exon deletion). The number of amino acid residues in each amino acid sequence present on the N-terminal side and C-terminal side relative to the insert amino acid sequence of a polypeptide of the present invention, contained in the specific partial peptide B of iii) above, is not particularly limited, as far as it is a number that ensures the specificity of the specific partial peptide B of iii) above; the number can be, for example, at least 3, preferably at least 4, more preferably at least 5, still more preferably at least 6, and most preferably at least 7, 8, 9 or 10, respectively.

The specific partial peptide B of the present invention can be useful as, for example, a target for specifically detecting a known polypeptide, and as a marker specific for the brain/nerves or specific for nerve differentiation, or as a marker not specific therefor. The specific partial peptide B of the present invention can also be useful in developing a substance capable of specifically recognizing a known polypeptide, or a substance incapable of specifically recognizing a known polypeptide, or developing a substance capable of specifically regulating a function of a known polypeptide, or a substance incapable of specifically regulating a function of a known polypeptide.

A shared partial peptide of the present invention can be a non-specific partial peptide that is present in both a polypeptide of the present invention and a known polypeptide. Such partial peptides are obvious from the disclosure herein. A shared partial peptide of the present invention can be useful as, for example, a target for comprehensively detecting both a polypeptide of the present invention and a known polypeptide, and as a marker specific for the brain/nerves or specific for nerve differentiation, or as a marker not specific therefor. A shared partial peptide of the present invention can also be useful in developing a substance capable of comprehensively recognizing both a polypeptide of the present invention and a known polypeptide, or a substance capable of comprehensively regulating functions of both a polypeptide of the present invention and a known polypeptide.

A polypeptide of the present invention or a specific partial peptide thereof may be fused with a polypeptide consisting of a heterologous amino acid sequence. As such a polypeptide, a polypeptide that facilitates purification or solubilization can be mentioned. In detail, as such polypeptides, histidine tag, maltose-binding protein (MBP), glutathione-S-transferase (GST), calmodulin-binding peptide (CBP), FLAG, and the Fc region of IgG molecule can be mentioned.

A polypeptide of the present invention and a partial peptide thereof may be provided in the form of a salt. As examples of the salt, salts with inorganic bases (e.g., alkali metals such as sodium and potassium; alkaline earth metals such as calcium and magnesium; aluminum, ammonium), salts with organic bases (e.g., trimethylamine, triethylamine, pyridine, picoline, ethanolamine, diethanolamine, triethanolamine, dicyclohexylamine, N,N-dibenzylethylenediamine), salts with inorganic acids (e.g., hydrochloric acid, hydrobromic acid, nitric acid, sulfuric acid, phosphoric acid), salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), salts with basic amino acids (e.g., arginine, lysine, ornithine) or salts with acidic amino acids (e.g., aspartic acid, glutamic acid) and the like can be mentioned.

A polypeptide of the present invention and a partial peptide thereof can be prepared by a method known per se. For example, a polypeptide of the present invention and a partial peptide thereof 1) may be recovered from an expression site, 2) may be recovered from a transformant described below, which expresses a polypeptide of the present invention and a partial peptide thereof, or a culture supernatant thereof, 3) may be synthesized using a cell-free system based on a rabbit reticulocyte lysate, wheat germ lysate, *Escherichia coli* lysate and the like, or 4) may be synthesized organochemically (e.g., solid phase synthesis). A polypeptide of the present invention and a partial peptide thereof are purified as appropriate by methods based on differences in solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography and use of antibody; methods based on differences in hydrophobicity, such as reverse phase high performance liquid chromatography; methods based on differences in isoelectric point, such as isoelectric focusing; and combinations thereof the like.

1.2. Polynucleotides and Partial Nucleotides Thereof

The present invention provides a polynucleotide having a nucleic acid sequence shown by SEQ ID NO:Y, or the nucleic acid sequence Y1 or the nucleic acid sequence Y2, or substantially the same nucleic acid sequence thereas (abbreviated as "nucleic acid sequence shown by SEQ ID NO:Y and the like" as required).

"SEQ ID NO:Y" denotes the SEQ ID NO of an optionally chosen nucleic acid sequence disclosed herein. A polynucleotide "having" SEQ ID NO:Y and the like means a polynucleotide "consisting of" SEQ ID NO:Y and the like, or a polynucleotide "comprising" the nucleic acid sequence and the like.

"The nucleic acid sequence Y1" denotes a nucleic acid sequence corresponding to the coding portion (that is, the entire open reading frame (ORF) or a portion thereof) in a nucleic acid sequence shown by SEQ ID NO:Y. In other words, "the nucleic acid sequence Y1" denotes a nucleic acid sequence shown by SEQ ID NO:Y when the nucleic acid sequence shown by SEQ ID NO:Y consists of a nucleic acid sequence corresponding to the coding portion only, and it denotes a nucleic acid sequence corresponding to the coding portion only when the nucleic acid sequence shown by SEQ ID NO:Y comprises nucleic acid sequences corresponding to both the coding portion and the non-coding portion.

"The nucleic acid sequence Y2" denotes a nucleic acid sequence corresponding to a non-coding portion (e.g., 5' or 3' noncoding region) in a nucleic acid sequence shown by SEQ ID NO:Y. In other words, "the nucleic acid sequence Y2" denotes a nucleic acid sequence shown by SEQ ID NO:Y when the nucleic acid sequence shown by SEQ ID NO:Y consists of a nucleic acid sequence corresponding to the non-coding portion only, and it denotes a nucleic acid sequence corresponding to the non-coding portion only when the nucleic acid sequence shown by SEQ ID NO:Y comprises nucleic acid sequences corresponding to both the non-coding portion and the coding portion.

Therefore, a nucleic acid sequence denoted by "SEQ ID NO:Y" can be denoted by any one of i) the nucleic acid sequence Y1 (when the nucleic acid sequence shown by SEQ ID NO:Y as a whole is a nucleic acid sequence corresponding to the coding portion), ii) the nucleic acid sequence Y2 (when the nucleic acid sequence shown by SEQ ID NO:Y as a whole is a nucleic acid sequence corresponding to the non-coding portion), or iii) a nucleic acid sequence comprising the nucleic acid sequence Y1 and the nucleic acid sequence Y2 (when the nucleic acid sequence shown by SEQ ID NO:Y comprises nucleic acid sequences corresponding to the coding portion and the non-coding portion).

In one embodiment, substantially the same nucleic acid sequence as a nucleic acid sequence shown by SEQ ID NO:Y, or the nucleic acid sequence Y1 or the nucleic acid sequence Y2 can be a nucleic acid sequence having a specified sequence identity to the nucleic acid sequence shown by SEQ ID NO:Y, or the nucleic acid sequence Y1 or the nucleic acid sequence Y2. The degree of nucleic acid sequence identity can be about 90% or more, preferably about 92% or more, more preferably about 95% or more, still more preferably about 96% or more, and most preferably about 97% or more, about 98% or more or about 99% or more. Nucleic acid sequence identity can be determined by a method known per se. For example, nucleic acid sequence identity (%) can be determined by the same method as that described above for amino acid sequence identity (%).

In another embodiment, substantially the same nucleic acid sequence as a nucleic acid sequence shown by SEQ ID NO:Y or the nucleic acid sequence Y1 or the nucleic acid sequence Y2 can be the nucleic acid sequence shown by SEQ ID NO:Y or the nucleic acid sequence Y1 or the nucleic acid sequence Y2, wherein one or more nucleotides have one or more modifications selected from among substitutions, additions, deletions and insertions. The number of nucleotides modified is not particularly limited, as far as it is one or more, and the number can be, for example, 1 to about 100, preferably 1 to about 70, more preferably 1 to about 50, still more preferably 1 to about 30, and most preferably 1 to about 20, 1 to about 10 or 1 to about 5 (e.g., 1 or 2).

In still another embodiment, substantially the same nucleic acid sequence as a nucleic acid sequence shown by SEQ ID NO:Y, or the nucleic acid sequence Y1 or the nucleic acid sequence Y2 can be a polynucleotide that can be hybridized to a nucleic acid sequence complementary to the nucleic acid sequence shown by SEQ ID NO:Y, or the nucleic acid sequence Y1 or the nucleic acid sequence Y2 under high stringent conditions. Hybridization conditions under high stringent conditions can be set with reference to reported conditions (see, e.g., Current Protocols in Molecular Biology, John Wiley & Sons, 6.3.1-6.3.6 (1999)). For example, as hybridization conditions under high stringent conditions, hybridization with 6×SSC (sodium chloride/sodium citrate)/45° C., followed by washing with 0.2×SSC/0.1% SDS/50 to 65° C. once or twice or more, can be mentioned.

Substantially the same nucleic acid sequence as a nucleic acid sequence shown by SEQ ID NO:Y, or the nucleic acid sequence Y1 or the nucleic acid sequence Y2 may completely retain a characteristic portion thereof (e.g., a portion corresponding to a specific partial nucleotide described below), and may have another portion (e.g., a portion present in a known polynucleotide) being substantially the same as the corresponding portion of the nucleic acid sequence shown by SEQ ID NO:Y, or the nucleic acid sequence Y1 or the nucleic acid sequence Y2. Alternatively, substantially the same nucleic acid sequence as a nucleic acid sequence shown by SEQ ID NO:Y, or the nucleic acid sequence Y1 or the nucleic acid sequence Y2 may have a non-characteristic portion thereof being the same as the corresponding portion of the nucleic acid sequence shown by SEQ ID NO:Y, or the nucleic acid sequence Y1 or the nucleic acid sequence Y2, and a characteristic portion thereof being substantially the same as the corresponding portion of the nucleic acid sequence shown by SEQ ID NO:Y, or the nucleic acid sequence Y1 or the nucleic acid sequence Y2.

A polynucleotide of the present invention is capable of encoding a polypeptide of the present invention. Therefore, a polynucleotide of the present invention can be a polynucleotide such that the polypeptide encoded thereby is capable of being functionally equivalent to a polypeptide of the present invention.

In detail, for the brain/nerve-specific genes 1 to 10, the nucleic acid sequence Y of the polynucleotide, and the SEQ ID NO:Y and Ya-th to Yb-th of the ORF-corresponding portion thereof (Ya-th to Yb-th nucleotide residues in the nucleic acid sequence Y) are as follows.

1) Brain/Nerve-specific Gene 1
  D-BRACE3000012.1 (SEQ ID NO:16 or SEQ ID NO:17, and 465th to 2558th)
  D-UTERU2026184.1 (SEQ ID NO:8 or SEQ ID NO:9, and 191st to 2119th)
2) Brain/nerve-specific gene 2
  D-NT2RP8004156.1 (SEQ ID NO:41 or SEQ ID NO:42, and 131st to 1387th)
3) Brain/Nerve-specific Gene 3
  D-NT2RI3005525.1 (SEQ. ID NO:56 or SEQ ID NO:57, and 45th to 1292nd)
4) Brain/Nerve-specific Gene 4
  D-NT2RP8004592.1 (SEQ ID NO:72 or SEQ ID NO:73, and 620th to 1183rd)
5) Brain/Nerve-specific Gene 5
  D-NT2RI2014164.1 (SEQ ID NO:87 or SEQ ID NO:88, and 162nd to 1397th)
  D-BRAMY2029564.1 (SEQ ID NO:97 or SEQ ID NO:98, and 143rd 35 to 1657th)
6) Brain/Nerve-specific Gene 6
  D-BRHIP2003515.1 (SEQ ID NO:116 or SEQ ID NO:117, and 84th to 707th)
7) Brain/Nerve-specific Gene 7
  D-BRACE2044661.1 (SEQ ID NO:131 or SEQ ID NO:132, and 297th to 878th)
8) Brain/Nerve-specific Gene 8
  D-3NB692002462.1 (SEQ ID NO:150 or SEQ ID NO:151, and 343rd to 951st)
  D-BRCAN2027778.1 (SEQ ID NO:157 or SEQ ID NO:158, and 52nd to 1086th)
9) Brain/Nerve-specific Gene 9
  D-NT2RI3001005.1 (SEQ ID NO:182 or SEQ ID NO:183, and 22nd to 1629th)
  D-NT2RI3005261.1 (SEQ ID NO:188 or SEQ ID NO:189, and 22nd to 1629th)
10) Brain/Nerve-specific Gene 10
  D-OCBBF2010718.1 (SEQ ID NO:205 or SEQ ID NO:206, and 144th to 2495th)
  D-OCBBF3004194.1 (SEQ ID NO:211 or SEQ ID NO:212, and 129th to 2480th)
  D-NT2RP8000826.1 (SEQ ID NO:217 or SEQ ID NO:218, and 95th to 2461st)
  D-NT2RP7007268.1 (SEQ ID NO:223 or SEQ ID NO:224, and 95th to 2461st)
  D-BRAWH3008172.1 (SEQ ID NO:229 or SEQ ID NO:330, and 281st to 2452nd)
  D-BRAWH3011965.1 (SEQ ID NO:234 or SEQ ID NO:235, and 300th to 1574th)

A polynucleotide of the present invention can be useful in, for example, developing a substance capable of specifically recognizing a polynucleotide of the present invention, a substance incapable of specifically recognizing a polynucleotide of the present invention, or a substance capable of comprehensively recognizing both a polynucleotide of the present invention and a known polynucleotide, and developing a substance capable of specifically regulating the expression of a polypeptide of the present invention, a substance incapable of specifically regulating the expression of a polypeptide of the present invention, or a substance capable of comprehensively regulating the expression of both a polypeptide of the present invention and a known polypeptide.

The present invention also provides a partial nucleotide.

"A partial nucleotide" consists of at least 15, preferably at least 16, more preferably at least 18, still more preferably at least 20, and most preferably at least 22, 23, 24 or 25, consecutive nucleotide residues selected from among subject polynucleotides, that can have a specified utility (e.g., use as a probe, a primer, a polynucleotide that encodes an immunogenic or antigenic peptide, a polynucleotide that encodes a functional peptide having a particular domain and the like).

"An insert nucleic acid sequence of a polynucleotide of the present invention" refers to a nucleic acid sequence that is incorporated in a polynucleotide of the present invention (e.g., novel variant), but lacked in a known polynucleotide (e.g., known variant). Meanwhile, "an insert nucleic acid sequence of a known polynucleotide" refers to a nucleic acid sequence that is incorporated in a known polynucleotide (e.g., known variant), but lacked in a polynucleotide of the present invention (e.g., novel variant). These insert nucleic acid sequences are obvious from the disclosure herein.

"A deletion nucleic acid sequence of a polynucleotide of the present invention" refers to a nucleic acid sequence that is lacked in a polynucleotide of the present invention (e.g., novel variant), but inserted in a known polynucleotide (e.g., known variant). Meanwhile, "a deletion nucleic acid sequence of a known polynucleotide" refers to a nucleic acid sequence that is lacked in a known polynucleotide (e.g., known variant), but inserted in a polynucleotide of the present invention (e.g., novel variant). These deletion nucleic acid sequences are obvious from the disclosure herein. "A deletion nucleic acid sequence of a polynucleotide of the present invention" can have the same definition as that for "an insert nucleic acid sequence of a known polynucleotide"; "a deletion nucleic acid sequence of a known polynucleotide" can have the same definition as that for "an insert nucleic acid sequence of a polynucleotide of the present invention".

A partial nucleotide of the present invention can be a) a specific partial nucleotide of a polynucleotide of the present invention, capable of distinguishing a polynucleotide of the present invention from a known polynucleotide (abbreviated as "specific partial nucleotide A" as required), b) a specific partial nucleotide of a known polynucleotide, capable of distinguishing a known polynucleotide from a polynucleotide of the present invention (abbreviated as "specific partial nucleotide B" as required, or c) a partial nucleotide common to both a polynucleotide of the present invention and a known polynucleotide (abbreviated as "shared partial nucleotide" as required). For these particular partial nucleotides, there appears a motivation for preparing them or utilizing them as markers on the basis of the present inventors' findings, but without these findings, there is no motivation for preparing them or utilizing them as markers. Being partial nucleotides specific for polynucleotides encoded by brain/nerve-specific genes 1 to 10, the specific partial nucleotides A and B are abbreviated as "specific partial nucleotides of the present invention" or "specific partial nucleotides" as required.

The specific partial nucleotide A of the present invention is a partial nucleotide that is present only in a polynucleotide having a nucleic acid sequence shown by SEQ ID NO:Y and the like, and that is not present in any known polynucleotide. As examples of the specific partial nucleotide A, i) a partial nucleotide consisting of an insert nucleic acid sequence of a polynucleotide of the present invention or a partial nucleic acid sequence thereof, ii) a partial nucleotide consisting of an insert nucleic acid sequence of a polynucleotide of the present invention or a terminal partial nucleic acid sequence thereof and an adjacent nucleic acid sequence thereof, and iii) a partial nucleotide consisting of a nucleic acid sequence wherein both nucleic acid sequences present on the 5' and 3' sides relative to an insert nucleic acid sequence of a known polynucleotide are linked together, formed as a result of exon deletion, can be mentioned.

The specific partial nucleotide A of i) above consists of an insert nucleic acid sequence of a polynucleotide of the present invention or a partial nucleic acid sequence thereof. Such partial nucleic acid sequences are obvious from the disclosure herein.

The specific partial nucleotide A of ii) above consists of an insert nucleic acid sequence of a polynucleotide of the present invention or a terminal partial nucleic acid sequence thereof and an adjacent nucleic acid sequence thereof. As such terminal partial nucleic acid sequences, a nucleic acid sequence corresponding to a 5'-terminal portion in an insert nucleic acid sequence of a polynucleotide of the present invention (abbreviated as "5'-terminal partial nucleic acid sequence A" as required), and a nucleic acid sequence corresponding to a 3'-terminal portion in an insert nucleic acid sequence of a polypeptide of the present invention (abbreviated as "3'-terminal partial nucleic acid sequence A" as required) can be mentioned. As such adjacent nucleic acid sequences, a nucleic acid sequence present on the 5' side relative to an insert nucleic acid sequence of a polynucleotide of the present invention (abbreviated as "5' adjacent nucleic acid sequence A" as required), and a nucleic acid sequence present on the 3' side relative to an insert nucleic acid sequence of a polynucleotide of the present invention (abbreviated as "3' adjacent nucleic acid sequence A" as required) can be mentioned. Therefore, the specific partial nucleotide A of ii) above can be a partial nucleotide consisting of a nucleic acid sequence spanning from a specified position of the 5' adjacent nucleic acid sequence A to a specified position of an insert nucleic acid sequence of a polynucleotide of the present invention, a partial nucleotide consisting of a nucleic acid sequence spanning from a specified position of an insert nucleic acid sequence of a polynucleotide of the present invention to a specified position of the 3' adjacent nucleic acid sequence A, or a partial nucleotide consisting of a nucleic acid sequence comprising the whole insert nucleic acid sequence of a polynucleotide of the present invention, spanning from a specified position of the 5' adjacent nucleic acid sequence A to a specified position of the 3' adjacent nucleic acid sequence A. The number of nucleotide residues in the insert nucleic acid sequence (or 5'-terminal or 3'-terminal partial nucleic acid sequence A) or adjacent nucleic acid sequence (or 5'-terminal or 3'-terminal adjacent nucleic acid sequence A), contained in the specific partial nucleotide A of ii) above, is not particularly limited, as far as it is a number that ensures the specificity of the specific partial nucleotide A of ii) above; the number can be, for example, at least 3, preferably at least 4, more preferably at least 5, still more preferably at least 6, and most preferably at least 7, 8, 9 or 10. Such terminal partial nucleic acid sequences and such adjacent nucleic acid sequences are obvious from the disclosure herein.

The specific partial nucleotide A of iii) above is a partial nucleotide not present in a known polynucleotide, which nucleotide consisting of a nucleic acid sequence wherein both nucleic acid sequences present on the 5' and 3' sides relative to an insert nucleic acid sequence of a known polynucleotide are linked together (in a polynucleotide of the present invention, these nucleic acid sequences are linked together as a result of exon deletion). The number of nucleotide residues in each nucleic acid sequence present on the 5' and 3' sides relative to an insert nucleic acid sequence of a known polynucleotide, contained in the specific partial nucleotide A of iii) above, is not particularly limited, as far as it is a number that ensures the specificity of the specific partial nucleotide A of iii) above; the number can be, for example, at least 3, preferably at least 4, more preferably at least 5, still more preferably at least 6, and most preferably at least 7, 8, 9 or 10, respectively.

The specific partial nucleotide A of the present invention can be useful as, for example, a target for specifically detecting a polynucleotide of the present invention, and as a biomarker specific for the brain/nerves or specific for nerve differentiation. The specific partial nucleotide A of the present invention can also be useful in developing a substance capable of specifically recognizing a polynucleotide of the present invention, or a substance incapable of specifically recognizing a polynucleotide of the present invention, or developing a substance capable of specifically regulating the expression of a polypeptide of the present invention, or a substance incapable of specifically regulating the expression of a polypeptide of the present invention.

The specific partial nucleotide B of the present invention is a partial nucleotide that is present only in a known polynucleotide, and not present in a polynucleotide having a nucleic acid sequence shown by SEQ ID NO:X and the like. As examples of the specific partial nucleotide B, i) a partial nucleotide consisting of an insert nucleic acid sequence of a known polynucleotide or a partial nucleic acid sequence thereof, ii) a partial nucleotide consisting of an insert nucleic acid sequence of a known polynucleotide or a terminal partial nucleic acid sequence thereof and an adjacent nucleic acid sequence thereof, and iii) a partial nucleotide consisting of a nucleic acid sequence wherein both nucleic acid sequences present on the 5' and 3' sides relative to an insert nucleic acid sequence of a polynucleotide of the present invention are linked together, formed as a result of exon deletion, can be mentioned.

The specific partial nucleotide B of i) above consists of an insert nucleic acid sequence of a known polynucleotide or a partial nucleic acid sequence thereof. Such partial nucleic acid sequences are obvious from the disclosure herein.

The specific partial nucleotide B of ii) above consists of an insert nucleic acid sequence of a known polynucleotide or a terminal partial nucleic acid sequence thereof and an adjacent nucleic acid sequence thereof. As such terminal partial nucleic acid sequences, a nucleic acid sequence corresponding to a 5'-terminal portion in an insert nucleic acid sequence of a known polynucleotide (abbreviated as "5'-terminal partial nucleic acid sequence B" as required), and a nucleic acid sequence corresponding to a 3'-terminal portion in an insert nucleic acid sequence of a known polynucleotide (abbreviated as "3'-terminal partial nucleic acid sequence B" as required) can be mentioned. As such adjacent nucleic acid sequences, a nucleic acid sequence present on the 5' side relative to an insert nucleic acid sequence of a known polynucleotide (abbreviated as "5' adjacent nucleic acid sequence B" as required), and a nucleic acid sequence present on the 3' side relative to an insert nucleic acid sequence of a known polynucleotide (abbreviated as "3' adjacent nucleic acid sequence B" as required) can be mentioned. Therefore, the specific partial nucleotide B of ii) above can be a partial nucleotide consisting of a nucleic acid sequence spanning from a specified position of the 5' adjacent nucleic acid sequence B to a specified position of an insert nucleic acid sequence of a known polynucleotide, a partial nucleotide consisting of a nucleic acid sequence spanning from a specified position of an insert nucleic acid sequence of a known polynucleotide to a specified position of the 3' adjacent nucleic acid sequence B, or a partial nucleotide consisting of a nucleic acid sequence comprising the whole insert nucleic acid sequence of a known polynucleotide, spanning from a specified position of the 5' adjacent nucleic acid sequence B to a specified position of the 3' adjacent nucleic acid sequence B. The number of nucleotide residues in the insert nucleic acid sequence (or 5'-terminal or 3'-terminal partial nucleic acid sequence B) or adjacent nucleic acid sequence (or 5'-terminal or 3'-terminal adjacent nucleic acid sequence B), contained in the specific partial nucleotide B of ii) above, is not particularly limited, as far as it is a number that ensures the specificity of the specific partial nucleotide B of ii) above; the number can be, for example, at least 3, preferably at least 4, more preferably at least 5, still more preferably at least 6, and most preferably at least 7, 8, 9 or 10. Such terminal partial nucleic acid sequences and such adjacent nucleic acid sequences are obvious from the disclosure herein.

The specific partial nucleotide B of iii) above is a partial nucleotide not present in a polynucleotide of the present invention, consisting of a nucleic acid sequence wherein both nucleic acid sequences present on the 5' and 3' sides relative to an insert nucleic acid sequence of a polynucleotide of the present invention are linked together (in a known polynucleotide, these nucleic acid sequences are linked together as a result of exon deletion). The number of nucleotide residues in each nucleic acid sequence present on the 5' and 3' sides relative to an insert nucleic acid sequence of a polynucleotide of the present invention, contained in the specific partial nucleotide B of iii) above, is not particularly limited, as far as it is a number that ensures the specificity of the specific partial nucleotide B of iii) above, and the number can be, for example, at least 3, preferably at least 4, more preferably at least 5, still more preferably at least 6, and most preferably at least 7, 8, 9 or 10, respectively.

The specific partial nucleotide B of the present invention can be useful as, for example, as a target for specifically detecting a known polynucleotide, and as a biomarker specific for the brain/nerves or specific for nerve differentiation, or as a marker not specific therefor. The specific partial nucleotide B of the present invention can also be useful in developing a substance capable of specifically recognizing a known polynucleotide, or a substance incapable of specifically recognizing a known polynucleotide, or developing a substance capable of specifically regulating the expression of a known polypeptide, or a substance incapable of specifically regulating the expression of a known polypeptide.

A shared partial nucleotide of the present invention can be a nonspecific partial nucleotide that is present in both a polynucleotide of the present invention and a known polynucleotide. Such partial nucleotides are obvious from the disclosure herein. A shared partial nucleotide of the present invention can be useful as, for example, a target for comprehensively detecting both a polynucleotide of the present invention and a known polynucleotide, and as a biomarker specific for the brain/nerves or specific for nerve differentiation, or as a marker not specific therefor. A shared partial nucleotide of the present invention can also be useful in developing a substance capable of comprehensively recognizing both a polynucleotide of the present invention and a known polynucleotide, or a substance capable of comprehensively regulating the expression of both a polypeptide of the present invention and a known polypeptide.

A polynucleotide of the present invention and a partial nucleotide thereof are capable of encoding a polypeptide of the present invention or a partial peptide of the present invention. A polynucleotide of the present invention or a partial nucleotide of the present invention may be fused with a polynucleotide consisting of a heterologous nucleic acid sequence. As such heterologous nucleic acid sequences, those that encode the above-described heterologous amino acid sequences can be mentioned.

A polynucleotide of the present invention and a partial nucleotide thereof may be provided in the form of a salt. As the salt, those described above can be mentioned.

A polynucleotide of the present invention and a partial nucleotide thereof can be prepared by a method known per se. For example, the same nucleic acid sequence as a nucleic acid sequence shown by SEQ ID NO:Y, or the nucleic acid sequence Y1 or the nucleic acid sequence Y2 can be cloned using a specified tissue or cell. Moreover, substantially the same nucleic acid sequence as a nucleic acid sequence shown by SEQ ID NO:Y or the nucleic acid sequence Y1 or the nucleic acid sequence Y2 can be prepared by introducing a mutation into a polynucleotide cloned as described above. As examples of the method of mutagenesis, methods such as the synthetic oligonucleotide site-directed mutagenesis method, the gapped duplex method, a method of randomly introducing point mutations (for example, treatment with nitrous acid or sulfurous acid), the cassette mutation method, the linker scanning method, and the mismatch primer method can be mentioned.

2. Related Substances

The present invention provides a series of related substances that can be developed on the basis of a polypeptide of the present invention and a partial peptide of the present invention, and a polynucleotide of the present invention and a partial nucleotide of the present invention. The related substances of the present invention described below can be useful as, for example, pharmaceuticals. When a related substance of the present invention is a pharmaceutical, the target disease can be, for example, a disease based on a nerve cell disorder. In detail, as such diseases, Parkinson's disease, Huntington's chorea, Alzheimer's disease, ischemic cerebral diseases (e.g., cerebral stroke), epilepsy, brain trauma, motor nerve disease, multiple sclerosis, amyotrophic lateral sclerosis, diseases caused by nerve toxic disorders and the like can be mentioned.

2.1. Antisense Molecules

The present invention provides antisense molecules.

The type of the antisense molecule may be a DNA or an RNA, or may be a DNA/RNA chimera. The antisense molecule may be one having a phosphodiester bond of the natural type, or a modified nucleotide of the thiophosphate type (P=O in phosphate bond replaced with P=S), 2'-O-methyl type or the like, which are stable to degrading enzymes. Other important factors for the designing of the antisense molecule include increases in water-solubility and cell membrane permeability and the like; these can also be cleared by choosing appropriate dosage forms such as those using liposome or microspheres. The length of the antisense molecule is not particularly limited, as far as the molecule is capable of specifically hybridizing to the transcription product; the antisense molecule may be of a sequence of about 15 nucleotides for the shortest, or of a sequence complementary to the entire sequence of the transcription product for the longest. Considering the ease of synthesis, antigenicity issue and the like, for example, oligonucleotides consisting of about 15 nucleotides or more, preferably about 15 to about 100 nucleotides, and more preferably about 18 to about 50 nucleotides, can be mentioned. Furthermore, the antisense molecule may be one capable of not only inhibiting the translation of the transcription product by hybridizing thereto, but also binding to a double-stranded DNA to form a triple strand (triplex) to inhibit the transcription into mRNA.

An antisense molecule of the present invention can comprise a nucleic acid sequence complementary to a nucleic acid sequence corresponding to a partial nucleotide of the present invention (e.g., specific partial nucleotides A and B of the present invention, a shared partial nucleotide of the present invention). Therefore, an antisense molecule of the present invention can be an antisense molecule specific for a polynucleotide of the present invention, an antisense molecule specific for a known polynucleotide, or an antisense molecule common to both a polynucleotide of the present invention and a known polynucleotide. An antisense molecule of the present invention can be useful in specifically suppressing the expression of a polypeptide of the present invention or a known polypeptide, or comprehensively suppressing the expression of both a polypeptide of the present invention and a known polypeptide.

2.2. RNAi-Inducing Nucleic Acids

The present invention provides RNAi-inducing nucleic acids.

An RNAi-inducible nucleic acid refers to a polynucleotide, preferably an RNA, capable of inducing the RNA interference (RNAi) effect when transferred into cells. The RNAi effect refers to the phenomenon in which a double-stranded RNA comprising the same nucleic acid sequence as that of mRNA, or a partial sequence thereof, suppresses the expression of the mRNA. To obtain the RNAi effect, it is preferable to use, for example, a double-stranded RNA having the same nucleic acid sequence as that of a target mRNA comprising at least 20 or more continuous bases (or a partial sequence thereof). The double-stranded structure may be configured by different strands, or may be a double strand conferred by stem loop structure of a single RNA. As examples of the RNAi-inducing nucleic acid, siRNA, miRNA and the like can be mentioned, and siRNA is preferable. The siRNA is not particularly limited, as far as it can induce RNAi, and the siRNA can be, for example, 21 to 27 bases long, preferably 21 to 25 bases long.

An RNAi-inducing nucleic acid of the present invention can be a double-stranded polynucleotide configured by a sense strand consisting of a nucleic acid sequence corresponding to a partial nucleotide of the present invention (e.g., specific partial nucleotides A and B of the present invention, a shared partial nucleotide of the present invention), and an antisense strand consisting of a nucleic acid sequence complementary thereto. An RNAi-inducing nucleic acid of the present invention may also have an overhang at the 5' terminus and/or 3' terminus of one or both of the sense strand and the antisense strand. The overhang can be one formed as a result of the addition of one to several (e.g., 1, 2 or 3) bases at the 5' terminus and/or 3' terminus of the sense strand and/or antisense strand. An RNAi-inducing nucleic acid of the present invention can be an RNAi-inducing nucleic acid specific for a polynucleotide of the present invention, an RNAi-inducing nucleic acid specific for a known polynucleotide, or an RNAi-inducing nucleic acid common to both a polynucleotide of the present invention and a known polynucleotide. An RNAi-inducing nucleic acid of the present invention can be useful in specifically suppressing the expression of a polypeptide of the present invention or a known polypeptide, or comprehensively suppressing the expression of both a polypeptide of the present invention and a known polypeptide.

2.3. Aptamers

The present invention provides aptamers.

An aptamer refers to a polynucleotide having a binding activity (or inhibitory activity) on a specified target molecule. An aptamer of the present invention can be an RNA, a DNA, a modified nucleotide or a mixture thereof. An aptamer of the present invention can also be in a linear or circular form. The length of the aptamer is not particularly limited, and can normally be about 16 to about 200 nucleotides, and can be, for example, about 100 nucleotides or less, preferably about 50 nucleotides or less, and more preferably about 40 nucleotides or less. The length of an aptamer of the present invention may be, for example, about 18, about 20, about 25 or about 30 nucleotides or more. The aptamer, for increasing the bindability, stability, drug delivering quality and the like, may be one wherein a sugar residue (e.g., ribose) of each nucleotide is modified. As examples of a portion of the sugar residue modified, ones wherein the oxygen atom at the 2'-position, 3'-position and/or 4'-position of the sugar residue is replaced with another atom and the like can be mentioned. As examples of types of modifications, fluorination, O-alkylation, O-allylation, S-alkylation, S-allylation and amination can be mentioned (see, e.g., Sproat et al., (1991) Nucle. Acid. Res. 19, 733-738; Cotton et al., (1991) Nucl. Acid. Res. 19, 2629-2635). The aptamer may be one wherein a purine or pyrimidine is altered. As examples of such alterations, alteration of the 5-position pyrimidine, alteration of the 8-position purine, alteration by an exocyclic amine, substitution by 4-thiouridine, and substitution by 5-bromo or 5-iodo-uracil can be mentioned. The phosphate group contained in an aptamer of the present invention may be altered to make it resistant to nuclease and hydrolysis. For example, the phosphate group may be substituted by a thioate, a dithioate or an amidate. An aptamer can be prepared according to available reports (for example, Ellington et al., (1990) Nature, 346, 818-822; Tuerk et al., (1990) Science, 249, 505-510).

An aptamer of the present invention is capable of binding specifically to a polypeptide of the present invention or a known polypeptide, or both a polypeptide of the present invention and a known polypeptide, via a region corresponding to a partial peptide of the present invention. Therefore, an aptamer of the present invention can be an aptamer specific for a polypeptide of the present invention, an aptamer specific for a known polypeptide, or an aptamer common to both a polypeptide of the present invention and a known polypeptide. Such a specific aptamer can be prepared by, for example, selecting (a) a polynucleotide that binds to a polypeptide of the present invention or a specific partial peptide thereof, and that does not bind to a known polypeptide, (b) a polynucleotide that binds to a known polypeptide or a specific partial peptide thereof, and that does not bind to a polypeptide of the present invention, or (c) a polynucleotide that binds to both a polypeptide of the present invention and a known polypeptide or to a shared partial peptide of the present invention, by the SELEX method.

2.4. Antibodies

The present invention provides antibodies.

An antibody of the present invention may be a polyclonal antibody (antiserum) or a monoclonal antibody, and can be prepared by a commonly known immunological technique. Although the monoclonal antibody may be of any isotype, IgG, IgM, IgA, IgD, IgE, or the like, IgG or IgM is preferable.

For example, the polyclonal antibody can be acquired by administering the above-described antigen (as required, may be prepared as a complex crosslinked to a carrier protein such as bovine serum albumin or KLH ((Keyhole Limpet Hemocyanin)), along with a commercially available adjuvant (for example, Freund's complete or incomplete adjuvant), to an animal subcutaneously or intraperitoneally about 2 to 4 times at intervals of 2 to 3 weeks (the antibody titer of partially drawn serum has been determined by a known antigen-antibody reaction and its elevation has been confirmed in advance), collecting whole blood about 3 to about 10 days after final immunization, and purifying the antiserum. As the animal to receive the antigen, mammals such as rats, mice, rabbits, goat, guinea pigs, and hamsters can be mentioned.

The monoclonal antibody can also be prepared by a cell fusion method. For example, the above-described antigen, along with a commercially available adjuvant, is subcutaneously or intraperitoneally administered to a mouse 2 to 4 times, and 3 days after final administration, the spleen or lymph nodes are collected, and leukocytes are collected. These leukocytes and myeloma cells (for example, NS-1, P3X63Ag8 and the like) are cell-fused to obtain a hybridoma that produces a monoclonal antibody against the factor. This cell fusion may be performed by the PEG method or the voltage pulse method. A hybridoma that produces the desired monoclonal antibody can be selected by detecting an antibody that binds specifically to the antigen, in the culture supernatant, using a widely known EIA or RIA method and the like. Cultivation of the hybridoma that produces the monoclonal antibody can be performed in vitro, or in vivo such as in ascitic fluid of a mouse or rat, preferably a mouse, and the antibody can be acquired from the culture supernatant of the hybridoma and the ascitic fluid of the animal.

An antibody of the present invention may also be a chimeric antibody, a humanized antibody or a human antibody.

A chimeric antibody means a monoclonal antibody derived from immunoglobulins of animal species having mutually different variable regions and constant regions. For example, a chimeric antibody can be a mouse/human chimeric monoclonal antibody whose variable region is a variable region derived from a mouse immunoglobulin, and whose constant region is a constant region derived from a human immunoglobulin. The constant region derived from a human immunoglobulin has an amino acid sequence unique depending on the isotype, such as IgG, IgM, IgA, IgD, and IgE, and the constant region of a recombinant chimeric monoclonal antibody in the present invention may be the constant region of a human immunoglobulin belonging to any isotype. The constant region of human IgG is preferable.

A chimeric antibody can be prepared by a method known per se. For example, a mouse/human chimeric monoclonal antibody can be prepared according to available reports (e.g., Jikken Igaku (extra issue), Vol. 6, No. 10, 1988 and JP-B-HEI-3-73280). In detail, a chimeric antibody can be prepared by inserting the $C_H$ gene acquired from the DNA that encodes a human immunoglobulin (C gene that encodes H chain constant region) downstream of the active $V_H$ gene acquired from the DNA that encodes a mouse monoclonal antibody isolated from a hybridoma that produces the mouse monoclonal antibody (rearranged VDJ gene that encodes H chain variable region), and inserting the $C_L$ gene acquired from the DNA that encodes a human immunoglobulin (C gene that encodes L chain constant region) downstream of the active $V_L$ gene acquired from the DNA that encodes a mouse monoclonal antibody isolated from the hybridoma (rearranged VJ gene that encodes L chain variable region), in a way that allows the expression of each gene, into one or separate expression vectors, transforming a host cell with the expression vector, and culturing the transformant cell.

A humanized antibody means a monoclonal antibody prepared by a gene engineering technique, for example, a human type monoclonal antibody wherein a portion or all of the complementarity-determining region of the ultra-variable region thereof is derived from a mouse monoclonal antibody, and the framework region of the variable region thereof and the constant region thereof are derived from a human immunoglobulin. The complementarity-determining regions of the ultra-variable region are three regions that are present in the ultra-variable region in the variable region of the antibody, and that complementarily directly bind to the antigen (Complementarity-determining regions; CDR1, CDR2, CDR3), and the framework regions of the variable region are four relatively highly conserved regions locating in the front and back of the three complementarity-determining regions (Framework; FR1, FR2, FR3, FR4). In other words, a humanized antibody means, for example, a monoclonal antibody wherein all regions other than a portion or all of the complementarity-determining region of the ultra-variable region of a mouse monoclonal antibody is replaced with a corresponding region of a human immunoglobulin.

A humanized antibody can be prepared by a method known per se. For example, a recombinant humanized antibody derived from a mouse monoclonal antibody can be prepared according to available reports (e.g., Japanese Patent Application Kohyo Publication No. HEI-4-506458 and JP-A-SHO-62-296890). In detail, from a hybridoma that produces a mouse monoclonal antibody, at least one mouse H chain CDR gene and at least one mouse L chain CDR gene corresponding to the mouse H chain CDR gene are isolated, and from a human immunoglobulin gene, the human H chain gene that encodes all regions other than the human H chain CDR corresponding to the mouse H chain gene and the human L chain gene that encodes all regions other than the human L chain CDR corresponding to the mouse L chain CDR are isolated. The mouse H chain CDR gene and human H chain gene isolated are introduced into an appropriate expression vector expressibly; likewise, the mouse L chain CDR gene and the human L chain gene are introduced into another appropriate expression vector expressively. Alternatively, the mouse H chain CDR gene/human H chain gene and the mouse L chain CDR gene/human L chain gene can be introduced into the same expression vector expressively. By transforming a host cell with the expression vector thus prepared to obtain a cell that produces a humanized antibody, and culturing the cell, a desired humanized antibody can be obtained from the culture supernatant.

A human antibody means an antibody wherein all regions comprising the variable regions and constant regions of the H chain and L chain constituting an immunoglobulin are derived from the gene that encodes a human immunoglobulin.

A human antibody can be prepared by a method known per se. For example, a human antibody can be produced by immunologically sensitizing with an antigen a transgenic animal prepared by incorporating at least a human immunoglobulin gene into a gene locus of a non-human mammal such as a mouse, in the same way as the above-described method of preparing a polyclonal antibody or a monoclonal antibody. For example, a transgenic mouse that produces a human antibody can be prepared according to available reports (Nature Genetics, Vol. 15, p. 146-156, 1997; Nature Genetics, Vol. 7, p. 13-21, 1994; Japanese Patent Application Kohyo Publication No. HEI-4-504365; International Patent Application Publication WO94/25585; Nature, Vol. 368, p. 856-859, 1994; and Japanese Patent Application Kohyo Publication No. HEI-6-500233).

An antibody of the present invention can also be a portion of an antibody of the present invention described above (e.g., monoclonal antibody). As examples of such antibodies, F(ab')$_2$, Fab', Fab, and Fv fragments, and single-chain antibodies can be mentioned.

An antibody of the present invention is capable of binding specifically to a polypeptide of the present invention or a known polypeptide, or both a polypeptide of the present invention and a known polypeptide, via a region corresponding to a partial peptide of the present invention. Therefore, an antibody of the present invention can be an antibody specific for a polypeptide of the present invention, an antibody specific for a known polypeptide, or an antibody common to both a polypeptide of the present invention and a known polypeptide. Such a specific antibody can be prepared by, for example, using a specific partial peptide of a polypeptide of the present invention, a specific partial peptide of a known polypeptide, or a shared partial peptide of the present invention as an antigen.

2.5. Expression Vectors

The present invention provides expression vectors for the above-described substances.

An expression vector of the present invention can comprise a polynucleotide that encodes a desired polypeptide to be expressed or a desired polynucleotide to be expressed, and a promoter operably linked to the polynucleotide. "A promoter is operably linked to a polynucleotide" means that the promoter is bound to a polynucleotide that encodes the gene in a way such that allows the expression of the polynucleotide under the control thereof, or the expression of the polypeptide encoded by the polynucleotide.

The backbone for an expression vector of the present invention is not particularly limited, as far as it allows production of a desired substance in a specified cell; for example, plasmid vectors and viral vectors can be mentioned. When an expression vector is used as a pharmaceutical, as vectors suitable for administration to mammals, viral vectors such as adenovirus, retrovirus, adeno-associated virus, herpesvirus, vaccinia virus, poxvirus, poliovirus, Sindbis virus, and Sendai virus can be mentioned.

When a prokaryotic cell is used as the host cell, an expression vector allowing the prokaryotic cell to be utilized as the host cell can be used. Such an expression vector can comprise, for example, elements such as a promoter-operator region, an initiation codon, a polynucleotide that encods a polypeptide of the present invention or a partial peptide thereof, a stop codon, a terminator region and a replication origin. A promoter-operator region for expressing a polypeptide of the present invention in a bacterium comprises a promoter, an operator and a Shine-Dalgarno (SD) sequence. These elements may be ones known per se.

When a eukaryotic cell is used as the host cell, an expression vector allowing the eukaryotic cell to be utilized as the host cell can be used. In this case, the promoter used is not particularly limited, as far as it is capable of functioning in eukaryotic organisms such as mammals. When the expression of a polypeptide is desired, as examples of such promoters, viral promoters such as SV40-derived initial promoter, cytomegalovirus LTR, Rous sarcoma virus LTR, MoMuLV-derived LTR, and adenovirus-derived initial promoter, and mammalian constituent protein gene promoters such as β-actin gene promoter, PGK gene promoter, and transferrin gene promoter, and the like can be mentioned. When the expression of a polynucleotide is desired, the promoter can be a polIII promoter (e.g., tRNA promoter, U6 promoter, H1 promoter).

An expression vector of the present invention can further comprise sites for transcription initiation and transcription termination, and a ribosome-binding site required for translation in the transcription region, a replication origin and a selection marker gene (e.g., ampicillin, tetracycline, kanamycin, spectinomycin, erythromycin, chloramphenicol) and the like. An expression vector of the present invention can be prepared by a method known per se (see, e.g., Molecular Cloning, $2^{nd}$ edition, Sambrook et al., Cold Spring Harbor Lab. Press (1989)).

3. Compositions

The present invention provides compositions comprising the above-described substances.

A composition of the present invention can comprise, in addition to the above-described substances, an optionally chosen carrier, for example, a pharmaceutically acceptable carrier. As examples of the pharmaceutically acceptable carrier, excipients such as sucrose, starch, mannitol, sorbitol, lactose, glucose, cellulose, talc, calcium phosphate, and calcium carbonate, binders such as cellulose, methylcellulose, hydroxypropylcellulose, polypropylpyrrolidone, gelatin, gum arabic, polyethylene glycol, sucrose, and starch, disintegrants such as starch, carboxymethylcellulose, hydroxypropylstarch, sodium-glycol-starch, sodium hydrogen carbonate, calcium phosphate, and calcium citrate, lubricants such as magnesium stearate, Aerosil, talc, and sodium lauryl sulfate, flavoring agents such as citric acid, menthol, glycyrrhizin ammonium salt, glycine, and orange flour, preservatives such as sodium benzoate, sodium hydrogen sulfite, methylparaben, and propylparaben, stabilizing agents such as citric acid, sodium citrate, and acetic acid, suspending agents such as methyl cellulose, polyvinylpyrrolidone, and aluminum stearate, dispersing agents such as surfactants, diluents such as water, physiological saline, and orange juice, and base waxes such as cacao butter, polyethylene glycol, and kerosene, and the like can be mentioned, which, however, are not to be construed as limiting.

Preparations suitable for oral administration are liquids prepared by dissolving an effective amount of a substance in a diluent such as water, physiological saline or orange juice, capsules, saches or tablets containing an effective amount of a substance in the form of solids or granules, suspensions prepared by suspending an effective amount of a substance in an appropriate dispersant, emulsions prepared by dispersing and emulsifying a solution, an effective amount of a substance is dissolved therein, in an appropriate dispersant, and the like.

Preparations suitable for parenteral administration (for example, intravenous injection, subcutaneous injection, intramuscular injection, topical injection, intraperitoneal administration and the like) are aqueous and non-aqueous isotonic sterile injectable liquids, which may contain an antioxidant, a buffer solution, a bacteriostatic agent, an isotonizing agent and the like. Aqueous and non-aqueous sterile suspensions can also be mentioned, which may contain a suspending agent, a solubilizer, a thickening agent, a stabilizer, an antiseptic and the like. These preparations can be enclosed in containers such as ampoules and vials for unit dosage or a plurality of dosages. It is also possible to freeze-dry the active ingredient and a pharmaceutically acceptable carrier, and store the preparation in a state that may be dissolved or suspended in an appropriate sterile vehicle just before use.

Although the dosage of a composition of the present invention varies depending on the activity and kind of active ingredient, seriousness of illness, recipient animal species, the recipient's drug tolerance, body weight, age, and the like, it is normally about 0.001 to about 500 mg/kg as the amount of active ingredient per day for an adult.

A composition of the present invention enables a regulation (e.g., promotion or suppression) of the expression or a function of a polypeptide of the present invention. A composition of the present invention can be useful as, for example, a pharmaceutical (e.g., a prophylactic or therapeutic drug for a disease as described above), reagent or food.

4. Cells

The present invention provides transformants that produce a polypeptide of the present invention or a partial peptide of the present invention, cells that produce an antibody of the present invention, and cells wherein the expression or a function of a polynucleotide or polypeptide of the present invention is regulated.

4.1. Transformants

A transformant of the present invention can be a cell transformed with an expression vector of the present invention, that expresses a polypeptide of the present invention or a partial peptide of the present invention. The host cell used to prepare the transformant is not particularly limited, as far as it is compatible with the expression vector, and capable of expressing the desired polynucleotide or polypeptide and the like; for example, primary culture cells or cell lines can be mentioned. In detail, as examples of such host cells, cells of prokaryotic organisms such as *Escherichia coli*, bacteria of the genus *Bacillus* (e.g., *Bacillus subtilis*), and *actinomyces*, and cells of eukaryotic organisms, such as yeast, insect cells, bird cells, and mammalian cells (e.g., cells derived from the above-described mammals: e.g., CHO cells) can be mentioned. A transformant of the present invention can be prepared by a method known per se (see, e.g., Molecular Cloning, $2^{nd}$ edition, Sambrook et al., Cold Spring Harbor Lab. Press (1989)).

Cultivation of the transformant can be performed in a nutrient medium such as a liquid medium by a method known per se. The medium preferably contains a carbon source, a nitrogen source, an inorganic substance and the like necessary for the growth of the transformant. Here, as examples of the carbon source, glucose, dextrin, soluble starch, sucrose and the like can be mentioned; as examples of the nitrogen source, inorganic or organic substances such as an ammonium salt, a nitrate salt, corn steep liquor, peptone, casein, meat extract, soybean cake, potato extract and the like can be mentioned; as examples of the inorganic substance, calcium chloride, sodium dihydrogen phosphate, magnesium chloride and the like can be mentioned. In addition, the medium may be supplemented with yeast extract, vitamins and the like. Culturing conditions, for example, temperature, medium pH and culturing time, are chosen as appropriate to allow a polypeptide of the present invention to be produced in a large amount. Culturing temperature is, for example, 30 to 37° C.

4.2. Antibody Producing Cells

An antibody-producing cell of the present invention can be an optionally chosen cell that produces an antibody of the present invention. As antibody-producing cells of the present invention, the above-described hybridomas, and a transformant cell incorporating an expression vector for one of the above-described antibodies can be mentioned. When an antibody-producing cell of the present invention is a transformant cell, details of the expression vector, host cell, cell culture and the like used to prepare the transformant cell can be the same as those described above.

4.3. Cells Wherein the Expression or a Function of a Polypeptide of the Present Invention is Regulated The present invention provides cells wherein the expression or a function of a polypeptide of the present invention is regulated.

A cell of the present invention can be an isolated and/or purified one. A cell of the present invention can be a cell derived from one of the above-described tissues, or a cell of one of the above-described kinds. A cell of the present invention can be derived from one of the above-described mammals. A cell of the present invention can be a primary culture cell or cell line, or a normal cell, or a cell derived from a mammal with one of the above-described diseases. A cell of the present invention can be a cell wherein the expression or a function of a polypeptide of the present invention is regulated specifically. A cell of the present invention can have a nerve cell-related action or nerve cell-related phenotype thereof being variable as a result of a regulation (e.g., promotion, suppression) of the expression or a function of a polypeptide of the present invention. A cell of the present invention can be a cell wherein the expression of a polypeptide of the present invention is regulated transiently, or a cell wherein the expression is regulated permanently (e.g., homozygousity- or heterozygousity-deficient cells). A cell of the present invention can also be a transformant or a non-transformant.

A cell of the present invention can be prepared by, for example, treating a cell with one of the above-described substances capable of regulating the expression or a function of a polynucleotide of the present invention or a polypeptide of the present invention (e.g., polypeptides of the present invention, antisense molecules, RNAi-inducing nucleic acids, antibodies, or expression vectors therefor). A cell of the present invention can also be prepared by isolating and/or purifying a cell from a transgenic animal or gene-deficient (so-called knockout) animal described below.

A cell wherein the expression or a function of a polypeptide of the present invention is regulated can be useful in, for example, developing a pharmaceutical (e.g., a prophylactic or therapeutic drug as described above), reagent or food, identifying a further marker gene specific for the brain/nerves or specific for nerve cell differentiation, and analyzing mechanisms associated with nerve cell differentiation. These can be performed by, for example, an expression profile analysis comprising measuring the expression profile in a cell of the present invention using a microarray, protein chip (e.g., antibody chip, or non-antibody chip such as chip manufactured by Ciphergen) and the like, and comparing the profile with the expression profile of a control cell. A cell of the present invention can also be useful as a cell model of a disease as described above.

5. Animals

The present invention provides animals wherein the expression or a function of a polypeptide of the present invention is regulated.

An animal of the present invention can be an animal with or without a genome alteration. The species of an animal of the present invention can be, for example, the same as one of the above-described non-human mammals.

In one embodiment, an animal of the present invention can be a transgenic animal with a genome alteration. A transgenic animal of the present invention is capable of expressing a polypeptide of the present invention. A transgenic animal of the present invention is also capable of expressing a polypeptide of the present invention specifically in one of the above-described cells or tissues.

A transgenic animal of the present invention can be prepared by a method known per se. In more detail, a transgenic animal of the present invention can be prepared by, for example, introducing a polynucleotide of the present invention linked operably to a specified promoter (e.g., a promoter that is non-specific or specific for one of the above-described cells or tissues) (e.g., may be in the form of an expression vector of the present invention) into a fertilized egg of an animal or another cell (e.g., unfertilized egg, spermatozoon or a progenitor cell thereof) in the initial stage of development. As examples of the method of gene introduction, the electroporation method, lipofection method, aggregation method, calcium phosphate coprecipitation method, and microinjection method can be mentioned. A transgenic animal of the present invention may be an animal prepared by mating a thus-prepared animal and another animal of the same species (e.g., animal model of a disease as described above).

In another embodiment, an animal of the present invention can be a gene-deficient animal with a genome alteration. A gene-deficient animal of the present invention is incapable of expressing a polypeptide of the present invention. A gene-deficient animal of the present invention is also incapable of expressing a polypeptide of the present invention specifically in one of the above-described cells or tissues.

A gene-deficient animal of the present invention can be prepared by a method known per se. In more detail, a gene-deficient animal of the present invention can be prepared using an embryonic stem cell (ES cell) specifically lacking a brain/nerve-specific gene. Such an ES cell can be prepared by, for example, introducing a specified targeting vector into ES cells, and selecting an ES cell showing homologous recombination from among the ES cells incorporating the targeting vector.

As a targeting vector, a targeting vector capable of inducing homologous recombination that causes specific expressional failure of a polynucleotide or polypeptide of the present invention can be used. Such a targeting vector comprises a first polynucleotide and second polynucleotide that are homologous or specifically homologous to a brain/nerve-specific gene (of the polynucleotides, at least one comprises a splicing donor signal for the brain/nerve-specific gene, and comprises a mutation that nullifies the splicing that produces at least one isoform in the signal), and, as required, a selection marker. A splicing donor signal for the brain/nerve-specific gene, and a mutation that nullifies the splicing that produces at least one isoform in the signal can be easily determined by a person skilled in the art. The first and second polynucleotides are polynucleotides having a sequence identity and length that are sufficient to produce homologous recombination in the genomic DNA associated with the brain/nerve-specific gene. The first and second polynucleotides are chosen in a way such that specific deficiency of a particular isoform is produced. As selection markers, positive selection markers (e.g., neomycin resistance gene, hygromycin B phosphotransferase (BPH) gene, blasticidin S deaminase gene, puromycin resistance gene), negative selection markers (e.g., herpes simplex virus (HSV) thymidine kinase (tk) gene, diphtheria toxin A fragment (DTA) gene) and the like can be mentioned. The targeting vector can comprise either a positive selection marker or a negative selection marker or both. The targeting vector may comprise two or more recombinase target sequences (e.g., loxP sequence, which is used in the Cre/loxP system derived from bacteriophage P1, FRT sequence, which is used in yeast-derived FLP/FRT system). The present invention also provides such a targeting vector.

As the method for introducing a targeting vector into an ES cell, a method known per se can be used. As examples of such methods, the calcium phosphate method, lipofection method/liposome method, electroporation method and the like can be mentioned. When a targeting vector is introduced into a cell, homologous recombination of the genomic DNA associated with the brain/nerve-specific gene occurs in the cell. Although an ES cell may be established by culturing an inner cell mass separated from a blastocyst of an optionally chosen animal on feeder cells, an existing ES cell may be utilized.

To select an ES cell showing homologous recombination, cells after introduction of a targeting vector are screened for. For example, after selection is performed by positive selection, negative selection and the like, screening based on genotype (for example, PCR method, Southern blot hybridization method) is performed. It is also preferable to further perform karyotype analysis on the ES cell obtained. In the karyotype analysis, the absence of chromosome aberrations in the selected ES cell is checked. Karyotype analysis can be performed by a method known per se. It is preferable that the karyotype of the ES cell be confirmed in advance before introducing the targeting vector.

A gene-deficient animal of the present invention can be prepared by transplanting to an animal a chimeric embryo obtained by introducing an ES cell obtained as described above into an embryo, and then mating the chimeric animal obtained. As examples of the embryo, blastocysts, 8-cell stage embryos and the like can be mentioned. The embryo can be obtained by mating a female animal undergoing an overovulation treatment with a hormone preparation (for example, PMSG, which has FSH-like action, and hCG, which has LH action, are used) and the like with a male animal, and the like. As methods of introducing an ES cell into an embryo, the micromanipulation method, aggregation method and the like can be mentioned.

The animal receiving a chimeric embryo transplanted is preferably a pseudo-pregnant animal. A pseudo-pregnant animal can be obtained by mating a female animal in the normal sexual cycle with a male animal emasculated by vasoligation and the like. The animal incorporating the chimeric embryo becomes pregnant and delivers a chimeric animal. Next, it is determined whether or not the animal born is a chimeric animal. Whether or not the animal born is a chimeric animal can be determined by a method known per se, for example, by the body color or coat color. For the determination, a DNA may be extracted from a portion of the body and subjected to Southern blot analysis or PCR assay. The mating can be performed preferably between a wild-type animal and a chimeric animal, or between chimeric animals. Whether or not the deficiency of the brain/nerve-specific gene has been introduced into the germ cell line of the chimeric animal and heterozygous offspring lacking the brain/nerve-specific gene has been obtained can be determined by a method known per se with various characters as indexes; for example, this can be determined by the body color or coat color of the offspring animal. For the determination, a DNA may be extracted from a portion of the body and subjected to Southern blot analysis or PCR assay. Furthermore, by mating thus-obtained heterozygotes, a homozygote can be prepared. A gene-deficient animal of the present invention may also be an animal prepared by mating an animal thus prepared and another animal of the same species (e.g., animal model of disease based on nerve cell disorder, transgenic animal).

In a still another embodiment, an animal of the present invention can be an animal without a genome alteration. Such an animal can be prepared by treating an animal with one of the above-described substances capable of regulating the expression or a function of a polynucleotide of the present invention or a polypeptide of the present invention (e.g., polypeptides of the present invention, antisense molecules, RNAi-inducing nucleic acids, antibodies, or expression vectors therefor). Such an animal can also be an animal capable or incapable of expressing a polypeptide of the present invention specifically in one of the above-described tissues by topical treatment. The animal treatment can be performed using a method mentioned with respect to a composition of the present invention.

An animal of the present invention can be useful in, for example, developing a pharmaceutical (e.g., a prophylactic or therapeutic drug as described above), reagent or food, identifying a further marker gene specific for the brain/nerves or specific for nerve cell differentiation, and analyzing mechanisms associated with nerve cell differentiation. These can be performed by, for example, an expression profile analysis comprising measuring an expression profile (particularly expression profile of a nerve cell or a tissue in the brain) using a microarray, protein chip (e.g., antibody chip, or non-antibody chip such as a chip manufactured by Ciphergen) and the like in an animal of the present invention, and comparing the profile with the expression profile of a control animal. An animal of the present invention can also be useful as an animal model of a disease as described above.

6. Measuring Means and Measuring Method

The present invention provides measuring means (e.g., primer set, nucleic acid probe, antibody, aptamer) and measuring methods for target polynucleotides and polypeptides.

6.1. Primer Set and Method of Use Thereof.

A primer set of the present invention can be used for specific detection and quantitation of a polynucleotide of the present invention or a known polynucleotide, or comprehensive detection and quantitation of both a polynucleotide of the present invention and a known polynucleotide. For example, such detection and quantitation can be achieved, after preparing total RNA from a biological sample, by utilizing a method of gene amplification such as a PCR (e.g., RT-PCR, real-time PCR, quantitative PCR), LAMP (Loop-mediated isothermal amplification) (see, e.g., WO00/28082), or ICAN (Isothermal and Chimeric primer-initiated Amplification of Nucleic acids) (see, e.g., WO00/56877). Because the number of primers required differs depending on the kind of the method of gene amplification, the number of primers is not particularly limited; for example, a primer set of the present invention can comprise two or more primers constituted by a sense and antisense primer. The two or more primers may be mixed in advance or not. Each of the sense and antisense primers is not particularly limited, as far as it is of a size enabling specific amplification of the target region; each primer consists of 12 (for example, at least about 15, preferably at least about 18, more preferably at least about 20 and the like) consecutive nucleotide residues. The sense and antisense primer, when the size of the polynucleotide amplified thereby is to be visually detected, can be designed to allow it to be visually detectable. The visually detectable size is not particularly limited, and can be, for example, at least about 50, preferably at least 70, more preferably at least about 100, still more preferably at least about 150, and most preferably at least about 200, about 300, about 400, about 500 or more nucleotide residues long. The sense and antisense primer do not require that the polynucleotide amplified thereby be visually detected, and may be detected by a fluorescence signal and the like, as is commonly used in real-time PCR.

A primer set of the present invention can be a) a primer set specific for a polynucleotide of the present invention, capable of distinguishing a polynucleotide of the present invention from a known polynucleotide (abbreviated as "specific primer set A" as required), b) a primer set specific for a known polynucleotide, capable of distinguishing a known polynucleotide from a polynucleotide of the present invention (abbreviated as "specific primer set B" as required), or c) a primer set common to both a polynucleotide of the present invention and a known polynucleotide (abbreviated as "shared primer set" as required) wherein a polynucleotide of the present invention and a known polynucleotide do not distinguish each other.

The specific primer set A of the present invention can comprise i) a sense and antisense primer designed to make it possible to distinguish the size of the polynucleotide of the present invention or partial nucleotide thereof to be amplified from the size of the known polynucleotide or partial nucleotide thereof to be amplified, or ii) a sense and antisense primer designed to allow a polynucleotide of the present invention or a partial nucleotide thereof alone to be amplified, and not to allow a known polynucleotide to be amplified.

The sense and antisense primers of i) above are preferably, for example, a) a sense primer corresponding to a nucleic acid sequence present on the 5' side relative to the nucleic acid sequence of the above-described specific partial nucleotide A (particularly an insert nucleic acid sequence of a polynucleotide of the present invention), and an antisense primer corresponding to a nucleic acid sequence complementary to a nucleic acid sequence present on the 3' side relative to the nucleic acid sequence, or b) a sense primer corresponding to a nucleic acid sequence present on the 5' side relative to the nucleic acid sequence of the above-described specific partial nucleotide B (particularly an insert nucleic acid sequence of a known polynucleotide), and an antisense primer corresponding to a nucleic acid sequence complementary to a nucleic acid sequence present on the 3' side relative to the nucleic acid sequence.

The sense and antisense primers of ii) above are preferably, for example, a) a sense primer corresponding to the nucleic acid sequence of the above-described specific partial nucleotide A (particularly an insert nucleic acid sequence of a polynucleotide of the present invention), and a specified antisense primer, b) a specified sense primer, and a sense primer corresponding to the nucleic acid sequence of the above-described specific partial nucleotide A (particularly an insert nucleic acid sequence of a polynucleotide of the present invention), or c) a sense and antisense primer corresponding to the nucleic acid sequence of the above-described specific partial nucleotide A (particularly an insert nucleic acid sequence of a polynucleotide of the present invention).

The specific primer set B of the present invention can comprise i) a sense and antisense primer designed to make it possible to distinguish the size of the known polynucleotide or partial nucleotide thereof to be amplified from the size of the polynucleotide of the present invention or partial nucleotide thereof to be amplified, or ii) a sense and antisense primer designed to allow a known polynucleotide or a partial nucleotide thereof alone to be amplified, and not to allow a polynucleotide of the present invention to be amplified.

The sense and antisense primers of i) above are preferably, for example, a) a sense primer corresponding to a nucleic acid sequence present on the 5' side relative to the nucleic acid sequence of the above-described specific partial nucleotide B (particularly an insert nucleic acid sequence of a known polynucleotide), and an antisense primer corresponding to a nucleic acid sequence complementary to a nucleic acid sequence present on the 3' side relative to the nucleic acid sequence, or b) a sense primer corresponding to a nucleic acid sequence present on the 5' side relative to the nucleic acid sequence of the above-described specific partial nucleotide A (particularly an insert nucleic acid sequence of a polynucleotide of the present invention), and an antisense primer corresponding to a nucleic acid sequence complementary to a nucleic acid sequence present on the 3' side relative to the nucleic acid sequence.

The sense and antisense primers of ii) above are preferably, for example, a) a sense primer corresponding to the nucleic acid sequence of the above-described specific partial nucleotide B (particularly an insert nucleic acid sequence of a known polynucleotide), and a specified antisense primer, b) a specified sense primer, and a sense primer corresponding to the nucleic acid sequence of the above-described specific partial nucleotide B (particularly an insert nucleic acid sequence of a known polynucleotide), or c) a sense and antisense primer corresponding to the nucleic acid sequence of the above-described specific partial nucleotide B (particularly an insert nucleic acid sequence of a known polynucleotide).

A shared primer set of the present invention can comprise a sense and antisense primer designed to equalize the size of the known polynucleotide or partial nucleotide thereof to be amplified to the size of the polynucleotide of the present invention or partial nucleotide thereof to be amplified. Such a sense and antisense primer are preferably, for example, a sense and antisense primer designed not to allow the polynucleotide of the present invention or partial nucleotide thereof to be amplified, and the known polynucleotide or partial nucleotide thereof to be amplified, to comprise the nucleic acid sequences of the above-described specific partial nucleotides A and B.

6.2. Nucleic Acid Probe and Method of Use Thereof

A nucleic acid probe of the present invention can be used for specific detection and quantitation of a polynucleotide of the present invention or a known polynucleotide, or comprehensive detection and quantitation of both a polynucleotide of the present invention and a known polynucleotide. For example, such a detection and quantitation can be achieved, after preparing total RNA from a biological sample, by utilizing Northern blotting, a nucleic acid array wherein a nucleic acid probe of the present invention is immobilized, and the like. Although the nucleic acid probe can be a DNA, an RNA, a modified nucleic acid or a chimeric molecule thereof and the like, a DNA is preferable in consideration of safety, convenience and the like. The nucleic acid probe may also be any one of a single-stranded or a double-stranded polynucleotide. The size of the nucleic acid probe is not particularly limited, as far as it is capable of specifically hybridizing to the transcription product of the target gene; the size is, for example, at least about 15 or 16, preferably about 15 to about 1000, more preferably about 20 to about 500, and still more preferably about 25 to about 300. When a nucleic acid probe of the present invention is a single-stranded polynucleotide, the nucleic acid probe of the present invention can be the same as an antisense molecule of the present invention. When a nucleic acid probe of the present invention is a double-stranded polynucleotide, the nucleic acid probe of the present invention can be configured by an antisense molecule of the present invention and a polynucleotide molecule complementary thereto.

A nucleic acid probe of the present invention can be a) a nucleic acid probe specific for a polynucleotide of the present invention, capable of distinguishing a polynucleotide of the present invention from a known polynucleotide (abbreviated as "specific nucleic acid probe A" as required), b) a nucleic acid probe specific for a known polynucleotide, capable of distinguishing a known polynucleotide from a polynucleotide of the present invention (abbreviated as "specific nucleic acid probe B" as required), or c) a nucleic acid probe common to both a polynucleotide of the present invention and a known polynucleotide, wherein a polynucleotide of the present invention and a known polynucleotide do not distinguish each other (abbreviated as "shared nucleic acid probe" as required).

The specific nucleic acid probe A of the present invention can be a polynucleotide having a nucleic acid sequence complementary to the nucleic acid sequence of the above-described specific partial nucleotide A (particularly an insert nucleic acid sequence of a polynucleotide of the present invention) (a single-stranded polynucleotide), or a polynucleotide having the nucleic acid sequence of the above-described specific partial nucleotide A (particularly an insert nucleic acid sequence of a polynucleotide of the present invention) and a nucleic acid sequence complementary to the nucleic acid sequence (a double-stranded polynucleotide).

The specific nucleic acid probe B of the present invention can be a polynucleotide having a nucleic acid sequence complementary to the nucleic acid sequence of the above-described specific partial nucleotide B (particularly an insert nucleic acid sequence of a known polynucleotide) (a single-stranded polynucleotide), or a polynucleotide having the nucleic acid sequence of the above-described specific partial nucleotide B (particularly an insert nucleic acid sequence of a known polynucleotide) and a nucleic acid sequence complementary to the nucleic acid sequence (a double-stranded polynucleotide).

A shared nucleic acid probe of the present invention can be a polynucleotide having a nucleic acid sequence complementary to the nucleic acid sequence of the above-described shared partial nucleotide (a single-stranded polynucleotide), or a polynucleotide having a nucleic acid sequence complementary to the nucleic acid sequence of the above-described shared partial nucleotide and the nucleic acid sequence (a double-stranded polynucleotide).

A nucleic acid probe of the present invention may be provided in a state immobilized on a support (i.e., as an array). The support for such a nucleic acid array is not particularly limited, as far as it is a support in common use in the art; for example, membranes (e.g., nylon membranes), glass, plastics, metals, plates and the like can be mentioned. A nucleic acid array in the present invention can assume a form known per se; for example, an array wherein a nucleic acid is directly synthesized on a support (so-called affimetrix type), an array wherein a nucleic acid is immobilized on a support (so-called Stanford type), fiber-type array, and electrochemical array (ECA) can be mentioned.

6.3. Antibodies and Aptamers and Method of Use Thereof.

An antibody and aptamer of the present invention can be used for specific detection and quantitation of a polypeptide of the present invention, a known polypeptide, or both a polypeptide of the present invention and a known polypeptide. For example, such a detection and quantitation can be achieved, after preparing an extract from a biological sample, or using a biological sample, by an immunological technique or an affinity-based method. As examples of such immunological techniques, enzyme immunoassay (EIA) (e.g., direct competitive ELISA, indirect competitive ELISA, sandwich ELISA), radioimmunoassay (RIA), fluorescent immunoassay (FIA), immunochromatography, luminescence immunoassay, spin immunoassay, Western blotting, and immunohistochemical staining can be mentioned. An affinity-based method can be performed in accordance with one of the above-described immunological techniques. The antibody and aptamer used for a measurement of a polypeptide of the present invention, a known polypeptide, or both a polypeptide of the present invention and a known polypeptide can be the same as the above-described antibody and aptamer of the present invention.

An antibody and aptamer of the present invention can be a) an antibody and aptamer specific for a polypeptide of the present invention, that make it possible to distinguish a polypeptide of the present invention from a known polypeptide (abbreviated as "specific antibody and aptamer A" as required), b) an antibody and aptamer specific for a known polypeptide, that make it possible to distinguish a known polypeptide from a polypeptide of the present invention (abbreviated as "specific antibody and aptamer B" as required), or c) an antibody and an aptamer common to both a polypeptide of the present invention and a known polypeptide, that do not distinguish between a polypeptide of the present invention and a known polypeptide (abbreviated as "shared antibody and aptamer" as required). The specific antibody and aptamer A of the present invention are capable of binding to the above-described specific partial peptide A (particularly a partial peptide consisting of an insert amino acid sequence of a polypeptide of the present invention). The specific antibody and aptamer B of the present invention are capable of binding to the above-described specific partial peptide B (particularly a partial peptide consisting of an insert amino acid sequence of a known polypeptide). A shared antibody and aptamer of the present invention are capable of binding to the above-described shared partial peptide.

An antibody and aptamer of the present invention may be provided in a form immobilized on a support (i.e., as an array). The support for such a nucleic acid array is not particularly limited, as far as it is a support in common use in the art; for example, membranes (e.g., nitrocellulose membranes), glass, plastics, metals, and plates (e.g., multiwell plates) can be mentioned.

6.4. Supplementary Matters Concerning Measuring Means of the Present Invention

A measuring means of the present invention can be provided in a form labeled with a labeling substance as required. As examples of the labeling substance, fluorescent substances such as FITC and FAM, luminescent substances such as luminol, luciferin and lucigenin, radioisotopes such as $^3$H, $^{14}$C, $^{32}$P, $^{35}$S, and $^{123}$I, affinity substances such as biotin and streptavidin, and the like can be mentioned.

A measuring means of the present invention may be provided in the form of a kit comprising an additional constituent, in addition to the measuring means. In this case, the various constituents contained in the kit can be provided in mutually isolated forms, for example, in forms housed in different containers. For example, when the measuring means is not labeled with a labeling substance, the kit can further comprise a labeling substance. A kit of the present invention can comprise two or more measuring means for two or more target genes (e.g., a combination of a brain/nerve-specific gene and a known gene, a combination of two or more brain/nerve-specific genes). When the measuring means of the present invention is provided in the form of an array, the array of the present invention can be one wherein two or more measuring means for two or more target genes are immobilized. A kit and array of the present invention can also comprise a measuring means as described above with respect to a housekeeping gene (e.g., GAPDH, β-actin).

6.5. Measuring Methods of the Present Invention

The present invention also provides a method of detecting or quantifying a target polypeptide or polynucleotide using a measuring means of the present invention.

A measurement of a target polynucleotide and polypeptide can be properly performed according to the kind of the measuring means by the above-described method.

In a method of the present invention, the expression level of a target polynucleotide or polypeptide in a biological sample obtained from one of the above-described mammals (e.g., human) or a culture (e.g., cell or tissue culture) can be measured. The biological sample is not particularly limited, as far as it is, for example, a sample containing a cell or tissue expressing the target polynucleotide or polynucleotide, or, if the target polynucleotide or polypeptide is secreted or oozed or the like, an animal-derived sample (e.g., blood, plasma, serum, saliva, cerebrospinal fluid, tear, urine) containing the polynucleotide or polypeptide secreted or oozed or the like. The biological sample can be one containing one of the above-described cells or tissues (e.g., nerve cell or a tissue in the brain). The biological sample used in the present invention, unless otherwise specified, can be a biological sample collected from a mammal in advance; in a particular aspect, a method of the present invention can comprise collecting a biological sample from a mammal.

In one embodiment, a method of the present invention can be utilized to identify a nerve cell, to determine a nerve cell differentiation state, or to diagnose a disease based on a nerve cell disorder (e.g., determination of onset or likelihood of onset). This method can comprise measuring the expression level of a target polynucleotide or polypeptide in a biological sample collected from an animal, and evaluating the onset or likelihood of onset of a target disease on the basis of the measured expression level or relative expression rate. For example, the measured expression level or relative expression rate is compared with the expression level in a mammal not suffering the target disease (e.g., normal animal). The expression level or expression rate in a mammal not suffering the target disease can be determined by a method known per se. By such a comparison, it is determined whether or not the animal possibly has the target disease, or whether or not the animal is likely to suffer the disease. It is known that in a mammal having a particular disease manifested, an expressional change in the gene associated with the disease is often observed. It is also known that before the onset of a particular disease, an expressional change in a particular gene is often observed. Therefore, by such an analysis, it is possible to determine the onset or likelihood of onset of a target disease. Such a method can be useful in, for example, conveniently determining and early detecting a target disease. Of course, a measuring means of the present invention and a reagent or kit of the present invention can also be utilized for such a determination.

In detail, the changes in the expression profiles of the brain/nerve-specific genes 1 to 10 in nerve cells or tissues in the brain are as described in Examples. Therefore, using a measuring means of the present invention that enables a specific measurement of a polynucleotide of the present invention and a partial nucleotide of the present invention (e.g., specific partial nucleotide A of the present invention, specific partial nucleotide B of the present invention, shared partial nucleotide of the present invention), and a polypeptide of the present invention and a partial peptide of the present invention (e.g., specific partial peptide A of the present invention, specific partial peptide B of the present invention, shared partial peptide of the present invention), by evaluating the degree of the expression of the brain/nerve-specific genes 1 to 10 and/or relative expression ratios thereof, it is possible to identify a nerve cell, to determine a differentiation state of a nerve cell, or to diagnose a disease based on a nerve cell disorder.

In another embodiment, a method of the present invention can be utilized for screening for a pharmaceutical, reagent or food and the like. For example, in one methodology, the screening method can comprise determining whether or not a test material is capable of regulating (e.g., increasing or decreasing) the number of nerve cells. Because the number of nerve cells and the expression level of a brain/nerve-specific gene can correlate with each other, such a screening can be performed by measuring the expression level of the brain/nerve-specific gene. In another methodology, the screening method can comprise determining whether or not a test material is capable of regulating the expression or a function of a target polynucleotide or polypeptide. Such a screening method can be utilized as, for example, a screening method for a pharmaceutical effective for a specified disease (e.g., disease based on a nerve cell disorder) and the like, comprising selecting a test substance capable of regulating the expression or a function of a target, and a screening method for a pharmaceutical with a decreased specified action (e.g., adverse reactions such as nerve cell differentiation regulatory action) and the like, comprising selecting a test substance incapable of regulating the expression or a function of a target. The test material subjected to the screening method can be a commonly known compound or a novel compound or a composition; as examples, nucleic acids, glucides, lipids, proteins, peptides, organic low molecular compounds, compound libraries prepared using combinatorial chemistry technology, random peptide libraries prepared by solid phase synthesis or the phage display method, or naturally occurring ingredients derived from microorganisms, animals, plants, marine organisms and the like, existing pharmaceuticals, reagents or foods and the like can be mentioned. In the screening method, mammals, cells and tissues (e.g., nerve cell and a tissue in the brain), or reconstitution systems (non-cell systems) as described above can be used. Pharmaceuticals and the like obtained by the screening method are also provided by the present invention.

The disclosures in all publications mentioned herein, including patents and patent application specifications, are incorporated herein by reference to the extent that all of them have been given expressly.

EXAMPLES

The present invention is hereinafter described in further detail with reference to Examples; however, the present invention is not limited to the Examples and the like by any means.

Example 1

Preparation and Sequence Analysis of Human cDNA Libraries (1) Preparation and Sequence Analysis of cDNA Libraries by the Improved Oligocap Method
1) Extraction and Purchase of mRNAs From human tissues (shown below), by a method described in a literature document (J. Sambrook, E. F. Fritsch & T. Maniatis, Molecular Cloning Second edition, Cold Spring harbor Laboratory Press, 1989), mRNAs were extracted as total RNAs. After cultivation of cultured human cells or primary culture human cells (shown below) by the methods described in the catalogues thereof, mRNAs were extracted as total RNAs by a method described in a literature document (J. Sambrook, E. F. Fritsch & T. Maniatis, Molecular Cloning Second edition, Cold Spring harbor Laboratory Press, 1989).

Hereinafter, the relationships between the names of libraries and the derivations thereof are shown in the order of "name of library: derivation". If a library was generated by subtraction, how to generate the subtraction library is also shown.
<Extraction of mRNAs from Human Tissues>
NTONG: Tongue; CTONG: Tongue, Tumor; FCBBF: Brain, Fetal; OCBBF: Brain, Fetal; PLACE: Placenta; SYNOV: Synovial membrane tissue from rheumatoid arthritis; CORDB: Cord blood.
<Extraction of mRNAs from Cultured Cells>
BNGH4: H4 cell (ATCC #HTB-148); IMR32: IMR32 cell (ATCC #CCL-127); SKNMC: SK-N-MC cell (ATCC #HTB-10); 3NB69: NB69 cell (RCB #RCB0480); BGGI1: GI1 cell (RCB #RCB0763); NB9N4: NB9 cell (RCB #RCB0477);

SKNSH: SK-N-SH cell (RCB #RCB0426); AHMSC: HMSC cell (Human mesenchymal cell); CHONS: Chondrocyte; ERLTF: TF-1 cell (erythroleukemia); HELAC: HeLa cell; JCMLC: leukemia cell (Leukemia, myelogenous); MESTC: Mesenchyme stem cell; N1ESE: Mesenchymal stem cell; NCRRM: Embryonal carcinoma; NCRRP: Embryonal carcinoma treated with retinoic acid (RA) to induce differentiation; T1ESE: Mesenchymal stem cell treated with trichostatin and 5-azacytidine to induce differentiation; NT2RM: NT2 cell (STARATAGENE #204101); NT2RP: NT2 cell treated with retinoic acid (RA) to induce differentiation for 5 weeks; NT2RI: NT2 cell treated with RA to induce differentiation for 5 weeks, and thereafter treated with a growth inhibitor for 2 weeks; NT2NE: NT2 cell treated with RA and treated with a growth inhibitor to induce nerve differentiation, followed by nerve concentration and recovery (NT2 Neuron); NTISM: a library generated by subtracting cDNAs that overlap with the mRNA of undifferentiated NT2 cells from a cDNA library prepared from an mRNA of NT2 cell (STARATAGENE #204101) treated with RA to induce differentiation for 5 weeks, and thereafter treated with a growth inhibitor for 2 weeks, using Subtract Kit (Invitrogen #K4320-01) (NT2RI-NT2RM). RCB indicates that the cell line was supplied by the RIKEN Gene Bank—Cell Development Bank, and ATCC indicates that the cell line was supplied by the American Type Culture Collection.

<Extraction of mRNAs from Primary Culture Cells>
ASTRO: Normal Human Astrocyte NHA5732, Takara Shuzo #CC2565; DFNES: Normal Human Dermal Fibroblasts (Neonatal Skin); NHDF-Neo) NHDF2564, Takara Shuzo #CC2509; MESAN: Normal human mesangial cells NHMC56046-2, Takara Shuzo #CC2559; NHNPC: Normal human neural progenitor cells NHNP5958, Takara Shuzo #CC2599; PEBLM: Human peripheral blood mononuclear cells HPBMC5939, Takara Shuzo #CC2702; HSYRA: HS-RA (Human synoviocytes from rheumatioid arthritis), Toyobo #T404K-05; PUAEN: Human pulmonary artery endothelial cells, Toyobo #T302K-05; UMVEN: Human umbilical vein endothelial cells HUVEC, Toyobo #T200K-05; HCASM: HCASMC (Human coronary artery smooth muscle cells), Toyobo #T305K-05; HCHON: HC (Human Chondrocytes), Toyobo #T402K-05; HHDPC: HDPC (Human dermal papilla cells), Toyobo #THPCK-001; CD34C: CD34+ cell (AllCells, LLC #CB14435M); D30ST: CD34+ cells treated with osteoclast differentiation factor (ODF) to induce differentiation for 3 days; D60ST: CD34+ cells treated with an ODF to induce differentiation for 6 days; D9OST: CD34+ cells treated with ODF to induce differentiation for 9 days; ACTVT: activated T-cell; LYMPB: Lymphoblast, EB virus transferred B cell; NETRP: Neutrophil.

Next, mRNAs extracted as total RNAs from the human tissues shown below were purchased. Hereinafter, the relationships between the names of libraries and the derivations thereof are shown in the order of "name of library: derivation". If a library was generated by subtraction, how to generate the subtraction library is also shown.

<mRNAs from Human Tissues Purchased as Total RNAs>
ADRGL: Adrenal gland, CLONTECH #64016-1; BRACE: Brain, cerebellum, CLONTECH #64035-1; BRAWH: Brain, whole, CLONTECH #64020-1; FEBRA: Brain, Fetal, CLONTECH #64019-1; FELIV: Liver, Fetal, CLONTECH #64018-1; HEART: Heart, CLONTECH #64025-1; HLUNG: Lung, CLONTECH #64023-1; KIDNE: Kidney, CLONTECH #64030-1; LIVER: Liver, CLONTECH #64022-1; MAMGL: Mammary Gland, CLONTECH #64037-1; PANCR: Pancreas, CLONTECH #64031-1; PROST: Prostate, CLONTECH #64038-1; SALGL: Salivary Gland, CLONTECH #64026-1; SKMUS: Skeletal Muscle, CLONTECH #64033-1; SMINT: Small Intestine, CLONTECH #64039-1; SPLEN: Spleen, CLONTECH #64034-1; STOMA: Stomach, CLONTECH #64090-1; TBAES: Breast, Tumor, CLONTECH #64015-1; TCERX: Cervix, Tumor, CLONTECH #64010-1; TCOLN: Colon, Tumor, CLONTECH #64014-1; TESTI: Testis, CLONTECH #64027-1; THYMU: Thymus, CLONTECH #64028-1; TLUNG: Lung, Tumor, CLONTECH #64013-1; TOVAR: Ovary, Tumor, CLONTECH #64011-1; TRACH: Trachea, CLONTECH #64091-1; TUTER: Uterus, Tumor, CLONTECH #64008-1; UTERU: Uterus, CLONTECH #64029-1; ADIPS: Adipose, Invitrogen #D6005-01; BLADE: Bladder, Invitrogen #D6020-01; BRALZ: Brain, cortex, Alzheimer, Invitrogen #D6830-01; CERVX: Cervix, Invitrogen #D6047-01; COLON: Colon, Invitrogen #D6050-0; NESOP: Esophagus, Invitrogen #D6060-01; PERIC: Pericardium, Invitrogen #D6105-01; RECTM: Rectum, Invitrogen #D6110-01; TESOP: Esophageal, Tumor, Invitrogen #D6860-01; TKIDN: Kidney, Tumor, Invitrogen #D6870-01; TLIVE: Liver, Tumor, Invitrogen #D6880-01; TSTOM: Stomach, Tumor, Invitrogen #D6920-01; BEAST: Adult Breast, STARATAGENE #735044; FEHRT: Heart, Fetal, STARATAGENE #738012; FEKID: Kidney, Fetal, STARATAGENE #738014; FELNG: Lung, Fetal, STARATAGENE #738020; NOVAR: Adult Ovary, STARATAGENE #735260; BRASW: a library generated by subtracting cDNAs that overlap with the mRNA of BRAWH (Brain, whole, CLONTECH #64020-1) from a cDNA library prepared from the mRNA of BRALZ (Brain, cortex, Alzheimer, Invitrogen #D6830-01), using Subtract Kit (Invitrogen #K4320-01) (BRALZ-BRAWH).

Furthermore, mRNAs extracted and purified as polyA(+) RNAs from the human tissues shown below were purchased. From an RNA prepared by mixing polyA(+) RNA derived from each tissue with polyA(−) RNA, a cDNA library was prepared. The polyA(−) RNA was prepared by removing the polyA(+) RNA from the total RNA of Brain, whole, CLONTECH #64020-1 by means of oligo dT cellulose. Hereinafter, the relationships between the names of libraries and the derivations thereof are shown in the order of "name of library: derivation".

<mRNAs from Human Tissues Purchased as polyA(+) RNAs>
BRAMY: Brain, amygdala, CLONTECH #6574-1; BRCAN: Brain, caudate nucleus, CLONTECH #6575-1; BRCOC: Brain, corpus callosum, CLONTECH #6577-1; BRHIP: Brain, hippocampus, CLONTECH #6578-1; BRSSN: Brain, substantia nigra, CLONTECH #6580-1; BRSTN: Brain, subthalamic nucleus, CLONTECH #6581-1; BRTHA: Brain, thalamus, CLONTECH #6582-1.

2) Preparation of cDNA Libraries by the Improved Oligocap Method

From each RNA, by a method (WO 01/04286) developed by improving the oligocap method [M. Maruyama and S. Sugano, Gene, 138: 171-174 (1994)], a cDNA library was prepared. Using an Oligo-cap linker (SEQ ID NO:1) and an Oligo dT primer (SEQ ID NO:2), as described in WO 01/04286, BAP (Bacterial Alkaline Phosphatase) treatment, TAP (Tobacco Acid Pyrophosphatase) treatment, RNA ligation, synthesis of first strand cDNA and removal of RNA were performed. Next, using 5' (SEQ ID NO:3) and 3' (SEQ ID NO:4) PCR primers, by PCR (polymerase chain reaction), the first strand cDNA was converted to a double-stranded cDNA, and cleaved with SfiI. Next, the cDNA fragment, usually fractionated into 2 kb or more (3 kb or more as the case may be), was cloned into the vector pME18SFL3 (GenBank AB009864, Expression vector), previously cleaved with DraIII, in a determined orientation of the cDNA, whereby a cDNA library was prepared.

The relationships between the names of the cDNA libraries used for 5'-terminal sequence analysis of the cDNAs and the derivations thereof are shown in Tables 1-1 to 1-6. The number of the 5'-terminal sequences of the cDNAs in each cDNA library after mapping onto the human genome are also shown in Table 1.

3) 5'-Terminal Sequence Analysis of cDNAs from cDNA Libraries Prepared by the Improved Oligocap Method The 5'-terminal nucleic acid sequences of cDNAs acquired from each cDNA library, after a sequencing reaction using a DNA sequencing reagent (BigDye Terminator Cycle Sequencing FS Ready Reaction Kit, manufactured by PE Biosystems) according to the manual, were analyzed using a DNA sequencer (ABI PRISM 3700, manufactured by PE Biosystems). For the data obtained, a database was constructed. The 5'-terminus full-length rate of each cDNA library prepared by the improved oligocap method was 90% on average, being a high full-length rate (calculated with the protein coding region of a known mRNA as an index).

4) Full-Length cDNA Nucleic Acid Analysis

For cDNAs selected for full-length cDNA nucleic acid analysis, the nucleic acid sequence of each full-length cDNA was determined. The nucleic acid sequences were determined mainly by a primer walking method based on the dideoxy terminator method using a custom-synthesized DNA primer. Specifically, a sequencing reaction was performed using a custom-synthesized DNA primer with a DNA sequencing reagent manufactured by PE Biosystem as directed in the manual, after which the DNA nucleic acid sequence was analyzed using a sequencer manufactured by the same company. The full-length nucleic acid sequence was finally established by completely overlapping the partial nucleic acid sequences determined by the above-described method. Next, the region of translation into protein was predicted from the determined full-length cDNA nucleic acid sequence, and the amino acid sequence was determined.

(2) Preparation of cDNA Libraries by the Oligocap Method and Sequence Analysis

1) Preparation of cDNA Libraries by the Oligocap Method

Being human fetal testis derived teratocarcinoma cells, NT-2 neuronal precursor cells (purchased from Stratagene), which can be differentiated into nerve cells by retinoic acid treatment, were used after being treated per the attached manual as follows.

NT-2 cells cultured without differentiation induction with retinoic acid (NT2RM)

NT-2 cells cultured, followed by differentiation induction by the addition of retinoic acid, then cultured for 2 days and 2 weeks (NT2RP)

Cultured human cell SK-N-MC (ATCC HTB-10) (SKNMC), cultured human cell Y79 (ATCC HTB-18) (Y79AA), cultured human cell GI1 (RCB RCB0763) (BGGI1), cultured human cell H4 (ATCC HTB-148) (BNGH4), cultured human cell IMR32 (ATCC CCL-127) (IMR32), and cultured human cell NB9 (RCB #RCB0477) (NB9N4) were cultured by the methods described in the catalogues thereof. RCB indicates that the cell line was supplied by the RIKEN Gene Bank—Cell Development Bank, and ATCC indicates that the cell line was supplied by the American Type Culture Collection.

The cultured cells of each line were collected, and by a method described in a literature document (J. Sambrook, E. F. Fritsch & T. Maniatis, Molecular Cloning Second edition, Cold Spring harbor Laboratory Press 1989), mRNAs were extracted. Furthermore, poly(A)+ RNAs were purified by means of oligo dT cellulose.

Likewise, from human placenta tissue (PLACE), human ovarian cancer tissue (OVARC), tissue rich in head portion from 10-week-gestional fetal human (HEMBA), tissue rich in trunk portion from 10-week-gestional fetal human (HEMBB), human mammary gland tissue (MAMMA), human thyroid tissue (THYRO), and human vascular endothelial tissue primary culture cell (VESEN), by a method described in a literature document (J. Sambrook, E. F. Fritsch & T. Maniatis, Molecular Cloning Second edition, Cold Spring harbor Laboratory Press, 1989), mRNAs were extracted. Furthermore, poly(A)+ RNAs were purified by means of oligo dT cellulose.

From all these poly(A)+ RNAs, by the oligocap method [M. Maruyama and S. Sugano, Gene, 138: 171-174 (1994)], respective cDNA libraries were prepared. Using an Oligo-cap linker (SEQ ID NO:1) and an Oligo dT primer (SEQ ID NO:2), as directed in a literature document [Suzuki and Sugano, Protein, Nucleic Acid and Enzyme, 41: 197-201 (1996), Y. Suzuki et al., Gene, 200: 149-156 (1997)], BAP (Bacterial Alkaline Phosphatase) treatment, TAP (Tobacco Acid Phosphatase) treatment, RNA ligation, synthesis of first strand cDNA and removal of RNA were performed. Next, using 5' (SEQ ID NO:3) and 3' (SEQ ID NO:4) PCR primers, the first strand cDNA was converted to a double-stranded cDNA by PCR (polymerase chain reaction), and cleaved with SfiI. Next, the cDNA was cloned into the vector pUC19FL3 (for some cases of NT2RM and NT2RP) or pME18SFL3 (GenBank AB009864, Expression vector), previously cleaved with DraIII, in a determined orientation of the cDNA, whereby a cDNA library was prepared.

The relationships between the names of the cDNA libraries used for 5'-terminal sequence analysis of the cDNAs and the derivations thereof are shown in Tables 1-1 to 1-6. The number of 5'-terminal sequences of the cDNAs in each cDNA library after mapping onto the human genome are also shown in Tables 1-1 to 1-6.

TABLES 1-1 to 1-6

| | | | | number of 5'-terminal sequences (only those which permitted mapping onto human genome) |
|---|---|---|---|---|
| Improved oligocap method | | | | |
| CORDB | Cord blood | | Extraction of mRNAs from human tissues | 708 |
| CTONG | Tongue, Cancer | | Extraction of mRNAs from human tissues | 31,371 |
| FCBBF | Brain, Fetal | | Extraction of mRNAs from human tissues | 31,986 |
| NTONG | Tongue | | Extraction of mRNAs from human tissues | 7,125 |
| OCBBF | Brain, Fetal | | Extraction of mRNAs from human tissues | 47,574 |
| PLACE | Placenta | | Extraction of mRNAs from human tissues | 33,231 |

TABLES 1-1 to 1-6-continued

| | | | number of 5'-terminal sequences (only those which permitted mapping onto human genome) |
|---|---|---|---|
| SYNOV | Synovial membrane tissue from rheumatoid arthritis | Extraction of mRNAs from human tissues | 27,489 |
| BRAMY | Brain, amygdala, CLONTECH #6574-1 | mRNAs from human tissues purchased as polyA(+) RNAs | 58,640 |
| BRCAN | Brain, caudate nucleus, CLONTECH #6575-1 | mRNAs from human tissues purchased as polyA(+) RNAs | 25,786 |
| BRCOC | Brain, corpus callosum, CLONTECH #6577-1 | mRNAs from human tissues purchased as polyA(+) RNAs | 16,718 |
| BRHIP | Brain, hippocampus, CLONTECH #6578-1 | mRNAs from human tissues purchased as polyA(+) RNAs | 57,918 |
| BRSSN | Brain, substantia nigra, CLONTECH #6580-1 | mRNAs from human tissues purchased as polyA(+) RNAs | 15,897 |
| BRSTN | Brain, subthalamic nucleus, CLONTECH #6581-1 | mRNAs from human tissues purchased as polyA(+) RNAs | 16,308 |
| BRTHA | Brain, thalamus, CLONTECH #6582-1 | mRNAs from human tissues purchased as polyA(+) RNAs | 53,267 |
| ADIPS | Adipose, Invitrogen #D6005-01 | mRNAs from human tissues purchased as total RNAs | 608 |
| ADRGL | Adrenal gland, CLONTECH #64016-1 | mRNAs from human tissues purchased as total RNAs | 10,223 |
| BEAST | Adult Breast, STARATAGENE #735044 | mRNAs from human tissues purchased as total RNAs | 2,731 |
| BLADE | Bladder, Invitrogen #D6020-01 | mRNAs from human tissues purchased as total RNAs | 8,431 |
| BRACE | Brain, cerebellum, CLONTECH #64035-1 | mRNAs from human tissues purchased as total RNAs | 82,880 |
| BRALZ | Brain, cortex, Alzheimer, Invitrogen #D6830-01 | mRNAs from human tissues purchased as total RNAs | 16,360 |
| BRASW | A library generated by subtracting cDNAs that overlap with the mRNA of BRAWH (Brain, whole, CLONTECH #64020-1) from a cDNA library prepared from the mRNA of BRALZ (Brain, cortex, Alzheimer, Invitrogen #D6830-01), using Subtract Kit (Invitrogen #K4320-01) (BRALZ-BRAWH) | mRNAs from human tissues purchased as total RNAs | 157 |
| BRAWH | Brain, whole, CLONTECH #64020-1 | mRNAs from human tissues purchased as total RNAs | 59,069 |
| CERVX | Cervix, Invitrogen #D6047-01 | mRNAs from human tissues purchased as total RNAs | 2,836 |
| COLON | Colon, Invitrogen #D6050-0 | mRNAs from human tissues purchased as total RNAs | 8,398 |
| FEBRA | Brain, Fetal, CLONTECH #64019-1 | mRNAS from human tissues purchased as total RNAs | 23,578 |
| FEHRT | Heart, Fetal, STARATAGENE #738012 | mRNAs from human tissues purchased as total RNAs | 2,859 |
| FEKID | Kidney, Fetal, STARATAGENE #738014 | mRNAs from human tissues purchased as total RNAs | 2,747 |
| FELIV | Liver, Fetal, CLONTECH #64018-1 | mRNAs from human tissues purchased as total RNAs | 186 |
| FELNG | Lung, Fetal, STARATAGENE #738020 | mRNAs from human tissues purchased as total RNAs | 2,764 |
| HEART | Heart, CLONTECH #64025-1 | mRNAs from human tissues purchased as total RNAs | 8,889 |
| HLUNG | Lung, CLONTECH #64023-1 | mRNAs from human tissues purchased as total RNAs | 16,146 |
| KIDNE | Kidney, CLONTECH #64030-1 | mRNAs from human tissues purchased as total RNAs | 17,008 |
| LIVER | Liver, CLONTECH #64022-1 | mRNAs from human tissues purchased as total RNAs | 6,843 |
| MAMGL | Mammary Gland, CLONTECH #64037-1 | mRNAs from human tissues purchased as total RNAs | 182 |
| NESOP | Esophagus, Invitrogen #D6060-01 | mRNAs from human tissues purchased as total RNAs | 2,690 |
| NOVAR | Adult Ovary, STARATAGENE #735260 | mRNAs from human tissues purchased as total RNAs | 2,486 |

TABLES 1-1 to 1-6-continued

| | | | number of 5'-terminal sequences (only those which permitted mapping onto human genome) |
|---|---|---|---|
| PANCR | Pancreas, CLONTECH #64031-1 | mRNAS from human tissues purchased as total RNAs | 179 |
| PERIC | Pericardium, Invitrogen #D6105-01 | mRNAs from human tissues purchased as total RNAs | 8,781 |
| PROST | Prostate, CLONTECH #64038-1 | mRNAS from human tissues purchased as total RNAs | 16,671 |
| RECTM | Rectum, Invitrogen #D6110-01 | mRNAs from human tissues purchased as total RNAs | 2,723 |
| SALGL | Salivary Gland, CLONTECH #64026-1 | mRNAs from human tissues purchased as total RNAs | 183 |
| SKMUS | Skeletal Muscle, CLONTECH #64033-1 | mRNAs from human tissues purchased as total RNAs | 8,424 |
| SMINT | Small Intestine, CLONTECH #64039-1 | mRNAs from human tissues purchased as total RNAs | 16,767 |
| SPLEN | Spleen, CLONTECH #64034-1 | mRNAs from human tissues purchased as total RNAs | 33,950 |
| STOMA | Stomach, CLONTECH #64090-1 | mRNAs from human tissues purchased as total RNAs | 8,685 |
| TBAES | Breast, Tumor, CLONTECH #64015-1 | mRNAs from human tissues purchased as total RNAs | 8,416 |
| TCERX | Cervix, Tumor, CLONTECH #64010-1 | mRNAs from human tissues purchased as total RNAs | 2,797 |
| TCOLN | Colon, Tumor, CLONTECH #64014-1 | mRNAs from human tissues purchased as total RNAs | 2,798 |
| TESOP | Esophageal, Tumor, Invitrogen #D6860-01 | mRNAs from human tissues purchased as total RNAs | 8,500 |
| TESTI | Testis, CLONTECH #64027-1 | mRNAs from human tissues purchased as total RNAs | 90,188 |
| THYMU | Thymus, CLONTECH #64028-1 | mRNAs from human tissues purchased as total RNAs | 70,578 |
| TKIDN | Kidney, Tumor, Invitrogen #D6870-01 | mRNAs from human tissues purchased as total RNAs | 15,970 |
| TLIVE | Liver, Tumor, Invitrogen #D6880-01 | mRNAs from human tissues purchased as total RNAs | 8,627 |
| TLUNG | Lung, Tumor, CLONTECH #64013-1 | mRNAs from human tissues purchased as total RNAs | 2,844 |
| TOVAR | Ovary, Tumor, CLONTECH #64011-1 | mRNAs from human tissues purchased as total RNAs | 2,722 |
| TRACH | Trachea, CLONTECH #64091-1 | mRNAs from human tissues purchased as total RNAs | 52,352 |
| TSTOM | Stomach, Tumor, Invitrogen #D6920-01 | mRNAs from human tissues purchased as total RNAs | 2,757 |
| TUTER | Uterus, Tumor, CLONTECH #64008-1 | mRNAs from human tissues purchased as total RNAs | 2,668 |
| UTERU | Uterus, CLONTECH #64029-1 | mRNAs from human tissues purchased as total RNAs | 49,561 |
| ACTVT | Activated T-cell | Extraction of mRNAs from primary culture human cells | 679 |
| ASTRO | Normal Human Astrocyte NHA5732, Takara Shuzo #CC2565 | Extraction of mRNAs from primary culture human cells | 17,162 |
| CD34C | CD34+ cell (AllCells, LLC #CB14435M) | Extraction of mRNAs from primary culture human cells | 1,420 |
| D3OST | CD34+ cells treated with osteoclast differentiation factor (ODF) to induce differentiation for 3 days | Extraction of mRNAs from primary culture human cells | 5,092 |
| D6OST | CD34+ cells treated with osteoclast differentiation factor (ODF) to induce differentiation for 6 days | Extraction of mRNAs from primary culture human cells | 888 |
| D9OST | CD34+ cells treated with osteoclast differentiation factor (ODF) to induce differentiation for 9 days | Extraction of mRNAs from primary culture human cells | 4,407 |
| DFNES | Normal Human Dermal Fibroblasts (Neonatal Skin; NHDF-Neo) NHDF2564, Takara Shuzo #CC2509 | Extraction of mRNAs from primary culture human cells | 10,103 |
| HCASM | HCASMC (Human coronary artery smooth muscle cells), Toyobo #T305K-05 | Extraction of mRNAs from primary culture human cells | 8,949 |
| HCHON | HC (Human Chondrocytes), Toyobo #T402K-05 | Extraction of mRNAs from primary culture human cells | 9,397 |
| HHDPC | HDPC (Human dermal papilla cells), Toyobo #THPCK-001 | Extraction of mRNAs from primary culture human cells | 8,453 |
| HSYRA | HS-RA (Human synoviocytes from rheumatoid arthritis), Toyobo #T404K-05 | Extraction of mRNAs from primary culture human cells | 7,955 |

TABLES 1-1 to 1-6-continued

| | | | number of 5'-terminal sequences (only those which permitted mapping onto human genome) |
|---|---|---|---|
| LYMPB | Lymphoblast, EB virus transferred B cell | Extraction of mRNAs from primary culture human cells | 2,617 |
| MESAN | Normal human mesangial cells NHMC56046-2, Takara Shuzo | Extraction of mRNAs from primary culture human cells | 16,053 |
| NETRP | Neutrophil | Extraction of mRNAs from primary culture human cells | 9,170 |
| NHNPC | Normal human neural progenitor cells NHNP5958, Takara Shuzo | Extraction of mRNAs from primary culture human cells | 2,377 |
| PEBLM | Human peripheral blood mononuclear cells HPBMC5939, Takara Shuzo #CC2702 | Extraction of mRNAs from primary culture human cells | 7,900 |
| PUAEN | Human pulmonary artery endothelial cells, Toyobo #T302K-05 | Extraction of mRNAs from primary culture human cells | 10,544 |
| UMVEN | Human umbilical vein endothelial cells HUVEC, Toyobo | Extraction of mRNAs from primary culture human cells | 631 |
| 3NB69 | NB69 cell (RCB #RCB0480) | Extraction of mRNAs from cultured human cells | 8,153 |
| AHMSC | HMSC cell (Human mesenchymal cell) | Extraction of mRNAs from cultured human cells | 668 |
| BGGI1 | GI1 cell (Gioma separated from gliosarcoma; RCB #RCB0763) | Extraction of mRNAs from cultured human cells | 1,899 |
| BNGH4 | H4 cell (Neuroglioma; ATCC #HTB-148) | Extraction of mRNAs from cultured human cells | 7,699 |
| CHONS | Chondrocyte; Cell Applications, Inc. #1205F | Extraction of mRNAs from cultured human cells | 2,687 |
| ERLTF | TF-1 cell (erythroleukemia) | Extraction of mRNAs from cultured human cells | 2,169 |
| HELAC | HeLa cell (from cervical cancer) | Extraction of mRNAs from cultured human cells | 676 |
| IMR32 | IMR32 cell (Neuroblastoma; ATCC #CCL-127) | Extraction of mRNAs from cultured human cells | 16,867 |
| JCMLC | Leukemia, myelogenous | Extraction of mRNAs from cultured human cells | 2,156 |
| MESTC | Mesenchyme stem cell | Extraction of mRNAs from cultured human cells | 687 |
| N1ESE | Mesenchymal stem cell | Extraction of mRNAs from cultured human cells | 2,624 |
| NB9N4 | NB9 cell (Neuroblastoma; RCB #RCB0477) | Extraction of mRNAs from cultured human cells | 1,759 |
| NCRRM | Embryonal carcinoma | Extraction of mRNAs from cultured human cells | 698 |
| NCRRP | Embryonal carcinoma treated with retinoic acid (RA) to induce differentiation | Extraction of mRNAs from cultured human cells | 691 |
| NT2NE | NT2 cell treated with RA and treated with a growth inhibitor to induce nerve differentiation, followed by nerve concentration and recovery (NT2 Neuron) | Extraction of mRNAs from cultured human cells | 16,337 |
| NT2RI | NT2 cell treated with RA to induce differentiation for 5 weeks, and thereafter treated with a growth inhibitor for 2 weeks | Extraction of mRNAs from cultured human cells | 32,662 |
| NT2RM | NT2 cell (STARATAGENE #204101) | Extraction of mRNAs from cultured human cells | 2,026 |
| NT2RP | NT2 cell treated with retinoic acid (RA) to induce differentiation for 5 weeks | Extraction of mRNAs from cultured human cells | 24,634 |
| NTISM | a library generated by subtracting cDNAs that overlap with the mRNA of undifferentiated NT2 cells from a cDNA library prepared from an mRNA of NT2 cell (STARATAGENE #204101) treated with RA to induce differentiation for 5 weeks, and thereafter treated with a growth inhibitor for 2 weeks, using Subtract Kit (Invitrogen #K4320-01) (NT2RI-NT2RM) | Extraction of mRNAs from cultured human cells | 180 |
| SKNMC | SK-N-MC cell (Neuroepithelioma; ATCC #HTB-10) | Extraction of mRNAs from cultured human cells | 7,607 |
| SKNSH | SK-N-SH cell (Neuroblastoma; RCB #RCB0426) | Extraction of mRNAs from cultured human cells | 8,662 |
| T1ESE | Mesenchymal stem cell treated with trichostatin and 5-azacytidine to induce differentiation | Extraction of mRNAs from cultured human cells | 2,685 |

TABLES 1-1 to 1-6-continued

| | | | number of 5'-terminal sequences (only those which permitted mapping onto human genome) |
|---|---|---|---|
| Oligocap method | | | |
| HEMBA | tissue rich in head portion from 10-week-gestational fetal human (whole embryo, mainly head) | mRNAs from human tissues | 7,033 |
| HEMBB | tissue rich in trunk portion from 10-week-gestational fetal human (whole embryo, mainly body) | mRNAs from human tissues | 2,581 |
| MAMMA | Mammary Gland | mRNAs from human tissues | 2,987 |
| OVARC | Ovary, Tumor | mRNAs from human tissues | 2,058 |
| PLACE | Placenta | mRNAs from human tissues | 12,859 |
| THYRO | Thyroid gland | mRNAs from human tissues | 1,863 |
| VESEN | Human umbilical vein endothelial cells | Extraction of mRNAs from primary culture human cells | 1,309 |
| NB9N3 | NB9 cell (Neuroblastoma; RCB #RCB0477) | Extraction of mRNAs from cultured human cells | 96 |
| NT2RM | NT2 cell (STARATAGENE #204101) | Extraction of mRNAs from cultured human cells | 5,375 |
| NT2RP | NT2 cell treated with retinoic acid (RA) to induce differentiation for 2 days and 2 weeks | Extraction of mRNAs from cultured human cells | 14,608 |
| Y79AA | Y79 cell (Retinoblastoma; ATCC HTB-18) | Extraction of mRNAs from cultured human cells | 2,377 |
| BGGI1 | GI1 cell (Gioma separated from gliosarcoma; RCB #RCB0763) | Extraction of mRNAs from cultured human cells | 62 |
| BNGH4 | H4 cell (Neuroglioma; ATCC #HTB-148) | Extraction of mRNAs from cultured human cells | 89 |
| IMR32 | IMR32 cell (Neuroblastoma; ATCC #CCL-127) | Extraction of mRNAs from cultured human cells | 94 |
| SKNMC | SK-N-MC cell (Neuroepithelioma; ATCC #HTB-10) | Extraction of mRNAs from cultured human cells | 92 |
| either oligocap method or improved oligocap method, not distinguished | | | |
| BGGI1 | GI1 cell (Gioma separated from gliosarcoma; RCB #RCB0763) | Extraction of mRNAs from cultured human cells | 1 |
| BNGH4 | H4 cell (Neuroglioma; ATCC #HTB-148) | Extraction of mRNAs from cultured human cells | 3 |
| IMR32 | IMR32 cell (Neuroblastoma; ATCC #CCL-127) | Extraction of mRNAs from cultured human cells | 1 |
| SKNMC | SK-N-MC cell (Neuroepithelioma; ATCC #HTB-10) | Extraction of mRNAs from cultured human cells | 1 |
| NT2RM | NT2 cell (STARATAGENE #204101) | Extraction of mRNAs from cultured human cells | 48 |
| Total | | | 1,440,790 |

2) 5'-Terminal Sequence Analysis of cDNAs from cDNA Libraries Prepared by the Oligocap Method The 5'-terminal or 3'-terminal nucleic acid sequences of cDNAs acquired from each cDNA library, after a sequencing reaction using a DNA sequencing reagent (Dye Terminator Cycle Sequencing FS Ready Reaction Kit, dRhodamine Terminator Cycle Sequencing FS Ready Reaction Kit or BigDye Terminator Cycle Sequencing FS Ready Reaction Kit, manufactured by PE Biosystems) according to the manual, were analyzed for DNA nucleic acid sequences using a DNA sequencer (ABI PRISM 377, manufactured by PE Biosystems). For the data obtained, a database was constructed. The 5'-terminus full-length rate of each cDNA library prepared by the oligocap method was 60% on average (calculated with the protein coding region of a known mRNA as an index).

3) Full-Length cDNA Nucleic Acid Analysis

For cDNAs selected for full-length cDNA nucleic acid analysis, the nucleic acid sequence of each full-length cDNA was determined. The nucleic acid sequences were determined mainly by a primer walking method based on the dideoxy terminator method using a custom-synthesized DNA primer. Specifically, a sequencing reaction was performed using a custom-synthesized DNA primer with a DNA sequencing reagent manufactured by PE Biosystem as directed in the manual, after which the DNA nucleic acid sequence was analyzed using a sequencer manufactured by the same company. For some clones, a DNA sequencer manufactured by Licor was also utilized. For some cDNAs, no custom primer was used, but the shotgun method, in which cDNA-containing plasmids are randomly cleaved, was used with a DNA sequencer to determine the DNA nucleic acid sequence. The full-length nucleic acid sequence was finally established by completely overlapping the partial nucleic acid sequences determined by the above-described method. Next, the region of translation into protein was predicted from the determined full-length nucleic acid sequence, and the amino acid sequence was determined.

Example 2

Genome Mapping and Clustering (1) Sequence Data Set
The following sequences were used as a data set.
Human genome sequence: UCSC hg 17 (NCBI Build 35) (http://www.genome.ucsc.edu/)
Human full-length cDNAs, 19,265 sequences, newly acquired and subjected to full-length cDNA sequence analysis by us
Out of human full-length cDNA sequences acquired and subjected to full-length cDNA sequence analysis by us, and registered with an existing public database (DDBJ/GenBank/EMBL) (accession numbers: AB038269, AB045981, AB056476, AB056477, AK000001 to AK002212, AK021413 to AK027260, AK027263 to AK027902, AK054561 to AK058202, AK074029 to AK074481, AK074483 to AK075325, AK075326 to AK075566, AK090395 to AK098842, AK122580 to AK129030, AK129488 to AK131107, AK131190 to AK131575, AK160364 to AK160386, AK172724 to AK172740, AK172741 to AK172866), 30,754 sequences that can be used for genome mapping
2039 sequences that had been registered with the database HUGE of Kazusa DNA Research Institute by Feb. 3, 2005 (http://www.kazusa.or.jp/huge/)
Human full-length cDNAs, 20,878 sequences, that had been listed on the Full Length Clone List on the website of Mammalian Gene Collection (http://mgc.nci.nih.gov/) and included in GenBank gbpri (ftp://ftp.ncbi.nih.gov/genbank/) by Jan. 30, 2005
Human full-length cDNAs, 9,280 sequences, that had been registered as Deutsches Krebsforschungszentrum (DKFZ) in GenBank gbpri before Jan. 30, 2005
Human full-length cDNAs, 13,984 sequences, being constituent sequences of the human RefSeq sequences of the Jan. 31, 2005 version (http://www.ncbi.nlm.nih.gov/RefSeq/), registered as mRNAs, and included in GenBank gbpri
Human RefSeq sequences of the Jan. 31, 2005 version (http://www.ncbi.nlm.nih.gov/RefSeq/), 28,931 sequences
Out of the human genome assemble sequences in Feb. 10, 2005 Ensembl (http://www.ensembl.org/) (NCBI35.nov_26.35), 33,666 sequences of NCBI35.nov_26.35 that had been mapped to the hg 17 human genome in UCSC (University of California, Santa Cruz, http://www.genome.ucsc.edu/)
Human cDNA 5'-terminal sequence, 1,456,213 sequences, and 3'-terminal sequence, 109,283 sequences, subjected to sequence analysis in our project (including published sequences with accession numbers: AU116788 to AU160826, AU279383 to AU280837, DA000001 to DA999999, DB000001 to DB384947)

(2) Genome Mapping
The above-described data set was subjected to genome mapping using BLASTN (ftp://ftp.ncbi.nih.gov/blast/), under the conditions of Identity of 95% or more and consensus length of 50 base pairs (bp) or more. About 99% of the sequences in the data set used for the mapping permitted genome mapping.

(3) Clustering
After the genome mapping, a sequence group contained in a genome region, as a single assembly, was allowed to form a cluster. Hence, each cluster was chosen in a way such that the outer sides of both ends of each genome region in the sequence group would not overlap the sequences mapped on each genome region. As a result, a total of 87,173 clusters existed. Therefrom, 17,535 clusters configured solely with human cDNA 3'-terminal sequences that were acquired and subjected to sequence analysis in our project were excluded, leaving 69,638 clusters. Of these clusters, 36,782 clusters were excluded since they were configured solely with human cDNA 5'-terminal sequences that were acquired and subjected to sequence analysis in our project (those having none of full-length cDNA, RefSeq, and Ensembl sequences were excluded). As a result, 32,856 clusters were found to comprise at least one of full-length cDNAs, RefSeq, and Ensembl sequences. By selecting clusters comprising one or more of full-length cDNAs, RefSeq, and Ensembl sequences, which are expected to have an ORF (open reading frame, coding region) with a reliability above a given level, 21,703 clusters were acquired. For these 21,703 clusters, expression specificity was determined.

Example 3

Experimental Procedures for Real-Time PCR (1) Synthesis of Template cDNAs
1) Human mRNA (Human Total RNA) Used as Template
A reaction was carried out with 50 µg of Human Total RNA per 150 µl of the system.
To 50 µg of Total RNA dissolved in 87 µl of $H_2O$, 10 µl of a random primer (concentration 65 ng/µl) and 7.5 µl of dNTP Mix (concentration 10 mM each dNTP Mix) were added. This was followed by incubation at 65° C. for 5 minutes and on ice for 1 minute. 30 µl of 5× reaction buffer solution (attached to the Invitrogen SuperScript III RT kit) and 7.5 µl of 0.1M DTT and 3 µl of RNase Inhibitor (STRATAGENE) and 5 µl of SuperScript III RT (Invitrogen) were added. This was followed by incubation at 25° C. for 5 minutes, incubation at 50° C. for 60 minutes, and incubation at 70° C. for 15 minutes. After the reaction, phenol-chloroform extraction was performed to deactivate the enzyme. By adding 3 µl of EDTA (0.5M) and 22.5 µl of 0.1N NaOH, alkali treatment was performed to degrade the RNA. After 30 µl of Tris (1M pH 7.8) was added to neutralize the reaction liquid, ethanol precipitation was performed, and the precipitate was dissolved in 100 µl of TE buffer solution.
Human mRNAs from the mRNA sources (Human Total RNAs) were acquired by the method described in Example 1.
A list of the human mRNAs used in the experiments is shown in Table 2.
2) Human mRNA (Human PolyA(+) RNA) Used as Template
A reaction was carried out with 5 µg of human PolyA RNA per 100 µl of the system.
To 5 µg of PolyA(+) RNA dissolved in 58 µl of $H_2O$, 5 µl of a random primer (concentration 65 ng/µl) and 5 µl of dNTP Mix (concentration 10 mM each dNTP Mix) were added. This was followed by incubation at 65° C. for 5 minutes and incubation on ice for 1 minute. 20 µl of 5× reaction buffer solution (attached to the Invitrogen SuperScript III RTkit), 5 µl of 0.1M DTT, 2 µl of RNase Inhibitor (STRATAGENE) and 5 µl of SuperScript III RT (Invitrogens) were added. This was followed by incubation at 25° C. for 5 minutes, incubation at 50° C. for 60 minutes, and incubation at 70° C. for 15 minutes. After the reaction, phenol-chloroform extraction was performed to deactivate the enzyme. By adding 2 µl of EDTA (0.5M) and 15 µl of 0.1N NaOH, alkali treatment was performed to degrade the RNA. After 20 µl of Tris (1M pH 7.8) was added to neutralize the reaction liquid, ethanol precipitation was performed, and the precipitate was dissolved in 50 µl of TE buffer solution.

A list of the human mRNAs used in the experiments is shown in Table 2.

TABLE 2

|   | Product name | Manufacturer | Catalog number |
|---|---|---|---|
| Human total RNA purchased | | | |
| 1 Bone Marrow | Human Bone Marrow Total RNA | Clontech | 636548 |
| 2 Brain, whole | Human Brain Total RNA | Clontech | 636530 |
| 3 Fetal Brain | Human Fetal Brain Total RNA | Clontech | 636526 |
| 4 Heart | Human Heart Total RNA | Clontech | 636532 |
| 5 Kidney | Human Kidney Total RNA | Clontech | 636529/636514 |
| 6 Liver | Human Liver Total RNA | Clontech | 636531 |
| 7 Lung | Human Lung Total RNA | Clontech | 636524 |
| 8 Thymus | Human Thymus Total RNA | Clontech | 636549 |
| 9 Uterus | Human Uterus Total RNA | Clontech | 636551/636513 |
| 10 Spinal Cord | Human Spinal Cord Total RNA | Clontech | 636554 |
| 11 Colon | Human Colon Total RNA | Clontech | 636521 |
| 12 Colon Tumor | Human Colon Tumor Total RNA | Clontech | 636634 |
| 13 Kidney Tumor | Human Kidney Tumor Total RNA | Clontech | 636632 |
| 14 Liver Tumor | Human Liver Total RNA | CHEMICOM | RNA569 |
| 15 Lung Tumor | Human Lung Tumor Total RNA | Clontech | 636633 |
| 16 Ovary | Human Ovary Total RNA | Clontech | 636555 |
| 17 Ovary Tumor | Human Ovary Tumor Total RNA | Clontech | 636631 |
| 18 Spleen | Human Spleen Total RNA | Clontech | 636525 |
| 19 Stomach | Human Stomach Total RNA | Clontech | 636522 |
| 20 Stomach Tumor | Human Stomach Tumor Total RNA | Clontech | 636629 |
| 21 Uterus Tumor | Human Uterus Tumor Total RNA | Clontech | 636628 |
| 22 ALZ Visual Cortex Occipital | Human Visual Cortex Occipital ALZ Total RNA | Ambion | B6336 |
| Human polyA(+) RNA purchased | | | |
| 1 Brain, whole | Human Brain, whole PolyARNA | Clontech | 636102 |
| 2 Brain cerebellum | Brain, cerebellum | Clontech | 636122 |
| 3 Brain, amygdala | Brain, amygdala | Clontech | 6574-1 |
| 4 Brain, caudate nucleus | Brain, caudate nucleus | Clontech | 6575-1 |
| 5 Brain, corpus callosum | Brain, corpus callosum | Clontech | 636133 |
| 6 Brain, hippocampus | Brain, hippocampus | Clontech | 636134 |
| 7 Brain, substantia nigra | Brain, substantia nigra | Clontech | 6580-1 |
| 8 Brain, thalamus | Brain, thalamus | Clontech | 636135 |
| 9 Brain, subthalamic nucleus | Brain, subthalamic nucleus | Clontech | 636167 |

| | Extraction of human total RNA from an RNA source | Explanation of the derivation of mRNA |
|---|---|---|
| 1 | Tongue (normal) | Normal tongue tissue |
| 2 | Tongue Tumor | Tongue tumor tissue |
| 3 | NT2 cell (STARATAGENE #204101) | Before treatment with NT2 retinoic acid (RA(−)) |
| 4 | NT2 cell treated with retinoic acid (RA) to induce differentiation | NT2 cell treated with retinoic acid (RA) to induce differentiation for 5 weeks |
| 5 | NT2 cell treated with RA to induce differentiation followed by treatment with a growth inhibitor (Inh) | NT2 cell treated with RA to induce differentiation for 5 weeks, and thereafter treated with a growth inhibitor for 2 weeks |
| 6 | NT2 cell treated with RA to induce differentiation | NT2 cell treated with retinoic acid (RA) to induce differentiation for 1 day |
| 7 | NT2 cell treated with RA to induce differentiation | NT2 cell treated with retinoic acid (RA) to induce differentiation for 2 days |
| 8 | NT2 cell treated with RA to induce differentiation | NT2 cell treated with retinoic acid (RA) to induce differentiation for 1 week |

TABLE 2-continued

| 9 | NT2 cell treated with RA and treated with a-Inh to induce nerve differentiation | NT2 cell treated with RA and treated with a growth inhibitor to induce nerve differentiation, followed by nerve cell concentration and recovery |
|---|---|---|

(2) Design of Primers and Probes

Using Primer Express software 3.0, the primer design software attached to the Applied Biosystems real-time PCR 7500 Fast, with the sequences of portions that serve as the borders of the changing region, primers and probes were designed to allow the individual detection of cDNAs having other splice patterns transcribed from the same chromosome region as the cDNA to be comparatively examined under the conditions recommended by the software. Using the designed primers, real-time PCR was performed, and they were confirmed to produce a single band and to be capable of specifically detecting only one kind of cDNA.

(3) Expressional Analysis Using Real-Time PCR 1) mRNAs Used

All mRNAs used were of human derivation.

The experiments on the four clusters chr14-45, chr7-2007, chr12-1875, and chr3-1507, out of the 10 experimental systems, were performed using SYBR GREEN as a real-time PCR reaction system, with 16 kinds of samples as template cDNAs: NT2 cells [NT2 RA(−)], NT2 cells treated with retinoic acid (RA) to induce differentiation for 24 hours [NT2 RA(+) 24 hr], NT2 cells treated with retinoic acid (RA) to induce differentiation for 48 hours [NT2 RA(+) 48 hr], NT2 cells treated with retinoic acid (RA) to induce differentiation for 1 week [NT2 RA(+) 1 week], NT2 cells treated with retinoic acid (RA) to induce differentiation for 5 weeks [NT2 RA(+)], NT2 cells treated with RA to induce differentiation for 5 weeks, and thereafter treated with a growth inhibitor for 2 weeks [NT2 RA(+) Inh(+)], NT2 cells treated with RA and treated with a growth inhibitor to induce nerve differentiation, followed by nerve concentration and recovery (NT2 Neuron), Brain, Fetal, Brain, whole, Alzheimer patient cerebral cortex (ALZ Visual Cortex Occipital), Mix, viscus tissues [Heart, Kidney, Liver, Lung, Colon, Stomach], Mix, blood cells and related tissues [Bone Marrow, Thymus, Spinal Cord, Spleen], Mix, tumor tissues [Colon Tumor, Kidney Tumor, Liver Tumor, Lung Tumor, Ovary Tumor, Stomach Tumor, Uterus Tumor, Tongue Tumor], Mix, normal tissues [Colon, Kidney, Liver, Lung, Ovary, Stomach, Uterus, Tongue], whole brain polyA(+)RNA [Brain, whole PolyA(+) RNA], and Brain, hippocampus.

For the cluster chr12-1875, experiments were also performed with, in addition to the foregoing 16 kinds, additional samples: Colon, Kidney, Liver, Lung, Ovary, Stomach, Uterus, Tongue, Colon Tumor, Kidney Tumor, Liver Tumor, Lung Tumor, Ovary Tumor, Stomach Tumor, Uterus Tumor, and Tongue Tumor.

For the cluster chr3-1507, experiments were also performed with, in addition to the foregoing 16 kinds, additional samples: Brain cerebellum, Brain, amygdala, Brain, caudate nucleus, Brain, corpus callosum, Brain, substantia nigra, Brain, thalamus, and Brain, subthalamic nucleus.

The experiments on the 2 clusters chr19-32 and chr12+1658, out of the 10 experimental systems, were performed using TaqMan manufactured by Applied Biosystems as a real-time PCR reaction system, with a total of 16 kinds of samples as template cDNAs: NT2 cells [NT2 RA(−)], NT2 cells treated with retinoic acid (RA) to induce differentiation for 24 hours [NT2 RA(+) 24 hr], NT2 cells treated with retinoic acid (RA) to induce differentiation for 48 hours [NT2 RA(+) 48 hr], NT2 cells treated with retinoic acid (RA) to induce differentiation for 1 week [NT2 RA(+) 1 week], NT2 cells treated with retinoic acid (RA) to induce differentiation for 5 weeks [NT2 RA(+)], NT2 cells treated with RA to induce differentiation for 5 weeks, and thereafter treated with a growth inhibitor for 2 weeks [NT2 RA(+) Inh(+)], NT2 cells treated with RA and treated with a growth inhibitor to induce nerve differentiation, followed by nerve concentration and recovery (NT2 Neuron), Brain, Fetal, Brain, whole, Alzheimer patient cerebral cortex (ALZ Visual Cortex Occipital), Mix, viscus tissues [Heart, Kidney, Liver, Lung, Colon, Stomach], Mix, blood cells and related tissues [Bone Marrow, Thymus, Spinal Cord, Spleen], Mix, tumor tissues [Colon Tumor, Kidney Tumor, Liver Tumor, Lung Tumor, Ovary Tumor, Stomach Tumor, Uterus Tumor, Tongue Tumor], Mix, normal tissues [Colon, Kidney, Liver, Lung, Ovary, Stomach, Uterus, Tongue], Brain, whole PolyA(+) RNA, and Brain, hippocampus.

The experiments on the 4 clusters chr2-2324, chrX-900, chr8-916, and chr3+2014, out of the 10 experimental systems, were performed using SYBR GREEN as a real-time PCR reaction system, with a total of 23 kinds of samples as template cDNAs: NT2 cells [NT2 RA(−)], NT2 cells treated with retinoic acid (RA) to induce differentiation for 24 hours [NT2 RA(+) 24 hr], NT2 cells treated with retinoic acid (RA) to induce differentiation for 48 hours [NT2 RA(+) 48 hr], NT2 cells treated with retinoic acid (RA) to induce differentiation for 1 week [NT2 RA(+) 1 week], NT2 cells treated with retinoic acid (RA) to induce differentiation for 5 weeks [NT2 RA(+)], NT2 cells treated with RA to induce differentiation for 5 weeks, and thereafter treated with a growth inhibitor for 2 weeks [NT2 RA(+) Inh(+)], NT2 cells treated with RA and treated with a growth inhibitor to induce nerve differentiation, followed by nerve concentration and recovery (NT2 Neuron), Brain, Fetal, Brain, whole, Alzheimer patient cerebral cortex (ALZ Visual Cortex Occipital), Mix, viscus tissues [Heart, Kidney, Liver, Lung, Colon, Stomach], Mix, blood cells and related tissues [Bone Marrow, Thymus, Spinal Cord, Spleen], Mix, tumor tissues [Colon Tumor, Kidney Tumor, Liver Tumor, Lung Tumor, Ovary Tumor, Stomach Tumor, Uterus Tumor, Tongue Tumor], Mix, normal tissues [Colon, Kidney, Liver, Lung, Ovary, Stomach, Uterus, Tongue], Brain, whole PolyA(+) RNA, Brain, hippocampus, Brain cerebellum, Brain, amygdala, Brain, caudate nucleus, Brain, corpus callosum, Brain, substantia nigra, Brain, thalamus, and Brain, subthalamic nucleus.

2) Reaction System Using SYBR GREEN

The SYBR GREEN I Dye assay chemistry is an experimental system based on the characteristic of SYBR GREEN to emit strong fluorescence by binding to a double-stranded DNA. When the DNA denatures to single-stranded during the PCR reaction, SYBR GREEN leaves from the DNA and the fluorescence decreases rapidly; however, with the subsequent annealing/extension reaction, it binds to the double-stranded DNA to emit fluorescence again. In the SYBR GREEN I Dye assay chemistry, fluorescence intensity, which increases with every PCR cycle, is detected.

To a cDNA derived from each tissue, 0.2 μl (equivalent to 100 ng of Total RNA), as the template, Forward Primer (final concentration 250 nM), Reverse Primer (final concentration 250 nM), and SYBR Green PCR Master Mix (ABI 4309155) were added, to make a total volume of 20 μl. For endogenous control, GAPDH (Accession No; NM_002046.2) always served as a reaction control for all templates.

A PCR was performed under the conditions shown below, which represent the standard protocol for Applied Biosystems real-time PCR 7500 Fast. After an initial step at 50° C. for 2 minutes and at 95° C. for 10 minutes, denaturation at 95° C. for 15 seconds and annealing elongation at 60° C. for 1 minute were repeated in 40 cycles.

GAPDH-F (SEQ ID NO:5): Forward Primer for endogenous control GAPDH
GAPDH-R (SEQ ID NO:6): Reverse Primer for endogenous control GAPDH 3) Reaction System Using TaqMan The TaqMan assay chemistry is an experimental system employing the TaqMan probe, a probe phosphorylated at the 3' terminus and labeled with a Fluorescenin-series fluorescent dye (reporter) at the 5' terminus, and a Rhodamine-series fluorescent dye (quencher) at the 3' terminus. When the TaqMan probe occurs alone, the fluorescence energy of the reporter is consumed as excitation energy for the quencher, and the fluorescence of the reporter is suppressed, because the fluorescence wavelength is close to that of the quencher even if reporter excitation light is irradiated. However, when the TaqMan probe is degraded by the 5'-3' exonuclease activity of DNA polymerase during the elongation from the primer in the PCR reaction, the fluorescent dye of the reporter leaves from the 5' terminus of the TaqMan probe, and the distance from the fluorescent dye of the quencher increases, resulting in the emission of fluorescence. In the TaqMan assay chemistry, the fluorescence intensity from the reporter, which increases with every PCR cycle, is detected.

To 0.2 μl (equivalent to 100 ng as converted to Total RNA) of a cDNA derived from each tissue as a template, Forward Primer (final concentration 900 nM), Reverse Primer (final concentration 900 nM), TaqMan Probe (final concentration 250 nM), and TaqMan Fast Universal PCR Master Mix (ABI 466073) were added, to make a total volume of 20 μl. For endogenous control, GAPDH always served as a reaction control for all templates.

A PCR was performed under the conditions shown below, which represent the Fast protocol for Applied Biosystems real-time PCR 7500 Fast. After enzyme activation 95° C. for 20 seconds, denaturation at 95° C. for 3 seconds and annealing elongation at 60° C. for 30 seconds were repeated in 40 cycles. GAPDH-Probe (SEQ ID NO:7): TaqMan Probe for endogenous control GAPDH ps (4) Method of Statistical Analysis of Data The results were analyzed using a relative quantitation method.

Using the RQ study software for Applied Biosystems real-time PCR 7500 Fast, a threshold was set in an exponential functional amplification region of the amplification curve. The number of cycles at that time was used as the Ct (threshold cycle). To make a correction for initial RNA content, the Ct of the endogenous control GAPDH was subtracted from the Ct obtained, and this value was used as the dCt [dCt=Target Ct−ENDOGENUS Ct (GAPDH)]. The dCt of the sample serving as the reference standard (control) was further subtracted from the dCt obtained, and this value was used as the ddCt [ddCt=Target dCt−Control dCt]. On the basis of this value, relative value was calculated, and this was used as the RQ [RQ=$2^{-ddCt}$]. On the basis of this result, a logarithmic graph was generated, and the amounts amplified and hence expression levels with each primer and probe were compared.

In each Example, analytical results for RQ and $\log_{10}$RQ are shown. RQ scores are shown to the first decimal point. For samples not allowing detection by real-time PCR, "Undet." was written in the fields for RQ score and the score of $\log_{10}$RQ. $\log_{10}$RQ scores are shown to the second decimal point. However, for a mixed sample of control normal visceral tissues (Mix, viscus tissues) (RQ value "1.0"), "0.0" was written in the field for $\log_{10}$RQ scores.

Example 4

Cluster chr19-32 (Data Set: 103)

(1) Cluster Analysis
1) Cluster Characteristics

An analysis was performed on 8 sequences of full-length cDNAs subjected to genome mapping onto the cluster chr19-32 (Human genome UCSC hg18 (NCBI Build34) chromosome 19, 63,124,000 bp to 63,140,000 bp) [D-UTERU2026184.1, D-BRACE3000012.1, AB075836.1, AY695825.1, C-NT2RI2001083, ENST00000358502, ENST00000361044, NM_133460.1]. They were classifiable according to expression pattern difference into the following 3 kinds.

[1] D-UTERU2026184.1
[2] D-BRACE3000012.1
[3] AB075836.1, AY695825.1, C-NT2RI2001083 (AK056113.1), ENST00000358502, ENST00000361044, NM_133460.1

[1] and [2] are cDNAs that were newly acquired and subjected to full-length cDNA sequence analysis by us, having an ORF different from that of [3], which had been registered in an existing public DB (DDBJ/Genbank/EMBL).

[1], compared with the known [3], had a different ORF region because of the deletion of portions corresponding to the second and third exons of [3] in the ORF region.

[2], compared with the known [3], had an altered translation initiation point and a different ORF region because of the insertion of an exon different from the other patterns into the ORF region.

It was found that the ORF regions present in the 3 kinds of cDNA patterns [1] to [3] undergo splicing in different patterns, such as exon deletions and insertions, from the same chromosome region, resulting in alterations of the amino acid sequences to produce diverse proteins and mRNAs.

2) Characteristics of D-UTERU2026184.1 ([1]), which was Newly Acquired and Subjected to Full-Length cDNA Sequence Analysis by Us 103_[1]_1-N0 (SEQ ID NO:8): The entire nucleic acid sequence region of D-UTERU2026184.1
103_[1]_1-NA0 (SEQ ID NO:9): Both the entire nucleic acid sequence region and amino acid sequence of D-UTERU2026184.1
103_[1]_1-A0 (SEQ ID NO:10): The entire amino acid sequence region of D-UTERU2026184.1

The 213-base exon present at the 213th to 425th bases of NM_133460.1 (SEQ ID NO:13), which is registered with an existing public DB, and serves for control, is deleted and not present in the region at the 223rd to 224th bases of D-UTERU2026184.1. The 2 bases present at the 520th to 521st bases of NM_133460.1 (SEQ ID NO:14) are also deleted and not present in the region at the 317th to 318th bases of D-UTERU2026184.1 (SEQ ID NO:11). Although the translation initiation point of NM_133460.1 is present on the 128-base insertion exon, D-UTERU2026184.1 is present on the first exon, which is shared by NM_133460.1; therefore, compared with NM_133460.1, the N-terminal amino acids differed by 43 residues.

103_[1]_1-N1 (SEQ ID NO:11): Deletion nucleic acid sequence region of D-UTERU2026184.1

103_[1]_1-A1 (SEQ ID NO:12): Amino acid region altered as a result of deletion of D-UTERU2026184.1

103_[1]_1-N2 (identical to SEQ ID NO:11): ORF nucleic acid region in the deletion nucleic acid region of D-UTERU2026184.1

103_[1]_1-A2 (identical to SEQ ID NO:12): ORF amino acid region related to the deletion nucleic acid region of D-UTERU2026184.1

103_[1]_C-N1 (SEQ ID NO:13): 213-base insert nucleic acid sequence present at the 213th to 425th bases of NM_133460.1 inserted into the region at the 223rd to 224th bases of D-UTERU2026184.1

103_[1]_C-N2 (SEQ ID NO:14): 2-base insert nucleic acid sequence present at the 520th to 521 bases of NM_133460.1 inserted into the region at the 317th to 318th bases of D-UTERU2026184.1

103_[1]_C-A1 (SEQ ID NO:15): Amino acid region related to the insert nucleic acid sequences at the 213th to 425th bases and the 520th to 521st bases of NM_133460.1, inserted into the region at the 223rd to 224th bases and the region at the 317th to 318th bases of D-UTERU2026184.1.

With this change, the Pfam motif "KRAB box", which is present at the 5th to 45th amino acids of NM_133460.1, which serves for control, disappeared in D-UTERU2026184.1 (http://pfam.janelia.org/).

3) Characteristics of D-BRACE3000012.1 ([2]), which was Newly Acquired and Subjected to Full-Length cDNA Sequence Analysis by Us 103_[2]_1-N0 (SEQ ID NO:16): The entire nucleic acid sequence region of D-BRACE3000012.1

103_[2]_1-NA0 (SEQ ID NO:17): Both the entire nucleic acid sequence region and amino acid sequence of D-BRACE3000012.1

103_[2]_1-A0 (SEQ ID NO:18): The entire amino acid sequence region of D-BRACE3000012.1

The sequence at the 314th to 533rd bases of D-BRACE3000012.1 (SEQ ID NO:19) is a variant with insertion of an exon not present in NM_133460.1, which is registered with an existing public DB and serves for control; because of its presence on the exon inserted, along with the translation initiation point, compared with the NM_133460.1, the N-terminal amino acids differed by 23 residues (SEQ ID NO:20).

103_[2]_1-N1 (SEQ ID NO:19): 220-base insert nucleic acid sequence region of D-BRACE3000012.1

103_[2]_1-A1 (SEQ ID NO:20): 23-residue insert amino acid sequence region of D-BRACE3000012.1

103_[2]_1-N2 (SEQ ID NO:21): ORF nucleic acid sequence region in 220-base insert region of D-BRACE3000012.1

103_[2]_1-A2 (SEQ ID NO:22): ORF amino acid region related to 220-base insert region of D-BRACE3000012.1

4) Expression Specificity Analysis and Design of Primers and TaqMan Probes for Real-Time PCR To clearly distinguish between the characteristic regions shown above, and examine the respective expression levels thereof, the following regions were used as detection regions. It seemed possible to compare the expression levels of the individual characteristic regions by comparing the expression levels of the detection regions.

103_01—A region specifically extracted by means of the sequence information at the border of a region lacking an exon in the cDNA pattern [1]: an ORF-altering region with exon deletion in the cDNA pattern [1], which was newly subjected to full-length cDNA sequence analysis by us →Fragment 103_01 (SEQ ID NO:25) amplified by Primer103_01F (SEQ ID NO:23) and Primer103_01R (SEQ ID NO:24)

TaqMan probe used 103_01TP: (SEQ ID NO:26)

103_02—A region specifically extracted by means of the sequence information on a region with exon insertion in the cDNA pattern [2]: an ORF-altering region with exon insertion in the cDNA pattern [2], which was newly subjected to full-length cDNA sequence analysis by us →Fragment 103_02 (SEQ ID NO:29) amplified by Primer103_02F (SEQ ID NO:27) and Primer103_02R (SEQ ID NO:28)

TaqMan probe used 103_02TP: (SEQ ID NO:30)

103_03—A specific region that is distinguishable from both the deletion region [1] and insert region of [2] in the cDNA pattern [3] registered with an existing public DB, serving as a control for comparing [1] and [2]

→Fragment 103_03 (SEQ ID NO:33) amplified by Primer103_03F (SEQ ID NO:31) and Primer103_03R (SEQ ID NO:32)

TaqMan probe used 103_03TP: (SEQ ID NO:34)

103_04—A common region shared by all of [1] to [3]: a region common to all patterns, serving for control to compare the overall expression levels of the cDNA patterns [1] and [2], which were newly subjected to full-length cDNA sequence analysis by us, and the cDNA pattern [3], registered with an existing public DB →Fragment 103_04 (SEQ ID NO:37) amplified by Primer103_04F (SEQ ID NO:35) and Primer103_04R (SEQ ID NO:36)

TaqMan probe 103_04TP used: (SEQ ID NO:38)

By mapping the 5'-terminal sequences of about 1.44 million sequences acquired using the oligocap method onto the human genome sequence, and comparatively analyzing them, the exon regions specific for the cDNA patterns [1], [2], and [3] shown above, respectively, were found to be expressed at the following frequencies.

In the cDNA pattern [1], which was newly acquired and analyzed by us, one 5'-terminal sequence was present, the derivation thereof being Uterus for 1 sequence (analytical parameter 49,561).

In the cDNA pattern [2], which was newly acquired and analyzed by us, two 5'-terminal sequences were present, the derivations thereof being Brain, cerebellum for 1 sequence (analytical parameter 82,880), and NT2 cells treated with retinoic acid (RA) to induce differentiation (NT2RP) for 1 sequence (analytical parameter 39,242).

In the cDNA pattern [3], which is registered with an existing public DB, fourteen 5'-terminal sequences were present, the derivations thereof being NT2 cells treated with retinoic acid (RA) to induce differentiation for 5 weeks (NT2RP) for 4 sequences (analytical parameter 39,242), NT2 cells treated with RA to induce differentiation for 5 weeks, and thereafter treated with a growth inhibitor for 2 weeks (NT2RI) for 2 sequences (analytical parameter 32,662), Brain, cerebellum for 1 sequence (analytical parameter 82,880), Brain, amygdala for 1 sequence (analytical parameter 58,640), Brain, hippocampus for 1 sequence (analytical parameter 57,918), Brain, substantia nigra for 1 sequence (analytical parameter 15,897), Normal Human Dermal Fibroblasts for 1 sequence (analytical parameter 10,103), Brain, Fetal for 2 sequences (analytical parameter 79,560), and Uterus for 1 sequence (analytical parameter 49,561).

From this result, it was found that the exon-deletion pattern [1] was expressed in Uterus, and that the exon-insertion pattern [2] was expressed in Brain, cerebellum and NT2 cells treated with retinoic acid to induce differentiation (NT2RP). It was found that the known sequence [3] was abundantly expressed in NT2 cells treated with retinoic acid to induce differentiation (NT2RP) and in brain tissues.

(2) Analysis of Expression Specificity by Real-Time PCR

To detect protein expression diversity changes due to exon selectivity, details of expression levels were analyzed by real-time PCR. The results are shown in Table 3.

weeks, Inh (+); the expression was low in NT2 Neuron (Table 3). Not only in Fetal Brain, but also in the whole brain, the expression was low (Table 3).

These results demonstrated that by comparing the expression of selective exon regions 103_[1]_1-N1 (SEQ ID NO:11) and 103_[2]_1-N1 (SEQ ID NO:19) of newly acquired cDNAs shown by the detection regions 103_01 (SEQ ID NO:25) and 103_02 (SEQ ID NO:29), it is possible to use these regions as differentiation markers for detecting stages of nerve cell differentiation or regeneration. It also seems possible to develop a new drug by means of a compound, antibody, siRNA or the like that targets a region that exhibits specificity.

TABLE 3

|  | RQ Score | | | | Log$_{10}$RQ Score | | | |
| --- | --- | --- | --- | --- | --- | --- | --- | --- |
|  | 103_01 | 103_02 | 103_03 | 103_04 | 103_01 | 103_02 | 103_03 | 103_04 |
| 01 NT2RA(−) | 0.1 | 6.3 | 0.9 | 0.4 | −0.86 | 0.80 | −0.04 | −0.45 |
| 02 NT2RA(+) 24 hr | 0.3 | 2.7 | 0.6 | 0.3 | −0.54 | 0.42 | −0.19 | −0.59 |
| 03 NT2RA(+) 48 hr | 0.2 | 2.0 | 0.7 | 0.3 | −0.68 | 0.29 | −0.14 | −0.52 |
| 04 NT2RA(+) 1 week | 1.9 | 1.5 | 0.9 | 0.8 | 0.27 | 0.17 | −0.03 | −0.11 |
| 05 NT2RA(+) 5 weeks | 6.7 | 8.6 | 2.9 | 1.1 | 0.83 | 0.93 | 0.46 | 0.05 |
| 06 NT2RA(+) 5 weeks, Inh(+) | 2.1 | 1.5 | 1.1 | 0.5 | 0.32 | 0.19 | 0.05 | −0.30 |
| 07 NT2 Neuron | 0.2 | 0.2 | 0.5 | 1.3 | −0.77 | −0.74 | −0.30 | 0.10 |
| 08 Brain, Fetal | 4.0 | 5.0 | 17.3 | 8.4 | 0.60 | 0.70 | 1.24 | 0.92 |
| 09 Brain, whole | 8.6 | 3.2 | 6.1 | 5.3 | 0.93 | 0.51 | 0.78 | 0.73 |
| 10 ALZ Visual Cortex Occipital | 1.2 | 0.7 | 2.2 | 3.0 | 0.08 | −0.18 | 0.34 | 0.47 |
| 11 Mix, viscus tissues | 1.0 | 1.0 | 1.0 | 1.0 | 0.0 | 0.0 | 0.0 | 0.0 |
| 12 Mix, blood cells and related tissues | 12.7 | 6.0 | 2.7 | 2.6 | 1.11 | 0.78 | 0.43 | 0.42 |
| 13 Mix, tumor tissues | 2.3 | 0.9 | 0.5 | 0.7 | 0.36 | −0.02 | −0.28 | −0.17 |
| 14 Mix, normal tissues | 2.4 | 1.9 | 1.2 | 1.8 | 0.37 | 0.29 | 0.09 | 0.24 |
| 15 Brain, whole PolyA(+) RNA | 4.8 | 2.2 | 5.9 | 3.1 | 0.68 | 0.34 | 0.77 | 0.49 |
| 16 Brain, hippocampus | 2.4 | 1.9 | 4.1 | 2.6 | 0.39 | 0.28 | 0.61 | 0.42 |

Expression levels were compared using the 16 samples shown in Example 3, including Brain, hippocampus, Brain, whole, Brain, Fetal, Alzheimer patient cerebral cortex (ALZ Visual Cortex Occipital), and NT2 cells in 7 differentiation stages. For experimental control, comparisons were made using the sample prepared by mixing normal visceral tissues in Example 3 (Mix, viscus tissues).

The ratio of ORF alteration due to exon insertion/deletion selectivity as compared between 103_01 (SEQ ID NO:25) and 103_02 (SEQ ID NO:29) changed greatly among the following differentiation stages of the brain and NT2 cells.

The expression of the exon-deletion pattern shown by 103_01 (SEQ ID NO:25) was low in undifferentiated NT2 cells NT2RA (−) and NT2RA (+) 48 hr, which represents the initial stage in which retinoic acid was added to induce differentiation; the expression was high in NT2RA(+) 1 week to NT2RA (+) 5 weeks, Inh (+), which represent the late stage of differentiation induction, and was low in NT2 Neuron. The expression in Brain, Fetal was also low (Table 3).

The expression of the exon insertion pattern shown by 103_02 (SEQ ID NO:29) was abundant in undifferentiated NT2 cells NT2RA(−) and the initial stage in which retinoic acid was added to induce differentiation, to NT2RA (+) 5

The following regions also seem to be useful as differentiation markers for detecting nerve cell differentiation or regeneration stages.

Upstream sequence 062_[1]_1-N3 (SEQ ID NO:39), which comprises the 285th to 306th bases undergoing priming by Primer103_01R (SEQ ID NO:24) in D-UTERU2026184.1 of the cDNA pattern [1].

Upstream sequence 062_[1]_1-N3 (SEQ ID NO:40), which comprises the 521st to 541st bases undergoing priming by Primer103_02R (SEQ ID NO:28) in D-BRACE3000012.1 of the cDNA pattern [2]. Region 103_01 (SEQ ID NO:25) amplified by Primer103_01F (SEQ ID NO:23) and Primer103_01R (SEQ ID NO:24) in the cDNA pattern [1] Region 103_02 (SEQ ID NO:29) amplified by Primer103_02F (SEQ ID NO:27) and Primer103_02R (SEQ ID NO:28) in the cDNA pattern [2]

Example 5

Cluster chr14-45 (Data Set: 019)

(1) Cluster Analysis
1) Cluster Characteristics

An analysis was performed on 13 sequences of full-length cDNAs subjected to genome mapping onto the cluster chr14-

45 (Human genome UCSC hg18 (NCBI Build34) chromosome 14, 104,305,000 bp to 104,335,000 bp) [D-NT2RP8004156.1, BC000479.2, BC084538.1, BX647722.1, BX648205.1, C-BRACE2006105, C-BRHIP2019884, C-PLACE7003657, C-TESTI4021482, ENST00000310523, ENST00000349310, M63167.1, NM_005163.1]. They were classified according to expression pattern difference into 7 kinds, which mainly included the following 2 kinds.

[1] D-NT2RP8004156.1

[2] BC000479.2, BC084538.1, BX648205.1, C-PLACE7003657 (AK122894.1), ENST00000310523, M63167.1, NM_005163.1

[1] is a cDNA which was newly acquired and subjected to full-length cDNA sequence analysis by us, having an ORF different from that of [2] registered in an existing public DB.

[1] had a different ORF region because of its expression from a chromosome region located downstream of the known [2].

It was found that the ORF regions present in the 2 kinds of cDNA patterns [1] to [2] cause expression starting at different transcription initiation points, from the same chromosome region, resulting in alterations of the amino acid sequences to produce diverse proteins and mRNAs.

2) Characteristics of D-NT2RP8004156.1 ([1]), which was Newly Acquired and Subjected to Full-Length cDNA Sequence Analysis by Us 019_[1]_1-N0 (SEQ ID NO:41): The entire nucleic acid sequence region of D-NT2RP8004156.1

019_[1]_1-NA0 (SEQ ID NO:42): Both the entire nucleic acid sequence region and amino acid sequence of D-NT2RP8004156.1

019_[1]_1-A0 (SEQ ID NO:43): The entire amino acid sequence region of D-NT2RP8004156.1

The 1st to 119th bases of D-NT2RP8004156.1 (SEQ ID NO:44) is an exon that is not present in NM_005163.1, which is registered in an existing public DB and serves as a control, lacking homology to NM_005163.1.

With this change, the translation initiation point of D-NT2RP8004156.1 shifts toward the 3' side relative to NM_005163.1, and the 131st base of D-NT2RP8004156.1 becomes the translation initiation point. For this reason, the N-terminal amino acid sequence shortened by 62 residues compared with NM_005163.1 (SEQ ID NO:264).

019_[1]_1-N1 (SEQ ID NO:44): A 119-base insert nucleic acid sequence region of D-NT2RP8004156.1

019_[1]_1-N2 (SEQ ID NO:45): A 130-base 5'UTR region of an ORF whose translation initiation point is the 131st base of D-NT2RP8004156.1

019_[1]_C-A1 (SEQ ID NO:264): Amino acid sequence region lacking 62 residues of D-NT2RP8004156.1 present in NM_005163.1

With this change, the Pfam motif "PH domain" present at the 6th to 108th amino acids of NM_005163.1 disappeared in D-NT2RP8004156.1.

3) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

019_01—A specific region present on the N-terminal side of the cDNA pattern [1]: a translation initiation region of the cDNA pattern [1], which was newly subjected to full-length cDNA sequence analysis by us, being a novel region not registered with an existing public DB
→Fragment 019_01 (SEQ ID NO:48) amplified by Primer019_01F (SEQ ID NO:46) and Primer01901R (SEQ ID NO:47)

019_02—A transcription initiation point region of [2], which is registered with an existing public DB, serving as a control for comparing [1]
→Fragment 019_02 (SEQ ID NO:51) amplified by Primer019_02F (SEQ ID NO:49) and Primer01902R (SEQ ID NO:50)

019_03—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB
→Fragment 019_03 (SEQ ID NO:54) amplified by Primer019_03F (SEQ ID NO:52) and Primer019_03R (SEQ ID NO:53)

By mapping the 5'-terminal sequences of about 1.44 million sequences acquired using the oligocap method onto the human genome sequence, and comparatively analyzing them, the exon regions specific for the respective cDNA patterns [1] to [2] shown above, respectively, were found to be expressed at the following frequencies.

In the cDNA pattern [1], which was newly acquired and analyzed by us, four 5'-terminal sequences were present, the derivation thereof being NT2 cells treated with retinoic acid (RA) to induce differentiation (NT2RP) for all sequences.

It was found that in the cDNA pattern [2], which is registered with an existing public DB, eleven 5'-terminal sequences were present: 4 sequences derived from brain tissues and 7 sequences from a plurality of other organs and the like were expressed.

From this result, it was found that the transcription initiation point of [1] was expressed specifically in NT2 cells after differentiation. From the transcription initiation point of [2], expression in a variety of organs was observed. Hence, it was thought that the mechanism of transcription in this chromosome region might be unique to the nerve cell differentiation stage of NT2 cells after differentiation, with a different transcription initiation point being used.

(2) Analysis of Expression Specificity by Real-Time PCR

To determine what are the states in which the transcription initiation point used for the expression changes, details of expression levels were analyzed by real-time PCR. The results are shown in Table 4 and Table 5.

TABLE 4

| | RQ Score | | | Log$_{10}$RQ Score | | |
|---|---|---|---|---|---|---|
| | 019_01 | 019_02 | 019_03 | 019_01 | 019_02 | 019_03 |
| 01 NT2RA(−) | 0.2 | 0.1 | 0.1 | −0.73 | −1.02 | −1.03 |
| 02 NT2RA(+) 24 hr | 0.5 | 0.1 | 0.1 | −0.29 | −1.16 | −1.15 |
| 03 NT2RA(+) 48 hr | 0.2 | 0.1 | 0.1 | −0.71 | −1.05 | −1.10 |
| 04 NT2RA(+) 1 week | 1.4 | 0.1 | 0.2 | 0.16 | −0.84 | −0.75 |

TABLE 4-continued

| | RQ Score | | | Log₁₀RQ Score | | |
|---|---|---|---|---|---|---|
| | 019_01 | 019_02 | 019_03 | 019_01 | 019_02 | 019_03 |
| 05 NT2RA(+) 5 weeks | 94.2 | 0.4 | 0.5 | 1.97 | −0.35 | −0.34 |
| 06 NT2RA(+) 5 weeks, Inh(+) | 4.7 | 0.4 | 0.5 | 0.67 | −0.37 | −0.32 |
| 07 NT2 Neuron | 0.0 | 0.1 | 0.0 | −1.40 | −1.03 | −1.80 |
| 08 Brain, Fetal | 1.1 | 1.5 | 1.4 | 0.03 | 0.17 | 0.16 |
| 09 Brain, whole | 0.1 | 0.6 | 0.6 | −1.06 | −0.24 | −0.25 |
| 10 ALZ Visual Cortex Occipital | 0.1 | 0.2 | 0.2 | −1.00 | −0.74 | −0.72 |
| 11 Mix, viscus tissues | 1.0 | 1.0 | 1.0 | 0.0 | 0.0 | 0.0 |
| 12 Mix, blood cells and related tissues | 1.7 | 0.7 | 0.4 | 0.23 | −0.15 | −0.38 |
| 13 Mix, tumor tissues | 2.2 | 0.7 | 0.8 | 0.35 | −0.18 | −0.09 |
| 14 Mix, normal tissues | 1.3 | 0.9 | 0.9 | 0.10 | −0.02 | −0.04 |
| 15 Brain, whole PolyA(+) RNA | 0.2 | 0.4 | 0.3 | −0.75 | −0.35 | −0.46 |
| 16 Brain, hippocampus | 0.2 | 0.4 | 0.3 | −0.81 | −0.43 | −0.51 |

TABLE 5

| | RQ Score | | | Log₁₀RQ Score | | |
|---|---|---|---|---|---|---|
| | 019_01 | 019_02 | 019_03 | 019_01 | 019_02 | 019_03 |
| 01 NT2RA(−) | 0.1 | 0.1 | 0.1 | −1.01 | −1.01 | −1.01 |
| 02 NT2RA(+) 24 hr | 0.2 | 0.1 | 0.1 | −0.66 | −1.23 | −1.11 |
| 03 NT2RA(+) 48 hr | 0.0 | 0.1 | 0.1 | −1.66 | −1.02 | −1.08 |
| 04 NT2RA(+) 1 week | 0.6 | 0.2 | 0.2 | −0.22 | −0.80 | −0.72 |
| 05 NT2RA(+) 5 weeks | 40.2 | 0.5 | 0.5 | 1.60 | −0.32 | −0.29 |
| 06 NT2RA(+) 5 weeks, Inh(+) | 2.0 | 0.5 | 0.6 | 0.30 | −0.29 | −0.25 |
| 07 NT2 Neuron | 0.0 | 0.1 | 0.0 | −1.52 | −1.04 | −1.80 |
| 08 Brain, Fetal | 0.4 | 1.5 | 1.5 | −0.36 | 0.19 | 0.17 |
| 09 Brain, whole | 0.2 | 0.6 | 0.6 | −0.73 | −0.21 | −0.22 |
| 10 ALZ Visual Cortex Occipital | 0.0 | 0.2 | 0.2 | −1.40 | −0.72 | −0.72 |
| 11 Mix, viscus tissues | 1.0 | 1.0 | 1.0 | 0.0 | 0.0 | 0.0 |
| 12 Mix, blood cells and related tissues | 1.1 | 0.9 | 0.7 | 0.03 | −0.07 | −0.13 |
| 13 Mix, tumor tissues | 0.7 | 0.6 | 0.6 | −0.17 | −0.25 | −0.19 |
| 14 Mix, normal tissues | 0.3 | 0.9 | 0.9 | −0.59 | −0.03 | −0.04 |
| 15 Brain, whole PolyA(+) RNA | 0.1 | 0.6 | 0.4 | −1.11 | −0.25 | −0.36 |
| 16 Brain, hippocampus | 0.1 | 0.5 | 0.4 | −1.08 | −0.29 | −0.40 |

Expression levels were compared using the 16 samples shown in Example 3, including Brain, hippocampus, Brain, whole, Brain, Fetal, ALZ Visual Cortex Occipital, and NT2 cells at 7 different differentiation stages. The comparison was made using the mixed sample of normal visceral tissues shown in Example 3 (Mix, viscus tissues) as an experimental control.

The ratio of ORF alteration due to transcription initiation point selectivity as compared between 019_01 (SEQ ID NO:48) and 019_02 (SEQ ID NO:51) changed greatly depending on NT2 cell differentiation stage. When compared in detail with respect to NT2 cell differentiation, no major difference was observed between the 2 kinds of transcription initiation points shown by 019_01 (SEQ ID NO:48) and 019_02 (SEQ ID NO:51) in undifferentiated NT2 cells NT2RA (−) and NT2RA (+) 48 hr, which represents the initial stage in which retinoic acid was added to induce differentiation (Table 4 and Table 5). However, in NT2RA (+) 1 week, which represents an advanced stage of differentiation, the difference widened; in NT2RA (+) 5 weeks, the ratio of transcription from the downstream transcription initiation point shown by 019_01 (SEQ ID NO:48) increased considerably (Table 4 and Table 5). However, thereafter in NT2RA (+) 5 weeks, Inh (+), the difference decreased; in NT2Neuron, on the contrary, the ratio of transcription from the known transcription initiation point shown by 019_02 (SEQ ID NO:51) increased (Table 4 and Table 5). In other tissues, no major difference was observed.

These results demonstrated that by comparing the expression of the 5'-terminal region of a newly acquired cDNA region shown by the detection region 019_01 (sequence No. 019-8) (a region close to the transcription initiation point) 019_[1]_1-N1 (SEQ ID NO:44), it is possible to use the 5'-terminal region as a differentiation marker for detecting cells in nerve cell differentiation or regeneration stages, particularly in the late stage of nerve differentiation or regeneration. It also seems possible to develop a new drug by means of a compound, antibody, siRNA or the like that targets a region that exhibits specificity.

The following regions also seem to be useful as differentiation markers for detecting cells in the late stage of nerve differentiation or regeneration.

Upstream sequence 019_[1]_1-N3 (SEQ ID NO:55), which comprises the 195th to 213th bases undergoing priming by Primer019_01R (SEQ ID NO:47) in D-NT2RP8004156.1 of the cDNA pattern [1]. Region 019_01 (SEQ ID NO:48) amplified by Primer019_01F (SEQ ID NO:46) and Primer019_01R (SEQ ID NO:47) in the cDNA pattern [1]

Example 6

Cluster chr2-2324 (Data Set: 031)

(1) Cluster Analysis
1) Cluster Characteristics

An analysis was performed on 7 sequences of full-length cDNAs subjected to genome mapping onto the cluster chr2-

2324 (Human genome UCSC hg18 (NCBI Build34) chromosome 2, 65,440,000 by to 65,580,000 bp) [D-NT2RI3005525.1, D-TRACH3029063.1, AY299090.1, C-HEP03447, C-NT2RP7004925, ENST00000356388, NM_181784.1]. They were classified according to expression pattern difference into 5 kinds, which mainly included the following 2 kinds.

[1] D-NT2RI3005525.1
[2] AY299090.1, C-NT2RP7004925 (AK056479.1), NM_181784.1

[1] is a cDNA which was newly acquired and subjected to full-length cDNA by us, and had a different ORF from [2] registered with an existing public DB.

[1] had a different ORF region because of its expression from a chromosome region located downstream of the known [2], and also because of the presence of the translation initiation point on a new exon lacking identity to [2].

It was found that the ORF regions present in the 2 kinds of cDNA patterns [1] to [2] cause expression starting at different transcription initiation points, from the same chromosome region, resulting in alterations of the amino acid sequences to produce diverse proteins and mRNAs.

2) Characteristics of D-NT2RI3005525.1 ([1]), which was Newly Acquired and Subjected to Full-Length cDNA by Us 031_[1]_1-N0 (SEQ ID NO:56): The entire nucleic acid sequence region of D-NT2RI3005525.1

031_[1]_1-NA0 (SEQ ID NO:57): Both the entire nucleic acid sequence region and amino acid sequence of D-NT2RI3005525.1

031_[1]_1-A0 (SEQ ID NO:58): The entire amino acid sequence region of D-NT2RI3005525.1

The sequence at the 1st to 61st bases of D-NT2RI3005525.1 (SEQ ID NO:59) is a variant incorporating an exon that is not present in NM_181784.1, which is registered with an existing public DB, and serves for control; because of the presence thereof along with the translation initiation point on the exon inserted, the N-terminal amino acids differed by 6 residues, compared with NM_181784.1 (SEQ ID NO:60).

031_[1]_1-N1 (SEQ ID NO:59): 61-base insert nucleic acid sequence region of D-NT2RI3005525.1

031_[1]_1-A1 (SEQ ID NO:60): 6-residue insert amino acid sequence region of D-NT2RI3005525.1

031_[1]_1-N2 (SEQ ID NO:61): ORF nucleic acid sequence region in 61-base insert region of D-NT2RI3005525.1

031_[1]_1-A2 (identical to SEQ ID NO:60): ORF amino acid region related to 61-base insert region of D-NT2RI3005525.1

3) Expression Specificity Analysis and Design of Primer for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

031_01—A specific region present on the N-terminal side of the cDNA pattern [1]: a translation initiation region of the cDNA pattern [1], which was newly subjected to full-length cDNA sequence analysis by us, being a novel region not registered with an existing public DB
→Fragment 031_01 (SEQ ID NO:64) amplified by Primer031_01F (SEQ ID NO:62) and Primer031_01R (SEQ ID NO:63)

031_02—A transcription initiation point region of [2], registered with an existing public DB, serving as a control for comparing [1]
→Fragment 031_02 (SEQ ID NO:67) amplified by Primer031_02F (SEQ ID NO:65) and Primer03102R (SEQ ID NO:66)

031_03—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB
→Fragment 031_03 (SEQ ID NO:70) amplified by Primer031_03F (SEQ ID NO:68) and Primer03103R (SEQ ID NO:69)

By mapping the 5'-terminal sequences of about 1.44 million sequences acquired using the oligocap method onto the human genome sequence, and comparatively analyzing them, the exon regions specific for the cDNA patterns [1] and [2] shown above, respectively, were found to be expressed at the following frequencies.

In the cDNA pattern [1], which was newly acquired and analyzed by us, twenty-eight 5'-terminal sequences were present, the derivations thereof being Brain, whole for 13 sequences (analytical parameter 59,069), Brain, hippocampus for 8 sequences (analytical parameter 57,918), Brain, amygdala for 5 sequences (analytical parameter 58,640), HDPC (Human dermal papilla cells) for 1 sequence (analytical parameter 8,453), and NT2 cells treated with retinoic acid (RA) to induce differentiation for 5 weeks, and thereafter treated with a growth inhibitor for 2 weeks (NT2RI) for 1 sequence (analytical parameter 32,662).

In the cDNA pattern [2], which is registered with an existing public DB, thirty-five 5'-terminal sequences were present, the derivations thereof being Brain, whole for 10 sequences (analytical parameter 59,069), Brain, cerebellum for 5 sequences (analytical parameter 82,880), Brain, Fetal for 5 sequences (analytical parameter 47,574), Brain, hippocampus for 3 sequences (analytical parameter 57,918), Trachea for 3 sequences (analytical parameter 52,352), Brain, thalamus for 2 sequences (analytical parameter 53,267), NT2 cells treated with retinoic acid (RA) to induce differentiation (NT2RP) for 2 sequences (analytical parameter 39,242), Thymus for 2 sequences (analytical parameter 70,578), NT2 cells treated with retinoic acid (RA) to induce differentiation for 5 weeks, and thereafter treated with a growth inhibitor for 2 weeks (NT2RI) for 1 sequence (analytical parameter 32,662), Testis for 1 sequence (analytical parameter 90,188), and Uterus for 1 sequence (analytical parameter 49,561).

From this result, it was found that the transcription initiation point of [1] was expressed abundantly in the brain, particularly in Brain, hippocampus and Brain, amygdala. It was found that the transcription initiation point of [2] was also abundantly expressed in the brain, but expressed in a wider variety of tissues compared with the transcription initiation point of [1]. From this result, it was thought that the mechanism of transcription in this chromosome region might be unique to particular portions of the brain, with a different is transcription initiation point being used.

(2) Analysis of Expression Specificity by Real-Time PCR

To determine what are the portions and states in which the transcription initiation point used for the expression changes, details of expression levels were analyzed by real-time PCR. The results are shown in Table 6 and Table 7.

TABLE 6

| | RQ Score | | | Log₁₀RQ Score | | |
|---|---|---|---|---|---|---|
| | 031_01 | 031_02 | 031_03 | 031_01 | 031_02 | 031_03 |
| 01 NT2RA(−) | 0.0 | 0.1 | 0.2 | −3.12 | −0.85 | −0.82 |
| 02 NT2RA(+) 24 hr | 0.0 | 0.5 | 0.8 | −2.48 | −0.34 | −0.09 |
| 03 NT2RA(+) 48 hr | 0.0 | 0.4 | 0.9 | −2.48 | −0.41 | −0.03 |
| 04 NT2RA(+) 1 week | 0.0 | 0.2 | 0.4 | −2.32 | −0.81 | −0.43 |
| 05 NT2RA(+) 5 weeks | 0.9 | 0.4 | 0.4 | −0.03 | −0.45 | −0.39 |
| 06 NT2RA(+) 5 weeks, Inh(+) | 2.3 | 0.4 | 0.5 | 0.36 | −0.37 | −0.29 |
| 07 NT2 Neuron | 0.1 | 0.0 | 0.1 | −1.00 | −1.51 | −0.83 |
| 08 Brain, Fetal | 0.5 | 1.7 | 2.1 | −0.33 | 0.22 | 0.32 |
| 09 Brain, whole | 15.4 | 1.4 | 2.1 | 1.19 | 0.16 | 0.31 |
| 10 ALZ Visual Cortex Occipital | 8.1 | 0.4 | 0.6 | 0.91 | −0.44 | −0.20 |
| 11 Mix, viscus tissues | 1.0 | 1.0 | 1.0 | 0.0 | 0.0 | 0.0 |
| 12 Mix, blood cells and related tissues | 0.6 | 0.7 | 0.9 | −0.21 | −0.17 | −0.06 |
| 13 Mix, tumor tissues | 0.5 | 0.4 | 0.5 | −0.31 | −0.35 | −0.29 |
| 14 Mix, normal tissues | 0.9 | 0.9 | 1.2 | −0.04 | −0.04 | 0.08 |
| 15 Brain, whole PolyA(+) RNA | 4.2 | 0.2 | 0.3 | 0.63 | −0.71 | −0.59 |
| 16 Brain, hippocampus | 2.8 | 0.1 | 0.2 | 0.44 | −0.87 | −0.74 |
| 17 Brain, cerebellum | 0.0 | 0.2 | 0.3 | −1.61 | −0.65 | −0.55 |
| 18 Brain, amygdala | 3.1 | 0.1 | 0.2 | 0.49 | −0.95 | −0.75 |
| 19 Brain, caudate nucleus | 0.2 | 0.1 | 0.1 | −0.78 | −1.00 | −0.88 |
| 20 Brain, corpus callosum | 0.2 | 0.1 | 0.1 | −0.61 | −1.10 | −1.02 |
| 21 Brain, substantia nigra | 0.2 | 0.1 | 0.2 | −0.72 | −0.85 | −0.78 |
| 22 Brain, thalamus | 0.2 | 0.1 | 0.1 | −0.75 | −1.16 | −1.05 |
| 23 Brain, subthalamic nucleus | 0.1 | 0.1 | 0.1 | −1.16 | −1.24 | −0.96 |

TABLE 7

| | RQ Score | | | Log₁₀RQ Score | | |
|---|---|---|---|---|---|---|
| | 031_01 | 031_02 | 031_03 | 031_01 | 031_02 | 031_03 |
| 01 Brain, Fetal | 0.3 | 1.9 | 1.8 | −0.46 | 0.28 | 0.27 |
| 02 Brain, whole | 10.2 | 1.3 | 1.8 | 1.01 | 0.10 | 0.26 |
| 03 ALZ Visual Cortex Occipital | 5.6 | 0.4 | 0.6 | 0.75 | −0.44 | −0.21 |
| 04 Mix, viscus tissues | 1.0 | 1.0 | 1.0 | 0.0 | 0.0 | 0.0 |
| 05 Mix, blood cells and related tissues | 0.5 | 0.8 | 0.9 | −0.31 | −0.11 | −0.03 |
| 06 Mix, tumor tissues | 0.8 | 0.7 | 0.8 | −0.11 | −0.17 | −0.08 |
| 07 Mix, normal tissues | 0.8 | 1.1 | 1.3 | −0.11 | 0.05 | 0.13 |
| 08 Brain, whole PolyA(+) RNA | 3.0 | 0.1 | 0.3 | 0.48 | −0.82 | −0.57 |
| 09 Brain, hippocampus | 2.1 | 0.1 | 0.2 | 0.32 | −0.88 | −0.72 |
| 10 Brain, cerebellum | 0.0 | 0.1 | 0.2 | −1.96 | −0.87 | −0.80 |
| 11 Brain, amygdala | 2.3 | 0.1 | 0.2 | 0.37 | −0.97 | −0.75 |
| 12 Brain, caudate nucleus | 0.1 | 0.1 | 0.1 | −0.96 | −1.06 | −0.96 |
| 13 Brain, corpus callosum | 0.2 | 0.1 | 0.1 | −0.82 | −1.16 | −1.09 |
| 14 Brain, substantia nigra | 0.1 | 0.1 | 0.1 | −0.99 | −1.01 | −0.95 |
| 15 Brain, thalamus | 0.1 | 0.0 | 0.1 | −1.05 | −1.34 | −1.23 |
| 16 Brain, subthalamic nucleus | 0.0 | 0.1 | 0.1 | −1.37 | −1.28 | −1.03 |

Expression levels were compared using the 23 kinds of samples shown in Example 3, including 11 kinds of brain tissues and NT2 cells at 7 different differentiation stages. The comparison was made using the mixed sample of normal visceral tissues shown in Example 3 (Mix, viscus tissues) as an experimental control.

The ratio of ORF alteration due to transcription initiation point selectivity as compared between 031_01 (SEQ ID NO:64) and 031_02 (SEQ ID NO:67) changed greatly among the following brain portions and NT2 cell differentiation stages.

In the brain, particularly in Brain, hippocampus and Brain, amygdala, the transcription from the downstream transcription initiation point shown by 031_01 (SEQ ID NO:64) was abundant (Table 6 and Table 7). No major difference was observed among the other portions of the brain.

Furthermore, when compared in detail with respect to NT2 cell differentiation, the expression of the mRNA transcribed from the transcription initiation point shown by 031_02 (SEQ ID NO:67), registered with an existing public DB, was abundant in undifferentiated NT2 cells NT2RA (−) and NT2RA (+) 1 week, which represents the initial stage in which retinoic acid was added to induce differentiation; however, in NT2RA (+) 5 weeks, predicted to be rich in nerve cells after differentiation, the expression level reversed; in the subsequent stages of NT2RA (+) 5 weeks, Inh (+), and NT2 Neuron, the expression of the mRNA transcribed from the downstream transcription initiation point shown by 031_01 (SEQ ID NO:64) was abundant (Table 6 and Table 7).

These results demonstrated that by comparing the expression of the 5'-terminal region 031_[1]-N1 (SEQ ID NO:59) of a newly acquired cDNA shown by the detection region 031_01 (SEQ ID NO:64) (a region close to the transcription initiation point), it is possible to use the 5'-terminal region as a marker specific for the brain, particularly for nerve-rich portions such as Brain, hippocampus (nerve differentiation, nerve regeneration marker and the like), and as a differentiation marker for detecting cells in nerve cell differentiation or regeneration stages, particularly those that have differentiated into a nerve. It also seems possible to develop a new drug by means of a compound, antibody, siRNA or the like that targets a region that exhibits specificity.

The following regions also seem to be useful as markers specific to the brain, particularly to the nerve-rich portions such as Brain, hippocampus (nerve differentiation, nerve regeneration marker and the like), and as differentiation markers for detecting nerve cells in differentiation or regeneration stages, particularly those that have differentiated into nerves.

Upstream sequence 031_[1]_1-N3 (SEQ ID NO:71), which comprises the 80th to 101st bases undergoing priming by Primer031_01R (SEQ ID NO:63) in D-NT2RI3005525.1 of the cDNA pattern [1]. Region 031_01 (SEQ ID NO:64) amplified by Primer031_01F (SEQ ID NO:62) and Primer031_01R (SEQ ID NO:63) in the cDNA pattern [1]

Example 7

Cluster chr7-2007 (Data Set: 067)

(1) Cluster Analysis
1) Cluster Characteristics

An analysis was performed on 10 sequences of full-length cDNAs subjected to genome mapping onto the cluster chr7-2007 (Human genome UCSC hg18 (NCBI Build34) chromosome 7, 26,400,000 bp to 26,850,000 bp) [D-NT2RP8004592.1, D-NT2RP7010844.1, Z-NT2RP7020087-01, BC002893.2, BC036044.1, ENST00000338865, ENST00000345317, NM_003930.3, XM_498174.1, XM_499-404.1]. They were classified according to expression pattern difference into 5 kinds, which mainly included the following 2 kinds.
[1] D-NT2RP8004592.1
[2] BC002893.2, BC036044.1, N_003930.3

[1] is a cDNA which was newly acquired and subjected to full-length cDNA sequence analysis by us, having a different ORF from [2], which is registered with an existing public DB.

[1] had a different ORF region from [2] because of its expression from a chromosome region located downstream of the known [2], and hence a shift of the translation initiation point toward the C-terminal side.

It was found that the ORF regions present in the 2 kinds of cDNA patterns [1] and [2] cause expression starting at different transcription initiation points, from the same chromosome region, resulting in alterations of the amino acid sequences to produce diverse proteins and mRNAs.

2) Characteristics of D-NT2RP8004592.1 ([1]), which was Newly Acquired and Subjected to Full-Length cDNA Sequence Analysis by Us 067_[1]_1-N0 (SEQ ID NO:72): The entire nucleic acid sequence region of D-NT2RP8004592.1
067_[1]_1-NA0 (SEQ ID NO:73): Both the entire nucleic acid sequence region and amino acid sequence of D-NT2RP8004592.1
067_[1]_1-A0 (SEQ ID NO:74): The entire amino acid sequence region of D-NT2RP8004592.1

The exon at the 1st to 169th bases of D-NT2RP8004592.1 (SEQ ID NO:75) (1st exon) is an exon that is not present in NM_003930.3, which is registered with an existing public DB, and serves for control, lacking homology thereto. The exon at the 1st to 359th bases of NM_003930.3 (first exon) is an exon that is not present in D-NT2RP8004592.1, lacking homology thereto. The second exon and beyond are present commonly in both cDNAs. The translation termination point of the ORF of NM_003930.3 is the same as that of D-NT2RP8004592.1; however, because the translation initiation point is present on the 1st exon, which is not present in D-NT2RP8004592.1, the N-terminus of the ORF differed. Because the translation initiation point of D-NT2RP8004592.1 is present on the 6th exon, which is shared by NM_003930.3, the amino acid sequence on the N-terminal side shortened by 172 residues, compared with NM_003930.3 (SEQ ID NO:265).

067_[1]_1-N 1 (SEQ ID NO:75): A 169-base insert nucleic acid sequence region of D-NT2RP8004592.1
067_[1]_1-N 2 (SEQ ID NO:76): A 619-base 5'UTR region of an ORF whose translation initiation point is the 620th base of D-NT2RP8004592.1
067_[1]_C-A1 (SEQ ID NO:265): A 172-residue deletion amino acid sequence region of D-NT2RP8004592.1 present in NM_003930.3

3) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

067_01—A specific region present on the N-terminal side of the cDNA pattern [1]: a translation initiation region of the cDNA pattern [1], which was newly subjected to full-length cDNA sequence analysis by us, being a novel region not registered with an existing public DB
→Fragment 067_01 (SEQ ID NO:79) amplified by Primer067_01F (SEQ ID NO:77) and Primer06701R (SEQ ID NO:78)

067_03—Transcription initiation point region of [2], which is registered with an existing public DB, serving as a control for comparing [1]
→Fragment 067_03 (SEQ ID NO:82) amplified by Primer067_03F (SEQ ID NO:80) and Primer06703R (SEQ ID NO:81)

067_04—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB
→Fragment 067_04 (SEQ ID NO:85) amplified by Primer067_04F (SEQ ID NO:83) and Primer06704R (SEQ ID NO:84)

By mapping the 5'-terminal sequences of about 1.44 million sequences acquired using the oligocap method onto the human genome sequence, and comparatively analyzing them, the exon regions specific for the cDNA patterns [1] to [2] shown above, respectively, were found to be expressed at the following frequencies.

In the cDNA pattern [1], which was newly acquired and analyzed by us, eighteen 5'-terminal sequences were present, the derivations thereof being NT2 cells treated with retinoic acid (RA) to induce differentiation (NR2RP) for 16 sequences (analytical parameter 39,242), and NT2 cells treated with retinoic acid (RA) to induce differentiation for 5 weeks, and thereafter treated with a growth inhibitor for 2 weeks (NT2RI) for 2 sequences (analytical parameter 32,662); all were derived from NT2 cells after differentiation.

In the cDNA pattern [2], which is registered with an existing public DB, one hundred twenty-two (122) 5'-terminal sequences were present, the derivations thereof being NT2 cells for 45 sequences, brain tissues for 25 sequences, and others for 47 sequences.

From this result, it was found that the transcription initiation point of [1] was expressed specifically in NT2 cells after differentiation. From the transcription initiation point of [2], expression was observed in NT2 cells, brain tissues and various other tissues. Hence, it was suggested that in this chromosome region, the mechanism of transcription may differ, and may result in different transcription initiation points being used only at the nerve cell differentiation states of NT2 cells after differentiation.

(2) Analysis of Expression Specificity by Real-Time PCR

To determine what are the states in which the transcription initiation point used for the expression changes, details of expression levels were analyzed by real-time PCR. The results are shown in Table 8 and Table 9.

in detail with respect to NT2 cell differentiation, the ratio of the transcription from the transcription initiation point shown by 067_01 (SEQ ID NO:79) was higher than that from the transcription initiation point shown by 067_03 (SEQ ID NO:82) in NT2RA (+) 1 week to NT2RA (+) 5 weeks, advanced stages of differentiation, compared with undifferentiated NT2 cells NT2RA (−) and NT2RA (+) 48 hr, which represents the initial stage in which retinoic acid was added to induce differentiation (Table 8 and Table 9). Subsequently, in NT2RA (+) 5 weeks, Inh (+), the difference narrowed, but in NT2 Neuron, the ratio of transcription represented by 067_01 (SEQ ID NO:79) increased again (Table 8 and Table 9).

TABLE 8

| | RQ Score | | | Log$_{10}$RQ Score | | |
|---|---|---|---|---|---|---|
| | 067_01 | 067_03 | 067_04 | 067_01 | 067_03 | 067_04 |
| 01 NT2RA(−) | 0.0 | 0.0 | 0.0 | −1.58 | −2.04 | −1.79 |
| 02 NT2RA(+) 24 hr | 3.1 | 0.5 | 0.6 | 0.49 | −0.29 | −0.19 |
| 03 NT2RA(+) 48 hr | 8.6 | 1.6 | 1.5 | 0.93 | 0.21 | 0.19 |
| 04 NT2RA(+) 1 week | 21.6 | 1.5 | 1.9 | 1.33 | 0.16 | 0.27 |
| 05 NT2RA(+) 5 weeks | 103.8 | 3.3 | 11.3 | 2.02 | 0.52 | 1.05 |
| 06 NT2RA(+) 5 weeks, Inh(+) | 3.2 | 1.2 | 2.6 | 0.51 | 0.07 | 0.41 |
| 07 NT2 Neuron | 30.3 | 0.7 | 0.4 | 1.48 | −0.16 | −0.37 |
| 08 Brain, Fetal | 0.1 | 0.2 | 0.3 | −0.95 | −0.66 | −0.51 |
| 09 Brain, whole | 0.9 | 0.6 | 1.0 | −0.05 | −0.19 | 0.01 |
| 10 ALZ Visual Cortex Occipital | 0.4 | 0.3 | 0.7 | −0.36 | −0.51 | −0.17 |
| 11 Mix, viscus tissues | 1.0 | 1.0 | 1.0 | 0.0 | 0.0 | 0.0 |
| 12 Mix, blood cells and related tissues | 2.3 | 1.9 | 2.5 | 0.36 | 0.27 | 0.40 |
| 13 Mix, tumor tissues | 0.7 | 0.3 | 0.3 | −0.14 | −0.46 | −0.49 |
| 14 Mix, normal tissues | 2.3 | 1.0 | 1.2 | 0.37 | −0.01 | 0.07 |
| 15 Brain, whole PolyA(+) RNA | 0.2 | 0.2 | 0.5 | −0.71 | −0.66 | −0.29 |
| 16 Brain, hippocampus | 0.1 | 0.2 | 0.4 | −0.94 | −0.75 | −0.35 |

TABLE 9

| | RQ Score | | | Log$_{10}$RQ Score | | |
|---|---|---|---|---|---|---|
| | 067_01 | 067_03 | 067_04 | 067_01 | 067_03 | 067_04 |
| 01 NT2RA(−) | 0.0 | 0.0 | 0.0 | −1.53 | −2.04 | −1.78 |
| 02 NT2RA(+) 24 hr | 3.2 | 0.6 | 0.8 | 0.50 | −0.23 | −0.11 |
| 03 NT2RA(+) 48 hr | 10.6 | 1.6 | 1.7 | 1.03 | 0.21 | 0.22 |
| 04 NT2RA(+) 1 week | 25.0 | 1.5 | 1.9 | 1.40 | 0.18 | 0.28 |
| 05 NT2RA(+) 5 weeks | 125.3 | 3.7 | 13.6 | 2.10 | 0.57 | 1.13 |
| 06 NT2RA(+) 5 weeks, Inh(+) | 4.4 | 1.3 | 3.4 | 0.64 | 0.11 | 0.53 |
| 07 NT2 Neuron | 25.5 | 0.6 | 0.4 | 1.41 | −0.19 | −0.37 |
| 08 Brain, Fetal | 0.2 | 0.2 | 0.3 | −0.63 | −0.64 | −0.48 |
| 09 Brain, whole | 1.0 | 0.7 | 1.2 | −0.01 | −0.16 | 0.10 |
| 10 ALZ Visual Cortex Occipital | 0.4 | 0.3 | 0.7 | −0.35 | −0.47 | −0.15 |
| 11 Mix, viscus tissues | 1.0 | 1.0 | 1.0 | 0.0 | 0.0 | 0.0 |
| 12 Mix, blood cells and related tissues | 2.1 | 2.1 | 3.2 | 0.32 | 0.32 | 0.50 |
| 13 Mix, tumor tissues | 0.4 | 0.3 | 0.4 | −0.45 | −0.48 | −0.42 |
| 14 Mix, normal tissues | 2.7 | 0.9 | 1.2 | 0.44 | −0.02 | 0.08 |
| 15 Brain, whole PolyA(+) RNA | 0.2 | 0.3 | 0.7 | −0.60 | −0.54 | −0.16 |
| 16 Brain, hippocampus | 0.1 | 0.2 | 0.6 | −0.88 | −0.62 | −0.22 |

Expression levels were compared using the 16 samples shown in Example 3, including Brain, hippocampus, Brain, whole, Brain, Fetal, Alzheimer patient cerebral cortex (ALZ Visual Cortex Occipital), and NT2 cells at 7 different differentiation stages and the like. The comparison was made using the mixed sample of normal visceral tissues shown in Example 3 (Mix, viscus tissues) as an experimental control.

The ratio of ORF alteration due to transcription initiation point selectivity as compared between 067_01 (SEQ ID NO:79) and 067_03 (SEQ ID NO:82) changed greatly depending on NT2 cell differentiation stage. When compared These results demonstrated that by comparing the expression of the 5′-terminal region (a region close to the transcription initiation point) 067_[1]-N1 (SEQ ID NO:75) of a newly acquired cDNA shown by the detection region 067_01 (SEQ ID NO:79), it is possible to use the 5′-terminal region as a differentiation marker for detecting cells in nerve cell differentiation or regeneration stages, particularly those that have differentiated into a nerve. It also seems possible to develop a new drug by means of a compound, antibody, siRNA or the like that targets a region that exhibits specificity.

The following regions also seem to be useful as differentiation markers for detecting nerve cells in differentiation or regeneration stages, particularly those that have differentiated into nerves.

Upstream sequence 067_[1]_1-N3 (SEQ ID NO:86), which comprises the 65th to 84th bases undergoing priming by Primer067_01R (SEQ ID NO:78) in D-NT2RP8004592.1 of the cDNA pattern [1]. Region 067_01 (SEQ ID NO:79) amplified by Primer067_01F (SEQ ID NO:77) and Primer06701R (SEQ ID NO:78) in the cDNA pattern [1].

Example 8

Cluster chrX-900 (Data Set: 122)

(1) Cluster Analysis
1) Cluster Characteristics

An analysis was performed on 7 full-length cDNAs subjected to genome mapping onto the cluster chrX-900 (Human genome UCSC hg18 (NCBI Build34) chromosome X, 43,380,000 by to 43,500,000 bp) [D-NT2RI2014164.1, D-BRAMY2029564.1, D-BRAMY2029564.1, BC022494.1, ENST00000265833, M69177.1, NM_000898.3]. They were classified according to expression pattern difference into 4 kinds, which mainly included the following 3 kinds.
[1] D-NT2RI2014164.1
[2] D-BRAMY2029564.1
[3] BC022494.1, ENST00000265833, M69177.1, NM_000898.3

[1] is a cDNA which was newly acquired and subjected to full-length cDNA sequence analysis by us, and had a different ORF from that of [3], which is registered with an existing public DB, because of the expression thereof from a chromosome region located downstream of the known [3].

[2] is a cDNA which was newly acquired and subjected to full-length cDNA sequence analysis by us, having a different ORF from that of the known [3] because of the insertion of an exon different from the other patterns in the ORF region [3].

It was found that the ORF regions present in the 3 kinds of cDNA patterns [1] to [3] cause expression starting at different transcription initiation points, from the same chromosome region, and have different splice patterns, such as exon insertions, resulting in alterations of the amino acid sequences to produce diverse proteins and mRNAs.

2) Characteristics of D-NT2RI2014164.1 ([1]), which was Newly Acquired and Subjected to Full-Length cDNA Sequence Analysis by Us 122_[1]_1-N0 (SEQ ID NO:87): The entire nucleic acid sequence region of D-NT2RI2014164.1

122_[1]_1-NA0 (SEQ ID NO:88): Both the entire nucleic acid sequence region and amino acid sequence of D-NT2RI2014164.1

122_[1]_1-A0 (SEQ ID NO:89): The entire amino acid sequence region of D-NT2RI2014164.1

The sequence at the 1st to 156th bases of D-NT2RI2014164.1 (SEQ ID NO:90) is an exon that is not present in NM_000898.3, which is registered with an existing public DB, and serves for control, lacking homology to NM_000898.3. With this change, the translation initiation point of D-NT2RI2014164.1 shifts toward the 3' side relative to NM_000898.3, and the 162nd base of D-NT2RI2014164.1 becomes the translation initiation point. For this reason, the amino acid sequence shortened by 16 residues, compared with NM_000898.3 (SEQ ID NO:266).

The 98-base exon present at the 1,274th to 1,371st bases of NM_000898.3 (SEQ ID NO:95) is lacked and not present in the region at the 1,250th to 1,251st bases of D-NT2RI2014164.1 (SEQ ID NO:92).

With this change, because of a translation frame change to cause the termination of the ORF at a stop codon different from that of NM_000898.3, the C-terminal amino acids differed by 48 residues, compared with NM_000898.3 (SEQ ID NO:93).

122_[1]_1-N1 (SEQ ID NO:90): A 156-base insert nucleic acid sequence region of D-NT2RI2014164.1

122_[1]_1-N2 (SEQ ID NO:91): A 161-base 5'UTR region of an ORF whose translation initiation point is the 162nd base of D-NT2RI2014164.1

122_[1]_1-N3 (SEQ ID NO:92): A deletion nucleic acid sequence region of D-NT2RI2014164.1

122_[1]_1-A1 (SEQ ID NO:93): Amino acid sequence region

122_[1]_1-N4 altered as a result of deletion of D-NT2RI2014164.1 (identical to SEQ ID NO:92): an ORF nucleic acid region in the deletion region of D-NT2RI2014164.1

122_[1]_1-A2 (SEQ ID NO:94): An ORF amino acid sequence region related to the deletion region of D-NT2RI2014164.1

122_[1]_C-N1 (SEQ ID NO:95): A 98-base exon nucleic acid sequence present at the 1,274th to 1,371th bases of NM_000898.3 inserted into the region at the 1,250th to 1,251st bases of D-NT2RI2014164.1

122_[1]_C-A1 (SEQ ID NO:96): A 33-residue amino acid sequence related to the 98-base exon nucleic acid sequence present at the 1,274th to 1,371st bases of NM_000898.3 inserted into the region at the 1,250th to 1,251st bases of D-NT2RI2014164.1

122_[1]_C-A2 (SEQ ID NO:266): A 16-residue deletion amino acid sequence region of D-NT2RI2014164.1 present in NM_000898.3

3) Characteristics of D-BRAMY2029564.1 ([2]), which was Newly Acquired and Subjected to Full-Length cDNA Sequence Analysis by Us 122_[2]_1-N0 (SEQ ID NO:97): The entire nucleic acid sequence region of D-BRAMY2029564.1

122_[2]_1-NA0 (SEQ ID NO:98): Both the entire nucleic acid sequence region and amino acid sequence of D-BRAMY2029564.1

122_[2]_1-A0 (SEQ ID NO:99): The entire amino acid sequence region of D-BRAMY2029564.1

The 90th to 140th bases of D-BRAMY2029564.1 (SEQ ID NO:100) is an exon that is not present in NM_000898.3, which is registered with an existing public DB, and serves for control, lacking homology to NM_000898.3. With this change, the translation initiation point of D-BRAMY2029564.1 shifts toward the 3' side, compared with NM_000898.3, and the 143rd base of D-BRAMY2029564.1 becomes a translation initiation point. For this reason, the amino acid sequence shortened by 16 residues, compared with NM_000898.3 (identical to SEQ ID NO:266).

122_[2]_1-N1 (SEQ ID NO:100): A 43-base insert nucleic acid sequence region of D-BRAMY2029564.1

122_[2]_1-N2 (SEQ ID NO:101): A 142-base 5'UTR region of an ORF whose translation initiation point is the 143rd base of D-BRAMY2029564.1

122_[2]_C-A1 (identical to SEQ ID NO:266): A 16-residue deletion amino acid sequence region of D-BRAMY2029564.1 present in NM_000898.3

4) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

122_01—A specific region present on the N-terminal side of the cDNA pattern [1]: a translation initiation region of the cDNA pattern [1], which was newly subjected to full-length cDNA sequence analysis by us, being a novel region not registered with an existing public DB
→Fragment 122_01 (SEQ ID NO:104) amplified by Primer122_01F (SEQ ID NO:102) and Primer122_01R (SEQ ID NO:103)

122_02—A region specifically extracted by means of the sequence information on regions of the exon insertion of cDNA pattern [2]: an ORF-altering exon insert region in the cDNA pattern [2], which was newly subjected to full-length cDNA sequence analysis by us
→Fragment 122_02 (SEQ ID NO:107) amplified by Primer122_02F (SEQ ID NO:105) and Primer122_02R (SEQ ID NO:106)

122_03—A transcription initiation point region of [3], which is registered with an existing public DB, serving as a control for comparing [1] and [2]
→Fragment 122_03 (SEQ ID NO:110) amplified by Primer122_03F (SEQ ID NO:108) and Primer122_03R (SEQ ID NO:109)

122_04—A common region shared by all of [1] to [3]: a region common to all patterns, serving for control to compare the overall expression levels of the cDNA patterns [1] and [2], which were newly subjected to full-length cDNA sequence analysis by us, and the cDNA pattern [3], which is registered with an existing public DB
→Fragment 122_04 (SEQ ID NO:113) amplified by Primer122_04F (SEQ ID NO:111) and Primer122_04R (SEQ ID NO:112)

By mapping the 5'-terminal sequences of about 1.44 million sequences acquired using the oligocap method onto the human genome sequence, and comparatively analyzing them, the exon regions specific to the cDNA patterns [1] to [3] shown above, respectively, were found to be expressed at the following frequencies.

In the cDNA pattern [1], which was newly acquired and analyzed by us, four 5'-terminal sequences were present, the derivations thereof being NT2 cells treated with retinoic acid (RA) and treated with a growth inhibitor to induce nerve differentiation, followed by nerve concentration and recovery (NT2NE) for 2 sequences (analytical parameter 16,337), and NT2 cells treated with retinoic acid (RA) to induce differentiation for 5 weeks, and thereafter treated with a growth inhibitor for 2 weeks (NT2RI) for 2 sequences (analytical parameter 32,662).

In the cDNA pattern [2], which was newly acquired and analyzed by us, two 5'-terminal sequences were present, the derivation thereof being Brain, amygdala for the 2 sequences (analytical parameter 58,640).

In the cDNA pattern [3], which is registered with an existing public DB, fifty-nine 5'-terminal sequences were present, the derivations thereof being Uterus for 11 sequence (analytical parameter 49,561), brain tissues for 19 sequences, and a variety of other tissues for the other sequences.

From this result, it was found that the transcription initiation point of [1] was abundantly expressed in differentiated NT2 cells. It was also found that the exon insertion pattern [2] was abundantly expressed in the brain. The transcription initiation point of [3] was expressed in various tissues. Hence, it was thought that the mechanism of transcription or splice pattern in this chromosome region might be unique to particular tissues such as the brain and nerve cells after differentiation, to alter amino acids, with a selection mechanism arising for mRNA pattern changes resulting in the expression of different proteins.

(2) Analysis of Expression Specificity by Real-Time PCR

To detect protein expression diversity changes due to transcription initiation point or exon selectivity among different tissues, details of expression levels were analyzed by real-time PCR. The results are shown in Table 10 and Table 11.

TABLE 10

|  | RQ Score | | | | $Log_{10}$RQ Score | | | |
| --- | --- | --- | --- | --- | --- | --- | --- | --- |
|  | 122_01 | 122_02 | 122_03 | 122_04 | 122_01 | 122_02 | 122_03 | 122_04 |
| 01 NT2RA(−) | 0.0 | 0.0 | 0.0 | 0.0 | −1.89 | −1.37 | −1.82 | −1.89 |
| 02 NT2RA(+) 24 hr | 0.3 | 0.1 | 0.0 | 0.0 | −0.59 | −0.99 | −2.55 | −2.85 |
| 03 NT2RA(+) 48 hr | 1.3 | 0.6 | 0.0 | 0.0 | 0.11 | −0.25 | −2.28 | −2.58 |
| 04 NT2RA(+) 1 week | 3.4 | 1.3 | 0.1 | 0.0 | 0.54 | 0.10 | −1.16 | −1.65 |
| 05 NT2RA(+) 5 weeks | 0.3 | 0.2 | 0.1 | 0.1 | −0.51 | −0.72 | −1.00 | −1.09 |
| 06 NT2RA(+) 5 weeks, Inh(+) | 0.5 | 0.3 | 0.2 | 0.2 | −0.28 | −0.59 | −0.61 | −0.69 |
| 07 NT2 Neuron | 5.1 | 0.6 | 0.0 | 0.0 | 0.71 | −0.19 | −1.34 | −2.21 |
| 08 Brain, Fetal | 0.6 | 1.7 | 0.4 | 0.2 | −0.19 | 0.22 | −0.43 | −0.73 |
| 09 Brain, whole | 2.3 | 13.4 | 1.1 | 0.5 | 0.36 | 1.13 | 0.02 | −0.26 |
| 10 ALZ Visual Cortex Occipital | 1.0 | 6.5 | 0.9 | 0.4 | −0.01 | 0.82 | −0.07 | −0.42 |
| 11 Mix, viscus tissues | 1.0 | 1.0 | 1.0 | 1.0 | 0.0 | 0.0 | 0.0 | 0.0 |
| 12 Mix, blood cells and related tissues | 1.1 | 2.1 | 1.1 | 0.7 | 0.06 | 0.33 | 0.03 | −0.13 |
| 13 Mix, tumor tissues | 0.5 | 0.2 | 0.2 | 0.3 | −0.33 | −0.61 | −0.67 | −0.53 |
| 14 Mix, normal tissues | 3.7 | 4.6 | 1.7 | 1.3 | 0.57 | 0.67 | 0.23 | 0.12 |
| 15 Brain, whole PolyA(+) RNA | 0.3 | 7.2 | 0.7 | 0.3 | −0.48 | 0.86 | −0.17 | −0.48 |
| 16 Brain, hippocampus | 0.4 | 4.6 | 0.9 | 0.5 | −0.44 | 0.66 | −0.05 | −0.35 |

TABLE 10-continued

|  | RQ Score | | | | Log₁₀RQ Score | | | |
| --- | --- | --- | --- | --- | --- | --- | --- | --- |
|  | 122_01 | 122_02 | 122_03 | 122_04 | 122_01 | 122_02 | 122_03 | 122_04 |
| 17 Brain, cerebellum | 0.2 | 2.9 | 0.5 | 0.2 | −0.81 | 0.47 | −0.31 | −0.68 |
| 18 Brain, amygdala | 0.5 | 4.2 | 1.0 | 0.5 | −0.32 | 0.62 | 0.00 | −0.29 |
| 19 Brain, caudate nucleus | 0.4 | 4.5 | 0.9 | 0.7 | −0.35 | 0.66 | −0.06 | −0.17 |
| 20 Brain, corpus callosum | 0.2 | 0.6 | 1.1 | 0.6 | −0.64 | −0.20 | 0.05 | −0.19 |
| 21 Brain, substantia nigra | 0.4 | 2.2 | 1.1 | 0.6 | −0.44 | 0.35 | 0.02 | −0.23 |
| 22 Brain, thalamus | 0.2 | 4.0 | 0.6 | 0.3 | −0.76 | 0.60 | −0.23 | −0.48 |
| 23 Brain, subthalamic nucleus | 0.1 | 0.8 | 0.8 | 0.4 | −1.12 | −0.09 | −0.07 | −0.43 |

TABLE 11

|  | RQ Score | | | | Log₁₀RQ Score | | | |
| --- | --- | --- | --- | --- | --- | --- | --- | --- |
|  | 122_01 | 122_02 | 122_03 | 122_04 | 122_01 | 122_02 | 122_03 | 122_04 |
| 01 NT2RA(−) | 0.0 | 0.0 | 0.0 | 0.0 | −1.68 | −1.42 | −1.85 | −1.83 |
| 02 NT2RA(+) 24 hr | 0.8 | 0.2 | 0.0 | 0.0 | −0.08 | −0.82 | −2.32 | −2.79 |
| 03 NT2RA(+) 48 hr | 3.4 | 0.7 | 0.0 | 0.0 | 0.54 | −0.15 | −2.32 | −2.70 |
| 04 NT2RA(+) 1 week | 8.5 | 2.3 | 0.1 | 0.0 | 0.93 | 0.36 | −1.23 | −1.65 |
| 05 NT2RA(+) 5 weeks | 0.8 | 0.3 | 0.1 | 0.1 | −0.11 | −0.52 | −0.98 | −1.15 |
| 06 NT2RA(+) 5 weeks, Inh(+) | 1.4 | 0.5 | 0.3 | 0.2 | 0.16 | −0.32 | −0.55 | −0.62 |
| 07 NT2 Neuron | 14.1 | 0.7 | 0.0 | 0.0 | 1.15 | −0.18 | −1.36 | −2.21 |
| 08 Brain, Fetal | 1.6 | 2.7 | 0.4 | 0.2 | 0.21 | 0.43 | −0.45 | −0.75 |
| 09 Brain, whole | 7.5 | 19.4 | 1.4 | 0.6 | 0.87 | 1.29 | 0.13 | −0.21 |
| 10 ALZ Visual Cortex Occipital | 3.0 | 10.9 | 1.0 | 0.4 | 0.48 | 1.04 | −0.02 | −0.40 |
| 11 Mix, viscus tissues | 1.0 | 1.0 | 1.0 | 1.0 | 0.0 | 0.0 | 0.0 | 0.0 |
| 12 Mix, blood cells and related tissues | 1.3 | 4.0 | 1.0 | 0.4 | 0.11 | 0.60 | 0.01 | −0.42 |
| 13 Mix, tumor tissues | 1.2 | 0.5 | 0.2 | 0.2 | 0.08 | −0.34 | −0.64 | −0.74 |
| 14 Mix, normal tissues | 5.0 | 11.8 | 2.0 | 1.8 | 0.70 | 1.07 | 0.30 | 0.25 |
| 15 Brain, whole PolyA(+) RNA | 1.1 | 12.0 | 0.7 | 0.4 | 0.04 | 1.08 | −0.13 | −0.45 |
| 16 Brain, hippocampus | 1.2 | 8.0 | 1.0 | 0.5 | 0.06 | 0.90 | −0.01 | −0.30 |
| 17 Brain, cerebellum | 0.4 | 4.0 | 0.5 | 0.2 | −0.43 | 0.60 | −0.30 | −0.69 |
| 18 Brain, amygdala | 0.9 | 5.6 | 0.9 | 0.5 | −0.03 | 0.75 | −0.03 | −0.31 |
| 19 Brain, caudate nucleus | 1.1 | 6.6 | 1.1 | 0.5 | 0.03 | 0.82 | 0.05 | −0.27 |
| 20 Brain, corpus callosum | 0.5 | 1.1 | 1.1 | 0.6 | −0.26 | 0.04 | 0.04 | −0.21 |
| 21 Brain, substantia nigra | 0.8 | 2.6 | 0.7 | 0.4 | −0.10 | 0.41 | −0.19 | −0.39 |
| 22 Brain, thalamus | 0.4 | 5.2 | 0.5 | 0.3 | −0.35 | 0.72 | −0.32 | −0.58 |
| 23 Brain, subthalamic nucleus | 0.2 | 0.9 | 0.6 | 0.3 | −0.77 | −0.06 | −0.25 | −0.57 |

Expression levels were compared using the 23 kinds of samples shown in Example 3, including 11 kinds of brain tissues and NT2 cells at 7 different differentiation stages. The comparison was made using the mixed sample of normal visceral tissues shown in Example 3 (Mix, viscus tissues) as an experimental control.

The ratio of ORF alteration due to transcription initiation point selectivity and exon selectivity as compared among 122_01 (SEQ ID NO:104), 122_02 (SEQ ID NO:107) and 122_03 (SEQ ID NO:110) changed greatly among the following differentiation stages of the brain and NT2 cells.

In all portions of the brain, the expression in the pattern of insertion of the exon shown by 122_02 (SEQ ID NO:107) was more abundant than 122_03 (SEQ ID NO:110) (Table 10 and Table 11).

For the downstream transcription initiation point shown by 122_01 (SEQ ID NO:104), it was found that the expression level varied greatly among the differentiation stages of NT2 cells. When compared in detail with respect to NT2 cell differentiation, it was found that the expression level of the pattern with an insertion was the same as that of the pattern without an insertion at the stage of undifferentiated NT2 cells NT2RA (−); however, in initial stages of differentiation such as NT2RA (+) 24 hr, NT2RA (+) 48 hr, and NT2RA (+) 1 week, which represent the initial stage in which retinoic acid was added to induce differentiation, the ratio of selection of the downstream transcription initiation point increased greatly, the difference being smaller in the late stage of differentiation (Table 10 and Table 11).

These results demonstrated that by comparing the expression of the 5'-terminal region of a newly acquired cDNA shown by the detection region 122_01 (SEQ ID NO:104) (a region close to the transcription initiation point), 122_[1]-N1 (SEQ ID NO:90), or the expression of a newly acquired cDNA region 122_[2]-N1 (SEQ ID NO:100), shown by the detection region 122_02 (SEQ ID NO:107), it is possible to use these regions as differentiation markers for detecting cells in nerve cell differentiation or regeneration stages, particularly those in an early stage of differentiation into nerve cells. It also seems possible to develop a new drug by means of a compound, antibody, siRNA or the like that targets a region that exhibits specificity.

The following regions also seem to be useful as differentiation markers for detecting nerve cell differentiation or regeneration stages, particularly initial stages of differentiation into nerve cells.

Upstream sequence 031_[1]_1-N3 (SEQ ID NO:114), which comprises the 138th to 162nd bases undergoing priming by Primer122_01R (SEQ ID NO:103) in D-NT2RI2014164.1 of the cDNA pattern [1]. Upstream sequence 031_[1]_1-N3 (SEQ ID NO:115), which comprises the 177th to 198th bases undergoing priming by Primer122_02R (SEQ ID NO:106) in D-BRAMY2029564.1 of the cDNA pattern [2].

Region 122_01 (SEQ ID NO:104) amplified by Primer122_01F (SEQ ID NO:102) and Primer122_01R (SEQ ID NO:103) in the cDNA pattern [1].

Region 122_02 (SEQ ID NO:107) amplified by Primer122_02F (SEQ ID NO:105) and Primer122_02R (SEQ ID NO:106) in the cDNA pattern [2].

Example 9

Cluster chr8-916 (Data Set: 124)

(1) Cluster Analysis
1) Cluster Characteristics

An analysis was performed on 10 sequences of full-length cDNAs subjected to genome mapping onto the cluster chr8-916 (Human genome UCSC hg18 (NCBI Build34) chromosome 8, 81,100,000 by to 81,325,000 bp) [D-BRHIP2003515.1, D-COLON2003937.1, Z-BRCOC2013886-01, BC018117.1, BX640835.1, C-SMINT1000078, ENST00000263850, NM_005079.1, U18914.1, XM_374275.1]. They were classified according to expression pattern difference into 4 kinds, which mainly included the following 2 kinds.
[1] D-BRHIP2003515.1
[2] BC018117.1, NM_005079.1, U18914.1

[1] is a cDNA newly acquired and subjected to full-length cDNA sequence analysis by us, and having a different ORF from [2], which had been registered with an existing public DB.

[1], compared with the known [2], had a different ORF region because of amino acid sequence alteration due to the insertion of an exon different from other patterns in the ORF region.

It was found that the ORF regions present in the 2 kinds of cDNA patterns [1] to [2] have different splice patterns, from the same chromosome region, resulting in alterations of the amino acid sequences to produce diverse proteins and mRNAs.

2) Characteristics of D-BRHIP2003515.1 ([1]), which was Newly Acquired and Subjected to Full-Length cDNA Sequence Analysis by Us 124_[1]_1-N0 (SEQ ID NO:116): The entire nucleic acid sequence region of D-BRHIP2003515.1
124_[1]_1-NA0 (SEQ ID NO:117): Both the entire nucleic acid sequence region and amino acid sequence of D-BRHIP2003515.1
124_[1]_1-A0 (SEQ ID NO:118): The entire amino acid sequence region of D-BRHIP2003515.1

The sequence at the 471st to 539th bases of D-BRHIP2003515.1 (SEQ ID NO:119) is a variant incorporating an exon that is not present in NM_005079.1, which is registered with an existing public DB, and serves for control. The translation initiation point and translation termination point of D-BRHIP2003515.1 are the same as those of NM_005079.1; however, because of the insertion of a 69-base exon into D-BRHIP2003515.1, the amino acid length increased by 23 residues, compared with NM_005079.1 (SEQ ID NO:120).

124_[1]_1-N1 (SEQ ID NO:119): A 69-base insert nucleic acid sequence region of D-BRHIP2003515.1
124_[1]_1-A 1 (SEQ ID NO:120): A 23-residue insert amino acid sequence region of D-BRHIP2003515.1
124_[1]_1-N 2 (identical to SEQ ID NO:119): An ORF nucleic acid sequence region in the 69-base insert region of D-BRHIP2003515.1
124_[1]_1-A 2 (identical to SEQ ID NO:120): An ORF amino acid region related to the 69-base insert region of D-BRHIP2003515.1

3) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

124_04—A region specifically extracted by means of the sequence information at the border of a region having an exon inserted therein in the cDNA pattern [1]: an insert region of an ORF altering exon in the cDNA pattern [1], which was newly subjected to full-length cDNA sequence analysis by us
→Fragment 124_04 (SEQ ID NO:123) amplified by Primer124_04F (SEQ ID NO:121) and Primer12404R (SEQ ID NO:122)

124_05—A specific region corresponding to a deletion region of the cDNA pattern [2], which is registered with an existing public DB, compared with the insertion region of [1], serving as a control for comparing [1]
→Fragment 124_05 (SEQ ID NO:126) amplified by Primer124_05F (SEQ ID NO:124) and Primer12405R (SEQ ID NO:125)

124_06—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB
→Fragment 124_06 (SEQ ID NO:129) amplified by Primer124_06F (SEQ ID NO:127) and Primer12406R (SEQ ID NO:128)

By mapping the 5'-terminal sequences of about 1.44 million sequences acquired using the oligocap method onto the human genome sequence, and comparatively analyzing them, the exon regions specific to the cDNA patterns [1] to [2] shown above, respectively, were found to be expressed at the following frequencies.

In the cDNA pattern [1], which was newly acquired and analyzed by us, twenty-one 5'-terminal sequences were present, the derivations thereof being brain tissues such as Brain, amygdala, Brain, cerebellum, and Brain, hippocampus for 18 sequences and Kidney, Tumor for 3 sequences.

In the cDNA pattern [2], which is registered with an existing public DB, fifty-one 5'-terminal sequences were present, the derivations thereof being brain tissues such as Brain, substantia nigra, Brain, hippocampus, Brain, amygdala, and Brain, corpus callosum for 17 sequences, tumor tissues such as Tongue, Tumor, and Kidney, Tumor for 9 sequences, and other normal tissues such as Lung, Small Intestine, and Trachea for 25 sequences.

From this result, it was found that the exon insertion pattern [1] was abundantly expressed in the brain. It was also found that the exon deletion pattern [2] was expressed not only in the brain, but also in other various tissues. Hence, it was thought that the mechanism for amino acid alteration due to exon insertion in this chromosome region to cause the expression of different proteins, as with the pattern [1], might be unique to particular tissues.

(2) Analysis of Expression Specificity by Real-Time PCR

To detect protein expression diversity changes due to exon selectivity among different tissues, details of expression levels were analyzed by real-time PCR. The results are shown in Table 12 and Table 13.

TABLE 12

|  | RQ Score | | | $Log_{10}$RQ Score | | |
| --- | --- | --- | --- | --- | --- | --- |
|  | 124_04 | 124_05 | 124_06 | 124_04 | 124_05 | 124_06 |
| 01 NT2RA(−) | 0.1 | 0.1 | 0.1 | −1.28 | −1.07 | −1.06 |
| 02 NT2RA(+) 24 hr | 0.2 | 0.1 | 0.1 | −0.74 | −1.21 | −1.22 |
| 03 NT2RA(+) 48 hr | 0.0 | 0.1 | 0.1 | −1.47 | −1.25 | −1.27 |
| 04 NT2RA(+) 1 week | 0.1 | 0.0 | 0.0 | −0.83 | −1.58 | −1.60 |
| 05 NT2RA(+) 5 weeks | 8.6 | 0.0 | 0.1 | 0.93 | −1.32 | −1.07 |
| 06 NT2RA(+) 5 weeks, Inh(+) | 4.7 | 0.1 | 0.1 | 0.67 | −1.15 | −1.03 |
| 07 NT2 Neuron | 1.1 | 0.0 | 0.0 | 0.04 | −2.08 | −1.79 |
| 08 Brain, Fetal | 148.6 | 0.0 | 0.4 | 2.17 | −1.59 | −0.38 |
| 09 Brain, whole | 465.6 | 0.3 | 2.1 | 2.67 | −0.47 | 0.32 |
| 10 ALZ Visual Cortex Occipital | 286.6 | 0.3 | 1.1 | 2.46 | −0.49 | 0.05 |
| 11 Mix, viscus tissues | 1.0 | 1.0 | 1.0 | 0.0 | 0.0 | 0.0 |
| 12 Mix, blood cells and related tissues | 14.6 | 0.5 | 0.6 | 1.16 | −0.34 | −0.26 |
| 13 Mix, tumor tissues | 0.4 | 0.9 | 0.8 | −0.40 | −0.04 | −0.09 |
| 14 Mix, normal tissues | 1.0 | 0.9 | 0.8 | −0.01 | −0.06 | −0.10 |
| 15 Brain, whole PolyA(+) RNA | 190.4 | 0.3 | 1.3 | 2.28 | −0.54 | 0.12 |
| 16 Brain, hippocampus | 189.2 | 0.3 | 1.1 | 2.28 | −0.50 | 0.06 |
| 17 Brain, cerebellum | 247.5 | 0.1 | 1.6 | 2.39 | −0.84 | 0.21 |
| 18 Brain, amygdala | 191.9 | 0.2 | 0.9 | 2.28 | −0.74 | −0.03 |
| 19 Brain, caudate nucleus | 134.8 | 0.4 | 0.9 | 2.13 | −0.45 | −0.05 |
| 20 Brain, corpus callosum | 25.0 | 1.1 | 1.2 | 1.40 | 0.03 | 0.09 |
| 21 Brain, substantia nigra | 70.3 | 0.5 | 0.9 | 1.85 | −0.29 | −0.06 |
| 22 Brain, thalamus | 194.7 | 0.3 | 1.0 | 2.29 | −0.57 | 0.01 |
| 23 Brain, subthalamic nucleus | 22.2 | 0.6 | 0.6 | 1.35 | −0.25 | −0.25 |

TABLE 13

|  | RQ Score | | | $Log_{10}$RQ Score | | |
| --- | --- | --- | --- | --- | --- | --- |
|  | 124_04 | 124_05 | 124_06 | 124_04 | 124_05 | 124_06 |
| 01 NT2RA(−) | 0.2 | 0.1 | 0.1 | −0.72 | −1.19 | −0.99 |
| 02 NT2RA(+) 24 hr | 1.0 | 0.1 | 0.1 | −0.02 | −1.19 | −1.14 |
| 03 NT2RA(+) 48 hr | 0.3 | 0.1 | 0.1 | −0.48 | −1.24 | −1.14 |
| 04 NT2RA(+) 1 week | 0.7 | 0.0 | 0.0 | −0.17 | −1.56 | −1.47 |
| 05 NT2RA(+) 5 weeks | 41.4 | 0.0 | 0.1 | 1.62 | −1.33 | −0.97 |
| 06 NT2RA(+) 5 weeks, Inh(+) | 30.7 | 0.1 | 0.1 | 1.49 | −1.09 | −0.89 |
| 07 NT2 Neuron | 6.2 | 0.0 | 0.0 | 0.79 | −1.95 | −1.59 |
| 08 Brain, Fetal | 839.9 | 0.0 | 0.5 | 2.92 | −1.62 | −0.27 |
| 09 Brain, whole | 3655.9 | 0.3 | 2.6 | 3.56 | −0.50 | 0.41 |
| 10 ALZ Visual Cortex Occipital | 1899.0 | 0.3 | 1.6 | 3.28 | −0.46 | 0.19 |
| 11 Mix, viscus tissues | 1.0 | 1.0 | 1.0 | 0.0 | 0.0 | 0.0 |
| 12 Mix, blood cells and related tissues | 100.9 | 0.5 | 0.7 | 2.00 | −0.28 | −0.17 |
| 13 Mix, tumor tissues | 1.9 | 0.8 | 0.9 | 0.28 | −0.11 | −0.05 |
| 14 Mix, normal tissues | 8.9 | 0.7 | 1.2 | 0.95 | −0.16 | 0.08 |
| 15 Brain, whole PolyA(+) RNA | 1539.2 | 0.3 | 1.7 | 3.19 | −0.55 | 0.22 |
| 16 Brain, hippocampus | 1524.4 | 0.3 | 1.5 | 3.18 | −0.48 | 0.16 |
| 17 Brain, cerebellum | 2130.5 | 0.2 | 2.3 | 3.33 | −0.80 | 0.36 |
| 18 Brain, amygdala | 1379.6 | 0.2 | 1.2 | 3.14 | −0.75 | 0.09 |
| 19 Brain, caudate nucleus | 804.0 | 0.4 | 1.1 | 2.91 | −0.45 | 0.04 |
| 20 Brain, corpus callosum | 163.7 | 1.1 | 1.4 | 2.21 | 0.04 | 0.16 |
| 21 Brain, substantia nigra | 386.9 | 0.5 | 1.1 | 2.59 | −0.32 | 0.04 |
| 22 Brain, thalamus | 1285.4 | 0.3 | 1.3 | 3.11 | −0.59 | 0.10 |
| 23 Brain, subthalamic nucleus | 181.6 | 0.6 | 0.8 | 2.26 | −0.26 | −0.11 |

Expression levels were compared using the 23 kinds of samples shown in Example 3, including 11 kinds of brain tissues and NT2 cells at 7 different differentiation stages. The comparison was made using the mixed sample of normal visceral tissues shown in Example 3 (Mix, viscus tissues) as an experimental control.

The ratio of ORF alteration due to exon insertion/deletion selectivity as compared between 124_04 (SEQ ID NO:123) and 124_05 (SEQ ID NO:126) changed greatly among the following tissues and NT2 cell differentiation stages.

In all portions of the brain, the expression of the pattern for insertion of the exon shown by 124_04 (SEQ ID NO:123) was abundant (Table 12 and Table 13).

It was found that in NT2 cells, exon selectivity changed greatly depending on the stage of differentiation. When compared in detail with respect to NT2 cell differentiation, almost no difference was observed between the two patterns 124_04 (SEQ ID NO:123) and 124_05 (SEQ ID NO:126) in undifferentiated NT2 cells NT2RA (−) and NT2RA (+) 1 week, which represent the initial stage in which retinoic acid was added to NT2 cells to induce differentiation; however, in NT2RA (+) 5 weeks to NT2 Neuron, the expression of the pattern of insertion of the exon shown by 12404 (SEQ ID NO:123) was considerably abundant (Table 12 and Table 13).

These results demonstrated that by comparing the expression of the selective exon region 124_[1]_1-N1 (SEQ ID NO:119) of a newly acquired cDNA shown by the detection region 124_04 (SEQ ID NO:123), it is possible to use the exon region as a brain-specific marker, and as a differentiation marker for detecting cells in nerve cell differentiation or regeneration stages, particularly those after nerve differentiation or nerve regeneration. It also seems possible to develop a new drug by means of a compound, antibody, siRNA or the like that targets a region that exhibits specificity.

The following regions also seem to be useful as markers specific for the brain, and as differentiation markers for detecting nerve cells in differentiation or regeneration stages, particularly those after nerve differentiation or after nerve regeneration.

Upstream sequence 124_[1]_1-N3 (SEQ ID NO:130), which comprises the 472nd to 491st bases undergoing priming by Primer124_04R (SEQ ID NO:122) in D-BRHIP2003515.1 of the cDNA pattern [1]. Region 124_04 (SEQ ID NO:123) amplified by Primer124_04F (SEQ ID NO:121) and Primer12404R (SEQ ID NO:122) in the cDNA pattern [1]

Example 10

Cluster chr3+2014 (Data Set: 112)

(1) Cluster Analysis
1) Cluster Characteristics

An analysis was performed on 7 full-length cDNAs subjected to genome mapping onto the cluster chr3+2014 (Human genome UCSC hg18 (NCBI Build34) chromosome 3, 143,070,000 by to 143,130,000 bp) [D-BRACE2044661.1, BC011835.2, C-BRAMY2022929, C-PRS09188, ENST00000286371, NM_001679.2, U51478.1]. They were classified according to expression pattern difference into 4 kinds, which mainly included the following 2 kinds.
[1] D-BRACE2044661.1
[2] BC011835.2, ENST00000286371, NM_001679.2, U51478.1

[1] is a cDNA newly acquired and subjected to full-length cDNA sequence analysis by us, and having a different ORF from [2], which had been registered with an existing public DB.

[1], compared with the known [2], had a different ORF because of translation initiation point alteration due to the insertion of an exon different from other patterns in the ORF region.

It was found that the ORF regions present in the 2 kinds of cDNA patterns [1] to [2] have different splice patterns, from the same chromosome region, resulting in alterations of the amino acid sequences to produce diverse proteins and mRNAs.

2) Characteristics of D-BRACE2044661.1 ([1]), which was Newly Acquired and Subjected to Full-Length cDNA Sequence Analysis by Us
112_[1]_1-N0 (SEQ ID NO:131): The entire nucleic acid sequence region of D-BRACE2044661.1
112_[1]_1-NA0 (SEQ ID NO:132): Both the entire nucleic acid sequence region and amino acid sequence of D-BRACE2044661.1
112_[1]_1-A0 (SEQ ID NO:133): The entire amino acid sequence region of D-BRACE2044661.1

The 272nd to 363rd bases of D-BRACE2044661.1 (SEQ ID NO:134) is an exon that is not present in NM_001679.2, which is registered with an existing public DB, and serves for control, lacking homology to NM_001679.2. Because a translation initiation point is present on this exon, the amino acids on the N-terminal side changed by 23 residues (SEQ ID NO:135).

112_[1]_1-N1 (SEQ ID NO:134): A 92-base insert nucleic acid sequence region of D-BRACE2044661.1
112_[1]_1-A1 (SEQ ID NO:135): A 23-residue insert amino acid sequence region D-BRACE2044661.1
112_[1]_1-N2 (SEQ ID NO:136): An ORF nucleic acid sequence region in the 92-base insert region of D-BRACE2044661.1
112_[1]_1-A2 (identical to SEQ ID NO:135): An ORF amino acid sequence region in the 92-base insert region of D-BRACE2044661.1

The sequence at the 837th to 856th bases of D-BRACE2044661.1 (SEQ ID NO:137) is an exon that is not present in NM_001679.2, which is registered with an existing public DB, and serves for control, lacking homology to NM_001679.2. Because of a change in the translation frame by this insert sequence, the amino acids on the C-terminal side changed by 13 residues (SEQ ID NO:138).

112_[1]_1-N3 (SEQ ID NO:137): A 20-base insert nucleic acid sequence region of D-BRACE2044661.1
112_[1]_1-A3 (SEQ ID NO:138): A 13-residue insert amino acid sequence region of D-BRACE2044661.1
112_[1]_1-N4 (identical to SEQ ID NO:137): An ORF nucleic acid sequence region in the 20-base insert region of D-BRACE2044661.1
112_[1]_1-A4 (SEQ ID NO:139): An ORF amino acid sequence region in the 20-base insert region of D-BRACE2044661.1

3) Expression Specificity Analysis and Design of Primers for Real-Time PCR

To clearly distinguish between the characteristic regions shown above, and examine the respective expression levels thereof, the following regions were used as detection regions.

It seemed possible to compare the expression levels of the individual characteristic regions by comparing the expression levels of the detection regions.

112_01—A region incorporating an exon of the cDNA pattern [1], specifically extracted by means of the sequence information at the border: an ORF-altering exon insert region in the cDNA pattern [1], which was newly subjected to full-length cDNA sequence analysis by us
→Fragment 112_01 (SEQ ID NO:142) amplified by Primer112_01F (SEQ ID NO:140) and Primer112_01R (SEQ ID NO:141)

112_02—A specific region corresponding to a deletion region of the cDNA pattern [2], which is registered with an existing public DB, compared with the insert region of [1], serving as a control for comparatively examining [1]
→Fragment 112_02 (SEQ ID NO:145) amplified by Primer112_02F (SEQ ID NO:143) and Primer112_02R (SEQ ID NO:144)

112_03—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB
→Fragment 112_03 (SEQ ID NO:148) amplified by Primer112_03F (SEQ ID NO:146) and Primer112_03R (SEQ ID NO:147)

By mapping the 5'-terminal sequences of about 1.44 million sequences acquired using the oligocap method onto the human genome sequence, and comparatively analyzing them, the regions specific for the 2 kinds of cDNA patterns [1] to [2] shown above, respectively, were found to be expressed at the following frequencies.

In the cDNA pattern [1], which was newly acquired and analyzed by us, six 5'-terminal sequences were present, the derivations thereof being Brain, cerebellum for 3 sequences (analytical parameter 82,880), Brain, cortex, Alzheimer for 1 sequence (analytical parameter 16,360), Brain, amygdala for 1 sequence (analytical parameter 58,640), and tissues rich in head portion from 10-week-gestional fetal human (whole embryo, mainly head) for 1 sequence (analytical parameter 7,033).

In the cDNA pattern [2], which is registered with an existing public DB, twenty-four 5'-terminal sequences were present, the derivations thereof being Placenta for 4 sequences (analytical parameter 46,090), NT2 cells treated with retinoic acid (RA) to induce differentiation (NT2RP) for 3 sequences (analytical parameter 39,242), Tongue, Tumor for 2 sequences (analytical parameter 31,371), IMR32 cells (Neuroblastoma) for 2 sequences (analytical parameter 16964), NT2 cells treated with retinoic acid and a growth inhibitor to induce nerve differentiation, followed by nerve concentration and recovery (NT2NE) for 2 sequences (analytical parameter 16,337) and the like; this pattern was expressed in various tissues.

From this result, it was found that the exon insertion pattern [1] was abundantly expressed in the brain. It was also found that the exon deletion pattern [2] was expressed not only in the brain, but also in other various tissues. Hence, it was thought that the selection mechanism for mRNA pattern change in this chromosome region, which alters N-terminal amino acids and results in the expression of different proteins because of exon insertion as with the pattern [1], might be unique to particular tissues.

(2) Analysis of Expression Specificity by Real-Time PCR

To detect protein expression diversity changes due to exon selectivity among different tissues, details of expression levels were analyzed by real-time PCR. The results are shown in Table 14.

TABLE 14

|  | RQ Score | | | $Log_{10}$RQ Score | | |
| --- | --- | --- | --- | --- | --- | --- |
|  | 112_01 | 112_02 | 112_03 | 112_01 | 112_02 | 112_03 |
| 01 NT2RA(−) | 0.4 | 0.5 | 1.2 | −0.35 | −0.26 | 0.09 |
| 02 NT2RA(+) 24 hr | 0.5 | 0.3 | 0.5 | −0.33 | −0.48 | −0.33 |
| 03 NT2RA(+) 48 hr | 0.4 | 0.5 | 0.6 | −0.41 | −0.32 | −0.22 |
| 04 NT2RA(+) 1 week | 0.2 | 0.5 | 0.6 | −0.74 | −0.32 | −0.21 |
| 05 NT2RA(+) 5 weeks | 2.0 | 0.9 | 2.0 | 0.29 | −0.03 | 0.31 |
| 06 NT2RA(+) 5 weeks, Inh(+) | 4.1 | 0.8 | 1.5 | 0.62 | −0.12 | 0.18 |
| 07 NT2 Neuron | 7.6 | 0.9 | 1.3 | 0.88 | −0.03 | 0.11 |
| 08 Brain, Fetal | 23.3 | 1.2 | 2.3 | 1.37 | 0.08 | 0.36 |
| 09 Brain, whole | 158.2 | 0.6 | 1.8 | 2.20 | −0.21 | 0.26 |
| 10 ALZ Visual Cortex Occipital | 109.3 | 0.3 | 1.2 | 2.04 | −0.55 | 0.08 |
| 11 Mix, viscus tissues | 1.0 | 1.0 | 1.0 | 0.0 | 0.0 | 0.0 |
| 12 Mix, blood cells and related tissues | 10.1 | 0.8 | 1.2 | 1.00 | −0.12 | 0.07 |
| 13 Mix, tumor tissues | 0.9 | 1.6 | 1.2 | −0.03 | 0.22 | 0.06 |
| 14 Mix, normal tissues | 2.4 | 1.3 | 1.6 | 0.37 | 0.10 | 0.20 |
| 15 Brain, whole PolyA(+) RNA | 114.0 | 0.3 | 0.9 | 2.06 | −0.56 | −0.03 |
| 16 Brain, hippocampus | 56.4 | 0.3 | 0.7 | 1.75 | −0.55 | −0.15 |
| 17 Brain, cerebellum | 149.9 | 0.6 | 1.6 | 2.18 | −0.20 | 0.21 |
| 18 Brain, amygdala | 47.5 | 0.3 | 0.9 | 1.68 | −0.47 | −0.06 |
| 19 Brain, caudate nucleus | 47.9 | 0.3 | 0.8 | 1.68 | −0.59 | −0.11 |
| 20 Brain, corpus callosum | 8.7 | 0.3 | 0.6 | 0.94 | −0.53 | −0.19 |
| 21 Brain, substantia nigra | 56.7 | 0.4 | 1.0 | 1.75 | −0.37 | 0.01 |
| 22 Brain, thalamus | 124.0 | 0.3 | 1.2 | 2.09 | −0.60 | 0.07 |
| 23 Brain, subthalamic nucleus | 26.1 | 0.4 | 0.7 | 1.42 | −0.37 | −0.16 |

Expression levels were compared using the 23 kinds of samples shown in Example 3, including 11 kinds of brain tissues and NT2 cells at 7 different differentiation stages. The comparison was made using the mixed sample of normal visceral tissues shown in Example 3 (Mix, viscus tissues) as an experimental control.

The ratio of ORF alteration due to exon insertion/deletion selectivity as compared between 112_01 (SEQ ID NO:142) and 112_02 (SEQ ID NO:145) changed greatly among the following brain portions and NT2 cell differentiation stages.

In the brain, particularly in Brain, cerebellum, Brain, hippocampus, Brain, amygdala, Brain, caudate nucleus, Brain, substantia nigra, and Brain, thalamus, the pattern of insertion of the exon shown by 112_01 (SEQ ID NO:142) was abundantly observed (Table 14).

It was also found that in NT2 cells, exon selectivity varied greatly depending on the stage of differentiation. When compared in detail with respect to NT2 cell differentiation, the expression of the exon deletion pattern shown by 112_02 (SEQ ID NO:145), which is registered with an existing public DB was more abundant in undifferentiated NT2 cells NT2RA (−) and NT2RA (+) 48 hr, NT2RA (+) 1 week, which represents the initial stage in which retinoic acid was added to induce differentiation; however, in NT2RA (+) 5 weeks, which is predicted to be rich in nerve cells after differentiation, the expression level reversed; even in NT2RA (+) 5 weeks, Inh (+) and NT2 Neuron, the expression of the exon insertion pattern shown by 112_01 (SEQ ID NO:142) was abundantly observed (Table 14).

These results demonstrated that by comparing the expression of the selective exon region 112_[1]-N1 (SEQ ID NO:134) of a newly acquired cDNA shown by the detection region 112_01 (SEQ ID NO:142), it is possible to use the exon region as a marker specific for the brain, particularly for portions such as Brain, cerebellum, Brain, hippocampus, Brain, amygdala, Brain, caudate nucleus, Brain, substantia nigra, and Brain, thalamus, and as a differentiation marker for detecting cells in nerve cell differentiation or regeneration stages, particularly those that have differentiated or regenerated into a nerve. It also seems possible to develop a new drug by means of a compound, antibody, siRNA or the like that targets a region that exhibits specificity.

The following regions also seem to be useful as differentiation markers.

Upstream sequence 112_[1]_1-N5 (SEQ ID NO:149), which comprises the 363rd to 390th bases undergoing priming by Primer112_01R (SEQ ID NO:141) in D-BRACE2044661.1 of the cDNA pattern [1].

Region 112_01 (SEQ ID NO:142) amplified by Primer112_01F (SEQ ID NO:140) and Primer112_01R (SEQ ID NO:141) in the cDNA pattern [1].

Example 11

Cluster chr12+1658 (Data Set: 095)

(1) Cluster Analysis
1) Cluster Characteristics

An analysis was performed on 7 sequences of full-length cDNAs subjected to genome mapping onto the cluster chr12+1658 (Human genome UCSC hg18 (NCBI Build34) chromosome 12, 108,470,000 by to 108,500,000 bp) [D-BRCAN2027778.1, D-3NB692002462.1, BC016140.1, C-NT2RP3000875, ENST00000228510, M88468.1, NM_000431.1]. They were classifiable according to expression pattern difference mainly into the following 3 kinds.

[1] D-3NB692002462.1
[2] D-BRCAN2027778.1
[3] BC016140.1, ENST00000228510, M88468.1, NM_000431.1

[1] and [2] are cDNAs which were newly acquired and subjected to full-length cDNA sequence analysis by us, and had a different ORF from [3], which had been registered with an existing public DB.

[1], compared with the known [3], had a different ORF region because of the deletion of portions corresponding to the third and fourth exons of [3] in the ORF region.

[2], compared with the known [3], had a different ORF region because of the deletion of a portion corresponding to the fourth exon of [3] in the ORF region.

It was found that the ORF regions present in the 3 kinds of cDNA patterns [1] to [3] have different splice patterns, such as exon deletions, from the same chromosome region, resulting in alterations of the amino acid sequences to produce diverse proteins and mRNAs.

2) Characteristics of D-3NB692002462.1 ([1]), which was Newly Acquired and Subjected to Full-Length cDNA Sequence Analysis by Us 095_[1]_1-N0 (SEQ ID NO:150): The entire nucleic acid sequence region of D-3NB692002462.1

095_[1]_1-NA0 (SEQ ID NO:151): Both the entire nucleic acid sequence region and amino acid sequence of D-3NB692002462.1

095_[1]_1-A0 (SEQ ID NO:152): The entire amino acid sequence region of D-3NB692002462.1

The 301-base exon present at the 303rd to 603rd bases of NM_000431.1, which is registered with an existing public DB, and serves for control (SEQ ID NO:155), is lacked and not present in the region at the 287th to 288th bases of D-3NB692002462.1 (SEQ ID NO:153). The translation initiation point of NM_000431.1 is present on the first exon, shared by D-3NB692002462.1; however, in D-3NB692002462.1, because of the alteration of the frame due to deletion of the 301 bases, the translation initiation point shifts toward the 3' side, compared with NM_000431.1, and the 343rd base of D-3NB692002462.1 becomes the translation initiation point. For this reason, the N-terminal amino acid sequence shortened by 194 residues, compared with NM_000431.1.

095_[1]_1-N1 (SEQ ID NO:153): A deletion nucleic acid sequence region of D-3NB692002462.1

095_[1]_1-N2 (SEQ ID NO:154): A 342-base 5'UTR region of an ORF whose translation initiation point is the 343rd base of D-3NB692002462.1

095_[1]_C-N1 (SEQ ID NO:155): A 301-base exon nucleic acid sequence present in the region at the 303rd to 603rd bases of NM_000431.1 inserted into the region at the 287th to 288th bases of D-3NB692002462.1

095_[1]_C-A1 (SEQ ID NO:156): A 101-residue amino acid sequence related to the 301-base exon nucleic acid sequence present in the region at the 303rd to 603rd bases of NM_000431.1 inserted into the region at the 1,250th to 1,251st bases of D-3NB692002462.1

With this change, "GHMP kinase putative ATP-binding protein", the Pfam motif present at the 128th to 346th amino acids of NM_000431.1, disappeared in D-3NB692002462.1.

3) Characteristics of D-BRCAN2027778.1 ([2]), which was Newly Acquired and Subjected to Full-Length cDNA Sequence Analysis by Us 095_[2]_1-N0 (SEQ ID NO:157): The entire nucleic acid sequence region of D-BRCAN2027778.1

095_[2]_1-NA0 (SEQ ID NO:158): Both the entire nucleic acid sequence region and amino acid sequence of D-BRCAN2027778.1

095_[2]_1-A0 (SEQ ID NO:159): The entire amino acid sequence region of D-BRCAN2027778.1

The 156-base exon present at the 448th to 603rd bases of NM_000431.1, which is registered with an existing public DB, and serves for control (SEQ ID NO:162), is lacked and not present in the region at the 422nd to 423rd bases of D-BRCAN2027778.1 (SEQ ID NO:160).

095_[2]_1-N1 (SEQ ID NO:160): A deletion nucleic acid sequence region of D-BRCAN2027778.1

095_[2]_1-A1 (SEQ ID NO:161): An altered amino acid sequence region of D-BRCAN2027778.1

095_[2]_1-N2 (identical to SEQ ID NO:160): An ORF nucleic acid sequence region in the deletion region of D-BRCAN2027778.1

095_[2]_1-A2 (identical to SEQ ID NO:161): An ORF amino acid region related to the deletion region of D-BRCAN2027778.1

095_[2]_C-N1 (SEQ ID NO:162): A 156-base exon nucleic acid sequence present in the region at the 448th to 603rd bases of NM_000431.1 inserted into the region at the 422nd to 423rd bases of D-BRCAN2027778.1

095_[2]_C-A1 (SEQ ID NO:163): A 101-residue amino acid sequence related to the 156-base exon nucleic acid sequence present in the region at the 448th to 603rd bases of NM_000431.1 inserted into the region at the 423rd to 424th bases of D-BRCAN2027778.1

4) Expression Specificity Analysis and Design of Primers for Real-Time PCR and Taqman Probe To clearly distinguish between the characteristic regions shown above, and examine the respective expression levels thereof, the following regions were used as detection regions. It seemed possible to compare the expression levels of the individual characteristic regions by comparing the expression levels of the detection regions.

095_01—A region specifically extracted by means of the sequence information at the border of regions of the exon deletion of cDNA pattern [1]: an ORF-altering exon deletion region in the cDNA pattern [1], which was newly subjected to full-length cDNA sequence analysis by us
→Fragment 095_01 (SEQ ID NO:166) amplified by Primer095_01F (SEQ ID NO:164) and Primer09501R (SEQ ID NO:165)
TaqMan probe used 095_01TP: (SEQ ID NO:167)

095_02—A region specifically extracted by means of the sequence information at the border of regions of the exon deletion of cDNA pattern [2]: an ORF-altering exon deletion in the cDNA pattern [2], which was newly subjected to full-length cDNA sequence analysis by us
→Fragment 095_02 (SEQ ID NO:170) amplified by Primer095_02F (SEQ ID NO:168) and Primer09502R (SEQ ID NO:169)
TaqMan probe used 095_02TP: (SEQ ID NO:171)

095_03—A specific region of the cDNA pattern [3], which is registered with an existing public DB, that can be distinguished from both the deletion regions of [1] and [2], serving as a control for comparing [1] and [2]
→Fragment 095_03 (SEQ ID NO:174) amplified by Primer095_03F (SEQ ID NO:172) and Primer09503R (SEQ ID NO:173)
TaqMan probe used 095_03TP: (SEQ ID NO:175)

095_04—A common region shared by all of [1] to [3]: a region common to all patterns, serving for control to compare the overall expression levels of the cDNA patterns [1] and [2], which were newly subjected to full-length cDNA sequence analysis by us, and the cDNA pattern [3], which is registered with an existing public DB
→Fragment 095_04 (SEQ ID NO:178) amplified by Primer095_04F (SEQ ID NO:176) and Primer095_04R (SEQ ID NO:177)
TaqMan probe used 095_04TP: (SEQ ID NO:179)

By mapping the 5'-terminal sequences of about 1.44 million sequences acquired using the oligocap method onto the human genome sequence, and comparatively analyzing them, the exon regions specific for the cDNA patterns [1] to [3] shown above, respectively, were found to be expressed at the following frequencies.

In the cDNA pattern [1], which was newly acquired and analyzed by us, three 5'-terminal sequences were present, the derivations thereof being NB69 cells for 1 sequence (analytical parameter 8,153), NT2 cells treated with retinoic acid (RA) to induce differentiation (NT2RP) for 1 sequence (analytical parameter 39,242), and SK-N-MC cells (Neuroepithelioma) for 1 sequence (analytical parameter 7,700).

In the cDNA pattern [2], which was newly acquired and analyzed by us, three 5'-terminal sequences were present, the derivations thereof being a library generated by subtracting cDNAs that overlap with the mRNA of BRAWH: Brain, whole from a cDNA library prepared from the mRNA of BRALZ [Alzheimer patient cerebral cortex (Brain, cortex, Alzheimer)] (BRALZ-BRAWH) for 1 sequence (analytical parameter 157), Brain, caudate nucleus for 1 sequence (analytical parameter 25,786), and NT2 cells treated with retinoic acid and a growth inhibitor to induce nerve differentiation, followed by nerve concentration and recovery (NT2NE) for 1 sequence (analytical parameter 16,337).

In the cDNA pattern [3], which is registered with an existing public DB, thirty-four 5'-terminal sequences were present, and expression was observed in various tissues, the derivations thereof being Brain, cerebellum for 4 sequences (analytical parameter 82,880), Testis for 4 sequences (analytical parameter 90,188), NT2 cells treated with RA and treated with a growth inhibitor to induce nerve differentiation, followed by nerve concentration and recovery (NT2NE) for 3 sequences (analytical parameter 16,337), Brain, whole for 2 sequences (analytical parameter 59,069), Brain, subthalamic nucleus for 2 sequences (analytical parameter 16,308), Kidney for 2 sequences (analytical parameter 17,008), and Thymus for 2 sequences (analytical parameter 70,578).

From this result, it was found that the exon deletion pattern [1] was expressed in differentiated NT2 cells and the like. It was also found that the exon deletion pattern [2] was abundantly expressed in the brain. The known sequence [3], compared with the patterns [1] and [2], was expressed in a wider variety of organs. Hence, it was thought that the selection mechanism for mRNA pattern change in this chromosome region, which alters amino acid sequences and results in the expression of different proteins because of exon selectivity as with the patterns [1] and [2], might be unique to particular tissues.

(2) Analysis of Expression Specificity by Real-Time PCR

To detect protein expression diversity changes due to exon selectivity among different tissues, details of expression levels were analyzed by real-time PCR. The results are shown in Table 15.

TABLE 15

|  | RQ Score | | | | $Log_{10}$ RQ Score | | | |
| --- | --- | --- | --- | --- | --- | --- | --- | --- |
|  | 095_01 | 095_02 | 095_03 | 095_04 | 095_01 | 095_02 | 095_03 | 095_04 |
| 01 NT2RA(−) | 0.5 | 0.3 | 0.2 | 0.2 | −0.34 | −0.49 | −0.78 | −0.66 |
| 02 NT2RA(+) 24 hr | 0.8 | 0.4 | 0.2 | 0.3 | −0.11 | −0.43 | −0.78 | −0.52 |
| 03 NT2RA(+) 48 hr | 0.3 | 0.2 | 0.2 | 0.4 | −0.49 | −0.66 | −0.70 | −0.37 |

TABLE 15-continued

|  | RQ Score | | | | Log₁₀RQ Score | | | |
| --- | --- | --- | --- | --- | --- | --- | --- | --- |
|  | 095_01 | 095_02 | 095_03 | 095_04 | 095_01 | 095_02 | 095_03 | 095_04 |
| 04 NT2RA(+) 1 week | 0.9 | 0.4 | 0.7 | 1.2 | −0.03 | −0.36 | −0.18 | 0.07 |
| 05 NT2RA(+) 5 weeks | 0.2 | 0.2 | 0.3 | 0.3 | −0.71 | −0.80 | −0.58 | −0.48 |
| 06 NT2RA(+) 5 weeks, Inh(+) | 0.1 | 0.2 | 0.3 | 0.2 | −0.88 | −0.64 | −0.58 | −0.63 |
| 07 NT2 Neuron | 0.2 | 0.0 | 0.1 | 1.7 | −0.72 | −1.36 | −1.16 | 0.23 |
| 08 Brain, Fetal | 2.3 | 0.7 | 0.5 | 1.2 | 0.36 | −0.16 | −0.26 | 0.09 |
| 09 Brain, whole | 1.0 | 0.3 | 0.4 | 0.7 | −0.01 | −0.52 | −0.41 | −0.16 |
| 10 ALZ Visual Cortex Occipital | 0.5 | 0.2 | 0.2 | 0.3 | −0.30 | −0.73 | −0.80 | −0.60 |
| 11 Mix, viscus tissues | 1.0 | 1.0 | 1.0 | 1.0 | 0.0 | 0.0 | 0.0 | 0.0 |
| 12 Mix, blood cells and related tissues | 2.1 | 1.0 | 0.9 | 1.0 | 0.33 | 0.01 | −0.05 | 0.01 |
| 13 Mix, tumor tissues | 0.4 | 0.3 | 0.5 | 0.5 | −0.45 | −0.53 | −0.30 | −0.31 |
| 14 Mix, normal tissues | 1.3 | 0.8 | 1.2 | 1.0 | 0.11 | −0.11 | 0.07 | 0.00 |
| 15 Brain, whole PolyA(+) RNA | 3.6 | 0.9 | 1.2 | 1.3 | 0.55 | −0.05 | 0.09 | 0.10 |
| 16 Brain, hippocampus | 1.9 | 0.4 | 0.7 | 0.7 | 0.27 | −0.36 | −0.13 | −0.17 |

Expression levels were compared using the 16 samples shown in Example 3, including Brain, hippocampus, Brain, whole, Brain, Fetal, Alzheimer patient cerebral cortex (ALZ Visual Cortex Occipital) and NT2 cells at 7 different differentiation stages. The comparison was made using the mixed sample of normal visceral tissues shown in Example 3 (Mix, viscus tissues) as an experimental control.

The ratio of ORF alteration due to exon deletion selectivity as compared between 095_01 (SEQ ID NO:166) and 095_02 (SEQ ID NO:170) changed greatly among the following differentiation stages of the brain and NT2 cells. The expression of the pattern of deletion of the exon shown by 095_01 (SEQ ID NO:166) was abundant in undifferentiated NT2 cells NT2RA (−) and NT2RA (+) 1 week, which represents the initial stage in which retinoic acid was added to induce differentiation. Although the expression decreased in NT2RA (+) 5 weeks to NT2RA(+) 5 weeks, Inh (+), which represent the late stage of differentiation induction, this pattern was again abundantly expressed in NT2 Neuron (Table 15).

The expression of the pattern of deletion of the exon shown by 095_02 (SEQ ID NO:170) was abundant in undifferentiated NT2 cells NT2RA (−) and NT2RA (+) 24 hr, which represents the initial stage in which retinoic acid was added to induce differentiation. In NT2RA (+) 5 weeks to NT2RA (+) 5 weeks, Inh (+), which represent the late stage of differentiation, and NT2 Neuron, the expression level decreased (Table 15).

These results demonstrated that by comparing the expression of the selective exon regions 095_[1]_1-N1 (SEQ ID NO:153) and 095_[2]1-N1 (SEQ ID NO:160) of newly acquired cDNAs shown by the detection regions 095_01 (SEQ ID NO:166) and 095_02 (SEQ ID NO:170), it is possible to use the exon regions as differentiation markers for detecting nerve cell differentiation or regeneration stages, particularly initial stages of differentiation into nerve cells.

Furthermore, it was demonstrated that the selective exon region 095_[1]_1-N1 (SEQ ID NO:153) of a newly acquired cDNA shown by the detection region 095_01 (sequence No. 095-17), as a brain-specific marker, can be used as one of differentiation markers for detecting cells in nerve cell differentiation or regeneration stages, particularly those after nerve differentiation or nerve regeneration. It also seems possible to develop a new drug by means of a compound, antibody, siRNA or the like that targets a region that exhibits specificity.

The following regions also seem to be useful as differentiation markers for detecting nerve cell differentiation or regeneration.

Upstream sequence 095_[1]_1-N3 (SEQ ID NO:180), which comprises the 304th to 326th bases undergoing priming by Primer095_01R (SEQ ID NO:165) in D-3NB692002462.1 of the cDNA pattern [1].

Upstream sequence 095_[2]_1-N3 (SEQ ID NO:181), which comprises the 444th to 466th bases undergoing priming by Primer095_02R (SEQ ID NO:169) in D-BR-CAN2027778.1 of the cDNA pattern [2].

Region 095_01 (SEQ ID NO:166) amplified by Primer095_01F (SEQ ID NO:164) and Primer09501R (SEQ ID NO:165) in the cDNA pattern [1]

Region 095_92 (SEQ ID NO:170) amplified by Primer095_02F (SEQ ID NO:168) and Primer09502R (SEQ ID NO:169) in the cDNA pattern [2]

Example 12

Cluster chr12-1875 (Data Set: 017)

(1) Cluster Analysis
1) Cluster Characteristics

Analysis was performed on 10 sequences of full-length cDNAs genome-mapped to the cluster chr12-1875 (Human genome UCSC hg18 (NCBI Build34) chromosome 12, 7,840,000 by to 7,960,000 bp) [D-NT2RI3001005.1, D-NT2RI3005261.1, AF481879.1, AL110298.1, AL832448.1, BC060766.1, C-TESTI1000257, C-TESTI4028880, ENST00000340749, NM_153449.2]. They were classified according to expression pattern difference into 4 kinds, which mainly included the following 2 kinds.

[1] D-NT2RI3001005.1, D-NT2RI3005261.1
[2] AF481879.1, C-TEST14028880 (AK126026.1), NM_153449.2

[1] is a cDNA which was newly acquired and subjected to full-length cDNA sequence analysis by us, and had a different ORF region because of the expression thereof from a chromosome region upstream of the known [2], and also because of the presence of the translation initiation point on a new exon lacking identity to [2].

It was found that the ORF regions present in the 2 kinds of cDNA patterns [1] and [2] cause expression starting at different initiation points, from the same chromosome region, resulting in alterations of the amino acid sequences to produce diverse proteins and mRNAs.

2) Characteristics of D-NT2RI3001005.1 ([1]), which was Newly Acquired and Subjected to Full-Length cDNA Sequence Analysis by Us 017_[1]_1-N0 (SEQ ID NO:182): The entire nucleic acid sequence region of D-NT2RI3001005.1

017_[1]_1-NA0 (SEQ ID NO:183): Both the entire nucleic acid sequence region and amino acid sequence of D-NT2RI3001005.1

017_[1]_1-A0 (SEQ ID NO:184): The entire amino acid sequence region of D-NT2RI3001005.1

The sequence at the 1st to 153rd bases of D-NT2RI3001005.1 (SEQ ID NO:185) is an exon that is not present in NM_153449.2, which is registered with an existing public DB, and serves for control, lacking homology to NM_153449.2. Because the translation initiation point is present on this exon, the amino acids on the N-terminal side changed by 44 residues (SEQ ID NO:186).

017_[1]_1-N1 (SEQ ID NO:185): A 153-base insert nucleic acid sequence region of D-NT2RI3001005.1

017_[1]_1-A1 (SEQ ID NO:186): A 44-residue insert amino acid sequence region of D-NT2RI3001005.1

017_[1]_1-N2 (SEQ ID NO:187): An ORF nucleic acid sequence region in the 153-base insert region of D-NT2RI3001005.1

017_[1]_1-A2 (identical to SEQ ID NO:186): An ORF amino acid sequence region in the 153-base insert region of D-NT2RI3001005.1

3) Characteristics of D-NT2RI3005261.1 ([1]), which was Newly Acquired and Subjected to Full-Length cDNA Sequence Analysis by Us 017_[1]_2-N0 (SEQ ID NO:188): The entire nucleic acid sequence region of D-NT2RI3005261.1

017_[1]_2-NA0 (SEQ ID NO:189): Both the entire nucleic acid sequence region and amino acid sequence of D-NT2RI3005261.1

017_[1]_2-A0 (SEQ ID NO:190): The entire amino acid sequence region of D-NT2RI3005261.1

The sequence at the 1st to 153rd bases of D-NT2RI3005261.1 (SEQ ID NO:191) is an exon that is not present in NM_153449.2, which is registered with an existing public DB, and serves for control, lacking homology to NM_153449.2. Because the translation initiation point is present on this exon, the amino acids on the N-terminal side changed by 44 residues (SEQ ID NO:192).

017_[1]_2-N1 (SEQ ID NO:191): A 153-base insert nucleic acid sequence region of D-NT2RI3005261.1

017_[1]_2-A1 (SEQ ID NO:192): A 44-residue insert amino acid sequence region of D-NT2RI3005261.1

017_[1]_2-N2 (SEQ ID NO:193): An ORF nucleic acid sequence region in the 153-base insert region of D-NT2RI3005261.1

017_[1]_2-A2 (identical to SEQ ID NO:192): An ORF amino acid sequence region in the 153-base insert region of D-NT2RI3005261.1

4) Characteristics of C-TESTI4028880 (AK126026.1) ([2]), which was Acquired and Subjected to Full-Length cDNA Sequence Analysis by Us, and is Already Registered with a Public DB 017_[2]_1-N0 (SEQ ID NO:194): The entire nucleic acid sequence region of C-TESTI4028880

017_[2]_1-NA0 (SEQ ID NO:195): Both the entire nucleic acid sequence region and amino acid sequence of C-TESTI4028880

017_[2]_1-A0 (SEQ ID NO:196): The entire amino acid sequence region of C-TESTI4028880

5) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

017_01—A specific region present on the N-terminal side of the cDNA pattern [1]: a translation initiation region of the cDNA pattern [1], which was newly subjected to full-length cDNA sequence analysis by us, being a novel region not registered with an existing public DB →Fragment 017_01 (SEQ. ID NO:199) amplified by Primer017_01F (SEQ ID NO:197) and Primer01701R (SEQ ID NO:198)

017_03—A common region shared by all of [1] to [2]: a region common to all patterns, serving for control to compare the overall expression levels of the cDNA pattern [1], which was newly subjected to full-length cDNA sequence analysis by us, and the cDNA pattern [2], which is registered with an existing public DB →Fragment 017_03 (SEQ ID NO:202) amplified by Primer017_03F (SEQ ID NO:200) and Primer01703R (SEQ ID NO:201)

By mapping the 5'-terminal sequences of about 1.44 million sequences acquired using the oligocap method onto the human genome sequence, and comparatively analyzing them, the regions specific for the 2 kinds of cDNA patterns [1] to [2] shown above, respectively, were found to be expressed at the following frequencies.

In the cDNA pattern [1], which was newly acquired and analyzed by us, fourteen 5'-terminal sequences were present, the derivations thereof being NT2 cells treated with retinoic acid (RA) to induce differentiation for 5 weeks, and thereafter treated with a growth inhibitor for 2 weeks (NT2RI) for 13 sequences (analytical parameter 32,662), and NT2 cells treated with retinoic acid (RA) to induce differentiation (NT2RP) for 1 sequence (analytical parameter 39,242).

In the cDNA pattern [2], which is registered with an existing public DB, eighty-six 5'-terminal sequences were present, the derivations thereof being Testis for 85 sequences (analytical parameter 90,188), and NT2 cells treated with RA to induce differentiation for 5 weeks, and thereafter treated with a growth inhibitor for 2 weeks (NT2RI) for 1 sequence (analytical parameter 32,662).

From this result, it was found that the transcription initiation point of [1] was expressed specifically in NT2 cells after differentiation. From the transcription initiation point of [2], the expression in Testis was very abundant. Hence, it was thought that the mechanism of transcription in this chromosome region might be different only it the situation of nerve cell differentiation of NT2 cells after differentiation, is with a different transcription initiation point being used.

(2) Analysis of Expression Specificity by Real-Time PCR

To determine what are the states in which the transcription initiation point used for the expression changes, details of expressions level were analyzed by real-time PCR. The results are shown in Table 16 and Table 17.

TABLE 16

| | RQ Score | | Log$_{10}$RQ Score | |
|---|---|---|---|---|
| | 017_01 | 017_03 | 017_01 | 017_03 |
| 01 NT2RA(−) | 81.1 | 4.7 | 1.91 | 0.67 |
| 02 NT2RA(+) 24 hr | 29.4 | 1.8 | 1.47 | 0.25 |
| 03 NT2RA(+) 48 hr | 34.8 | 1.6 | 1.54 | 0.21 |
| 04 NT2RA(+) 1 week | 177.5 | 2.6 | 2.25 | 0.41 |
| 05 NT2RA(+) 5 weeks | 39.2 | 0.8 | 1.59 | −0.07 |
| 06 NT2RA(+) 5 weeks, Inh(+) | 1250.2 | 7.0 | 3.10 | 0.85 |
| 07 NT2 Neuron | 319.1 | 0.6 | 2.50 | −0.19 |
| 08 Brain, Fetal | 1.2 | 1.5 | 0.07 | 0.18 |
| 09 Brain, whole | 0.6 | 2.3 | −0.25 | 0.35 |
| 10 ALZ Visual Cortex Occipital | 0.6 | 0.6 | −0.23 | −0.21 |
| 11 Mix, viscus tissues | 1.0 | 1.0 | 0.0 | 0.0 |
| 12 Mix, blood cells and related tissues | 1.4 | 2.1 | 0.15 | 0.32 |
| 13 Mix, tumor tissues | 0.6 | 0.3 | −0.24 | −0.60 |
| 14 Mix, normal tissues | 32.4 | 1.1 | 1.51 | 0.06 |
| 15 Brain, whole PolyA(+) RNA | 0.1 | 0.5 | −0.88 | −0.27 |
| 16 Brain, hippocampus | 0.7 | 0.5 | −0.15 | −0.31 |

TABLE 17

| | RQ Score | | Log$_{10}$RQ Score | |
|---|---|---|---|---|
| | 017_01 | 017_03 | 017_01 | 017_03 |
| 01 NT2RA(−) | 30.9 | 5.2 | 1.49 | 0.72 |
| 02 NT2RA(+) 24 hr | 11.3 | 1.7 | 1.05 | 0.22 |
| 03 NT2RA(+) 48 hr | 15.5 | 1.6 | 1.19 | 0.22 |
| 04 NT2RA(+) 1 week | 77.1 | 2.9 | 1.89 | 0.46 |
| 05 NT2RA(+) 5 weeks | 17.5 | 1.0 | 1.24 | −0.02 |
| 06 NT2RA(+) 5 weeks, Inh(+) | 497.7 | 7.6 | 2.70 | 0.88 |
| 07 NT2 Neuron | 145.3 | 0.6 | 2.16 | −0.20 |
| 08 Brain, Fetal | 1.0 | 1.8 | −0.02 | 0.24 |
| 09 Brain, whole | 0.3 | 2.6 | −0.57 | 0.41 |
| 10 ALZ Visual Cortex Occipital | 0.3 | 0.7 | −0.46 | −0.14 |
| 11 Mix, viscus tissues | 1.0 | 1.0 | 0.0 | 0.0 |
| 12 Mix, blood cells and related tissues | 0.9 | 2.7 | −0.02 | 0.43 |
| 13 Mix, tumor tissues | 1.7 | 0.3 | 0.24 | −0.57 |
| 14 Mix, normal tissues | 19.8 | 1.2 | 1.30 | 0.07 |
| 15 Brain, whole PolyA(+) RNA | 0.2 | 0.7 | −0.79 | −0.16 |
| 16 Brain, hippocampus | 0.5 | 0.7 | −0.29 | −0.16 |
| 17 Colon | 0.8 | 0.1 | −0.12 | −0.92 |
| 18 Colon Tumor | Undet. | 0.0 | Undet. | −1.65 |
| 19 Kidney | 0.7 | 0.3 | −0.15 | −0.50 |
| 20 Kidney Tumor | 0.0 | 0.2 | −1.60 | −0.61 |
| 21 Liver | 2.2 | 0.1 | 0.34 | −0.94 |
| 22 Liver Tumor | 14.8 | 0.1 | 1.17 | −0.94 |
| 23 Lung | 0.1 | 2.0 | −0.91 | 0.30 |
| 24 Lung Tumor | 0.3 | 0.6 | −0.60 | −0.25 |
| 25 Ovary | 93.4 | 2.0 | 1.97 | 0.29 |
| 26 Ovary Tumor | 6.7 | 0.2 | 0.83 | −0.70 |
| 27 Stomach | 1.1 | 0.7 | 0.04 | −0.17 |
| 28 Stomach Tumor | Undet. | 0.1 | Undet. | −1.25 |
| 29 Uterus | 2.5 | 1.6 | 0.40 | 0.21 |
| 30 Uterus Tumor | 0.6 | 0.3 | −0.21 | −0.53 |
| 31 Tongue | 33.7 | 0.2 | 1.53 | −0.65 |
| 32 Tumor Tongue | 15.6 | 0.1 | 1.19 | −0.91 |

Expression levels were compared using the 32 samples shown in Example 3, including Brain, hippocampus, Brain, whole, Brain, Fetal, Alzheimer patient cerebral cortex (ALZ Visual Cortex Occipital), NT2 cells at 7 different differentiation stages, 8 kinds of normal tissues, and 8 kinds of tumor tissues and the like. The comparison was made using the mixed sample of normal visceral tissues shown in Example 3 (Mix, viscus tissues) as an experimental control.

The transcription initiation point shown by 017_01 (SEQ ID NO:199) is used selectively in NT2 cells. Hence, in NT2 cells at all stages, whether undifferentiated or differentiated, the ratio of transcription from the upstream transcription initiation point was considerably high (Table 16 and Table 17).

These results demonstrated that by detecting the is expression of the 5'-terminal regions (regions close to the transcription initiation point) 017_[1]_1-N1 (SEQ ID NO:185) and 017_[1]_2-N1 (SEQ ID NO:191) of a newly acquired cDNA region shown by the detection region 017_01 (SEQ ID NO:199), it is possible to use the 5'-terminal regions as nerve cell markers. It also seems possible to develop a new drug by means of a compound, antibody, siRNA or the like that targets a region that exhibits specificity.

The following regions also seem to be useful as nerve cell markers.

Upstream sequence 017_[1]_1-N3 (SEQ ID NO:203), which comprises the 143rd to 159th bases undergoing priming by Primer01701R (SEQ ID NO:198) in D-NT2RI3001005.1 of the cDNA pattern [1].

Upstream sequence 017_[1]_2-N3 (SEQ ID NO:204), which comprises the 143rd to 159th bases undergoing priming by Primer01701R (SEQ ID NO:198) in D-NT2RI3005261.1 of the cDNA pattern [1].

Region 017_01 (SEQ ID NO:199) amplified by Primer017_01F (SEQ ID NO:197) and Primer01701R (SEQ ID NO:198) in the cDNA pattern [1].

Example 13

Cluster chr3-1507 (Data Set: 023)

(1) Cluster Analysis
1) Cluster Characteristics

An analysis was performed on 15 sequences of full-length cDNAs subjected to genome mapping onto the cluster chr3-1507 (Human genome UCSC hg18 (NCBI Build34) chromosome 3, 73,500,000 by to 73,800,000 bp) [D-OCBBF2010718.1, D-OCBBF3004194.1, D-NT2RP8000826.1, D-NT2RP7007268.1, D-BRAWH3008172.1, D-BRAWH3011965.1, AB029018.1, AL049958.1, AL157498.1, BC014432.1, C-HEMBA1005489, ENST00000263666, ENST00000308537, ENST00000319719, NM_015009.1]. They were classified according to expression pattern difference into 8 kinds, which mainly included the following 5 kinds.

[1] D-OCBBF2010718.1, D-OCBBF3004194.1
[2] D-NT2RP8000826.1, D-NT2RP7007268.1
[3] D-BRAWH3008172.1
[4] D-BRAWH3011965.1
[5] AB029018.1, ENST00000263666, NM_015009.1

[1], [2], [3], and [4] are cDNAs which were newly acquired and subjected to full-length cDNA sequence analysis by us, and had a different ORF from [5], which had been registered with an existing public DB.

[1], [2], [3], and [4] had a different ORF region because of the expression thereof from a chromosome region located downstream of the known [5], and also because of the presence of a translation initiation point different from [5].

It was found that the ORF regions present in the 5 kinds of cDNA patterns [1] to [5] cause expression starting at different transcription initiation points, from the same chromosome region, resulting in alterations of the amino acid sequences to produce diverse proteins and mRNAs.

2) Characteristics of D-OCBBF2010718.1 ([1]), which was Newly Acquired and Subjected to Full-Length cDNA Sequence Analysis by Us 023_[1]_1-N0 (SEQ ID NO:205): The entire nucleic acid sequence region of D-OCBBF2010718.1

023_[1]_1-NA0 (SEQ ID NO:206): Both the entire nucleic acid sequence region and amino acid sequence of D-OCBBF2010718.1

023_[1]_1-A0 (SEQ ID NO:207): The entire amino acid sequence region of D-OCBBF2010718.1

The 1st to 212th bases of D-OCBBF2010718.1 (SEQ ID NO:208) is an exon that is not present in NM_015009.1, which is registered with an existing public DB, and serves for control, lacking homology to NM_015009.1. Because the translation initiation point is present on this exon, the amino acids on the N-terminal side changed by 23 residues (SEQ ID NO:209).

023_[1]_1-N1 (SEQ ID NO:208): A 212-base insert nucleic acid sequence region of D-OCBBF2010718.1

023_[1]_1-A1 (SEQ ID NO:209): A 23-residue insert amino acid sequence region of D-OCBBF2010718.1

023_[1]_1-N2 (SEQ ID NO:210): An ORF nucleic acid sequence region in the 212-base insert region of D-OCBBF2010718.1

023_[1]_1-A2 (identical to SEQ ID NO:209): An ORF amino acid sequence region in the 212-base insert region of D-OCBBF2010718.1

3) Characteristics of D-OCBBF3004194.1 ([1]), which was Newly Acquired and Subjected to Full-Length cDNA Sequence Analysis by Us 023_[1]_2-N0 (SEQ ID NO:211): The entire nucleic acid sequence region of D-OCBBF3004194.1

023_[1]_2-NA0 (SEQ ID NO:212): Both the entire nucleic acid sequence region and amino acid sequence of D-OCBBF3004194.1

023_[1]_2-A0 (SEQ ID NO:213): The entire amino acid sequence region of D-OCBBF3004194.1

The sequence at the 1st to 197th bases of D-OCBBF3004194.1 (SEQ ID NO:214) is an exon that is not present in NM_015009.1, which is registered with an existing public DB, and serves for control, lacking homology to NM_015009.1. Because the translation initiation point is present on this exon, the amino acids on the N-terminal side changed by 23 residues (SEQ ID NO:215).

023_[1]_2-N1 (SEQ ID NO:214): A 197-base insert nucleic acid sequence region of D-OCBBF3004194.1

023_[1]_2-A1 (SEQ ID NO:215): A 23-residue insert amino acid sequence region of D-OCBBF3004194.1

023_[1]_2-N2 (SEQ ID NO:216): An ORF nucleic acid sequence region in the 197-base insert region of D-OCBBF3004194.1

023_[1]_2-A2 (identical to SEQ ID NO:215): An ORF amino acid sequence region in the 197-base insert region of D-OCBBF3004194.1

4) Characteristics of D-NT2RP8000826.1 ([2]), which was Newly Acquired and Subjected to Full-Length cDNA Sequence Analysis by Us 023_[2]_1-N0 (SEQ ID NO:217): The entire nucleic acid sequence region of D-NT2RP8000826.1

023_[2]_1-NA0 (SEQ ID NO:218): Both the entire nucleic acid sequence region and amino acid sequence of D-NT2RP8000826.1

023_[2]_1-A0 (SEQ ID NO:219): The entire amino acid sequence region of D-NT2RP8000826.1

The sequence at the 1st to 178th bases of D-NT2RP8000826.1 (SEQ ID NO:220) is an exon that is not present in NM_015009.1, which is registered with an existing public DB, and serves for control, lacking homology to NM_015009.1. Because the translation initiation point is present on this exon, the amino acids on the N-terminal side changed by 28 residues (SEQ ID NO:221).

023_[2]_1-N1 (SEQ ID NO:220): A 178-base insert nucleic acid sequence region of D-NT2RP8000826.1

023_[2]_1-A1 (SEQ ID NO:221): A 28-residue insert amino acid sequence region of D-NT2RP8000826.1

023_[2]_1-N2 (SEQ ID NO:222): An ORF nucleic acid sequence region in the 178-base insert region of D-NT2RP8000826.1

023_[2]_1-A2 (identical to SEQ ID NO:221): An ORF amino acid sequence region in the 178-base insert region of D-NT2RP8000826.1

5) Characteristics of D-NT2RP7007268.1 ([2]), which was Newly Acquired and Subjected to Full-Length cDNA Sequence Analysis by Us 023_[2]_2-N0 (SEQ ID NO:223): The entire nucleic acid sequence region of D-NT2RP7007268.1

023_[2]_2-NA0 (SEQ ID NO:224): Both the entire nucleic acid sequence region and amino acid sequence of D-NT2RP7007268.1

023_[2]_2-A0 (SEQ ID NO:225): The entire amino acid sequence region of D-NT2RP7007268.1

The sequence at the 1st to 178th bases of D-NT2RP7007268.1 (SEQ ID NO:226) is an exon that is not present in NM_015009.1, which is registered with an existing public DB, and serve for control, lacking homology to NM_015009.1. Because the translation initiation point is present on this exon, the amino acids on the N-terminal side changed by 28 residues (SEQ ID NO:227).

023_[2]_2-N1 (SEQ ID NO:226): A 178-base insert nucleic acid sequence region of D-NT2RP7007268.1

023_[2]_2-A1 (SEQ ID NO:227): A 28-residue insert amino acid sequence region of D-NT2RP7007268.1

023_[2]_2-N2 (SEQ ID NO:228): An ORF nucleic acid sequence region in the 178-base insert region of D-NT2RP7007268.1

023_[2]_2-A2 (identical to SEQ ID NO:227): An ORF amino acid sequence region in the 178-base insert region of D-NT2RP7007268.1

6) Characteristics of D-BRAWH3008172.1 ([3]), which was Newly Acquired and Subjected to Full-Length cDNA Sequence Analysis by Us 023_[3]_1-N0 (SEQ ID NO:229): The entire nucleic acid sequence region of D-BRAWH3008172.1

023_[3]_1-NA0 (SEQ ID NO:230): Both the entire nucleic acid sequence region and amino acid sequence of D-BRAWH3008172.1

023_[3]_1-A0 (SEQ ID NO:231): The entire amino acid sequence region of D-BRAWH3008172.1

The sequence at the 1st to 169th bases of D-BRAWH3008172.1 (SEQ ID NO:232) is an exon that is not present in NM_015009.1, which is registered with an existing public DB, and serves for control, lacking homology to NM_015009.1. With this change, the translation initiation point of D-BRAWH3008172.1 shifts toward the 3' side relative to NM_015009.1, and the 281st base of D-BRAWH3008172.1 becomes the translation initiation point. For this reason, the amino acid sequence shortened by 343 residues compared with NM_015009.1.

023_[3]1-N1 (SEQ ID NO:232): A 169-base insert nucleic acid sequence region of D-BRAWH3008172.1

023_[3]_1-N2 (SEQ ID NO:233): A 280-base 5'UTR region of an ORF whose translation initiation point is the 281st base of D-BRAWH3008172.1

7) Characteristics of D-BRAWH3011965.1 ([4]), which was Newly Acquired and Subjected to Full-Length cDNA Sequence Analysis by Us 023_[4]_1-N0 (SEQ ID NO:234): The entire nucleic acid sequence region of D-BRAWH3011965.1

023_[4]_1-NA0 (SEQ ID NO:235): Both the entire nucleic acid sequence region and amino acid sequence of D-BRAWH3011965.1

023_[4]_1-A0 (SEQ ID NO:236): The entire amino acid sequence region of D-BRAWH3011965.1

The sequence at the 1st to 311th bases of D-BRAWH3011965.1 (SEQ ID NO:237) is an exon that is not present in NM_015009.1, which is registered in an existing public DB and serves as a control, lacking homology to NM_015009.1. Because the translation initiation point is present on this exon, the amino acids on the N-terminal side changed by 4 residues (SEQ ID NO:238).

023_[4]_1-N1 (SEQ ID NO:237): A 311-base insert nucleic acid sequence region of D-BRAWH3011965.1

023_[4]_1-A1 (SEQ ID NO:238): A 4-residue insert amino acid sequence region of D-BRAWH3011965.1

023_[4]_1-N2 (SEQ ID NO:239): An ORF nucleic acid sequence region in the 311-base insert region of D-BRAWH3011965.1

023_[4]_1-A2 (identical to SEQ ID NO:238): An ORF amino acid sequence region in the 311-base insert region of D-BRAWH3011965.1

8) Expression Specificity Analysis and Design of Primers for Real-Time PCR

To clearly distinguish between the characteristic regions shown above, and examine the respective expression levels thereof, the following regions were used as detection regions. It seemed possible to compare the expression levels of the individual characteristic regions by comparing the expression levels of the detection regions.

023_01—A specific region present on the N-terminal side of the cDNA pattern [1]: a translation initiation region of the cDNA pattern [1], which was newly subjected to full-length cDNA sequence analysis by us, being a novel region not registered with an existing public DB →Fragment 023_01 (SEQ ID NO:242) amplified by Primer023_01F (SEQ ID NO:240) and Primer023_01R (SEQ ID NO:241)

023_02—A specific region present on the N-terminal side of the cDNA pattern [2]: a translation initiation region of the cDNA pattern [2], which was newly subjected to full-length cDNA sequence analysis by us, being a novel region not registered with an existing public DB →Fragment 023_02 (SEQ ID NO:245) amplified by Primer023_02F (SEQ ID NO:243) and Primer023_02R (SEQ ID NO:244)

023_03—A specific region present on the N-terminal side of the cDNA pattern [3]: a translation initiation region of the cDNA pattern [3], which was newly subjected to full-length cDNA sequence analysis by us, being a novel region not registered with an existing public DB →Fragment 023_03 (SEQ ID NO:248) amplified by Primer023_03F (SEQ ID NO:246) and Primer023 03R (SEQ ID NO:247)

023_04—A specific region present on the N-terminal side of the cDNA pattern [4]: a translation initiation region of the cDNA pattern [4], which was newly subjected to full-length cDNA sequence analysis by us, being a novel region not registered with an existing public DB →Fragment 023_04 (SEQ ID NO:251) amplified by Primer023_04F (SEQ ID NO:249) and Primer02304R (SEQ ID NO:250)

023_05—A specific region of the cDNA pattern [5], which is registered with an existing public DB, that can be distinguished from all of [1], [2], [3], and [4], serving as a control for comparing [1], [2], [3], and [4]

→Fragment 023_05 (SEQ ID NO:254) amplified by Primer023_05F (SEQ ID NO:252) and Primer023_05R (SEQ ID NO:253)

023_06—A common region shared by all of [1] to [5]: a region common to all patterns, serving for control to compare the overall expression levels of the cDNA patterns [1], [2], [3], and [4], which were newly subjected to full-length cDNA sequence analysis by us, and the cDNA pattern [5] registered with an existing public DB →Fragment 023_06 (SEQ ID NO:257) amplified by Primer023_06F (SEQ ID NO:255) and Primer023 06R (SEQ ID NO:256)

By mapping the 5'-terminal sequences of about 1.44 million sequences acquired using the oligocap method onto the human genome sequence, and comparatively analyzing them, the regions specific for the 2 kinds of cDNA patterns [1] to [2] shown above, respectively, were found to be expressed at the following frequencies.

In the cDNA pattern [1], which was newly acquired and analyzed by us, thirty-two 5'-terminal sequences were present, the derivations thereof being NT2 cells treated with retinoic acid (RA) to induce differentiation (NT2RP) for 21 sequences (analytical parameter 39,242), Brain, Fetal for 8 sequences (analytical parameter 103,138), NT2 cells treated with retinoic acid (RA) to induce differentiation for 5 weeks, and thereafter treated with a growth inhibitor for 2 weeks (NT2RI) for 1 sequence (analytical parameter 32,662), Brain, hippocampus for 1 sequence (analytical parameter 57,918), and Brain, amygdala for 1 sequence (analytical parameter 58,640).

In the cDNA pattern [2], which was newly acquired and analyzed by us, twenty 5'-terminal sequences were present, the derivation thereof being NT2 cells treated with retinoic acid (RA) to induce differentiation (NT2RP) for the 20 sequences (analytical parameter 39,242).

In the cDNA pattern [3], which was newly acquired and analyzed by us, sixteen 5'-terminal sequences were present, the derivations thereof being Brain, whole for 8 sequences (analytical parameter 59,069), Brain, amygdala for 5 sequences (analytical parameter 58,640), Kidney, Tumor for 1 sequence (analytical parameter 15,970), Brain, thalamus for 1 sequence (analytical parameter 53,267), and Testis for 1 sequence (analytical parameter 90,188).

In the cDNA pattern [4], which was newly acquired and analyzed by us, five 5'-terminal sequences were present, the derivations thereof being Brain, whole for 3 sequences (analytical parameter 59,069), Brain, hippocampus for 1 sequence (analytical parameter 57,918), and Brain, thalamus for 1 sequence (analytical parameter 53,267).

In the cDNA pattern [5], which is registered with an existing public DB, two 5'-terminal sequences were present, the derivations thereof being Stomach, Tumor for 1 sequence (analytical parameter 2,757), and Prostate for 1 sequence (analytical parameter 16,671).

From this result, it was found that the transcription initiation point of [1] was abundantly expressed in differentiated NT2 cells and the fetal brain. It was found that the transcription initiation point of [2] was abundantly expressed in differentiated NT2 cells. It was found that the transcription initiation points of [3] and [4] were abundantly expressed in the brain. The known sequence [5] was expressed in gastric cancer and the prostate. Hence, it was thought that the mechanism of transcription in this chromosome region might differ among various organs and cell conditions, with different transcription initiation points being used.

(2) Analysis of Expression Specificity by Real-Time PCR

To determine what are the states in which the transcription initiation point used for expression changes, details of expression levels were analyzed by real-time PCR. The results are shown in Tables 18-1 and 18-2 and Tables 19-1 and 19-2.

Expression levels were compared using the 23 samples shown in Example 3, including Brain, hippocampus, Brain, whole, Brain, Fetal, Alzheimer patient cerebral cortex (ALZ Visual Cortex Occipital), NT2 cells at 7 different differentiation stages, and 7 kinds of brain tissues. The comparison was made using the mixed sample of normal visceral tissues shown in Example 3 (Mix, viscus tissues) as an experimental control.

The transcription initiation points shown by 023_01 (SEQ ID NO:242), 023_02 (SEQ ID NO:245), and 023_04 (SEQ ID NO:251) were abundantly expressed in NT2 cells after differentiation, particularly in NT2RA (+) 1 week, which represents an advanced stage of differentiation, whereas 023_01 (SEQ ID NO:242) was most abundantly expressed in NT2RA (+) 5 weeks (Tables 18-1 and 18-2 and Tables 19-1

TABLES 18-1, 18-2

| | RQ Score | | | | | | $Log_{10}$RQ Score | | | | | |
|---|---|---|---|---|---|---|---|---|---|---|---|---|
| | 023_01 | 023_02 | 023_03 | 023_04 | 023_05 | 023_06 | 023_01 | 023_02 | 023_03 | 023_04 | 023_05 | 023_06 |
| 01 NT2RA(−) | 0.0 | 0.0 | Undet | 0.0 | 0.0 | 0.0 | −2.32 | −2.82 | Undet | −2.07 | −1.63 | −1.54 |
| 02 NT2RA(+) 24 hr | 0.1 | 0.1 | 0.0 | 0.2 | 0.0 | 0.0 | −1.11 | −1.22 | −3.03 | −0.71 | −1.62 | −1.40 |
| 03 NT2RA(+) 48 hr | 1.3 | 0.4 | 0.0 | 0.8 | 0.1 | 0.2 | 0.12 | −0.38 | −2.12 | −0.11 | −1.13 | −0.81 |
| 04 NT2RA(+) 1 week | 19.1 | 1.8 | 0.1 | 5.6 | 0.3 | 1.8 | 1.28 | 0.25 | −1.24 | 0.75 | −0.55 | 0.25 |
| 05 NT2RA(+) 5 weeks | 39.7 | 1.2 | 0.0 | 0.2 | 0.4 | 1.9 | 1.60 | 0.08 | −1.58 | −0.63 | −0.43 | 0.27 |
| 06 NT2RA(+) 5 weeks, Inh(+) | 2.0 | 0.0 | 0.0 | 0.1 | 0.1 | 0.3 | 0.30 | −1.64 | −1.65 | −1.29 | −0.84 | −0.55 |
| 07 NT2 Neuron | 2.9 | 0.7 | 0.0 | 1.4 | 0.0 | 0.2 | 0.46 | −0.17 | −1.95 | 0.16 | −1.77 | −0.66 |
| 08 Brain, Fetal | 53.3 | 3.5 | 34.6 | 11.3 | 1.7 | 3.5 | 1.73 | 0.54 | 1.54 | 1.05 | 0.23 | 0.54 |
| 09 Brain, whole | 0.8 | 1.0 | 58.9 | 2.7 | 0.4 | 1.0 | −0.12 | −0.01 | 1.77 | 0.42 | −0.46 | 0.01 |
| 10 ALZ Visual Cortex Occipital | 0.5 | 0.6 | 27.6 | 1.2 | 0.2 | 0.6 | −0.26 | −0.24 | 1.44 | 0.07 | −0.71 | −0.20 |
| 11 Mix, viscus tissues | 1.0 | 1.0 | 1.0 | 1.0 | 1.0 | 1.0 | 0.0 | 0.0 | 0.0 | 0.0 | 0.0 | 0.0 |
| 12 Mix, blood cells and related tissues | 1.0 | 0.3 | 0.3 | 0.6 | 0.3 | 0.4 | −0.02 | −0.54 | −0.51 | −0.20 | −0.46 | −0.40 |
| 13 Mix, tumor tissues | 1.0 | 0.1 | 0.0 | 0.0 | 0.1 | 0.3 | −0.01 | −1.22 | −1.36 | −1.41 | −0.87 | −0.50 |
| 14 Mix, normal tissues | 2.1 | 2.9 | 3.0 | 4.2 | 2.3 | 2.4 | 0.33 | 0.47 | 0.48 | 0.63 | 0.36 | 0.37 |
| 15 Brain, whole PolyA(+) RNA | 0.2 | 0.1 | 19.0 | 0.8 | 0.1 | 0.4 | −0.71 | −0.99 | 1.28 | −0.12 | −1.01 | −0.38 |
| 16 Brain, hippocampus | 0.3 | 0.0 | 9.7 | 0.4 | 0.1 | 0.3 | −0.55 | −1.39 | 0.98 | −0.40 | −0.96 | −0.48 |

TABLES 19-1, 19-2

| | RQ Score | | | | | | $Log_{10}$RQ Score | | | | | |
|---|---|---|---|---|---|---|---|---|---|---|---|---|
| | 023_01 | 023_02 | 023_03 | 023_04 | 023_05 | 023_06 | 023_01 | 023_02 | 023_03 | 023_04 | 023_05 | 023_06 |
| 01 NT2RA(−) | 0.0 | 0.0 | Undet | 0.0 | 0.0 | 0.0 | −2.22 | −2.59 | Undet | −1.70 | −1.59 | −1.53 |
| 02 NT2RA(+) 24 hr | 0.1 | 0.1 | 0.0 | 0.5 | 0.0 | 0.0 | −1.02 | −0.91 | −2.71 | −0.31 | −1.54 | −1.34 |
| 03 NT2RA(+) 48 hr | 1.7 | 0.6 | 0.0 | 1.2 | 0.1 | 0.2 | 0.23 | −0.20 | −2.18 | 0.08 | −0.96 | −0.65 |
| 04 NT2RA(+) 1 week | 25.8 | 3.2 | 0.1 | 10.6 | 0.4 | 2.6 | 1.41 | 0.51 | −0.96 | 1.03 | −0.39 | 0.42 |
| 05 NT2RA(+) 5 weeks | 48.9 | 1.8 | 0.0 | 0.2 | 0.5 | 3.0 | 1.69 | 0.26 | −1.37 | −0.62 | −0.29 | 0.48 |
| 06 NT2RA(+) 5 weeks, Inh(+) | 2.8 | 0.0 | 0.0 | 0.1 | 0.2 | 0.5 | 0.45 | −1.36 | −1.66 | −1.02 | −0.66 | −0.32 |
| 07 NT2 Neuron | 3.1 | 0.9 | 0.0 | 2.3 | 0.0 | 0.3 | 0.49 | −0.02 | −1.45 | 0.35 | −1.85 | −0.58 |
| 08 Brain, Fetal | 67.9 | 6.0 | 54.2 | 25.8 | 1.9 | 4.3 | 1.83 | 0.78 | 1.73 | 1.41 | 0.29 | 0.63 |
| 09 Brain, whole | 0.8 | 1.5 | 90.6 | 5.4 | 0.4 | 1.0 | −0.10 | 0.17 | 1.96 | 0.74 | −0.44 | 0.02 |
| 10 ALZ Visual Cortex Occipital | 0.6 | 0.9 | 40.4 | 2.5 | 0.2 | 0.6 | −0.21 | −0.07 | 1.61 | 0.40 | −0.65 | −0.26 |
| 11 Mix, viscus tissues | 1.0 | 1.0 | 1.0 | 1.0 | 1.0 | 1.0 | 0.0 | 0.0 | 0.0 | 0.0 | 0.0 | 0.0 |
| 12 Mix, blood cells and related tissues | 1.2 | 0.4 | 0.7 | 1.2 | 0.3 | 0.4 | 0.06 | −0.35 | −0.16 | 0.07 | −0.50 | −0.42 |
| 13 Mix, tumor tissues | 1.0 | 0.1 | 0.0 | 0.0 | 0.1 | 0.3 | −0.02 | −1.29 | −1.53 | −1.41 | −0.92 | −0.58 |
| 14 Mix, normal tissues | 2.2 | 4.0 | 4.3 | 6.6 | 2.2 | 2.3 | 0.34 | 0.60 | 0.63 | 0.82 | 0.35 | 0.37 |
| 15 Brain, whole PolyA(+) RNA | 0.3 | 0.2 | 31.4 | 1.3 | 0.1 | 0.5 | −0.54 | −0.75 | 1.50 | 0.12 | −0.88 | −0.28 |
| 16 Brain, hippocampus | 0.4 | 0.1 | 16.0 | 0.7 | 0.1 | 0.5 | −0.40 | −1.13 | 1.20 | −0.15 | −0.86 | −0.30 |
| 17 Brain, cerebellum | 0.1 | 0.0 | 0.1 | 0.0 | 0.1 | 0.2 | −0.86 | −1.81 | −0.86 | −1.80 | −1.09 | −0.79 |
| 18 Brain, amygdala | 1.4 | 0.1 | 11.9 | 0.5 | 0.1 | 0.5 | 0.14 | −1.11 | 1.08 | −0.33 | −1.02 | −0.31 |
| 19 Brain, caudate nucleus | 0.1 | 0.0 | 1.3 | 0.1 | 0.1 | 0.2 | −1.15 | −1.56 | 0.12 | −0.84 | −1.13 | −0.70 |
| 20 Brain, corpus callosum | 0.1 | 0.0 | 1.1 | 0.2 | 0.1 | 0.2 | −1.14 | −1.61 | 0.05 | −0.64 | −1.05 | −0.64 |
| 21 Brain, substantia nigra | 0.1 | 0.1 | 2.4 | 0.3 | 0.1 | 0.2 | −0.83 | −1.13 | 0.39 | −0.56 | −1.04 | −0.73 |
| 22 Brain, thalamus | 0.2 | 0.0 | 4.4 | 0.2 | 0.0 | 0.2 | −0.78 | −1.57 | 0.65 | −0.77 | −1.41 | −0.82 |
| 23 Brain, subthalamic nucleus | 0.0 | 0.0 | 0.3 | 0.0 | 0.1 | 0.2 | −1.70 | −2.49 | −0.55 | −1.82 | −1.24 | −0.77 | and 19-2). In the brain tissues, the expression from the transcription initiation points shown by 023_01 (SEQ ID NO:242), 023_03 (SEQ ID NO:248), and 023_04 (SEQ ID NO:251) was abundant, with the expression in Brain, Fetal being particularly abundant (Tables 18-1 and 18-2 and Tables 19-1 and 19-2).

These results demonstrated that by comparing the expression of transcription initiation point regions 023_[1]_1-N1 (SEQ ID NO:208), 023_[1]_2-N1 (SEQ ID NO:214), 023_[2]_1-N1 (SEQ ID NO:220), 023_[2]_2-N1 (SEQ ID NO:226), 023_[3]_1-N1 (SEQ ID NO:232), and 023_[4]_1-N1 (SEQ ID NO:237) of newly acquired cDNAs shown by the detection regions 023_01 (SEQ ID NO:242), 023_02 (SEQ ID NO:245), 023_03 (SEQ ID NO:248), and 023_04 (SEQ ID NO:251), it is possible to use these regions as differentiation markers for detecting nerve cell differentiation or regeneration stages, or as brain-specific markers. It also seems possible to develop a new drug by means of a compound, antibody, siRNA or the like that targets a region that exhibits specificity.

The following regions also seem to be useful as differentiation markers for detecting stages of nerve cell differentiation or regeneration and brain-specific markers.

Upstream sequence 023_[1]_1-N3 (SEQ ID NO:258), which comprises the 191st to 219th bases undergoing priming by Primer023_01R (SEQ ID NO:241) in D-OCBBF2010718.1 of the cDNA pattern [1].

Upstream sequence 023_[1]_2-N3 (SEQ ID NO:259), which comprises the 181st to 204th bases undergoing priming by Primer023_01R (SEQ ID NO:241) in D-OCBBF3004194.1 of the cDNA pattern [1].

Upstream sequence 023_[2]_1-N3 (SEQ ID NO:260), which comprises the 158th to 179th bases undergoing priming by Primer023_02R (SEQ ID NO:244) in D-NT2RP8000826.1 of the cDNA pattern [2].

Upstream sequence 023_[2]_2-N3 (SEQ ID NO:261), which comprises the 161st to 180th bases undergoing priming by Primer023_02R (SEQ ID NO:244) in D-NT2RP7007268.1 of the cDNA pattern [2].

Upstream sequence 023_[3]_1-N3 (SEQ ID NO:262), which comprises the 293rd to 316th bases undergoing priming by Primer023_03R (SEQ ID NO:247) in D-BRAWH3008172.1 of the cDNA pattern [3].

Upstream sequence 023_[4]_1-N3 (SEQ ID NO:263), which comprises the 65th to 84th bases undergoing priming by Primer023_04R (SEQ ID NO:250) in D-BRAWH3011965.1 of the cDNA pattern [4].

Region 023_01 (SEQ ID NO:242) amplified by Primer023_01F (SEQ ID NO:240) and Primer023_01R (SEQ ID NO:241) in the cDNA pattern [1].

Region 023_02 (SEQ ID NO:245) amplified by Primer023_02F (SEQ ID NO:243) and Primer02302R (SEQ ID NO:244) in the cDNA pattern [2].

Region 023_03 (SEQ ID NO:248) amplified by Primer023_03F (SEQ ID NO:246) and Primer02303R (SEQ ID NO:247) in the cDNA pattern [3].

Region 023_04 (SEQ ID NO:251) amplified by Primer023_04F (SEQ ID NO:249) and Primer02304R (SEQ ID NO:250) in the cDNA pattern [4].

Example 14

OFR Information on Full-Length cDNA Sequences and Results of Homology Analysis and Results of Analysis of Motif and the Like To determine the functions of 19 sequences of full-length cDNAs that were newly acquired and subjected to full-length cDNA sequence analysis by us, ORF prediction and annotation analysis were performed. Results of the annotation analysis can be updated when the database or analytical software for comparison is upgraded. Thereby, it is sometimes possible to newly add an annotation to sequences with no annotation given under the same conditions.

1) Prediction of ORFs of cDNAs Undergoing Full-Length cDNA Sequence Analysis

Using ORF prediction/evaluation systems such as ATGpr (A. Salamov et al. (1998) Bioinformatics 14: 384-390) and TRins (K. Kimura et al. (2003) Genome Informatics 14: 456-457), ORFs were predicted from full-length cDNA sequences. The ORF region information predicted from the full-length cDNA sequences is shown below.

The ORF regions were denoted in compliance with the rules of "DDBJ/EMBL/GenBank Feature Table Definition" (http://www.ncbi.nlm.nih.gov/collab/FT/index.html). The ORF start position is the first character of the methionine-encoding base "ATG", and the stop position represents the third character of the stop codon. These are indicated by a partition "..". However, for the ORFs that do not have a stop codon, the stop position is indicated with the use of ">" in compliance with the denotation rules.

| Name of cDNA sequence | ORF region |
|---|---|
| D-UTERU2026184.1 | 191 . . . 2119 |
| D-BRACE3000012.1 | 465 . . . 2558 |
| D-NT2RP8004156.1 | 131 . . . 1387 |
| D-NT2RI3005525.1 | 45 . . . 1292 |
| D-NT2RP8004592.1 | 620 . . . 1183 |
| D-NT2RI2014164.1 | 162 . . . 1397 |
| D-BRAMY2029564.1 | 143 . . . 1657 |
| D-BRHIP2003515.1 | 84 . . . 707 |
| D-BRACE2044661.1 | 297 . . . 878 |
| D-3NB692002462.1 | 343 . . . 951 |
| D-BRCAN2027778.1 | 52 . . . 1086 |
| D-NT2RI3001005.1 | 22 . . . 1629 |
| D-NT2RI3005261.1 | 22 . . . 1629 |
| D-OCBBF2010718.1 | 144 . . . 2495 |
| D-OCBBF3004194.1 | 129 . . . 2480 |
| D-NT2RP8000826.1 | 95 . . . 2461 |
| D-NT2RP7007268.1 | 95 . . . 2461 |
| D-BRAWH3008172.1 | 281 . . . 2452 |
| D-BRAWH3011965.1 | 300 . . . >1574 |

2) Results of Homology Analysis Using BLASTP (Swissprot)

Homology analysis was performed on the 19 ORF sequences shown in Example 14-1, using BLASTP (blastall 2.2.6; ftp://ftp.ncbi.nih.gov/blast/), for SwissProt of the Aug. 22, 2006 version (ftp://us.expasy.org/databases/swiss-prot/). Based on the results of the homology analysis, the sequences showing the highest homology with an E-value of 1E-10 or less are shown below. In the following cases, however, the applicable candidate is not selected, but the next candidate is shown.

Having a definition beginning with "ALU SUBFAMILY"
Having a definition beginning with "Alu subfamily"
Having a definition beginning with "!!!! ALU SUBFAMILY"
Having a definition beginning with "B-CELL GROWTH FACTOR PRECURSOR"
Having a definition including "NRK2"
Having a definition beginning with "PROLINE-RICH"
Having a definition beginning with "GLYCINE-RICH"
Having a definition beginning with "EXTENSIN PRECURSOR"
Having a definition beginning with "COLLAGEN"
Having a definition beginning with "100 KD"

Having a definition beginning with "RETROVIRUS-RELATED POL POLYPROTEIN"
Having a definition beginning with "CUTICLE COLLAGEN"
Having a definition beginning with "HYPOTHETICAL"
Having a definition beginning with "Hypothetical"
Having a definition beginning with "SALIVARY PROLINE-RICH PROTEIN"
Having a definition beginning with "IMMEDIATE-EARLY PROTEIN"
Having the accession No "P49646"

Individual data are shown with the name of cDNA sequence, ORF region, hit data accession number, hit data definition, hit data keyword, E-value, consensus length (amino acid length), and identity, separated by "//" in this order.

D-UTERU2026184.1//191..2119//Q8TF45//Zinc finger protein 418//DNA-binding; Metal-binding; Nuclear protein; Repeat; Repressor; Transcription; Transcription regulation; Zinc; Zinc-finger.//0//601//100

D-BRACE3000012.1//465..2558//Q8TF45//Zinc finger protein 418//DNA-binding; Metal-binding; Nuclear protein; Repeat; Repressor; Transcription; Transcription regulation; Zinc; Zinc-finger.//0//674//99

D-NT2RP8004156.1//131..1387//P31749//RAC-alpha serine/threonine-protein kinase (EC2.7.11.1) (RAC-PK-alpha) (Protein kinase B) (PKB) (C-AKT)//3D-structure; Apoptosis; ATP-binding; Carbohydrate metabolism; Glucose metabolism; Glycogen biosynthesis; Glycogen metabolism; Kinase; Nuclear protein; Nucleotide-binding; Phosphorylation; Serine/threonine-protein kinase; Sugar transport; Transferase; Translation regulation; Transport.//0//418//100

D-NT2RI3005525.1//45..1292//Q7Z698//Sprouty-related, EVH1 domain-containing protein 2 (Spred-2)//Membrane; Phosphorylation.//0//409//99

D-NT2RI2014164.1//162..1397//P27338//Amine oxidase [flavin-containing] B (EC1.4.3.4) (Monoamine oxidase type B) (MAO-B)//3D-structure; Acetylation; Direct protein sequencing; FAD; Flavoprotein; Membrane; Mitochondrion; Oxidoreductase; Transmembrane.//0//367//93

D-BRAMY2029564.1//143..1657//P27338//Amine oxidase [flavin-containing] B (EC1.4.3.4) (Monoamine oxidase type B) (MAO-B)//3D-structure; Acetylation; Direct protein sequencing; FAD; Flavoprotein; Membrane; Mitochondrion; Oxidoreductase; Transmembrane.//0//504//100

D-BRHIP2003515.1//84..707//P55327//Tumor protein D52 (N8 protein)//Coiled coil.//7E-93//184//88

D-BRACE2044661.1//297..878//P54709//Sodium/potassium-transporting ATPase subunitbeta-3 (Sodium/potassium-dependent ATPase beta-3subunit) (ATPB-3) (CD298 antigen)//Glycoprotein; Ion transport; Membrane; Potassium; Potassium transport; Signal-anchor; Sodium; Sodium transport; Sodium/potassium transport; Transmembrane; Transport.//1E-90//158//97

D-3NB692002462.1//343..951//Q03426//Mevalonate kinase (EC 2.7.1.36) (MK)//ATP-binding; Cataract; Cholesterol biosynthesis; Disease mutation; Kinase; Lipid synthesis; Nucleotide-binding; Peroxisome; Polymorphism; Steroid biosynthesis; Sterol biosynthesis; Transferase.//1E-112//202//100

D-BRCAN2027778.1//52..1086//Q03426//Mevalonate kinase (EC 2.7.1.36) (MK)//ATP-binding; Cataract; Cholesterol biosynthesis; Disease mutation; Kinase; Lipid synthesis; Nucleotide-binding; Peroxisome; Polymorphism; Steroid biosynthesis; Sterol biosynthesis; Transferase.//0//343//86

D-NT2RI3001005.1//22..1629//Q8TDB8//Solute carrier family 2, facilitated glucosetransporter member 14 (Glucose transporter type 14)//Alternative splicing; Developmental protein; Differentiation; Glycoprotein; Membrane; Spermatogenesis; Sugar transport; Transmembrane; Transport.//0//490//99

D-NT2RI3005261.1//22..1629//Q8TDB8//Solute carrier family 2, facilitated glucosetransporter member 14 (Glucose transporter type 14)//Alternative splicing; Developmental protein; Differentiation; Glycoprotein; Membrane; Spermatogenesis; Sugar transport; Transmembrane; Transport.//0//491//100

D-OCBBF2010718.1//144..2495//Q9UPQ7//PDZ domain-containing RING finger protein 3 (Ligand of Numb-protein X 3) (Semaphorin cytoplasmicdomain-associated protein 3) (SEMACAP3 protein)//3D-structure; Alternative splicing; Coiled coil; Metal-binding; Polymorphism; Repeat; Zinc; Zinc-finger.//0//758//99

D-OCBBF3004194.1//129..2480//Q9UPQ7//PDZ domain-containing RING finger protein 3 (Ligand of Numb-protein X 3) (Semaphorin cytoplasmicdomain-associated protein 3) (SEMACAP3 protein)//3D-structure; Alternative splicing; Coiled coil; Metal-binding; Polymorphism; Repeat; Zinc; Zinc-finger.//0//760//99

D-NT2RP8000826.1//95..2461//Q9UPQ7//PDZ domain-containing RING finger protein 3 (Ligand of Numb-protein X 3) (Semaphorin cytoplasmicdomain-associated protein 3) (SEMACAP3 protein)//3D-structure; Alternative splicing; Coiled coil; Metal-binding; Polymorphism; Repeat; Zinc; Zinc-finger.//0//759//99

D-NT2RP7007268.1//95..2461//Q9UPQ7//PDZ domain-containing RING finger protein 3 (Ligand of Numb-protein X 3) (Semaphorin cytoplasmicdomain-associated protein 3) (SEMACAP3 protein)//3D-structure; Alternative splicing; Coiled coil; Metal-binding; Polymorphism; Repeat; Zinc; Zinc-finger.//0//759//99

D-BRAWH3008172.1//281..2452//Q9UPQ7//PDZ domain-containing RING finger protein 3 (Ligand of Numb-protein X 3) (Semaphorin cytoplasmicdomain-associated protein 3) (SEMACAP3 protein)//3D-structure; Alternative splicing; Coiled coil; Metal-binding; Polymorphism; Repeat; Zinc; Zinc-finger.//0//722//99

D-BRAWH3011965.1//300.>1574//Q9UPQ7//PDZ domain-containing RING finger protein 3 (Ligand of Numb-protein X 3) (Semaphorin cytoplasmicdomain-associated protein 3) (SEMACAP3 protein)//3D-structure; Alternative splicing; Coiled coil; Metal-binding; Polymorphism; Repeat; Zinc; Zinc-finger.//0//421//99

3) Results of Homology Analysis Using BLASTP (RefSeq)

Homology analysis was performed on the 19 ORF sequences shown in Example 14-1), using BLASTP (blastall 2.2.6; ftp://ftp.ncbi.nih.gov/blast/), for RefSeq of the Jul. 15, 2006 version (human, mouse, rat; ftp://ftp.ncbi.nih.gov/refseq/). Based on the results of the homology analysis, the sequences showing the highest homology with an E-value of 1E-10 or less are shown below. In the following cases, however, the applicable candidate is not selected, but the next candidate is shown.

Having a definition beginning with "hypothetical protein FLJ"
Having a definition beginning with "KIAA"
Having a definition beginning with "hypothetical protein DKFZ"
Having a definition beginning with "DKFZ"

Having a definition beginning with "RIKEN cDNA"
Having a definition beginning with "hypothetical protein MGC"
Having a definition of "hypothetical protein"
Having a definition beginning with "hypothetical protein PP"
Having the definition as "neuronal thread protein"
Having a definition beginning with "clone FLB"
Having a definition beginning with "hypothetical protein PRO"
Having the definition as "PR00483 protein"
Having a definition including "MNC"
Having a definition including "MOST-1"
Having a definition beginning with "similar to"
Having a definition including "TPR gene on Y"
Having a definition beginning with "HSPC"
Having a definition beginning with "CGI-"

Individual data are shown with the name of cDNA sequence, ORF region, hit data accession number, hit data definition, E-value, consensus length (amino acid length), and identity separated by "//" in this order.

D-UTERU2026184.1//191..2119//NP_597717.1//zinc finger protein 418 [Homo sapiens]//0//601//100
D-BRACE3000012.1//465..2558//NP_597717.1//zinc finger protein 418 [Homo sapiens]//0//674//99
D-NT2RP8004156.1//131..1387//NP_005154.2//v-akt murine thymoma viral oncogene homolog 1 [Homo sapiens]//0//418//100
D-NT2RI3005525.1//45..1292//NP_861449.1//sprouty-related protein with EVH-1 domain 2 [Homo sapiens]//0//408//99
D-NT2RP8004592.1//620..1183//NP_003921.2//src family associated phosphoprotein 2 [Homo sapiens]//1E-110//187//100
D-NT2RI2014164.1//162..1397//NP_000889.3//amine oxidase (flavin-containing) [Homo sapiens]//0//367//93
D-BRAMY2029564.1//143..1657//NP_000889.3//amine oxidase (flavin-containing) [Homo sapiens]//0//504//100
D-BRHIP2003515.1//84..707//NP_001020424.1//tumor protein D52 isoform 2 [Homo sapiens]//1E-110//207//100
D-BRACE2044661.1//297..878//NP_001670.1//Na+/K+-ATPase beta 3 subunit [Homo sapiens]//5E-91//158//97
D-3NB692002462.1//343..951//NP_000422.1//mevalonate kinase [Homo sapiens]//1E-112//202//100
D-BRCAN2027778.1//52..1086//NP_000422.1//mevalonate kinase [Homo sapiens]//0//343//86
D-NT2RI3001005.1//22..1629//NP_703150.1//glucose transporter 14 [Homo sapiens]//0//490//99
D-NT2RI3005261.1//22..1629//NP_703150.1//glucose transporter 14 [Homo sapiens]//0//491//100
D-OCBBF2010718.1//144..2495//NP_055824.1//PDZ domain containing RING finger 3 [Homo sapiens]//0//758//99
D-OCBBF3004194.1//129..2480//NP_055824.1//PDZ domain containing RING finger 3 [Homo sapiens]//0//760//99
D-NT2RP8000826.1//95..2461//NP_055824.1//PDZ domain containing RING finger 3 [Homo sapiens]//0//759//99
D-NT2RP7007268.1//95..2461//NP_055824.1//PDZ domain containing RING finger 3 [Homo sapiens]//0//759//99
D-BRAWH3008172.1//281..2452//NP_055824.1//PDZ domain containing RING finger 3 [Homo sapiens]//0//722//99
D-BRAWH3011965.1//300.>1574//NP_055824.1//PDZ domain containing RING finger 3 [Homo sapiens]//0//421//99

4) Results of Motif Homology Analysis Using Pfam

Motif homology analysis was performed on the 19 ORF sequences shown in Example 14-1), using Pfam (ftp://ftp.sanger.ac.uk/pub/databases/Pfam/). The analytical program used was hmmpfam v2.3.2, and the analysis was performed for the November 2005 version of Pfam19.0. Based on the results of the homology analysis, the sequences showing the highest homology with an E-value of 1E-10 or less are shown below.

Individual data are shown with the name of cDNA sequence and ORF region, followed by hit data accession number, hit data name, hit data description, E-value, and InterPro ID, separated by "¥" in this order, presented repeatedly using as many "//" partitions as the hit data.

D-BRACE3000012.1//465..2558//
  PF01352.15¥KRAB¥KRAB box¥2.1e-20¥IPR001909
D-NT2RP8004156.1//131..1387//
  PF00069.14¥Pkinase¥Protein kinase domain¥1.6e-113¥IPR000719//PF07714.5¥Pkinase_Tyr¥Protein tyrosine kinase¥1.3e-18¥//PF00433.12¥Pkinase_C¥Protein kinase C terminal domain¥1.4e-11¥IPR000961
D-NT2RI3005525.1//45..1292//
  PF05210.2¥Sprouty¥Sprouty protein (Spry) ¥2.7e-11¥IPR007875
D-NT2RI2014164.1//162..1397//
  PF01593.12¥Amino_oxidase—Flavin containing amine oxidoreductase¥9.2e-57¥IPR002937
D-BRAMY2029564.1//143..1657//
  PF01593.12¥Amino_oxidase¥Flavin containing amine oxidoreductase¥5.8e-103¥IPR002937
D-BRHIP2003515.1//84..707//PF04201.4¥TPD52¥Tumour protein D52 family¥1.5e-119¥IPR007327
D-BRACE2044661.1//297..878//PF00287.7¥Na_K-ATPase¥Sodium/potassium ATPase beta chain¥3.1e-32¥IPR000402
D-NT2RI3001005.1//22..1629//
  PF00083.13¥Sugar_tr¥Sugar (and other) transporter¥6.3e-200¥IPR005828//PF07690.5¥MFS_1¥Major Facilitator Superfamily¥1.1e-14¥IPR011701
D-NT2RI3005261.1//22..1629//
  PF00083.13¥Sugar_tr¥Sugar (and other) transporter¥5.5e-200¥IPR005828//PF07690.5¥MFS_1¥Major Facilitator Superfamily¥1.1e-14¥IPR011701
D-OCBBF2010718.1//144..2495//PF00595.12¥PDZ¥PDZ domain (Also known as DHR or GLGF) ¥2e-14¥IPR001478
D-OCBBF3004194.1//129..2480//PF00595.12¥PDZ¥PDZ domain (Also known as DHR or GLGF) ¥7.1e-16¥IPR001478
D-NT2RP8000826.1//95..2461//PF00595.12¥PDZ¥PDZ domain (Also known as DHR or GLGF) ¥7.1e-16¥IPR001478
D-NT2RP7007268.1//95..2461//PF00595.12¥PDZ¥PDZ domain (Also known as DHR or GLGF) ¥7.1e-16¥IPR001478
D-BRAWH3008172.1//281..2452//PF00595.12¥PDZ¥PDZ domain (Also known as DHR or GLGF) ¥7.1e-16¥IPR001478
D-BRAWH3011965.1//300.>1574//PF00595.12¥PDZ¥PDZ domain (Also known as DHR or GLGF) 17.1e-16¥IPR001478

5) Transmembrane Domain Prediction Analysis Using SOSUI

Transmembrane domain prediction analysis was performed on the 19 ORF sequences shown in Example 14-1), using SOSUI (http://bp.nuap.nagoya-u.ac.jp/sosui/). For the analysis, SOSUI version 1.5 was used. The sequences that permitted prediction of the transmembrane domain in the SOSUI analysis are shown below.

Individual data are shown with the name of cDNA sequence, ORF region, and number of transmembrane domain separated by "//".
D-NT2RI3005525.1//45..1292//1
D-BRACE2044661.1//297..878//2
D-NT2RI3001005.1//22..1629//11
D-NT2RI3005261.1//22..1629//11

6) N-Terminal Secretion Signal Sequence Prediction Analysis Using PSORT

N-terminal secretion signal sequence prediction was performed on the 19 ORF sequences shown in Example 14-1), using PSORT (http://psort.nibb.ac.jp/). PSORT II was used for the analysis.

In the PSORT analysis, no sequences permitted prediction of the N-terminal secretion signal sequence.

7) N-Terminal Secretion Signal Sequence Prediction Analysis Using SignalP Ver.3.0

N-terminal secretion signal sequence prediction was performed on the 19 ORF sequences shown in Example 14-1), using SignalP (http://www.cbs.dtu.dk/services/SignalP/). SignalP version 3.0 was used for the analysis. Sequences that permitted prediction of the N-terminal secretion signal sequence in the SignalP analysis are shown below.

Individual data are shown with the name of cDNA sequence and ORF region separated by "//".
D-BRACE2044661.1//297..878

Summary of Examples 1 to 14

Although there have been remarkable advances in the analysis of human chromosome sequences thanks to the progress in human genome research, this does not mean that all the human genetic functions have been clarified. We analyzed human genes with a focus on the diversity thereof, and showed that the diversity is largely associated with gene functional changes.

By comparing human genome sequence information and data on human cDNAs, which are products of transcription therefrom, it was found that a plurality of mRNAs are transcribed from certain regions of chromosome. They occur in two cases: a case wherein there are different ORF regions predicted to encode and produce different proteins, and another case wherein there are different 5'UTR regions or 3'UTR regions, which are noncoding regions, and the same protein is produced. With an emphasis on cDNAs predicted to encode proteins different from those of known cDNAs that have already been analyzed, in particular, we performed search and sequence analysis of such cDNAs. Hence, it was found that the cause of the diversity resides mainly in transcription initiation point selectivity and exon selectivity. Regarding transcription initiation point selectivity, a change of the transcription factor used in a certain chromosome region produced a different position for transcription initiation, resulting in the cDNA diversity. As for exon selectivity, an increase or decrease in the exon used, despite transcription from the same chromosome region, at the time of transcription and splicing, resulted in the cDNA diversity.

How the genetic diversity is associated with gene functions was analyzed on the basis of our own information on the expression frequencies of mRNAs by the 5'-terminal sequences of about 1.50 million human cDNAs (5'-onepass sequences). Hence, a large number of cases were found wherein gene functions seemed to be significantly influenced by diversity features, including variation of transcription initiation region selective in a certain organ, and deletion of exon in a certain condition. We discovered genes whose diversity varies depending on the brain tissue portion and nerve cell differentiation stage, and conducted extensive analyses.

Regarding the analytical method, the expression levels were compared using real-time PCR (polymerase chain reaction). For example, assuming an exon predicted to be inserted selectively only after differentiation into nerve cells, a primer that specifically detects the exon region (01) is designed, a primer that specifically detects the pattern in which the exon is not inserted (02) is designed, and a primer that detects a region having both patterns in common (03) is designed. With the use of these 3 kinds of primers, the amounts amplified at the various stages of nerve cell differentiation are compared. The specific region detection results for 01 and 02 are compared with the amount amplified for the shared region 03 as the control at various stages of nerve cell differentiation, whereby it is possible to know how the exon selectivity was changed by nerve cell differentiation. Hence, the correlation between exon selectivity and tissue specific expression can be assessed.

By this method, we discovered many genes whose diversity is associated with tissue-specific expression. Being specific for the tissue in which the gene is expressed suggests that the diversity may significantly influence the function of the gene. Hence, by using a specific region with diversity as a gene is marker, it seems possible to elucidate the function of a particular portion of the brain, and to detect nerve cell differentiation or regeneration stages in detail. Furthermore, for example, by proceeding to develop a pharmaceutical with a protein having a specific region expressed only at a certain stage of nerve cell differentiation or regeneration as the target, it seems possible to develop a pharmaceutical that is more effective with lower prevalence of adverse reactions.

<Explanation of Nerve Cell Differentiation>

The mRNAs related to nerve cell differentiation (mRNAs that induce differentiation of nervous system cells and exhibit an expressional change) are thought to be useful as therapeutic/diagnostic markers for nerve disease. By searching for an mRNA that exhibits an expressional change during the process of inducing differentiation of cultured human cells NT2 into nerve cells (retinoic acid (RA) stimulation or RA stimulation followed by treatment with growth inhibitor), such an mRNA can be discovered. These mRNAs are also thought to be associated with nerve regeneration.

<Explanation of Various Portions of the Brain>

1) Hippocampus

Among the brain tissues, the hippocampus is a very important portion that controls memory, having the function of fixing memory by determining whether or not the information obtained is necessary, and allowing other brain portions to store the memory. Clinical findings show that if the hippocampus is disordered, or, in the worst case, if the hippocampus is lacked, one is only able to remember new things for a short time. Some patients with dementia are thought to have an abnormality in the hippocampus. When comparing the whole brain tissue and the hippocampus, the mRNAs exhibiting expressional variation are mRNAs involved in memory or associated with dementia, and are thought to be useful in elucidating the mechanism for memory and as therapeutic/diagnostic markers.

2) Caudate Nucleus

The hippocampal system is a portion that is important to memory associated with spatial cognition. Spatial cognition is also said to be memory of remembering places. By contrast, the caudate nucleus is said to be a portion that is important to memory acquired through habits (habitual memory).

3) Amygdala

The amygdala is the emotional center of the brain. The information that has passed the amygdala causes emotional reactions, for example, panic and fear reactions. If a strong fear is produced upon affect assessment of a stimulus by the amygdala, the amygdala transmits warning signals to various portions of the brain. As a result, reactions such as palm sweating, palpitation, blood pressure elevation, and rapid secretion of adrenaline occur. The amygdala can also be said to be a tissue that controls a kind of instinct of defense in which warning signals are transmitted to the body to make the body in a warning state. When comparing the whole brain tissue and the amygdala, the mRNAs exhibiting expressional variation are mRNAs involved in emotional reactions, and are thought to be useful in elucidating the molecular mechanisms for emotional reactions, fear reactions, panic and the like.

4) Cerebellum

The cerebellum is the center of equilibrium, muscle movement, and motor learning. This region is thought to be involved in motor regulation; as the cerebellum acts, one can make smooth motions involuntarily. There is also increasing evidence for the involvement of the cerebellum not only in physical movement, but also in the habituation of higher movements such as reading and writing. When comparing the brain tissue as a whole and the cerebellum, the mRNAs exhibiting expressional variation are mRNAs involved in equilibrium and motor functions, and are thought to be useful in elucidating the molecular mechanisms for the motor functions under the control of the brain.

5) Thalamus

The thalamus is a portion where nerve cells that are highly associated with the cerebrum gather, transferring sensory information from the spinal cord and the like to the relevant portions of the cerebrum, and regulating the motor commands of the cerebrum. For example, in visual sensation, images are separated into size, shape, and color, and in auditory sensation, sounds are separated into volume and comfortability and sent to the sensory area of cerebral cortex. When comparing the whole brain tissue and the thalamus, the mRNAs exhibiting expressional variation are mRNAs involved in signal transduction from sensory organs, and are thought to be useful in elucidating the molecular mechanism for the signal transduction under the control of the brain.

6) Substantia Nigra

The substantia nigra is a nerve nucleus that occupies a portion of the midbrain. The substantia nigra is roughly divided into two portions: pars compacta and pars reticulata (and lateral portion), both of which are central constituents of the basal ganglion. The basal ganglion, along with the cerebellum, is known as a higher center responsible for important roles in the onset and control of voluntary movement. The basal ganglion roughly consists of the four nerve nuclei, i.e., striate body, pallidum, substantia nigra, and subthalamic nucleus, the striate body being divided into the caudate nucleus and the putamen, the pallidum into the lateral segment and the medial segment, and the substantia nigra into the pars compacta and the pars reticulata. When these nerve nuclei are re-classified from the viewpoint of the signal transduction modes of "input", "output", and "mutual communication", the striate body corresponds to the input portion of the basal ganglion, and the pallidal medial segment and the substantia nigra pars reticulata correspond to the output portion thereof. Connecting the input portion and the output portion indirectly, the pallidal lateral segment and the subthalamic nucleus are thought to be an interface of the basal ganglion; modifying the nervous activity of the striate body by dopamine, the substantia nigra pars compacta is thought to be a modifying portion of the basal ganglion.

An illness of the cerebro-nervous system characterized by an insufficient production of a neurotransmitter produced in the substantia nigra in the brain, known as dopamine, resulting in motor disorders such as hand tremor and stiffening of muscles making physical movement dull, is said to be Parkinson's disease. Brain nerve cells usually decrease little by little with aging; in Parkinson's disease, nerve cells of the substantia nigra decrease remarkably at higher rates than usual.

When comparing the whole brain tissue and the substantia nigra, the mRNAs exhibiting expressional variation are thought to be mRNAs involved in the above events.

7) Alzheimer Patient's Cerebral Cortex

Alzheimer's disease is an illness of the cerebro-nervous system characterized by loss of memory, that hampers daily activities and necessitates nursing care in advanced cases, eventually leading to atrophy of the brain. Although the causes of the onset thereof are said to be associated with environmental factors such as stress, as well as vascular factors such as hypertension and cholesterolemia, they have not been investigated in full. Therefore, when comparing normal brain tissue and Alzheimer pathologic tissues, the mRNAs exhibiting expressional variation are mRNAs associated with Alzheimer's disease, and are thought to be useful in elucidating the mechanisms for the onset of pathologic conditions, and as therapeutic/diagnostic markers.

This application is based on a patent application No. 2007-066430 filed in Japan (filing date: Mar. 15, 2007), the contents of which are incorporated in full herein by this reference.

[Sequence Listing]

SEQUENCE LISTING

```
<160> NUMBER OF SEQ ID NOS: 266

<210> SEQ ID NO 1
<211> LENGTH: 30
<212> TYPE: RNA
<213> ORGANISM: Artificial Sequence
<220> FEATURE:
<223> OTHER INFORMATION: synthesized oligo-cap linker used for oligo-cap
      method

<400> SEQUENCE: 1
agcaucgagu cggccuuguu ggccuacugg                                      30
```

```
<210> SEQ ID NO 2
<211> LENGTH: 42
<212> TYPE: DNA
<213> ORGANISM: Artificial Sequence
<220> FEATURE:
<223> OTHER INFORMATION: synthesized oligo(dT) primer used for oligo-cap
      method

<400> SEQUENCE: 2
gcggctgaag acggcctatg tggcctttttt tttttttttt tt                           42

<210> SEQ ID NO 3
<211> LENGTH: 21
<212> TYPE: DNA
<213> ORGANISM: Artificial Sequence
<220> FEATURE:
<223> OTHER INFORMATION: forward primer used for preparing cDNA library

<400> SEQUENCE: 3
agcatcgagt cggccttgtt g                                                   21

<210> SEQ ID NO 4
<211> LENGTH: 21
<212> TYPE: DNA
<213> ORGANISM: Artificial Sequence
<220> FEATURE:
<223> OTHER INFORMATION: reverse primer used for preparing cDNA library

<400> SEQUENCE: 4
gcggctgaag acggcctatg t                                                   21

<210> SEQ ID NO 5
<211> LENGTH: 22
<212> TYPE: DNA
<213> ORGANISM: Artificial Sequence
<220> FEATURE:
<223> OTHER INFORMATION: forward primer used for detecting a
      polynucleotide encoding GAPDH

<400> SEQUENCE: 5
ccaggtggtc tcctctgact tc                                                  22

<210> SEQ ID NO 6
<211> LENGTH: 19
<212> TYPE: DNA
<213> ORGANISM: Artificial Sequence
<220> FEATURE:
<223> OTHER INFORMATION: reverse primer used for detecting a
      polynucleotide encoding GAPDH

<400> SEQUENCE: 6
gtggtcgttg agggcaatg                                                      19

<210> SEQ ID NO 7
<211> LENGTH: 25
<212> TYPE: DNA
<213> ORGANISM: Artificial Sequence
<220> FEATURE:
<223> OTHER INFORMATION: probe used for detecting a polynucleotide
      encoding GAPDH

<400> SEQUENCE: 7
acagcgacac ccactcctcc acctt                                               25

<210> SEQ ID NO 8
<211> LENGTH: 2499
<212> TYPE: DNA
<213> ORGANISM: Homo sapiens
```

```
<400> SEQUENCE: 8
ggtagcgacc attttggtta atgttgggtg tgtttctgcg gtttgtgagg tgagaggcgc      60
tggagctatg ggtccgaacc gcggtgtctg aacccagaag gtgaagagtc cttcttgctg     120
cacagaggca gatcttaggc cccgtaacgg cgcccgccgc tcccggcagt gctttccccg     180
cgtactcggg atggcggcgg ccgcgctgag gctcccggct caggttgttg gtgtggatca     240
gaagatgagg aggcaccttc taagaagagc atttctatac aaagagtgtc tcaggtcagc     300
actcctgggg caggtgtctc ccaagaaggc tcactcttgt gaaatgtgtg gcgcgatctt     360
gggagacatt ttgcacttgg cagatcatca ggggacacat cacaagcaga aactgcacag     420
gtgtgaggca tgggggaata aattgtatga tagttcaaac cgtccgcacc agaatcagta     480
ccttggagag aaaccctata gaagcagtgt tgaggaagca ttgtttgtga agaggtgtaa     540
gttccatgtg tcagaggagt catctatctt cattcagagt ggaaaggact ttttgcccag     600
ctcaggatta ctgctgcagg aggccactca cactggggag aagtcaaaca gcaaacctga     660
gtgtgagtct ccctttcagt ggggagatac tcattacagc tgtggagaat gcatgaaaca     720
ttctagcacc aaacacgtat tgttcaaca gcagagactt ccctctagag aggaatgtta     780
ttgctgggaa tgtgggaaat cctttagcaa atatgatagc gtcagtaatc atcagagagt     840
tcacactggg aaaagacctt atgaatgtgg agaatgtggg aaatctttta gtcataaggg     900
cagccttgtt cagcatcagc gagttcacac tgggaaaaga ccttatgaat gtggagaatg     960
tgggaaatct tttagtcata agggcagcct tgttcagcat cagcgagttc atactggaga    1020
aagaccttat gagtgtggag aatgtgggaa atcttttagt caaaatggta ctctcattaa    1080
acatcaacga gttcacactg gagaaagacc ttatgagtgt gaagaatgtg ggaaatgttt    1140
tactcagaag ggcaatctca ttcaacatca acgaggtcac actagtgaaa gaccttatga    1200
gtgtgaagaa tgtggaaaat gttttagtca aaagggcacc ctaactgaac atcatcgagt    1260
tcacactaga gaacgacctt atgagtgtgg agaatgtggg aaatctttta gtcgaaaggg    1320
acacctttagg aaccatcagc gaggtcacac tggagaaaga ccttacgagt gtggagaatg    1380
tgggaaatct tttagtcgaa agggcaacct cattcagcat cagcgaagcc acactggaga    1440
aaggccttat gagtgtagag agtgtaggaa attatttagg ggcaagtccc acctcattga    1500
acaccagaga gttcacactg gagaaaggcc atatgaatgt aatgaatgtg ggaaatcatt    1560
tcaagacagc tctgggtttc gtgttcatca gagagttcac actggagaaa accgtttga    1620
gtgtagtgaa tgtgggaagt catttcctca aagctgttcc ctccttcgac atcggagagt    1680
tcatactgga gaaaggcctt atgaatgtgg agaatgtgga aagtcatttc atcagagctc    1740
ttccctcctt cgacatcaga aaacccacac tgcagaaaga ccttatgagt gcagagaatg    1800
tgggaaattc ttctccagtc tccttgaaca caggagagtt cacactggag aaaggcctta    1860
tgagtgcagg aatgtggaa aaacatttac tcgaaggtct gcgcattttaa acatcagag    1920
acttcatact cgaggaaagc cttacgagtg cagcgaatgt gggaaatcct tgctgaaac    1980
cttcagtctt actgaacaca ggagagtaca cactggagaa aggccttatg agtgcagtga    2040
atgtggaaaa tcatttcatc gaagctcttc tctccttcga catcagagag ttcacacaga    2100
aagaagtcct tacaagtgaa aagaaatttg ggaaattctt tagctaaacc tctgtgcatc    2160
ttcttgatca gagggttctt actggatcag gacctatga gtgtgacaaa cgtgggatat    2220
tctttatgca gaagtcttgt tttattacat acagaagagc tcccactgca gaagggcctc    2280
ttgagtgcga tgaatgtgag aaagccttct gccttctgtc attggataac agattgttct    2340
```

```
cataaggaaa acactgtaca cgtacaggaa atattatttc ttgtaaaaca taacactgga    2400
ggagatgcct tatgacggag ccatctgcct aaattgacat accttcagca tctgcataaa    2460
ctcaattatg ttggagctgt gtggcatttt tcaccctgc                           2499

<210> SEQ ID NO 9
<211> LENGTH: 2499
<212> TYPE: DNA
<213> ORGANISM: Homo sapiens
<221> NAME/KEY: CDS
<222> LOCATION: (191)..(2119)

<400> SEQUENCE: 9
ggtagcgacc attttggtta atgttgggtg tgtttctgcg gtttgtgagg tgagaggcgc       60
tggagctatg ggtccgaacc gcggtgtctg aacccagaag gtgaagagtc cttcttgctg      120
cacagaggca gatcttaggc cccgtaacgg cgcccgccgc tcccggcagt gctttccccg      180
cgtactcggg atg gcg gcg gcc gcg ctg agg ctc ccg gct cag gtt gtt         229
            Met Ala Ala Ala Ala Leu Arg Leu Pro Ala Gln Val Val
              1               5                  10 ggt gtg gat cag aag atg agg agg cac ctt cta aga aga gca ttt cta       277
Gly Val Asp Gln Lys Met Arg Arg His Leu Leu Arg Arg Ala Phe Leu
 15                  20                  25 tac aaa gag tgt ctc agg tca gca ctc ctg ggg cag gtg tct ccc aag       325
Tyr Lys Glu Cys Leu Arg Ser Ala Leu Leu Gly Gln Val Ser Pro Lys
 30                  35                  40                  45 aag gct cac tct tgt gaa atg tgt ggc gcg atc ttg gga gac att ttg       373
Lys Ala His Ser Cys Glu Met Cys Gly Ala Ile Leu Gly Asp Ile Leu
                 50                  55                  60 cac ttg gca gat cat cag ggg aca cat cac aag cag aaa ctg cac agg       421
His Leu Ala Asp His Gln Gly Thr His His Lys Gln Lys Leu His Arg
         65                  70                  75 tgt gag gca tgg ggg aat aaa ttg tat gat agt tca aac cgt ccg cac       469
Cys Glu Ala Trp Gly Asn Lys Leu Tyr Asp Ser Ser Asn Arg Pro His
     80                  85                  90 cag aat cag tac ctt gga gag aaa ccc tat aga agc agt gtt gag gaa       517
Gln Asn Gln Tyr Leu Gly Glu Lys Pro Tyr Arg Ser Ser Val Glu Glu
 95                 100                 105 gca ttg ttt gtg aag agg tgt aag ttc cat gtg tca gag gag tca tct       565
Ala Leu Phe Val Lys Arg Cys Lys Phe His Val Ser Glu Glu Ser Ser
110                 115                 120                 125 atc ttc att cag agt gga aag gac ttt ttg ccc agc tca gga tta ctg       613
Ile Phe Ile Gln Ser Gly Lys Asp Phe Leu Pro Ser Ser Gly Leu Leu
                130                 135                 140 ctg cag gag gcc act cac act ggg gag aag tca aac agc aaa cct gag       661
Leu Gln Glu Ala Thr His Thr Gly Glu Lys Ser Asn Ser Lys Pro Glu
        145                 150                 155 tgt gag tct ccc ttt cag tgg gga gat act cat tac agc tgt gga gaa       709
Cys Glu Ser Pro Phe Gln Trp Gly Asp Thr His Tyr Ser Cys Gly Glu
    160                 165                 170 tgc atg aaa cat tct agc acc aaa cac gta ttt gtt caa cag cag aga       757
Cys Met Lys His Ser Ser Thr Lys His Val Phe Val Gln Gln Gln Arg
175                 180                 185 ctt ccc tct aga gag gaa tgt tat tgc tgg gaa tgt ggg aaa tcc ttt       805
Leu Pro Ser Arg Glu Glu Cys Tyr Cys Trp Glu Cys Gly Lys Ser Phe
190                 195                 200                 205 agc aaa tat gat agc gtc agt aat cat cag aga gtt cac act ggg aaa       853
Ser Lys Tyr Asp Ser Val Ser Asn His Gln Arg Val His Thr Gly Lys
                210                 215                 220 aga cct tat gaa tgt gga gaa tgt ggg aaa tct ttt agt cat aag ggc       901
```

```
                Arg Pro Tyr Glu Cys Gly Glu Cys Gly Lys Ser Phe Ser His Lys Gly
                                225                 230                 235 agc ctt gtt cag cat cag cga gtt cac act ggg aaa aga cct tat gaa        949
Ser Leu Val Gln His Gln Arg Val His Thr Gly Lys Arg Pro Tyr Glu
        240                 245                 250 tgt gga gaa tgt ggg aaa tct ttt agt cat aag ggc agc ctt gtt cag        997
Cys Gly Glu Cys Gly Lys Ser Phe Ser His Lys Gly Ser Leu Val Gln
255                 260                 265 cat cag cga gtt cat act gga gaa aga cct tat gag tgt gga gaa tgt       1045
His Gln Arg Val His Thr Gly Glu Arg Pro Tyr Glu Cys Gly Glu Cys
270                 275                 280                 285 ggg aaa tct ttt agt caa aat ggt act ctc att aaa cat caa cga gtt       1093
Gly Lys Ser Phe Ser Gln Asn Gly Thr Leu Ile Lys His Gln Arg Val
                290                 295                 300 cac act gga gaa aga cct tat gag tgt gaa gaa tgt ggg aaa tgt ttt       1141
His Thr Gly Glu Arg Pro Tyr Glu Cys Glu Glu Cys Gly Lys Cys Phe
                305                 310                 315 act cag aag ggc aat ctc att caa cat caa cga ggt cac act agt gaa       1189
Thr Gln Lys Gly Asn Leu Ile Gln His Gln Arg Gly His Thr Ser Glu
        320                 325                 330 aga cct tat gag tgt gaa gaa tgt gga aaa tgt ttt agt caa aag ggc       1237
Arg Pro Tyr Glu Cys Glu Glu Cys Gly Lys Cys Phe Ser Gln Lys Gly
335                 340                 345 acc cta act gaa cat cat cga gtt cac act aga gaa cga cct tat gag       1285
Thr Leu Thr Glu His His Arg Val His Thr Arg Glu Arg Pro Tyr Glu
350                 355                 360                 365 tgt gga gaa tgt ggg aaa tct ttt agt cga aag gga cac ctt agg aac       1333
Cys Gly Glu Cys Gly Lys Ser Phe Ser Arg Lys Gly His Leu Arg Asn
                370                 375                 380 cat cag cga ggt cac act gga gaa aga cct tac gag tgt gga gaa tgt       1381
His Gln Arg Gly His Thr Gly Glu Arg Pro Tyr Glu Cys Gly Glu Cys
                385                 390                 395 ggg aaa tct ttt agt cga aag ggc aac ctc att cag cat cag cga agc       1429
Gly Lys Ser Phe Ser Arg Lys Gly Asn Leu Ile Gln His Gln Arg Ser
                400                 405                 410 cac act gga gaa agg cct tat gag tgt aga gag tgt agg aaa tta ttt       1477
His Thr Gly Glu Arg Pro Tyr Glu Cys Arg Glu Cys Arg Lys Leu Phe
        415                 420                 425 agg ggc aag tcc cac ctc att gaa cac cag aga gtt cac act gga gaa       1525
Arg Gly Lys Ser His Leu Ile Glu His Gln Arg Val His Thr Gly Glu
430                 435                 440                 445 agg cca tat gaa tgt aat gaa tgt ggg aaa tca ttt caa gac agc tct       1573
Arg Pro Tyr Glu Cys Asn Glu Cys Gly Lys Ser Phe Gln Asp Ser Ser
                450                 455                 460 ggg ttt cgt gtt cat cag aga gtt cac act gga gaa aaa ccg ttt gag       1621
Gly Phe Arg Val His Gln Arg Val His Thr Gly Glu Lys Pro Phe Glu
                465                 470                 475 tgt agt gaa tgt ggg aag tca ttt cct caa agc tgt tcc ctc ctt cga       1669
Cys Ser Glu Cys Gly Lys Ser Phe Pro Gln Ser Cys Ser Leu Leu Arg
                480                 485                 490 cat cgg aga gtt cat act gga gaa agg cct tat gaa tgt gga gaa tgt       1717
His Arg Arg Val His Thr Gly Glu Arg Pro Tyr Glu Cys Gly Glu Cys
        495                 500                 505 gga aag tca ttt cat cag agc tct tcc ctc ctt cga cat cag aaa acc       1765
Gly Lys Ser Phe His Gln Ser Ser Ser Leu Leu Arg His Gln Lys Thr
510                 515                 520                 525 cac act gca gaa aga cct tat gag tgc aga gaa tgt ggg aaa ttc ttc       1813
His Thr Ala Glu Arg Pro Tyr Glu Cys Arg Glu Cys Gly Lys Phe Phe
                530                 535                 540 tcc agt ctc ctt gaa cac agg aga gtt cac act gga gaa agg cct tat       1861
```

```
Ser Ser Leu Leu Glu His Arg Arg Val His Thr Gly Glu Arg Pro Tyr
            545                 550                 555 gag tgc agg gaa tgt gga aaa aca ttt act cga agg tct gcg cat ttt      1909
Glu Cys Arg Glu Cys Gly Lys Thr Phe Thr Arg Arg Ser Ala His Phe
        560                 565                 570 aaa cat cag aga ctt cat act cga gga aag cct tac gag tgc agc gaa      1957
Lys His Gln Arg Leu His Thr Arg Gly Lys Pro Tyr Glu Cys Ser Glu
575                 580                 585 tgt ggg aaa tcc ttt gct gaa acc ttc agt ctt act gaa cac agg aga      2005
Cys Gly Lys Ser Phe Ala Glu Thr Phe Ser Leu Thr Glu His Arg Arg
590                 595                 600                 605 gta cac act gga gaa agg cct tat gag tgc agt gaa tgt gga aaa tca      2053
Val His Thr Gly Glu Arg Pro Tyr Glu Cys Ser Glu Cys Gly Lys Ser
                610                 615                 620 ttt cat cga agc tct tct ctc ctt cga cat cag aga gtt cac aca gaa      2101
Phe His Arg Ser Ser Ser Leu Leu Arg His Gln Arg Val His Thr Glu
                625                 630                 635 aga agt cct tac aag tga aaagaaattt gggaaattct ttagctaaac             2149
Arg Ser Pro Tyr Lys
                640 ctctgtgcat cttcttgatc agagggttct tactggatca ggaccttatg agtgtgacaa    2209 acgtgggata ttctttatgc agaagtcttg ttttattaca tacagaagag ctcccactgc    2269 agaagggcct cttgagtgcg atgaatgtga gaaagccttc tgccttctgt cattggataa    2329 cagattgttc tcataaggaa aacactgtac acgtacagga aatattattt cttgtaaaac    2389 ataacactgg aggagatgcc ttatgacgga gccatctgcc taaattgaca taccttcagc    2449 atctgcataa actcaattat gttggagctg tgtggcattt ttcaccctgc               2499

<210> SEQ ID NO 10
<211> LENGTH: 642
<212> TYPE: PRT
<213> ORGANISM: Homo sapiens

<400> SEQUENCE: 10

Met Ala Ala Ala Leu Arg Leu Pro Ala Gln Val Val Gly Val Asp
1               5                   10                  15

Gln Lys Met Arg Arg His Leu Leu Arg Arg Ala Phe Leu Tyr Lys Glu
            20                  25                  30

Cys Leu Arg Ser Ala Leu Leu Gly Gln Val Ser Pro Lys Lys Ala His
        35                  40                  45

Ser Cys Glu Met Cys Gly Ala Ile Leu Gly Asp Ile Leu His Leu Ala
    50                  55                  60

Asp His Gln Gly Thr His His Lys Gln Lys Leu His Arg Cys Glu Ala
65                  70                  75                  80

Trp Gly Asn Lys Leu Tyr Asp Ser Ser Asn Arg Pro His Gln Asn Gln
                85                  90                  95

Tyr Leu Gly Glu Lys Pro Tyr Arg Ser Ser Val Glu Glu Ala Leu Phe
            100                 105                 110

Val Lys Arg Cys Lys Phe His Val Ser Glu Glu Ser Ile Phe Ile
        115                 120                 125

Gln Ser Gly Lys Asp Phe Leu Pro Ser Ser Gly Leu Leu Gln Glu
    130                 135                 140

Ala Thr His Thr Gly Glu Lys Ser Asn Ser Lys Pro Glu Cys Glu Ser
145                 150                 155                 160

Pro Phe Gln Trp Gly Asp Thr His Tyr Ser Cys Gly Glu Cys Met Lys
                165                 170                 175
```

-continued

```
His Ser Ser Thr Lys His Val Phe Val Gln Gln Arg Leu Pro Ser
            180                 185                 190

Arg Glu Glu Cys Tyr Cys Trp Glu Cys Gly Lys Ser Phe Ser Lys Tyr
            195                 200                 205

Asp Ser Val Ser Asn His Gln Arg Val His Thr Gly Lys Arg Pro Tyr
210                 215                 220

Glu Cys Gly Glu Cys Gly Lys Ser Phe Ser His Lys Gly Ser Leu Val
225                 230                 235                 240

Gln His Gln Arg Val His Thr Gly Lys Arg Pro Tyr Glu Cys Gly Glu
            245                 250                 255

Cys Gly Lys Ser Phe Ser His Lys Gly Ser Leu Val Gln His Gln Arg
            260                 265                 270

Val His Thr Gly Glu Arg Pro Tyr Glu Cys Gly Glu Cys Gly Lys Ser
            275                 280                 285

Phe Ser Gln Asn Gly Thr Leu Ile Lys His Gln Arg Val His Thr Gly
            290                 295                 300

Glu Arg Pro Tyr Glu Cys Glu Cys Gly Lys Cys Phe Thr Gln Lys
305                 310                 315                 320

Gly Asn Leu Ile Gln His Gln Arg Gly His Thr Ser Glu Arg Pro Tyr
            325                 330                 335

Glu Cys Glu Cys Gly Lys Cys Phe Ser Gln Lys Gly Thr Leu Thr
            340                 345                 350

Glu His His Arg Val His Thr Arg Glu Arg Pro Tyr Glu Cys Gly Glu
            355                 360                 365

Cys Gly Lys Ser Phe Ser Arg Lys Gly His Leu Arg Asn His Gln Arg
            370                 375                 380

Gly His Thr Gly Glu Arg Pro Tyr Glu Cys Gly Glu Cys Gly Lys Ser
385                 390                 395                 400

Phe Ser Arg Lys Gly Asn Leu Ile Gln His Gln Arg Ser His Thr Gly
            405                 410                 415

Glu Arg Pro Tyr Glu Cys Arg Glu Cys Arg Lys Leu Phe Arg Gly Lys
            420                 425                 430

Ser His Leu Ile Glu His Gln Arg Val His Thr Gly Glu Arg Pro Tyr
            435                 440                 445

Glu Cys Asn Glu Cys Gly Lys Ser Phe Gln Asp Ser Ser Gly Phe Arg
            450                 455                 460

Val His Gln Arg Val His Thr Gly Glu Lys Pro Phe Glu Cys Ser Glu
465                 470                 475                 480

Cys Gly Lys Ser Phe Pro Gln Ser Cys Ser Leu Leu Arg His Arg Arg
            485                 490                 495

Val His Thr Gly Glu Arg Pro Tyr Glu Cys Gly Glu Cys Gly Lys Ser
            500                 505                 510

Phe His Gln Ser Ser Leu Leu Arg His Gln Lys Thr His Thr Ala
            515                 520                 525

Glu Arg Pro Tyr Glu Cys Arg Glu Cys Gly Lys Phe Phe Ser Ser Leu
            530                 535                 540

Leu Glu His Arg Arg Val His Thr Gly Glu Arg Pro Tyr Glu Cys Arg
545                 550                 555                 560

Glu Cys Gly Lys Thr Phe Thr Arg Arg Ser Ala His Phe Lys His Gln
            565                 570                 575

Arg Leu His Thr Arg Gly Lys Pro Tyr Glu Cys Ser Glu Cys Gly Lys
            580                 585                 590

Ser Phe Ala Glu Thr Phe Ser Leu Thr Glu His Arg Arg Val His Thr
            595                 600                 605
```

```
Gly Glu Arg Pro Tyr Glu Cys Ser Glu Cys Gly Lys Ser Phe His Arg
    610                 615                 620

Ser Ser Ser Leu Leu Arg His Gln Arg Val His Thr Glu Arg Ser Pro
625                 630                 635                 640

Tyr Lys

<210> SEQ ID NO 11
<211> LENGTH: 42
<212> TYPE: DNA
<213> ORGANISM: Homo sapiens

<400> SEQUENCE: 11
gcgctgaggc tcccggctca ggttgttggt gtggatcaga ag                           42

<210> SEQ ID NO 12
<211> LENGTH: 43
<212> TYPE: PRT
<213> ORGANISM: Homo sapiens

<400> SEQUENCE: 12

Met Ala Ala Ala Ala Leu Arg Leu Pro Ala Gln Val Val Gly Val Asp
1               5                   10                  15

Gln Lys Met Arg Arg His Leu Leu Arg Arg Ala Phe Leu Tyr Lys Glu
            20                  25                  30

Cys Leu Arg Ser Ala Leu Leu Gly Gln Val Ser
        35                  40

<210> SEQ ID NO 13
<211> LENGTH: 213
<212> TYPE: DNA
<213> ORGANISM: Homo sapiens

<400> SEQUENCE: 13
gcatcatctg gctgcaaaga agagaacaca ctgtgtttga gggaggagga aggaggatca       60
gagtttaaac tcctgccata atgcagggca ctgtggcatt tgaagatgtg ctgtgaact       120 tttcccagga ggagtggagt ctccttagtg aggttcagag atgcctttac catgacgtga      180
tgctggagaa ctgggtactt atatcctccc tgg                                   213

<210> SEQ ID NO 14
<211> LENGTH: 2
<212> TYPE: DNA
<213> ORGANISM: Homo sapiens

<400> SEQUENCE: 14 gt                                                                       2

<210> SEQ ID NO 15
<211> LENGTH: 77
<212> TYPE: PRT
<213> ORGANISM: Homo sapiens

<400> SEQUENCE: 15

Met Gln Gly Thr Val Ala Phe Glu Asp Val Ala Val Asn Phe Ser Gln
1               5                   10                  15

Glu Glu Trp Ser Leu Leu Ser Val Gln Arg Cys Tyr His Asp
            20                  25                  30

Val Met Leu Glu Asn Trp Val Leu Ile Ser Ser Leu Gly Cys Trp Cys
        35                  40                  45

Gly Ser Glu Asp Glu Glu Ala Pro Ser Lys Lys Ser Ile Ser Ile Gln
```

```
                    50                  55                  60
Arg Val Ser Gln Val Ser Thr Pro Gly Ala Gly Val Ser
 65                  70                  75

<210> SEQ ID NO 16
<211> LENGTH: 3551
<212> TYPE: DNA
<213> ORGANISM: Homo sapiens

<400> SEQUENCE: 16
ctctggtagc gaccattttg gttaatgttg ggtgtgtttc tgcggtttgt gaggtgagag      60
gcgctggagc tatgggtccg aaccgcggtg tctgaaccca gaaggtgaag agtccttctt     120
gctgcacaga ggcagatcct aggccccgta acggcgcccg ccgctcccgg cagtgctttc     180
cccgcgtact cgggatggcg gcggccgcgc tgaggctccc ggctcaggca tcatctggct     240
gcaaagaaga gaacacactg tgtttgaggg aggaggaagg aggatcagag tttaaactcc     300
tgccataatg cagaccattc tccataacaa gggagtggga tttaaatgac tctaggtgga     360
cagaggaaag tcgtcattgt agaggggtca ccaagtgcaa cacagaagtg aatagggcc      420 atggatatct aaagccccac ctggttctgt ggggatgtgg agccatgcaa gaaggccttc     480
atagaatgac ttgggactgc attgctattg ggagccatga gaattctgtg cagggcactg     540
tggcatttga agatgtggct gtgaactttt cccaggagga gtggagtctc cttagtgagg     600
ttcagagatg cctttaccat gacgtgatgc tggagaactg ggtacttata tcctccctgg     660
gttgttggtg tggatcagaa gatgaggagg caccttctaa gaagagcatt tctatacaaa     720
gagtgtctca ggtcagcact cctggggcag gtgtgtctcc caagaaggct cactcttgtg     780
aaatgtgtgg cgcgatcttg ggagacattt tgcacttggc agatcatcag ggacacatc      840 acaagcagaa actgcacagg tgtgaggcat ggggaataa attgtatgat agttcaaacc      900
gtccgcacca gaatcagtac cttggagaga aaccctatag aagcagtgtt gaggaagcat     960
tgtttgtgaa gaggtgtaag ttccatgtgt cagaggagtc atctatcttc attcagagtg    1020
gaaaggactt tttgcccagc tcaggattac tgctgcagga ggccactcac actggggaga    1080
agtcaaacag caaacctgag tgtgagtctc cctttcagtg gggagatact cgttacagct    1140
gtggagaatg catgaaacat tctagcacca aacacgtatt tgttcaacag cagagacttc    1200
cctctagaga ggaatgttat tgctgggaat gtgggaaatc ctttagcaaa tatgatagcg    1260
tcagtaatca tcagagagtt cacactggga aaagacctta tgaatgtgga atgtgggga    1320 aatcttttag tcataagggc agccttgttc agcatcagcg agttcacact gggaaaagac    1380
cttatgaatg tggagaatgt gggaaatctt ttagtcataa gggcagcctt gttcagcatc    1440
agcgagttca tactggagaa agaccttatg agtgtggaga atgtgggaaa tcttttagtc    1500
aaaatggtac tctcattaaa catcaacgag ttcacactgg agaaagacct tatgagtgtg    1560
aagaatgtgg gaaatgtttt actcagaagg gcaatctcat tcaacatcaa cgaggtcaca    1620
ctagtgaaag accttatgag tgtgaagaat gtggaaatg ttttagtcaa aagggcaccc    1680
taactgaaca tcatcgagtt cacactagag aacgaccta tgagtgtgga atgtgggga    1740 aatcttttag tcgaaaggga caccttagga ccatcagcg gggtcacact ggagaaagac    1800
cttacgagtg tggagaatgt gggaaatctt ttagtcgaaa gggcaacctc attcagcatc    1860
agcgaagcca cactggagaa aggccttatg agtgtagaga gtgtaggaaa ttatttaggg    1920
gcaagtccca cctcattgaa caccagagag ttcacactgg agaaaggcca tatgaatgta    1980
atgaatgtgg gaaatcattt caagacagct ctgggttcg tgttcatcag agagttcaca    2040
```

```
ctggagaaaa accgtttgag tgtagtgaat gtgggaagtc atttcctcaa agctgttccc   2100
tccttcgaca tcggagagtt catactggag aaaggcctta tgaatgtgga gaatgtggaa   2160
agtcatttca tcagagctct tccctccttc gacatcagaa aactcacact gcagaaagac   2220
cttatgagtg cagagaatgt gggaaattct tctccagtct ccttgaacac aggagagttc   2280
acactggaga aaggccttat gaatgcaggg aatgtggaaa acatttact cgaaggtctg   2340 cgcattttaa acatcagaga cttcatactc gaggaaagcc ttacgagtgc agcgaatgtg   2400
ggaaatcctt tgctgaaacc ttcagtctta ctgaacacag gagagtacac actggagaaa   2460
ggccttatga gtgcagtgaa tgtggaaaat catttcatcg aagctcttct ctccttcgac   2520
atcagagagt tcacacagaa agaagtcctt acaagtgaaa agaaatttgg gaaattcttt   2580
agctaaacct ctgtgcatct tcttgatcag agggttctta ctggatcagg accttatgag   2640
tgtgacaaac gtgggatatt ctttatgcag aagtcttgtt ttattacata cagaagagct   2700
cccactgcag aagggcctct tgagtgcgat gaatgtgaga agccttctg ccttctgtca   2760 ttggataaca gattgttctc ataaggaaaa cactgtacac gtacaggaaa tattatttct   2820
tgtaaaacat aacactggag gagatgcctt atgacggagc catctgccta aattggcata   2880
ccttcagcat ctgcataaac tcaattatgt tggagctgtg tggcattttt caccctgccg   2940
ggttcccttg ccagacatga tgtcggttat ctggcaaaag ccatttatg tcggccacga   3000 ggcaggtgtt cactgtgcat cattcattca ccccatgatg ttctggaagt aaaccttggt   3060
tgtctttcgt tggccagagg aattgaatgt ccgtctgtct gcccaggctg gagtggcacg   3120
atctcagctc actgcagcct ccacctccag ggttcaagcg attctcctgc ctcagcctcc   3180
cggggatctc aagggcattt ccctttgccc acctcgcctt ttcatatttg gtaaactgta   3240
tgcatttgcc tccagcccaa gattataaat atgaactgat tatgatctgc atgttctctc   3300
tttgggttca agcatttcct tacagaagag ccaccgtgga agtcatgggt aaatatgtgt   3360
tgaattggta actccctctt ggagaatttc ttgtgaatta cacagcaata ggggaactca   3420
tttaactgga gacataatct caatttgtaa agtgtggccc attttctaac attttattt   3480 tgcataccct cccctctctt ctcgattgat gaaactaaca aagaggttaa taaaagccca   3540
tctcgtcatg t                                                       3551
```

<210> SEQ ID NO 17
<211> LENGTH: 3551
<212> TYPE: DNA
<213> ORGANISM: Homo sapiens
<221> NAME/KEY: CDS
<222> LOCATION: (465)..(2558)

<400> SEQUENCE: 17

```
ctctggtagc gaccattttg gttaatgttg ggtgtgtttc tgcggtttgt gaggtgagag    60
gcgctggagc tatgggtccg aaccgcggtg tctgaaccca gaaggtgaag agtccttctt   120
gctgcacaga ggcagatcct aggccccgta acgcgcccg ccgctcccgg cagtgctttc   180
cccgcgtact cggatggcg gcggccgcgc tgaggctccc ggctcaggca tcatctggct   240
gcaaagaaga gaacacactg tgtttgaggg aggaggaagg aggatcagag tttaaactcc   300
tgccataatg cagaccattc tccataacaa gggagtggga tttaaatgac tctaggtgga   360
cagaggaaag tcgtcattgt agaggggtca ccaagtgcaa cacagaagtg gaatagggcc   420
atggatatct aaagccccac ctggttctgt ggggatgtgg agcc atg caa gaa ggc    476
                                                 Met Gln Glu Gly
                                                 1
```

```
ctt cat aga atg act tgg gac tgc att gct att ggg agc cat gag aat        524
Leu His Arg Met Thr Trp Asp Cys Ile Ala Ile Gly Ser His Glu Asn
 5              10                  15                  20 tct gtg cag ggc act gtg gca ttt gaa gat gtg gct gtg aac ttt tcc        572
Ser Val Gln Gly Thr Val Ala Phe Glu Asp Val Ala Val Asn Phe Ser
                     25                  30                  35 cag gag gag tgg agt ctc ctt agt gag gtt cag aga tgc ctt tac cat        620
Gln Glu Glu Trp Ser Leu Leu Ser Glu Val Gln Arg Cys Leu Tyr His
                 40                  45                  50 gac gtg atg ctg gag aac tgg gta ctt ata tcc tcc ctg ggt tgt tgg        668
Asp Val Met Leu Glu Asn Trp Val Leu Ile Ser Ser Leu Gly Cys Trp
             55                  60                  65 tgt gga tca gaa gat gag gag gca cct tct aag aag agc att tct ata        716
Cys Gly Ser Glu Asp Glu Glu Ala Pro Ser Lys Lys Ser Ile Ser Ile
 70                  75                  80 caa aga gtg tct cag gtc agc act cct ggg gca ggt gtg tct ccc aag        764
Gln Arg Val Ser Gln Val Ser Thr Pro Gly Ala Gly Val Ser Pro Lys
 85                  90                  95                 100 aag gct cac tct tgt gaa atg tgt ggc gcg atc ttg gga gac att ttg        812
Lys Ala His Ser Cys Glu Met Cys Gly Ala Ile Leu Gly Asp Ile Leu
                105                 110                 115 cac ttg gca gat cat cag ggg aca cat cac aag cag aaa ctg cac agg        860
His Leu Ala Asp His Gln Gly Thr His His Lys Gln Lys Leu His Arg
            120                 125                 130 tgt gag gca tgg ggg aat aaa ttg tat gat agt tca aac cgt ccg cac        908
Cys Glu Ala Trp Gly Asn Lys Leu Tyr Asp Ser Ser Asn Arg Pro His
                135                 140                 145 cag aat cag tac ctt gga gag aaa ccc tat aga agc agt gtt gag gaa        956
Gln Asn Gln Tyr Leu Gly Glu Lys Pro Tyr Arg Ser Ser Val Glu Glu
            150                 155                 160 gca ttg ttt gtg aag agg tgt aag ttc cat gtg tca gag gag tca tct       1004
Ala Leu Phe Val Lys Arg Cys Lys Phe His Val Ser Glu Glu Ser Ser
165                 170                 175                 180 atc ttc att cag agt gga aag gac ttt ttg ccc agc tca gga tta ctg       1052
Ile Phe Ile Gln Ser Gly Lys Asp Phe Leu Pro Ser Ser Gly Leu Leu
                    185                 190                 195 ctg cag gag gcc act cac act ggg gag aag tca aac agc aaa cct gag       1100
Leu Gln Glu Ala Thr His Thr Gly Glu Lys Ser Asn Ser Lys Pro Glu
                200                 205                 210 tgt gag tct ccc ttt cag tgg gga gat act cgt tac agc tgt gga gaa       1148
Cys Glu Ser Pro Phe Gln Trp Gly Asp Thr Arg Tyr Ser Cys Gly Glu
            215                 220                 225 tgc atg aaa cat tct agc acc aaa cac gta ttt gtt caa cag cag aga       1196
Cys Met Lys His Ser Ser Thr Lys His Val Phe Val Gln Gln Gln Arg
230                 235                 240 ctt ccc tct aga gag gaa tgt tat tgc tgg gaa tgt ggg aaa tcc ttt       1244
Leu Pro Ser Arg Glu Glu Cys Tyr Cys Trp Glu Cys Gly Lys Ser Phe
245                 250                 255                 260 agc aaa tat gat agc gtc agt aat cat cag aga gtt cac act ggg aaa       1292
Ser Lys Tyr Asp Ser Val Ser Asn His Gln Arg Val His Thr Gly Lys
                265                 270                 275 aga cct tat gaa tgt gga gaa tgt ggg aaa tct ttt agt cat aag ggc       1340
Arg Pro Tyr Glu Cys Gly Glu Cys Gly Lys Ser Phe Ser His Lys Gly
                280                 285                 290 agc ctt gtt cag cat cag cga gtt cac act ggg aaa aga cct tat gaa       1388
Ser Leu Val Gln His Gln Arg Val His Thr Gly Lys Arg Pro Tyr Glu
            295                 300                 305 tgt gga gaa tgt ggg aaa tct ttt agt cat aag ggc agc ctt gtt cag       1436
Cys Gly Glu Cys Gly Lys Ser Phe Ser His Lys Gly Ser Leu Val Gln
310                 315                 320
```

| | | |
|---|---|---|
| cat cag cga gtt cat act gga gaa aga cct tat gag tgt gga gaa tgt<br>His Gln Arg Val His Thr Gly Glu Arg Pro Tyr Glu Cys Gly Glu Cys<br>325                               330                           335                     340 | 1484 |
| ggg aaa tct ttt agt caa aat ggt act ctc att aaa cat caa cga gtt<br>Gly Lys Ser Phe Ser Gln Asn Gly Thr Leu Ile Lys His Gln Arg Val<br>                 345                          350                          355 | 1532 |
| cac act gga gaa aga cct tat gag tgt gaa gaa tgt ggg aaa tgt ttt<br>His Thr Gly Glu Arg Pro Tyr Glu Cys Glu Glu Cys Gly Lys Cys Phe<br>                   360                          365                       370 | 1580 |
| act cag aag ggc aat ctc att caa cat caa cga ggt cac act agt gaa<br>Thr Gln Lys Gly Asn Leu Ile Gln His Gln Arg Gly His Thr Ser Glu<br>375                               380                           385 | 1628 |
| aga cct tat gag tgt gaa gaa tgt gga aaa tgt ttt agt caa aag ggc<br>Arg Pro Tyr Glu Cys Glu Glu Cys Gly Lys Cys Phe Ser Gln Lys Gly<br>               390                          395                       400 | 1676 |
| acc cta act gaa cat cat cga gtt cac act aga gaa cga cct tat gag<br>Thr Leu Thr Glu His His Arg Val His Thr Arg Glu Arg Pro Tyr Glu<br>405                               410                           415                   420 | 1724 |
| tgt gga gaa tgt ggg aaa tct ttt agt cga aag gga cac ctt agg aac<br>Cys Gly Glu Cys Gly Lys Ser Phe Ser Arg Lys Gly His Leu Arg Asn<br>                          425                          430                       435 | 1772 |
| cat cag cgg ggt cac act gga gaa aga cct tac gag tgt gga gaa tgt<br>His Gln Arg Gly His Thr Gly Glu Arg Pro Tyr Glu Cys Gly Glu Cys<br>                   440                          445                       450 | 1820 |
| ggg aaa tct ttt agt cga aag ggc aac ctc att cag cat cag cga agc<br>Gly Lys Ser Phe Ser Arg Lys Gly Asn Leu Ile Gln His Gln Arg Ser<br>                 455                          460                          465 | 1868 |
| cac act gga gaa agg cct tat gag tgt aga gag tgt agg aaa tta ttt<br>His Thr Gly Glu Arg Pro Tyr Glu Cys Arg Glu Cys Arg Lys Leu Phe<br>               470                          475                       480 | 1916 |
| agg ggc aag tcc cac ctc att gaa cac cag aga gtt cac act gga gaa<br>Arg Gly Lys Ser His Leu Ile Glu His Gln Arg Val His Thr Gly Glu<br>485                               490                           495                   500 | 1964 |
| agg cca tat gaa tgt aat gaa tgt ggg aaa tca ttt caa gac agc tct<br>Arg Pro Tyr Glu Cys Asn Glu Cys Gly Lys Ser Phe Gln Asp Ser Ser<br>                   505                          510                       515 | 2012 |
| ggg ttt cgt gtt cat cag aga gtt cac act gga gaa aaa ccg ttt gag<br>Gly Phe Arg Val His Gln Arg Val His Thr Gly Glu Lys Pro Phe Glu<br>               520                          525                       530 | 2060 |
| tgt agt gaa tgt ggg aag tca ttt cct caa agc tgt tcc ctc ctt cga<br>Cys Ser Glu Cys Gly Lys Ser Phe Pro Gln Ser Cys Ser Leu Leu Arg<br>             535                          540                       545 | 2108 |
| cat cgg aga gtt cat act gga gaa agg cct tat gaa tgt gga gaa tgt<br>His Arg Arg Val His Thr Gly Glu Arg Pro Tyr Glu Cys Gly Glu Cys<br>550                               555                           560 | 2156 |
| gga aag tca ttt cat cag agc tct tcc ctc ctt cga cat cag aaa act<br>Gly Lys Ser Phe His Gln Ser Ser Ser Leu Leu Arg His Gln Lys Thr<br>565                               570                           575                   580 | 2204 |
| cac act gca gaa aga cct tat gag tgc aga gaa tgt ggg aaa ttc ttc<br>His Thr Ala Glu Arg Pro Tyr Glu Cys Arg Glu Cys Gly Lys Phe Phe<br>                   585                          590                       595 | 2252 |
| tcc agt ctc ctt gaa cac agg aga gtt cac act gga gaa agg cct tat<br>Ser Ser Leu Leu Glu His Arg Arg Val His Thr Gly Glu Arg Pro Tyr<br>               600                          605                       610 | 2300 |
| gaa tgc agg gaa tgt gga aaa aca ttt act cga agg tct gcg cat ttt<br>Glu Cys Arg Glu Cys Gly Lys Thr Phe Thr Arg Arg Ser Ala His Phe<br>             615                          620                       625 | 2348 |
| aaa cat cag aga ctt cat act cga gga aag cct tac gag tgc agc gaa<br>Lys His Gln Arg Leu His Thr Arg Gly Lys Pro Tyr Glu Cys Ser Glu<br>               630                          635                       640 | 2396 |

```
tgt ggg aaa tcc ttt gct gaa acc ttc agt ctt act gaa cac agg aga      2444
Cys Gly Lys Ser Phe Ala Glu Thr Phe Ser Leu Thr Glu His Arg Arg
645                 650                 655                 660 gta cac act gga gaa agg cct tat gag tgc agt gaa tgt gga aaa tca      2492
Val His Thr Gly Glu Arg Pro Tyr Glu Cys Ser Glu Cys Gly Lys Ser
                665                 670                 675 ttt cat cga agc tct tct ctc ctt cga cat cag aga gtt cac aca gaa      2540
Phe His Arg Ser Ser Ser Leu Leu Arg His Gln Arg Val His Thr Glu
            680                 685                 690 aga agt cct tac aag tga aagaaattt gggaaattct ttagctaaac              2588
Arg Ser Pro Tyr Lys
                695 ctctgtgcat cttcttgatc agagggttct tactggatca ggaccttatg agtgtgacaa    2648 acgtgggata ttctttatgc agaagtcttg ttttattaca tacagaagag ctcccactgc    2708 agaagggcct cttgagtgcg atgaatgtga gaaagccttc tgccttctgt cattggataa    2768 cagattgttc tcataaggaa aacactgtac acgtacagga atatatttt cttgtaaaac     2828 ataacactgg aggagatgcc ttatgacgga gccatctgcc taaattgca taccttcagc     2888 atctgcataa actcaattat gttggagctg tgtggcattt ttcaccctgc cgggttccct    2948 tgccagacat gatgtcggtt atctggcaaa agccatttta tgtcggccac gaggcaggtg    3008 ttcactgtgc atcattcatt cacccccatga tgttctggaa gtaaaccttg ttgtctttc    3068 gttggccaga ggaattgaat gtccgtctgt ctgcccaggc tggagtggca cgatctcagc    3128 tcactgcagc ctccacctcc agggttcaag cgattctcct gcctcagcct cccgggatc    3188 tcaagggcat ttccctttgc ccacctcgcc ttttcatatt tggtaaactg tatgcatttg    3248 cctccagccc aagattataa atatgaactg attatgatct gcatgttctc tctttgggtt    3308 caagcatttc cttacagaag agccaccgtg gaagtcatgg gtaaatatgt gttgaattgg    3368 taactccctc ttggagaatt tcttgtgaat tacacagcaa tagggaact catttaactg     3428 gagacataat ctcaatttgt aaagtgtggc ccattttcta acattttat tttgcatacc     3488 ctcccctctc ttctcgattg atgaaactaa caaagaggtt aataaaagcc catctcgtca    3548 tgt                                                                  3551

<210> SEQ ID NO 18
<211> LENGTH: 697
<212> TYPE: PRT
<213> ORGANISM: Homo sapiens

<400> SEQUENCE: 18

Met Gln Glu Gly Leu His Arg Met Thr Trp Asp Cys Ile Ala Ile Gly
1               5                   10                  15

Ser His Glu Asn Ser Val Gln Gly Thr Val Ala Phe Glu Asp Val Ala
                20                  25                  30

Val Asn Phe Ser Gln Glu Glu Trp Ser Leu Leu Ser Glu Val Gln Arg
            35                  40                  45

Cys Leu Tyr His Asp Val Met Leu Glu Asn Trp Val Leu Ile Ser Ser
        50                  55                  60

Leu Gly Cys Trp Cys Gly Ser Glu Asp Glu Glu Ala Pro Ser Lys Lys
65                  70                  75                  80

Ser Ile Ser Ile Gln Arg Val Ser Gln Val Ser Thr Pro Gly Ala Gly
                85                  90                  95

Val Ser Pro Lys Lys Ala His Ser Cys Glu Met Cys Gly Ala Ile Leu
            100                 105                 110
```

```
Gly Asp Ile Leu His Leu Ala Asp His Gln Gly Thr His His Lys Gln
            115                 120                 125

Lys Leu His Arg Cys Glu Ala Trp Gly Asn Lys Leu Tyr Asp Ser Ser
130                 135                 140

Asn Arg Pro His Gln Asn Gln Tyr Leu Gly Glu Lys Pro Tyr Arg Ser
145                 150                 155                 160

Ser Val Glu Glu Ala Leu Phe Val Lys Arg Cys Lys Phe His Val Ser
                165                 170                 175

Glu Glu Ser Ser Ile Phe Ile Gln Ser Gly Lys Asp Phe Leu Pro Ser
            180                 185                 190

Ser Gly Leu Leu Leu Gln Glu Ala Thr His Thr Gly Glu Lys Ser Asn
            195                 200                 205

Ser Lys Pro Glu Cys Glu Ser Pro Phe Gln Trp Gly Asp Thr Arg Tyr
        210                 215                 220

Ser Cys Gly Glu Cys Met Lys His Ser Ser Thr Lys His Val Phe Val
225                 230                 235                 240

Gln Gln Gln Arg Leu Pro Ser Arg Glu Glu Cys Tyr Cys Trp Glu Cys
                245                 250                 255

Gly Lys Ser Phe Ser Lys Tyr Asp Ser Val Ser Asn His Gln Arg Val
            260                 265                 270

His Thr Gly Lys Arg Pro Tyr Glu Cys Gly Glu Cys Gly Lys Ser Phe
        275                 280                 285

Ser His Lys Gly Ser Leu Val Gln His Gln Arg Val His Thr Gly Lys
        290                 295                 300

Arg Pro Tyr Glu Cys Gly Glu Cys Gly Lys Ser Phe Ser His Lys Gly
305                 310                 315                 320

Ser Leu Val Gln His Gln Arg Val His Thr Gly Glu Arg Pro Tyr Glu
                325                 330                 335

Cys Gly Glu Cys Gly Lys Ser Phe Ser Gln Asn Gly Thr Leu Ile Lys
            340                 345                 350

His Gln Arg Val His Thr Gly Glu Arg Pro Tyr Glu Cys Glu Glu Cys
        355                 360                 365

Gly Lys Cys Phe Thr Gln Lys Gly Asn Leu Ile Gln His Gln Arg Gly
    370                 375                 380

His Thr Ser Glu Arg Pro Tyr Glu Cys Glu Glu Cys Gly Lys Cys Phe
385                 390                 395                 400

Ser Gln Lys Gly Thr Leu Thr Glu His His Arg Val His Thr Arg Glu
                405                 410                 415

Arg Pro Tyr Glu Cys Gly Glu Cys Gly Lys Ser Phe Ser Arg Lys Gly
            420                 425                 430

His Leu Arg Asn His Gln Arg Gly His Thr Gly Glu Arg Pro Tyr Glu
        435                 440                 445

Cys Gly Glu Cys Gly Lys Ser Phe Ser Arg Lys Gly Asn Leu Ile Gln
    450                 455                 460

His Gln Arg Ser His Thr Gly Glu Arg Pro Tyr Glu Cys Arg Glu Cys
465                 470                 475                 480

Arg Lys Leu Phe Arg Gly Lys Ser His Leu Ile Glu His Gln Arg Val
                485                 490                 495

His Thr Gly Glu Arg Pro Tyr Glu Cys Asn Glu Cys Gly Lys Ser Phe
            500                 505                 510

Gln Asp Ser Ser Gly Phe Arg Val His Gln Arg Val His Thr Gly Glu
        515                 520                 525

Lys Pro Phe Glu Cys Ser Glu Cys Gly Lys Ser Phe Pro Gln Ser Cys
    530                 535                 540
```

```
Ser Leu Leu Arg His Arg Arg Val His Thr Gly Glu Arg Pro Tyr Glu
545                 550                 555                 560

Cys Gly Glu Cys Gly Lys Ser Phe His Gln Ser Ser Leu Leu Arg
        565                 570                 575

His Gln Lys Thr His Thr Ala Glu Arg Pro Tyr Glu Cys Arg Glu Cys
    580                 585                 590

Gly Lys Phe Phe Ser Ser Leu Leu Glu His Arg Arg Val His Thr Gly
        595                 600                 605

Glu Arg Pro Tyr Glu Cys Arg Glu Cys Gly Lys Thr Phe Thr Arg Arg
    610                 615                 620

Ser Ala His Phe Lys His Gln Arg Leu His Thr Arg Gly Lys Pro Tyr
625                 630                 635                 640

Glu Cys Ser Glu Cys Gly Lys Ser Phe Ala Glu Thr Phe Ser Leu Thr
                645                 650                 655

Glu His Arg Arg Val His Thr Gly Glu Arg Pro Tyr Glu Cys Ser Glu
            660                 665                 670

Cys Gly Lys Ser Phe His Arg Ser Ser Leu Leu Arg His Gln Arg
        675                 680                 685

Val His Thr Glu Arg Ser Pro Tyr Lys
    690                 695

<210> SEQ ID NO 19
<211> LENGTH: 220
<212> TYPE: DNA
<213> ORGANISM: Homo sapiens

<400> SEQUENCE: 19
accattctcc ataacaaggg agtgggattt aaatgactct aggtggacag aggaaagtcg      60
tcattgtaga ggggtcacca agtgcaacac agaagtggaa tagggccatg atatctaaa     120 gccccacctg gttctgtggg gatgtggagc catgcaagaa ggccttcata gaatgacttg     180
ggactgcatt gctattggga gccatgagaa ttctgtgcag                           220

<210> SEQ ID NO 20
<211> LENGTH: 23
<212> TYPE: PRT
<213> ORGANISM: Homo sapiens

<400> SEQUENCE: 20

Met Gln Glu Gly Leu His Arg Met Thr Trp Asp Cys Ile Ala Ile Gly
1               5                   10                  15

Ser His Glu Asn Ser Val Gln
            20

<210> SEQ ID NO 21
<211> LENGTH: 69
<212> TYPE: DNA
<213> ORGANISM: Homo sapiens

<400> SEQUENCE: 21
atgcaagaag gccttcatag aatgacttgg gactgcattg ctattgggag ccatgagaat      60
tctgtgcag                                                              69

<210> SEQ ID NO 22
<211> LENGTH: 23
<212> TYPE: PRT
<213> ORGANISM: Homo sapiens

<400> SEQUENCE: 22
```

```
Met Gln Glu Gly Leu His Arg Met Thr Trp Asp Cys Ile Ala Ile Gly
1               5                   10                  15

Ser His Glu Asn Ser Val Gln
            20
```

<210> SEQ ID NO 23
<211> LENGTH: 18
<212> TYPE: DNA
<213> ORGANISM: Artificial Sequence
<220> FEATURE:
<223> OTHER INFORMATION: forward primer used for specifically detecting
      the variant of the present invention (D-UTERU2026184.1)

<400> SEQUENCE: 23
gtgctttccc cgcgtact                                                   18

<210> SEQ ID NO 24
<211> LENGTH: 22
<212> TYPE: DNA
<213> ORGANISM: Artificial Sequence
<220> FEATURE:
<223> OTHER INFORMATION: reverse primer used for specifically detecting
      the variant of the present invention (D-UTERU2026184.1)

<400> SEQUENCE: 24
aggagtgctg acctgagaca ct                                              22

<210> SEQ ID NO 25
<211> LENGTH: 138
<212> TYPE: DNA
<213> ORGANISM: Artificial Sequence
<220> FEATURE:
<223> OTHER INFORMATION: partial polynucleotide specific to the variant
      of the present invention (D-UTERU2026184.1), which is obtained by
      PCR using forward primer (SEQ ID NO:23) and reverse primer (SEQ ID
      NO:24)

<400> SEQUENCE: 25
gtgctttccc cgcgtactcg ggatggcggc ggccgcgctg aggctcccgg ctcaggttgt     60
tggtgtggat cagaagatga ggaggcacct tctaagaaga gcatttctat acaaagagtg    120
tctcaggtca gcactcct                                                  138

<210> SEQ ID NO 26
<211> LENGTH: 22
<212> TYPE: DNA
<213> ORGANISM: Artificial Sequence
<220> FEATURE:
<223> OTHER INFORMATION: probe used for detecting the variants of the
      present invention (D-UTERU2026184.1)

<400> SEQUENCE: 26
ctcccggctc aggttgttgg tg                                              22

<210> SEQ ID NO 27
<211> LENGTH: 23
<212> TYPE: DNA
<213> ORGANISM: Artificial Sequence
<220> FEATURE:
<223> OTHER INFORMATION: forward primer used for specifically detecting
      the variant of the present invention (D-BRACE3000012.1)

<400> SEQUENCE: 27
gatatctaaa gccccacctg gtt                                             23

<210> SEQ ID NO 28

```
<211> LENGTH: 21
<212> TYPE: DNA
<213> ORGANISM: Artificial Sequence
<220> FEATURE:
<223> OTHER INFORMATION: reverse primer used for specifically detecting
      the variant of the present invention (D-BRACE3000012.1)

<400> SEQUENCE: 28
acagtgccct gcacagaatt c                                              21

<210> SEQ ID NO 29
<211> LENGTH: 118
<212> TYPE: DNA
<213> ORGANISM: Artificial Sequence
<220> FEATURE:
<223> OTHER INFORMATION: partial polynucleotide specific to the variant
      of the present invention (D-BRACE3000012.1), which is obtained by
      PCR using forward primer (SEQ ID NO:27) and reverse primer (SEQ ID
      NO:28)

<400> SEQUENCE: 29
gatatctaaa gccccacctg gttctgtggg gatgtggagc catgcaagaa ggccttcata    60
gaatgacttg gactgcatt gctattggga gccatgagaa ttctgtgcag ggcactgt     118

<210> SEQ ID NO 30
<211> LENGTH: 28
<212> TYPE: DNA
<213> ORGANISM: Artificial Sequence
<220> FEATURE:
<223> OTHER INFORMATION: probe used for detecting the variants of the
      present invention (D-BRACE3000012.1)

<400> SEQUENCE: 30
atgacttggg actgcattgc tattggga                                       28

<210> SEQ ID NO 31
<211> LENGTH: 22
<212> TYPE: DNA
<213> ORGANISM: Artificial Sequence
<220> FEATURE:
<223> OTHER INFORMATION: forward primer used for specifically detecting
      the known variant of the gene of the present invention
      (NM_133460.1)

<400> SEQUENCE: 31
ggaggaagga ggatcagagt tt                                             22

<210> SEQ ID NO 32
<211> LENGTH: 20
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_133460.1)

<400> SEQUENCE: 32
agccacatct tcaaatgcca                                                20

<210> SEQ ID NO 33
<211> LENGTH: 69
<212> TYPE: DNA
<213> ORGANISM: Artificial Sequence
<220> FEATURE:
<223> OTHER INFORMATION: partial polynucleotide specific to the known
      variant of the gene of the present invention (NM_133460.1), which
      is obtained by PCR using forward primer (SEQ ID NO:31) and reverse
      primer (SEQ ID NO:32)
```

```
<400> SEQUENCE: 33
ggaggaagga ggatcagagt ttaaactcct gccataatgc agggcactgt ggcatttgaa      60
gatgtggct                                                             69

<210> SEQ ID NO 34
<211> LENGTH: 25
<212> TYPE: DNA
<213> ORGANISM: Artificial Sequence
<220> FEATURE:
<223> OTHER INFORMATION: probe used for specifically detecting the known
      variant of the gene of the present invention (NM_133460.1)

<400> SEQUENCE: 34
aactcctgcc ataatgcagg gcact                                           25

<210> SEQ ID NO 35
<211> LENGTH: 24
<212> TYPE: DNA
<213> ORGANISM: Artificial Sequence
<220> FEATURE:
<223> OTHER INFORMATION: forward primer used for detecting the variants
      of the gene of the present invention (D-UTERU2026184.1,
      D-BRACE3000012.1 and NM_133460.1)

<400> SEQUENCE: 35
ttccatgtgt cagaggagtc atct                                            24

<210> SEQ ID NO 36
<211> LENGTH: 24
<212> TYPE: DNA
<213> ORGANISM: Artificial Sequence
<220> FEATURE:
<223> OTHER INFORMATION: reverse primer used for detecting the variants
      of the gene of the present invention (D-UTERU2026184.1,
      D-BRACE3000012.1 and NM_133460.1)

<400> SEQUENCE: 36
cactcaggtt tgctgtttga cttc                                            24

<210> SEQ ID NO 37
<211> LENGTH: 122
<212> TYPE: DNA
<213> ORGANISM: Artificial Sequence
<220> FEATURE:
<223> OTHER INFORMATION: partial polynucleotide common to the variants
      of the gene of the present invention (D-UTERU2026184.1,
      D-BRACE3000012.1 and NM_133460.1), which is obtained by PCR using
      forward primer (SEQ ID NO:35) and reverse primer (SEQ ID NO:36)

<400> SEQUENCE: 37
ttccatgtgt cagaggagtc atctatcttc attcagagtg gaaaggactt tttgcccagc     60
tcaggattac tgctgcagga ggccactcac actggggaga agtcaaacag caaacctgag   120
tg                                                                   122

<210> SEQ ID NO 38
<211> LENGTH: 27
<212> TYPE: DNA
<213> ORGANISM: Artificial Sequence
<220> FEATURE:
<223> OTHER INFORMATION: probe used for detecting the variants of the
      gene of the present invention (D-UTERU2026184.1, D-BRACE3000012.1
      and NM_133460.1)

<400> SEQUENCE: 38
ttttgcccag ctcaggatta ctgctgc                                         27
```

<210> SEQ ID NO 39
<211> LENGTH: 306
<212> TYPE: DNA
<213> ORGANISM: Homo sapiens

<400> SEQUENCE: 39

| | | | | | | |
|---|---|---|---|---|---|---|
| ggtagcgacc | attttggtta | atgttgggtg | tgtttctgcg | gtttgtgagg | tgagaggcgc | 60 |
| tggagctatg | ggtccgaacc | gcggtgtctg | aacccagaag | gtgaagagtc | cttcttgctg | 120 |
| cacagaggca | gatcttaggc | cccgtaacgg | cgcccgccgc | tcccggcagt | gctttccccg | 180 |
| cgtactcggg | atggcggcgg | ccgcgctgag | gctcccggct | caggttgttg | gtgtggatca | 240 |
| gaagatgagg | aggcaccttc | taagaagagc | atttctatac | aaagagtgtc | tcaggtcagc | 300 |
| actcct | | | | | | 306 |

<210> SEQ ID NO 40
<211> LENGTH: 541
<212> TYPE: DNA
<213> ORGANISM: Homo sapiens

<400> SEQUENCE: 40

| | | | | | | |
|---|---|---|---|---|---|---|
| ctctggtagc | gaccattttg | gttaatgttg | ggtgtgtttc | tgcggtttgt | gaggtgagag | 60 |
| gcgctggagc | tatgggtccg | aaccgcggtg | tctgaaccca | gaaggtgaag | agtccttctt | 120 |
| gctgcacaga | ggcagatcct | aggccccgta | acggcgcccg | ccgctcccgg | cagtgctttc | 180 |
| cccgcgtact | cgggatggcg | gcggccgcgc | tgaggctccc | ggctcaggca | tcatctggct | 240 |
| gcaaagaaga | gaacacactg | tgtttgaggg | aggaggaagg | aggatcagag | tttaaactcc | 300 |
| tgccataatg | cagaccattc | tccataacaa | gggagtggga | tttaaatgac | tctaggtgga | 360 |
| cagaggaaag | tcgtcattgt | agaggggtca | ccaagtgcaa | cacagaagtg | gaatagggcc | 420 |
| atggatatct | aaagccccac | ctggttctgt | ggggatgtgg | agccatgcaa | gaaggccttc | 480 |
| atagaatgac | ttgggactgc | attgctattg | ggagccatga | gaattctgtg | cagggcactg | 540 |
| t | | | | | | 541 |

<210> SEQ ID NO 41
<211> LENGTH: 1573
<212> TYPE: DNA
<213> ORGANISM: Homo sapiens

<400> SEQUENCE: 41

| | | | | | | |
|---|---|---|---|---|---|---|
| aaaaaaaaac | tgccacggag | ccccagcggc | tacacactcc | actcactcac | acctctcagg | 60 |
| gccccgcacg | ttcccacagc | cctcagggtg | tacgtgctgt | aggtgtggct | gtgccccaga | 120 |
| gtgccagctg | atgaagacgg | agcggccccg | gcccaacacc | ttcatcatcc | gctgcctgca | 180 |
| gtggaccact | gtcatcgaac | gcaccttcca | tgtggagact | cctgaggagc | gggaggagtg | 240 |
| gacaaccgcc | atccagactg | tggctgacgg | cctcaagaag | caggaggagg | aggagatgga | 300 |
| cttccggtcg | ggctcaccca | gtgacaactc | aggggctgaa | gagatggagg | tgtccctggc | 360 |
| caagcccaag | caccgcgtga | ccatgaacga | gtttgagtac | ctgaagctgc | tgggcaaggg | 420 |
| cactttcggc | aaggtgatcc | tggtgaagga | gaaggccaca | ggccgctact | acgccatgaa | 480 |
| gatcctcaag | aaggaagtca | tcgtggccaa | ggacgaggtg | gcccacacac | tcaccgagaa | 540 |
| ccgcgtcctg | cagaactcca | ggcacccctt | cctcacagcc | ctgaagtact | ctttccagac | 600 |
| ccacgaccgc | ctctgctttg | tcatggagta | cgccaacggg | ggcgagctgt | tcttccacct | 660 |
| gtcccgggaa | cgtgtgttct | ccgaggaccg | ggcccgcttc | tatggcgctg | agattgtgtc | 720 |

```
agccctggac tacctgcact cggagaagaa cgtggtgtac cgggacctca agctggagaa    780
cctcatgctg gacaaggacg ggcacattaa gatcacagac ttcgggctgt gcaaggaggg    840
gatcaaggac ggtgccacca tgaagacctt ttgcggcaca cctgagtacc tggccccga    900 ggtgctggag gacaatgact acggccgtgc agtggactgg tgggggctgg gcgtggtcat    960
gtacgagatg atgtgcggtc gcctgcccct ctacaaccag gaccatgaga agcttttga   1020 gctcatcctc atggaggaga tccgcttccc gcgcacgctt ggtcccgagg ccaagtcctt   1080
gctttcaggg ctgctcaaga aggaccccaa gcagaggctt ggcgggggct ccgaggacgc   1140
caaggagatc atgcagcatc gcttctttgc cggtatcgtg tggcagcacg tgtacgagaa   1200
gaagctcagc ccaccCttca agccccaggt cacgtcggag actgacacca ggtattttga   1260
tgaggagttc acggcccaga tgatcaccat cacaccacct gaccaagatg acagcatgga   1320
gtgtgtggac agcgagcgca ggccccactt ccccagttc tcctactcgg ccagcggcac    1380
ggcctgaggc ggcggtggac tgcgctggac gatagcttgg agggatggag aggcggcctc   1440
gtgccatgat ctgtatttaa tggtttttat ttctcgggtg catttgagag aagccacgct   1500
gtcctctcga gcccagatgg aaagacgttt ttgtgctgtg ggcagcaccc tcccccgcag   1560
cggggtaggg aag                                                      1573

<210> SEQ ID NO 42
<211> LENGTH: 1573
<212> TYPE: DNA
<213> ORGANISM: Homo sapiens
<221> NAME/KEY: CDS
<222> LOCATION: (131)..(1387)

<400> SEQUENCE: 42 aaaaaaaac tgccacggag ccccagcggc tacacactcc actcactcac acctctcagg     60
gccccgcacg ttcccacagc cctcagggtg tacgtgctgt aggtgtggct gtgccccaga   120
gtgccagctg atg aag acg gag cgg ccc cgg ccc aac acc ttc atc atc      169
            Met Lys Thr Glu Arg Pro Arg Pro Asn Thr Phe Ile Ile
              1               5                  10 cgc tgc ctg cag tgg acc act gtc atc gaa cgc acc ttc cat gtg gag    217
Arg Cys Leu Gln Trp Thr Thr Val Ile Glu Arg Thr Phe His Val Glu
 15                  20                  25 act cct gag gag cgg gag gag tgg aca acc gcc atc cag act gtg gct    265
Thr Pro Glu Glu Arg Glu Glu Trp Thr Thr Ala Ile Gln Thr Val Ala
 30                  35                  40                  45 gac ggc ctc aag aag cag gag gag gag gag atg gac ttc cgg tcg ggc    313
Asp Gly Leu Lys Lys Gln Glu Glu Glu Glu Met Asp Phe Arg Ser Gly
                 50                  55                  60 tca ccc agt gac aac tca ggg gct gaa gag atg gag gtg tcc ctg gcc    361
Ser Pro Ser Asp Asn Ser Gly Ala Glu Glu Met Glu Val Ser Leu Ala
             65                  70                  75 aag ccc aag cac cgc gtg acc atg aac gag ttt gag tac ctg aag ctg    409
Lys Pro Lys His Arg Val Thr Met Asn Glu Phe Glu Tyr Leu Lys Leu
         80                  85                  90 ctg ggc aag ggc act ttc ggc aag gtg atc ctg gtg aag gag aag gcc    457
Leu Gly Lys Gly Thr Phe Gly Lys Val Ile Leu Val Lys Glu Lys Ala
     95                 100                 105 aca ggc cgc tac tac gcc atg aag atc ctc aag aag gaa gtc atc gtg    505
Thr Gly Arg Tyr Tyr Ala Met Lys Ile Leu Lys Lys Glu Val Ile Val
110                 115                 120                 125 gcc aag gac gag gtg gcc cac aca ctc acc gag aac cgc gtc ctg cag    553
Ala Lys Asp Glu Val Ala His Thr Leu Thr Glu Asn Arg Val Leu Gln
                130                 135                 140
```

```
aac tcc agg cac ccc ttc ctc aca gcc ctg aag tac tct ttc cag acc      601
Asn Ser Arg His Pro Phe Leu Thr Ala Leu Lys Tyr Ser Phe Gln Thr
            145                 150                 155 cac gac cgc ctc tgc ttt gtc atg gag tac gcc aac ggg ggc gag ctg      649
His Asp Arg Leu Cys Phe Val Met Glu Tyr Ala Asn Gly Gly Glu Leu
        160                 165                 170 ttc ttc cac ctg tcc cgg gaa cgt gtg ttc tcc gag gac cgg gcc cgc      697
Phe Phe His Leu Ser Arg Glu Arg Val Phe Ser Glu Asp Arg Ala Arg
        175                 180                 185 ttc tat ggc gct gag att gtg tca gcc ctg gac tac ctg cac tcg gag      745
Phe Tyr Gly Ala Glu Ile Val Ser Ala Leu Asp Tyr Leu His Ser Glu
190                 195                 200                 205 aag aac gtg gtg tac cgg gac ctc aag ctg gag aac ctc atg ctg gac      793
Lys Asn Val Val Tyr Arg Asp Leu Lys Leu Glu Asn Leu Met Leu Asp
                210                 215                 220 aag gac ggg cac att aag atc aca gac ttc ggg ctg tgc aag gag ggg      841
Lys Asp Gly His Ile Lys Ile Thr Asp Phe Gly Leu Cys Lys Glu Gly
            225                 230                 235 atc aag gac ggt gcc acc atg aag acc ttt tgc ggc aca cct gag tac      889
Ile Lys Asp Gly Ala Thr Met Lys Thr Phe Cys Gly Thr Pro Glu Tyr
        240                 245                 250 ctg gcc ccc gag gtg ctg gag gac aat gac tac ggc cgt gca gtg gac      937
Leu Ala Pro Glu Val Leu Glu Asp Asn Asp Tyr Gly Arg Ala Val Asp
        255                 260                 265 tgg tgg ggg ctg ggc gtg gtc atg tac gag atg atg tgc ggt cgc ctg      985
Trp Trp Gly Leu Gly Val Val Met Tyr Glu Met Met Cys Gly Arg Leu
270                 275                 280                 285 ccc ttc tac aac cag gac cat gag aag ctt ttt gag ctc atc ctc atg     1033
Pro Phe Tyr Asn Gln Asp His Glu Lys Leu Phe Glu Leu Ile Leu Met
                290                 295                 300 gag gag atc cgc ttc ccg cgc acg ctt ggt ccc gag gcc aag tcc ttg     1081
Glu Glu Ile Arg Phe Pro Arg Thr Leu Gly Pro Glu Ala Lys Ser Leu
            305                 310                 315 ctt tca ggg ctg ctc aag aag gac ccc aag cag agg ctt ggg ggc         1129
Leu Ser Gly Leu Leu Lys Lys Asp Pro Lys Gln Arg Leu Gly Gly Gly
        320                 325                 330 tcc gag gac gcc aag gag atc atg cag cat cgc ttc ttt gcc ggt atc     1177
Ser Glu Asp Ala Lys Glu Ile Met Gln His Arg Phe Phe Ala Gly Ile
335                 340                 345 gtg tgg cag cac gtg tac gag aag aag ctc agc cca ccc ttc aag ccc     1225
Val Trp Gln His Val Tyr Glu Lys Lys Leu Ser Pro Pro Phe Lys Pro
350                 355                 360                 365 cag gtc acg tcg gag act gac acc agg tat ttt gat gag gag ttc acg     1273
Gln Val Thr Ser Glu Thr Asp Thr Arg Tyr Phe Asp Glu Glu Phe Thr
                370                 375                 380 gcc cag atg atc acc atc aca cca cct gac caa gat gac agc atg gag     1321
Ala Gln Met Ile Thr Ile Thr Pro Pro Asp Gln Asp Asp Ser Met Glu
            385                 390                 395 tgt gtg gac agc gag cgc agg ccc cac ttc ccc cag ttc tcc tac tcg     1369
Cys Val Asp Ser Glu Arg Arg Pro His Phe Pro Gln Phe Ser Tyr Ser
        400                 405                 410 gcc agc ggc acg gcc tga ggcggcggtg gactgcgctg gacgatagct            1417
Ala Ser Gly Thr Ala
        415 tggagggatg gagaggcggc ctcgtgccat gatctgtatt taatggtttt tatttctcgg   1477 gtgcatttga gagaagccac gctgtcctct cgagcccaga tggaaagacg ttttttgtgct  1537 gtgggcagca ccctccccccg cagcggggta gggaag                            1573

<210> SEQ ID NO 43
```

```
<211> LENGTH: 418
<212> TYPE: PRT
<213> ORGANISM: Homo sapiens

<400> SEQUENCE: 43
```

| | | | | | | | | | | | | | | |
|---|---|---|---|---|---|---|---|---|---|---|---|---|---|---|
| Met | Lys | Thr | Glu | Arg | Pro | Arg | Pro | Asn | Thr | Phe | Ile | Ile | Arg | Cys | Leu |
| 1 | | | | 5 | | | | | 10 | | | | | 15 | |
| Gln | Trp | Thr | Thr | Val | Ile | Glu | Arg | Thr | Phe | His | Val | Glu | Thr | Pro | Glu |
| | | | 20 | | | | | 25 | | | | | 30 | | |
| Glu | Arg | Glu | Glu | Trp | Thr | Thr | Ala | Ile | Gln | Thr | Val | Ala | Asp | Gly | Leu |
| | | 35 | | | | | 40 | | | | | 45 | | | |
| Lys | Lys | Gln | Glu | Glu | Glu | Met | Asp | Phe | Arg | Ser | Gly | Ser | Pro | Ser | |
| 50 | | | | | 55 | | | | | 60 | | | | | |
| Asp | Asn | Ser | Gly | Ala | Glu | Glu | Met | Glu | Val | Ser | Leu | Ala | Lys | Pro | Lys |
| 65 | | | | 70 | | | | | 75 | | | | | 80 | |
| His | Arg | Val | Thr | Met | Asn | Glu | Phe | Glu | Tyr | Leu | Lys | Leu | Leu | Gly | Lys |
| | | | | 85 | | | | | 90 | | | | | 95 | |
| Gly | Thr | Phe | Gly | Lys | Val | Ile | Leu | Val | Lys | Glu | Lys | Ala | Thr | Gly | Arg |
| | | | 100 | | | | | 105 | | | | | 110 | | |
| Tyr | Tyr | Ala | Met | Lys | Ile | Leu | Lys | Lys | Glu | Val | Ile | Val | Ala | Lys | Asp |
| | | | 115 | | | | | 120 | | | | | 125 | | |
| Glu | Val | Ala | His | Thr | Leu | Thr | Glu | Asn | Arg | Val | Leu | Gln | Asn | Ser | Arg |
| | 130 | | | | | 135 | | | | | 140 | | | | |
| His | Pro | Phe | Leu | Thr | Ala | Leu | Lys | Tyr | Ser | Phe | Gln | Thr | His | Asp | Arg |
| 145 | | | | | 150 | | | | | 155 | | | | | 160 |
| Leu | Cys | Phe | Val | Met | Glu | Tyr | Ala | Asn | Gly | Gly | Glu | Leu | Phe | Phe | His |
| | | | | 165 | | | | | 170 | | | | | 175 | |
| Leu | Ser | Arg | Glu | Arg | Val | Phe | Ser | Glu | Asp | Arg | Ala | Arg | Phe | Tyr | Gly |
| | | | 180 | | | | | 185 | | | | | 190 | | |
| Ala | Glu | Ile | Val | Ser | Ala | Leu | Asp | Tyr | Leu | His | Ser | Glu | Lys | Asn | Val |
| | | | 195 | | | | | 200 | | | | | 205 | | |
| Val | Tyr | Arg | Asp | Leu | Lys | Leu | Glu | Asn | Leu | Met | Leu | Asp | Lys | Asp | Gly |
| | 210 | | | | | 215 | | | | | 220 | | | | |
| His | Ile | Lys | Ile | Thr | Asp | Phe | Gly | Leu | Cys | Lys | Glu | Gly | Ile | Lys | Asp |
| 225 | | | | | 230 | | | | | 235 | | | | | 240 |
| Gly | Ala | Thr | Met | Lys | Thr | Phe | Cys | Gly | Thr | Pro | Glu | Tyr | Leu | Ala | Pro |
| | | | | 245 | | | | | 250 | | | | | 255 | |
| Glu | Val | Leu | Glu | Asp | Asn | Asp | Tyr | Gly | Arg | Ala | Val | Asp | Trp | Trp | Gly |
| | | | 260 | | | | | 265 | | | | | 270 | | |
| Leu | Gly | Val | Val | Met | Tyr | Glu | Met | Met | Cys | Gly | Arg | Leu | Pro | Phe | Tyr |
| | | | 275 | | | | | 280 | | | | | 285 | | |
| Asn | Gln | Asp | His | Glu | Lys | Leu | Phe | Glu | Leu | Ile | Leu | Met | Glu | Glu | Ile |
| | 290 | | | | | 295 | | | | | 300 | | | | |
| Arg | Phe | Pro | Arg | Thr | Leu | Gly | Pro | Glu | Ala | Lys | Ser | Leu | Leu | Ser | Gly |
| 305 | | | | | 310 | | | | | 315 | | | | | 320 |
| Leu | Leu | Lys | Lys | Asp | Pro | Lys | Gln | Arg | Leu | Gly | Gly | Ser | Glu | Asp | |
| | | | | 325 | | | | | 330 | | | | | 335 | |
| Ala | Lys | Glu | Ile | Met | Gln | His | Arg | Phe | Phe | Ala | Gly | Ile | Val | Trp | Gln |
| | | | 340 | | | | | 345 | | | | | 350 | | |
| His | Val | Tyr | Glu | Lys | Lys | Leu | Ser | Pro | Pro | Phe | Lys | Pro | Gln | Val | Thr |
| | | | 355 | | | | | 360 | | | | | 365 | | |
| Ser | Glu | Thr | Asp | Thr | Arg | Tyr | Phe | Asp | Glu | Glu | Phe | Thr | Ala | Gln | Met |
| | 370 | | | | | 375 | | | | | 380 | | | | |
| Ile | Thr | Ile | Thr | Pro | Pro | Asp | Gln | Asp | Asp | Ser | Met | Glu | Cys | Val | Asp |
| 385 | | | | | 390 | | | | | 395 | | | | | 400 |

Ser Glu Arg Arg Pro His Phe Pro Gln Phe Ser Tyr Ser Ala Ser Gly
            405                 410                 415

Thr Ala

<210> SEQ ID NO 44
<211> LENGTH: 119
<212> TYPE: DNA
<213> ORGANISM: Homo sapiens

<400> SEQUENCE: 44
aaaaaaaaac tgccacggag ccccagcggc tacacactcc actcactcac acctctcagg      60
gccccgcacg ttcccacagc cctcagggtg tacgtgctgt aggtgtggct gtgcccag       119

<210> SEQ ID NO 45
<211> LENGTH: 130
<212> TYPE: DNA
<213> ORGANISM: Homo sapiens

<400> SEQUENCE: 45
aaaaaaaaac tgccacggag ccccagcggc tacacactcc actcactcac acctctcagg      60
gccccgcacg ttcccacagc cctcagggtg tacgtgctgt aggtgtggct gtgcccaga     120 gtgccagctg                                                            130

<210> SEQ ID NO 46
<211> LENGTH: 22
<212> TYPE: DNA
<213> ORGANISM: Artificial Sequence
<220> FEATURE:
<223> OTHER INFORMATION: forward primer used for specifically detecting
      the variant of the present invention (D-NT2RP8004156.1)

<400> SEQUENCE: 46
tcagggtgta cgtgctgtag gt                                               22

<210> SEQ ID NO 47
<211> LENGTH: 19
<212> TYPE: DNA
<213> ORGANISM: Artificial Sequence
<220> FEATURE:
<223> OTHER INFORMATION: reverse primer used for specifically detecting
      the variant of the present invention (D-NT2RP8004156.1)

<400> SEQUENCE: 47
acatggaagg tgcgttcga                                                   19

<210> SEQ ID NO 48
<211> LENGTH: 131
<212> TYPE: DNA
<213> ORGANISM: Artificial Sequence
<220> FEATURE:
<223> OTHER INFORMATION: partial polynucleotide specific to the variant
      of the present invention (D-NT2RP8004156.1), which is obtained by
      PCR using forward primer (SEQ ID NO:46) and reverse primer (SEQ ID
      NO:47)

<400> SEQUENCE: 48
tcagggtgta cgtgctgtag gtgtggctgt gccccagagt gccagctgat gaagacggag      60 cggcccggc ccaacacctt catcatccgc tgcctgcagt ggaccactgt catcgaacgc     120
accttccatg t                                                          131

<210> SEQ ID NO 49
<211> LENGTH: 18

-continued

```
<212> TYPE: DNA
<213> ORGANISM: Artificial Sequence
<220> FEATURE:
<223> OTHER INFORMATION: forward primer used for specifically detecting
      the known variant of the gene of the present invention
      (NM_005163.1)

<400> SEQUENCE: 49
ggttggctgc acaaacga                                                   18

<210> SEQ ID NO 50
<211> LENGTH: 21
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_005163.1)

<400> SEQUENCE: 50
gagcctcacg ttggtccaca t                                               21

<210> SEQ ID NO 51
<211> LENGTH: 124
<212> TYPE: DNA
<213> ORGANISM: Artificial Sequence
<220> FEATURE:
<223> OTHER INFORMATION: partial polynucleotide specific to the known
      variant of the gene of the present invention (NM_005163.1), which
      is obtained by PCR using forward primer (SEQ ID NO:49) and reverse
      primer (SEQ ID NO:50)

<400> SEQUENCE: 51
ggttggctgc acaaacgagg ggagtacatc aagacctggc ggccacgcta cttcctcctc     60
aagaatgatg gcaccttcat tggctacaag gagcggccgc aggatgtgga ccaacgtgag    120
gctc                                                                 124

<210> SEQ ID NO 52
<211> LENGTH: 18
<212> TYPE: DNA
<213> ORGANISM: Artificial Sequence
<220> FEATURE:
<223> OTHER INFORMATION: forward primer used for detecting the variants
      of the gene of the present invention (D-NT2RP8004156.1 and
      NM_005163.1)

<400> SEQUENCE: 52
ccgcgtcctg cagaactc                                                   18

<210> SEQ ID NO 53
<211> LENGTH: 18
<212> TYPE: DNA
<213> ORGANISM: Artificial Sequence
<220> FEATURE:
<223> OTHER INFORMATION: reverse primer used for detecting the variants
      of the gene of the present invention (D-NT2RP8004156.1 and
      NM_005163.1)

<400> SEQUENCE: 53
cccgttggcg tactccat                                                   18

<210> SEQ ID NO 54
<211> LENGTH: 100
<212> TYPE: DNA
<213> ORGANISM: Artificial Sequence
<220> FEATURE:
<223> OTHER INFORMATION: partial polynucleotide common to the variants
      of the gene of the present invention (D-NT2RP8004156.1 and
```

NM_005163.1), which is obtained by PCR using forward primer (SEQ
ID NO:52) and reverse primer (SEQ ID NO:53)

<400> SEQUENCE: 54
ccgcgtcctg cagaactcca ggcacccctt cctcacagcc ctgaagtact ctttccagac    60
ccacgaccgc ctctgctttg tcatggagta cgccaacggg                          100

<210> SEQ ID NO 55
<211> LENGTH: 213
<212> TYPE: DNA
<213> ORGANISM: Homo sapiens

<400> SEQUENCE: 55
aaaaaaaaac tgccacggag ccccagcggc tacacactcc actcactcac acctctcagg    60
gccccgcacg ttcccacagc cctcagggtg tacgtgctgt aggtgtggct gtgcccaga    120 gtgccagctg atgaagacgg agcggccccg gcccaacacc ttcatcatcc gctgcctgca   180
gtggaccact gtcatcgaac gcaccttcca tgt                                213

<210> SEQ ID NO 56
<211> LENGTH: 1800
<212> TYPE: DNA
<213> ORGANISM: Homo sapiens

<400> SEQUENCE: 56
aataatgcta atacccagca ctcgggctcc acaatgtaga ggaaatggca tcgcctggca    60
gtgacagcta tattgtgcgt gtcaaggctg tggttatgac agagatgac tccagcgggg    120 gatggttccc acgggaagga ggcgggatca gtcgcgtcgg ggtctgtaag gtcatgcacc   180
ccgaaggcaa tggacgaagc ggcttttctca tccatggtga acgacagaaa gacaaactgg   240
tggtattgga atgctatgta agaaaggact tggtctacac caaagccaat ccaacgtttc   300
atcactggaa ggtcgataat aggaagtttg gacttacttt ccaaagccct gctgatgccc   360
gagcctttga caggggagta aggaaagcaa tcgaagacct tatagaaggt tcaacaacgt   420
catcttccac catccataat gaagctgagc ttggcgatga tgacgttttt acaacagcta   480
cagacagttc ttctaattcc tctcagaaga gagagcaacc tactcggaca atctcctctc   540
ccacatcctg tgagcaccgg aggatttata ccctgggcca cctccacgac tcataccca   600 cagaccacta tcacctcgat cagccgatgc caaggcccta ccgccaggtg agcttcccgg   660
acgacgacga ggagatcgtg cgcatcaacc cccgggagaa gatctggatg acggggtacg   720
aggattaccg gcacgcaccc gtcaggggca agtacccgga cccctcggag gacgcggact   780
cctcctacgt gcgcttcgcc aagggcgagg tccccaagca tgactacaac taccctacg   840 tggactcctc agactttggc ctaggcgagg acccaaagg ccgcggggc agcgtgatca   900 agacgcagcc ctcccgggc aagtcgcggc ggcggaagga ggacgagag cgctcgcggt   960 gcgtgtactg cagggacatg ttcaaccacg aggagaaccg ccggggccac tgccaggacg   1020
cgcccgactc cgtgagaact tgcatccgcc gggtgagctg catgtggtgc gcggacagca   1080
tgctctatca ctgtatgtcg gaccccgagg gagactatac agacccttgc tcgtgcgata   1140
ctagcgacga gaagttttgc ctccggtgga tggctcttat tgccttgtct ttcctggccc   1200
cctgtatgtg ctgttacctg cccccttcggg cctgctacca ctgcggagtg atgtgcaggt   1260
gctgtggcgg gaagcacaaa gcggccgcgt gactcagttt ccctcccttc tccctccatc   1320
cgcagccaca ggggaactcg tctcttacat actctcatct tctcccccgc tcccttccac   1380
tccaaggagc gaggagggca agcggcctcc cagctccctg gtacctcgag gcaccattcc   1440

-continued

```
agccagggac gctgccgggt agactctcca ctcccctgc cgcccacact gcagcagcca    1500
catccataca cacacgctcg cacagtgttc tgaggaagga accttcgcca cagactcctg    1560
tactattaac aatctgtaac caagctaact gtctcatcca tgtgttgatt cctgtttcc     1620 tcctcccccg cctcttccag ttcaaaggag tctgcaattg gaactgctga ttttcggtgg    1680
gttttgtagt tgatttttcc aagagcgtcg aagactctct ttctcttggt tcaccttgcc    1740
tgtcgctagc aagcatctgg ttcagcggaa atgggatgtg agaatgatga aacccgacag    1800
```

<210> SEQ ID NO 57
<211> LENGTH: 1800
<212> TYPE: DNA
<213> ORGANISM: Homo sapiens
<221> NAME/KEY: CDS
<222> LOCATION: (45)..(1292)

<400> SEQUENCE: 57

```
aataatgcta atacccagca ctcgggctcc acaatgtaga ggaa atg gca tcg cct         56
                                                Met Ala Ser Pro
                                                  1 ggc agt gac agc tat att gtg cgt gtc aag gct gtg gtt atg acc aga         104
Gly Ser Asp Ser Tyr Ile Val Arg Val Lys Ala Val Val Met Thr Arg
  5                  10                  15                  20 gat gac tcc agc ggg gga tgg ttc cca cgg gaa gga ggc ggg atc agt         152
Asp Asp Ser Ser Gly Gly Trp Phe Pro Arg Glu Gly Gly Gly Ile Ser
                 25                  30                  35 cgc gtc ggg gtc tgt aag gtc atg cac ccc gaa ggc aat gga cga agc         200
Arg Val Gly Val Cys Lys Val Met His Pro Glu Gly Asn Gly Arg Ser
             40                  45                  50 ggc ttt ctc atc cat ggt gaa cga cag aaa gac aaa ctg gtg gta ttg         248
Gly Phe Leu Ile His Gly Glu Arg Gln Lys Asp Lys Leu Val Val Leu
         55                  60                  65 gaa tgc tat gta aga aag gac ttg gtc tac acc aaa gcc aat cca acg         296
Glu Cys Tyr Val Arg Lys Asp Leu Val Tyr Thr Lys Ala Asn Pro Thr
 70                  75                  80 ttt cat cac tgg aag gtc gat aat agg aag ttt gga ctt act ttc caa         344
Phe His His Trp Lys Val Asp Asn Arg Lys Phe Gly Leu Thr Phe Gln
 85                  90                  95                 100 agc cct gct gat gcc cga gcc ttt gac agg gga gta agg aaa gca atc         392
Ser Pro Ala Asp Ala Arg Ala Phe Asp Arg Gly Val Arg Lys Ala Ile
                105                 110                 115 gaa gac ctt ata gaa ggt tca aca acg tca tct tcc acc atc cat aat         440
Glu Asp Leu Ile Glu Gly Ser Thr Thr Ser Ser Ser Thr Ile His Asn
            120                 125                 130 gaa gct gag ctt ggc gat gat gac gtt ttt aca aca gct aca gac agt         488
Glu Ala Glu Leu Gly Asp Asp Asp Val Phe Thr Thr Ala Thr Asp Ser
        135                 140                 145 tct tct aat tcc tct cag aag aga gag caa cct act cgg aca atc tcc         536
Ser Ser Asn Ser Ser Gln Lys Arg Glu Gln Pro Thr Arg Thr Ile Ser
    150                 155                 160 tct ccc aca tcc tgt gag cac cgg agg att tat acc ctg ggc cac ctc         584
Ser Pro Thr Ser Cys Glu His Arg Arg Ile Tyr Thr Leu Gly His Leu
165                 170                 175                 180 cac gac tca tac ccc aca gac cac tat cac ctc gat cag ccg atg cca         632
His Asp Ser Tyr Pro Thr Asp His Tyr His Leu Asp Gln Pro Met Pro
                185                 190                 195 agg ccc tac cgc cag gtg agc ttc ccg gac gac gac gag gag atc gtg         680
Arg Pro Tyr Arg Gln Val Ser Phe Pro Asp Asp Asp Glu Glu Ile Val
            200                 205                 210 cgc atc aac ccc cgg gag aag atc tgg atg acg ggg tac gag gat tac         728
Arg Ile Asn Pro Arg Glu Lys Ile Trp Met Thr Gly Tyr Glu Asp Tyr
```

```
                Arg Ile Asn Pro Arg Glu Lys Ile Trp Met Thr Gly Tyr Glu Asp Tyr
                    215                 220                 225 cgg cac gca ccc gtc agg ggc aag tac ccg gac ccc tcg gag gac gcg          776
Arg His Ala Pro Val Arg Gly Lys Tyr Pro Asp Pro Ser Glu Asp Ala
    230                 235                 240 gac tcc tcc tac gtg cgc ttc gcc aag ggc gag gtc ccc aag cat gac          824
Asp Ser Ser Tyr Val Arg Phe Ala Lys Gly Glu Val Pro Lys His Asp
245                 250                 255                 260 tac aac tac ccc tac gtg gac tcc tca gac ttt ggc cta ggc gag gac          872
Tyr Asn Tyr Pro Tyr Val Asp Ser Ser Asp Phe Gly Leu Gly Glu Asp
                265                 270                 275 ccc aaa ggc cgc ggg ggc agc gtg atc aag acg cag ccc tcc cgg ggc          920
Pro Lys Gly Arg Gly Gly Ser Val Ile Lys Thr Gln Pro Ser Arg Gly
            280                 285                 290 aag tcg cgg cgg cgg aag gag gac gga gag cgc tcg cgg tgc gtg tac          968
Lys Ser Arg Arg Arg Lys Glu Asp Gly Glu Arg Ser Arg Cys Val Tyr
        295                 300                 305 tgc agg gac atg ttc aac cac gag gag aac cgc cgg ggc cac tgc cag         1016
Cys Arg Asp Met Phe Asn His Glu Glu Asn Arg Arg Gly His Cys Gln
    310                 315                 320 gac gcg ccc gac tcc gtg aga act tgc atc cgc cgg gtg agc tgc atg         1064
Asp Ala Pro Asp Ser Val Arg Thr Cys Ile Arg Arg Val Ser Cys Met
325                 330                 335                 340 tgg tgc gcg gac agc atg ctc tat cac tgt atg tcg gac ccc gag gga         1112
Trp Cys Ala Asp Ser Met Leu Tyr His Cys Met Ser Asp Pro Glu Gly
                345                 350                 355 gac tat aca gac cct tgc tcg tgc gat act agc gac gag aag ttt tgc         1160
Asp Tyr Thr Asp Pro Cys Ser Cys Asp Thr Ser Asp Glu Lys Phe Cys
            360                 365                 370 ctc cgg tgg atg gct ctt att gcc ttg tct ttc ctg gcc ccc tgt atg         1208
Leu Arg Trp Met Ala Leu Ile Ala Leu Ser Phe Leu Ala Pro Cys Met
        375                 380                 385 tgt tgt tac ctg ccc ctt cgg gcc tgc tac cac tgc gga gtg atg tgc         1256
Cys Cys Tyr Leu Pro Leu Arg Ala Cys Tyr His Cys Gly Val Met Cys
    390                 395                 400 agg tgc tgt ggc ggg aag cac aaa gcg gcc gcg tga ctcagtttcc              1302
Arg Cys Cys Gly Gly Lys His Lys Ala Ala Ala
405                 410                 415 ctcccttctc cctccatccg cagccacagg ggaactcgtc tcttacatac tctcatcttc       1362
tcccccgctc ccttccactc caaggagcga ggagggcaag cggcctccca gctccctggt       1422
acctcgaggc accattccag ccagggacgc tgccgggtag actctccact cccctgccg        1482 cccacactgc agcagccaca tccatacaca cacgctcgca cagtgttctg aggaaggaac       1542
cttcgccaca gactcctgta ctattaacaa tctgtaacca agctaactgt ctcatccatg       1602
tgttgatttc ctgtttcctc ctcccccgcc tcttccagtt caaaggagtc tgcaattgga       1662
actgctgatt tcggtgggt tttgtagttg attttttccaa gagcgtcgaa gactctcttt       1722
ctcttggttc accttgcctg tcgctagcaa gcatctggtt cagcggaaat gggatgtgag       1782
aatgatgaaa cccgacag                                                    1800

<210> SEQ ID NO 58
<211> LENGTH: 415
<212> TYPE: PRT
<213> ORGANISM: Homo sapiens

<400> SEQUENCE: 58

Met Ala Ser Pro Gly Ser Asp Tyr Ile Val Arg Val Lys Ala Val
1               5                   10                  15
```

-continued

Val Met Thr Arg Asp Asp Ser Ser Gly Gly Trp Phe Pro Arg Glu Gly
        20                  25                  30

Gly Gly Ile Ser Arg Val Gly Val Cys Lys Val Met His Pro Glu Gly
            35                  40                  45

Asn Gly Arg Ser Gly Phe Leu Ile His Gly Glu Arg Gln Lys Asp Lys
50                      55                  60

Leu Val Val Leu Glu Cys Tyr Val Arg Lys Asp Leu Val Tyr Thr Lys
65                  70                  75                  80

Ala Asn Pro Thr Phe His His Trp Lys Val Asp Asn Arg Lys Phe Gly
                85                  90                  95

Leu Thr Phe Gln Ser Pro Ala Asp Ala Arg Ala Phe Asp Arg Gly Val
            100                 105                 110

Arg Lys Ala Ile Glu Asp Leu Ile Glu Gly Ser Thr Thr Ser Ser Ser
        115                 120                 125

Thr Ile His Asn Glu Ala Glu Leu Gly Asp Asp Val Phe Thr Thr
    130                 135                 140

Ala Thr Asp Ser Ser Ser Asn Ser Ser Gln Lys Arg Glu Gln Pro Thr
145                 150                 155                 160

Arg Thr Ile Ser Ser Pro Thr Ser Cys Glu His Arg Arg Ile Tyr Thr
                165                 170                 175

Leu Gly His Leu His Asp Ser Tyr Pro Thr Asp His Tyr His Leu Asp
            180                 185                 190

Gln Pro Met Pro Arg Pro Tyr Arg Gln Val Ser Phe Pro Asp Asp Asp
        195                 200                 205

Glu Glu Ile Val Arg Ile Asn Pro Arg Glu Lys Ile Trp Met Thr Gly
210                 215                 220

Tyr Glu Asp Tyr Arg His Ala Pro Val Arg Gly Lys Tyr Pro Asp Pro
225                 230                 235                 240

Ser Glu Asp Ala Asp Ser Ser Tyr Val Arg Phe Ala Lys Gly Glu Val
                245                 250                 255

Pro Lys His Asp Tyr Asn Tyr Pro Tyr Val Asp Ser Ser Asp Phe Gly
            260                 265                 270

Leu Gly Glu Asp Pro Lys Gly Arg Gly Gly Ser Val Ile Lys Thr Gln
        275                 280                 285

Pro Ser Arg Gly Lys Ser Arg Arg Lys Glu Asp Gly Glu Arg Ser
290                 295                 300

Arg Cys Val Tyr Cys Arg Asp Met Phe Asn His Glu Glu Asn Arg Arg
305                 310                 315                 320

Gly His Cys Gln Asp Ala Pro Asp Ser Val Arg Thr Cys Ile Arg Arg
                325                 330                 335

Val Ser Cys Met Trp Cys Ala Ser Met Leu Tyr His Cys Met Ser
            340                 345                 350

Asp Pro Glu Gly Asp Tyr Thr Asp Pro Cys Ser Cys Asp Thr Ser Asp
        355                 360                 365

Glu Lys Phe Cys Leu Arg Trp Met Ala Leu Ile Ala Leu Ser Phe Leu
370                 375                 380

Ala Pro Cys Met Cys Cys Tyr Leu Pro Leu Arg Ala Cys Tyr His Cys
385                 390                 395                 400

Gly Val Met Cys Arg Cys Cys Gly Gly Lys His Lys Ala Ala Ala
                405                 410                 415

<210> SEQ ID NO 59
<211> LENGTH: 61
<212> TYPE: DNA
<213> ORGANISM: Homo sapiens

<400> SEQUENCE: 59
aataatgcta atacccagca ctcgggctcc acaatgtaga ggaaatggca tcgcctggca    60
g    61

<210> SEQ ID NO 60
<211> LENGTH: 6
<212> TYPE: PRT
<213> ORGANISM: Homo sapiens

<400> SEQUENCE: 60

Met Ala Ser Pro Gly Ser
1               5

<210> SEQ ID NO 61
<211> LENGTH: 17
<212> TYPE: DNA
<213> ORGANISM: Homo sapiens

<400> SEQUENCE: 61
atggcatcgc ctggcag    17

<210> SEQ ID NO 62
<211> LENGTH: 22
<212> TYPE: DNA
<213> ORGANISM: Artificial Sequence
<220> FEATURE:
<223> OTHER INFORMATION: forward primer used for specifically detecting
      the variant of the present invention (D-NT2RI3005525.1)

<400> SEQUENCE: 62
ggctccacaa tgtagaggaa at    22

<210> SEQ ID NO 63
<211> LENGTH: 22
<212> TYPE: DNA
<213> ORGANISM: Artificial Sequence
<220> FEATURE:
<223> OTHER INFORMATION: reverse primer used for specifically detecting
      the variant of the present invention (D-NT2RI3005525.1)

<400> SEQUENCE: 63
ggtcataacc acagccttga ca    22

<210> SEQ ID NO 64
<211> LENGTH: 77
<212> TYPE: DNA
<213> ORGANISM: Artificial Sequence
<220> FEATURE:
<223> OTHER INFORMATION: partial polynucleotide specific to the variant
      of the present invention (D-NT2RI3005525.1), which is obtained by
      PCR using forward primer (SEQ ID NO:62) and reverse primer (SEQ ID
      NO:63)

<400> SEQUENCE: 64
ggctccacaa tgtagaggaa atggcatcgc ctggcagtga cagctatatt gtgcgtgtca    60
aggctgtggt tatgacc    77

<210> SEQ ID NO 65
<211> LENGTH: 23
<212> TYPE: DNA
<213> ORGANISM: Artificial Sequence
<220> FEATURE:
<223> OTHER INFORMATION: forward primer used for specifically detecting
      the known variant of the gene of the present invention
      (NM_181784.1)

```
<400> SEQUENCE: 65
acaggcgtct aggtaacaag aaa                                              23

<210> SEQ ID NO 66
<211> LENGTH: 20
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_181784.1)

<400> SEQUENCE: 66
cagccttgac acgcacaata                                                  20

<210> SEQ ID NO 67
<211> LENGTH: 78
<212> TYPE: DNA
<213> ORGANISM: Artificial Sequence
<220> FEATURE:
<223> OTHER INFORMATION: partial polynucleotide specific to the known
      variant of the gene of the present invention (NM_181784.1), which
      is obtained by PCR using forward primer (SEQ ID NO:65) and reverse
      primer (SEQ ID NO:66)

<400> SEQUENCE: 67
acaggcgtct aggtaacaag aaaatgaccg aagaaacaca cccagacgat gacagctata      60
ttgtgcgtgt caaggctg                                                    78

<210> SEQ ID NO 68
<211> LENGTH: 23
<212> TYPE: DNA
<213> ORGANISM: Artificial Sequence
<220> FEATURE:
<223> OTHER INFORMATION: forward primer used for detecting the variants
      of the gene of the present invention (D-NT2RI3005525.1 and
      NM_181784.1)

<400> SEQUENCE: 68
gaccccgagg gagactatac aga                                              23

<210> SEQ ID NO 69
<211> LENGTH: 19
<212> TYPE: DNA
<213> ORGANISM: Artificial Sequence
<220> FEATURE:
<223> OTHER INFORMATION: reverse primer used for detecting the variants
      of the gene of the present invention (D-NT2RI3005525.1 and
      NM_181784.1)

<400> SEQUENCE: 69
atccaccgga ggcaaaact                                                   19

<210> SEQ ID NO 70
<211> LENGTH: 71
<212> TYPE: DNA
<213> ORGANISM: Artificial Sequence
<220> FEATURE:
<223> OTHER INFORMATION: partial polynucleotide common to the variants
      of the gene of the present invention (D-NT2RI3005525.1 and
      NM_181784.1), which is obtained by PCR using forward primer (SEQ
      ID NO:68) and reverse primer (SEQ ID NO:69)

<400> SEQUENCE: 70
gaccccgagg gagactatac agacccttgc tcgtgcgata ctagcgacga gaagttttgc      60
ctccggtgga t                                                           71
```

<210> SEQ ID NO 71
<211> LENGTH: 101
<212> TYPE: DNA
<213> ORGANISM: Homo sapiens

<400> SEQUENCE: 71

```
aataatgcta atacccagca ctcgggctcc acaatgtaga ggaaatggca tcgcctggca      60
gtgacagcta tattgtgcgt gtcaaggctg tggttatgac c                        101
```

<210> SEQ ID NO 72
<211> LENGTH: 1420
<212> TYPE: DNA
<213> ORGANISM: Homo sapiens

<400> SEQUENCE: 72

```
agagctggag catctcgcag ccctacaact tctttgcggc gcttggtctg tctttgcgtt      60
gcgagatcag gatcggtgtg ttgctcagac accggccgaa cgccaccggc acgtctagga    120
gtctcctgtg cctggaagag gctggtttca ttcgattcta aaagaaacgg atgttgaaac    180
atttgtagca gatatactga aaggagaaaa tttatccaag aaagcaaagg aaaagagaga    240
atcccttatt aagaagataa agatgtaaa gtctatctat cttcaggaat ttcaagacaa     300
aggtgatgca gaagatgggg aagaatatga tgacccttt gctgggcctc cagacactat    360
ttcattagcc tcagaacgat atgataaaga cgatgaagcc ccctctgatg agcccagtt     420 tcctccaatt gcagcacaag accttccttt tgttctaaag gctggctacc ttgaaaaacg    480
cagaaaagat cacagctttc tgggatttga atggcagaaa cggtggtgtg ctctcagtaa    540
aacggtattc tattattatg gaagtgataa agacaaacaa cagaaaggtg aatttgcaat    600
agatggctac agtgtcagaa tgaataacac tctaagaaag gatggaaaga aagattgctg    660
ttttgaaatc tctgctcctg ataaacgtat atatcagttt acagcagctt ctcccaaaga    720
tgctgaagaa tgggtacagc agctgaaatt tgtattgcaa gatatggaat ctgatattat    780
tcctgaggat tatgatgaga gggagaatt atatgatgat gttgatcatc ctctaccaat    840
aagcaatcca ctaacaagca gtcaaccaat agatgatgaa atttatgaag aacttccaga    900
agaagaagag gacagtgctc cagtgaaagt ggaagaacaa aggaagatga gtcaggatag    960
tgtccatcac acctcagggg ataagagcac tgattatgct aattttacc agggattgtg   1020 ggattgtact ggagcttttt ctgatgagtt gtcatttaag cgtggtgatg tgatttacat   1080
tcttagcaag gaatacaata gatatggctg gtgggtagga gaaatgaagg gagccattgg   1140
cttggtgcct aaagcctaca taatggagat gtatgatatt tgagagtcct ggaaaaggaa   1200
aattcttctg cttgtctgca aatgctctgg atttagaagc gtcatgaaag cacgagtgac   1260
agctcctaac ctctccttgt tttattaaac attacttatc tttgactgtt atttatgca   1320 gtcgctcatt aaaatattcc tctgatgtga aattaaatga aggatattaa tgtaaattag   1380
atgcaaccag ttaagttata cctgttgcta ttttgcaaag                         1420
```

<210> SEQ ID NO 73
<211> LENGTH: 1420
<212> TYPE: DNA
<213> ORGANISM: Homo sapiens
<221> NAME/KEY: CDS
<222> LOCATION: (620)..(1183)

<400> SEQUENCE: 73

```
agagctggag catctcgcag ccctacaact tctttgcggc gcttggtctg tctttgcgtt      60
```

```
gcgagatcag gatcggtgtg ttgctcagac accggccgaa cgccaccggc acgtctagga      120
gtctcctgtg cctggaagag gctggtttca ttcgattcta aaagaaacgg atgttgaaac      180
atttgtagca gatatactga aaggagaaaa tttatccaag aaagcaaagg aaaagagaga      240
atcccttatt aagaagataa aagatgtaaa gtctatctat cttcaggaat ttcaagacaa      300
aggtgatgca gaagatgggg aagaatatga tgaccctttt gctgggcctc cagacactat      360
ttcattagcc tcagaacgat atgataaaga cgatgaagcc ccctctgatg agcccagtt       420 tcctccaatt gcagcacaag accttccttt tgttctaaag gctggctacc ttgaaaaacg      480
cagaaaagat cacagctttc tgggatttga atggcagaaa cggtggtgtg ctctcagtaa      540
aacggtattc tattattatg gaagtgataa agacaaacaa cagaaaggtg aatttgcaat      600
agatggctac agtgtcaga atg aat aac act cta aga aag gat gga aag aaa      652
              Met Asn Asn Thr Leu Arg Lys Asp Gly Lys Lys
                1               5                  10 gat tgc tgt ttt gaa atc tct gct cct gat aaa cgt ata tat cag ttt       700
Asp Cys Cys Phe Glu Ile Ser Ala Pro Asp Lys Arg Ile Tyr Gln Phe
         15                  20                  25 aca gca gct tct ccc aaa gat gct gaa gaa tgg gta cag cag ctg aaa       748
Thr Ala Ala Ser Pro Lys Asp Ala Glu Glu Trp Val Gln Gln Leu Lys
     30                  35                  40 ttt gta ttg caa gat atg gaa tct gat att att cct gag gat tat gat       796
Phe Val Leu Gln Asp Met Glu Ser Asp Ile Ile Pro Glu Asp Tyr Asp
 45                  50                  55 gag aga gga gaa tta tat gat gat gtt gat cat cct cta cca ata agc       844
Glu Arg Gly Glu Leu Tyr Asp Asp Val Asp His Pro Leu Pro Ile Ser
 60                  65                  70                  75 aat cca cta aca agc agt caa cca ata gat gat gaa att tat gaa gaa       892
Asn Pro Leu Thr Ser Ser Gln Pro Ile Asp Asp Glu Ile Tyr Glu Glu
                 80                  85                  90 ctt cca gaa gaa gaa gag gac agt gct cca gtg aaa gtg gaa gaa caa       940
Leu Pro Glu Glu Glu Glu Asp Ser Ala Pro Val Lys Val Glu Glu Gln
             95                 100                 105 agg aag atg agt cag gat agt gtc cat cac acc tca ggg gat aag agc       988
Arg Lys Met Ser Gln Asp Ser Val His His Thr Ser Gly Asp Lys Ser
        110                 115                 120 act gat tat gct aat ttt tac cag gga ttg tgg gat tgt act gga gct      1036
Thr Asp Tyr Ala Asn Phe Tyr Gln Gly Leu Trp Asp Cys Thr Gly Ala
    125                 130                 135 ttt tct gat gag ttg tca ttt aag cgt ggt gat gtg att tac att ctt      1084
Phe Ser Asp Glu Leu Ser Phe Lys Arg Gly Asp Val Ile Tyr Ile Leu
140                 145                 150                 155 agc aag gaa tac aat aga tat ggc tgg tgg gta gga gaa atg aag gga      1132
Ser Lys Glu Tyr Asn Arg Tyr Gly Trp Trp Val Gly Glu Met Lys Gly
                160                 165                 170 gcc att ggc ttg gtg cct aaa gcc tac ata atg gag atg tat gat att      1180
Ala Ile Gly Leu Val Pro Lys Ala Tyr Ile Met Glu Met Tyr Asp Ile
            175                 180                 185 tga gagtcctgga aaggaaaat tcttctgctt gtctgcaaat gctctggatt             1233
tagaagcgtc atgaaagcac gagtgacagc tcctaacctc ccttgtttt attaaacatt     1293 acttatcttt gactgttatt ttatgcagtc gctcattaaa atattcctct gatgtgaaat     1353
taaatgaagg atattaatgt aaattagatg caaccagtta agttatacct gttgctattt     1413
tgcaaag                                                                1420

<210> SEQ ID NO 74
<211> LENGTH: 187
```

```
<212> TYPE: PRT
<213> ORGANISM: Homo sapiens

<400> SEQUENCE: 74

Met Asn Asn Thr Leu Arg Lys Asp Gly Lys Lys Asp Cys Cys Phe Glu
1               5                   10                  15

Ile Ser Ala Pro Asp Lys Arg Ile Tyr Gln Phe Thr Ala Ala Ser Pro
            20                  25                  30

Lys Asp Ala Glu Glu Trp Val Gln Gln Leu Lys Phe Val Leu Gln Asp
        35                  40                  45

Met Glu Ser Asp Ile Ile Pro Glu Asp Tyr Asp Glu Arg Gly Glu Leu
    50                  55                  60

Tyr Asp Val Asp His Pro Leu Pro Ile Ser Asn Pro Leu Thr Ser
65                  70                  75                  80

Ser Gln Pro Ile Asp Asp Glu Ile Tyr Glu Glu Leu Pro Glu Glu Glu
                85                  90                  95

Glu Asp Ser Ala Pro Val Lys Val Glu Glu Arg Lys Met Ser Gln
            100                 105                 110

Asp Ser Val His His Thr Ser Gly Asp Lys Ser Thr Asp Tyr Ala Asn
            115                 120                 125

Phe Tyr Gln Gly Leu Trp Asp Cys Thr Gly Ala Phe Ser Asp Glu Leu
130                 135                 140

Ser Phe Lys Arg Gly Asp Val Ile Tyr Ile Leu Ser Lys Glu Tyr Asn
145                 150                 155                 160

Arg Tyr Gly Trp Trp Val Gly Glu Met Lys Gly Ala Ile Gly Leu Val
                165                 170                 175

Pro Lys Ala Tyr Ile Met Glu Met Tyr Asp Ile
            180                 185

<210> SEQ ID NO 75
<211> LENGTH: 169
<212> TYPE: DNA
<213> ORGANISM: Homo sapiens

<400> SEQUENCE: 75
agagctggag catctcgcag ccctacaact tctttgcggc gcttggtctg tctttgcgtt      60
gcgagatcag gatcggtgtg ttgctcagac accggccgaa cgccaccggc acgtctagga    120
gtctcctgtg cctggaagag gctggtttca ttcgattcta aaagaaacg                169

<210> SEQ ID NO 76
<211> LENGTH: 619
<212> TYPE: DNA
<213> ORGANISM: Homo sapiens

<400> SEQUENCE: 76
agagctggag catctcgcag ccctacaact tctttgcggc gcttggtctg tctttgcgtt      60
gcgagatcag gatcggtgtg ttgctcagac accggccgaa cgccaccggc acgtctagga    120
gtctcctgtg cctggaagag gctggtttca ttcgattcta aaagaaacgg atgttgaaac    180
atttgtagca gatatactga aaggagaaaa tttatccaag aaagcaaagg aaaagagaga    240
atcccttatt aagaagataa agatgtaaa gtctatctat cttcaggaat tcaagacaa      300 aggtgatgca gaagatgggg aagaatatga tgaccctttt gctgggcctc agacactat     360 ttcattagcc tcagaacgat atgataaaga cgatgaagcc ccctctgatg agcccagtt     420 tcctccaatt gcagcacaag accttccttt tgttctaaag gctggctacc ttgaaaaacg    480
cagaaaagat cacagctttc tgggatttga atggcagaaa cggtggtgtg ctctcagtaa    540
```

-continued

```
aacggtattc tattattatg gaagtgataa agacaaacaa cagaaaggtg aatttgcaat      600
agatggctac agtgtcaga                                                  619
```

<210> SEQ ID NO 77
<211> LENGTH: 20
<212> TYPE: DNA
<213> ORGANISM: Artificial Sequence
<220> FEATURE:
<223> OTHER INFORMATION: forward primer used for specifically detecting
      the variant of the present invention (D-NT2RP8004592.1)

<400> SEQUENCE: 77

```
tctcgcagcc ctacaacttc                                                  20
```

<210> SEQ ID NO 78
<211> LENGTH: 20
<212> TYPE: DNA
<213> ORGANISM: Artificial Sequence
<220> FEATURE:
<223> OTHER INFORMATION: reverse primer used for specifically detecting
      the variant of the present invention (D-NT2RP8004592.1)

<400> SEQUENCE: 78

```
gcaacacacc gatcctgatc                                                  20
```

<210> SEQ ID NO 79
<211> LENGTH: 72
<212> TYPE: DNA
<213> ORGANISM: Artificial Sequence
<220> FEATURE:
<223> OTHER INFORMATION: partial polynucleotide specific to the variant
      of the present invention (D-NT2RP8004592.1), which is obtained by
      PCR using forward primer (SEQ ID NO:77) and reverse primer (SEQ ID
      NO:78)

<400> SEQUENCE: 79

```
tctcgcagcc ctacaacttc tttgcggcgc ttggtctgtc tttgcgttgc gagatcagga      60
tcggtgtgtt gc                                                          72
```

<210> SEQ ID NO 80
<211> LENGTH: 18
<212> TYPE: DNA
<213> ORGANISM: Artificial Sequence
<220> FEATURE:
<223> OTHER INFORMATION: forward primer used for specifically detecting
      the known variant of the gene of the present invention
      (NM_003930.3)

<400> SEQUENCE: 80

```
cctgcgctcc ctaacatg                                                    18
```

<210> SEQ ID NO 81
<211> LENGTH: 22
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_003930.3)

<400> SEQUENCE: 81

```
tgccaacagg ttcctaattt cc                                               22
```

<210> SEQ ID NO 82
<211> LENGTH: 81
<212> TYPE: DNA

<213> ORGANISM: Artificial Sequence
<220> FEATURE:
<223> OTHER INFORMATION: partial polynucleotide specific to the known
      variant of the gene of the present invention (NM_003930.3), which
      is obtained by PCR using forward primer (SEQ ID NO:80) and reverse
      primer (SEQ ID NO:81)

<400> SEQUENCE: 82
cctgcgctcc ctaacatgcc caaccccagc agcacctcct ctccctaccc cctccctgag     60
gaaattagga acctgttggc a                                               81

<210> SEQ ID NO 83
<211> LENGTH: 24
<212> TYPE: DNA
<213> ORGANISM: Artificial Sequence
<220> FEATURE:
<223> OTHER INFORMATION: forward primer used for detecting the variants
      of the gene of the present invention (D-NT2RP8004592.1 and
      NM_003930.3)

<400> SEQUENCE: 83
catcctctac caataagcaa tcca                                            24

<210> SEQ ID NO 84
<211> LENGTH: 27
<212> TYPE: DNA
<213> ORGANISM: Artificial Sequence
<220> FEATURE:
<223> OTHER INFORMATION: reverse primer used for detecting the variants
      of the gene of the present invention (D-NT2RP8004592.1 and
      NM_003930.3)

<400> SEQUENCE: 84
ctatcctgac tcatcttcct ttgttct                                         27

<210> SEQ ID NO 85
<211> LENGTH: 134
<212> TYPE: DNA
<213> ORGANISM: Artificial Sequence
<220> FEATURE:
<223> OTHER INFORMATION: partial polynucleotide common to the variants
      of the gene of the present invention (D-NT2RP8004592.1 and
      NM_003930.3), which is obtained by PCR using forward primer (SEQ
      ID NO:83) and reverse primer (SEQ ID NO:84)

<400> SEQUENCE: 85
catcctctac caataagcaa tccactaaca agcagtcaac caatagatga tgaaatttat     60
gaagaacttc cagaagaaga agaggacagt gctccagtga agtggaaga acaaaggaag     120 atgagtcagg atag                                                      134

<210> SEQ ID NO 86
<211> LENGTH: 84
<212> TYPE: DNA
<213> ORGANISM: Homo sapiens

<400> SEQUENCE: 86
agagctggag catctcgcag ccctacaact tctttgcggc gcttggtctg tctttgcgtt     60
gcgagatcag gatcggtgtg ttgc                                            84

<210> SEQ ID NO 87
<211> LENGTH: 1660
<212> TYPE: DNA
<213> ORGANISM: Homo sapiens

<400> SEQUENCE: 87

-continued

```
aagccagttt gaacttcagg aggaggaact atttggccaa acacctcct aatatgtagt      60
tcagtagaga tgccctggag aatgctgcac tgttccacat gcctgcaaat attcctctaa    120
tgatacagtc ccaaggcttt ggacattgat agactccagg tatggcagca gccaaacttc    180
tgcatgactc tggactgaat gtggttgttc tggaagcccg gaccgtgtg ggaggcagga     240
cttacactct taggaaccaa aaggttaaat atgtggacct tggaggatcc tatgttggac    300
caacccagaa tcgtatcttg agattagcca aggagctagg attggagacc tacaaagtga    360
atgaggttga gcgtctgatc caccatgtaa agggcaaatc ataccccttc agggggccat    420
tcccacctgt atggaatcca attacctact tagatcataa caacttttgg aggacaatgg    480
atgacatggg gcgagagatt ccgagtgatg ccccatggaa ggctccccctt gcagaagagt    540
gggacaacat gacaatgaag gagctactgg acaagctctg ctggactgaa tctgcaaagc    600
agcttgccac tctctttgtg aacctgtgtg tcactgcaga gacccatgag gtctctgctc    660
tctggttcct gtggtatgtg aagcagtgtg gaggcacaac aagaatcatc tcgacaacaa    720
atggaggaca ggagaggaaa tttgtgggcg atctggtca agtgagtgag cggataatgg     780
acctccttgg agaccgagtg aagctggaga ggcctgtgat ctacattgac cagacaagag    840
aaaatgtcct tgtggagacc ctaaaccatg agatgtatga ggctaaatat gtgattagtg    900
ctattcctcc tactctgggc atgaagattc acttcaatcc ccctctgcca atgatgagaa    960
accagatgat cactcgtgtg cctttgggtt cagtcatcaa gtgtatagtt tattataaag   1020
agcctttctg gaggaaaaag gattactgtg gaaccatgat tattgatgga gaagaagctc   1080
cagttgccta cacgttggat gataccaaac ctgaaggcaa ctatgctgcc ataatgggat   1140
ttatcctggc ccacaaagcc agaaaactgg cacgtcttac caaagaggaa aggttgaaga   1200
aactttgtga actctatgcc aaggttctgg gttccctaga agctctggag ggttctacgc   1260
cagccagtgg acaggattta ctttgcaggc accgagactg ccacacactg gagcggctac   1320
atggagggg ctgtagaggc cggggagaga gcagcccgag agatcctgca tgccatgggg    1380
aagattccag aggatgaaat ctggcagtca gaaccagagt ctgtggatgt ccctgcacag   1440
cccatcacca ccaccttttt ggagagacat ttgccctccg tgccaggcct gctcaggctg   1500
attggattga ccaccatctt ttcagcaacg gctcttggct tcctggccca caaaaggggg   1560
ctacttgtga gagtctaaag agagagggtg tctgtaatca cactctcttc ttactgtatt   1620
tgggatatga gtttggggaa agagttgcag taaagttcca                         1660
```

<210> SEQ ID NO 88
<211> LENGTH: 1660
<212> TYPE: DNA
<213> ORGANISM: Homo sapiens
<221> NAME/KEY: CDS
<222> LOCATION: (162)..(1397)

<400> SEQUENCE: 88

```
aagccagttt gaacttcagg aggaggaact atttggccaa acacctcct aatatgtagt      60 tcagtagaga tgccctggag aatgctgcac tgttccacat gcctgcaaat attcctctaa    120
tgatacagtc ccaaggcttt ggacattgat agactccagg t atg gca gca gcc aaa    176
                                              Met Ala Ala Ala Lys
                                                1               5 ctt ctg cat gac tct gga ctg aat gtg gtt gtt ctg gaa gcc cgg gac      224
Leu Leu His Asp Ser Gly Leu Asn Val Val Val Leu Glu Ala Arg Asp
         10                  15                  20 cgt gtg gga ggc agg act tac act ctt agg aac caa aag gtt aaa tat      272
Arg Val Gly Gly Arg Thr Tyr Thr Leu Arg Asn Gln Lys Val Lys Tyr
```

```
                   25                  30                  35
gtg gac ctt gga gga tcc tat gtt gga cca acc cag aat cgt atc ttg      320
Val Asp Leu Gly Gly Ser Tyr Val Gly Pro Thr Gln Asn Arg Ile Leu
         40                  45                  50 aga tta gcc aag gag cta gga ttg gag acc tac aaa gtg aat gag gtt      368
Arg Leu Ala Lys Glu Leu Gly Leu Glu Thr Tyr Lys Val Asn Glu Val
 55                  60                  65 gag cgt ctg atc cac cat gta aag ggc aaa tca tac ccc ttc agg ggg      416
Glu Arg Leu Ile His His Val Lys Gly Lys Ser Tyr Pro Phe Arg Gly
 70                  75                  80                  85 cca ttc cca cct gta tgg aat cca att acc tac tta gat cat aac aac      464
Pro Phe Pro Pro Val Trp Asn Pro Ile Thr Tyr Leu Asp His Asn Asn
                 90                  95                 100 ttt tgg agg aca atg gat gac atg ggg cga gag att ccg agt gat gcc      512
Phe Trp Arg Thr Met Asp Asp Met Gly Arg Glu Ile Pro Ser Asp Ala
            105                 110                 115 cca tgg aag gct ccc ctt gca gaa gag tgg gac aac atg aca atg aag      560
Pro Trp Lys Ala Pro Leu Ala Glu Glu Trp Asp Asn Met Thr Met Lys
        120                 125                 130 gag cta ctg gac aag ctc tgc tgg act gaa tct gca aag cag ctt gcc      608
Glu Leu Leu Asp Lys Leu Cys Trp Thr Glu Ser Ala Lys Gln Leu Ala
    135                 140                 145 act ctc ttt gtg aac ctg tgt gtc act gca gag acc cat gag gtc tct      656
Thr Leu Phe Val Asn Leu Cys Val Thr Ala Glu Thr His Glu Val Ser
150                 155                 160                 165 gct ctc tgg ttc ctg tgg tat gtg aag cag tgt gga ggc aca aca aga      704
Ala Leu Trp Phe Leu Trp Tyr Val Lys Gln Cys Gly Gly Thr Thr Arg
                170                 175                 180 atc atc tcg aca aca aat gga gga cag gag agg aaa ttt gtg ggc gga      752
Ile Ile Ser Thr Thr Asn Gly Gly Gln Glu Arg Lys Phe Val Gly Gly
            185                 190                 195 tct ggt caa gtg agt gag cgg ata atg gac ctc ctt gga gac cga gtg      800
Ser Gly Gln Val Ser Glu Arg Ile Met Asp Leu Leu Gly Asp Arg Val
        200                 205                 210 aag ctg gag agg cct gtg atc tac att gac cag aca aga gaa aat gtc      848
Lys Leu Glu Arg Pro Val Ile Tyr Ile Asp Gln Thr Arg Glu Asn Val
    215                 220                 225 ctt gtg gag acc cta aac cat gag atg tat gag gct aaa tat gtg att      896
Leu Val Glu Thr Leu Asn His Glu Met Tyr Glu Ala Lys Tyr Val Ile
230                 235                 240                 245 agt gct att cct cct act ctg ggc atg aag att cac ttc aat ccc cct      944
Ser Ala Ile Pro Pro Thr Leu Gly Met Lys Ile His Phe Asn Pro Pro
                250                 255                 260 ctg cca atg atg aga aac cag atg atc act cgt gtg cct ttg ggt tca      992
Leu Pro Met Met Arg Asn Gln Met Ile Thr Arg Val Pro Leu Gly Ser
            265                 270                 275 gtc atc aag tgt ata gtt tat tat aaa gag cct ttc tgg agg aaa aag     1040
Val Ile Lys Cys Ile Val Tyr Tyr Lys Glu Pro Phe Trp Arg Lys Lys
        280                 285                 290 gat tac tgt gga acc atg att att gat gga gaa gaa gct cca gtt gcc     1088
Asp Tyr Cys Gly Thr Met Ile Ile Asp Gly Glu Glu Ala Pro Val Ala
    295                 300                 305 tac acg ttg gat gat acc aaa cct gaa ggc aac tat gct gcc ata atg     1136
Tyr Thr Leu Asp Asp Thr Lys Pro Glu Gly Asn Tyr Ala Ala Ile Met
310                 315                 320                 325 gga ttt atc ctg gcc cac aaa gcc aga aaa ctg gca cgt ctt acc aaa     1184
Gly Phe Ile Leu Ala His Lys Ala Arg Lys Leu Ala Arg Leu Thr Lys
                330                 335                 340 gag gaa agg ttg aag aaa ctt tgt gaa ctc tat gcc aag gtt ctg ggt     1232
Glu Glu Arg Leu Lys Lys Leu Cys Glu Leu Tyr Ala Lys Val Leu Gly
```

```
                                          345                   350                   355
tcc cta gaa gct ctg gag ggt tct acg cca gcc agt gga cag gat tta                         1280
Ser Leu Glu Ala Leu Glu Gly Ser Thr Pro Ala Ser Gly Gln Asp Leu
            360                   365                   370 ctt tgc agg cac cga gac tgc cac aca ctg gag cgg cta cat gga ggg                         1328
Leu Cys Arg His Arg Asp Cys His Thr Leu Glu Arg Leu His Gly Gly
        375                   380                   385 ggc tgt aga ggc cgg gga gag agc agc ccg aga gat cct gca tgc cat                         1376
Gly Cys Arg Gly Arg Gly Glu Ser Ser Pro Arg Asp Pro Ala Cys His
390                   395                   400                   405 ggg gaa gat tcc aga gga tga aatctggcag tcagaaccag agtctgtgga                            1427
Gly Glu Asp Ser Arg Gly
                410 tgtccctgca cagcccatca ccaccacctt tttggagaga catttgccct ccgtgccagg                       1487 cctgctcagg ctgattggat tgaccaccat cttttcagca acggctcttg gcttcctggc                       1547 ccacaaaagg gggctacttg tgagagtcta aagagagagg gtgtctgtaa tcacactctc                       1607 ttcttactgt atttgggata tgagtttggg gaaagagttg cagtaaagtt cca                              1660

<210> SEQ ID NO 89
<211> LENGTH: 411
<212> TYPE: PRT
<213> ORGANISM: Homo sapiens

<400> SEQUENCE: 89

Met Ala Ala Ala Lys Leu Leu His Asp Ser Gly Leu Asn Val Val
1               5                   10                  15

Leu Glu Ala Arg Asp Arg Val Gly Gly Arg Thr Tyr Thr Leu Arg Asn
                20                  25                  30

Gln Lys Val Lys Tyr Val Asp Leu Gly Gly Ser Tyr Val Gly Pro Thr
            35                  40                  45

Gln Asn Arg Ile Leu Arg Leu Ala Lys Glu Leu Gly Leu Glu Thr Tyr
        50                  55                  60

Lys Val Asn Glu Val Glu Arg Leu Ile His His Val Lys Gly Lys Ser
65                  70                  75                  80

Tyr Pro Phe Arg Gly Pro Phe Pro Pro Val Trp Asn Pro Ile Thr Tyr
                85                  90                  95

Leu Asp His Asn Asn Phe Trp Arg Thr Met Asp Met Gly Arg Glu
                100                 105                 110

Ile Pro Ser Asp Ala Pro Trp Lys Ala Pro Leu Ala Glu Glu Trp Asp
            115                 120                 125

Asn Met Thr Met Lys Glu Leu Leu Asp Lys Leu Cys Trp Thr Glu Ser
        130                 135                 140

Ala Lys Gln Leu Ala Thr Leu Phe Val Asn Leu Cys Val Thr Ala Glu
145                 150                 155                 160

Thr His Glu Val Ser Ala Leu Trp Phe Leu Trp Tyr Val Lys Gln Cys
                165                 170                 175

Gly Gly Thr Thr Arg Ile Ile Ser Thr Thr Asn Gly Gly Gln Glu Arg
            180                 185                 190

Lys Phe Val Gly Gly Ser Gly Gln Val Ser Glu Arg Ile Met Asp Leu
        195                 200                 205

Leu Gly Asp Arg Val Lys Leu Glu Arg Pro Val Ile Tyr Ile Asp Gln
    210                 215                 220

Thr Arg Glu Asn Val Leu Val Glu Thr Leu Asn His Glu Met Tyr Glu
225                 230                 235                 240

Ala Lys Tyr Val Ile Ser Ala Ile Pro Pro Thr Leu Gly Met Lys Ile
```

```
                    245                 250                 255
His Phe Asn Pro Pro Leu Pro Met Met Arg Asn Gln Met Ile Thr Arg
            260                 265                 270

Val Pro Leu Gly Ser Val Ile Lys Cys Ile Val Tyr Tyr Lys Glu Pro
        275                 280                 285

Phe Trp Arg Lys Lys Asp Tyr Cys Gly Thr Met Ile Ile Asp Gly Glu
    290                 295                 300

Glu Ala Pro Val Ala Tyr Thr Leu Asp Asp Thr Lys Pro Glu Gly Asn
305                 310                 315                 320

Tyr Ala Ala Ile Met Gly Phe Ile Leu Ala His Lys Ala Arg Lys Leu
                325                 330                 335

Ala Arg Leu Thr Lys Glu Glu Arg Leu Lys Lys Leu Cys Glu Leu Tyr
            340                 345                 350

Ala Lys Val Leu Gly Ser Leu Glu Ala Leu Glu Gly Ser Thr Pro Ala
        355                 360                 365

Ser Gly Gln Asp Leu Leu Cys Arg His Arg Asp Cys His Thr Leu Glu
    370                 375                 380

Arg Leu His Gly Gly Gly Cys Arg Gly Arg Gly Glu Ser Ser Pro Arg
385                 390                 395                 400

Asp Pro Ala Cys His Gly Glu Asp Ser Arg Gly
                405                 410

<210> SEQ ID NO 90
<211> LENGTH: 156
<212> TYPE: DNA
<213> ORGANISM: Homo sapiens

<400> SEQUENCE: 90
aagccagttt gaacttcagg aggaggaact atttggccaa acacctcct aatatgtagt      60 tcagtagaga tgccctggag aatgctgcac tgttccacat gcctgcaaat attcctctaa    120
tgatacagtc ccaaggcttt ggacattgat agactc                              156

<210> SEQ ID NO 91
<211> LENGTH: 161
<212> TYPE: DNA
<213> ORGANISM: Homo sapiens

<400> SEQUENCE: 91
aagccagttt gaacttcagg aggaggaact atttggccaa acacctcct aatatgtagt      60 tcagtagaga tgccctggag aatgctgcac tgttccacat gcctgcaaat attcctctaa    120
tgatacagtc ccaaggcttt ggacattgat agactccagg t                        161

<210> SEQ ID NO 92
<211> LENGTH: 42
<212> TYPE: DNA
<213> ORGANISM: Homo sapiens

<400> SEQUENCE: 92
ggttccctag aagctctgga gggttctacg ccagccagtg ga                        42

<210> SEQ ID NO 93
<211> LENGTH: 48
<212> TYPE: PRT
<213> ORGANISM: Homo sapiens

<400> SEQUENCE: 93

Gly Ser Thr Pro Ala Ser Gly Gln Asp Leu Leu Cys Arg His Arg Asp
1               5                   10                  15
```

```
Cys His Thr Leu Glu Arg Leu His Gly Gly Gly Cys Arg Gly Arg Gly
            20                  25                  30

Glu Ser Ser Pro Arg Asp Pro Ala Cys His Gly Glu Asp Ser Arg Gly
        35                  40                  45
```

<210> SEQ ID NO 94
<211> LENGTH: 14
<212> TYPE: PRT
<213> ORGANISM: Homo sapiens

<400> SEQUENCE: 94

```
Gly Ser Leu Glu Ala Leu Glu Gly Ser Thr Pro Ala Ser Gly
1               5                   10
```

<210> SEQ ID NO 95
<211> LENGTH: 98
<212> TYPE: DNA
<213> ORGANISM: Homo sapiens

<400> SEQUENCE: 95

```
ccagtgcatt atgaagaaaa gaactggtgt gaggagcagt actctggggg ctgctacaca    60
acttatttcc cccctgggat cctgactcaa tatggaag                           98
```

<210> SEQ ID NO 96
<211> LENGTH: 33
<212> TYPE: PRT
<213> ORGANISM: Homo sapiens

<400> SEQUENCE: 96

```
Pro Val His Tyr Glu Glu Lys Asn Trp Cys Glu Glu Gln Tyr Ser Gly
1               5                   10                  15

Gly Cys Tyr Thr Thr Tyr Phe Pro Pro Gly Ile Leu Thr Gln Tyr Gly
            20                  25                  30

Arg
```

<210> SEQ ID NO 97
<211> LENGTH: 1864
<212> TYPE: DNA
<213> ORGANISM: Homo sapiens

<400> SEQUENCE: 97

```
aaagaaaacg gagcagcggg caccagggag gcctggaacg gggcgagcgc catgagcaac    60
aaatgcgacg tggtcgtggt gggggggcggc atctcagaaa catcagactc tgggcctcta   120
ttgacaaacc gtatccactt gtatggcagc agccaaactt ctgcatgact ctggactgaa   180
tgtggttgtt ctggaagccc gggaccgtgt ggaggcagg acttacactc ttaggaacca    240
aaaggttaaa tatgtggacc ttggaggatc ctatgttgga ccaacccaga atcgtatctt   300
gagattagcc aaggagctag gattggagac ctacaaagtg aatgaggttg agcgtctgat   360
ccaccatgta aagggcaaat cataccccctt caggggggcca ttcccacctg tatggaatcc   420
aattacctac ttagatcata caacttttg gaggacaatg gatgacatgg ggcgagagat    480
tccgagtgat gccccatgga aggctcccct tgcagaagag tgggacaaca tgacaatgaa    540
ggagctactg gacaagctct gctggactga atctgcaaag cagcttgcca ctctctttgt    600
gaacctgtgt gtcactgcag agacccatga ggtctctgct ctctggttcc tgtggtatgt    660
gaagcagtgt ggaggcacaa caagaatcat ctcgacaaca aatggaggac aggagaggaa    720
atttgtgggc ggatctggtc aagtgagtga gcggataatg gacctccttg agaccgagt    780
```

```
gaagctggag aggcctgtga tctacattga ccagacaaga gaaaatgtcc ttgtggagac    840
cctaaaccat gagatgtatg aggctaaata tgtgattagt gctattcctc ctactctggg    900
catgaagatt cacttcaatc cccctctgcc aatgatgaga aaccagatga tcactcgtgt    960
gcctttgggt tcagtcatca agtgtatagt ttattataaa gagcctttct ggaggaaaaa   1020
ggattactgt ggaaccatga ttattgatgg agaagaagct ccagttgcct acacgttgga   1080
tgacaccaaa cctgaaggca actatgctgc cataatggga tttatcctgg cccacaaagc   1140
cagaaaactg gcacgtctta ccaaagagga aaggttgaag aaactttgtg aactctatgc   1200
caaggttctg ggttccctag aagctctgga gccagtgcat tatgaagaaa agaactggtg   1260
tgaggagcag tactctgggg gctgctacac aacttatttc ccccctggga tcctgactca   1320
atatggaagg gttctacgcc agccagtgga caggatttac tttgcaggca ccgagactgc   1380
cacacactgg agcggctaca tggaggggggc tgtagaggcc ggggagagag cagcccgaga   1440
gatcctgcat gccatgggga agattccaga ggatgaaatc tggcagtcag aaccagagtc   1500
tgtggatgtc cctgcacagc ccatcaccac cacctttttg gagagacatt tgccctccgt   1560
gccaggcctg ctcaggctga ttggattgac caccatcttt tcagcaacgg ctcttggctt   1620
cctggcccac aaaaggggggc tacttgtgag agtctaaaga gagagggtgt ctgtaatcac   1680
actctcttct tactgtattt gggatatgag tttggggaaa gagttgcagt aaagttccat   1740
gaagacaaat agtgtggagt gaggcgggga gcatgaagat aaatccaact ctgactgtaa   1800
aatacatggt atctctttct ccgttgtggc ccctgcttag tgtcccttac ctggcttagc   1860
gttc                                                                1864

<210> SEQ ID NO 98
<211> LENGTH: 1864
<212> TYPE: DNA
<213> ORGANISM: Homo sapiens
<221> NAME/KEY: CDS
<222> LOCATION: (143)..(1657)

<400> SEQUENCE: 98
aaagaaaacg gagcagcggg caccagggag gcctggaacg gggcgagcgc catgagcaac     60
aaatgcgacg tggtcgtggt ggggggcggc atctcagaaa catcagactc tgggcctcta    120
ttgacaaacc gtatccactt gt atg gca gca gcc aaa ctt ctg cat gac tct    172
                          Met Ala Ala Ala Lys Leu Leu His Asp Ser
                           1               5                  10 gga ctg aat gtg gtt gtt ctg gaa gcc cgg gac cgt gtg gga ggc agg     220
Gly Leu Asn Val Val Val Leu Glu Ala Arg Asp Arg Val Gly Gly Arg
                 15                  20                  25 act tac act ctt agg aac caa aag gtt aaa tat gtg gac ctt gga gga     268
Thr Tyr Thr Leu Arg Asn Gln Lys Val Lys Tyr Val Asp Leu Gly Gly
         30                  35                  40 tcc tat gtt gga cca acc cag aat cgt atc ttg aga tta gcc aag gag     316
Ser Tyr Val Gly Pro Thr Gln Asn Arg Ile Leu Arg Leu Ala Lys Glu
     45                  50                  55 cta gga ttg gag acc tac aaa gtg aat gag gtt gag cgt ctg atc cac     364
Leu Gly Leu Glu Thr Tyr Lys Val Asn Glu Val Glu Arg Leu Ile His
 60                  65                  70 cat gta aag ggc aaa tca tac ccc ttc agg ggg cca ttc cca cct gta     412
His Val Lys Gly Lys Ser Tyr Pro Phe Arg Gly Pro Phe Pro Pro Val
 75                  80                  85                  90 tgg aat cca att acc tac tta gat cat aac aac ttt tgg agg aca atg     460
Trp Asn Pro Ile Thr Tyr Leu Asp His Asn Asn Phe Trp Arg Thr Met
                 95                 100                 105
```

```
gat gac atg ggg cga gag att ccg agt gat gcc cca tgg aag gct ccc      508
Asp Asp Met Gly Arg Glu Ile Pro Ser Asp Ala Pro Trp Lys Ala Pro
        110                 115                 120 ctt gca gaa gag tgg gac aac atg aca atg aag gag cta ctg gac aag      556
Leu Ala Glu Glu Trp Asp Asn Met Thr Met Lys Glu Leu Leu Asp Lys
            125                 130                 135 ctc tgc tgg act gaa tct gca aag cag ctt gcc act ctc ttt gtg aac      604
Leu Cys Trp Thr Glu Ser Ala Lys Gln Leu Ala Thr Leu Phe Val Asn
        140                 145                 150 ctg tgt gtc act gca gag acc cat gag gtc tct gct ctc tgg ttc ctg      652
Leu Cys Val Thr Ala Glu Thr His Glu Val Ser Ala Leu Trp Phe Leu
155                 160                 165                 170 tgg tat gtg aag cag tgt gga ggc aca aca aga atc atc tcg aca aca      700
Trp Tyr Val Lys Gln Cys Gly Gly Thr Thr Arg Ile Ile Ser Thr Thr
                175                 180                 185 aat gga gga cag gag agg aaa ttt gtg ggc gga tct ggt caa gtg agt      748
Asn Gly Gly Gln Glu Arg Lys Phe Val Gly Gly Ser Gly Gln Val Ser
            190                 195                 200 gag cgg ata atg gac ctc ctt gga gac cga gtg aag ctg gag agg cct      796
Glu Arg Ile Met Asp Leu Leu Gly Asp Arg Val Lys Leu Glu Arg Pro
        205                 210                 215 gtg atc tac att gac cag aca aga gaa aat gtc ctt gtg gag acc cta      844
Val Ile Tyr Ile Asp Gln Thr Arg Glu Asn Val Leu Val Glu Thr Leu
    220                 225                 230 aac cat gag atg tat gag gct aaa tat gtg att agt gct att cct cct      892
Asn His Glu Met Tyr Glu Ala Lys Tyr Val Ile Ser Ala Ile Pro Pro
235                 240                 245                 250 act ctg ggc atg aag att cac ttc aat ccc cct ctg cca atg atg aga      940
Thr Leu Gly Met Lys Ile His Phe Asn Pro Pro Leu Pro Met Met Arg
                255                 260                 265 aac cag atg atc act cgt gtg cct ttg ggt tca gtc atc aag tgt ata      988
Asn Gln Met Ile Thr Arg Val Pro Leu Gly Ser Val Ile Lys Cys Ile
            270                 275                 280 gtt tat tat aaa gag cct ttc tgg agg aaa aag gat tac tgt gga acc     1036
Val Tyr Tyr Lys Glu Pro Phe Trp Arg Lys Lys Asp Tyr Cys Gly Thr
        285                 290                 295 atg att att gat gga gaa gaa gct cca gtt gcc tac acg ttg gat gac     1084
Met Ile Ile Asp Gly Glu Glu Ala Pro Val Ala Tyr Thr Leu Asp Asp
300                 305                 310 acc aaa cct gaa ggc aac tat gct gcc ata atg gga ttt atc ctg gcc     1132
Thr Lys Pro Glu Gly Asn Tyr Ala Ala Ile Met Gly Phe Ile Leu Ala
315                 320                 325                 330 cac aaa gcc aga aaa ctg gca cgt ctt acc aaa gag gaa agg ttg aag     1180
His Lys Ala Arg Lys Leu Ala Arg Leu Thr Lys Glu Glu Arg Leu Lys
                335                 340                 345 aaa ctt tgt gaa ctc tat gcc aag gtt ctg ggt tcc cta gaa gct ctg     1228
Lys Leu Cys Glu Leu Tyr Ala Lys Val Leu Gly Ser Leu Glu Ala Leu
            350                 355                 360 gag cca gtg cat tat gaa gaa aag aac tgg tgt gag gag cag tac tct     1276
Glu Pro Val His Tyr Glu Glu Lys Asn Trp Cys Glu Glu Gln Tyr Ser
        365                 370                 375 ggg ggc tgc tac aca act tat ttc ccc cct ggg atc ctg act caa tat     1324
Gly Gly Cys Tyr Thr Thr Tyr Phe Pro Pro Gly Ile Leu Thr Gln Tyr
380                 385                 390 gga agg gtt cta cgc cag cca gtg gac agg att tac ttt gca ggc acc     1372
Gly Arg Val Leu Arg Gln Pro Val Asp Arg Ile Tyr Phe Ala Gly Thr
395                 400                 405                 410 gag act gcc aca cac tgg agc ggc tac atg gag ggg gct gta gag gcc     1420
Glu Thr Ala Thr His Trp Ser Gly Tyr Met Glu Gly Ala Val Glu Ala
                415                 420                 425
```

```
                                                    -continued
ggg gag aga gca gcc cga gag atc ctg cat gcc atg ggg aag att cca    1468
Gly Glu Arg Ala Ala Arg Glu Ile Leu His Ala Met Gly Lys Ile Pro
            430                 435                 440 gag gat gaa atc tgg cag tca gaa cca gag tct gtg gat gtc cct gca    1516
Glu Asp Glu Ile Trp Gln Ser Glu Pro Glu Ser Val Asp Val Pro Ala
        445                 450                 455 cag ccc atc acc acc acc ttt ttg gag aga cat ttg ccc tcc gtg cca    1564
Gln Pro Ile Thr Thr Thr Phe Leu Glu Arg His Leu Pro Ser Val Pro
460                 465                 470 ggc ctg ctc agg ctg att gga ttg acc acc atc ttt tca gca acg gct    1612
Gly Leu Leu Arg Leu Ile Gly Leu Thr Thr Ile Phe Ser Ala Thr Ala
475                 480                 485                 490 ctt ggc ttc ctg gcc cac aaa agg ggg cta ctt gtg aga gtc taa        1657
Leu Gly Phe Leu Ala His Lys Arg Gly Leu Leu Val Arg Val
                495                 500 agagagaggg tgtctgtaat cacactctct tcttactgta tttgggatat gagtttgggg  1717
aaagagttgc agtaaagttc catgaagaca aatagtgtgg agtgaggcgg ggagcatgaa  1777
gataaatcca actctgactg taaaatacat ggtatctctt tctccgttgt ggcccctgct  1837
tagtgtccct tacctggctt agcgttc                                     1864

<210> SEQ ID NO 99
<211> LENGTH: 504
<212> TYPE: PRT
<213> ORGANISM: Homo sapiens

<400> SEQUENCE: 99

Met Ala Ala Ala Lys Leu Leu His Asp Ser Gly Leu Asn Val Val
1               5                   10                  15

Leu Glu Ala Arg Asp Arg Val Gly Gly Arg Thr Tyr Thr Leu Arg Asn
            20                  25                  30

Gln Lys Val Lys Tyr Val Asp Leu Gly Gly Ser Tyr Val Gly Pro Thr
        35                  40                  45

Gln Asn Arg Ile Leu Arg Leu Ala Lys Glu Leu Gly Leu Glu Thr Tyr
    50                  55                  60

Lys Val Asn Glu Val Glu Arg Leu Ile His His Val Lys Gly Lys Ser
65                  70                  75                  80

Tyr Pro Phe Arg Gly Pro Phe Pro Pro Val Trp Asn Pro Ile Thr Tyr
                85                  90                  95

Leu Asp His Asn Asn Phe Trp Arg Thr Met Asp Asp Met Gly Arg Glu
            100                 105                 110

Ile Pro Ser Asp Ala Pro Trp Lys Ala Pro Leu Ala Glu Glu Trp Asp
        115                 120                 125

Asn Met Thr Met Lys Glu Leu Leu Asp Lys Leu Cys Trp Thr Glu Ser
    130                 135                 140

Ala Lys Gln Leu Ala Thr Leu Phe Val Asn Leu Cys Val Thr Ala Glu
145                 150                 155                 160

Thr His Glu Val Ser Ala Leu Trp Phe Leu Trp Tyr Val Lys Gln Cys
                165                 170                 175

Gly Gly Thr Thr Arg Ile Ile Ser Thr Thr Asn Gly Gly Gln Glu Arg
            180                 185                 190

Lys Phe Val Gly Gly Ser Gly Gln Val Ser Glu Arg Ile Met Asp Leu
        195                 200                 205

Leu Gly Asp Arg Val Lys Leu Glu Arg Pro Val Ile Tyr Ile Asp Gln
    210                 215                 220

Thr Arg Glu Asn Val Leu Val Glu Thr Leu Asn His Glu Met Tyr Glu
225                 230                 235                 240
```

Ala Lys Tyr Val Ile Ser Ala Ile Pro Pro Thr Leu Gly Met Lys Ile
                245                 250                 255

His Phe Asn Pro Pro Leu Pro Met Met Arg Asn Gln Met Ile Thr Arg
            260                 265                 270

Val Pro Leu Gly Ser Val Ile Lys Cys Ile Val Tyr Tyr Lys Glu Pro
        275                 280                 285

Phe Trp Arg Lys Lys Asp Tyr Cys Gly Thr Met Ile Ile Asp Gly Glu
    290                 295                 300

Glu Ala Pro Val Ala Tyr Thr Leu Asp Asp Thr Lys Pro Glu Gly Asn
305                 310                 315                 320

Tyr Ala Ala Ile Met Gly Phe Ile Leu Ala His Lys Ala Arg Lys Leu
                325                 330                 335

Ala Arg Leu Thr Lys Glu Glu Arg Leu Lys Lys Leu Cys Glu Leu Tyr
            340                 345                 350

Ala Lys Val Leu Gly Ser Leu Glu Ala Leu Glu Pro Val His Tyr Glu
        355                 360                 365

Glu Lys Asn Trp Cys Glu Glu Gln Tyr Ser Gly Gly Cys Tyr Thr Thr
    370                 375                 380

Tyr Phe Pro Pro Gly Ile Leu Thr Gln Tyr Gly Arg Val Leu Arg Gln
385                 390                 395                 400

Pro Val Asp Arg Ile Tyr Phe Ala Gly Thr Glu Thr Ala Thr His Trp
                405                 410                 415

Ser Gly Tyr Met Glu Gly Ala Val Glu Ala Gly Glu Arg Ala Ala Arg
            420                 425                 430

Glu Ile Leu His Ala Met Gly Lys Ile Pro Glu Asp Glu Ile Trp Gln
        435                 440                 445

Ser Glu Pro Glu Ser Val Asp Val Pro Ala Gln Pro Ile Thr Thr Thr
    450                 455                 460

Phe Leu Glu Arg His Leu Pro Ser Val Pro Gly Leu Leu Arg Leu Ile
465                 470                 475                 480

Gly Leu Thr Thr Ile Phe Ser Ala Thr Ala Leu Gly Phe Leu Ala His
                485                 490                 495

Lys Arg Gly Leu Leu Val Arg Val
            500

<210> SEQ ID NO 100
<211> LENGTH: 43
<212> TYPE: DNA
<213> ORGANISM: Homo sapiens

<400> SEQUENCE: 100
aaacatcaga ctctgggcct ctattgacaa accgtatcca ctt                    43

<210> SEQ ID NO 101
<211> LENGTH: 142
<212> TYPE: DNA
<213> ORGANISM: Homo sapiens

<400> SEQUENCE: 101
aaagaaaacg gagcagcggg caccagggag gcctggaacg gggcgagcgc catgagcaac    60
aaatgcgacg tggtcgtggt ggggggcggc atctcagaaa catcagactc tgggcctcta   120 ttgacaaaacc gtatccactt gt                                          142

<210> SEQ ID NO 102
<211> LENGTH: 23
<212> TYPE: DNA

```
<213> ORGANISM: Artificial Sequence
<220> FEATURE:
<223> OTHER INFORMATION: forward primer used for specifically detecting
      the variant of the present invention (D-NT2RI2014164.1)

<400> SEQUENCE: 102
tggccaaaac acctcctaat atg                                              23

<210> SEQ ID NO 103
<211> LENGTH: 26
<212> TYPE: DNA
<213> ORGANISM: Artificial Sequence
<220> FEATURE:
<223> OTHER INFORMATION: reverse primer used for specifically detecting
      the variant of the present invention (D-NT2RI2014164.1)

<400> SEQUENCE: 103
atacctggag tctatcaatg tccaaa                                           26

<210> SEQ ID NO 104
<211> LENGTH: 130
<212> TYPE: DNA
<213> ORGANISM: Artificial Sequence
<220> FEATURE:
<223> OTHER INFORMATION: partial polynucleotide specific to the variant
      of the present invention (D-NT2RI2014164.1), which is obtained by
      PCR using forward primer (SEQ ID NO:102) and reverse primer (SEQ
      ID NO:103)

<400> SEQUENCE: 104
tggccaaaac acctcctaat atgtagttca gtagagatgc cctggagaat gctgcactgt      60
tccacatgcc tgcaaatatt cctctaatga tacagtccca aggctttgga cattgataga    120
ctccaggtat                                                           130

<210> SEQ ID NO 105
<211> LENGTH: 24
<212> TYPE: DNA
<213> ORGANISM: Artificial Sequence
<220> FEATURE:
<223> OTHER INFORMATION: forward primer used for specifically detecting
      the variant of the present invention (D-BRAMY2029564.1)

<400> SEQUENCE: 105
ggcatctcag aaacatcaga ctct                                             24

<210> SEQ ID NO 106
<211> LENGTH: 22
<212> TYPE: DNA
<213> ORGANISM: Artificial Sequence
<220> FEATURE:
<223> OTHER INFORMATION: reverse primer used for specifically detecting
      the variant of the present invention (D-BRAMY2029564.1)

<400> SEQUENCE: 106
gcttccagaa caaccacatt ca                                               22

<210> SEQ ID NO 107
<211> LENGTH: 111
<212> TYPE: DNA
<213> ORGANISM: Artificial Sequence
<220> FEATURE:
<223> OTHER INFORMATION: partial polynucleotide specific to the variant
      of the present invention (D-BRAMY2029564.1), which is obtained by
      PCR using forward primer (SEQ ID NO:105) and reverse primer (SEQ
      ID NO:106)

<400> SEQUENCE: 107
```

```
ggcatctcag aaacatcaga ctctgggcct ctattgacaa accgtatcca cttgtatggc    60
agcagccaaa cttctgcatg actctggact gaatgtggtt gttctggaag c            111
```

<210> SEQ ID NO 108
<211> LENGTH: 18
<212> TYPE: DNA
<213> ORGANISM: Artificial Sequence
<220> FEATURE:
<223> OTHER INFORMATION: forward primer used for specifically detecting
      the known variant of the gene of the present invention
      (NM_000898.3)

<400> SEQUENCE: 108

```
gagcgccatg agcaacaa                                                  18
```

<210> SEQ ID NO 109
<211> LENGTH: 22
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_000898.3)

<400> SEQUENCE: 109

```
tccagagtca tgcagaagtt tg                                             22
```

<210> SEQ ID NO 110
<211> LENGTH: 88
<212> TYPE: DNA
<213> ORGANISM: Artificial Sequence
<220> FEATURE:
<223> OTHER INFORMATION: partial polynucleotide specific to the known
      variant of the gene of the present invention (NM_000898.3), which
      is obtained by PCR using forward primer (SEQ ID NO:108) and
      reverse primer (SEQ ID NO:109)

<400> SEQUENCE: 110

```
gagcgccatg agcaacaaat gcgacgtggt cgtggtgggg ggcggcatct caggtatggc    60
agcagccaaa cttctgcatg actctgga                                       88
```

<210> SEQ ID NO 111
<211> LENGTH: 23
<212> TYPE: DNA
<213> ORGANISM: Artificial Sequence
<220> FEATURE:
<223> OTHER INFORMATION: forward primer used for detecting the variants
      of the gene of the present invention (D-NT2RI2014164.1,
      D-BRAMY2029564.1 and NM_000898.3)

<400> SEQUENCE: 111

```
gctctctggt tcctgtggta tgt                                            23
```

<210> SEQ ID NO 112
<211> LENGTH: 20
<212> TYPE: DNA
<213> ORGANISM: Artificial Sequence
<220> FEATURE:
<223> OTHER INFORMATION: reverse primer used for detecting the variants
      of the gene of the present invention (D-NT2RI2014164.1,
      D-BRAMY2029564.1 and NM_000898.3)

<400> SEQUENCE: 112

```
gatccgccca caaatttcct                                                20
```

<210> SEQ ID NO 113
<211> LENGTH: 98

```
<212> TYPE: DNA
<213> ORGANISM: Artificial Sequence
<220> FEATURE:
<223> OTHER INFORMATION: partial polynucleotide common to the variants
      of the gene of the present invention (D-NT2RI2014164.1,
      D-BRAMY2029564.1 and NM_000898.3), which is obtained by PCR using
      forward primer (SEQ ID NO:111) and reverse primer (SEQ ID NO:112)

<400> SEQUENCE: 113
gctctctggt tcctgtggta tgtgaagcag tgtggaggca caacaagaat catctcgaca    60
acaaatggag gacaggagag gaaatttgtg gcggatc                             98

<210> SEQ ID NO 114
<211> LENGTH: 162
<212> TYPE: DNA
<213> ORGANISM: Homo sapiens

<400> SEQUENCE: 114
aagccagttt gaacttcagg aggaggaact atttggccaa acacctcct aatatgtagt     60 tcagtagaga tgccctggag aatgctgcac tgttccacat gcctgcaaat attcctctaa   120
tgatacagtc ccaaggcttt ggacattgat agactccagg ta                      162

<210> SEQ ID NO 115
<211> LENGTH: 198
<212> TYPE: DNA
<213> ORGANISM: Homo sapiens

<400> SEQUENCE: 115
aaagaaaacg gagcagcggg caccagggag gcctggaacg gggcgagcgc catgagcaac    60
aaatgcgacg tggtcgtggt gggggcggc atctcagaaa catcagactc tgggcctcta   120
ttgacaaacc gtatccactt gtatggcagc agccaaactt ctgcatgact ctggactgaa   180
tgtggttgtt ctggaagc                                                 198

<210> SEQ ID NO 116
<211> LENGTH: 1422
<212> TYPE: DNA
<213> ORGANISM: Homo sapiens

<400> SEQUENCE: 116
ctgcgcggcg cggcgggcga tccgagccgg gacgggctgc aggcgggggt gctgcagagg    60
acacgaggcg gcgggctgga gacatggacc gcggcgagca aggtctgctg agaacagacc   120
cagtccctga ggaaggagaa gatgttgctg ccacgatcag tgccacagag accctctcgg   180
aagaggagca ggaagagcta agaagagaac ttgcaaaggt agaagaagaa atccagactc   240
tgtctcaagt gttagcagca aaagagaagc atctagcaga gatcaagcgg aaacttggaa   300
tcaattctct acaggaacta aaacagaaca ttgccaaagg gtggcaagac gtgacagcaa   360
catctgctta caagaagaca tctgaaacct tatcccaggc tggacagaag gcctcagctg   420 cttttttcgtc tgttggctca gtcatcacca aaaagctgga agatgtaaaa ttgcaagcct   480
tttcacattc ctttagtata cgttccattc agcattcaat tagcatgcct gctatgagaa   540
actccccaac tttttaaatca tttgaagaaa aggtcgaaaa cttaaagtct aaagtagggg   600
gaaccaagcc tgctggtggt gatttttggag aagtcttgaa ttcggctgca aatgctagtg   660
ccaccaccac ggagcctctt ccagaaaaga cacaggagag cctgtgagat tcctaccttt   720
gttctgctac ccactgccag atgctgcaag cgaggtccaa gcacatcttg tcaacatgca   780
ttgccatgaa tttctaccag atgtgctttt atttagcttt acatattcct ttgaccaaat   840
```

```
agtttgtggg ttaaacaaaa tgaaaatatc ttcacctcta ttcttgggaa acacccttta      900
gtgtacattt atgttccttt atttaggaaa caccattata aaaacactta tagtaaatgg      960
ggacattcac tataatgatc taagaagcta cagattgtca tagttgtttt cctgctttac     1020
aaaattgctc cagatctgga atgccagttt gacccttgtc ttctataata tttcctttt      1080 ttcccctctt tgaatctctg tatatttgat tcttaactaa aattgttctc ttaaatattc     1140
tgaatcctgg taattaaaag tttgggtgta ttttctttac ctccaaggaa agaactacta     1200
gctacaaaaa atattttgga ataagcattg ttttggtata aggtacatat tttggttgaa     1260
gacaccagac tgaagtaaac agctgtgcat ccaatttatt atagttttgt aagtaacaat     1320
atgtaatcaa acttctaggt gacttgagag tggaacctcc tatatcatta tttagcaccg     1380
tttgtgacag taaccatttc agtgtattgt ttattatacc ac                        1422

<210> SEQ ID NO 117
<211> LENGTH: 1422
<212> TYPE: DNA
<213> ORGANISM: Homo sapiens
<221> NAME/KEY: CDS
<222> LOCATION: (84)..(707)

<400> SEQUENCE: 117
ctgcgcggcg cggcgggcga tccgagccgg gacgggctgc aggcgggggt gctgcagagg       60
acacgaggcg gcgggctgga gac atg gac cgc ggc gag caa ggt ctg ctg aga      113
                          Met Asp Arg Gly Glu Gln Gly Leu Leu Arg
                           1               5                  10 aca gac cca gtc cct gag gaa gga gaa gat gtt gct gcc acg atc agt        161
Thr Asp Pro Val Pro Glu Glu Gly Glu Asp Val Ala Ala Thr Ile Ser
                15                  20                  25 gcc aca gag acc ctc tcg gaa gag gag cag gaa gag cta aga aga gaa        209
Ala Thr Glu Thr Leu Ser Glu Glu Glu Gln Glu Glu Leu Arg Arg Glu
         30                  35                  40 ctt gca aag gta gaa gaa gaa atc cag act ctg tct caa gtg tta gca        257
Leu Ala Lys Val Glu Glu Glu Ile Gln Thr Leu Ser Gln Val Leu Ala
     45                  50                  55 gca aaa gag aag cat cta gca gag atc aag cgg aaa ctt gga atc aat        305
Ala Lys Glu Lys His Leu Ala Glu Ile Lys Arg Lys Leu Gly Ile Asn
 60                  65                  70 tct cta cag gaa cta aaa cag aac att gcc aaa ggg tgg caa gac gtg        353
Ser Leu Gln Glu Leu Lys Gln Asn Ile Ala Lys Gly Trp Gln Asp Val
 75                  80                  85                  90 aca gca aca tct gct tac aag aag aca tct gaa acc tta tcc cag gct        401
Thr Ala Thr Ser Ala Tyr Lys Lys Thr Ser Glu Thr Leu Ser Gln Ala
                 95                 100                 105 gga cag aag gcc tca gct gct ttt tcg tct gtt ggc tca gtc atc acc        449
Gly Gln Lys Ala Ser Ala Ala Phe Ser Ser Val Gly Ser Val Ile Thr
            110                 115                 120 aaa aag ctg gaa gat gta aaa ttg caa gcc ttt tca cat tcc ttt agt        497
Lys Lys Leu Glu Asp Val Lys Leu Gln Ala Phe Ser His Ser Phe Ser
        125                 130                 135 ata cgt tcc att cag cat tca att agc atg cct gct atg aga aac tcc        545
Ile Arg Ser Ile Gln His Ser Ile Ser Met Pro Ala Met Arg Asn Ser
    140                 145                 150 cca act ttt aaa tca ttt gaa gaa aag gtc gaa aac tta aag tct aaa        593
Pro Thr Phe Lys Ser Phe Glu Glu Lys Val Glu Asn Leu Lys Ser Lys
155                 160                 165                 170 gta ggg gga acc aag cct gct ggt ggt gat ttt gga gaa gtc ttg aat        641
Val Gly Gly Thr Lys Pro Ala Gly Gly Asp Phe Gly Glu Val Leu Asn
                175                 180                 185
```

```
tcg gct gca aat gct agt gcc acc acc acg gag cct ctt cca gaa aag        689
Ser Ala Ala Asn Ala Ser Ala Thr Thr Thr Glu Pro Leu Pro Glu Lys
            190                 195                 200 aca cag gag agc ctg tga gattcctacc tttgttctgc tacccactgc                737
Thr Gln Glu Ser Leu
            205 cagatgctgc aagcgaggtc caagcacatc ttgtcaacat gcattgccat gaatttctac       797 cagatgtgct tttatttagc tttacatatt cctttgacca aatagtttgt gggttaaaca       857 aaatgaaaat atcttcacct ctattcttgg gaaacaccct ttagtgtaca tttatgttcc       917 tttatttagg aaacaccatt ataaaaacac ttatagtaaa tggggacatt cactataatg       977 atctaagaag ctacagattg tcatagttgt tttcctgctt tacaaaattg ctccagatct      1037 ggaatgccag tttgaccttt gtcttctata atatttcctt ttttttcccct ctttgaatct     1097 ctgtatattt gattcttaac taaaattgtt ctcttaaata ttctgaatcc tggtaattaa      1157 aagtttgggt gtattttctt tacctccaag gaaagaacta ctagctacaa aaaatatttt      1217 ggaataagca ttgttttggt ataaggtaca tatttggtt gaagacacca gactgaagta       1277 aacagctgtg catccaattt attatagttt tgtaagtaac aatatgtaat caaacttcta      1337 ggtgacttga gagtggaacc tcctatatca ttatttagca ccgtttgtga cagtaaccat      1397 ttcagtgtat tgtttattat accac                                             1422

<210> SEQ ID NO 118
<211> LENGTH: 207
<212> TYPE: PRT
<213> ORGANISM: Homo sapiens

<400> SEQUENCE: 118

Met Asp Arg Gly Glu Gln Gly Leu Leu Arg Thr Asp Pro Val Pro Glu
1               5                   10                  15

Glu Gly Glu Asp Val Ala Ala Thr Ile Ser Ala Thr Glu Thr Leu Ser
            20                  25                  30

Glu Glu Glu Gln Glu Glu Leu Arg Arg Glu Leu Ala Lys Val Glu Glu
        35                  40                  45

Glu Ile Gln Thr Leu Ser Gln Val Leu Ala Ala Lys Glu Lys His Leu
    50                  55                  60

Ala Glu Ile Lys Arg Lys Leu Gly Ile Asn Ser Leu Gln Glu Leu Lys
65                  70                  75                  80

Gln Asn Ile Ala Lys Gly Trp Gln Asp Val Thr Ala Thr Ser Ala Tyr
                85                  90                  95

Lys Lys Thr Ser Glu Thr Leu Ser Gln Ala Gly Gln Lys Ala Ser Ala
            100                 105                 110

Ala Phe Ser Ser Val Gly Ser Val Ile Thr Lys Lys Leu Glu Asp Val
        115                 120                 125

Lys Leu Gln Ala Phe Ser His Ser Phe Ser Ile Arg Ser Ile Gln His
    130                 135                 140

Ser Ile Ser Met Pro Ala Met Arg Asn Ser Pro Thr Phe Lys Ser Phe
145                 150                 155                 160

Glu Glu Lys Val Glu Asn Leu Lys Ser Lys Val Gly Gly Thr Lys Pro
                165                 170                 175

Ala Gly Gly Asp Phe Gly Glu Val Leu Asn Ser Ala Ala Asn Ala Ser
            180                 185                 190

Ala Thr Thr Thr Glu Pro Leu Pro Glu Lys Thr Gln Glu Ser Leu
        195                 200                 205
```

<210> SEQ ID NO 119
<211> LENGTH: 69
<212> TYPE: DNA
<213> ORGANISM: Homo sapiens

<400> SEQUENCE: 119
ttgcaagcct tttcacattc ctttagtata cgttccattc agcattcaat tagcatgcct    60
gctatgaga                                                            69

<210> SEQ ID NO 120
<211> LENGTH: 23
<212> TYPE: PRT
<213> ORGANISM: Homo sapiens

<400> SEQUENCE: 120

Leu Gln Ala Phe Ser His Ser Phe Ser Ile Arg Ser Ile Gln His Ser
1               5                   10                  15

Ile Ser Met Pro Ala Met Arg
            20

<210> SEQ ID NO 121
<211> LENGTH: 21
<212> TYPE: DNA
<213> ORGANISM: Artificial Sequence
<220> FEATURE:
<223> OTHER INFORMATION: forward primer used for specifically detecting
      the variant of the present invention (D-BRHIP2003515.1)

<400> SEQUENCE: 121
tcagctgctt tttcgtctgt t                                              21

<210> SEQ ID NO 122
<211> LENGTH: 20
<212> TYPE: DNA
<213> ORGANISM: Artificial Sequence
<220> FEATURE:
<223> OTHER INFORMATION: reverse primer used for specifically detecting
      the variant of the present invention (D-BRHIP2003515.1)

<400> SEQUENCE: 122
ggaatgtgaa aaggcttgca                                                20

<210> SEQ ID NO 123
<211> LENGTH: 78
<212> TYPE: DNA
<213> ORGANISM: Artificial Sequence
<220> FEATURE:
<223> OTHER INFORMATION: partial polynucleotide specific to the variant
      of the present invention (D-BRHIP2003515.1), which is obtained by
      PCR using forward primer (SEQ ID NO:121) and reverse primer (SEQ
      ID NO:122)

<400> SEQUENCE: 123
tcagctgctt tttcgtctgt tggctcagtc atcaccaaaa agctggaaga tgtaaaattg    60
caagcctttt cacattcc                                                  78

<210> SEQ ID NO 124
<211> LENGTH: 20
<212> TYPE: DNA
<213> ORGANISM: Artificial Sequence
<220> FEATURE:
<223> OTHER INFORMATION: forward primer used for specifically detecting
      the known variant of the gene of the present invention
      (NM_005079.1)

<400> SEQUENCE: 124

```
cctcagctgc tttttcgtct                                                    20
```

<210> SEQ ID NO 125
<211> LENGTH: 25
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_005079.1)

<400> SEQUENCE: 125

```
aaaagttggg gagtttttta catct                                              25
```

<210> SEQ ID NO 126
<211> LENGTH: 74
<212> TYPE: DNA
<213> ORGANISM: Artificial Sequence
<220> FEATURE:
<223> OTHER INFORMATION: partial polynucleotide specific to the known
      variant of the gene of the present invention (NM_005079.1), which
      is obtained by PCR using forward primer (SEQ ID NO:124) and
      reverse primer (SEQ ID NO:125)

<400> SEQUENCE: 126

```
cctcagctgc tttttcgtct gttggctcag tcatcaccaa aaagctggaa gatgtaaaaa        60
actccccaac tttt                                                          74
```

<210> SEQ ID NO 127
<211> LENGTH: 25
<212> TYPE: DNA
<213> ORGANISM: Artificial Sequence
<220> FEATURE:
<223> OTHER INFORMATION: forward primer used for detecting the variants
      of the gene of the present invention (D-BRHIP2003515.1 and
      NM_005079.1)

<400> SEQUENCE: 127

```
gacagcaaca tctgcttaca agaag                                              25
```

<210> SEQ ID NO 128
<211> LENGTH: 22
<212> TYPE: DNA
<213> ORGANISM: Artificial Sequence
<220> FEATURE:
<223> OTHER INFORMATION: reverse primer used for detecting the variants
      of the gene of the present invention (D-BRHIP2003515.1 and
      NM_005079.1)

<400> SEQUENCE: 128

```
atgactgagc caacagacga aa                                                 22
```

<210> SEQ ID NO 129
<211> LENGTH: 93
<212> TYPE: DNA
<213> ORGANISM: Artificial Sequence
<220> FEATURE:
<223> OTHER INFORMATION: partial polynucleotide common to the variants
      of the gene of the present invention (D-BRHIP2003515.1 and
      NM_005079.1), which is obtained by PCR using forward primer (SEQ
      ID NO:127) and reverse primer (SEQ ID NO:128)

<400> SEQUENCE: 129

```
gacagcaaca tctgcttaca agaagacatc tgaaacctta tcccaggctg gacagaaggc        60
ctcagctgct tttcgtctg ttggctcagt cat                                      93
```

<210> SEQ ID NO 130

```
<211> LENGTH: 491
<212> TYPE: DNA
<213> ORGANISM: Homo sapiens

<400> SEQUENCE: 130
ctgcgcggcg cggcgggcga tccgagccgg gacgggctgc aggcgggggt gctgcagagg      60
acacgaggcg gcgggctgga gacatggacc gcggcgagca aggtctgctg agaacagacc     120
cagtccctga ggaaggagaa gatgttgctg ccacgatcag tgccacagag accctctcgg     180
aagaggagca ggaagagcta agaagagaac ttgcaaaggt agaagaagaa atccagactc     240
tgtctcaagt gttagcagca aaagagaagc atctagcaga gatcaagcgg aaacttggaa     300
tcaattctct acaggaacta aaacagaaca ttgccaaagg gtggcaagac gtgacagcaa     360
catctgctta caagaagaca tctgaaacct tatcccaggc tggacagaag gcctcagctg     420 cttttttcgtc tgttggctca gtcatcacca aaaagctgga agatgtaaaa ttgcaagcct     480
tttcacattc c                                                          491

<210> SEQ ID NO 131
<211> LENGTH: 1926
<212> TYPE: DNA
<213> ORGANISM: Homo sapiens

<400> SEQUENCE: 131
aaaagtcggc tcgagtactc cccgtaacga ggaggtgttc tcggccgtcc caccccttcac     60 tgccgtctcc gggctgcgcc gccggagccg ggacgcgcct ccgcagccct cgccgcctcc    120
atccccgcgg ccgcagctcc tctcgccgtc cgcgcgcaca ccatgacgaa gaacgagaag    180
aagtccctca accagagcct ggccgagtgg aagctcttca tctacaaccc gaccaccgga    240
gaattcctgg ggcgcaccgc caagagctgg ggatcgcagt atgtggtagg gaagtgatgc    300
tgtctgaagg tgacatcctg ttctcctctc ttctgtcctc tccatcctta ttttggccac    360
ctggtttgat cttgctcttc tacctagttt tttatgggtt cctggctgca ctcttctcat    420
tcacgatgtg ggttatgctt cagactctca cgatgaggt tccaaaatac cgtgaccaga    480
ttcctagccc aggactcatg gttttttccaa aaccagtgac cgcattggaa tatacattca    540
gtaggtctga tccaacttcg tatgcagggt acattgaaga cccttaagaag tttctaaaac    600 catatacttt agaagaacag aagaacctca cagtctgtcc tgatggagca ctttttgaac    660
agaagggtcc agtttatgtt gcatgtcagt ttcctatttc attacttcaa gcatgcagtg    720
gtatgaatga tcctgatttt ggctattctc aaggaaaccc ttgtattctt gtgaaaatga    780
acagaataat tggattaaag cctgaaggag tgccaaggat agattgtgtt tcaaagacaa    840
ataatgtaaa agatggaatg aagatatacc aaatgtagca gtttatcctc ataatggaat    900
gatagactta aaatatttcc catattatgg gaaaaaactg catgttgggt atctacagcc    960
attggttgct gttcaggtca gctttgctcc taacaacact gggaaagaag taacagttga   1020
gtgcaagatt gatggatcag ccaacctaaa aagtcaggat gatcgtgaca gttttttggg   1080
acgagttatg ttcaaaatca cagcacgtgc atagtatgag taggatatct ccacagtta    1140 aatgttgtgt tgtctgtctt cattttgtaa cagctggacc ttccattcta gaattatgag   1200
accaccttgg agaaaggtgt gtggtacatg acattgggtt acatcataac gtgcttccag   1260
atcatagtgt tcagtgtcct ctgaagtaac tgcctgttgc ctctgctgcc ctttgaacca   1320
gtgtacagtc gccagatagg gaccggtgaa cacctgattc caaacatgta ggatgggggt   1380
cttgtcctct tttatgtgg tttaattgcc aagtgtctaa agcttaatat gccgtgctat    1440
```

```
gtaaatattt tatggatata acaactgtca tattttgatg tcaacagagt tttagggata    1500
aaatggtacc cggccaacat caagtgactt tatagctgca agaaatgtgg tatgtggaga    1560
agttctgtat gtgaggaagg aaaaaaagaa aataaaagtg tgtttgaaaa atattatctt    1620
gggttctttg taaaatttat ttttttacatg ctgaattagc ctcgatcttt ttgattaaga    1680
gcacaaactt tttttttgtaa aacatgtaaa aaaaaaactg ggattaattt ttagtgttgg    1740
aactgcctct tattttaggc tgtagataaa atagcatttt taggttagcc agtgtgacta    1800
tgcacctaat tttttatgag attaaattca taagacttaa tttgtacaat agtttgtgaa    1860
atatcttgtt actgctttta tttagcagac tgtggactgt aataaagtat ataaattgtg    1920
aaatat                                                              1926

<210> SEQ ID NO 132
<211> LENGTH: 1926
<212> TYPE: DNA
<213> ORGANISM: Homo sapiens
<221> NAME/KEY: CDS
<222> LOCATION: (297)..(878)

<400> SEQUENCE: 132
aaaagtcggc tcgagtactc cccgtaacga ggaggtgttc tcggccgtcc cacccttcac     60
tgccgtctcc gggctgcgcc gccggagccg ggacgcgcct ccgcagccct cgccgcctcc    120
atccccgcgg ccgcagctcc tctcgccgtc cgcgcgcaca ccatgacgaa gaacgagaag    180
aagtccctca accagagcct ggccgagtgg aagctcttca tctacaaccc gaccaccgga    240
gaattcctgg ggcgcaccgc caagagctgg ggatcgcagt atgtggtagg gaagtg atg    299
                                                                 Met
                                                                  1 ctg tct gaa ggt gac atc ctg ttc tcc tct ctt ctg tcc tct cca tcc      347
Leu Ser Glu Gly Asp Ile Leu Phe Ser Ser Leu Leu Ser Ser Pro Ser
          5                   10                  15 tta ttt tgg cca cct ggt ttg atc ttg ctc ttc tac cta gtt ttt tat      395
Leu Phe Trp Pro Pro Gly Leu Ile Leu Leu Phe Tyr Leu Val Phe Tyr
         20                  25                  30 ggg ttc ctg gct gca ctc ttc tca ttc acg atg tgg gtt atg ctt cag      443
Gly Phe Leu Ala Ala Leu Phe Ser Phe Thr Met Trp Val Met Leu Gln
     35                  40                  45 act ctc aac gat gag gtt cca aaa tac cgt gac cag att cct agc cca      491
Thr Leu Asn Asp Glu Val Pro Lys Tyr Arg Asp Gln Ile Pro Ser Pro
 50                  55                  60                  65 gga ctc atg gtt ttt cca aaa cca gtg acc gca ttg gaa tat aca ttc      539
Gly Leu Met Val Phe Pro Lys Pro Val Thr Ala Leu Glu Tyr Thr Phe
                 70                  75                  80 agt agg tct gat cca act tcg tat gca ggg tac att gaa gac ctt aag      587
Ser Arg Ser Asp Pro Thr Ser Tyr Ala Gly Tyr Ile Glu Asp Leu Lys
             85                  90                  95 aag ttt cta aaa cca tat act tta gaa gaa cag aag aac ctc aca gtc      635
Lys Phe Leu Lys Pro Tyr Thr Leu Glu Glu Gln Lys Asn Leu Thr Val
        100                 105                 110 tgt cct gat gga gca ctt ttt gaa cag aag ggt cca gtt tat gtt gca      683
Cys Pro Asp Gly Ala Leu Phe Glu Gln Lys Gly Pro Val Tyr Val Ala
    115                 120                 125 tgt cag ttt cct att tca tta ctt caa gca tgc agt ggt atg aat gat      731
Cys Gln Phe Pro Ile Ser Leu Leu Gln Ala Cys Ser Gly Met Asn Asp
130                 135                 140                 145 cct gat ttt ggc tat tct caa gga aac cct tgt att ctt gtg aaa atg      779
Pro Asp Phe Gly Tyr Ser Gln Gly Asn Pro Cys Ile Leu Val Lys Met
                150                 155                 160
```

```
aac aga ata att gga tta aag cct gaa gga gtg cca agg ata gat tgt      827
Asn Arg Ile Ile Gly Leu Lys Pro Glu Gly Val Pro Arg Ile Asp Cys
        165                 170                 175 gtt tca aag aca aat aat gta aaa gat gga atg aag ata tac caa atg      875
Val Ser Lys Thr Asn Asn Val Lys Asp Gly Met Lys Ile Tyr Gln Met
    180                 185                 190 tag cagtttatcc tcataatgga atgatagact aaaatatttt cccatattat           928
gggaaaaaac tgcatgttgg gtatctacag ccattggttg ctgttcaggt cagctttgct    988
cctaacaaca ctgggaaaga agtaacagtt gagtgcaaga ttgatggatc agccaaccta   1048
aaaagtcagg atgatcgtga caagttttg ggacgagtta tgttcaaaat cacagcacgt    1108
gcatagtatg agtaggatat ctccacagag taaatgttgt gttgtctgtc ttcattttgt   1168
aacagctgga ccttccattc tagaattatg agaccacctt ggagaaaggt gtgtggtaca   1228
tgacattggg ttacatcata acgtgcttcc agatcatagt gttcagtgtc ctctgaagta   1288
actgcctgtt gcctctgctg ccctttgaac cagtgtacag tcgccagata gggaccggtg   1348
aacacctgat ccaaacatg taggatgggg gtcttgtcct cttttatgt ggtttaattg     1408
ccaagtgtct aaagcttaat atgccgtgct atgtaaatat tttatggata taacaactgt   1468
catattttga tgtcaacaga gttttaggga taaaatggta cccggccaac atcaagtgac   1528
tttatagctg caagaaatgt ggtatgtgga aagttctgt atgtgaggaa ggaaaaaaag    1588
aaaataaaag tgtgtttgaa aaatattatc ttgggttctt tgtaaaattt attttttaca   1648
tgctgaatta gcctcgatct ttttgattaa gagcacaaac ttttttttgt aaaacatgta   1708
aaaaaaaac tgggattaat ttttagtgtt ggaactgcct cttattttag gctgtagata    1768
aaatagcatt tttaggttag ccagtgtgac tatgcaccta atttttttatg agattaaatt  1828
cataagactt aatttgtaca atagtttgtg aaatatcttg ttactgcttt tatttagcag   1888
actgtggact gtaataaagt atataaattg tgaaatat                           1926
```

<210> SEQ ID NO 133
<211> LENGTH: 193
<212> TYPE: PRT
<213> ORGANISM: Homo sapiens

<400> SEQUENCE: 133

```
Met Leu Ser Glu Gly Asp Ile Leu Phe Ser Leu Leu Ser Ser Pro
1               5                   10                  15

Ser Leu Phe Trp Pro Pro Gly Leu Ile Leu Leu Phe Tyr Leu Val Phe
            20                  25                  30

Tyr Gly Phe Leu Ala Ala Leu Phe Ser Phe Thr Met Trp Val Met Leu
        35                  40                  45

Gln Thr Leu Asn Asp Glu Val Pro Lys Tyr Arg Asp Gln Ile Pro Ser
    50                  55                  60

Pro Gly Leu Met Val Phe Pro Lys Pro Val Thr Ala Leu Glu Tyr Thr
65                  70                  75                  80

Phe Ser Arg Ser Asp Pro Thr Ser Tyr Ala Gly Tyr Ile Glu Asp Leu
                85                  90                  95

Lys Lys Phe Leu Lys Pro Tyr Thr Leu Glu Glu Gln Lys Asn Leu Thr
            100                 105                 110

Val Cys Pro Asp Gly Ala Leu Phe Glu Gln Lys Gly Pro Val Tyr Val
        115                 120                 125

Ala Cys Gln Phe Pro Ile Ser Leu Leu Gln Ala Cys Ser Gly Met Asn
    130                 135                 140

Asp Pro Asp Phe Gly Tyr Ser Gln Gly Asn Pro Cys Ile Leu Val Lys
```

```
                145                 150                 155                 160

Met Asn Arg Ile Ile Gly Leu Lys Pro Glu Gly Val Pro Arg Ile Asp
                    165                 170                 175

Cys Val Ser Lys Thr Asn Asn Val Lys Asp Gly Met Lys Ile Tyr Gln
            180                 185                 190

Met

<210> SEQ ID NO 134
<211> LENGTH: 92
<212> TYPE: DNA
<213> ORGANISM: Homo sapiens

<400> SEQUENCE: 134
gatcgcagta tgtggtaggg aagtgatgct gtctgaaggt gacatcctgt tctcctctct      60
tctgtcctct ccatccttat tttggccacc tg                                   92

<210> SEQ ID NO 135
<211> LENGTH: 23
<212> TYPE: PRT
<213> ORGANISM: Homo sapiens

<400> SEQUENCE: 135

Met Leu Ser Glu Gly Asp Ile Leu Phe Ser Ser Leu Leu Ser Ser Pro
1               5                   10                  15

Ser Leu Phe Trp Pro Pro Gly
            20

<210> SEQ ID NO 136
<211> LENGTH: 67
<212> TYPE: DNA
<213> ORGANISM: Homo sapiens

<400> SEQUENCE: 136
atgctgtctg aaggtgacat cctgttctcc tctcttctgt cctctccatc cttattttgg      60
ccacctg                                                               67

<210> SEQ ID NO 137
<211> LENGTH: 20
<212> TYPE: DNA
<213> ORGANISM: Homo sapiens

<400> SEQUENCE: 137
acaaataatg taaaagatgg                                                 20

<210> SEQ ID NO 138
<211> LENGTH: 13
<212> TYPE: PRT
<213> ORGANISM: Homo sapiens

<400> SEQUENCE: 138

Thr Asn Asn Val Lys Asp Gly Met Lys Ile Tyr Gln Met
1               5                   10

<210> SEQ ID NO 139
<211> LENGTH: 7
<212> TYPE: PRT
<213> ORGANISM: Homo sapiens

<400> SEQUENCE: 139

Thr Asn Asn Val Lys Asp Gly
1               5
```

```
<210> SEQ ID NO 140
<211> LENGTH: 22
<212> TYPE: DNA
<213> ORGANISM: Artificial Sequence
<220> FEATURE:
<223> OTHER INFORMATION: forward primer used for specifically detecting
      the variant of the present invention (D-BRACE2044661.1)

<400> SEQUENCE: 140
cgcagtatgt ggtagggaag tg                                              22

<210> SEQ ID NO 141
<211> LENGTH: 28
<212> TYPE: DNA
<213> ORGANISM: Artificial Sequence
<220> FEATURE:
<223> OTHER INFORMATION: reverse primer used for specifically detecting
      the variant of the present invention (D-BRACE2044661.1)

<400> SEQUENCE: 141
aaactaggta gaagagcaag atcaaacc                                        28

<210> SEQ ID NO 142
<211> LENGTH: 116
<212> TYPE: DNA
<213> ORGANISM: Artificial Sequence
<220> FEATURE:
<223> OTHER INFORMATION: partial polynucleotide specific to the variant
      of the present invention (D-BRACE2044661.1), which is obtained by
      PCR using forward primer (SEQ ID NO:141) and reverse primer (SEQ
      ID NO:142)

<400> SEQUENCE: 142
cgcagtatgt ggtagggaag tgatgctgtc tgaaggtgac atcctgttct cctctcttct     60
gtcctctcca tccttatttt ggccacctgg tttgatcttg ctcttctacc tagttt        116

<210> SEQ ID NO 143
<211> LENGTH: 22
<212> TYPE: DNA
<213> ORGANISM: Artificial Sequence
<220> FEATURE:
<223> OTHER INFORMATION: forward primer used for specifically detecting
      the known variant of the gene of the present invention
      (NM_001679.2)

<400> SEQUENCE: 143
ccgagtggaa gctcttcatc ta                                              22

<210> SEQ ID NO 144
<211> LENGTH: 21
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_001679.2)

<400> SEQUENCE: 144
aagatcaaac cccagctctt g                                               21

<210> SEQ ID NO 145
<211> LENGTH: 79
<212> TYPE: DNA
<213> ORGANISM: Artificial Sequence
<220> FEATURE:
<223> OTHER INFORMATION: partial polynucleotide specific to the known
      variant of the gene of the present invention (NM_001679.2), which
      is obtained by PCR using forward primer (SEQ ID NO:143) and
``` reverse primer (SEQ ID NO:144)

<400> SEQUENCE: 145
ccgagtggaa gctcttcatc tacaacccga ccaccggaga attcctgggg cgcaccgcca    60
agagctgggg tttgatctt    79

<210> SEQ ID NO 146
<211> LENGTH: 23
<212> TYPE: DNA
<213> ORGANISM: Artificial Sequence
<220> FEATURE:
<223> OTHER INFORMATION: forward primer used for detecting the variants
      of the gene of the present invention (D-BRACE2044661.1 and
      NM_001679.2)

<400> SEQUENCE: 146
tcgtatgcag ggtacattga aga    23

<210> SEQ ID NO 147
<211> LENGTH: 23
<212> TYPE: DNA
<213> ORGANISM: Artificial Sequence
<220> FEATURE:
<223> OTHER INFORMATION: reverse primer used for detecting the variants
      of the gene of the present invention (D-BRACE2044661.1 and
      NM_001679.2)

<400> SEQUENCE: 147
tgcaacataa actggaccct tct    23

<210> SEQ ID NO 148
<211> LENGTH: 126
<212> TYPE: DNA
<213> ORGANISM: Artificial Sequence
<220> FEATURE:
<223> OTHER INFORMATION: partial polynucleotide common to the variants
      of the gene of the present invention (D-BRACE2044661.1 and
      NM_001679.2), which is obtained by PCR using forward primer (SEQ
      ID NO:146) and reverse primer (SEQ ID NO:147)

<400> SEQUENCE: 148
tcgtatgcag ggtacattga agaccttaag aagtttctaa aaccatatac tttagaagaa    60
cagaagaacc tcacagtctg tcctgatgga gcacttttg aacagaaggg tccagtttat   120
gttgca    126

<210> SEQ ID NO 149
<211> LENGTH: 390
<212> TYPE: DNA
<213> ORGANISM: Homo sapiens

<400> SEQUENCE: 149
aaaagtcggc tcgagtactc cccgtaacga ggaggtgttc tcggccgtcc caccctttcac    60 tgccgtctcc gggctgcgcc gccggagccg ggacgcgcct ccgcagccct cgccgcctcc   120
atccccgcgg ccgcagctcc tctcgccgtc cgcgcgcaca ccatgacgaa gaacgagaag   180
aagtccctca accagagcct ggccgagtgg aagctcttca tctacaaccc gaccaccgga   240
gaattcctgg ggcgcaccgc caagagctgg ggatcgcagt atgtggtagg gaagtgatgc   300
tgtctgaagg tgacatcctg ttctcctctc ttctgtcctc tccatcctta ttttggccac   360
ctggtttgat cttgctcttc tacctagttt    390

<210> SEQ ID NO 150
<211> LENGTH: 1120

```
<212> TYPE: DNA
<213> ORGANISM: Homo sapiens

<400> SEQUENCE: 150
tattcggcgc ggaggggcgg cggccgggga ggcggcggcg gcggcaggat tcccaggagc     60
catgttgtca gaagtcctac tggtgtctgc tccggggaaa gtcatccttc atggagaaca    120
tgccgtggta catggcaagg tagcactggc tgtatccttg aacttgagaa cattcctccg    180
gcttcaaccc cacagcaatg ggaaagtgga cctcagctta cccaacattg gtatcaagcg    240
ggcctgggat gtggccaggc ttcagtcact ggacacaagc tttctgggtg gaccaaggag    300
gatttggagc taattaacaa gtgggccttc aaggggaga gaatgattca cgggaacccc    360
tccggagtgg acaatgctgt cagcacctgg ggaggagccc tccgatacca tcaagggaag    420
atttcatcct taaagaggtc gccagctctc cagatcctgc tgaccaacac caaagtccct    480
cgcaatacca gggcccttgt ggctggcgtc agaaacaggc tgctcaagtt cccagagatc    540 gtggccccc tcctgacctc aatagatgcc atctccctgg agtgtgagcg cgtgctggga    600
gagatggggg aagccccagc cccggagcag tacctcgtgc tggaagagct cattgacatg    660
aaccagcacc atctgaatgc cctcggcgtg gccacgcct ctctggacca gctctgccag    720
gtgaccaggg cccgcggact tcacagcaag ctgactggcg caggcggtgg tggctgtggc    780
atcacactcc tcaagccagg gctggagcag ccagaagtgg aggccacgaa gcaggccctg    840
accagctgtg gctttgactg cttggaaacc agcatcggtg ccccggcgt ctccatccac    900 tcagccacct ccctggacag ccgagtccag caagccctgg atggcctctg agaggagccc    960
acgacactgc agccccaccc agatgccct ttctggatta ttctgggggc tgcagttcga   1020
ctctgtgctg ccagcgagc gcccagctcc tgacactgct ggagaggccc cagccgcttg   1080
gcgatgccag ccaagctctg cagtcccagc ggtgggacct                          1120

<210> SEQ ID NO 151
<211> LENGTH: 1120
<212> TYPE: DNA
<213> ORGANISM: Homo sapiens
<221> NAME/KEY: CDS
<222> LOCATION: (343)..(951)

<400> SEQUENCE: 151
tattcggcgc ggaggggcgg cggccgggga ggcggcggcg gcggcaggat tcccaggagc     60
catgttgtca gaagtcctac tggtgtctgc tccggggaaa gtcatccttc atggagaaca    120
tgccgtggta catggcaagg tagcactggc tgtatccttg aacttgagaa cattcctccg    180
gcttcaaccc cacagcaatg ggaaagtgga cctcagctta cccaacattg gtatcaagcg    240
ggcctgggat gtggccaggc ttcagtcact ggacacaagc tttctgggtg gaccaaggag    300
gatttggagc taattaacaa gtgggccttc aaggggaga ga atg att cac ggg         354
                                              Met Ile His Gly
                                                1 aac ccc tcc gga gtg gac aat gct gtc agc acc tgg gga gga gcc ctc      402
Asn Pro Ser Gly Val Asp Asn Ala Val Ser Thr Trp Gly Gly Ala Leu
 5              10                  15                  20 cga tac cat caa ggg aag att tca tcc tta aag agg tcg cca gct ctc      450
Arg Tyr His Gln Gly Lys Ile Ser Ser Leu Lys Arg Ser Pro Ala Leu
            25                  30                  35 cag atc ctg ctg acc aac acc aaa gtc cct cgc aat acc agg gcc ctt      498
Gln Ile Leu Leu Thr Asn Thr Lys Val Pro Arg Asn Thr Arg Ala Leu
    40                  45                  50 gtg gct ggc gtc aga aac agg ctg ctc aag ttc cca gag atc gtg gcc      546
```

```
Val Ala Gly Val Arg Asn Arg Leu Leu Lys Phe Pro Glu Ile Val Ala
         55                  60                  65 ccc ctc ctg acc tca ata gat gcc atc tcc ctg gag tgt gag cgc gtg       594
Pro Leu Leu Thr Ser Ile Asp Ala Ile Ser Leu Glu Cys Glu Arg Val
 70                  75                  80 ctg gga gag atg ggg gaa gcc cca gcc ccg gag cag tac ctc gtg ctg       642
Leu Gly Glu Met Gly Glu Ala Pro Ala Pro Glu Gln Tyr Leu Val Leu
 85                  90                  95                 100 gaa gag ctc att gac atg aac cag cac cat ctg aat gcc ctc ggc gtg       690
Glu Glu Leu Ile Asp Met Asn Gln His His Leu Asn Ala Leu Gly Val
                    105                 110                 115 ggc cac gcc tct ctg gac cag ctc tgc cag gtg acc agg gcc cgc gga       738
Gly His Ala Ser Leu Asp Gln Leu Cys Gln Val Thr Arg Ala Arg Gly
            120                 125                 130 ctt cac agc aag ctg act ggc gca ggt ggt ggc tgt ggc atc aca           786
Leu His Ser Lys Leu Thr Gly Ala Gly Gly Gly Cys Gly Ile Thr
        135                 140                 145 ctc ctc aag cca ggg ctg gag cag cca gaa gtg gag gcc acg aag cag       834
Leu Leu Lys Pro Gly Leu Glu Gln Pro Glu Val Glu Ala Thr Lys Gln
150                 155                 160 gcc ctg acc agc tgt ggc ttt gac tgc ttg gaa acc agc atc ggt gcc       882
Ala Leu Thr Ser Cys Gly Phe Asp Cys Leu Glu Thr Ser Ile Gly Ala
165                 170                 175                 180 ccc ggc gtc tcc atc cac tca gcc acc tcc ctg gac agc cga gtc cag       930
Pro Gly Val Ser Ile His Ser Ala Thr Ser Leu Asp Ser Arg Val Gln
                    185                 190                 195 caa gcc ctg gat ggc ctc tga gaggagccca cgacactgca gccccaccca          981
Gln Ala Leu Asp Gly Leu
                200 gatgcccctt tctggattat tctgggggct gcagttcgac tctgtgctgg ccagcgagcg    1041 cccagctcct gacactgctg gagaggcccc agccgcttgg cgatgccagc caagctctgc   1101 agtcccagcg gtgggacct                                                  1120

<210> SEQ ID NO 152
<211> LENGTH: 202
<212> TYPE: PRT
<213> ORGANISM: Homo sapiens

<400> SEQUENCE: 152

Met Ile His Gly Asn Pro Ser Gly Val Asp Asn Ala Val Ser Thr Trp
  1               5                  10                  15

Gly Gly Ala Leu Arg Tyr His Gln Gly Lys Ile Ser Ser Leu Lys Arg
             20                  25                  30

Ser Pro Ala Leu Gln Ile Leu Leu Thr Asn Thr Lys Val Pro Arg Asn
         35                  40                  45

Thr Arg Ala Leu Val Ala Gly Val Arg Asn Arg Leu Leu Lys Phe Pro
 50                  55                  60

Glu Ile Val Ala Pro Leu Leu Thr Ser Ile Asp Ala Ile Ser Leu Glu
 65                  70                  75                  80

Cys Glu Arg Val Leu Gly Glu Met Gly Glu Ala Pro Ala Pro Glu Gln
                 85                  90                  95

Tyr Leu Val Leu Glu Glu Leu Ile Asp Met Asn Gln His His Leu Asn
            100                 105                 110

Ala Leu Gly Val Gly His Ala Ser Leu Asp Gln Leu Cys Gln Val Thr
        115                 120                 125

Arg Ala Arg Gly Leu His Ser Lys Leu Thr Gly Ala Gly Gly Gly Gly
    130                 135                 140
```

Cys Gly Ile Thr Leu Leu Lys Pro Gly Leu Glu Gln Pro Glu Val Glu
145                 150                 155                 160

Ala Thr Lys Gln Ala Leu Thr Ser Cys Gly Phe Asp Cys Leu Glu Thr
                165                 170                 175

Ser Ile Gly Ala Pro Gly Val Ser Ile His Ser Ala Thr Ser Leu Asp
            180                 185                 190

Ser Arg Val Gln Gln Ala Leu Asp Gly Leu
        195                 200

<210> SEQ ID NO 153
<211> LENGTH: 42
<212> TYPE: DNA
<213> ORGANISM: Homo sapiens

<400> SEQUENCE: 153
cactggacac aagctttctg ggtggaccaa ggaggatttg ga                          42

<210> SEQ ID NO 154
<211> LENGTH: 342
<212> TYPE: DNA
<213> ORGANISM: Homo sapiens

<400> SEQUENCE: 154
tattcggcgc ggaggggcgg cggccgggga ggcggcggcg gcggcaggat tcccaggagc        60
catgttgtca gaagtcctac tggtgtctgc tccggggaaa gtcatccttc atggagaaca       120
tgccgtggta catggcaagg tagcactggc tgtatccttg aacttgagaa cattcctccg       180
gcttcaaccc cacagcaatg ggaaagtgga cctcagctta cccaacattg gtatcaagcg       240
ggcctgggat gtggccaggc ttcagtcact ggacacaagc tttctgggtg gaccaaggag       300
gatttggagc taattaacaa gtgggccttc aagggagaga                             342

<210> SEQ ID NO 155
<211> LENGTH: 301
<212> TYPE: DNA
<213> ORGANISM: Homo sapiens

<400> SEQUENCE: 155
agcaaggtga tgtcacaaca cccacctcag agcaagtgga gaagctaaag gaggttgcag        60
gcttgcctga cgactgtgct gtcaccgagc gcctggctgt gctggccttt ctttacttat       120
acctgtccat ctgccggaag cagagggccc tgccgagcct ggatatcgta gtgtggtcgg       180
agctgccccc cggggcgggc ttgggctcca gcgccgccta ctcggtgtgt ctggcagcag       240
ccctcctgac tgtgtgcgag gagatcccaa acccgctgaa ggacggggat tgcgtcaaca       300
g                                                                       301

<210> SEQ ID NO 156
<211> LENGTH: 101
<212> TYPE: PRT
<213> ORGANISM: Homo sapiens

<400> SEQUENCE: 156

Glu Gln Gly Asp Val Thr Thr Pro Thr Ser Glu Gln Val Glu Lys Leu
1               5                   10                  15

Lys Glu Val Ala Gly Leu Pro Asp Asp Cys Ala Val Thr Glu Arg Leu
            20                  25                  30

Ala Val Leu Ala Phe Leu Tyr Leu Tyr Leu Ser Ile Cys Arg Lys Gln
        35                  40                  45

Arg Ala Leu Pro Ser Leu Asp Ile Val Val Trp Ser Glu Leu Pro Pro

```
        50                  55                  60
Gly Ala Gly Leu Gly Ser Ser Ala Ala Tyr Ser Val Cys Leu Ala Ala
65                  70                  75                  80

Ala Leu Leu Thr Val Cys Glu Glu Ile Pro Asn Pro Leu Lys Asp Gly
                85                  90                  95

Asp Cys Val Asn Arg
            100

<210> SEQ ID NO 157
<211> LENGTH: 1130
<212> TYPE: DNA
<213> ORGANISM: Homo sapiens

<400> SEQUENCE: 157
ggaggggcgg cggccgggga ggcggcggcg gcggcaggat tcccaggagc catgttgtca      60
gaagtcctac tggtgtctgc tccggggaaa gtcatccttc atggagaaca tgccgtggta     120
catggcaagg tagcactggc tgtatccttg aacttgagaa cattcctccg cttcaaccc      180 cacagcaatg ggaaagtgga cctcagctta cccaacattg gtatcaagcg ggcctgggat     240
gtggccaggc ttcagtcact ggacacaagc tttctggagc aaggtgatgt cacaacaccc     300
acctcagagc aagtggagaa gctaaaggag gttgcaggct tgcctgacga ctgtgctgtc     360
accgagcgct ggctgtgct ggccttcctt tacttatacc tgtccatctg ccggaagcag     420
aggtggacca aggaggattt ggagctaatt aacaagtggg ccttccaagg ggagagaatg     480
attcacggga ccccctccgg agtggacaat gctgtcagca cctggggagg agccctccga     540
taccatcaag ggaagatttc atccttaaag aggtcgccag ctctcctgat cctgctgacc     600
aacaccaaag tccctcgcaa taccagggcc ttgtggctg cgtcagaaaa caggctgctc      660
aagttcccag agatcgtggc ccccctcctg acctcaatag atgccatctc cctggagtgt     720
gagcgcgtgc tgggagagat ggggggaagcc ccagccccgg agcagtacct cgtgctggaa    780
gagctcatcg acatgaacca gcaccatctg aatgccctcg gcgtgggcca cgcctctctg     840
gaccagctct gccaggtgac cagggcccgc ggacttcaca gcaagctgac tggcgcaggc     900
ggtggtggct gtggcatcac actcctcaag ccagggctgg agcagccaga agtggaggcc     960
acgaagcagg ccctgaccag ctgtggcttt gactgcttgg aaaccagcat cggtgccccc    1020
ggcgtctcca tccactcagc cacctccctg gacagccgag tccagcaagc cctggatggc    1080
ctctgagagg agcccacgac actgcagccc cacccagatg ccccttctg               1130

<210> SEQ ID NO 158
<211> LENGTH: 1130
<212> TYPE: DNA
<213> ORGANISM: Homo sapiens
<221> NAME/KEY: CDS
<222> LOCATION: (52)..(1086)

<400> SEQUENCE: 158
ggaggggcgg cggccgggga ggcggcggcg gcggcaggat tcccaggagc c atg ttg       57
                                                         Met Leu
                                                           1 tca gaa gtc cta ctg gtg tct gct ccg ggg aaa gtc atc ctt cat gga       105
Ser Glu Val Leu Leu Val Ser Ala Pro Gly Lys Val Ile Leu His Gly
         5                  10                  15 gaa cat gcc gtg gta cat ggc aag gta gca ctg gct gta tcc ttg aac       153
Glu His Ala Val Val His Gly Lys Val Ala Leu Ala Val Ser Leu Asn
     20                  25                  30 ttg aga aca ttc ctc cgg ctt caa ccc cac agc aat ggg aaa gtg gac       201
```

```
Leu Arg Thr Phe Leu Arg Leu Gln Pro His Ser Asn Gly Lys Val Asp
 35                  40                  45                  50 ctc agc tta ccc aac att ggt atc aag cgg gcc tgg gat gtg gcc agg        249
Leu Ser Leu Pro Asn Ile Gly Ile Lys Arg Ala Trp Asp Val Ala Arg
                 55                  60                  65 ctt cag tca ctg gac aca agc ttt ctg gag caa ggt gat gtc aca aca        297
Leu Gln Ser Leu Asp Thr Ser Phe Leu Glu Gln Gly Asp Val Thr Thr
             70                  75                  80 ccc acc tca gag caa gtg gag aag cta aag gag gtt gca ggc ttg cct        345
Pro Thr Ser Glu Gln Val Glu Lys Leu Lys Glu Val Ala Gly Leu Pro
         85                  90                  95 gac gac tgt gct gtc acc gag cgc ctg gct gtg ctg gcc ttt ctt tac        393
Asp Asp Cys Ala Val Thr Glu Arg Leu Ala Val Leu Ala Phe Leu Tyr
     100                 105                 110 tta tac ctg tcc atc tgc cgg aag cag agg tgg acc aag gag gat ttg        441
Leu Tyr Leu Ser Ile Cys Arg Lys Gln Arg Trp Thr Lys Glu Asp Leu
 115                 120                 125                 130 gag cta att aac aag tgg gcc ttc caa ggg gag aga atg att cac ggg        489
Glu Leu Ile Asn Lys Trp Ala Phe Gln Gly Glu Arg Met Ile His Gly
                 135                 140                 145 aac ccc tcc gga gtg gac aat gct gtc agc acc tgg gga gga gcc ctc        537
Asn Pro Ser Gly Val Asp Asn Ala Val Ser Thr Trp Gly Gly Ala Leu
             150                 155                 160 cga tac cat caa ggg aag att tca tcc tta aag agg tcg cca gct ctc        585
Arg Tyr His Gln Gly Lys Ile Ser Ser Leu Lys Arg Ser Pro Ala Leu
         165                 170                 175 ctg atc ctg ctg acc aac acc aaa gtc cct cgc aat acc agg gcc ctt        633
Leu Ile Leu Leu Thr Asn Thr Lys Val Pro Arg Asn Thr Arg Ala Leu
     180                 185                 190 gtg gct ggc gtc aga aac agg ctg ctc aag ttc cca gag atc gtg gcc        681
Val Ala Gly Val Arg Asn Arg Leu Leu Lys Phe Pro Glu Ile Val Ala
 195                 200                 205                 210 ccc ctc ctg acc tca ata gat gcc atc tcc ctg gag tgt gag cgc gtg        729
Pro Leu Leu Thr Ser Ile Asp Ala Ile Ser Leu Glu Cys Glu Arg Val
                 215                 220                 225 ctg gga gag atg ggg gaa gcc cca gcc ccg gag cag tac ctc gtg ctg        777
Leu Gly Glu Met Gly Glu Ala Pro Ala Pro Glu Gln Tyr Leu Val Leu
             230                 235                 240 gaa gag ctc atc gac atg aac cag cac cat ctg aat gcc ctc ggc gtg        825
Glu Glu Leu Ile Asp Met Asn Gln His His Leu Asn Ala Leu Gly Val
         245                 250                 255 ggc cac gcc tct ctg gac cag ctc tgc cag gtg acc agg gcc cgc gga        873
Gly His Ala Ser Leu Asp Gln Leu Cys Gln Val Thr Arg Ala Arg Gly
     260                 265                 270 ctt cac agc aag ctg act ggc gca ggc ggt ggc tgt ggc atc aca            921
Leu His Ser Lys Leu Thr Gly Ala Gly Gly Gly Cys Gly Ile Thr
 275                 280                 285                 290 ctc ctc aag cca ggg ctg gag cag cca gaa gtg gag gcc acg aag cag        969
Leu Leu Lys Pro Gly Leu Glu Gln Pro Glu Val Glu Ala Thr Lys Gln
                 295                 300                 305 gcc ctg acc agc tgt ggc ttt gac tgc ttg gaa acc agc atc ggt gcc       1017
Ala Leu Thr Ser Cys Gly Phe Asp Cys Leu Glu Thr Ser Ile Gly Ala
             310                 315                 320 ccc ggt gtc tcc atc cac tca gcc acc tcc ctg gac agc cga gtc cag       1065
Pro Gly Val Ser Ile His Ser Ala Thr Ser Leu Asp Ser Arg Val Gln
         325                 330                 335 caa gcc ctg gat ggc ctc tga gaggagccca cgacactgca gccccaccca          1116
Gln Ala Leu Asp Gly Leu
     340 gatgcccctt tctg                                                       1130
```

<210> SEQ ID NO 159
<211> LENGTH: 344
<212> TYPE: PRT
<213> ORGANISM: Homo sapiens

<400> SEQUENCE: 159

Met Leu Ser Glu Val Leu Leu Val Ser Ala Pro Gly Lys Val Ile Leu
1               5                   10                  15

His Gly Glu His Ala Val Val His Gly Lys Val Ala Leu Ala Val Ser
            20                  25                  30

Leu Asn Leu Arg Thr Phe Leu Arg Leu Gln Pro His Ser Asn Gly Lys
        35                  40                  45

Val Asp Leu Ser Leu Pro Asn Ile Gly Ile Lys Arg Ala Trp Asp Val
    50                  55                  60

Ala Arg Leu Gln Ser Leu Asp Thr Ser Phe Leu Glu Gln Gly Asp Val
65                  70                  75                  80

Thr Thr Pro Thr Ser Glu Gln Val Glu Lys Leu Lys Glu Val Ala Gly
                85                  90                  95

Leu Pro Asp Asp Cys Ala Val Thr Glu Arg Leu Ala Val Leu Ala Phe
            100                 105                 110

Leu Tyr Leu Tyr Leu Ser Ile Cys Arg Lys Gln Arg Trp Thr Lys Glu
        115                 120                 125

Asp Leu Glu Leu Ile Asn Lys Trp Ala Phe Gln Gly Glu Arg Met Ile
    130                 135                 140

His Gly Asn Pro Ser Gly Val Asp Asn Ala Val Ser Thr Trp Gly Gly
145                 150                 155                 160

Ala Leu Arg Tyr His Gln Gly Lys Ile Ser Ser Leu Lys Arg Ser Pro
                165                 170                 175

Ala Leu Leu Ile Leu Leu Thr Asn Thr Lys Val Pro Arg Asn Thr Arg
            180                 185                 190

Ala Leu Val Ala Gly Val Arg Asn Arg Leu Leu Lys Phe Pro Glu Ile
        195                 200                 205

Val Ala Pro Leu Leu Thr Ser Ile Asp Ala Ile Ser Leu Glu Cys Glu
    210                 215                 220

Arg Val Leu Gly Glu Met Gly Glu Ala Pro Pro Glu Gln Tyr Leu
225                 230                 235                 240

Val Leu Glu Glu Leu Ile Asp Met Asn Gln His Leu Asn Ala Leu
                245                 250                 255

Gly Val Gly His Ala Ser Leu Asp Gln Leu Cys Gln Val Thr Arg Ala
            260                 265                 270

Arg Gly Leu His Ser Lys Leu Thr Gly Ala Gly Gly Gly Cys Gly
        275                 280                 285

Ile Thr Leu Leu Lys Pro Gly Leu Glu Gln Pro Glu Val Glu Ala Thr
    290                 295                 300

Lys Gln Ala Leu Thr Ser Cys Gly Phe Asp Cys Leu Glu Thr Ser Ile
305                 310                 315                 320

Gly Ala Pro Gly Val Ser Ile His Ser Ala Thr Ser Leu Asp Ser Arg
                325                 330                 335

Val Gln Gln Ala Leu Asp Gly Leu
            340

<210> SEQ ID NO 160
<211> LENGTH: 42
<212> TYPE: DNA
<213> ORGANISM: Homo sapiens

```
<400> SEQUENCE: 160
gtccatctgc cggaagcaga ggtggaccaa ggaggatttg ga                              42

<210> SEQ ID NO 161
<211> LENGTH: 15
<212> TYPE: PRT
<213> ORGANISM: Homo sapiens

<400> SEQUENCE: 161

Leu Ser Ile Cys Arg Lys Gln Arg Trp Thr Lys Glu Asp Leu Glu
1               5                   10                  15

<210> SEQ ID NO 162
<211> LENGTH: 156
<212> TYPE: DNA
<213> ORGANISM: Homo sapiens

<400> SEQUENCE: 162
ggccctgccg agcctggata tcgtagtgtg gtcggagctg ccccccgggg cgggcttggg          60
ctccagcgcc gcctactcgg tgtgtctggc agcagccctc ctgactgtgt gcgaggagat         120
cccaaacccg ctgaaggacg gggattgcgt caacag                                  156

<210> SEQ ID NO 163
<211> LENGTH: 53
<212> TYPE: PRT
<213> ORGANISM: Homo sapiens

<400> SEQUENCE: 163

Arg Ala Leu Pro Ser Leu Asp Ile Val Val Trp Ser Glu Leu Pro Pro
1               5                   10                  15

Gly Ala Gly Leu Gly Ser Ser Ala Ala Tyr Ser Val Cys Leu Ala Ala
                20                  25                  30

Ala Leu Leu Thr Val Cys Glu Glu Ile Pro Asn Pro Leu Lys Asp Gly
        35                  40                  45

Asp Cys Val Asn Arg
    50

<210> SEQ ID NO 164
<211> LENGTH: 19
<212> TYPE: DNA
<213> ORGANISM: Artificial Sequence
<220> FEATURE:
<223> OTHER INFORMATION: forward primer used for specifically detecting
      the variant of the present invention (D-3NB692002462.1)

<400> SEQUENCE: 164
tggccaggct tcagtcact                                                       19

<210> SEQ ID NO 165
<211> LENGTH: 23
<212> TYPE: DNA
<213> ORGANISM: Artificial Sequence
<220> FEATURE:
<223> OTHER INFORMATION: reverse primer used for specifically detecting
      the variant of the present invention (D-3NB692002462.1)

<400> SEQUENCE: 165
gcccacttgt taattagctc caa                                                  23

<210> SEQ ID NO 166
<211> LENGTH: 75
<212> TYPE: DNA
```

```
<213> ORGANISM: Artificial Sequence
<220> FEATURE:
<223> OTHER INFORMATION: partial polynucleotide specific to the variant
      of the present invention (D-3NB692002462.1), which is obtained by
      PCR using forward primer (SEQ ID NO:164) and reverse primer (SEQ
      ID NO:165)

<400> SEQUENCE: 166
tggccaggct tcagtcactg gacacaagct ttctgggtgg accaaggagg atttggagct    60
aattaacaag tgggc                                                    75

<210> SEQ ID NO 167
<211> LENGTH: 29
<212> TYPE: DNA
<213> ORGANISM: Artificial Sequence
<220> FEATURE:
<223> OTHER INFORMATION: probe used for detecting the variants of the
      present invention (D-3NB692002462.1)

<400> SEQUENCE: 167
acacaagctt tctgggtgga ccaaggagg                                     29

<210> SEQ ID NO 168
<211> LENGTH: 19
<212> TYPE: DNA
<213> ORGANISM: Artificial Sequence
<220> FEATURE:
<223> OTHER INFORMATION: forward primer used for specifically detecting
      the variant of the present invention (D-BRCAN2027778.1)

<400> SEQUENCE: 168
aggcttgcct gacgactgt                                                19

<210> SEQ ID NO 169
<211> LENGTH: 23
<212> TYPE: DNA
<213> ORGANISM: Artificial Sequence
<220> FEATURE:
<223> OTHER INFORMATION: reverse primer used for specifically detecting
      the variant of the present invention (D-BRCAN2027778.1)

<400> SEQUENCE: 169
ggaaggccca cttgttaatt agc                                           23

<210> SEQ ID NO 170
<211> LENGTH: 131
<212> TYPE: DNA
<213> ORGANISM: Artificial Sequence
<220> FEATURE:
<223> OTHER INFORMATION: partial polynucleotide specific to the variant
      of the present invention (D-BRCAN2027778.1), which is obtained by
      PCR using forward primer (SEQ ID NO:168) and reverse primer (SEQ
      ID NO:169)

<400> SEQUENCE: 170
aggcttgcct gacgactgtg ctgtcaccga gcgcctggct gtgctggcct tctttactt    60 atacctgtcc atctgccgga agcagaggtg gaccaaggag gatttggagc taattaacaa  120
gtgggccttc c                                                       131

<210> SEQ ID NO 171
<211> LENGTH: 27
<212> TYPE: DNA
<213> ORGANISM: Artificial Sequence
<220> FEATURE:
<223> OTHER INFORMATION: probe used for detecting the variants of the
      present invention (D-BRCAN2027778.1)
```

<400> SEQUENCE: 171
agcagaggtg gaccaaggag gatttgg 27

<210> SEQ ID NO 172
<211> LENGTH: 19
<212> TYPE: DNA
<213> ORGANISM: Artificial Sequence
<220> FEATURE:
<223> OTHER INFORMATION: forward primer used for specifically detecting
      the known variant of the gene of the present invention
      (NM_000431.1)

<400> SEQUENCE: 172
gatcccaaac ccgctgaag 19

<210> SEQ ID NO 173
<211> LENGTH: 22
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_000431.1)

<400> SEQUENCE: 173
gaatcattct ctccccttgg aa 22

<210> SEQ ID NO 174
<211> LENGTH: 101
<212> TYPE: DNA
<213> ORGANISM: Artificial Sequence
<220> FEATURE:
<223> OTHER INFORMATION: partial polynucleotide specific to the known
      variant of the gene of the present invention (NM_000431.1), which
      is obtained by PCR using forward primer (SEQ ID NO:172) and
      reverse primer (SEQ ID NO:173)

<400> SEQUENCE: 174
gatcccaaac ccgctgaagg acggggattg cgtcaacagg tggaccaagg aggatttgga 60
gctaattaac aagtgggcct tccaagggga gagaatgatt c 101

<210> SEQ ID NO 175
<211> LENGTH: 27
<212> TYPE: DNA
<213> ORGANISM: Artificial Sequence
<220> FEATURE:
<223> OTHER INFORMATION: probe used for specifically detecting the known
      variant of the gene of the present invention (NM_000431.1)

<400> SEQUENCE: 175
cgtcaacagg tggaccaagg aggattt 27

<210> SEQ ID NO 176
<211> LENGTH: 19
<212> TYPE: DNA
<213> ORGANISM: Artificial Sequence
<220> FEATURE:
<223> OTHER INFORMATION: forward primer used for detecting the variants
      of the gene of the present invention (D-3NB692002462.1,
      D-BRCAN2027778.1 and NM_000431.1)

<400> SEQUENCE: 176
cgccagctct ccagatcct 19

<210> SEQ ID NO 177
<211> LENGTH: 21
<212> TYPE: DNA

```
<213> ORGANISM: Artificial Sequence
<220> FEATURE:
<223> OTHER INFORMATION: reverse primer used for detecting the variants
      of the gene of the present invention (D-3NB692002462.1,
      D-BRCAN2027778.1 and NM_000431.1)

<400> SEQUENCE: 177
gggaacttga gcagcctgtt t                                              21

<210> SEQ ID NO 178
<211> LENGTH: 94
<212> TYPE: DNA
<213> ORGANISM: Artificial Sequence
<220> FEATURE:
<223> OTHER INFORMATION: partial polynucleotide common to the variants
      of the gene of the present invention (D-3NB692002462.1,
      D-BRCAN2027778.1 and NM_000431.1), which is obtained by PCR using
      forward primer (SEQ ID NO:176) and reverse primer (SEQ ID NO:177)

<400> SEQUENCE: 178
cgccagctct ccagatcctg ctgaccaaca ccaaagtccc tcgcaatacc agggcccttg    60
tggctggcgt cagaaacagg ctgctcaagt tccc                                94

<210> SEQ ID NO 179
<211> LENGTH: 25
<212> TYPE: DNA
<213> ORGANISM: Artificial Sequence
<220> FEATURE:
<223> OTHER INFORMATION: probe used for detecting the variants of the
      gene of the present invention (D-3NB692002462.1, D-BRCAN2027778.1
      and NM_000431.1)

<400> SEQUENCE: 179
ctgaccaaca ccaaagtccc tcgca                                          25

<210> SEQ ID NO 180
<211> LENGTH: 326
<212> TYPE: DNA
<213> ORGANISM: Homo sapiens

<400> SEQUENCE: 180
tattcggcgc ggaggggcgg cggccgggga ggcggcggcg gcggcaggat tcccaggagc    60
catgttgtca gaagtcctac tggtgtctgc tccggggaaa gtcatccttc atggagaaca   120
tgccgtggta catggcaagg tagcactggc tgtatccttg aacttgagaa cattcctccg   180
gcttcaaccc cacagcaatg ggaaagtgga cctcagctta cccaacattg gtatcaagcg   240
ggcctgggat gtggccaggc ttcagtcact ggacacaagc tttctgggtg gaccaaggag   300
gatttggagc taattaacaa gtgggc                                        326

<210> SEQ ID NO 181
<211> LENGTH: 466
<212> TYPE: DNA
<213> ORGANISM: Homo sapiens

<400> SEQUENCE: 181
ggaggggcgg cggccgggga ggcggcggcg gcggcaggat tcccaggagc catgttgtca    60
gaagtcctac tggtgtctgc tccggggaaa gtcatccttc atggagaaca tgccgtggta   120
catggcaagg tagcactggc tgtatccttg aacttgagaa cattcctccg gcttcaaccc   180
cacagcaatg ggaaagtgga cctcagctta cccaacattg gtatcaagcg ggcctgggat   240
gtggccaggc ttcagtcact ggacacaagc tttctggagc aaggtgatgt cacaacaccc   300
acctcagagc aagtggagaa gctaaaggag gttgcaggct tgcctgacga ctgtgctgtc   360
```

```
accgagcgcc tggctgtgct ggcctttctt tacttatacc tgtccatctg ccggaagcag    420
aggtggacca aggaggattt ggagctaatt aacaagtggg ccttcc                   466
```

<210> SEQ ID NO 182
<211> LENGTH: 1872
<212> TYPE: DNA
<213> ORGANISM: Homo sapiens

<400> SEQUENCE: 182

```
acaacctgac ttttgtccac aatgcaaaga ctccaactgt tgagagtaga agtactgctg     60
ggtgtgaaac aaggagatga aatgcggcat ttcttttttt cttctcagac ctccactctg    120
gagaagagtc agaatggggg cgtcggggag gaggtcaccc cagctctgat ctttgccatc    180
acagttgcta caatcggctc tttccagttt ggctacaaca ctggggtcat caatgctcct    240
gagacgatca taaaggaatt tatcaataaa actttgacgg acaaggcaaa tgcccctccc    300
tctgaggtgc tgctcacgaa tctctggtcc ttgtctgtgg ccatatttc cgtcgggggt    360 atgatcggct cctttccgt cggactcttt gttaaccgct ttggcaggcg caattcaatg    420
ctgattgtca acctgttggc tgccactggt ggctgcctta tgggactgtg taaaatagct    480
gagtcagttg aaatgctgat cctgggccgc ttggttattg gcctcttctg cggactctgc    540
acaggttttg tgcccatgta cattggagag atctcgccta ctgccctgag gggtgccttt    600
ggcactctca accagctggg catagttatt ggaattctgg tggcccagat ctttggtctg    660
gaactcatcc ttgggtctaa agagctatgg ccggtgctat taggctttac catccttcca    720
gctatcctgc aaagtgcagc ccttccatgt tgccctgaaa gtcccagatt tttgctcatt    780
aacagaaaaa aagaggagaa tgctacgcgg atcctccagc ggttgtgggg cacccaggat    840
gtatcccaag acatccagga tgaaagat gagagtgcaa ggatgtcaca agaaaagcaa    900
gtcaccgtgc tggagctctt tagagtgtcc agctaccgac agcccatcat catttccatt    960
gtgctccagc tctctcagca gctctctggg atcaatgctg tgttctatta ctcaacagga   1020
atcttcaagg atgcaggtgt tcaacagccc atctatgcca ccatcagcgc gggtgtggtt   1080
aatactatct tcactttact ttctctattt ctggtggaaa gggcaggaag aaggactctg   1140
catatgatag gccttggagg gatggctttt tgttccacgc tcatgactgt ttctttgtta   1200
ttaaagaatc actataatgg gatgagcttt gtctgtattg gggctatctt ggtctttgtg   1260
gcctgttttg aaattggacc aggccccatt ccctggttta ttgtggccga actcttcagc   1320
cagggccccc gcccagctgc gatggcagtg gccggctgct ccaactggac ctccaacttc   1380
ctagtcggat tgctcttccc ctctgctgct tactatttag gagcctacgt ttttattatc   1440
ttcaccggct tcctcattac cttcctggcc tttaccttct tcaaagtccc tgagacccgt   1500
ggcaggactt tgaggatat cacacgggcc ttttgaaggg caggcacacg tgcagataga   1560
tctggaaagg acggcgtcat ggggatgaac agcatcgagc ctgctaagga gaccaccacc   1620
aatgtctaag tcgtgcctcc ttccacctcc ctcccggcat gggaaggcca cctctccctc   1680
aacaagggag agacctcatc aggatgaacc caggacgctt ctgaatgctg ctacttgatt   1740 tcttttctcat cccacgcact ccatgagcac cccaaggctg cagtttgttg gatcttcaat   1800
ggctttttaa attttatttc ctggacatcc tcttctgctt aggagagacc gagtgaacct   1860
accttcattt ca                                                       1872
```

<210> SEQ ID NO 183
<211> LENGTH: 1872

-continued

```
<212> TYPE: DNA
<213> ORGANISM: Homo sapiens
<221> NAME/KEY: CDS
<222> LOCATION: (22)..(1629)

<400> SEQUENCE: 183
acaacctgac ttttgtccac a atg caa aga ctc caa ctg ttg aga gta gaa          51
                        Met Gln Arg Leu Gln Leu Leu Arg Val Glu
                          1               5                  10 gta ctg ctg ggt gtg aaa caa gga gat gaa atg cgg cat ttc ttt ttt          99
Val Leu Leu Gly Val Lys Gln Gly Asp Glu Met Arg His Phe Phe Phe
             15                  20                  25 tct tct cag acc tcc act ctg gag aag agt cag aat ggg ggc gtc ggg         147
Ser Ser Gln Thr Ser Thr Leu Glu Lys Ser Gln Asn Gly Gly Val Gly
         30                  35                  40 gag gag gtc acc cca gct ctg atc ttt gcc atc aca gtt gct aca atc         195
Glu Glu Val Thr Pro Ala Leu Ile Phe Ala Ile Thr Val Ala Thr Ile
     45                  50                  55 ggc tct ttc cag ttt ggc tac aac act ggg gtc atc aat gct cct gag         243
Gly Ser Phe Gln Phe Gly Tyr Asn Thr Gly Val Ile Asn Ala Pro Glu
 60                  65                  70 acg atc ata aag gaa ttt atc aat aaa act ttg acg gac aag gca aat         291
Thr Ile Ile Lys Glu Phe Ile Asn Lys Thr Leu Thr Asp Lys Ala Asn
 75                  80                  85                  90 gcc cct ccc tct gag gtg ctg ctc acg aat ctc tgg tcc ttg tct gtg         339
Ala Pro Pro Ser Glu Val Leu Leu Thr Asn Leu Trp Ser Leu Ser Val
                 95                 100                 105 gcc ata ttt tcc gtc ggg ggt atg atc ggc tcc ttt tcc gtc gga ctc         387
Ala Ile Phe Ser Val Gly Gly Met Ile Gly Ser Phe Ser Val Gly Leu
             110                 115                 120 ttt gtt aac cgc ttt ggc agg cgc aat tca atg ctg att gtc aac ctg         435
Phe Val Asn Arg Phe Gly Arg Arg Asn Ser Met Leu Ile Val Asn Leu
         125                 130                 135 ttg gct gcc act ggt ggc tgc ctt atg gga ctg tgt aaa ata gct gag         483
Leu Ala Ala Thr Gly Gly Cys Leu Met Gly Leu Cys Lys Ile Ala Glu
     140                 145                 150 tca gtt gaa atg ctg atc ctg ggc cgc ttg gtt att ggc ctc ttc tgc         531
Ser Val Glu Met Leu Ile Leu Gly Arg Leu Val Ile Gly Leu Phe Cys
155                 160                 165                 170 gga ctc tgc aca ggt ttt gtg ccc atg tac att gga gag atc tcg cct         579
Gly Leu Cys Thr Gly Phe Val Pro Met Tyr Ile Gly Glu Ile Ser Pro
                 175                 180                 185 act gcc ctg agg ggt gcc ttt ggc act ctc aac cag ctg ggc ata gtt         627
Thr Ala Leu Arg Gly Ala Phe Gly Thr Leu Asn Gln Leu Gly Ile Val
             190                 195                 200 att gga att ctg gtg gcc cag atc ttt ggt ctg gaa ctc atc ctt ggg         675
Ile Gly Ile Leu Val Ala Gln Ile Phe Gly Leu Glu Leu Ile Leu Gly
         205                 210                 215 tct aaa gag cta tgg ccg gtg cta tta ggc ttt acc atc ctt cca gct         723
Ser Lys Glu Leu Trp Pro Val Leu Leu Gly Phe Thr Ile Leu Pro Ala
     220                 225                 230 atc ctg caa agt gca gcc ctt cca tgt tgc cct gaa agt ccc aga ttt         771
Ile Leu Gln Ser Ala Ala Leu Pro Cys Cys Pro Glu Ser Pro Arg Phe
235                 240                 245                 250 ttg ctc att aac aga aaa aaa gag gag aat gct acg cgg atc ctc cag         819
Leu Leu Ile Asn Arg Lys Lys Glu Glu Asn Ala Thr Arg Ile Leu Gln
                 255                 260                 265 cgg ttg tgg ggc acc cag gat gta tcc caa gac atc cag gag atg aaa         867
Arg Leu Trp Gly Thr Gln Asp Val Ser Gln Asp Ile Gln Glu Met Lys
             270                 275                 280 gat gag agt gca agg atg tca caa gaa aag caa gtc acc gtg ctg gag         915
Asp Glu Ser Ala Arg Met Ser Gln Glu Lys Gln Val Thr Val Leu Glu
```

```
Asp Glu Ser Ala Arg Met Ser Gln Glu Lys Gln Val Thr Val Leu Glu
            285                 290                 295 ctc ttt aga gtg tcc agc tac cga cag ccc atc atc att tcc att gtg      963
Leu Phe Arg Val Ser Ser Tyr Arg Gln Pro Ile Ile Ile Ser Ile Val
300                 305                 310 ctc cag ctc tct cag cag ctc tct ggg atc aat gct gtg ttc tat tac     1011
Leu Gln Leu Ser Gln Gln Leu Ser Gly Ile Asn Ala Val Phe Tyr Tyr
315                 320                 325                 330 tca aca gga atc ttc aag gat gca ggt gtt caa cag ccc atc tat gcc     1059
Ser Thr Gly Ile Phe Lys Asp Ala Gly Val Gln Gln Pro Ile Tyr Ala
                335                 340                 345 acc atc agc gcg ggt gtg gtt aat act atc ttc act tta ctt tct cta     1107
Thr Ile Ser Ala Gly Val Val Asn Thr Ile Phe Thr Leu Leu Ser Leu
                350                 355                 360 ttt ctg gtg gaa agg gca gga aga agg act ctg cat atg ata ggc ctt     1155
Phe Leu Val Glu Arg Ala Gly Arg Arg Thr Leu His Met Ile Gly Leu
                365                 370                 375 gga ggg atg gct ttt tgt tcc acg ctc atg act gtt tct ttg tta tta     1203
Gly Gly Met Ala Phe Cys Ser Thr Leu Met Thr Val Ser Leu Leu Leu
380                 385                 390 aag aat cac tat aat ggg atg agc ttt gtc tgt att ggg gct atc ttg     1251
Lys Asn His Tyr Asn Gly Met Ser Phe Val Cys Ile Gly Ala Ile Leu
395                 400                 405                 410 gtc ttt gtg gcc tgt ttt gaa att gga cca ggc ccc att ccc tgg ttt     1299
Val Phe Val Ala Cys Phe Glu Ile Gly Pro Gly Pro Ile Pro Trp Phe
                415                 420                 425 att gtg gcc gaa ctc ttc agc cag ggc ccc cgc cca gct gcg atg gca     1347
Ile Val Ala Glu Leu Phe Ser Gln Gly Pro Arg Pro Ala Ala Met Ala
                430                 435                 440 gtg gcc ggc tgc tcc aac tgg acc tcc aac ttc cta gtc gga ttg ctc     1395
Val Ala Gly Cys Ser Asn Trp Thr Ser Asn Phe Leu Val Gly Leu Leu
                445                 450                 455 ttc ccc tct gct gct tac tat tta gga gcc tac gtt ttt att atc ttc     1443
Phe Pro Ser Ala Ala Tyr Tyr Leu Gly Ala Tyr Val Phe Ile Ile Phe
            460                 465                 470 acc ggc ttc ctc att acc ttc ctg gcc ttt acc ttc ttc aaa gtc cct     1491
Thr Gly Phe Leu Ile Thr Phe Leu Ala Phe Thr Phe Phe Lys Val Pro
475                 480                 485                 490 gag acc cgt ggc agg act ttt gag gat atc aca cgg gcc ttt gaa ggg     1539
Glu Thr Arg Gly Arg Thr Phe Glu Asp Ile Thr Arg Ala Phe Glu Gly
                495                 500                 505 cag gca cac ggt gca gat aga tct gga aag gac ggc gtc atg ggg atg     1587
Gln Ala His Gly Ala Asp Arg Ser Gly Lys Asp Gly Val Met Gly Met
                510                 515                 520 aac agc atc gag cct gct aag gag acc acc acc aat gtc taa             1629
Asn Ser Ile Glu Pro Ala Lys Glu Thr Thr Thr Asn Val
525                 530                 535 gtcgtgcctc cttccacctc cctcccggca tgggaaggcc acctctccct caacaaggga   1689
gagacctcat caggatgaac ccaggacgct tctgaatgct gctacttgat ttctttctca   1749
tcccacgcac tccatgagca ccccaaggct gcagtttgtt ggatcttcaa tggcttttta   1809
aattttattt cctggacatc ctcttctgct taggagagac cgagtgaacc taccttcatt   1869
tca                                                                 1872
```

<210> SEQ ID NO 184
<211> LENGTH: 535
<212> TYPE: PRT
<213> ORGANISM: Homo sapiens

<400> SEQUENCE: 184

-continued

```
Met Gln Arg Leu Gln Leu Leu Arg Val Glu Val Leu Gly Val Lys
1               5                   10                  15

Gln Gly Asp Glu Met Arg His Phe Phe Ser Ser Gln Thr Ser Thr
            20                  25                  30

Leu Glu Lys Ser Gln Asn Gly Val Gly Glu Val Thr Pro Ala
            35                  40                  45

Leu Ile Phe Ala Ile Thr Val Ala Thr Ile Gly Ser Phe Gln Phe Gly
50                      55                  60

Tyr Asn Thr Gly Val Ile Asn Ala Pro Glu Thr Ile Ile Lys Glu Phe
65                      70                  75                  80

Ile Asn Lys Thr Leu Thr Asp Lys Ala Asn Ala Pro Pro Ser Glu Val
                85                  90                  95

Leu Leu Thr Asn Leu Trp Ser Leu Ser Val Ala Ile Phe Ser Val Gly
                100                 105                 110

Gly Met Ile Gly Ser Phe Ser Val Gly Leu Phe Val Asn Arg Phe Gly
            115                 120                 125

Arg Arg Asn Ser Met Leu Ile Val Asn Leu Leu Ala Ala Thr Gly Gly
            130                 135                 140

Cys Leu Met Gly Leu Cys Lys Ile Ala Glu Ser Val Glu Met Leu Ile
145                 150                 155                 160

Leu Gly Arg Leu Val Ile Gly Leu Phe Cys Gly Leu Cys Thr Gly Phe
                165                 170                 175

Val Pro Met Tyr Ile Gly Glu Ile Ser Pro Thr Ala Leu Arg Gly Ala
                180                 185                 190

Phe Gly Thr Leu Asn Gln Leu Gly Ile Val Ile Gly Ile Leu Val Ala
                195                 200                 205

Gln Ile Phe Gly Leu Glu Leu Ile Leu Gly Ser Lys Glu Leu Trp Pro
210                 215                 220

Val Leu Leu Gly Phe Thr Ile Leu Pro Ala Ile Leu Gln Ser Ala Ala
225                 230                 235                 240

Leu Pro Cys Cys Pro Glu Ser Pro Arg Phe Leu Leu Ile Asn Arg Lys
                245                 250                 255

Lys Glu Glu Asn Ala Thr Arg Ile Leu Gln Arg Leu Trp Gly Thr Gln
                260                 265                 270

Asp Val Ser Gln Asp Ile Gln Glu Met Lys Asp Glu Ser Ala Arg Met
                275                 280                 285

Ser Gln Glu Lys Gln Val Thr Val Leu Glu Leu Phe Arg Val Ser Ser
290                 295                 300

Tyr Arg Gln Pro Ile Ile Ile Ser Ile Val Leu Gln Leu Ser Gln Gln
305                 310                 315                 320

Leu Ser Gly Ile Asn Ala Val Phe Tyr Tyr Ser Thr Gly Ile Phe Lys
                325                 330                 335

Asp Ala Gly Val Gln Gln Pro Ile Tyr Ala Thr Ile Ser Ala Gly Val
                340                 345                 350

Val Asn Thr Ile Phe Thr Leu Leu Ser Leu Phe Leu Val Glu Arg Ala
                355                 360                 365

Gly Arg Arg Thr Leu His Met Ile Gly Leu Gly Gly Met Ala Phe Cys
                370                 375                 380

Ser Thr Leu Met Thr Val Ser Leu Leu Leu Lys Asn His Tyr Asn Gly
385                 390                 395                 400

Met Ser Phe Val Cys Ile Gly Ala Ile Leu Val Phe Val Ala Cys Phe
                405                 410                 415

Glu Ile Gly Pro Gly Pro Ile Pro Trp Phe Ile Val Ala Glu Leu Phe
```

```
                420           425           430
Ser Gln Gly Pro Arg Pro Ala Ala Met Ala Val Ala Gly Cys Ser Asn
            435                 440                 445

Trp Thr Ser Asn Phe Leu Val Gly Leu Leu Phe Pro Ser Ala Ala Tyr
        450                 455                 460

Tyr Leu Gly Ala Tyr Val Phe Ile Ile Phe Thr Gly Phe Leu Ile Thr
465                 470                 475                 480

Phe Leu Ala Phe Thr Phe Phe Lys Val Pro Glu Thr Arg Gly Arg Thr
                485                 490                 495

Phe Glu Asp Ile Thr Arg Ala Phe Glu Gly Gln Ala His Gly Ala Asp
                500                 505                 510

Arg Ser Gly Lys Asp Gly Val Met Gly Met Asn Ser Ile Glu Pro Ala
            515                 520                 525

Lys Glu Thr Thr Thr Asn Val
        530                 535

<210> SEQ ID NO 185
<211> LENGTH: 153
<212> TYPE: DNA
<213> ORGANISM: Homo sapiens

<400> SEQUENCE: 185
acaacctgac ttttgtccac aatgcaaaga ctccaactgt tgagagtaga agtactgctg    60
ggtgtgaaac aaggagatga aatgcggcat tctttttttt cttctcagac ctccactctg   120
gagaagagtc agaatggggg cgtcggggag gag                                153

<210> SEQ ID NO 186
<211> LENGTH: 44
<212> TYPE: PRT
<213> ORGANISM: Homo sapiens

<400> SEQUENCE: 186

Met Gln Arg Leu Gln Leu Leu Arg Val Glu Val Leu Leu Gly Val Lys
1               5                   10                  15

Gln Gly Asp Glu Met Arg His Phe Phe Phe Ser Ser Gln Thr Ser Thr
            20                  25                  30

Leu Glu Lys Ser Gln Asn Gly Gly Val Gly Glu Glu
        35                  40

<210> SEQ ID NO 187
<211> LENGTH: 132
<212> TYPE: DNA
<213> ORGANISM: Homo sapiens

<400> SEQUENCE: 187
atgcaaagac tccaactgtt gagagtagaa gtactgctgg gtgtgaaaca aggagatgaa    60
atgcggcatt tcttttttc ttctcagacc tccactctgg agaagagtca gaatggggc    120 gtcggggagg ag                                                        132

<210> SEQ ID NO 188
<211> LENGTH: 1872
<212> TYPE: DNA
<213> ORGANISM: Homo sapiens

<400> SEQUENCE: 188
acaacctgac ttttgttcac aatgcaaaga ctccaactgt tgagagtaga agtactgctg    60
ggtgtgaaac aaggagatga aatgcggcat tctttttttt cttctcagac ctccactctg   120
```

-continued

```
gagaagagtc agaatggggg cgtcgggag gaggtcaccc cagctctgat ctttgccatc    180
acagttgcta caatcggctc tttccagttt ggctacaaca ctgggggtcat caatgctcct   240 gagacgatca taaaggaatt tatcaataaa actttgacgg acaaggcaaa tgccctccc    300 tctgaggtgc tgctcacgaa tctctggtcc ttgtctgtgg ccatattttc cgtcgggggt   360
atgatcggct ccttttccgt cggactcttt gttaaccgct ttggcaggcg caattcaatg   420
ctgattgtca acctgttggc tgccactggt ggctgcctta tgggactgtg taaaatagct   480
gagtcagttg aaatgctgat cctgggccgc ttggttattg gcctcttctg cggactctgc   540
acaggttttg tgcccatgta cattggagag atctcgccta ctgccctgag gggtgccttt   600
ggcactctca accagctggg catagttatt ggaattctgg tggcccagat ctttggtctg   660
gaactcatcc ttgggtctga agagctatgg ccggtgctat taggctttac catccttcca   720
gctatcctgc aaagtgcagc ccttccatgt tgccctgaaa gtcccagatt tttgctcatt   780
aacagaaaaa aagaggagaa tgctacgcgg atcctccagc ggttgtgggg cacccaggat   840
gtatcccaag acatccagga tgaaagat gagagtgcaa ggatgtcaca agaaaagcaa    900
gtcaccgtgc tggagctctt tagagtgtcc agctaccgac agcccatcat catttccatt   960
gtgctccagc tctctcagca gctctctggg atcaatgctg tgttctatta ctcaacagga  1020
atcttcaagg atgcaggtgt tcaacagccc atctatgcca ccatcagcgc gggtgtggtt  1080
aatactatct tcactttact ttctctattt ctggtggaaa gggcaggaag aaggactctg  1140
catatgatag gccttggagg gatggctttt tgttccacgc tcatgactgt ttctttgtta  1200
ttaaagaatc actataatgg gatgagcttt gtctgtattg gggctatctt ggtctttgtg  1260
gcctgttttg aaattggacc aggccccatt ccctggttta tgtggccga actcttcagc   1320 cagggccccc gcccagctgc gatggcagtg gccggctgct ccaactggac ctccaacttc  1380
ctagtcggat tgctcttccc ctctgctgct tactatttag gagcctacgt ttttattatc  1440
ttcaccggct tcctcattac cttcctggcc tttaccttct tcaaagtccc tgagacccgt  1500
ggcaggactt ttgaggatat cacacggggc tttgaagggc aggcacacgg tgcagataga  1560
tctggaaagg acggcgtcat ggggatgaac agcatcgagc tgctaaggga gaccaccacc  1620
aatgtctaag tcgtgcctcc ttccacctcc ctcccggcat gggaaagcca cctctccctc  1680 aacagggag agacctcatc aggatgaacc caggacgctt ctgaatgctg ctacttgatt   1740
tctttctcat cccacgcact ccatgagcac cccaaggctg cagtttgttg gatcttcaat  1800 ggcttttaa atttatttc ctggacatcc tcttctgctt aggagagacc gagtgaacct    1860
accttcattt ca                                                       1872
```

<210> SEQ ID NO 189
<211> LENGTH: 1872
<212> TYPE: DNA
<213> ORGANISM: Homo sapiens
<221> NAME/KEY: CDS
<222> LOCATION: (22)..(1629)

<400> SEQUENCE: 189

```
acaacctgac ttttgttcac a atg caa aga ctc caa ctg ttg aga gta gaa          51
                         Met Gln Arg Leu Gln Leu Leu Arg Val Glu
                         1               5                   10 gta ctg ctg ggt gtg aaa caa gga gat gaa atg cgg cat ttc ttt ttt          99
Val Leu Leu Gly Val Lys Gln Gly Asp Glu Met Arg His Phe Phe Phe
        15                  20                  25 tct tct cag acc tcc act ctg gag aag agt cag aat ggg ggc gtc ggg         147
Ser Ser Gln Thr Ser Thr Leu Glu Lys Ser Gln Asn Gly Gly Val Gly
```

```
                30                  35                  40
gag gag gtc acc cca gct ctg atc ttt gcc atc aca gtt gct aca atc        195
Glu Glu Val Thr Pro Ala Leu Ile Phe Ala Ile Thr Val Ala Thr Ile
            45                  50                  55 ggc tct ttc cag ttt ggc tac aac act ggg gtc atc aat gct cct gag        243
Gly Ser Phe Gln Phe Gly Tyr Asn Thr Gly Val Ile Asn Ala Pro Glu
    60                  65                  70 acg atc ata aag gaa ttt atc aat aaa act ttg acg gac aag gca aat        291
Thr Ile Ile Lys Glu Phe Ile Asn Lys Thr Leu Thr Asp Lys Ala Asn
75                  80                  85                  90 gcc cct ccc tct gag gtg ctg ctc acg aat ctc tgg tcc ttg tct gtg        339
Ala Pro Pro Ser Glu Val Leu Leu Thr Asn Leu Trp Ser Leu Ser Val
                95                  100                 105 gcc ata ttt tcc gtc ggg ggt atg atc ggc tcc ttt tcc gtc gga ctc        387
Ala Ile Phe Ser Val Gly Gly Met Ile Gly Ser Phe Ser Val Gly Leu
            110                 115                 120 ttt gtt aac cgc ttt ggc agg cgc aat tca atg ctg att gtc aac ctg        435
Phe Val Asn Arg Phe Gly Arg Arg Asn Ser Met Leu Ile Val Asn Leu
    125                 130                 135 ttg gct gcc act ggt ggc tgc ctt atg gga ctg tgt aaa ata gct gag        483
Leu Ala Ala Thr Gly Gly Cys Leu Met Gly Leu Cys Lys Ile Ala Glu
140                 145                 150 tca gtt gaa atg ctg atc ctg ggc cgc ttg gtt att ggc ctc ttc tgc        531
Ser Val Glu Met Leu Ile Leu Gly Arg Leu Val Ile Gly Leu Phe Cys
155                 160                 165                 170 gga ctc tgc aca ggt ttt gtg ccc atg tac att gga gag atc tcg cct        579
Gly Leu Cys Thr Gly Phe Val Pro Met Tyr Ile Gly Glu Ile Ser Pro
                175                 180                 185 act gcc ctg agg ggt gcc ttt ggc act ctc aac cag ctg ggc ata gtt        627
Thr Ala Leu Arg Gly Ala Phe Gly Thr Leu Asn Gln Leu Gly Ile Val
            190                 195                 200 att gga att ctg gtg gcc cag atc ttt ggt ctg gaa ctc atc ctt ggg        675
Ile Gly Ile Leu Val Ala Gln Ile Phe Gly Leu Glu Leu Ile Leu Gly
    205                 210                 215 tct gaa gag cta tgg ccg gtg cta tta ggc ttt acc atc ctt cca gct        723
Ser Glu Glu Leu Trp Pro Val Leu Leu Gly Phe Thr Ile Leu Pro Ala
220                 225                 230 atc ctg caa agt gca gcc ctt cca tgt tgc cct gaa agt ccc aga ttt        771
Ile Leu Gln Ser Ala Ala Leu Pro Cys Cys Pro Glu Ser Pro Arg Phe
235                 240                 245                 250 ttg ctc att aac aga aaa aaa gag gag aat gct acg cgg atc ctc cag        819
Leu Leu Ile Asn Arg Lys Lys Glu Glu Asn Ala Thr Arg Ile Leu Gln
                255                 260                 265 cgg ttg tgg ggc acc cag gat gta tcc caa gac atc cag gag atg aaa        867
Arg Leu Trp Gly Thr Gln Asp Val Ser Gln Asp Ile Gln Glu Met Lys
            270                 275                 280 gat gag agt gca agg atg tca caa gaa aag caa gtc acc gtg ctg gag        915
Asp Glu Ser Ala Arg Met Ser Gln Glu Lys Gln Val Thr Val Leu Glu
    285                 290                 295 ctc ttt aga gtg tcc agc tac cga cag ccc atc atc att tcc att gtg        963
Leu Phe Arg Val Ser Ser Tyr Arg Gln Pro Ile Ile Ile Ser Ile Val
300                 305                 310 ctc cag ctc tct cag cag ctc tct ggg atc aat gct gtg ttc tat tac       1011
Leu Gln Leu Ser Gln Gln Leu Ser Gly Ile Asn Ala Val Phe Tyr Tyr
315                 320                 325                 330 tca aca gga atc ttc aag gat gca ggt gtt caa cag ccc atc tat gcc       1059
Ser Thr Gly Ile Phe Lys Asp Ala Gly Val Gln Gln Pro Ile Tyr Ala
                335                 340                 345 acc atc agc gcg ggt gtg gtt aat act atc ttc act tta ctt tct cta       1107
Thr Ile Ser Ala Gly Val Val Asn Thr Ile Phe Thr Leu Leu Ser Leu
```

```
                           350                 355                 360
ttt ctg gtg gaa agg gca gga aga agg act ctg cat atg ata ggc ctt    1155
Phe Leu Val Glu Arg Ala Gly Arg Arg Thr Leu His Met Ile Gly Leu
            365                 370                 375 gga ggg atg gct ttt tgt tcc acg ctc atg act gtt tct ttg tta tta    1203
Gly Gly Met Ala Phe Cys Ser Thr Leu Met Thr Val Ser Leu Leu Leu
        380                 385                 390 aag aat cac tat aat ggg atg agc ttt gtc tgt att ggg gct atc ttg    1251
Lys Asn His Tyr Asn Gly Met Ser Phe Val Cys Ile Gly Ala Ile Leu
395                 400                 405                 410 gtc ttt gtg gcc tgt ttt gaa att gga cca ggc ccc att ccc tgg ttt    1299
Val Phe Val Ala Cys Phe Glu Ile Gly Pro Gly Pro Ile Pro Trp Phe
                415                 420                 425 att gtg gcc gaa ctc ttc agc cag ggc ccc cgc cca gct gcg atg gca    1347
Ile Val Ala Glu Leu Phe Ser Gln Gly Pro Arg Pro Ala Ala Met Ala
        430                 435                 440 gtg gcc ggc tgc tcc aac tgg acc tcc aac ttc cta gtc gga ttg ctc    1395
Val Ala Gly Cys Ser Asn Trp Thr Ser Asn Phe Leu Val Gly Leu Leu
            445                 450                 455 ttc ccc tct gct gct tac tat tta gga gcc tac gtt ttt att atc ttc    1443
Phe Pro Ser Ala Ala Tyr Tyr Leu Gly Ala Tyr Val Phe Ile Ile Phe
460                 465                 470 acc ggc ttc ctc att acc ttc ctg gcc ttt acc ttc ttc aaa gtc cct    1491
Thr Gly Phe Leu Ile Thr Phe Leu Ala Phe Thr Phe Phe Lys Val Pro
475                 480                 485                 490 gag acc cgt ggc agg act ttt gag gat atc aca cgg gcc ttt gaa ggg    1539
Glu Thr Arg Gly Arg Thr Phe Glu Asp Ile Thr Arg Ala Phe Glu Gly
                495                 500                 505 cag gca cac ggt gca gat aga tct gga aag gac ggc gtc atg ggg atg    1587
Gln Ala His Gly Ala Asp Arg Ser Gly Lys Asp Gly Val Met Gly Met
        510                 515                 520 aac agc atc gag cct gct aag gag acc acc acc aat gtc taa            1629
Asn Ser Ile Glu Pro Ala Lys Glu Thr Thr Thr Asn Val
            525                 530                 535 gtcgtgcctc cttccacctc cctcccggca tgggaaagcc acctctccct caacaaggga  1689
gagacctcat caggatgaac ccaggacgct tctgaatgct gctacttgat ttctttctca  1749
tcccacgcac tccatgagca ccccaaggct gcagtttgtt ggatcttcaa tggcttttta  1809
aattttattt cctggacatc ctcttctgct taggagagac cgagtgaacc taccttcatt  1869
tca                                                                1872

<210> SEQ ID NO 190
<211> LENGTH: 535
<212> TYPE: PRT
<213> ORGANISM: Homo sapiens

<400> SEQUENCE: 190

Met Gln Arg Leu Gln Leu Leu Arg Val Glu Val Leu Leu Gly Val Lys
1               5                   10                  15

Gln Gly Asp Glu Met Arg His Phe Phe Phe Ser Ser Gln Thr Ser Thr
            20                  25                  30

Leu Glu Lys Ser Gln Asn Gly Gly Val Gly Glu Val Thr Pro Ala
        35                  40                  45

Leu Ile Phe Ala Ile Thr Val Ala Thr Ile Gly Ser Phe Gln Phe Gly
    50                  55                  60

Tyr Asn Thr Gly Val Ile Asn Ala Pro Glu Thr Ile Ile Lys Glu Phe
65                  70                  75                  80

Ile Asn Lys Thr Leu Thr Asp Lys Ala Asn Ala Pro Pro Ser Glu Val
```

```
                85                  90                  95
Leu Leu Thr Asn Leu Trp Ser Leu Ser Val Ala Ile Phe Ser Val Gly
            100                 105                 110
Gly Met Ile Gly Ser Phe Ser Val Gly Leu Phe Val Asn Arg Phe Gly
            115                 120                 125
Arg Arg Asn Ser Met Leu Ile Val Asn Leu Leu Ala Thr Gly Gly
            130                 135                 140
Cys Leu Met Gly Leu Cys Lys Ile Ala Glu Ser Val Glu Met Leu Ile
145                 150                 155                 160
Leu Gly Arg Leu Val Ile Gly Leu Phe Cys Gly Leu Cys Thr Gly Phe
                165                 170                 175
Val Pro Met Tyr Ile Gly Glu Ile Ser Pro Thr Ala Leu Arg Gly Ala
            180                 185                 190
Phe Gly Thr Leu Asn Gln Leu Gly Ile Val Ile Gly Ile Leu Val Ala
            195                 200                 205
Gln Ile Phe Gly Leu Glu Leu Ile Leu Gly Ser Glu Glu Leu Trp Pro
            210                 215                 220
Val Leu Leu Gly Phe Thr Ile Leu Pro Ala Ile Leu Gln Ser Ala Ala
225                 230                 235                 240
Leu Pro Cys Cys Pro Glu Ser Pro Arg Phe Leu Leu Ile Asn Arg Lys
                245                 250                 255
Lys Glu Glu Asn Ala Thr Arg Ile Leu Gln Arg Leu Trp Gly Thr Gln
            260                 265                 270
Asp Val Ser Gln Asp Ile Gln Glu Met Lys Asp Glu Ser Ala Arg Met
            275                 280                 285
Ser Gln Glu Lys Gln Val Thr Val Leu Glu Leu Phe Arg Val Ser Ser
            290                 295                 300
Tyr Arg Gln Pro Ile Ile Ile Ser Ile Val Leu Gln Leu Ser Gln Gln
305                 310                 315                 320
Leu Ser Gly Ile Asn Ala Val Phe Tyr Tyr Ser Thr Gly Ile Phe Lys
                325                 330                 335
Asp Ala Gly Val Gln Gln Pro Ile Tyr Ala Thr Ile Ser Ala Gly Val
            340                 345                 350
Val Asn Thr Ile Phe Thr Leu Leu Ser Leu Phe Leu Val Glu Arg Ala
            355                 360                 365
Gly Arg Arg Thr Leu His Met Ile Gly Leu Gly Gly Met Ala Phe Cys
            370                 375                 380
Ser Thr Leu Met Thr Val Ser Leu Leu Leu Lys Asn His Tyr Asn Gly
385                 390                 395                 400
Met Ser Phe Val Cys Ile Gly Ala Ile Leu Val Phe Val Ala Cys Phe
                405                 410                 415
Glu Ile Gly Pro Gly Pro Ile Pro Trp Phe Ile Val Ala Glu Leu Phe
            420                 425                 430
Ser Gln Gly Pro Arg Pro Ala Ala Met Ala Val Ala Gly Cys Ser Asn
            435                 440                 445
Trp Thr Ser Asn Phe Leu Val Gly Leu Leu Phe Pro Ser Ala Ala Tyr
            450                 455                 460
Tyr Leu Gly Ala Tyr Val Phe Ile Ile Phe Thr Gly Phe Leu Ile Thr
465                 470                 475                 480
Phe Leu Ala Phe Thr Phe Lys Val Pro Glu Thr Arg Gly Arg Thr
                485                 490                 495
Phe Glu Asp Ile Thr Arg Ala Phe Glu Gly Gln Ala His Gly Ala Asp
            500                 505                 510
```

```
Arg Ser Gly Lys Asp Gly Val Met Gly Met Asn Ser Ile Glu Pro Ala
        515                 520                 525

Lys Glu Thr Thr Thr Asn Val
        530             535

<210> SEQ ID NO 191
<211> LENGTH: 153
<212> TYPE: DNA
<213> ORGANISM: Homo sapiens

<400> SEQUENCE: 191
acaacctgac ttttgttcac aatgcaaaga ctccaactgt tgagagtaga agtactgctg      60
ggtgtgaaac aaggagatga aatgcggcat tctttttttt cttctcagac ctccactctg     120
gagaagagtc agaatggggg cgtcggggag gag                                  153

<210> SEQ ID NO 192
<211> LENGTH: 44
<212> TYPE: PRT
<213> ORGANISM: Homo sapiens

<400> SEQUENCE: 192

Met Gln Arg Leu Gln Leu Leu Arg Val Glu Val Leu Leu Gly Val Lys
1               5                   10                  15

Gln Gly Asp Glu Met Arg His Phe Phe Phe Ser Ser Gln Thr Ser Thr
            20                  25                  30

Leu Glu Lys Ser Gln Asn Gly Gly Val Gly Glu Glu
        35                  40

<210> SEQ ID NO 193
<211> LENGTH: 132
<212> TYPE: DNA
<213> ORGANISM: Homo sapiens

<400> SEQUENCE: 193
atgcaaagac tccaactgtt gagagtagaa gtactgctgg gtgtgaaaca aggagatgaa      60
atgcggcatt tctttttttc ttctcagacc tccactctgg agaagagtca gaatggggggc    120 gtcggggagg ag                                                         132

<210> SEQ ID NO 194
<211> LENGTH: 4115
<212> TYPE: DNA
<213> ORGANISM: Homo sapiens

<400> SEQUENCE: 194
agtcgcgggg tctgggagga gacctgaatg aaatgaggga gccttgggag catgatccag      60
gcggagggaa ctggattcgg gaggaggaac tgccttggcc ttgaaagata cctaccagga     120
gttcaagtgc tgtgcgggtg catcagcttt gtagatttgt gcaagatgaa aattggaatt     180
gtcttaggaa attatggatc attcatttat tcagtgctgg attcattcag tgatttatgt     240
ctgaagtgtg acagaagggg agtaaggcca agtgtccttg ccctctattg gagattctgc     300
ctcccctggg acagatggct tcttgagcac actcccacga tgggtggctg ctctggtaca     360
tctcatccac ttcttcatct gtgaagctgt cacccatggt ggtgagcagc tcctggaggt     420
ggtcctcatg agtgaaacct gaggattcct cgttgaagca gtattcatc catggggttc      480 ttccgcggtg aagccagctt gtcgtgctgt ccccccttgtc aatgaagcca tcatggttct    540
ggtcaatcat gttgaaagcc tccttaaact cctggatgtg gaactggtca acatcacga     600 agacattgga tgtggccccc tgtgctgtgg tcgcttcttg gtcttggctt tggtccactt    660
```

```
gctgaacatt ttggcttcag gaagcagtac cttgaagaga aattggagag ggagtcaatt   720
cctaggatag cagagagatg gacaacagac agaatagatg gagtttcaca atggtggcca   780
tgtgtctgga attggtgggt tcttggtctc actgacttca agaatgaagc cgcacaccct   840
cgcagtcacc ccagctctga tctttgccat cacagttgct acaatcggct ctttccagtt   900
tggctacaac actggggtca tcaatgctcc tgagacgatc ataaaggaat ttatcaataa   960
aactttgacg gacaaggcaa atgcccctcc ctctgaggtg ctgctcacga atctctggtc  1020
cttgtctgtg gccatatttt ccgtcggggg tatgatcggc tccttttccg tcggactctt  1080
tgttaaccgc tttggcaggc gcaattcaat gctgattgtc aacctgttgg ctgccactgg  1140
tggctgcctt atgggactgt gtaaaatagc tgagtcagtt gaaatgctga tcctgggccg  1200
cttggttatt ggcctcttct gcggactctg cacaggtttt gtgcccatgt acattggaga  1260
gatctcgcct actgccctga ggggtgcctt tggcactctc aaccagctgg gcatagttat  1320
tggaattctg gtgcccaga tctttggtct ggaactcatc cttgggtctg aagagctatg  1380
gccggtgcta ttaggcttta ccatccttcc agctatcctg caaagtgcag cccttccatg  1440
ttgccctgaa agtcccagat ttttgctcat aacagaaaa aaagaggaga atgctacgcg  1500
gatcctccag cggttgtggg gcacccagga tgtatcccaa gacatccagg agatgaaaga  1560
tgagagtgca aggatgtcac aagaaaagca agtcaccgtg ctggagctct ttagagtgtc  1620
cagctaccga cagcccatca tcatttccat tgtgctccag ctctctcagc agctctctgg  1680
gatcaatgct gtgttctatt actcaacagg aatcttcaag gatgcaggtg ttcaacagcc  1740
catctatgcc accatcagcg cgggtgtggt taatactatc ttcactttac tttctctatt  1800
tctggtggaa agggcaggaa gaaggactct gcatatgata ggccttggag ggatggcttt  1860
ttgttccacg ctcatgactg tttctttgtt attaaagaat cactataatg ggatgagctt  1920
tgtctgtatt ggggctatct tggtctttgt ggcctgtttt gaaattggac caggccccat  1980
tccctggttt attgtggccg aactcttcag ccagggcccc cgcccagctg cgatggcagt  2040
ggccggctgc tccaactgga cctccaactt cctagtcgga ttgctcttcc cctctgctgc  2100
ttactattta ggagcctacg ttttttattat cttcaccggc ttcctcatta ccttcttggc  2160
ctttaccttc ttcaaagtcc ctgagacccg tggcaggact tttgaggata tcacacgggc  2220
ctttgaaggg caggcacacg gtgcagatag atctggaaag gacggcgtca tggggatgaa  2280
cagcatcgag cctgctaagg agaccaccac caatgtctaa gtcgtgcctc cttccacctc  2340
cctcccggca tgggaaagcc acctctccct caacaaggga gagactttat caggatgaac  2400
ccaggacgct tctgaatgct gctacttgat ttctttctca tcccacgcac tccatgagca  2460
ccccaaggct gcagtttgtt ggatcttcaa tggctttta aattttattt cctggacatc  2520
ctcttctgct taggagagac cgagtgaacc taccttcatt tcaggaggga ttggccgctt  2580
ggcacatgac aactttgcca gcttttcctc ccttgggttc tgatattgcc gcactagggg  2640
atataggaga ggaaaagtaa ggtgcagttg ccccaacctc agacttacca ggaagcagat  2700
acatgtgagt gtggaaggca gaggggtttt atgtaagagc accttcctca cttccataca  2760
gctctacgcg gcaaattaac ttgagtttta tttatcttat cctctggttt aattacataa  2820
atatttattt tttaagtgta attttgccaa ataataacaa cagaaggaaa ttgagattag  2880
agggaggtgt ttaaagagag gttatagagt aaaagatttg atgctggaga ggttaaggtg  2940
caataagaat tcaggagaa atgttgttca ttattggagg gtaaatgatg tggtgcctga  3000
ggtctgtaca ttacctctta acaatttctg tccttcagat gaaaactctt tgatttctca  3060
```

```
gaaaagttgt atgcctattt aataaagcta ctcatttcct ttggaacttt atctttaaga    3120
taatagttta catgtagtag tacttgaaat ctaggattat taactaatat gggcattgta    3180
gttaatggcg gttgatgggt tctaattttg gatggagtcc agggaagaga aagtgatttc    3240
tagaaagcct gttcccctca ctggacgaaa taactccttg tagtagtctc attacttttg    3300
aagtaatccc gccacctatc tagtgggaga gccatccaaa tgagaaacct aaaataattg    3360
gttcttggta gagattcatt atttctccac tttgttcttt aggagatttt aggtgttgat    3420
tttctgtttt attttaactc ataccttta aggaattccc caagaatgt ttatagcaaa     3480 cttggaattt gtaacctcag ctctgggaga ggattttttt ctgagcgatt attatctaaa    3540
gtgtgttgtt gctttaggct cacggcacgc ttgcgtatgt ctgttaccat gtcactgtgg    3600
tcctatgccg aatgccctca ggggacttga atctttccaa taaaccaggt ttagacagta    3660
tgagtcaatg tgcagtgcag cccacacttg agaggatgaa tgtatgtgca ctgtcacttt    3720
gctctgggtg aagtatgtt attgttgact tattttctct gtgtttgttc ctacagcccc    3780
tttttcatat gttgctcagt ctcccttttcc cttcttggtg cttacacatc tcagacccctt  3840 tagccaaacc cttgccagtg acagtatttt ggttctcagt tctcactgtt ccctctgctc    3900
ctggagcctt tgaataaaaa tgcacgtagc tatggagtgg ggtttagctg aaaggtggc    3960 cttccaactt cacgtcaact tctggctcct cagtttggca gtaaggcagg aagttgttt    4020 tcctatttct cactgagaag attgtgaata tttccatatg gattttccat tattgtttgt    4080
ttgattcttt gttttaaaat aaaaattctg aatgt                                4115

<210> SEQ ID NO 195
<211> LENGTH: 4115
<212> TYPE: DNA
<213> ORGANISM: Homo sapiens
<221> NAME/KEY: CDS
<222> LOCATION: (758)..(2320)

<400> SEQUENCE: 195
agtcgcgggg tctgggagga gacctgaatg aaatgaggga gccttgggag catgatccag     60
gcggagggaa ctgattcgg gaggaggaac tgccttggcc ttgaaagata cctaccagga    120
gttcaagtgc tgtgcgggtg catcagcttt gtagatttgt gcaagatgaa aattggaatt    180
gtcttaggaa attatggatc attcatttat tcagtgctgg attcattcag tgatttatgt    240
ctgaagtgtg acagaagggg agtaaggcca agtgtccttg ccctctattg gagattctgc    300
ctcccctggg acagatggct tcttgagcac actcccacga tgggtggctg ctctggtaca    360
tctcatccac ttcttcatct gtgaagctgt cacccatggt ggtgagcagc tcctggaggt    420
ggtcctcatg agtgaaacct gaggattcct cgttgaagca ggtattcatc catggggttc    480
ttccgcggtg aagccagctt gtcgtgctgt cccccttgtc aatgaagcca tcatggttct    540
ggtcaatcat gttgaaagcc tccttaaact cctggatgtg gaactggtca acatcacga    600 agacattgga tgtggccccc tgtgctgtgg tcgcttcttg gtcttggctt tggtccactt    660
gctgaacatt ttggcttcag gaagcagtac cttgaagaga aattggagag ggagtcaatt    720
cctaggatag cagagagatg gacaacagac agaatag atg gag ttt cac aat ggt    775
                                        Met Glu Phe His Asn Gly
                                         1               5 ggc cat gtg tct gga att ggt ggg ttc ttg gtc tca ctg act tca aga     823
Gly His Val Ser Gly Ile Gly Gly Phe Leu Val Ser Leu Thr Ser Arg
         10                  15                  20 atg aag ccg cac acc ctc gca gtc acc cca gct ctg atc ttt gcc atc     871
```

```
            Met Lys Pro His Thr Leu Ala Val Thr Pro Ala Leu Ile Phe Ala Ile
                    25                  30                  35 aca gtt gct aca atc ggc tct ttc cag ttt ggc tac aac act ggg gtc          919
Thr Val Ala Thr Ile Gly Ser Phe Gln Phe Gly Tyr Asn Thr Gly Val
 40                  45                  50 atc aat gct cct gag acg ata aag gaa ttt atc aat aaa act ttg             967
Ile Asn Ala Pro Glu Thr Ile Ile Lys Glu Phe Ile Asn Lys Thr Leu
 55                  60                  65                  70 acg gac aag gca aat gcc cct ccc tct gag gtg ctg ctc acg aat ctc        1015
Thr Asp Lys Ala Asn Ala Pro Pro Ser Glu Val Leu Leu Thr Asn Leu
                 75                  80                  85 tgg tcc ttg tct gtg gcc ata ttt tcc gtc ggg ggt atg atc ggc tcc        1063
Trp Ser Leu Ser Val Ala Ile Phe Ser Val Gly Gly Met Ile Gly Ser
                 90                  95                 100 ttt tcc gtc gga ctc ttt gtt aac cgc ttt ggc agg cgc aat tca atg        1111
Phe Ser Val Gly Leu Phe Val Asn Arg Phe Gly Arg Arg Asn Ser Met
                105                 110                 115 ctg att gtc aac ctg ttg gct gcc act ggt ggc tgc ctt atg gga ctg        1159
Leu Ile Val Asn Leu Leu Ala Ala Thr Gly Gly Cys Leu Met Gly Leu
                120                 125                 130 tgt aaa ata gct gag tca gtt gaa atg ctg atc ctg ggc cgc ttg gtt        1207
Cys Lys Ile Ala Glu Ser Val Glu Met Leu Ile Leu Gly Arg Leu Val
135                 140                 145                 150 att ggc ctc ttc tgc gga ctc tgc aca ggt ttt gtg ccc atg tac att        1255
Ile Gly Leu Phe Cys Gly Leu Cys Thr Gly Phe Val Pro Met Tyr Ile
                155                 160                 165 gga gag atc tcg cct act gcc ctg agg ggt gcc ttt ggc act ctc aac        1303
Gly Glu Ile Ser Pro Thr Ala Leu Arg Gly Ala Phe Gly Thr Leu Asn
                170                 175                 180 cag ctg ggc ata gtt att gga att ctg gtg gcc cag atc ttt ggt ctg        1351
Gln Leu Gly Ile Val Ile Gly Ile Leu Val Ala Gln Ile Phe Gly Leu
                185                 190                 195 gaa ctc atc ctt ggg tct gaa gag cta tgg ccg gtg cta tta ggc ttt        1399
Glu Leu Ile Leu Gly Ser Glu Glu Leu Trp Pro Val Leu Leu Gly Phe
                200                 205                 210 acc atc ctt cca gct atc ctg caa agt gca gcc ctt cca tgt tgc cct        1447
Thr Ile Leu Pro Ala Ile Leu Gln Ser Ala Ala Leu Pro Cys Cys Pro
215                 220                 225                 230 gaa agt ccc aga ttt ttg ctc att aac aga aaa aaa gag gag aat gct        1495
Glu Ser Pro Arg Phe Leu Leu Ile Asn Arg Lys Lys Glu Glu Asn Ala
                235                 240                 245 acg cgg atc ctc cag cgg ttg tgg ggc acc cag gat gta tcc caa gac        1543
Thr Arg Ile Leu Gln Arg Leu Trp Gly Thr Gln Asp Val Ser Gln Asp
                250                 255                 260 atc cag gag atg aaa gat gag agt gca agg atg tca caa gaa aag caa        1591
Ile Gln Glu Met Lys Asp Glu Ser Ala Arg Met Ser Gln Glu Lys Gln
                265                 270                 275 gtc acc gtg ctg gag ctc ttt aga gtg tcc agc tac cga cag ccc atc        1639
Val Thr Val Leu Glu Leu Phe Arg Val Ser Ser Tyr Arg Gln Pro Ile
280                 285                 290 atc att tcc att gtg ctc cag ctc tct cag cag ctc tct ggg atc aat        1687
Ile Ile Ser Ile Val Leu Gln Leu Ser Gln Gln Leu Ser Gly Ile Asn
295                 300                 305                 310 gct gtg ttc tat tac tca aca gga atc ttc aag gat gca ggt gtt caa        1735
Ala Val Phe Tyr Tyr Ser Thr Gly Ile Phe Lys Asp Ala Gly Val Gln
                315                 320                 325 cag ccc atc tat gcc acc atc agc gcg ggt gtg gtt aat act atc ttc        1783
Gln Pro Ile Tyr Ala Thr Ile Ser Ala Gly Val Val Asn Thr Ile Phe
                330                 335                 340 act tta ctt tct cta ttt ctg gtg gaa agg gca gga aga agg act ctg        1831
```

```
                    Thr Leu Leu Ser Leu Phe Leu Val Glu Arg Ala Gly Arg Arg Thr Leu
                            345                 350                 355 cat atg ata ggc ctt gga ggg atg gct ttt tgt tcc acg ctc atg act                   1879
His Met Ile Gly Leu Gly Gly Met Ala Phe Cys Ser Thr Leu Met Thr
        360                 365                 370 gtt tct ttg tta tta aag aat cac tat aat ggg atg agc ttt gtc tgt                   1927
Val Ser Leu Leu Leu Lys Asn His Tyr Asn Gly Met Ser Phe Val Cys
375                 380                 385                 390 att ggg gct atc ttg gtc ttt gtg gcc tgt ttt gaa att gga cca ggc                   1975
Ile Gly Ala Ile Leu Val Phe Val Ala Cys Phe Glu Ile Gly Pro Gly
                395                 400                 405 ccc att ccc tgg ttt att gtg gcc gaa ctc ttc agc cag ggc ccc cgc                   2023
Pro Ile Pro Trp Phe Ile Val Ala Glu Leu Phe Ser Gln Gly Pro Arg
        410                 415                 420 cca gct gcg atg gca gtg gcc ggc tgc tcc aac tgg acc tcc aac ttc                   2071
Pro Ala Ala Met Ala Val Ala Gly Cys Ser Asn Trp Thr Ser Asn Phe
425                 430                 435 cta gtc gga ttg ctc ttc ccc tct gct gct tac tat tta gga gcc tac                   2119
Leu Val Gly Leu Leu Phe Pro Ser Ala Ala Tyr Tyr Leu Gly Ala Tyr
                440                 445                 450 gtt ttt att atc ttc acc ggc ttc ctc att acc ttc ttg gcc ttt acc                   2167
Val Phe Ile Ile Phe Thr Gly Phe Leu Ile Thr Phe Leu Ala Phe Thr
455                 460                 465                 470 ttc ttc aaa gtc cct gag acc cgt ggc agg act ttt gag gat atc aca                   2215
Phe Phe Lys Val Pro Glu Thr Arg Gly Arg Thr Phe Glu Asp Ile Thr
                475                 480                 485 cgg gcc ttt gaa ggg cag gca cac ggt gca gat aga tct gga aag gac                   2263
Arg Ala Phe Glu Gly Gln Ala His Gly Ala Asp Arg Ser Gly Lys Asp
        490                 495                 500 ggc gtc atg ggg atg aac agc atc gag cct gct aag gag acc acc acc                   2311
Gly Val Met Gly Met Asn Ser Ile Glu Pro Ala Lys Glu Thr Thr Thr
                505                 510                 515 aat gtc taa gtcgtgcctc cttccacctc cctcccggca tgggaaagcc                           2360
Asn Val
    520 acctctccct caacaaggga gagactttat caggatgaac ccaggacgct tctgaatgct                 2420 gctacttgat ttctttctca tcccacgcac tccatgagca ccccaaggct gcagtttgtt                 2480 ggatcttcaa tggcttttta aattttattt cctggacatc ctcttctgct taggagagac                 2540 cgagtgaacc taccttcatt tcaggaggga ttggccgctt ggcacatgac aactttgcca                 2600 gcttttcctc ccttgggttc tgatattgcc gcactagggg atataggaga ggaaaagtaa                 2660 ggtgcagttg ccccaacctc agacttacca ggaagcagat acatgtgagt gtggaaggca                 2720 gaggggttt atgtaagagc accttcctca cttccataca gctctacgcg gcaaattaac                  2780 ttgagtttta tttatcttat cctctggttt aattacataa atatttattt tttaagtgta                 2840 attttgccaa ataataacaa cagaaggaaa ttgagattag agggaggtgt ttaaagagag                 2900 gttatagagt aaaagatttg atgctggaga ggttaaggtg caataagaat tcaggagaaa                 2960 atgttgttca ttattggagg gtaaatgatg tggtgcctga ggtctgtaca ttacctctta                 3020 acaatttctg tccttcagat gaaaactctt tgatttctca gaaagttgt atgcctattt                  3080 aataaagcta ctcatttcct ttggaacttt atctttaaga taatagttta catgtagtag                 3140 tacttgaaat ctaggattat taactaatat gggcattgta gttaatggcg ttgatgggt                  3200 tctaattttg gatggagtcc agggaagaga aagtgatttc tagaaagcct gttcccctca                 3260 ctggacgaaa taactccttg tagtagtctc attacttttg aagtaatccc gccacctatc                 3320 tagtgggaga gccatccaaa tgagaaacct aaaataattg gttcttggta gagattcatt                 3380
```

```
atttctccac tttgttcttt aggagatttt aggtgttgat tttctgtttt attttaactc    3440
atacctttaa aggaattccc caaagaatgt ttatagcaaa cttggaattt gtaacctcag    3500
ctctgggaga ggatttttt ctgagcgatt attatctaaa gtgtgttgtt gctttaggct     3560
cacggcacgc ttgcgtatgt ctgttaccat gtcactgtgg tcctatgccg aatgccctca    3620
ggggacttga atctttccaa taaaccaggt ttagacagta tgagtcaatg tgcagtgcag    3680
cccacacttg agaggatgaa tgtatgtgca ctgtcacttt gctctgggtg gaagtatgtt    3740
attgttgact tattttctct gtgtttgttc ctacagcccc ttttcatat gttgctcagt     3800 ctccctttcc cttcttggtg cttacacatc tcagacccct tagccaaacc cttgccagtg    3860
acagtatttt ggttctcagt tctcactgtt ccctctgctc ctggagcctt tgaataaaaa    3920
tgcacgtagc tatggagtgg ggtttagctg gaaaggtggc cttccaactt cacgtcaact    3980
tctggctcct cagtttggca gtaaggcagg gaagttgttt tcctatttct cactgagaag    4040
attgtgaata tttccatatg gattttccat tattgtttgt ttgattcttt gttttaaaat    4100
aaaaattctg aatgt                                                    4115
```

<210> SEQ ID NO 196
<211> LENGTH: 520
<212> TYPE: PRT
<213> ORGANISM: Homo sapiens

<400> SEQUENCE: 196

```
Met Glu Phe His Asn Gly Gly His Val Ser Gly Ile Gly Gly Phe Leu
1               5                   10                  15

Val Ser Leu Thr Ser Arg Met Lys Pro His Thr Leu Ala Val Thr Pro
            20                  25                  30

Ala Leu Ile Phe Ala Ile Thr Val Ala Thr Ile Gly Ser Phe Gln Phe
        35                  40                  45

Gly Tyr Asn Thr Gly Val Ile Asn Ala Pro Glu Thr Ile Ile Lys Glu
    50                  55                  60

Phe Ile Asn Lys Thr Leu Thr Asp Lys Ala Asn Ala Pro Pro Ser Glu
65                  70                  75                  80

Val Leu Leu Thr Asn Leu Trp Ser Leu Ser Val Ala Ile Phe Ser Val
                85                  90                  95

Gly Gly Met Ile Gly Ser Phe Ser Val Gly Leu Phe Val Asn Arg Phe
            100                 105                 110

Gly Arg Arg Asn Ser Met Leu Ile Val Asn Leu Leu Ala Ala Thr Gly
        115                 120                 125

Gly Cys Leu Met Gly Leu Cys Lys Ile Ala Glu Ser Val Glu Met Leu
    130                 135                 140

Ile Leu Gly Arg Leu Val Ile Gly Leu Phe Cys Gly Leu Cys Thr Gly
145                 150                 155                 160

Phe Val Pro Met Tyr Ile Gly Glu Ile Ser Pro Thr Ala Leu Arg Gly
                165                 170                 175

Ala Phe Gly Thr Leu Asn Gln Leu Gly Ile Val Ile Gly Ile Leu Val
            180                 185                 190

Ala Gln Ile Phe Gly Leu Glu Leu Ile Leu Gly Ser Glu Glu Leu Trp
        195                 200                 205

Pro Val Leu Leu Gly Phe Thr Ile Leu Pro Ala Ile Leu Gln Ser Ala
    210                 215                 220

Ala Leu Pro Cys Cys Pro Glu Ser Pro Arg Phe Leu Leu Ile Asn Arg
225                 230                 235                 240
```

-continued

```
Lys Lys Glu Glu Asn Ala Thr Arg Ile Leu Gln Arg Leu Trp Gly Thr
                245                 250                 255

Gln Asp Val Ser Gln Asp Ile Gln Glu Met Lys Asp Glu Ser Ala Arg
            260                 265                 270

Met Ser Gln Glu Lys Gln Val Thr Val Leu Glu Leu Phe Arg Val Ser
        275                 280                 285

Ser Tyr Arg Gln Pro Ile Ile Ile Ser Ile Val Leu Gln Leu Ser Gln
    290                 295                 300

Gln Leu Ser Gly Ile Asn Ala Val Phe Tyr Tyr Ser Thr Gly Ile Phe
305                 310                 315                 320

Lys Asp Ala Gly Val Gln Gln Pro Ile Tyr Ala Thr Ile Ser Ala Gly
                325                 330                 335

Val Val Asn Thr Ile Phe Thr Leu Leu Ser Leu Phe Leu Val Glu Arg
            340                 345                 350

Ala Gly Arg Arg Thr Leu His Met Ile Gly Leu Gly Gly Met Ala Phe
        355                 360                 365

Cys Ser Thr Leu Met Thr Val Ser Leu Leu Leu Lys Asn His Tyr Asn
    370                 375                 380

Gly Met Ser Phe Val Cys Ile Gly Ala Ile Leu Val Phe Val Ala Cys
385                 390                 395                 400

Phe Glu Ile Gly Pro Gly Pro Ile Pro Trp Phe Ile Val Ala Glu Leu
                405                 410                 415

Phe Ser Gln Gly Pro Arg Pro Ala Ala Met Ala Val Ala Gly Cys Ser
            420                 425                 430

Asn Trp Thr Ser Asn Phe Leu Val Gly Leu Leu Phe Pro Ser Ala Ala
        435                 440                 445

Tyr Tyr Leu Gly Ala Tyr Val Phe Ile Ile Phe Thr Gly Phe Leu Ile
    450                 455                 460

Thr Phe Leu Ala Phe Thr Phe Phe Lys Val Pro Glu Thr Arg Gly Arg
465                 470                 475                 480

Thr Phe Glu Asp Ile Thr Arg Ala Phe Glu Gly Gln Ala His Gly Ala
                485                 490                 495

Asp Arg Ser Gly Lys Asp Gly Val Met Gly Met Asn Ser Ile Glu Pro
            500                 505                 510

Ala Lys Glu Thr Thr Thr Asn Val
        515                 520

<210> SEQ ID NO 197
<211> LENGTH: 23
<212> TYPE: DNA
<213> ORGANISM: Artificial Sequence
<220> FEATURE:
<223> OTHER INFORMATION: forward primer used for specifically detecting
      the variant of the present invention (D-NT2RI3001005.1 and
      D-NT2RI3005261.1)

<400> SEQUENCE: 197
ggcatttctt ttttcttct cag                                           23

<210> SEQ ID NO 198
<211> LENGTH: 17
<212> TYPE: DNA
<213> ORGANISM: Artificial Sequence
<220> FEATURE:
<223> OTHER INFORMATION: reverse primer used for specifically detecting
      the variant of the present invention (D-NT2RI3001005.1 and
      D-NT2RI3005261.1)

<400> SEQUENCE: 198
```

```
ggtgacctcc tccccga                                                      17
```

<210> SEQ ID NO 199
<211> LENGTH: 74
<212> TYPE: DNA
<213> ORGANISM: Artificial Sequence
<220> FEATURE:
<223> OTHER INFORMATION: partial polynucleotide specific to the variant
      of the present invention (D-NT2RI3001005.1 and D-NT2RI3005261.1),
      which is obtained by PCR using forward primer (SEQ ID NO:197) and
      reverse primer (SEQ ID NO:198)

<400> SEQUENCE: 199

```
ggcatttctt tttttcttct cagacctcca ctctggagaa gagtcagaat ggggcgtcg       60 gggaggaggt cacc                                                         74
```

<210> SEQ ID NO 200
<211> LENGTH: 22
<212> TYPE: DNA
<213> ORGANISM: Artificial Sequence
<220> FEATURE:
<223> OTHER INFORMATION: forward primer used for detecting the variants
      of the gene of the present invention (D-NT2RI3001005.1,
      D-NT2RI3005261.1 and NM_153449.2)

<400> SEQUENCE: 200

```
tttattgtgg ccgaactctt ca                                                22
```

<210> SEQ ID NO 201
<211> LENGTH: 22
<212> TYPE: DNA
<213> ORGANISM: Artificial Sequence
<220> FEATURE:
<223> OTHER INFORMATION: reverse primer used for detecting the variants
      of the gene of the present invention (D-NT2RI3001005.1,
      D-NT2RI3005261.1 and NM_153449.2)

<400> SEQUENCE: 201

```
gcaatccgac taggaagttg ga                                                22
```

<210> SEQ ID NO 202
<211> LENGTH: 97
<212> TYPE: DNA
<213> ORGANISM: Artificial Sequence
<220> FEATURE:
<223> OTHER INFORMATION: partial polynucleotide common to the variants
      of the gene of the present invention (D-NT2RI3001005.1,
      D-NT2RI3005261.1 and NM_153449.2), which is obtained by PCR using
      forward primer (SEQ ID NO:200) and reverse primer (SEQ ID NO:201)

<400> SEQUENCE: 202

```
tttattgtgg ccgaactctt cagccagggc ccccgcccag ctgcgatggc agtggccggc       60
tgctccaact ggacctccaa cttcctagtc ggattgc                                97
```

<210> SEQ ID NO 203
<211> LENGTH: 159
<212> TYPE: DNA
<213> ORGANISM: Homo sapiens

<400> SEQUENCE: 203

```
acaacctgac ttttgtccac aatgcaaaga ctccaactgt tgagagtaga agtactgctg       60
ggtgtgaaac aaggagatga aatgcggcat ttcttttttt cttctcagac ctccactctg      120
gagaagagtc agaatggggg cgtcggggag gaggtcacc                             159
```

<210> SEQ ID NO 204

```
<211> LENGTH: 159
<212> TYPE: DNA
<213> ORGANISM: Homo sapiens

<400> SEQUENCE: 204
acaacctgac ttttgttcac aatgcaaaga ctccaactgt tgagagtaga agtactgctg      60
ggtgtgaaac aaggagatga aatgcggcat ttcttttttt cttctcagac ctccactctg     120
gagaagagtc agaatggggg cgtcggggag gaggtcacc                            159

<210> SEQ ID NO 205
<211> LENGTH: 2724
<212> TYPE: DNA
<213> ORGANISM: Homo sapiens

<400> SEQUENCE: 205
gagagcagcg ccaatgtgaa gcgttgcagt cgcttgactc acctgaggct ctccaaggat      60
accttcaatg cctgcactgt aagggagctg cttttcccgg gtgctggcga gaacggaagc     120
cttcctttga cgttttccta acatgggat gcagtctgtg cagcctgcag aagcaagagg     180
agcagtacaa attactctat gaagtttgtc aggtcaacgg cagagactta tccagagcaa     240
ctcatgacca ggctgtggaa gctttcaaga cagccaagga gcccatagtg gtgcaggtgt     300
tgagaagaac accaaggacc aaaatgttca cgcctccatc agagtctcag ctggtggaca     360
cgggaaccca aaccgacatc acctttgaac atatcatggc cctcactaag atgtcctctc     420
ccagcccacc cgtgctggat ccctatctct gccagagga gcatccctca gcccatgaat     480
actacgatcc aaatgactac attggagaca tccatcagga gatggacagg gaggagctgg     540
agctggagga gtggacctc tacagaatga acagccagga caagctgggc ctcactgtgt     600
gctaccggac ggacgatgaa gacgacattg ggatttatat cagtgagatt gaccctaaca     660
gcattgcagc caaggatggg cgcatccgag aaggagactg cattatccag attaatggga     720
tagaggtgca gaaccgtgaa gaggctgtgg ctcttctaac cagtgaagaa aataaaaact     780
tttcattgct gattgcaagg cctgaactcc agctggatga gggctggatg gatgatgaca     840
ggaacgactt tctggatgac ctgcacatgg acatgctgga ggagcagcac accaggcca     900 tgcaattcac agctagcgtg ctgcagcaga agaagcacga cgaagacggt gggaccacag     960
atacagccac catcttgtcc aaccagcacg agaaggacag cggtgtgggg cggaccgacg    1020
agagcacccg taatgacgag agctcggagc aagagaacaa tggcgacgac gccaccgcat    1080
cctccaaccc gctggcgggg cagaggaagc tcacctgcag ccaggacacc ttgggcagcg    1140
gcgacctgcc cttcagcaac gagtctttca tttcggccga ctgcacggac gccgactacc    1200 tgggatccc ggtggacgag tgcgagcgct tccgcgagct cctggagctc aagtgccagg    1260
tgaagagcgc caccccttac ggcctgtact accctagcgg ccccctggac gccggcaaga    1320
gtgaccctga gagcgtggac aaggagctgg agctgctgaa cgaagagctg cgcagcatcg    1380
agctggagtg cctgagcatc gtgcgcgccc acaagatgca gcagctcaag gagcagtacc    1440
gcgagtcctg gatgctgcac aacagcgcct ccgcaacta caacaccagc atcgacgtgc    1500
gcagacgcga gctctcagat atcaccgagc tcccggagaa atccgacaag gacagctcga    1560
gcgcctacaa cacaggcgag agctgccgca gcacccgct cacccctgag atctccccg    1620 acaactcctt gaggagagcg gcggagggca tcagctgccc gagcagcgaa ggggctgtgg    1680
ggaccacgga agcctacggg ccagcctcca agaatctgct ctccatcacg gaagatcccg    1740
aagtgggcac ccctacctat agcccgtccc tgaaggagct ggaccccaac cagccctgg    1800
```

-continued

```
aaagcaaaga gcggagagcc agcgacggga gccggagccc cacgcccagc cagaagctgg     1860
gcagcgccta cctgccctcc tatcaccact cccatacaa gcacgcgcac atcccggcgc       1920
acgcccagca ctaccagagc tacatgcagc tgatccagca gaagtcggcc gtggagtacg     1980
cgcaaagcca gatgagcctg gtgagcatgt gcaaggacct gagctctccc accccgtcgg    2040
agccgcgcat ggagtggaag gtgaagatcc gcagcgacgg gacgcgctac atcaccaaga    2100
ggcccgtgcg ggaccgcctg ctgcgggagc gcgccctgaa gatccgggaa gagcgcagcg    2160
gcatgaccac cgacgacgac gcggtgagcg agatgaagat ggggcgctac tggagcaagg    2220
aggagaggaa gcagcacttg gtgaaggcca aggagcagcg gcggcggcgc gagttcatga    2280
tgcagagcag gttggattgt ctcaaggagc agcaagcagc cgatgacagg aaggagatga    2340
acattctcga actgagccac aaaaagatga tgaagaagag gaataagaaa atcttcgata    2400
actggatgac gatccaagaa ctcttaaccc acggcacaaa atccccggac ggcactagag    2460
tatacaattc cttcctatcg gtgactactg tataattttc acttctgcat tatgtacata    2520
aaggagacca ctaccactgg ggtagaaatt cctgcctcgt tcaatgcggc aagttttgt     2580 atataagata agtacggtct tcatgtttat agtccaaatt tgcaaaccct acaactctgg    2640
gtgtcatagg tctattttaa gggaagagag agaaaaacac ccttactatc ttggaaggca    2700
atattaacaa acagagcttt tttc                                            2724
```

<210> SEQ ID NO 206
<211> LENGTH: 2724
<212> TYPE: DNA
<213> ORGANISM: Homo sapiens
<221> NAME/KEY: CDS
<222> LOCATION: (144)..(2495)

<400> SEQUENCE: 206

```
gagagcagcg ccaatgtgaa gcgttgcagt cgcttgactc acctgaggct ctccaaggat      60
accttcaatg cctgcactgt aagggagctg cttttcccgg gtgctggcga gaacggaagc    120
cttcctttga cgttttctca aac atg gga tgc agt ctg tgc agc ctg cag aag    173
                          Met Gly Cys Ser Leu Cys Ser Leu Gln Lys
                            1               5                  10 caa gag gag cag tac aaa tta ctc tat gaa gtt tgt cag gtc aac ggc      221
Gln Glu Glu Gln Tyr Lys Leu Leu Tyr Glu Val Cys Gln Val Asn Gly
            15                  20                  25 aga gac tta tcc aga gca act cat gac cag gct gtg gaa gct ttc aag      269
Arg Asp Leu Ser Arg Ala Thr His Asp Gln Ala Val Glu Ala Phe Lys
        30                  35                  40 aca gcc aag gag ccc ata gtg gtg cag gtg ttg aga aga aca cca agg      317
Thr Ala Lys Glu Pro Ile Val Val Gln Val Leu Arg Arg Thr Pro Arg
    45                  50                  55 acc aaa atg ttc acg cct cca tca gag tct cag ctg gtg gac acg gga      365
Thr Lys Met Phe Thr Pro Pro Ser Glu Ser Gln Leu Val Asp Thr Gly
 60                  65                  70 acc caa acc gac atc acc ttt gaa cat atc atg gcc ctc act aag atg      413
Thr Gln Thr Asp Ile Thr Phe Glu His Ile Met Ala Leu Thr Lys Met
75                  80                  85                  90 tcc tct ccc agc cca ccc gtg ctg gat ccc tat ctc ttg cca gag gag      461
Ser Ser Pro Ser Pro Pro Val Leu Asp Pro Tyr Leu Leu Pro Glu Glu
                 95                 100                 105 cat ccc tca gcc cat gaa tac tac gat cca aat gac tac att gga gac      509
His Pro Ser Ala His Glu Tyr Tyr Asp Pro Asn Asp Tyr Ile Gly Asp
            110                 115                 120 atc cat cag gag atg gac agg gag gag ctg gag ctg gag gaa gtg gac      557
Ile His Gln Glu Met Asp Arg Glu Glu Leu Glu Leu Glu Glu Val Asp
```

```
                    125                 130                 135
ctc tac aga atg aac agc cag gac aag ctg ggc ctc act gtg tgc tac    605
Leu Tyr Arg Met Asn Ser Gln Asp Lys Leu Gly Leu Thr Val Cys Tyr
140                 145                 150 cgg acg gac gat gaa gac gac att ggg att tat atc agt gag att gac    653
Arg Thr Asp Asp Glu Asp Asp Ile Gly Ile Tyr Ile Ser Glu Ile Asp
155                 160                 165                 170 cct aac agc att gca gcc aag gat ggg cgc atc cga gaa gga gac tgc    701
Pro Asn Ser Ile Ala Ala Lys Asp Gly Arg Ile Arg Glu Gly Asp Cys
                175                 180                 185 att atc cag att aat ggg ata gag gtg cag aac cgt gaa gag gct gtg    749
Ile Ile Gln Ile Asn Gly Ile Glu Val Gln Asn Arg Glu Glu Ala Val
                190                 195                 200 gct ctt cta acc agt gaa gaa aat aaa aac ttt tca ttg ctg att gca    797
Ala Leu Leu Thr Ser Glu Glu Asn Lys Asn Phe Ser Leu Leu Ile Ala
            205                 210                 215 agg cct gaa ctc cag ctg gat gag ggc tgg atg gat gat gac agg aac    845
Arg Pro Glu Leu Gln Leu Asp Glu Gly Trp Met Asp Asp Asp Arg Asn
        220                 225                 230 gac ttt ctg gat gac ctg cac atg gac atg ctg gag gag cag cac cac    893
Asp Phe Leu Asp Asp Leu His Met Asp Met Leu Glu Glu Gln His His
235                 240                 245                 250 cag gcc atg caa ttc aca gct agc gtg ctg cag cag aag aag cac gac    941
Gln Ala Met Gln Phe Thr Ala Ser Val Leu Gln Gln Lys Lys His Asp
                255                 260                 265 gaa gac ggt ggg acc aca gat aca gcc acc atc ttg tcc aac cag cac    989
Glu Asp Gly Gly Thr Thr Asp Thr Ala Thr Ile Leu Ser Asn Gln His
                270                 275                 280 gag aag gac agc ggt gtg ggg cgg acc gac gag agc acc cgt aat gac   1037
Glu Lys Asp Ser Gly Val Gly Arg Thr Asp Glu Ser Thr Arg Asn Asp
            285                 290                 295 gag agc tcg gag caa gag aac aat ggc gac gac gcc acc gca tcc tcc   1085
Glu Ser Ser Glu Gln Glu Asn Asn Gly Asp Asp Ala Thr Ala Ser Ser
        300                 305                 310 aac ccg ctg gcg ggg cag agg aag ctc acc tgc agc cag gac acc ttg   1133
Asn Pro Leu Ala Gly Gln Arg Lys Leu Thr Cys Ser Gln Asp Thr Leu
315                 320                 325                 330 ggc agc ggc gac ctg ccc ttc agc aac gag tct ttc att tcg gcc gac   1181
Gly Ser Gly Asp Leu Pro Phe Ser Asn Glu Ser Phe Ile Ser Ala Asp
                335                 340                 345 tgc acg gac gcc gac tac ctg ggg atc ccg gtg gac gag tgc gag cgc   1229
Cys Thr Asp Ala Asp Tyr Leu Gly Ile Pro Val Asp Glu Cys Glu Arg
                350                 355                 360 ttc cgc gag ctc ctg gag ctc aag tgc cag gtg aag agc gcc acc cct   1277
Phe Arg Glu Leu Leu Glu Leu Lys Cys Gln Val Lys Ser Ala Thr Pro
            365                 370                 375 tac ggc ctg tac tac cct agc ggc ccc ctg gac gcc ggc aag agt gac   1325
Tyr Gly Leu Tyr Tyr Pro Ser Gly Pro Leu Asp Ala Gly Lys Ser Asp
        380                 385                 390 cct gag agc gtg gac aag gag ctg gag ctg ctg aac gaa gag ctg cgc   1373
Pro Glu Ser Val Asp Lys Glu Leu Glu Leu Leu Asn Glu Glu Leu Arg
395                 400                 405                 410 agc atc gag ctg gag tgc ctg agc atc gtg cgc gcc cac aag atg cag   1421
Ser Ile Glu Leu Glu Cys Leu Ser Ile Val Arg Ala His Lys Met Gln
                415                 420                 425 cag ctc aag gag cag tac cgc gag tcc tgg atg ctg cac aac agc ggc   1469
Gln Leu Lys Glu Gln Tyr Arg Glu Ser Trp Met Leu His Asn Ser Gly
                430                 435                 440 ttc cgc aac tac aac acc agc atc gac gtg cgc aga cgc gag ctc tca   1517
Phe Arg Asn Tyr Asn Thr Ser Ile Asp Val Arg Arg Arg Glu Leu Ser
```

-continued

```
           445                 450                 455
gat atc acc gag ctc ccg gag aaa tcc gac aag gac agc tcg agc gcc      1565
Asp Ile Thr Glu Leu Pro Glu Lys Ser Asp Lys Asp Ser Ser Ser Ala
    460                 465                 470 tac aac aca ggc gag agc tgc cgc agc acc ccg ctc acc ctg gag atc      1613
Tyr Asn Thr Gly Glu Ser Cys Arg Ser Thr Pro Leu Thr Leu Glu Ile
475                 480                 485                 490 tcc ccc gac aac tcc ttg agg aga gcg gcg gag ggc atc agc tgc ccg      1661
Ser Pro Asp Asn Ser Leu Arg Arg Ala Ala Glu Gly Ile Ser Cys Pro
                495                 500                 505 agc agc gaa ggg gct gtg ggg acc acg gaa gcc tac ggg cca gcc tcc      1709
Ser Ser Glu Gly Ala Val Gly Thr Thr Glu Ala Tyr Gly Pro Ala Ser
            510                 515                 520 aag aat ctg ctc tcc atc acg gaa gat ccc gaa gtg ggc acc cct acc      1757
Lys Asn Leu Leu Ser Ile Thr Glu Asp Pro Glu Val Gly Thr Pro Thr
        525                 530                 535 tat agc ccg tcc ctg aag gag ctg gac ccc aac cag ccc ctg gaa agc      1805
Tyr Ser Pro Ser Leu Lys Glu Leu Asp Pro Asn Gln Pro Leu Glu Ser
    540                 545                 550 aaa gag cgg aga gcc agc gac ggg agc cgg agc ccc acg ccc agc cag      1853
Lys Glu Arg Arg Ala Ser Asp Gly Ser Arg Ser Pro Thr Pro Ser Gln
555                 560                 565                 570 aag ctg ggc agc gcc tac ctg ccc tcc tat cac cac tcc cca tac aag      1901
Lys Leu Gly Ser Ala Tyr Leu Pro Ser Tyr His His Ser Pro Tyr Lys
                575                 580                 585 cac gcg cac atc ccg gcg cac gcc cag cac tac cag agc tac atg cag      1949
His Ala His Ile Pro Ala His Ala Gln His Tyr Gln Ser Tyr Met Gln
            590                 595                 600 ctg atc cag cag aag tcg gcc gtg gag tac gcg caa agc cag atg agc      1997
Leu Ile Gln Gln Lys Ser Ala Val Glu Tyr Ala Gln Ser Gln Met Ser
        605                 610                 615 ctg gtg agc atg tgc aag gac ctg agc tct ccc acc ccg tcg gag ccg      2045
Leu Val Ser Met Cys Lys Asp Leu Ser Ser Pro Thr Pro Ser Glu Pro
    620                 625                 630 cgc atg gag tgg aag gtg aag atc cgc agc gac ggg acg cgc tac atc      2093
Arg Met Glu Trp Lys Val Lys Ile Arg Ser Asp Gly Thr Arg Tyr Ile
635                 640                 645                 650 acc aag agg ccc gtg cgg gac cgc ctg ctg cgg gag cgc gcc ctg aag      2141
Thr Lys Arg Pro Val Arg Asp Arg Leu Leu Arg Glu Arg Ala Leu Lys
                655                 660                 665 atc cgg gaa gag cgc agc ggc atg acc acc gac gac gac gcg gtg agc      2189
Ile Arg Glu Glu Arg Ser Gly Met Thr Thr Asp Asp Asp Ala Val Ser
            670                 675                 680 gag atg aag atg ggg cgc tac tgg agc aag gag gag agg aag cag cac      2237
Glu Met Lys Met Gly Arg Tyr Trp Ser Lys Glu Glu Arg Lys Gln His
        685                 690                 695 ttg gtg aag gcc aag gag cag cgg cgg cgg cgc gag ttc atg atg cag      2285
Leu Val Lys Ala Lys Glu Gln Arg Arg Arg Arg Glu Phe Met Met Gln
    700                 705                 710 agc agg ttg gat tgt ctc aag gag cag caa gca gcc gat gac agg aag      2333
Ser Arg Leu Asp Cys Leu Lys Glu Gln Gln Ala Ala Asp Asp Arg Lys
715                 720                 725                 730 gag atg aac att ctc gaa ctg agc cac aaa aag atg atg aag aag agg      2381
Glu Met Asn Ile Leu Glu Leu Ser His Lys Lys Met Met Lys Lys Arg
                735                 740                 745 aat aag aaa atc ttc gat aac tgg atg acg atc caa gaa ctc tta acc      2429
Asn Lys Lys Ile Phe Asp Asn Trp Met Thr Ile Gln Glu Leu Leu Thr
            750                 755                 760 cac ggc aca aaa tcc ccg gac ggc act aga gta tac aat tcc ttc cta      2477
His Gly Thr Lys Ser Pro Asp Gly Thr Arg Val Tyr Asn Ser Phe Leu
```

-continued

```
                765                 770                 775
tcg gtg act act gta taa ttttcacttc tgcattatgt acataaagga            2525
Ser Val Thr Thr Val
        780 gaccactacc actggggtag aaattcctgc ctcgttcaat gcggcaagtt tttgtatata   2585 agataagtac ggtcttcatg tttatagtcc aaatttgcaa accctacaac tctgggtgtc   2645 ataggtctat tttaagggaa gagagagaaa aacacccta ctatcttgga aggcaatatt   2705 aacaaacaga gctttttc                                                 2724

<210> SEQ ID NO 207
<211> LENGTH: 783
<212> TYPE: PRT
<213> ORGANISM: Homo sapiens

<400> SEQUENCE: 207

Met Gly Cys Ser Leu Cys Ser Leu Gln Lys Gln Glu Glu Gln Tyr Lys
1               5                   10                  15

Leu Leu Tyr Glu Val Cys Gln Val Asn Gly Arg Asp Leu Ser Arg Ala
                20                  25                  30

Thr His Asp Gln Ala Val Glu Ala Phe Lys Thr Ala Lys Glu Pro Ile
            35                  40                  45

Val Val Gln Val Leu Arg Arg Thr Pro Arg Thr Lys Met Phe Thr Pro
        50                  55                  60

Pro Ser Glu Ser Gln Leu Val Asp Thr Gly Thr Gln Thr Asp Ile Thr
65                  70                  75                  80

Phe Glu His Ile Met Ala Leu Thr Lys Met Ser Ser Pro Ser Pro Pro
                85                  90                  95

Val Leu Asp Pro Tyr Leu Leu Pro Glu Glu His Pro Ser Ala His Glu
                100                 105                 110

Tyr Tyr Asp Pro Asn Asp Tyr Ile Gly Asp Ile His Gln Glu Met Asp
            115                 120                 125

Arg Glu Glu Leu Glu Leu Glu Val Asp Leu Tyr Arg Met Asn Ser
        130                 135                 140

Gln Asp Lys Leu Gly Leu Thr Val Cys Tyr Arg Thr Asp Asp Glu Asp
145                 150                 155                 160

Asp Ile Gly Ile Tyr Ile Ser Glu Ile Asp Pro Asn Ser Ile Ala Ala
                165                 170                 175

Lys Asp Gly Arg Ile Arg Glu Gly Asp Cys Ile Ile Gln Ile Asn Gly
            180                 185                 190

Ile Glu Val Gln Asn Arg Glu Glu Ala Val Ala Leu Leu Thr Ser Glu
        195                 200                 205

Glu Asn Lys Asn Phe Ser Leu Leu Ile Ala Arg Pro Glu Leu Gln Leu
    210                 215                 220

Asp Glu Gly Trp Met Asp Asp Arg Asn Asp Phe Leu Asp Asp Leu
225                 230                 235                 240

His Met Asp Met Leu Glu Glu Gln His His Gln Ala Met Gln Phe Thr
                245                 250                 255

Ala Ser Val Leu Gln Gln Lys Lys His Asp Glu Asp Gly Gly Thr Thr
            260                 265                 270

Asp Thr Ala Thr Ile Leu Ser Asn Gln His Glu Lys Asp Ser Gly Val
        275                 280                 285

Gly Arg Thr Asp Glu Ser Thr Arg Asn Asp Glu Ser Ser Glu Gln Glu
    290                 295                 300

Asn Asn Gly Asp Asp Ala Thr Ala Ser Ser Asn Pro Leu Ala Gly Gln
```

```
            305                 310                 315                 320
Arg Lys Leu Thr Cys Ser Gln Asp Thr Leu Gly Ser Gly Asp Leu Pro
                325                 330                 335

Phe Ser Asn Glu Ser Phe Ile Ser Ala Asp Cys Thr Asp Ala Asp Tyr
                340                 345                 350

Leu Gly Ile Pro Val Asp Glu Cys Glu Arg Phe Arg Glu Leu Leu Glu
                355                 360                 365

Leu Lys Cys Gln Val Lys Ser Ala Thr Pro Tyr Gly Leu Tyr Tyr Pro
            370                 375                 380

Ser Gly Pro Leu Asp Ala Gly Lys Ser Asp Pro Glu Ser Val Asp Lys
385                 390                 395                 400

Glu Leu Glu Leu Leu Asn Glu Glu Leu Arg Ser Ile Glu Leu Glu Cys
                405                 410                 415

Leu Ser Ile Val Arg Ala His Lys Met Gln Leu Lys Glu Gln Tyr
                420                 425                 430

Arg Glu Ser Trp Met Leu His Asn Ser Gly Phe Arg Asn Tyr Asn Thr
            435                 440                 445

Ser Ile Asp Val Arg Arg Glu Leu Ser Asp Ile Thr Glu Leu Pro
        450                 455                 460

Glu Lys Ser Asp Lys Asp Ser Ser Ser Ala Tyr Asn Thr Gly Glu Ser
465                 470                 475                 480

Cys Arg Ser Thr Pro Leu Thr Leu Glu Ile Ser Pro Asn Ser Leu
                485                 490                 495

Arg Arg Ala Ala Glu Gly Ile Ser Cys Pro Ser Ser Glu Gly Ala Val
            500                 505                 510

Gly Thr Thr Glu Ala Tyr Gly Pro Ala Ser Lys Asn Leu Leu Ser Ile
        515                 520                 525

Thr Glu Asp Pro Glu Val Gly Thr Pro Thr Tyr Ser Pro Ser Leu Lys
        530                 535                 540

Glu Leu Asp Pro Asn Gln Pro Leu Glu Ser Lys Glu Arg Arg Ala Ser
545                 550                 555                 560

Asp Gly Ser Arg Ser Pro Thr Pro Ser Gln Lys Leu Gly Ser Ala Tyr
                565                 570                 575

Leu Pro Ser Tyr His His Ser Pro Tyr Lys His Ala His Ile Pro Ala
                580                 585                 590

His Ala Gln His Tyr Gln Ser Tyr Met Gln Leu Ile Gln Gln Lys Ser
            595                 600                 605

Ala Val Glu Tyr Ala Gln Ser Gln Met Ser Leu Val Ser Met Cys Lys
            610                 615                 620

Asp Leu Ser Ser Pro Thr Pro Ser Glu Pro Arg Met Glu Trp Lys Val
625                 630                 635                 640

Lys Ile Arg Ser Asp Gly Thr Arg Tyr Ile Thr Lys Arg Pro Val Arg
                645                 650                 655

Asp Arg Leu Leu Arg Glu Arg Ala Leu Lys Ile Arg Glu Glu Arg Ser
                660                 665                 670

Gly Met Thr Thr Asp Asp Ala Val Ser Glu Met Lys Met Gly Arg
            675                 680                 685

Tyr Trp Ser Lys Glu Glu Arg Lys Gln His Leu Val Lys Ala Lys Glu
            690                 695                 700

Gln Arg Arg Arg Glu Phe Met Met Gln Ser Arg Leu Asp Cys Leu
705                 710                 715                 720

Lys Glu Gln Gln Ala Ala Asp Asp Arg Lys Glu Met Asn Ile Leu Glu
                725                 730                 735
```

Leu Ser His Lys Lys Met Met Lys Lys Arg Asn Lys Lys Ile Phe Asp
                740                 745                 750

Asn Trp Met Thr Ile Gln Glu Leu Leu Thr His Gly Thr Lys Ser Pro
        755                 760                 765

Asp Gly Thr Arg Val Tyr Asn Ser Phe Leu Ser Val Thr Thr Val
        770                 775                 780

<210> SEQ ID NO 208
<211> LENGTH: 212
<212> TYPE: DNA
<213> ORGANISM: Homo sapiens

<400> SEQUENCE: 208
gagagcagcg ccaatgtgaa gcgttgcagt cgcttgactc acctgaggct ctccaaggat    60
accttcaatg cctgcactgt aagggagctg cttttcccgg gtgctggcga gaacggaagc   120
cttcctttga cgttttccta acatgggat gcagtctgtg cagcctgcag aagcaagagg    180
agcagtacaa attactctat gaagtttgtc ag                                  212

<210> SEQ ID NO 209
<211> LENGTH: 23
<212> TYPE: PRT
<213> ORGANISM: Homo sapiens

<400> SEQUENCE: 209

Met Gly Cys Ser Leu Cys Ser Leu Gln Lys Gln Glu Glu Gln Tyr Lys
1               5                   10                  15

Leu Leu Tyr Glu Val Cys Gln
            20

<210> SEQ ID NO 210
<211> LENGTH: 69
<212> TYPE: DNA
<213> ORGANISM: Homo sapiens

<400> SEQUENCE: 210
atgggatgca gtctgtgcag cctgcagaag caagaggagc agtacaaatt actctatgaa    60
gtttgtcag                                                            69

<210> SEQ ID NO 211
<211> LENGTH: 2570
<212> TYPE: DNA
<213> ORGANISM: Homo sapiens

<400> SEQUENCE: 211
gtgaagcgtt gcagtcgctt gactcacctg aggctctcca aggataccttt caatgcctgc    60 actgtaaggg agctgctttt cccgggtgct ggcgagaacg gaagccttcc tttgacgttt   120
ttctaaacat gggatgcagt ctgtgcagcc tgcagaagca agaggagcag tacaaattac   180
tctatgaagt ttgtcaggtc aacggcagag acttatccag agcaactcat gaccaggctg   240
tggaagcttt caagacagcc aaggagccca tagtggtgca ggtgttgaga agaacaccaa   300
ggaccaaaat gttcacgcct ccatcagagt ctcagctggt ggacacggga acccaaaccg   360
acatcacctt tgaacatatc atggccctca ctaagatgtc ctctcccagc ccacccgtac   420
tggatcccta tctcttgcca gaggagcatc cctcagccca tgaatactac gatccaaatg   480
actacattgg agacatccat caggagatgg acagggagga gctggagctg aggaagtgg    540 acctctacag aatgaacagc caggacaagc tgggcctcac tgtgtgctac cggacggacg   600
atgaagacga cattgggatt tatatcagtg agattgaccc taacagcatt gcagccaagg   660

```
atgggcgcat ccgagaagga gaccgcatta tccagattaa tgggatagag gtgcagaacc     720
gtgaagaggc tgtggctctt ctaaccagtg aagaaaataa aaacttttca ttgctgattg     780
caaggcctga actccagctg gatgagggct ggatggatga tgacaggaac gactttctgg     840
atgacctgca catggacatg ctggaggagc agcaccacca ggccatgcaa ttcacagcta     900
gcgtgctgca gcagaagaag cacgacgaag acggtgggac cacagataca gccaccatct     960
tgtccaacca gcacgagaag gacagtggtg tggggcggac cgacgagagc acccgtaatg    1020
acgagagctc ggagcaagag aacaatggcg acgacgccac cgcatcctcc aacccgctgg    1080
cggggcagag gaagctcacc tgcagccagg acaccttggg cagcggcgac ctgcccttca    1140
gcaacgagtc tttcatttcg gccgactgca cggacgccga ctacctgggg atcccggtgg    1200
acgagtgcga gcgcttccgc gagctcctgg agctcaagtg ccaggtgaag agcgccaccc    1260
cttacggcct gtactaccct agcggccccc tggacgccgg caagagtgac cctgagagcg    1320
tggacaagga gctggagctg ctgaacgaag agctgcgcag catcgagctg gagtgcctga    1380
gcatcgtgcg cgcccacaag atgcagcagc tcaaggagca gtaccgcgag tcctggatgc    1440
tgcacaacag cggcttccgc aactacaaca ccagcatcga cgtgcgcaga cacgagctct    1500
cagatatcac cgagctcccg gagaaatccg acaaggacag ctcgagcgcc tacaacacag    1560
gcgagagctg ccgcagcacc ccgctcaccc tggagatctc ccccgacaac tccttgagga    1620
gagcggcgga gggcatcagc tgcccgagca gcgaaggggc tgtggggacc acggaagcct    1680
acgggccagc tccaagaat ctgctctcca tcacggaaga tcccgaagtg gcacccccta    1740
cctatagccc gtccctgaag gagctggacc ccaaccagcc cctggaaagc aaagagcgga    1800
gagccagcga cgggagccgg agccccacgc ccagccagaa gctgggcagc gcctacctgc    1860
cctcctatca ccactcccca tacaagcacg cgcacatccc ggcgcacgcc cagcactacc    1920
agagctacat gcagctgatc cagcagaagt cggccgtgga gtacgcgcaa agccagatga    1980
gcctggtgag catgtgcaag gacctgagct ctcccacccc gtcggagccg cgcatggagt    2040
ggaaggtgaa gatccgcagc gacgggacgc gctacatcac caagaggccc gtgcgggacc    2100
gcctgctgcg ggagcgcgcc ctgaagatcc gggaagagcg cagcggcatg accaccgacg    2160
acgacgcggt gagcgagatg aagatggggc gctactggag caaggaggag aggaagcagc    2220
acctggtgaa ggccaaggag cagcggcggc ggcgcgagtt catgatgcag agcaggttgg    2280
attgtctcaa ggagcagcaa gcagccgatg acaggaagga gatgaacatt ctcgaactga    2340
gccacaaaaa gatgatgaag aagaggaata agaaaatctt cgataactgg atgacgatcc    2400
aagaactctt aacccacggc acaaaatccc cggacggcac tagagtatac aattccttcc    2460
tatcggtgac tactgtataa ttttcacttc tgcattatgt acataaagga gaccactacc    2520
actggggtag aaattcctgc ctcgttcaat gcggcaagtt tttgtatata              2570

<210> SEQ ID NO 212
<211> LENGTH: 2570
<212> TYPE: DNA
<213> ORGANISM: Homo sapiens
<221> NAME/KEY: CDS
<222> LOCATION: (129)..(2480)

<400> SEQUENCE: 212
gtgaagcgtt gcagtcgctt gactcacctg aggctctcca aggataccct caatgcctgc      60
actgtaaggg agctgctttt cccgggtgct ggcgagaacg gaagccttcc tttgacgttt     120 ttctaaac atg gga tgc agt ctg tgc agc ctg cag aag caa gag gag cag      170
```

|     |     |     |     |     |     |     |     |     |     |     |     |     |
| --- | --- | --- | --- | --- | --- | --- | --- | --- | --- | --- | --- | --- |
|     | Met | Gly | Cys | Ser | Leu | Cys | Ser | Leu | Gln | Lys | Gln | Glu Glu Gln |
|     | 1   |     |     | 5   |     |     |     |     | 10  |     |     |     |
| tac | aaa | tta | ctc | tat | gaa | gtt | tgt | cag | gtc | aac | ggc | aga gac tta tcc | 218 |
| Tyr | Lys | Leu | Leu | Tyr | Glu | Val | Cys | Gln | Val | Asn | Gly | Arg Asp Leu Ser |
| 15  |     |     |     | 20  |     |     |     | 25  |     |     |     | 30  |
| aga | gca | act | cat | gac | cag | gct | gtg | gaa | gct | ttc | aag | aca gcc aag gag | 266 |
| Arg | Ala | Thr | His | Asp | Gln | Ala | Val | Glu | Ala | Phe | Lys | Thr Ala Lys Glu |
|     |     |     | 35  |     |     |     | 40  |     |     |     | 45  |     |
| ccc | ata | gtg | gtg | cag | gtg | ttg | aga | aga | aca | cca | agg | acc aaa atg ttc | 314 |
| Pro | Ile | Val | Val | Gln | Val | Leu | Arg | Arg | Thr | Pro | Arg | Thr Lys Met Phe |
|     |     |     | 50  |     |     |     | 55  |     |     |     | 60  |     |
| acg | cct | cca | tca | gag | tct | cag | ctg | gtg | gac | acg | gga | acc caa acc gac | 362 |
| Thr | Pro | Pro | Ser | Glu | Ser | Gln | Leu | Val | Asp | Thr | Gly | Thr Gln Thr Asp |
|     |     | 65  |     |     |     | 70  |     |     |     | 75  |     |     |
| atc | acc | ttt | gaa | cat | atc | atg | gcc | ctc | act | aag | atg | tcc tct ccc agc | 410 |
| Ile | Thr | Phe | Glu | His | Ile | Met | Ala | Leu | Thr | Lys | Met | Ser Ser Pro Ser |
|     | 80  |     |     |     | 85  |     |     |     | 90  |     |     |     |
| cca | ccc | gta | ctg | gat | ccc | tat | ctc | ttg | cca | gag | gag | cat ccc tca gcc | 458 |
| Pro | Pro | Val | Leu | Asp | Pro | Tyr | Leu | Leu | Pro | Glu | Glu | His Pro Ser Ala |
| 95  |     |     |     | 100 |     |     |     | 105 |     |     |     | 110 |
| cat | gaa | tac | tac | gat | cca | aat | gac | tac | att | gga | gac | atc cat cag gag | 506 |
| His | Glu | Tyr | Tyr | Asp | Pro | Asn | Asp | Tyr | Ile | Gly | Asp | Ile His Gln Glu |
|     |     |     |     | 115 |     |     |     | 120 |     |     |     | 125 |
| atg | gac | agg | gag | gag | ctg | gag | ctg | gag | gaa | gtg | gac | ctc tac aga atg | 554 |
| Met | Asp | Arg | Glu | Glu | Leu | Glu | Leu | Glu | Glu | Val | Asp | Leu Tyr Arg Met |
|     |     | 130 |     |     |     | 135 |     |     |     | 140 |     |     |
| aac | agc | cag | gac | aag | ctg | ggc | ctc | act | gtg | tgc | tac | cgg acg gac gat | 602 |
| Asn | Ser | Gln | Asp | Lys | Leu | Gly | Leu | Thr | Val | Cys | Tyr | Arg Thr Asp Asp |
|     | 145 |     |     |     | 150 |     |     |     | 155 |     |     |     |
| gaa | gac | gac | att | ggg | att | tat | atc | agt | gag | att | gac | cct aac agc att | 650 |
| Glu | Asp | Asp | Ile | Gly | Ile | Tyr | Ile | Ser | Glu | Ile | Asp | Pro Asn Ser Ile |
| 160 |     |     |     | 165 |     |     |     | 170 |     |     |     |     |
| gca | gcc | aag | gat | ggg | cgc | atc | cga | gaa | gga | gac | cgc | att atc cag att | 698 |
| Ala | Ala | Lys | Asp | Gly | Arg | Ile | Arg | Glu | Gly | Asp | Arg | Ile Ile Gln Ile |
| 175 |     |     |     | 180 |     |     |     | 185 |     |     |     | 190 |
| aat | ggg | ata | gag | gtg | cag | aac | cgt | gaa | gag | gct | gtg | gct ctt cta acc | 746 |
| Asn | Gly | Ile | Glu | Val | Gln | Asn | Arg | Glu | Glu | Ala | Val | Ala Leu Leu Thr |
|     |     |     | 195 |     |     |     | 200 |     |     |     | 205 |     |
| agt | gaa | gaa | aat | aaa | aac | ttt | tca | ttg | ctg | att | gca | agg cct gaa ctc | 794 |
| Ser | Glu | Glu | Asn | Lys | Asn | Phe | Ser | Leu | Leu | Ile | Ala | Arg Pro Glu Leu |
|     |     | 210 |     |     |     | 215 |     |     |     | 220 |     |     |
| cag | ctg | gat | gag | ggc | tgg | atg | gat | gat | gac | agg | aac | gac ttt ctg gat | 842 |
| Gln | Leu | Asp | Glu | Gly | Trp | Met | Asp | Asp | Asp | Arg | Asn | Asp Phe Leu Asp |
|     |     | 225 |     |     |     | 230 |     |     |     | 235 |     |     |
| gac | ctg | cac | atg | gac | atg | ctg | gag | gag | cag | cac | cac | cag gcc atg caa | 890 |
| Asp | Leu | His | Met | Asp | Met | Leu | Glu | Glu | Gln | His | His | Gln Ala Met Gln |
|     | 240 |     |     |     | 245 |     |     |     | 250 |     |     |     |
| ttc | aca | gct | agc | gtg | ctg | cag | cag | aag | aag | cac | gac | gaa gac ggt ggg | 938 |
| Phe | Thr | Ala | Ser | Val | Leu | Gln | Gln | Lys | Lys | His | Asp | Glu Asp Gly Gly |
| 255 |     |     |     | 260 |     |     |     | 265 |     |     |     | 270 |
| acc | aca | gat | aca | gcc | acc | atc | ttg | tcc | aac | cag | cac | gag aag gac agt | 986 |
| Thr | Thr | Asp | Thr | Ala | Thr | Ile | Leu | Ser | Asn | Gln | His | Glu Lys Asp Ser |
|     |     |     | 275 |     |     |     | 280 |     |     |     | 285 |     |
| ggt | gtg | ggg | cgg | acc | gac | gag | agc | acc | cgt | aat | gac | gag agc tcg gag | 1034 |
| Gly | Val | Gly | Arg | Thr | Asp | Glu | Ser | Thr | Arg | Asn | Asp | Glu Ser Ser Glu |
|     |     | 290 |     |     |     | 295 |     |     |     | 300 |     |     |
| caa | gag | aac | aat | ggc | gac | gac | gcc | acc | gca | tcc | tcc | aac ccg ctg gcg | 1082 |
| Gln | Glu | Asn | Asn | Gly | Asp | Asp | Ala | Thr | Ala | Ser | Ser | Asn Pro Leu Ala |
|     |     | 305 |     |     |     | 310 |     |     |     | 315 |     |     |
| ggg | cag | agg | aag | ctc | acc | tgc | agc | cag | gac | acc | ttg | ggc agc ggc gac | 1130 |

-continued

```
Gly Gln Arg Lys Leu Thr Cys Ser Gln Asp Thr Leu Gly Ser Gly Asp
320                 325                 330 ctg ccc ttc agc aac gag tct ttc att tcg gcc gac tgc acg gac gcc    1178
Leu Pro Phe Ser Asn Glu Ser Phe Ile Ser Ala Asp Cys Thr Asp Ala
335                 340                 345                 350 gac tac ctg ggg atc ccg gtg gac gag tgc gag cgc ttc cgc gag ctc    1226
Asp Tyr Leu Gly Ile Pro Val Asp Glu Cys Glu Arg Phe Arg Glu Leu
                355                 360                 365 ctg gag ctc aag tgc cag gtg aag agc gcc acc cct tac ggc ctg tac    1274
Leu Glu Leu Lys Cys Gln Val Lys Ser Ala Thr Pro Tyr Gly Leu Tyr
        370                 375                 380 tac cct agc ggc ccc ctg gac gcc ggc aag agt gac cct gag agc gtg    1322
Tyr Pro Ser Gly Pro Leu Asp Ala Gly Lys Ser Asp Pro Glu Ser Val
            385                 390                 395 gac aag gag ctg gag ctg ctg aac gaa gag ctg cgc agc atc gag ctg    1370
Asp Lys Glu Leu Glu Leu Leu Asn Glu Glu Leu Arg Ser Ile Glu Leu
400                 405                 410 gag tgc ctg agc atc gtg cgc gcc cac aag atg cag cag ctc aag gag    1418
Glu Cys Leu Ser Ile Val Arg Ala His Lys Met Gln Gln Leu Lys Glu
415                 420                 425                 430 cag tac cgc gag tcc tgg atg ctg cac aac agc ggc ttc cgc aac tac    1466
Gln Tyr Arg Glu Ser Trp Met Leu His Asn Ser Gly Phe Arg Asn Tyr
                435                 440                 445 aac acc agc atc gac gtg cgc aga cac gag ctc tca gat atc acc gag    1514
Asn Thr Ser Ile Asp Val Arg Arg His Glu Leu Ser Asp Ile Thr Glu
        450                 455                 460 ctc ccg gag aaa tcc gac aag gac agc tcg agc gcc tac aac aca ggc    1562
Leu Pro Glu Lys Ser Asp Lys Asp Ser Ser Ser Ala Tyr Asn Thr Gly
            465                 470                 475 gag agc tgc cgc agc acc ccg ctc acc ctg gag atc tcc ccc gac aac    1610
Glu Ser Cys Arg Ser Thr Pro Leu Thr Leu Glu Ile Ser Pro Asp Asn
480                 485                 490 tcc ttg agg aga gcg gcg gag ggc atc agc tgc ccg agc agc gaa ggg    1658
Ser Leu Arg Arg Ala Ala Glu Gly Ile Ser Cys Pro Ser Ser Glu Gly
495                 500                 505                 510 gct gtg ggg acc acg gaa gcc tac ggg cca gcc tcc aag aat ctg ctc    1706
Ala Val Gly Thr Thr Glu Ala Tyr Gly Pro Ala Ser Lys Asn Leu Leu
                515                 520                 525 tcc atc acg gaa gat ccc gaa gtg ggc acc cct acc tat agc ccg tcc    1754
Ser Ile Thr Glu Asp Pro Glu Val Gly Thr Pro Thr Tyr Ser Pro Ser
        530                 535                 540 ctg aag gag ctg gac ccc aac cag ccc ctg gaa agc aaa gag cgg aga    1802
Leu Lys Glu Leu Asp Pro Asn Gln Pro Leu Glu Ser Lys Glu Arg Arg
            545                 550                 555 gcc agc gac ggg agc cgg agc ccc acg ccc agc cag aag ctg ggc agc    1850
Ala Ser Asp Gly Ser Arg Ser Pro Thr Pro Ser Gln Lys Leu Gly Ser
560                 565                 570 gcc tac ctg ccc tcc tat cac cac tcc cca tac aag cac gcg cac atc    1898
Ala Tyr Leu Pro Ser Tyr His His Ser Pro Tyr Lys His Ala His Ile
575                 580                 585                 590 ccg gcg cac gcc cag cac tac cag agc tac atg cag ctg atc cag cag    1946
Pro Ala His Ala Gln His Tyr Gln Ser Tyr Met Gln Leu Ile Gln Gln
                595                 600                 605 aag tcg gcc gtg gag tac gcg caa agc cag atg agc ctg gtg agc atg    1994
Lys Ser Ala Val Glu Tyr Ala Gln Ser Gln Met Ser Leu Val Ser Met
        610                 615                 620 tgc aag gac ctg agc tct ccc acc ccg tcg gag ccg cgc atg gag tgg    2042
Cys Lys Asp Leu Ser Ser Pro Thr Pro Ser Glu Pro Arg Met Glu Trp
            625                 630                 635 aag gtg aag atc cgc agc gac ggg acg cgc tac atc acc aag agg ccc    2090
```

```
Lys Val Lys Ile Arg Ser Asp Gly Thr Arg Tyr Ile Thr Lys Arg Pro
            640                 645                 650 gtg cgg gac cgc ctg ctg cgg gag cgc gcc ctg aag atc cgg gaa gag      2138
Val Arg Asp Arg Leu Leu Arg Glu Arg Ala Leu Lys Ile Arg Glu Glu
655                 660                 665                 670 cgc agc ggc atg acc acc gac gac gac gcg gtg agc gag atg aag atg      2186
Arg Ser Gly Met Thr Thr Asp Asp Asp Ala Val Ser Glu Met Lys Met
                675                 680                 685 ggg cgc tac tgg agc aag gag gag agg aag cag cac ctg gtg aag gcc      2234
Gly Arg Tyr Trp Ser Lys Glu Glu Arg Lys Gln His Leu Val Lys Ala
            690                 695                 700 aag gag cag cgg cgg cgc gag ttc atg atg cag agc agg ttg gat          2282
Lys Glu Gln Arg Arg Arg Glu Phe Met Met Gln Ser Arg Leu Asp
        705                 710                 715 tgt ctc aag gag cag caa gca gcc gat gac agg aag gag atg aac att      2330
Cys Leu Lys Glu Gln Gln Ala Ala Asp Asp Arg Lys Glu Met Asn Ile
720                 725                 730 ctc gaa ctg agc cac aaa aag atg atg aag aag agg aat aag aaa atc      2378
Leu Glu Leu Ser His Lys Lys Met Met Lys Lys Arg Asn Lys Lys Ile
735                 740                 745                 750 ttc gat aac tgg atg acg atc caa gaa ctc tta acc cac ggc aca aaa      2426
Phe Asp Asn Trp Met Thr Ile Gln Glu Leu Leu Thr His Gly Thr Lys
                755                 760                 765 tcc ccg gac ggc act aga gta tac aat tcc ttc cta tcg gtg act act      2474
Ser Pro Asp Gly Thr Arg Val Tyr Asn Ser Phe Leu Ser Val Thr Thr
            770                 775                 780 gta taa ttttcacttc tgcattatgt acataaagga gaccactacc actggggtag       2530
Val aaattcctgc ctcgttcaat gcggcaagtt tttgtatata                          2570

<210> SEQ ID NO 213
<211> LENGTH: 783
<212> TYPE: PRT
<213> ORGANISM: Homo sapiens

<400> SEQUENCE: 213

Met Gly Cys Ser Leu Cys Ser Leu Gln Lys Gln Glu Glu Gln Tyr Lys
1               5                   10                  15

Leu Leu Tyr Glu Val Cys Gln Val Asn Gly Arg Asp Leu Ser Arg Ala
            20                  25                  30

Thr His Asp Gln Ala Val Glu Ala Phe Lys Thr Ala Lys Glu Pro Ile
        35                  40                  45

Val Val Gln Val Leu Arg Arg Thr Pro Arg Thr Lys Met Phe Thr Pro
    50                  55                  60

Pro Ser Glu Ser Gln Leu Val Asp Thr Gly Thr Gln Thr Asp Ile Thr
65                  70                  75                  80

Phe Glu His Ile Met Ala Leu Thr Lys Met Ser Ser Pro Ser Pro Pro
                85                  90                  95

Val Leu Asp Pro Tyr Leu Leu Pro Glu Glu His Pro Ser Ala His Glu
            100                 105                 110

Tyr Tyr Asp Pro Asn Asp Tyr Ile Gly Asp Ile His Gln Glu Met Asp
        115                 120                 125

Arg Glu Glu Leu Glu Leu Glu Glu Val Asp Leu Tyr Arg Met Asn Ser
    130                 135                 140

Gln Asp Lys Leu Gly Leu Thr Val Cys Tyr Arg Thr Asp Asp Glu Asp
145                 150                 155                 160

Asp Ile Gly Ile Tyr Ile Ser Glu Ile Asp Pro Asn Ser Ile Ala Ala
                165                 170                 175
```

```
Lys Asp Gly Arg Ile Arg Glu Gly Asp Arg Ile Ile Gln Ile Asn Gly
            180                 185                 190
Ile Glu Val Gln Asn Arg Glu Glu Ala Val Ala Leu Leu Thr Ser Glu
            195                 200                 205
Glu Asn Lys Asn Phe Ser Leu Leu Ile Ala Arg Pro Glu Leu Gln Leu
210                 215                 220
Asp Glu Gly Trp Met Asp Asp Arg Asn Asp Phe Leu Asp Asp Leu
225                 230                 235                 240
His Met Asp Met Leu Glu Glu Gln His His Gln Ala Met Gln Phe Thr
                245                 250                 255
Ala Ser Val Leu Gln Gln Lys Lys His Asp Glu Asp Gly Gly Thr Thr
            260                 265                 270
Asp Thr Ala Thr Ile Leu Ser Asn Gln His Glu Lys Asp Ser Gly Val
            275                 280                 285
Gly Arg Thr Asp Glu Ser Thr Arg Asn Asp Glu Ser Ser Glu Gln Glu
        290                 295                 300
Asn Asn Gly Asp Asp Ala Thr Ala Ser Ser Asn Pro Leu Ala Gly Gln
305                 310                 315                 320
Arg Lys Leu Thr Cys Ser Gln Asp Thr Leu Gly Ser Gly Asp Leu Pro
                325                 330                 335
Phe Ser Asn Glu Ser Phe Ile Ser Ala Asp Cys Thr Asp Ala Asp Tyr
                340                 345                 350
Leu Gly Ile Pro Val Asp Glu Cys Glu Arg Phe Arg Glu Leu Leu Glu
            355                 360                 365
Leu Lys Cys Gln Val Lys Ser Ala Thr Pro Tyr Gly Leu Tyr Tyr Pro
370                 375                 380
Ser Gly Pro Leu Asp Ala Gly Lys Ser Asp Pro Glu Ser Val Asp Lys
385                 390                 395                 400
Glu Leu Glu Leu Leu Asn Glu Glu Leu Arg Ser Ile Glu Leu Glu Cys
                405                 410                 415
Leu Ser Ile Val Arg Ala His Lys Met Gln Gln Leu Lys Glu Gln Tyr
            420                 425                 430
Arg Glu Ser Trp Met Leu His Asn Ser Gly Phe Arg Asn Tyr Asn Thr
        435                 440                 445
Ser Ile Asp Val Arg Arg His Glu Leu Ser Asp Ile Thr Glu Leu Pro
        450                 455                 460
Glu Lys Ser Asp Lys Asp Ser Ser Ser Ala Tyr Asn Thr Gly Glu Ser
465                 470                 475                 480
Cys Arg Ser Thr Pro Leu Thr Leu Glu Ile Ser Pro Asp Asn Ser Leu
                485                 490                 495
Arg Arg Ala Ala Glu Gly Ile Ser Cys Pro Ser Ser Glu Gly Ala Val
            500                 505                 510
Gly Thr Thr Glu Ala Tyr Gly Pro Ala Ser Lys Asn Leu Leu Ser Ile
            515                 520                 525
Thr Glu Asp Pro Glu Val Gly Thr Pro Thr Tyr Ser Pro Ser Leu Lys
        530                 535                 540
Glu Leu Asp Pro Asn Gln Pro Leu Glu Ser Lys Glu Arg Arg Ala Ser
545                 550                 555                 560
Asp Gly Ser Arg Ser Pro Thr Pro Ser Gln Lys Leu Gly Ser Ala Tyr
                565                 570                 575
Leu Pro Ser Tyr His His Ser Pro Tyr Lys His Ala His Ile Pro Ala
            580                 585                 590
His Ala Gln His Tyr Gln Ser Tyr Met Gln Leu Ile Gln Gln Lys Ser
```

```
                595              600                605
Ala Val Glu Tyr Ala Gln Ser Gln Met Ser Leu Val Ser Met Cys Lys
610                 615                 620

Asp Leu Ser Ser Pro Thr Pro Ser Glu Pro Arg Met Glu Trp Lys Val
625                 630                 635                 640

Lys Ile Arg Ser Asp Gly Thr Arg Tyr Ile Thr Lys Arg Pro Val Arg
                645                 650                 655

Asp Arg Leu Leu Arg Glu Arg Ala Leu Lys Ile Arg Glu Glu Arg Ser
            660                 665                 670

Gly Met Thr Thr Asp Asp Ala Val Ser Glu Met Lys Met Gly Arg
        675                 680                 685

Tyr Trp Ser Lys Glu Glu Arg Lys Gln His Leu Val Lys Ala Lys Glu
690                 695                 700

Gln Arg Arg Arg Glu Phe Met Met Gln Ser Arg Leu Asp Cys Leu
705                 710                 715                 720

Lys Glu Gln Gln Ala Ala Asp Asp Arg Lys Glu Met Asn Ile Leu Glu
                725                 730                 735

Leu Ser His Lys Lys Met Met Lys Lys Arg Asn Lys Lys Ile Phe Asp
            740                 745                 750

Asn Trp Met Thr Ile Gln Glu Leu Leu Thr His Gly Thr Lys Ser Pro
        755                 760                 765

Asp Gly Thr Arg Val Tyr Asn Ser Phe Leu Ser Val Thr Val
    770                 775                 780

<210> SEQ ID NO 214
<211> LENGTH: 197
<212> TYPE: DNA
<213> ORGANISM: Homo sapiens

<400> SEQUENCE: 214
gtgaagcgtt gcagtcgctt gactcacctg aggctctcca aggatacctt caatgcctgc    60
actgtaaggg agctgctttt cccgggtgct ggcgagaacg gaagccttcc tttgacgttt   120
ttctaaacat gggatgcagt ctgtgcagcc tgcagaagca agaggagcag tacaaattac   180
tctatgaagt ttgtcag                                                  197

<210> SEQ ID NO 215
<211> LENGTH: 23
<212> TYPE: PRT
<213> ORGANISM: Homo sapiens

<400> SEQUENCE: 215

Met Gly Cys Ser Leu Cys Ser Leu Gln Lys Gln Glu Glu Gln Tyr Lys
1               5                   10                  15

Leu Leu Tyr Glu Val Cys Gln
            20

<210> SEQ ID NO 216
<211> LENGTH: 69
<212> TYPE: DNA
<213> ORGANISM: Homo sapiens

<400> SEQUENCE: 216
atgggatgca gtctgtgcag cctgcagaag caagaggagc agtacaaatt actctatgaa    60
gtttgtcag                                                           69

<210> SEQ ID NO 217
<211> LENGTH: 2698
```

<212> TYPE: DNA
<213> ORGANISM: Homo sapiens

<400> SEQUENCE: 217

```
agcatttgct cagtactctc aacataaacc aagcttagat cgcaatgaaa ctgcggacct      60
gcaggctgcc ttgcttcact gagtcaattt ttaaatgaag atggaacaca agaggatgat     120
cttattgttc agtaaattta ctctaataca taaaccccat ggtggaagat ggtatttggt     180
caacggcaga gacttatcca gagcaactca tgaccaggct gtggaagctt tcaagacagc     240
caaggagccc atagtggtgc aggtgttgag aagaacacca aggaccaaaa tgttcacgcc     300
tccatcagag tctcagctgg tggacacggg aacccaaacc gacatcacct ttgaacatat     360
catggccctc actaagatgt cctctcccag cccacccgta ctggatccct atctcttgcc     420
agaggagcat ccctcagccc atgaatacta cgatccaaat gactacattg gagacatcca     480
tcaggagatg gacagggagg agctggagct ggaggaagtg gacctctaca gaatgaacag     540
ccaggacaag ctgggcctca ctgtgtgcta ccggacggac gatgaagacg acattgggat     600
ttatatcagt gagattgacc ctaacagcat tgcagccaag gatgggcgca tccgagaagg     660
agaccgcatt atccagatta atgggataga ggtgcagaac cgtgaagagg ctgtggctct     720
tctaaccagt gaagaaaata aaaacttttc attgctgatt gcaaggcctg aactccagct     780
ggatgagggc tggatggatg atgacaggaa cgactttctg gatgacctgc acatggacat     840
gctggaggag cagcaccacc aggccatgca attcacagct agcgtgctgc agcagaagaa     900
gcacgacgaa gacggtggga ccacagatac agccaccatc ttgtccaacc agcacgagaa     960
ggacagcggt gtgggcgga ccgacgagag cacccgtaat gacgagagct cggagcaaga    1020
gaacaatggc gacgacgcca ccgcatcctc aacccgctg cgggggcaga ggaagctcac    1080
ctgcagccag gacaccttgg gcagcggcga cctgcccttc agcaacgagt ctttcatttc    1140
ggccgactgc acgacgccg actacctggg gatcccggtg gacgagtgcg agcgcttccg    1200
cgagctcctg gagctcaagt gccaggtgaa gagcgccacc ccttacggcc tgtactaccc    1260
tagcggcccc ctggacgccg gcaagagtga ccctgagagc gtggacaagg agctggagct    1320
gctgaacgaa gagctgcgca gcatcgagct ggagtgcctg agcatcgtgc gcgcccacaa    1380
gatgcagcag ctcaaggagc agtaccgcga gtcctggatg ctgcacaaca gcggcttccg    1440
caactacaac accagcatcg acgtgcgcag acacgagctc tcggatatca ccgagctccc    1500
ggagaaatcc gacaaggaca gctcgagcgc ctacaacaca ggcgagagct gccgcagcac    1560
cccgctcacc ctggagatct cccccgacaa ctccttgagg agagcggtgg agggcatcag    1620
ctgcccgagc agcgaagggg ctgtggggac cacggaagcc tacggccag cctccaagaa    1680
tctgctctcc atcacggaag atcccgaagt gggcacccct acctatagcc cgtccctgaa    1740
ggagctggac cccaaccagc ccctggaaag caaagagcgg agagccagcg acgggagccg    1800
gagccccacg cccagccaga agctgggcag cgcctacctg ccctcctatc accactcccc    1860
atacaagcac cgcgcacatcc cggcgcacgc ccagcactac cagagctaca tgcagctgat    1920
ccagcagaag tcggccgtgg agtacgcgca aagccagatg agcctggtga gcatgtgcaa    1980
ggacctgagc tctcccaccc cgtcggagcc gcgcatggag tggaaggtga agatccgcag    2040
cgacgggacg cgctacatca ccaagaggcc cgtgcggac cgcctgctgc gggagcgcgc    2100
cctgaagatc cggggaagagc gcagcggcat gaccaccgac gacgacgcgg tgagcgagat    2160
gaagatgggg cgctactgga gcaaggagga gaggaagcag cacctggtga aggccaagga    2220
gcagcggcgg cggcgcgagt tcatgatgca gagcaggttg gattgtctca aggagcagca    2280
```

```
agcagccgat gacaggaagg agatgaacat tctcgaactg agccacaaaa agatgatgaa    2340
gaagaggaat aagaaaatct tcgataactg gatgacgatc caagaactct taacccacgg    2400
cacaaaatcc ccggacggca ctagagtata caattccttc ctatcggtga ctactgtata    2460
attttcactt ctgcattatg tacataaagg agaccactac cactggggta gaaattcctg    2520
cctcgttcaa tgcggcaagt ttttgtatat aagataagta cggtcttcat gtttatagtc    2580
caaatttgca aacctacaa ctctgggtgt cataggtcta ttttaaggga agagagagaa    2640 aaacacccctt actatcttgg aaggcaatat taacaaacag agctttttc aaatagca    2698

<210> SEQ ID NO 218
<211> LENGTH: 2698
<212> TYPE: DNA
<213> ORGANISM: Homo sapiens
<221> NAME/KEY: CDS
<222> LOCATION: (95)..(2461)

<400> SEQUENCE: 218
agcatttgct cagtactctc aacataaacc aagcttagat cgcaatgaaa ctgcggacct    60
gcaggctgcc ttgcttcact gagtcaattt ttaa atg aag atg gaa cac aag agg    115
                                     Met Lys Met Glu His Lys Arg
                                       1               5 atg atc tta ttg ttc agt aaa ttt act cta ata cat aaa ccc cat ggt    163
Met Ile Leu Leu Phe Ser Lys Phe Thr Leu Ile His Lys Pro His Gly
        10                  15                  20 gga aga tgg tat ttg gtc aac ggc aga gac tta tcc aga gca act cat    211
Gly Arg Trp Tyr Leu Val Asn Gly Arg Asp Leu Ser Arg Ala Thr His
     25                  30                  35 gac cag gct gtg gaa gct ttc aag aca gcc aag gag ccc ata gtg gtg    259
Asp Gln Ala Val Glu Ala Phe Lys Thr Ala Lys Glu Pro Ile Val Val
 40                  45                  50                  55 cag gtg ttg aga aga aca cca agg acc aaa atg ttc acg cct cca tca    307
Gln Val Leu Arg Arg Thr Pro Arg Thr Lys Met Phe Thr Pro Pro Ser
             60                  65                  70 gag tct cag ctg gtg gac acg gga acc caa acc gac atc acc ttt gaa    355
Glu Ser Gln Leu Val Asp Thr Gly Thr Gln Thr Asp Ile Thr Phe Glu
         75                  80                  85 cat atc atg gcc ctc act aag atg tcc tct ccc agc cca ccc gta ctg    403
His Ile Met Ala Leu Thr Lys Met Ser Ser Pro Ser Pro Pro Val Leu
     90                  95                 100 gat ccc tat ctc ttg cca gag gag cat ccc tca gcc cat gaa tac tac    451
Asp Pro Tyr Leu Leu Pro Glu Glu His Pro Ser Ala His Glu Tyr Tyr
105                 110                 115 gat cca aat gac tac att gga gac atc cat cag gag atg gac agg gag    499
Asp Pro Asn Asp Tyr Ile Gly Asp Ile His Gln Glu Met Asp Arg Glu
120                 125                 130                 135 gag ctg gag ctg gag gaa gtg gac ctc tac aga atg aac agc cag gac    547
Glu Leu Glu Leu Glu Glu Val Asp Leu Tyr Arg Met Asn Ser Gln Asp
             140                 145                 150 aag ctg ggc ctc act gtg tgc tac cgg acg gac gat gaa gac gac att    595
Lys Leu Gly Leu Thr Val Cys Tyr Arg Thr Asp Asp Glu Asp Asp Ile
         155                 160                 165 ggg att tat atc agt gag att gac cct aac agc att gca gcc aag gat    643
Gly Ile Tyr Ile Ser Glu Ile Asp Pro Asn Ser Ile Ala Ala Lys Asp
     170                 175                 180 ggg cgc atc cga gaa gga gac cgc att atc cag att aat ggg ata gag    691
Gly Arg Ile Arg Glu Gly Asp Arg Ile Ile Gln Ile Asn Gly Ile Glu
185                 190                 195 gtg cag aac cgt gaa gag gct gtg gct ctt cta acc agt gaa gaa aat    739
Val Gln Asn Arg Glu Glu Ala Val Ala Leu Leu Thr Ser Glu Glu Asn
```

```
                Val Gln Asn Arg Glu Glu Ala Val Ala Leu Leu Thr Ser Glu Glu Asn
                200                 205                 210                 215 aaa aac ttt tca ttg ctg att gca agg cct gaa ctc cag ctg gat gag            787
Lys Asn Phe Ser Leu Leu Ile Ala Arg Pro Glu Leu Gln Leu Asp Glu
                        220                 225                 230 ggc tgg atg gat gat gac agg aac gac ttt ctg gat gac ctg cac atg            835
Gly Trp Met Asp Asp Asp Arg Asn Asp Phe Leu Asp Asp Leu His Met
                235                 240                 245 gac atg ctg gag gag cag cac cac cag gcc atg caa ttc aca gct agc            883
Asp Met Leu Glu Glu Gln His His Gln Ala Met Gln Phe Thr Ala Ser
            250                 255                 260 gtg ctg cag cag aag aag cac gac gaa gac ggt ggg acc aca gat aca            931
Val Leu Gln Gln Lys Lys His Asp Glu Asp Gly Gly Thr Thr Asp Thr
        265                 270                 275 gcc acc atc ttg tcc aac cag cac gag aag gac agc ggt gtg ggg cgg            979
Ala Thr Ile Leu Ser Asn Gln His Glu Lys Asp Ser Gly Val Gly Arg
    280                 285                 290                 295 acc gac gag agc acc cgt aat gac gag agc tcg gag caa gag aac aat           1027
Thr Asp Glu Ser Thr Arg Asn Asp Glu Ser Ser Glu Gln Glu Asn Asn
                    300                 305                 310 ggc gac gac gcc acc gca tcc tcc aac ccg ctg gcg ggg cag agg aag           1075
Gly Asp Asp Ala Thr Ala Ser Ser Asn Pro Leu Ala Gly Gln Arg Lys
                315                 320                 325 ctc acc tgc agc cag gac acc ttg ggc agc ggc gac ctg ccc ttc agc           1123
Leu Thr Cys Ser Gln Asp Thr Leu Gly Ser Gly Asp Leu Pro Phe Ser
            330                 335                 340 aac gag tct ttc att tcg gcc gac tgc acg gac gcc gac tac ctg ggg           1171
Asn Glu Ser Phe Ile Ser Ala Asp Cys Thr Asp Ala Asp Tyr Leu Gly
        345                 350                 355 atc ccg gtg gac gag tgc gag cgc ttc cgc gag ctc ctg gag ctc aag           1219
Ile Pro Val Asp Glu Cys Glu Arg Phe Arg Glu Leu Leu Glu Leu Lys
    360                 365                 370                 375 tgc cag gtg aag agc gcc acc cct tac ggc ctg tac tac cct agc ggc           1267
Cys Gln Val Lys Ser Ala Thr Pro Tyr Gly Leu Tyr Tyr Pro Ser Gly
                    380                 385                 390 ccc ctg gac gcc ggc aag agt gac cct gag agc gtg gac aag gag ctg           1315
Pro Leu Asp Ala Gly Lys Ser Asp Pro Glu Ser Val Asp Lys Glu Leu
                395                 400                 405 gag ctg ctg aac gaa gag ctg cgc agc atc gag ctg gag tgc ctg agc           1363
Glu Leu Leu Asn Glu Glu Leu Arg Ser Ile Glu Leu Glu Cys Leu Ser
            410                 415                 420 atc gtg cgc gcc cac aag atg cag cag ctc aag gag cag tac cgc gag           1411
Ile Val Arg Ala His Lys Met Gln Gln Leu Lys Glu Gln Tyr Arg Glu
        425                 430                 435 tcc tgg atg ctg cac aac agc ggc ttc cgc aac tac aac acc agc atc           1459
Ser Trp Met Leu His Asn Ser Gly Phe Arg Asn Tyr Asn Thr Ser Ile
440                 445                 450                 455 gac gtg cgc aga cac gag ctc tcg gat atc acc gag ctc ccg gag aaa           1507
Asp Val Arg Arg His Glu Leu Ser Asp Ile Thr Glu Leu Pro Glu Lys
                460                 465                 470 tcc gac aag gac agc tcg agc gcc tac aac aca ggc gag agc tgc cgc           1555
Ser Asp Lys Asp Ser Ser Ser Ala Tyr Asn Thr Gly Glu Ser Cys Arg
                475                 480                 485 agc acc ccg ctc acc ctg gag atc tcc ccc gac aac tcc ttg agg aga           1603
Ser Thr Pro Leu Thr Leu Glu Ile Ser Pro Asp Asn Ser Leu Arg Arg
            490                 495                 500 gcg gtg gag ggc atc agc tgc ccg agc agc gaa ggg gct gtg ggg acc           1651
Ala Val Glu Gly Ile Ser Cys Pro Ser Ser Glu Gly Ala Val Gly Thr
        505                 510                 515 acg gaa gcc tac ggg cca gcc tcc aag aat ctg ctc tcc atc acg gaa           1699
Thr Glu Ala Tyr Gly Pro Ala Ser Lys Asn Leu Leu Ser Ile Thr Glu
```

```
                Thr Glu Ala Tyr Gly Pro Ala Ser Lys Asn Leu Leu Ser Ile Thr Glu
                520                 525                 530                 535 gat ccc gaa gtg ggc acc cct acc tat agc ccg tcc ctg aag gag ctg          1747
Asp Pro Glu Val Gly Thr Pro Thr Tyr Ser Pro Ser Leu Lys Glu Leu
            540                 545                 550 gac ccc aac cag ccc ctg gaa agc aaa gag cgg aga gcc agc gac ggg          1795
Asp Pro Asn Gln Pro Leu Glu Ser Lys Glu Arg Arg Ala Ser Asp Gly
                555                 560                 565 agc cgg agc ccc acg ccc agc cag aag ctg ggc agc gcc tac ctg ccc          1843
Ser Arg Ser Pro Thr Pro Ser Gln Lys Leu Gly Ser Ala Tyr Leu Pro
        570                 575                 580 tcc tat cac cac tcc cca tac aag cac gcg cac atc ccg gcg cac gcc          1891
Ser Tyr His His Ser Pro Tyr Lys His Ala His Ile Pro Ala His Ala
585                 590                 595 cag cac tac cag agc tac atg cag ctg atc cag cag aag tcg gcc gtg          1939
Gln His Tyr Gln Ser Tyr Met Gln Leu Ile Gln Gln Lys Ser Ala Val
    600                 605                 610                 615 gag tac gcg caa agc cag atg agc ctg gtg agc atg tgc aag gac ctg          1987
Glu Tyr Ala Gln Ser Gln Met Ser Leu Val Ser Met Cys Lys Asp Leu
                620                 625                 630 agc tct ccc acc ccg tcg gag ccg cgc atg gag tgg aag gtg aag atc          2035
Ser Ser Pro Thr Pro Ser Glu Pro Arg Met Glu Trp Lys Val Lys Ile
            635                 640                 645 cgc agc gac ggg acg cgc tac atc acc aag agg ccc gtg cgg gac cgc          2083
Arg Ser Asp Gly Thr Arg Tyr Ile Thr Lys Arg Pro Val Arg Asp Arg
                650                 655                 660 ctg ctg cgg gag cgc gcc ctg aag atc cgg gaa gag cgc agc ggc atg          2131
Leu Leu Arg Glu Arg Ala Leu Lys Ile Arg Glu Glu Arg Ser Gly Met
        665                 670                 675 acc acc gac gac gac gcg gtg agc gag atg aag atg ggg cgc tac tgg          2179
Thr Thr Asp Asp Asp Ala Val Ser Glu Met Lys Met Gly Arg Tyr Trp
680                 685                 690                 695 agc aag gag gag agg aag cag cac ctg gtg aag gcc aag gag cag cgg          2227
Ser Lys Glu Glu Arg Lys Gln His Leu Val Lys Ala Lys Glu Gln Arg
                700                 705                 710 cgg cgg cgc gag ttc atg atg cag agc agg ttg gat tgt ctc aag gag          2275
Arg Arg Arg Glu Phe Met Met Gln Ser Arg Leu Asp Cys Leu Lys Glu
            715                 720                 725 cag caa gca gcc gat gac agg aag gag atg aac att ctc gaa ctg agc          2323
Gln Gln Ala Ala Asp Asp Arg Lys Glu Met Asn Ile Leu Glu Leu Ser
        730                 735                 740 cac aaa aag atg atg aag aag agg aat aag aaa atc ttc gat aac tgg          2371
His Lys Lys Met Met Lys Lys Arg Asn Lys Lys Ile Phe Asp Asn Trp
745                 750                 755 atg acg atc caa gaa ctc tta acc cac ggc aca aaa tcc ccg gac ggc          2419
Met Thr Ile Gln Glu Leu Leu Thr His Gly Thr Lys Ser Pro Asp Gly
760                 765                 770                 775 act aga gta tac aat tcc ttc cta tcg gtg act act gta taa                  2461
Thr Arg Val Tyr Asn Ser Phe Leu Ser Val Thr Thr Val
                780                 785 ttttcacttc tgcattatgt acataaagga gaccactacc actggggtag aaattcctgc          2521
ctcgttcaat gcggcaagtt tttgtatata agataagtac ggtcttcatg tttatagtcc          2581
aaatttgcaa accctacaac tctgggtgtc ataggtctat tttaaggaa gagagagaaa          2641 aacacccctta ctatccttgga aggcaatatt aacaaacaga gcttttttca aatagca           2698

<210> SEQ ID NO 219
<211> LENGTH: 788
<212> TYPE: PRT
<213> ORGANISM: Homo sapiens
```

<400> SEQUENCE: 219

```
Met Lys Met Glu His Lys Arg Met Ile Leu Leu Phe Ser Lys Phe Thr
1               5                   10                  15
Leu Ile His Lys Pro His Gly Gly Arg Trp Tyr Leu Val Asn Gly Arg
            20                  25                  30
Asp Leu Ser Arg Ala Thr His Asp Gln Ala Val Glu Ala Phe Lys Thr
        35                  40                  45
Ala Lys Glu Pro Ile Val Val Gln Val Leu Arg Arg Thr Pro Arg Thr
50                  55                  60
Lys Met Phe Thr Pro Pro Ser Glu Ser Gln Leu Val Asp Thr Gly Thr
65                  70                  75                  80
Gln Thr Asp Ile Thr Phe Glu His Ile Met Ala Leu Thr Lys Met Ser
                85                  90                  95
Ser Pro Ser Pro Pro Val Leu Asp Pro Tyr Leu Leu Pro Glu Glu His
            100                 105                 110
Pro Ser Ala His Glu Tyr Tyr Asp Pro Asn Asp Tyr Ile Gly Asp Ile
        115                 120                 125
His Gln Glu Met Asp Arg Glu Glu Leu Glu Leu Glu Glu Val Asp Leu
130                 135                 140
Tyr Arg Met Asn Ser Gln Asp Lys Leu Gly Leu Thr Val Cys Tyr Arg
145                 150                 155                 160
Thr Asp Asp Glu Asp Asp Ile Gly Ile Tyr Ile Ser Glu Ile Asp Pro
                165                 170                 175
Asn Ser Ile Ala Ala Lys Asp Gly Arg Ile Arg Glu Gly Asp Arg Ile
            180                 185                 190
Ile Gln Ile Asn Gly Ile Glu Val Gln Asn Arg Glu Glu Ala Val Ala
        195                 200                 205
Leu Leu Thr Ser Glu Glu Asn Lys Asn Phe Ser Leu Leu Ile Ala Arg
210                 215                 220
Pro Glu Leu Gln Leu Asp Glu Gly Trp Met Asp Asp Asp Arg Asn Asp
225                 230                 235                 240
Phe Leu Asp Asp Leu His Met Asp Met Leu Glu Glu Gln His His Gln
                245                 250                 255
Ala Met Gln Phe Thr Ala Ser Val Leu Gln Gln Lys Lys His Asp Glu
            260                 265                 270
Asp Gly Gly Thr Thr Asp Thr Ala Thr Ile Leu Ser Asn Gln His Glu
        275                 280                 285
Lys Asp Ser Gly Val Gly Arg Thr Asp Glu Ser Thr Arg Asn Asp Glu
290                 295                 300
Ser Ser Glu Gln Glu Asn Asn Gly Asp Asp Ala Thr Ala Ser Ser Asn
305                 310                 315                 320
Pro Leu Ala Gly Gln Arg Lys Leu Thr Cys Ser Gln Asp Thr Leu Gly
                325                 330                 335
Ser Gly Asp Leu Pro Phe Ser Asn Glu Ser Phe Ile Ser Ala Asp Cys
            340                 345                 350
Thr Asp Ala Asp Tyr Leu Gly Ile Pro Val Asp Glu Cys Glu Arg Phe
        355                 360                 365
Arg Glu Leu Leu Glu Leu Lys Cys Gln Val Lys Ser Ala Thr Pro Tyr
370                 375                 380
Gly Leu Tyr Tyr Pro Ser Gly Pro Leu Asp Ala Gly Lys Ser Asp Pro
385                 390                 395                 400
Glu Ser Val Asp Lys Glu Leu Glu Leu Leu Asn Glu Glu Leu Arg Ser
                405                 410                 415
```

```
Ile Glu Leu Glu Cys Leu Ser Ile Val Arg Ala His Lys Met Gln Gln
            420                 425                 430

Leu Lys Glu Gln Tyr Arg Ser Trp Met Leu His Asn Ser Gly Phe
        435                 440                 445

Arg Asn Tyr Asn Thr Ser Ile Asp Val Arg Arg His Glu Leu Ser Asp
450                 455                 460

Ile Thr Glu Leu Pro Glu Lys Ser Asp Lys Asp Ser Ser Ser Ala Tyr
465                 470                 475                 480

Asn Thr Gly Glu Ser Cys Arg Ser Thr Pro Leu Thr Leu Glu Ile Ser
                485                 490                 495

Pro Asp Asn Ser Leu Arg Arg Ala Val Glu Gly Ile Ser Cys Pro Ser
                500                 505                 510

Ser Glu Gly Ala Val Gly Thr Thr Glu Ala Tyr Gly Pro Ala Ser Lys
            515                 520                 525

Asn Leu Leu Ser Ile Thr Glu Asp Pro Glu Val Gly Thr Pro Thr Tyr
            530                 535                 540

Ser Pro Ser Leu Lys Glu Leu Asp Pro Asn Gln Pro Leu Glu Ser Lys
545                 550                 555                 560

Glu Arg Arg Ala Ser Asp Gly Ser Arg Ser Pro Thr Pro Ser Gln Lys
                565                 570                 575

Leu Gly Ser Ala Tyr Leu Pro Ser Tyr His His Ser Pro Tyr Lys His
            580                 585                 590

Ala His Ile Pro Ala His Ala Gln His Tyr Gln Ser Tyr Met Gln Leu
            595                 600                 605

Ile Gln Gln Lys Ser Ala Val Glu Tyr Ala Gln Ser Gln Met Ser Leu
    610                 615                 620

Val Ser Met Cys Lys Asp Leu Ser Pro Thr Pro Ser Glu Pro Arg
625                 630                 635                 640

Met Glu Trp Lys Val Lys Ile Arg Ser Asp Gly Thr Arg Tyr Ile Thr
                645                 650                 655

Lys Arg Pro Val Arg Asp Arg Leu Leu Arg Glu Arg Ala Leu Lys Ile
                660                 665                 670

Arg Glu Glu Arg Ser Gly Met Thr Thr Asp Asp Asp Ala Val Ser Glu
            675                 680                 685

Met Lys Met Gly Arg Tyr Trp Ser Lys Glu Glu Arg Lys Gln His Leu
            690                 695                 700

Val Lys Ala Lys Glu Gln Arg Arg Arg Glu Phe Met Met Gln Ser
705                 710                 715                 720

Arg Leu Asp Cys Leu Lys Glu Gln Gln Ala Ala Asp Asp Arg Lys Glu
                725                 730                 735

Met Asn Ile Leu Glu Leu Ser His Lys Lys Met Met Lys Lys Arg Asn
            740                 745                 750

Lys Lys Ile Phe Asp Asn Trp Met Thr Ile Gln Glu Leu Leu Thr His
            755                 760                 765

Gly Thr Lys Ser Pro Asp Gly Thr Arg Val Tyr Asn Ser Phe Leu Ser
        770                 775                 780

Val Thr Thr Val
785

<210> SEQ ID NO 220
<211> LENGTH: 178
<212> TYPE: DNA
<213> ORGANISM: Homo sapiens

<400> SEQUENCE: 220
```

```
agcatttgct cagtactctc aacataaacc aagcttagat cgcaatgaaa ctgcggacct    60
gcaggctgcc ttgcttcact gagtcaattt ttaaatgaag atggaacaca agaggatgat   120
cttattgttc agtaaattta ctctaataca taaaccccat ggtggaagat ggtatttg    178
```

<210> SEQ ID NO 221
<211> LENGTH: 28
<212> TYPE: PRT
<213> ORGANISM: Homo sapiens

<400> SEQUENCE: 221

```
Met Lys Met Glu His Lys Arg Met Ile Leu Leu Phe Ser Lys Phe Thr
1               5                   10                  15

Leu Ile His Lys Pro His Gly Gly Arg Trp Tyr Leu
            20                  25
```

<210> SEQ ID NO 222
<211> LENGTH: 84
<212> TYPE: DNA
<213> ORGANISM: Homo sapiens

<400> SEQUENCE: 222

```
atgaagatgg aacacaagag gatgatctta ttgttcagta aatttactct aatacataaa    60
ccccatggtg aagatggta tttg                                           84
```

<210> SEQ ID NO 223
<211> LENGTH: 2927
<212> TYPE: DNA
<213> ORGANISM: Homo sapiens

<400> SEQUENCE: 223

```
agcatttgct cagtactctc aacataaacc aagcttagat cgcaatgaaa ctgcggacct    60
gcaggctgcc ttgcttcact gagtcaattt ttaaatgaag atggaacaca agaggatgat   120
cttattgttc agtaaattta ctctaataca taaaccccat ggtggaagat ggtatttggt   180
caacggcaga gacttatcca gagcaactca tgaccaggct gtggaagctt tcaagacagc   240
caaggagccc atagtggtgc aggtgttgag aagaacacca aggaccaaaa tgttcacgcc   300
tccatcagag tctcagctgg tggacacggg aacccaaacc gacatcacct ttgaacatat   360
catggccctc actaagatgt cctctcccag cccacccgta ctggatccct atctcttgcc   420
agaggagcat ccctcagccc atgaatacta cgatccaaat gactacattg agacatccat   480
tcaggagatg gacagggagg agctggagct ggaggaagtg gacctctaca gaatgaacag   540
ccaggacaag ctgggcctca ctgtgtgcta ccggacggac gatgaagacg acattgggat   600
ttacatcagt gagattgacc ctaacagcat tgcagccaag gatgggcgca tccgagaagg   660
agaccgcatt atccagatta tgggataga ggtgcagaac cgtgaagagg ctgtggctct   720
tctaaccagt gaagaaaata aaactttttc attgctgatt gcaaggcctg aactccagct   780
ggatgagggc tggatggatg atgacaggaa cgactttctg gatgacctgc acatggacat   840
gctggaggag cagcaccacc aggccatgca attcacagct agcgtgctgc agcagaagaa   900 gcacgcgaa gacggtggga ccacagatac agccaccatc ttgtccaacc agcacgagaa   960
ggacagcggt gtgggcgga ccgacgagag caccgtaac gacgagagct cggagcaaga  1020
gaacaatggc gacgacgcca ccgcatcctc aacccgctg cgggcagaga ggaagctcac  1080
ctgcagccag gaccttggg cagcggga cctgcccttc agcaacgagt ctttcattc    1140 ggccgactgc acggacgccg actacctggg gatcacggtg gacgagtgcg agcgcttccg  1200
```

-continued

```
cgagctcctg gagctcaagt gccaggtgaa gagcgccacc ccttacggcc tgtactaccc      1260
tagcggcccc ctggacgccg gcaagagtga ccctgagagc gtggacaagg agctggagct      1320
gctgaacgaa gagctgcgca gcatcgagct ggagtgcctg agcatcgtgc gcgcccacaa      1380
gatgcagcag ctcaaggagc agtaccgcga gtcctggatg ctgcacaaca gcggcttccg      1440
caactacaac accagcatcg acgtgcgcag cacgagctc tcagatatca ccgagctccc       1500
ggagaaatcc gacaaggaca gctcgagcgc ctacaacaca ggcgagagct gccgcagcac      1560
cccgctcacc ctggagatct ccccgacaa ctccttgagg agagcggcgg agggcatcag       1620
ctgcccgagc agcgaagggg ctgtggggac cacggaagcc tacgggccag cctccaagaa      1680
tctgctctcc atcacggaag atcccgaagt gggcacccct acctatagcc cgtccctgaa      1740
ggagctggac cccaaccagc ccctggaaag caaagagcgg agagccagcg acgggagccg      1800
gagccccacg cccagccaga gctgggcag cgcctacctg ccctcctatc accactcccc       1860
atacaagcac gcgcacatcc cggcgcacgc ccagcactac cagagctaca tgcagctgat      1920
ccagcagaag tcggccgtgg agtacgcgca aagccagatg agcctggtga gcatgtgcaa      1980
ggacctgagc tctcccaccc cgtcggagcc gcgcatggag tggaaggtga agatccgcag      2040
cgacgggacg cgctacatca ccaagaggcc cgtgcgggac cgcctgctgc gggagcgcgc      2100
cctgaagatc cggaagagc gcagcggcat gaccaccgac gacgacgcgg tgagcgagat      2160
gaagatgggg cgctactgga gcaaggagga gaggaagcag cacctggtga aggccaagga      2220
gcagcggcgg cggcgcgagt tcatgatgca gagcaggttg gattgtctca aggagcagca      2280
agcagccgat gacaggaagg agatgaacat tctcgaactg agccacaaaa agatgatgaa      2340
gaagaggaat aagaaaatct tcgataactg gatgacgatc caagaactct aacccacgg      2400 cacaaaatcc ccggacggca ctagagtata caattccttc ctatcggtga ctactgtata      2460
attttcactt ctgcattatg tacataaagg agaccactac cactgggta gaaattcctg       2520 cctcgttcaa tgcggcaagt tttgtatat aagataagta cggtcttcat gtttacagtc       2580
caaatttgca aaccctacaa ctctgggtgt cataggtcta ttttaaggga agagagagaa      2640
aaacaccctt actatcttgg aaggcaatat taacaaacag atctttttc aaatagcaat      2700 tgtactttc tacctgtacc cttttacata aagtgtttaa atttcagaaa gatcttttat       2760
taagcatact ttcacagaat aacttgttta aactatattc atataaaaaa gttaaacacg      2820
ctttttttcc tgcctaaaac acaaatacaa ctgccagtat gtattttaa tggaacccta      2880 ttttataatg gtacgttact gaatgtgttt catatgcgtg accgtta                   2927
```

<210> SEQ ID NO 224
<211> LENGTH: 2927
<212> TYPE: DNA
<213> ORGANISM: Homo sapiens
<221> NAME/KEY: CDS
<222> LOCATION: (95)..(2461)

<400> SEQUENCE: 224

```
agcatttgct cagtactctc aacataaacc aagcttagat cgcaatgaaa ctgcggacct       60
gcaggctgcc ttgcttcact gagtcaattt ttaa atg aag atg gaa cac aag agg      115
                                    Met Lys Met Glu His Lys Arg
                                     1               5 atg atc tta ttg ttc agt aaa ttt act cta ata cat aaa ccc cat ggt        163
Met Ile Leu Leu Phe Ser Lys Phe Thr Leu Ile His Lys Pro His Gly
         10                  15                  20 gga aga tgg tat ttg gtc aac ggc aga gac tta tcc aga gca act cat        211
```

-continued

```
Gly Arg Trp Tyr Leu Val Asn Gly Arg Asp Leu Ser Arg Ala Thr His
     25                  30                  35 gac cag gct gtg gaa gct ttc aag aca gcc aag gag ccc ata gtg gtg       259
Asp Gln Ala Val Glu Ala Phe Lys Thr Ala Lys Glu Pro Ile Val Val
 40                  45                  50                  55 cag gtg ttg aga aga aca cca agg acc aaa atg ttc acg cct cca tca       307
Gln Val Leu Arg Arg Thr Pro Arg Thr Lys Met Phe Thr Pro Pro Ser
                 60                  65                  70 gag tct cag ctg gtg gac acg gga acc caa acc gac atc acc ttt gaa       355
Glu Ser Gln Leu Val Asp Thr Gly Thr Gln Thr Asp Ile Thr Phe Glu
             75                  80                  85 cat atc atg gcc ctc act aag atg tcc tct ccc agc cca ccc gta ctg       403
His Ile Met Ala Leu Thr Lys Met Ser Ser Pro Ser Pro Pro Val Leu
         90                  95                 100 gat ccc tat ctc ttg cca gag gag cat ccc tca gcc cat gaa tac tac       451
Asp Pro Tyr Leu Leu Pro Glu Glu His Pro Ser Ala His Glu Tyr Tyr
     105                 110                 115 gat cca aat gac tac att gga gac atc cat cag gag atg gac agg gag       499
Asp Pro Asn Asp Tyr Ile Gly Asp Ile His Gln Glu Met Asp Arg Glu
120                 125                 130                 135 gag ctg gag ctg gag gaa gtg gac ctc tac aga atg aac agc cag gac       547
Glu Leu Glu Leu Glu Glu Val Asp Leu Tyr Arg Met Asn Ser Gln Asp
                140                 145                 150 aag ctg ggc ctc act gtg tgc tac cgg acg gac gat gaa gac gac att       595
Lys Leu Gly Leu Thr Val Cys Tyr Arg Thr Asp Asp Glu Asp Asp Ile
            155                 160                 165 ggg att tac atc agt gag att gac cct aac agc att gca gcc aag gat       643
Gly Ile Tyr Ile Ser Glu Ile Asp Pro Asn Ser Ile Ala Ala Lys Asp
        170                 175                 180 ggg cgc atc cga gaa gga gac cgc att atc cag att aat ggg ata gag       691
Gly Arg Ile Arg Glu Gly Asp Arg Ile Ile Gln Ile Asn Gly Ile Glu
185                 190                 195 gtg cag aac cgt gaa gag gct gtg gct ctt cta acc agt gaa gaa aat       739
Val Gln Asn Arg Glu Glu Ala Val Ala Leu Leu Thr Ser Glu Glu Asn
200                 205                 210                 215 aaa aac ttt tca ttg ctg att gca agg cct gaa ctc cag ctg gat gag       787
Lys Asn Phe Ser Leu Leu Ile Ala Arg Pro Glu Leu Gln Leu Asp Glu
                220                 225                 230 ggc tgg atg gat gat gac agg aac gac ttt ctg gat gac ctg cac atg       835
Gly Trp Met Asp Asp Asp Arg Asn Asp Phe Leu Asp Asp Leu His Met
            235                 240                 245 gac atg ctg gag gag cag cac cac cag gcc atg caa ttc aca gct agc       883
Asp Met Leu Glu Glu Gln His His Gln Ala Met Gln Phe Thr Ala Ser
        250                 255                 260 gtg ctg cag cag aag aag cac gac gaa gac ggt ggg acc aca gat aca       931
Val Leu Gln Gln Lys Lys His Asp Glu Asp Gly Gly Thr Thr Asp Thr
265                 270                 275 gcc acc atc ttg tcc aac cag cac gag aag gac agc ggt gtg ggg cgg       979
Ala Thr Ile Leu Ser Asn Gln His Glu Lys Asp Ser Gly Val Gly Arg
280                 285                 290                 295 acc gac gag agc acc cgt aac gac gag agc tcg gag caa gag aac aat      1027
Thr Asp Glu Ser Thr Arg Asn Asp Glu Ser Ser Glu Gln Glu Asn Asn
                300                 305                 310 ggc gac gac gcc acc gca tcc tcc aac ccg ctg gcg ggg cag agg aag      1075
Gly Asp Asp Ala Thr Ala Ser Ser Asn Pro Leu Ala Gly Gln Arg Lys
            315                 320                 325 ctc acc tgc agc cag gac acc ttg ggc agc ggc gac ctg ccc ttc agc      1123
Leu Thr Cys Ser Gln Asp Thr Leu Gly Ser Gly Asp Leu Pro Phe Ser
        330                 335                 340 aac gag tct ttc att tcg gcc gac tgc acg gac gcc gac tac ctg ggg      1171
Asn Glu Ser Phe Ile Ser Ala Asp Cys Thr Asp Ala Asp Tyr Leu Gly
```

-continued

| | | | | | | | | | | | | | | | |
|---|---|---|---|---|---|---|---|---|---|---|---|---|---|---|---|
| Asn | Glu | Ser | Phe | Ile | Ser | Ala | Asp | Cys | Thr | Asp | Ala | Asp | Tyr | Leu | Gly |
| | 345 | | | | 350 | | | | | 355 | | | | | |

```
atc acg gtg gac gag tgc gag cgc ttc cgc gag ctc ctg gag ctc aag    1219
Ile Thr Val Asp Glu Cys Glu Arg Phe Arg Glu Leu Leu Glu Leu Lys
360             365                 370                 375 tgc cag gtg aag agc gcc acc cct tac ggc ctg tac tac cct agc ggc    1267
Cys Gln Val Lys Ser Ala Thr Pro Tyr Gly Leu Tyr Tyr Pro Ser Gly
            380                 385                 390 ccc ctg gac gcc ggc aag agt gac cct gag agc gtg gac aag gag ctg    1315
Pro Leu Asp Ala Gly Lys Ser Asp Pro Glu Ser Val Asp Lys Glu Leu
                395                 400                 405 gag ctg ctg aac gaa gag ctg cgc agc atc gag ctg gag tgc ctg agc    1363
Glu Leu Leu Asn Glu Glu Leu Arg Ser Ile Glu Leu Glu Cys Leu Ser
            410                 415                 420 atc gtg cgc gcc cac aag atg cag cag ctc aag gag cag tac cgc gag    1411
Ile Val Arg Ala His Lys Met Gln Gln Leu Lys Glu Gln Tyr Arg Glu
        425                 430                 435 tcc tgg atg ctg cac aac agc ggc ttc cgc aac tac aac acc agc atc    1459
Ser Trp Met Leu His Asn Ser Gly Phe Arg Asn Tyr Asn Thr Ser Ile
440                 445                 450                 455 gac gtg cgc aga cac gag ctc tca gat atc acc gag ctc ccg gag aaa    1507
Asp Val Arg Arg His Glu Leu Ser Asp Ile Thr Glu Leu Pro Glu Lys
                460                 465                 470 tcc gac aag gac agc tcg agc gcc tac aac aca ggc gag agc tgc cgc    1555
Ser Asp Lys Asp Ser Ser Ser Ala Tyr Asn Thr Gly Glu Ser Cys Arg
            475                 480                 485 agc acc ccg ctc acc ctg gag atc tcc ccc gac aac tcc ttg agg aga    1603
Ser Thr Pro Leu Thr Leu Glu Ile Ser Pro Asp Asn Ser Leu Arg Arg
        490                 495                 500 gcg gcg gag ggc atc agc tgc ccg agc agc gaa ggg gct gtg ggg acc    1651
Ala Ala Glu Gly Ile Ser Cys Pro Ser Ser Glu Gly Ala Val Gly Thr
    505                 510                 515 acg gaa gcc tac ggg cca gcc tcc aag aat ctg ctc tcc atc acg gaa    1699
Thr Glu Ala Tyr Gly Pro Ala Ser Lys Asn Leu Leu Ser Ile Thr Glu
520                 525                 530                 535 gat ccc gaa gtg ggc acc cct acc tat agc ccg tcc ctg aag gag ctg    1747
Asp Pro Glu Val Gly Thr Pro Thr Tyr Ser Pro Ser Leu Lys Glu Leu
                540                 545                 550 gac ccc aac cag ccc ctg gaa agc aaa gag cgg aga gcc agc gac ggg    1795
Asp Pro Asn Gln Pro Leu Glu Ser Lys Glu Arg Arg Ala Ser Asp Gly
            555                 560                 565 agc cgg agc ccc acg ccc agc cag aag ctg ggc agc gcc tac ctg ccc    1843
Ser Arg Ser Pro Thr Pro Ser Gln Lys Leu Gly Ser Ala Tyr Leu Pro
        570                 575                 580 tcc tat cac cac tcc cca tac aag cac gcg cac atc ccg gcg cac gcc    1891
Ser Tyr His His Ser Pro Tyr Lys His Ala His Ile Pro Ala His Ala
585                 590                 595 cag cac tac cag agc tac atg cag ctg atc cag cag aag tcg gcc gtg    1939
Gln His Tyr Gln Ser Tyr Met Gln Leu Ile Gln Gln Lys Ser Ala Val
600                 605                 610                 615 gag tac gcg caa agc cag atg agc ctg gtg agc atg tgc aag gac ctg    1987
Glu Tyr Ala Gln Ser Gln Met Ser Leu Val Ser Met Cys Lys Asp Leu
                620                 625                 630 agc tct ccc acc ccg tcg gag ccg cgc atg gag tgg aag gtg aag atc    2035
Ser Ser Pro Thr Pro Ser Glu Pro Arg Met Glu Trp Lys Val Lys Ile
            635                 640                 645 cgc agc gac ggg acg cgc tac atc acc aag agg ccc gtg cgg gac cgc    2083
Arg Ser Asp Gly Thr Arg Tyr Ile Thr Lys Arg Pro Val Arg Asp Arg
        650                 655                 660 ctg ctg cgg gag cgc gcc ctg aag atc cgg gaa gag cgc agc ggc atg    2131
```

-continued

```
Leu Leu Arg Glu Arg Ala Leu Lys Ile Arg Glu Glu Arg Ser Gly Met
    665                 670                 675 acc acc gac gac gac gcg gtg agc gag atg aag atg ggg cgc tac tgg      2179
Thr Thr Asp Asp Asp Ala Val Ser Glu Met Lys Met Gly Arg Tyr Trp
680                 685                 690                 695 agc aag gag gag agg aag cag cac ctg gtg aag gcc aag gag cag cgg      2227
Ser Lys Glu Glu Arg Lys Gln His Leu Val Lys Ala Lys Glu Gln Arg
            700                 705                 710 cgg cgg cgc gag ttc atg atg cag agc agg ttg gat tgt ctc aag gag      2275
Arg Arg Arg Glu Phe Met Met Gln Ser Arg Leu Asp Cys Leu Lys Glu
        715                 720                 725 cag caa gca gcc gat gac agg aag gag atg aac att ctc gaa ctg agc      2323
Gln Gln Ala Ala Asp Asp Arg Lys Glu Met Asn Ile Leu Glu Leu Ser
    730                 735                 740 cac aaa aag atg atg aag aag agg aat aag aaa atc ttc gat aac tgg      2371
His Lys Lys Met Met Lys Lys Arg Asn Lys Lys Ile Phe Asp Asn Trp
745                 750                 755 atg acg atc caa gaa ctc tta acc cac ggc aca aaa tcc ccg gac ggc      2419
Met Thr Ile Gln Glu Leu Leu Thr His Gly Thr Lys Ser Pro Asp Gly
760                 765                 770                 775 act aga gta tac aat tcc ttc cta tcg gtg act act gta taa              2461
Thr Arg Val Tyr Asn Ser Phe Leu Ser Val Thr Thr Val
                780                 785 ttttcacttc tgcattatgt acataaagga gaccactacc actggggtag aaattcctgc    2521
ctcgttcaat gcggcaagtt tttgtatata agataagtac ggtcttcatg tttacagtcc    2581
aaatttgcaa accctacaac tctgggtgtc ataggtctat tttaagggaa gagagagaaa    2641 aacacccttta ctatcttgga aggcaatatt aacaaacaga tctttttca aatagcaatt    2701 gtacttttct acctgtaccc ttttacataa agtgttaaa tttcagaaag atcttttatt    2761
aagcatactt tcacagaata acttgtttaa actatattca tataaaaaag ttaaacacgc    2821 ttttttttcct gcctaaaaca caaatacaac tgccagtatg tattttttaat ggaacccctat  2881 tttataatgg tacgttactg aatgtgtttc atatgcgtga ccgtta                   2927

<210> SEQ ID NO 225
<211> LENGTH: 788
<212> TYPE: PRT
<213> ORGANISM: Homo sapiens

<400> SEQUENCE: 225

Met Lys Met Glu His Lys Arg Met Ile Leu Leu Phe Ser Lys Phe Thr
1               5                   10                  15

Leu Ile His Lys Pro His Gly Gly Arg Trp Tyr Leu Val Asn Gly Arg
            20                  25                  30

Asp Leu Ser Arg Ala Thr His Asp Gln Ala Val Glu Ala Phe Lys Thr
        35                  40                  45

Ala Lys Glu Pro Ile Val Val Gln Val Leu Arg Arg Thr Pro Arg Thr
    50                  55                  60

Lys Met Phe Thr Pro Pro Ser Glu Ser Gln Leu Val Asp Thr Gly Thr
65                  70                  75                  80

Gln Thr Asp Ile Thr Phe Glu His Ile Met Ala Leu Thr Lys Met Ser
                85                  90                  95

Ser Pro Ser Pro Pro Val Leu Asp Pro Tyr Leu Pro Glu Glu His
            100                 105                 110

Pro Ser Ala His Glu Tyr Tyr Asp Pro Asn Asp Tyr Ile Gly Asp Ile
        115                 120                 125

His Gln Glu Met Asp Arg Glu Glu Leu Glu Leu Glu Glu Val Asp Leu
```

```
                130                 135                 140
Tyr Arg Met Asn Ser Gln Asp Lys Leu Gly Leu Thr Val Cys Tyr Arg
145                 150                 155                 160

Thr Asp Asp Glu Asp Asp Ile Gly Ile Tyr Ile Ser Glu Ile Asp Pro
                165                 170                 175

Asn Ser Ile Ala Ala Lys Asp Gly Arg Ile Arg Glu Gly Asp Arg Ile
                180                 185                 190

Ile Gln Ile Asn Gly Ile Glu Val Gln Asn Arg Glu Glu Ala Val Ala
                195                 200                 205

Leu Leu Thr Ser Glu Glu Asn Lys Asn Phe Ser Leu Leu Ile Ala Arg
210                 215                 220

Pro Glu Leu Gln Leu Asp Glu Gly Trp Met Asp Asp Arg Asn Asp
225                 230                 235                 240

Phe Leu Asp Asp Leu His Met Asp Met Leu Glu Glu Gln His His Gln
                245                 250                 255

Ala Met Gln Phe Thr Ala Ser Val Leu Gln Gln Lys Lys His Asp Glu
                260                 265                 270

Asp Gly Gly Thr Thr Asp Thr Ala Thr Ile Leu Ser Asn Gln His Glu
                275                 280                 285

Lys Asp Ser Gly Val Gly Arg Thr Asp Glu Ser Thr Arg Asn Asp Glu
290                 295                 300

Ser Glu Gln Glu Asn Gly Asp Asp Ala Thr Ala Ser Ser Asn
305                 310                 315                 320

Pro Leu Ala Gly Gln Arg Lys Leu Thr Cys Ser Gln Asp Thr Leu Gly
                325                 330                 335

Ser Gly Asp Leu Pro Phe Ser Asn Glu Ser Phe Ile Ser Ala Asp Cys
                340                 345                 350

Thr Asp Ala Asp Tyr Leu Gly Ile Thr Val Asp Glu Cys Glu Arg Phe
                355                 360                 365

Arg Glu Leu Leu Glu Leu Lys Cys Gln Val Lys Ser Ala Thr Pro Tyr
                370                 375                 380

Gly Leu Tyr Tyr Pro Ser Gly Pro Leu Asp Ala Gly Lys Ser Asp Pro
385                 390                 395                 400

Glu Ser Val Asp Lys Glu Leu Glu Leu Leu Asn Glu Glu Leu Arg Ser
                405                 410                 415

Ile Glu Leu Glu Cys Leu Ser Ile Val Arg Ala His Lys Met Gln Gln
                420                 425                 430

Leu Lys Glu Gln Tyr Arg Glu Ser Trp Met Leu His Asn Ser Gly Phe
                435                 440                 445

Arg Asn Tyr Asn Thr Ser Ile Asp Val Arg Arg His Glu Leu Ser Asp
450                 455                 460

Ile Thr Glu Leu Pro Glu Lys Ser Asp Lys Asp Ser Ser Ser Ala Tyr
465                 470                 475                 480

Asn Thr Gly Glu Ser Cys Arg Ser Thr Pro Leu Thr Leu Glu Ile Ser
                485                 490                 495

Pro Asp Asn Ser Leu Arg Arg Ala Ala Glu Gly Ile Ser Cys Pro Ser
                500                 505                 510

Ser Glu Gly Ala Val Gly Thr Thr Glu Ala Tyr Gly Pro Ala Ser Lys
                515                 520                 525

Asn Leu Leu Ser Ile Thr Glu Asp Pro Glu Val Gly Thr Pro Thr Tyr
                530                 535                 540

Ser Pro Ser Leu Lys Glu Leu Asp Pro Asn Gln Pro Leu Glu Ser Lys
545                 550                 555                 560
```

Glu Arg Arg Ala Ser Asp Gly Ser Arg Ser Pro Thr Pro Ser Gln Lys
                565                 570                 575

Leu Gly Ser Ala Tyr Leu Pro Ser Tyr His His Ser Pro Tyr Lys His
            580                 585                 590

Ala His Ile Pro Ala His Ala Gln His Tyr Gln Ser Tyr Met Gln Leu
        595                 600                 605

Ile Gln Gln Lys Ser Ala Val Glu Tyr Ala Gln Ser Gln Met Ser Leu
    610                 615                 620

Val Ser Met Cys Lys Asp Leu Ser Ser Pro Thr Pro Ser Glu Pro Arg
625                 630                 635                 640

Met Glu Trp Lys Val Lys Ile Arg Ser Asp Gly Thr Arg Tyr Ile Thr
                645                 650                 655

Lys Arg Pro Val Arg Asp Arg Leu Leu Arg Glu Arg Ala Leu Lys Ile
                660                 665                 670

Arg Glu Glu Arg Ser Gly Met Thr Thr Asp Asp Ala Val Ser Glu
            675                 680                 685

Met Lys Met Gly Arg Tyr Trp Ser Lys Glu Glu Arg Lys Gln His Leu
    690                 695                 700

Val Lys Ala Lys Glu Gln Arg Arg Arg Glu Phe Met Met Gln Ser
705                 710                 715                 720

Arg Leu Asp Cys Leu Lys Glu Gln Gln Ala Ala Asp Arg Lys Glu
                725                 730                 735

Met Asn Ile Leu Glu Leu Ser His Lys Lys Met Met Lys Lys Arg Asn
    740                 745                 750

Lys Lys Ile Phe Asp Asn Trp Met Thr Ile Gln Glu Leu Leu Thr His
                755                 760                 765

Gly Thr Lys Ser Pro Asp Gly Thr Arg Val Tyr Asn Ser Phe Leu Ser
770                 775                 780

Val Thr Thr Val
785

<210> SEQ ID NO 226
<211> LENGTH: 178
<212> TYPE: DNA
<213> ORGANISM: Homo sapiens

<400> SEQUENCE: 226
agcatttgct cagtactctc aacataaacc aagcttagat cgcaatgaaa ctgcggacct      60
gcaggctgcc ttgcttcact gagtcaattt ttaaatgaag atggaacaca agaggatgat     120
cttattgttc agtaaattta ctctaataca taaaccccat ggtggaagat ggtatttg      178

<210> SEQ ID NO 227
<211> LENGTH: 28
<212> TYPE: PRT
<213> ORGANISM: Homo sapiens

<400> SEQUENCE: 227

Met Lys Met Glu His Lys Arg Met Ile Leu Leu Phe Ser Lys Phe Thr
1               5                   10                  15

Leu Ile His Lys Pro His Gly Gly Arg Trp Tyr Leu
            20                  25

<210> SEQ ID NO 228
<211> LENGTH: 84
<212> TYPE: DNA
<213> ORGANISM: Homo sapiens

<400> SEQUENCE: 228

```
atgaagatgg aacacaagag gatgatctta ttgttcagta aatttactct aatacataaa    60
ccccatggtg aagatggta tttg                                           84

<210> SEQ ID NO 229
<211> LENGTH: 2738
<212> TYPE: DNA
<213> ORGANISM: Homo sapiens

<400> SEQUENCE: 229
atatataata gccttgcaag tgaacggata agcaaagtca gttgctgaga aataacactt    60
ccgagctgac gcatccaaat gtttaggata cacctgagat gtctctctta ctgaatagaa   120
acaacatccc tggaagctct agacttctga ggcaccccag ctttccctgg tcaacggcag   180
agacttatcc agagcaactc atgaccaggc tgtggaagct ttcaagacag ccaaggagcc   240
catagtggtg caggtgttga aagaacacc aaggaccaaa atgttcacgc ctccatcaga   300
gtctcagctg gtggacacgg aacccaaac cgacatcacc tttgaacata tcatggccct   360
cactaagatg tcctctccca gcccacccgt actggatccc tatctcttgc cagaggagca   420
tccctcagcc catgaatact acgatccaaa tgactacatt ggagacatcc atcaggagat   480
ggacagggag gagctggagc tggaggaagt ggacctctac agaatgaaca gccaggacaa   540
gctgggcctc actgtgtgct accggacgga cgatgaagac acattggga tttatatcag   600 tgagattgac cctaacagca ttgcagccaa ggatgggcgc atccgagaag gagaccgcat   660
tatccagatt aatgggatag aggtgcagaa ccgtgaagag gctgtggctc ttctaaccag   720
tgaagaaaat aaaaactttt cattgctgat tgcaaggcct gaactccagc tggatgaggg   780
ctggatggat gatgacagga acgactttct ggatgacctg cacatggaca tgctggagga   840
gcagcaccac caggccatgc aattcacagc tagcgtgctg cagcagaaga agcacgacga   900
agacggtggg accacagata cagccaccat cttgtccaac cagcacgaga aggacagcgg   960
tgtggggcgg accgacgaga gcacccgtaa tgacgagagc tcggagcaag agaacaatgg  1020
cgacgacgcc accgcatcct ccaacccgct ggcggggcag aggaagctca cctgcagcca  1080
ggacaccttg ggcagcggcg acctgccctt cagcaacgag tctttcattt cggccgactg  1140 cacgacgcc gactacctgg ggatcccggt ggacgagtgc gagcgcttcc gcgagctcct  1200
ggagctcaag tgccaggtga agagcgccac cccttacggc ctgtactacc ctagcggccc  1260
cctggacgcc ggcaagagtg accctgagag cgtggacaag gagctggagc tgctgaacga  1320
agagctgcgc agcatcgagc tggagtgcct gagcatcgtg cgcgcccaca agatgcagca  1380
gctcaaggag cagtaccgcg agtcctggat gctgcacaac agcggcttcc gcaactacaa  1440
caccagcatc gacgtgcgca gacacgagct ctcggatatc accgagctcc cggagaaatc  1500
cgacaaggac agctcgagcg cctacaacac aggcgagagc tgccgcagca ccccgctcac  1560
cctggagatc tcccccgaca actccttgag gagagcggtg gagggcatca gctgcccgag  1620
cagcgaaggg gctgtgggga ccacggaagc ctacggcca gcctccaaga atctgctctc  1680
catcacggaa gatcccgaag tgggcacccc tacctatagc ccgtccctga aggagctgga  1740
ccccaaccag cccctggaaa gcaaagagcg gagagccagc gacggagcc ggagccccac  1800 gcccagccaa aagctgggca gcgcctacct gccctcctat caccactccc catacaagca  1860
cgcgcacatc ccggcgcacg cccagcacta ccagagctac atgcagctga tccagcagaa  1920
gtcggccgtg gagtacgcgc aaagccagat gagcctggtg agcatgtgca aggacctgag  1980
ctctcccacc ccgtcggagc cgcgcatgga gtggaaggtg aagatccgca gcgacgggac  2040
```

```
gcgctacatc accaagaggc ccgtgcggga ccgcctgctg cgggagcgcg ccctgaagat    2100
ccgggaagag cgcagcggca tgaccaccga cgacgacgcg gtgagcgaga tgaagatggg    2160
gcgctactgg agcaaggagg agaggaagca gcacctggtg aaggccaagg agcagcggcg    2220
gcggcgcgag ttcatgatgc agagcaggtt ggattgtctc aaggagcagc aagcagccga    2280
tgacaggaag gagatgaaca ttctcgaact gagcccacaa aagatgatga agaagaggaa    2340
taagaaaatc ttcgataact ggatgacgat ccaagaactc ttaacccacg gcacaaaatc    2400
cccggacggc actagagtat acaattcctt cctatcggtg actactgtat aattttcact    2460
tctgcattat gtacataaag gagaccacta ccactggggt agaaattcct gcctcgttca    2520
atgcggcaag ttttttgtata taagataagt acggtcttca tgtttacagt ccaaatttgc    2580
aaaccccaca actctgggtg tcgtaggtct attttaaggg aagagagaga aaaacacccct   2640 tactatcttg gaaggcaata ttaacaaaca gagcttttt  caaatagcaa ttgtacttt     2700 ctacctgtac ccttttacat aaagtgttta aatttcag                            2738
```

<210> SEQ ID NO 230
<211> LENGTH: 2738
<212> TYPE: DNA
<213> ORGANISM: Homo sapiens
<221> NAME/KEY: CDS
<222> LOCATION: (281)..(2452)

<400> SEQUENCE: 230

```
atatataata gccttgcaag tgaacggata agcaaagtca gttgctgaga ataacactt     60 ccgagctgac gcatccaaat gtttaggata cacctgagat gtctctctta ctgaatagaa   120
acaacatccc tggaagctct agacttctga ggcaccccag cttccctgg  tcaacggcag   180 agacttatcc agagcaactc atgaccaggc tgtggaagct ttcaagacag ccaaggagcc   240
catagtggtg caggtgttga aagaacacc  aaggaccaaa atg ttc acg cct cca     295
                                                 Met Phe Thr Pro Pro
                                                  1               5 tca gag tct cag ctg gtg gac acg gga acc caa acc gac atc acc ttt    343
Ser Glu Ser Gln Leu Val Asp Thr Gly Thr Gln Thr Asp Ile Thr Phe
            10                   15                   20 gaa cat atc atg gcc ctc act aag atg tcc tct ccc agc cca ccc gta    391
Glu His Ile Met Ala Leu Thr Lys Met Ser Ser Pro Ser Pro Pro Val
        25                   30                   35 ctg gat ccc tat ctc ttg cca gag gag cat ccc tca gcc cat gaa tac    439
Leu Asp Pro Tyr Leu Leu Pro Glu Glu His Pro Ser Ala His Glu Tyr
    40                   45                   50 tac gat cca aat gac tac att gga gac atc cat cag gag atg gac agg    487
Tyr Asp Pro Asn Asp Tyr Ile Gly Asp Ile His Gln Glu Met Asp Arg
55                   60                   65 gag gag ctg gag ctg gag gaa gtg gac ctc tac aga atg aac agc cag    535
Glu Glu Leu Glu Leu Glu Glu Val Asp Leu Tyr Arg Met Asn Ser Gln
70                   75                   80                   85 gac aag ctg ggc ctc act gtg tgc tac cgg acg gat gat gaa gac gac    583
Asp Lys Leu Gly Leu Thr Val Cys Tyr Arg Thr Asp Asp Glu Asp Asp
                90                   95                  100 att ggg att tat atc agt gag att gac cct aac agc att gca gcc aag    631
Ile Gly Ile Tyr Ile Ser Glu Ile Asp Pro Asn Ser Ile Ala Ala Lys
            105                  110                  115 gat ggg cgc atc cga gaa gga gac cgc att atc cag att aat ggg ata    679
Asp Gly Arg Ile Arg Glu Gly Asp Arg Ile Ile Gln Ile Asn Gly Ile
        120                  125                  130 gag gtg cag aac cgt gaa gag gct gtg gct ctt cta acc agt gaa gaa    727
```

```
                                                         -continued

Glu Val Gln Asn Arg Glu Glu Ala Val Ala Leu Leu Thr Ser Glu Glu
        135                 140                 145 aat aaa aac ttt tca ttg ctg att gca agg cct gaa ctc cag ctg gat    775
Asn Lys Asn Phe Ser Leu Leu Ile Ala Arg Pro Glu Leu Gln Leu Asp
150                 155                 160                 165 gag ggc tgg atg gat gat gac agg aac gac ttt ctg gat gac ctg cac    823
Glu Gly Trp Met Asp Asp Asp Arg Asn Asp Phe Leu Asp Asp Leu His
                170                 175                 180 atg gac atg ctg gag gag cag cac cac cag gcc atg caa ttc aca gct    871
Met Asp Met Leu Glu Glu Gln His His Gln Ala Met Gln Phe Thr Ala
            185                 190                 195 agc gtg ctg cag cag aag aag cac gac gaa gac ggt ggg acc aca gat    919
Ser Val Leu Gln Gln Lys Lys His Asp Glu Asp Gly Gly Thr Thr Asp
        200                 205                 210 aca gcc acc atc ttg tcc aac cag cac gag aag gac agc ggt gtg ggg    967
Thr Ala Thr Ile Leu Ser Asn Gln His Glu Lys Asp Ser Gly Val Gly
215                 220                 225 cgg acc gac gag agc acc cgt aat gac gag agc tcg gag caa gag aac   1015
Arg Thr Asp Glu Ser Thr Arg Asn Asp Glu Ser Ser Glu Gln Glu Asn
230                 235                 240                 245 aat ggc gac gac gcc acc gca tcc tcc aac ccg ctg gcg ggg cag agg   1063
Asn Gly Asp Asp Ala Thr Ala Ser Ser Asn Pro Leu Ala Gly Gln Arg
                250                 255                 260 aag ctc acc tgc agc cag gac acc ttg ggc agc ggc gac ctg ccc ttc   1111
Lys Leu Thr Cys Ser Gln Asp Thr Leu Gly Ser Gly Asp Leu Pro Phe
            265                 270                 275 agc aac gag tct ttc att tcg gcc gac tgc acg gac gcc gac tac ctg   1159
Ser Asn Glu Ser Phe Ile Ser Ala Asp Cys Thr Asp Ala Asp Tyr Leu
        280                 285                 290 ggg atc ccg gtg gac gag tgc gag cgc ttc cgc gag ctc ctg gag ctc   1207
Gly Ile Pro Val Asp Glu Cys Glu Arg Phe Arg Glu Leu Leu Glu Leu
295                 300                 305 aag tgc cag gtg aag agc gcc acc cct tac ggc ctg tac tac cct agc   1255
Lys Cys Gln Val Lys Ser Ala Thr Pro Tyr Gly Leu Tyr Tyr Pro Ser
310                 315                 320                 325 ggc ccc ctg gac gcc ggc aag agt gac cct gag agc gtg gac aag gag   1303
Gly Pro Leu Asp Ala Gly Lys Ser Asp Pro Glu Ser Val Asp Lys Glu
                330                 335                 340 ctg gag ctg ctg aac gaa gag ctg cgc agc atc gag ctg gag tgc ctg   1351
Leu Glu Leu Leu Asn Glu Glu Leu Arg Ser Ile Glu Leu Glu Cys Leu
            345                 350                 355 agc atc gtg cgc gcc cac aag atg cag cag ctc aag gag cag tac cgc   1399
Ser Ile Val Arg Ala His Lys Met Gln Gln Leu Lys Glu Gln Tyr Arg
        360                 365                 370 gag tcc tgg atg ctg cac aac agc ggc ttc cgc aac tac aac acc agc   1447
Glu Ser Trp Met Leu His Asn Ser Gly Phe Arg Asn Tyr Asn Thr Ser
375                 380                 385 atc gac gtg cgc aga cac gag ctc tcg gat atc acc gag ctc ccg gag   1495
Ile Asp Val Arg Arg His Glu Leu Ser Asp Ile Thr Glu Leu Pro Glu
390                 395                 400                 405 aaa tcc gac aag gac agc tcg agc gcc tac aac aca ggc gag agc tgc   1543
Lys Ser Asp Lys Asp Ser Ser Ser Ala Tyr Asn Thr Gly Glu Ser Cys
                410                 415                 420 cgc agc acc ccg ctc acc ctg gag atc tcc ccc gac aac tcc ttg agg   1591
Arg Ser Thr Pro Leu Thr Leu Glu Ile Ser Pro Asp Asn Ser Leu Arg
            425                 430                 435 aga gcg gtg gag ggc atc agc tgc ccg agc agc gaa ggg gct gtg ggg   1639
Arg Ala Val Glu Gly Ile Ser Cys Pro Ser Ser Glu Gly Ala Val Gly
        440                 445                 450 acc acg gaa gcc tac ggg cca gcc tcc aag aat ctg ctc tcc atc acg   1687
```

|  |  |  |  |  |  |  |  |  |  |  |  |  |
|---|---|---|---|---|---|---|---|---|---|---|---|---|
| Thr | Thr | Glu | Ala | Tyr | Gly | Pro | Ala | Ser | Lys | Asn | Leu | Ser | Ile | Thr |
|  | 455 |  |  |  | 460 |  |  |  |  | 465 |  |  |  |  |

```
gaa gat ccc gaa gtg ggc acc cct acc tat agc ccg tcc ctg aag gag      1735
Glu Asp Pro Glu Val Gly Thr Pro Thr Tyr Ser Pro Ser Leu Lys Glu
470             475                 480                  485 ctg gac ccc aac cag ccc ctg gaa agc aaa gag cgg aga gcc agc gac      1783
Leu Asp Pro Asn Gln Pro Leu Glu Ser Lys Glu Arg Arg Ala Ser Asp
                490                 495                 500 ggg agc cgg agc ccc acg ccc agc cag aag ctg ggc agc gcc tac ctg      1831
Gly Ser Arg Ser Pro Thr Pro Ser Gln Lys Leu Gly Ser Ala Tyr Leu
            505                 510                 515 ccc tcc tat cac cac tcc cca tac aag cac gcg cac atc ccg gcg cac      1879
Pro Ser Tyr His His Ser Pro Tyr Lys His Ala His Ile Pro Ala His
        520                 525                 530 gcc cag cac tac cag agc tac atg cag ctg atc cag cag aag tcg gcc      1927
Ala Gln His Tyr Gln Ser Tyr Met Gln Leu Ile Gln Gln Lys Ser Ala
    535                 540                 545 gtg gag tac gcg caa agc cag atg agc ctg gtg agc atg tgc aag gac      1975
Val Glu Tyr Ala Gln Ser Gln Met Ser Leu Val Ser Met Cys Lys Asp
550                 555                 560                 565 ctg agc tct ccc acc ccg tcg gag ccg cgc atg gag tgg aag gtg aag      2023
Leu Ser Ser Pro Thr Pro Ser Glu Pro Arg Met Glu Trp Lys Val Lys
                570                 575                 580 atc cgc agc gac ggg acg cgc tac atc acc aag agg ccc gtg cgg gac      2071
Ile Arg Ser Asp Gly Thr Arg Tyr Ile Thr Lys Arg Pro Val Arg Asp
            585                 590                 595 cgc ctg ctg cgg gag cgc gcc ctg aag atc cgg gaa gag cgc agc ggc      2119
Arg Leu Leu Arg Glu Arg Ala Leu Lys Ile Arg Glu Glu Arg Ser Gly
        600                 605                 610 atg acc acc gac gac gac gcg gtg agc gag atg aag atg ggg cgc tac      2167
Met Thr Thr Asp Asp Asp Ala Val Ser Glu Met Lys Met Gly Arg Tyr
    615                 620                 625 tgg agc aag gag gag agg aag cag cac ctg gtg aag gcc aag gag cag      2215
Trp Ser Lys Glu Glu Arg Lys Gln His Leu Val Lys Ala Lys Glu Gln
630                 635                 640                 645 cgg cgg cgg cgc gag ttc atg atg cag agc agg ttg gat tgt ctc aag      2263
Arg Arg Arg Arg Glu Phe Met Met Gln Ser Arg Leu Asp Cys Leu Lys
                650                 655                 660 gag cag caa gca gcc gat gac agg aag gag atg aac att ctc gaa ctg      2311
Glu Gln Gln Ala Ala Asp Asp Arg Lys Glu Met Asn Ile Leu Glu Leu
            665                 670                 675 agc cac aaa aag atg atg aag aag agg aat aag aaa atc ttc gat aac      2359
Ser His Lys Lys Met Met Lys Lys Arg Asn Lys Lys Ile Phe Asp Asn
        680                 685                 690 tgg atg acg atc caa gaa ctc tta acc cac ggc aca aaa tcc ccg gac      2407
Trp Met Thr Ile Gln Glu Leu Leu Thr His Gly Thr Lys Ser Pro Asp
    695                 700                 705 ggc act aga gta tac aat tcc ttc cta tcg gtg act act gta taa          2452
Gly Thr Arg Val Tyr Asn Ser Phe Leu Ser Val Thr Thr Val
710                 715                 720 ttttcacttc tgcattatgt acataaagga gaccactacc actggggtag aaattcctgc    2512
ctcgttcaat gcggcaagtt tttgtatata agataagtac ggtcttcatg tttacagtcc    2572
aaatttgcaa accccacaac tctgggtgtc gtaggtctat tttaagggaa gagagagaaa    2632 aacacccttacctatcttgga aggcaatatt aacaaacaga gctttttca aatagcaatt    2692 gtacttttct acctgtaccc ttttacataa agtgtttaaa tttcag                   2738

<210> SEQ ID NO 231
<211> LENGTH: 723
```

<212> TYPE: PRT
<213> ORGANISM: Homo sapiens

<400> SEQUENCE: 231

```
Met Phe Thr Pro Pro Ser Glu Ser Gln Leu Val Asp Thr Gly Thr Gln
1               5                   10                  15

Thr Asp Ile Thr Phe Glu His Ile Met Ala Leu Thr Lys Met Ser Ser
            20                  25                  30

Pro Ser Pro Pro Val Leu Asp Pro Tyr Leu Leu Pro Glu His Pro
        35                  40                  45

Ser Ala His Glu Tyr Tyr Asp Pro Asn Asp Tyr Ile Gly Asp Ile His
    50                  55                  60

Gln Glu Met Asp Arg Glu Leu Glu Leu Glu Val Asp Leu Tyr
65                  70                  75                  80

Arg Met Asn Ser Gln Asp Lys Leu Gly Leu Thr Val Cys Tyr Arg Thr
                85                  90                  95

Asp Asp Glu Asp Asp Ile Gly Ile Tyr Ile Ser Glu Ile Asp Pro Asn
            100                 105                 110

Ser Ile Ala Ala Lys Asp Gly Arg Ile Arg Glu Gly Asp Arg Ile Ile
        115                 120                 125

Gln Ile Asn Gly Ile Glu Val Gln Asn Arg Glu Glu Ala Val Ala Leu
    130                 135                 140

Leu Thr Ser Glu Glu Asn Lys Asn Phe Ser Leu Leu Ile Ala Arg Pro
145                 150                 155                 160

Glu Leu Gln Leu Asp Glu Gly Trp Met Asp Asp Asp Arg Asn Asp Phe
                165                 170                 175

Leu Asp Asp Leu His Met Asp Met Leu Glu Glu Gln His His Gln Ala
            180                 185                 190

Met Gln Phe Thr Ala Ser Val Leu Gln Gln Lys Lys His Asp Glu Asp
        195                 200                 205

Gly Gly Thr Thr Asp Thr Ala Thr Ile Leu Ser Asn Gln His Glu Lys
    210                 215                 220

Asp Ser Gly Val Gly Arg Thr Asp Glu Ser Thr Arg Asn Asp Glu Ser
225                 230                 235                 240

Ser Glu Gln Glu Asn Asn Gly Asp Asp Ala Thr Ala Ser Ser Asn Pro
                245                 250                 255

Leu Ala Gly Gln Arg Lys Leu Thr Cys Ser Gln Asp Thr Leu Gly Ser
            260                 265                 270

Gly Asp Leu Pro Phe Ser Asn Glu Ser Phe Ile Ser Ala Asp Cys Thr
        275                 280                 285

Asp Ala Asp Tyr Leu Gly Ile Pro Val Asp Glu Cys Glu Arg Phe Arg
    290                 295                 300

Glu Leu Leu Glu Leu Lys Cys Gln Val Lys Ser Ala Thr Pro Tyr Gly
305                 310                 315                 320

Leu Tyr Tyr Pro Ser Gly Pro Leu Asp Ala Gly Lys Ser Asp Pro Glu
                325                 330                 335

Ser Val Asp Lys Glu Leu Glu Leu Leu Asn Glu Glu Leu Arg Ser Ile
            340                 345                 350

Glu Leu Glu Cys Leu Ser Ile Val Arg Ala His Lys Met Gln Gln Leu
        355                 360                 365

Lys Glu Gln Tyr Arg Glu Ser Trp Met Leu His Asn Ser Gly Phe Arg
    370                 375                 380

Asn Tyr Asn Thr Ser Ile Asp Val Arg Arg His Glu Leu Ser Asp Ile
385                 390                 395                 400
```

```
Thr Glu Leu Pro Glu Lys Ser Asp Lys Asp Ser Ser Ala Tyr Asn
            405                 410                 415

Thr Gly Glu Ser Cys Arg Ser Thr Pro Leu Thr Leu Glu Ile Ser Pro
        420                 425                 430

Asp Asn Ser Leu Arg Arg Ala Val Glu Gly Ile Ser Cys Pro Ser Ser
            435                 440                 445

Glu Gly Ala Val Gly Thr Thr Glu Ala Tyr Gly Pro Ala Ser Lys Asn
    450                 455                 460

Leu Leu Ser Ile Thr Glu Asp Pro Glu Val Gly Thr Pro Thr Tyr Ser
465                 470                 475                 480

Pro Ser Leu Lys Glu Leu Asp Pro Asn Gln Pro Leu Glu Ser Lys Glu
                485                 490                 495

Arg Arg Ala Ser Asp Gly Ser Arg Ser Pro Thr Pro Ser Gln Lys Leu
                500                 505                 510

Gly Ser Ala Tyr Leu Pro Ser Tyr His His Ser Pro Tyr Lys His Ala
        515                 520                 525

His Ile Pro Ala His Ala Gln His Tyr Gln Ser Tyr Met Gln Leu Ile
    530                 535                 540

Gln Gln Lys Ser Ala Val Glu Tyr Ala Gln Ser Gln Met Ser Leu Val
545                 550                 555                 560

Ser Met Cys Lys Asp Leu Ser Ser Pro Thr Pro Ser Glu Pro Arg Met
                565                 570                 575

Glu Trp Lys Val Lys Ile Arg Ser Asp Gly Thr Arg Tyr Ile Thr Lys
                580                 585                 590

Arg Pro Val Arg Asp Arg Leu Leu Arg Glu Arg Ala Leu Lys Ile Arg
            595                 600                 605

Glu Glu Arg Ser Gly Met Thr Thr Asp Asp Ala Val Ser Glu Met
    610                 615                 620

Lys Met Gly Arg Tyr Trp Ser Lys Glu Glu Lys Gln His Leu Val
625                 630                 635                 640

Lys Ala Lys Glu Gln Arg Arg Arg Glu Phe Met Gln Ser Arg
                645                 650                 655

Leu Asp Cys Leu Lys Glu Gln Gln Ala Ala Asp Arg Lys Glu Met
            660                 665                 670

Asn Ile Leu Glu Leu Ser His Lys Lys Met Met Lys Lys Arg Asn Lys
            675                 680                 685

Lys Ile Phe Asp Asn Trp Met Thr Ile Gln Glu Leu Leu Thr His Gly
            690                 695                 700

Thr Lys Ser Pro Asp Gly Thr Arg Val Tyr Asn Ser Phe Leu Ser Val
705                 710                 715                 720

Thr Thr Val

<210> SEQ ID NO 232
<211> LENGTH: 169
<212> TYPE: DNA
<213> ORGANISM: Homo sapiens

<400> SEQUENCE: 232
atatataata gccttgcaag tgaacggata agcaaagtca gttgctgaga aataacactt    60
ccgagctgac gcatccaaat gtttaggata cacctgagat gtctctctta ctgaatagaa   120
acaacatccc tggaagctct agacttctga ggcaccccag ctttccctg               169

<210> SEQ ID NO 233
<211> LENGTH: 280
<212> TYPE: DNA
```

<213> ORGANISM: Homo sapiens

<400> SEQUENCE: 233

| | | | | | |
|---|---|---|---|---|---|
| atatataata | gccttgcaag | tgaacggata | agcaaagtca | gttgctgaga | aataacactt | 60 |
| ccgagctgac | gcatccaaat | gtttaggata | cacctgagat | gtctctctta | ctgaatagaa | 120 |
| acaacatccc | tggaagctct | agacttctga | ggcaccccag | ctttccctgg | tcaacggcag | 180 |
| agacttatcc | agagcaactc | atgaccaggc | tgtggaagct | ttcaagacag | ccaaggagcc | 240 |
| catagtggtg | caggtgttga | agaacacc | aaggaccaaa | | | 280 |

<210> SEQ ID NO 234
<211> LENGTH: 1574
<212> TYPE: DNA
<213> ORGANISM: Homo sapiens

<400> SEQUENCE: 234

| | | | | | |
|---|---|---|---|---|---|
| gtagacgcct | cggggcttaa | gagaacgtga | catggaagag | acaggaaata | tgtactcttg | 60 |
| tacaggtatg | cggcacacat | gtggccccct | ccctcccagc | ctcctcacta | aagattatta | 120 |
| acctgcttat | tctcctggtt | cacctgaggc | tgttttgaga | gaatctcagt | atctcagtct | 180 |
| tcatttcata | cgacattctt | cgggctcctc | ttgttcatct | ttgcagactg | aagtatttat | 240 |
| gaaggacctt | cagaaatctg | attcctcctg | atgaatcaaa | gagtaaagaa | gaatcaaaca | 300 |
| tgattaacca | ggtcaacggc | agagacttat | ccagagcaac | tcatgaccag | gctgtggaag | 360 |
| ctttcaagac | agccaaggag | cccatagtgg | tgcaggtgtt | gagaagaaca | ccaaggacca | 420 |
| aaatgttcac | gcctccatca | gagtctcagc | tggtggacac | gggaacccaa | accgacatca | 480 |
| cctttgaaca | tatcatggcc | ctcactaaga | tgtcctctcc | cagccacccc | gtactggatc | 540 |
| cctatctctt | gccagaggag | catccctcag | cccatgaata | ctacgatcca | aatgactaca | 600 |
| ttggagacat | ccatcaggag | atggacaggg | aggagctgga | gctggaggaa | gtggacctct | 660 |
| acagaatgaa | cagccaggac | aagctgggcc | tcactgtgtg | ctaccggacg | gacgatgaag | 720 |
| acgacattgg | gatttatatc | agtgagattg | accctaacag | cattgcagcc | aaggatgggc | 780 |
| gcatccgaga | aggagaccgc | attatccaga | ttaatggat | agaggtgcag | aaccgtgaag | 840 |
| aggctgtggc | tcttctaacc | agtgaagaaa | ataaaaactt | ttcattgctg | attgcaaggc | 900 |
| ctgaactcca | gctggatgag | ggctggatgg | atgatgacag | gaacgacttt | ctggatgacc | 960 |
| tgcacatgga | catgctggag | gagcagcacc | accaggccat | gcaattcaca | gctagcgtgc | 1020 |
| tgcagcagaa | gaagcacgac | gaagacggtg | ggaccacaga | tacagccacc | atcttgtcca | 1080 |
| accagcacga | gaaggacagc | ggtgtggggc | ggaccgacga | gagcacccgt | aatgacgaga | 1140 |
| gctcggagca | agagagcaat | ggcgacacg | ccaccgcatc | ctccaacccg | ctggcggggc | 1200 |
| agaggaagct | cacctgcagc | caggacacct | gggcagcgg | cgacctgccc | ttcagcaacg | 1260 |
| agtctttcat | ttcggccgac | tgcacggacg | ccgactacct | ggggatcccg | gtggacgagt | 1320 |
| gcgagcgctt | ccgcgagctc | ctggagctca | agtgccaggt | gaagagcgcc | acccttacg | 1380 |
| gcctgtacta | ccctagcggc | cccctggacg | ccggcaagag | tgaccctgag | agcgtggaca | 1440 |
| aggagctgga | gctgctgaac | gaagagctgc | gcagcatcga | gctggagtgc | ctgagcatcg | 1500 |
| tgcgcgccca | caagatgcag | cagctcaagg | agcagtaccg | cgagtcctgg | atgctgcaca | 1560 |
| acagcggctt | ccgc | | | | | 1574 |

<210> SEQ ID NO 235
<211> LENGTH: 1574
<212> TYPE: DNA

```
<213> ORGANISM: Homo sapiens
<221> NAME/KEY: CDS
<222> LOCATION: (300)..(1574)

<400> SEQUENCE: 235
```

| | |
|---|---:|
| gtagacgcct cggggcttaa gagaacgtga catggaagag acaggaaata tgtactcttg | 60 |
| tacaggtatg cggcacacat gtggccccct ccctcccagc ctcctcacta aagattatta | 120 |
| acctgcttat tctcctggtt cacctgaggc tgttttgaga gaatctcagt atctcagtct | 180 |
| tcatttcata cgacattctt cgggctcctc ttgttcatct ttgcagactg aagtatttat | 240 |
| gaaggacctt cagaaatctg attcctcctg atgaatcaaa gagtaaagaa gaatcaaac | 299 |

| | | | | | | | | | | | | | | | | |
|---|---|---|---|---|---|---|---|---|---|---|---|---|---|---|---|---:|
| atg | att | aac | cag | gtc | aac | ggc | aga | gac | tta | tcc | aga | gca | act | cat | gac | 347 |
| Met | Ile | Asn | Gln | Val | Asn | Gly | Arg | Asp | Leu | Ser | Arg | Ala | Thr | His | Asp | |
| 1 | | | | 5 | | | | | 10 | | | | | 15 | | |
| cag | gct | gtg | gaa | gct | ttc | aag | aca | gcc | aag | gag | ccc | ata | gtg | gtg | cag | 395 |
| Gln | Ala | Val | Glu | Ala | Phe | Lys | Thr | Ala | Lys | Glu | Pro | Ile | Val | Val | Gln | |
| | | | 20 | | | | | 25 | | | | | 30 | | | |
| gtg | ttg | aga | aga | aca | cca | agg | acc | aaa | atg | ttc | acg | cct | cca | tca | gag | 443 |
| Val | Leu | Arg | Arg | Thr | Pro | Arg | Thr | Lys | Met | Phe | Thr | Pro | Pro | Ser | Glu | |
| | | 35 | | | | | 40 | | | | | 45 | | | | |
| tct | cag | ctg | gtg | gac | acg | gga | acc | caa | acc | gac | atc | acc | ttt | gaa | cat | 491 |
| Ser | Gln | Leu | Val | Asp | Thr | Gly | Thr | Gln | Thr | Asp | Ile | Thr | Phe | Glu | His | |
| 50 | | | | | 55 | | | | | 60 | | | | | | |
| atc | atg | gcc | ctc | act | aag | atg | tcc | tct | ccc | agc | cca | ccc | gta | ctg | gat | 539 |
| Ile | Met | Ala | Leu | Thr | Lys | Met | Ser | Ser | Pro | Ser | Pro | Pro | Val | Leu | Asp | |
| 65 | | | | 70 | | | | | 75 | | | | | 80 | | |
| ccc | tat | ctc | ttg | cca | gag | gag | cat | ccc | tca | gcc | cat | gaa | tac | tac | gat | 587 |
| Pro | Tyr | Leu | Leu | Pro | Glu | Glu | His | Pro | Ser | Ala | His | Glu | Tyr | Tyr | Asp | |
| | | | | 85 | | | | | 90 | | | | | 95 | | |
| cca | aat | gac | tac | att | gga | gac | atc | cat | cag | gag | atg | gac | agg | gag | gag | 635 |
| Pro | Asn | Asp | Tyr | Ile | Gly | Asp | Ile | His | Gln | Glu | Met | Asp | Arg | Glu | Glu | |
| | | | 100 | | | | | 105 | | | | | 110 | | | |
| ctg | gag | ctg | gag | gaa | gtg | gac | ctc | tac | aga | atg | aac | agc | cag | gac | aag | 683 |
| Leu | Glu | Leu | Glu | Glu | Val | Asp | Leu | Tyr | Arg | Met | Asn | Ser | Gln | Asp | Lys | |
| | | | 115 | | | | | 120 | | | | | 125 | | | |
| ctg | ggc | ctc | act | gtg | tgc | tac | cgg | acg | gac | gaa | gac | gac | att | ggg | | 731 |
| Leu | Gly | Leu | Thr | Val | Cys | Tyr | Arg | Thr | Asp | Asp | Glu | Asp | Asp | Ile | Gly | |
| | 130 | | | | | 135 | | | | | 140 | | | | | |
| att | tat | atc | agt | gag | att | gac | cct | aac | agc | att | gca | gcc | aag | gat | ggg | 779 |
| Ile | Tyr | Ile | Ser | Glu | Ile | Asp | Pro | Asn | Ser | Ile | Ala | Ala | Lys | Asp | Gly | |
| 145 | | | | | 150 | | | | | 155 | | | | | 160 | |
| cgc | atc | cga | gaa | gga | gac | cgc | att | atc | cag | att | aat | ggg | ata | gag | gtg | 827 |
| Arg | Ile | Arg | Glu | Gly | Asp | Arg | Ile | Ile | Gln | Ile | Asn | Gly | Ile | Glu | Val | |
| | | | 165 | | | | | 170 | | | | | 175 | | | |
| cag | aac | cgt | gaa | gag | gct | gtg | gct | ctt | cta | acc | agt | gaa | gaa | aat | aaa | 875 |
| Gln | Asn | Arg | Glu | Glu | Ala | Val | Ala | Leu | Leu | Thr | Ser | Glu | Glu | Asn | Lys | |
| | | 180 | | | | | 185 | | | | | 190 | | | | |
| aac | ttt | tca | ttg | ctg | att | gca | agg | cct | gaa | ctc | cag | ctg | gat | gag | ggc | 923 |
| Asn | Phe | Ser | Leu | Leu | Ile | Ala | Arg | Pro | Glu | Leu | Gln | Leu | Asp | Glu | Gly | |
| | | 195 | | | | | 200 | | | | | 205 | | | | |
| tgg | atg | gat | gat | gac | agg | aac | gac | ttt | ctg | gat | gac | ctg | cac | atg | gac | 971 |
| Trp | Met | Asp | Asp | Asp | Arg | Asn | Asp | Phe | Leu | Asp | Asp | Leu | His | Met | Asp | |
| | 210 | | | | | 215 | | | | | 220 | | | | | |
| atg | ctg | gag | gag | cag | cac | cac | cag | gcc | atg | caa | ttc | aca | gct | agc | gtg | 1019 |
| Met | Leu | Glu | Glu | Gln | His | His | Gln | Ala | Met | Gln | Phe | Thr | Ala | Ser | Val | |
| 225 | | | | | 230 | | | | | 235 | | | | | 240 | |
| ctg | cag | cag | aag | aag | cac | gac | gaa | gac | ggt | ggg | acc | aca | gat | aca | gcc | 1067 |
| Leu | Gln | Gln | Lys | Lys | His | Asp | Glu | Asp | Gly | Gly | Thr | Thr | Asp | Thr | Ala | |
| | | | 245 | | | | | 250 | | | | | 255 | | | |

```
acc atc ttg tcc aac cag cac gag aag gac agc ggt gtg ggg cgg acc    1115
Thr Ile Leu Ser Asn Gln His Glu Lys Asp Ser Gly Val Gly Arg Thr
        260                 265                 270 gac gag agc acc cgt aat gac gag agc tcg gag caa gag agc aat ggc    1163
Asp Glu Ser Thr Arg Asn Asp Glu Ser Ser Glu Gln Glu Ser Asn Gly
    275                 280                 285 gac gac gcc acc gca tcc tcc aac ccg ctg gcg ggg cag agg aag ctc    1211
Asp Asp Ala Thr Ala Ser Ser Asn Pro Leu Ala Gly Gln Arg Lys Leu
290                 295                 300 acc tgc agc cag gac acc ttg ggc agc ggc gac ctg ccc ttc agc aac    1259
Thr Cys Ser Gln Asp Thr Leu Gly Ser Gly Asp Leu Pro Phe Ser Asn
305                 310                 315                 320 gag tct ttc att tcg gcc gac tgc acg gac gcc gac tac ctg ggg atc    1307
Glu Ser Phe Ile Ser Ala Asp Cys Thr Asp Ala Asp Tyr Leu Gly Ile
                325                 330                 335 ccg gtg gac gag tgc gag cgc ttc cgc gag ctc ctg gag ctc aag tgc    1355
Pro Val Asp Glu Cys Glu Arg Phe Arg Glu Leu Leu Glu Leu Lys Cys
            340                 345                 350 cag gtg aag agc gcc acc cct tac ggc ctg tac tac cct agc ggc ccc    1403
Gln Val Lys Ser Ala Thr Pro Tyr Gly Leu Tyr Tyr Pro Ser Gly Pro
        355                 360                 365 ctg gac gcc ggc aag agt gac cct gag agc gtg gac aag gag ctg gag    1451
Leu Asp Ala Gly Lys Ser Asp Pro Glu Ser Val Asp Lys Glu Leu Glu
    370                 375                 380 ctg ctg aac gaa gag ctg cgc agc atc gag gag tgc ctg agc atc        1499
Leu Leu Asn Glu Glu Leu Arg Ser Ile Glu Glu Cys Leu Ser Ile
385                 390                 395                 400 gtg cgc gcc cac aag atg cag cag ctc aag gag cag tac cgc gag tcc    1547
Val Arg Ala His Lys Met Gln Gln Leu Lys Glu Gln Tyr Arg Glu Ser
                405                 410                 415 tgg atg ctg cac aac agc ggc ttc cgc                                1574
Trp Met Leu His Asn Ser Gly Phe Arg
            420                 425

<210> SEQ ID NO 236
<211> LENGTH: 425
<212> TYPE: PRT
<213> ORGANISM: Homo sapiens

<400> SEQUENCE: 236

Met Ile Asn Gln Val Asn Gly Arg Asp Leu Ser Arg Ala Thr His Asp
1               5                   10                  15

Gln Ala Val Glu Ala Phe Lys Thr Ala Lys Glu Pro Ile Val Val Gln
            20                  25                  30

Val Leu Arg Arg Thr Pro Arg Thr Lys Met Phe Thr Pro Pro Ser Glu
        35                  40                  45

Ser Gln Leu Val Asp Thr Gly Thr Gln Thr Asp Ile Thr Phe Glu His
    50                  55                  60

Ile Met Ala Leu Thr Lys Met Ser Ser Pro Ser Pro Val Leu Asp
65                  70                  75                  80

Pro Tyr Leu Leu Pro Glu Glu His Pro Ser Ala His Glu Tyr Asp
                85                  90                  95

Pro Asn Asp Tyr Ile Gly Asp Ile His Gln Glu Met Asp Arg Glu Glu
            100                 105                 110

Leu Glu Leu Glu Glu Val Asp Leu Tyr Arg Met Asn Ser Gln Asp Lys
        115                 120                 125

Leu Gly Leu Thr Val Cys Tyr Arg Thr Asp Asp Glu Asp Ile Gly
    130                 135                 140

Ile Tyr Ile Ser Glu Ile Asp Pro Asn Ser Ile Ala Ala Lys Asp Gly
```

```
                145                 150                 155                 160
Arg Ile Arg Glu Gly Asp Arg Ile Ile Gln Ile Asn Gly Ile Glu Val
                165                 170                 175
Gln Asn Arg Glu Glu Ala Val Ala Leu Leu Thr Ser Glu Glu Asn Lys
                180                 185                 190
Asn Phe Ser Leu Leu Ile Ala Arg Pro Glu Leu Gln Leu Asp Glu Gly
                195                 200                 205
Trp Met Asp Asp Asp Arg Asn Asp Phe Leu Asp Leu His Met Asp
        210                 215                 220
Met Leu Glu Glu Gln His His Gln Ala Met Gln Phe Thr Ala Ser Val
225                 230                 235                 240
Leu Gln Gln Lys Lys His Asp Glu Asp Gly Gly Thr Thr Asp Thr Ala
                245                 250                 255
Thr Ile Leu Ser Asn Gln His Glu Lys Asp Ser Gly Val Gly Arg Thr
                260                 265                 270
Asp Glu Ser Thr Arg Asn Asp Glu Ser Ser Gln Glu Ser Asn Gly
                275                 280                 285
Asp Asp Ala Thr Ala Ser Ser Asn Pro Leu Ala Gly Gln Arg Lys Leu
        290                 295                 300
Thr Cys Ser Gln Asp Thr Leu Gly Ser Gly Asp Leu Pro Phe Ser Asn
305                 310                 315                 320
Glu Ser Phe Ile Ser Ala Asp Cys Thr Asp Ala Asp Tyr Leu Gly Ile
                325                 330                 335
Pro Val Asp Glu Cys Glu Arg Phe Arg Glu Leu Leu Glu Leu Lys Cys
                340                 345                 350
Gln Val Lys Ser Ala Thr Pro Tyr Gly Leu Tyr Tyr Pro Ser Gly Pro
                355                 360                 365
Leu Asp Ala Gly Lys Ser Asp Pro Glu Ser Val Asp Lys Glu Leu Glu
        370                 375                 380
Leu Leu Asn Glu Glu Leu Arg Ser Ile Glu Leu Glu Cys Leu Ser Ile
385                 390                 395                 400
Val Arg Ala His Lys Met Gln Gln Leu Lys Glu Gln Tyr Arg Glu Ser
                405                 410                 415
Trp Met Leu His Asn Ser Gly Phe Arg
        420                 425

<210> SEQ ID NO 237
<211> LENGTH: 311
<212> TYPE: DNA
<213> ORGANISM: Homo sapiens

<400> SEQUENCE: 237
gtagacgcct cggggcttaa gagaacgtga catggaagag acaggaaata tgtactcttg     60
tacaggtatg cggcacacat gtggccccct ccctcccagc ctcctcacta aagattatta    120
acctgcttat tctcctggtt cacctgaggc tgttttgaga gaatctcagt atctcagtct    180
tcatttcata cgacattctt cgggctcctc ttgttcatct ttgcagactg aagtatttat    240
gaaggacctt cagaaatctg attcctcctg atgaatcaaa gagtaaagaa gaatcaaaca    300
tgattaacca g                                                         311

<210> SEQ ID NO 238
<211> LENGTH: 4
<212> TYPE: PRT
<213> ORGANISM: Homo sapiens

<400> SEQUENCE: 238
```

Met Ile Asn Gln
1

<210> SEQ ID NO 239
<211> LENGTH: 12
<212> TYPE: DNA
<213> ORGANISM: Homo sapiens

<400> SEQUENCE: 239
atgattaacc ag                                                         12

<210> SEQ ID NO 240
<211> LENGTH: 21
<212> TYPE: DNA
<213> ORGANISM: Artificial Sequence
<220> FEATURE:
<223> OTHER INFORMATION: forward primer used for specifically detecting
      the variant of the present invention (D-OCBBF2010718.1 and
      D-OCBBF3004194.1)

<400> SEQUENCE: 240
gccttccttt gacgtttttc t                                               21

<210> SEQ ID NO 241
<211> LENGTH: 24
<212> TYPE: DNA
<213> ORGANISM: Artificial Sequence
<220> FEATURE:
<223> OTHER INFORMATION: reverse primer used for specifically detecting
      the variant of the present invention (D-OCBBF2010718.1 and
      D-OCBBF3004194.1)

<400> SEQUENCE: 241
cgttgacctg acaaacttca taga                                            24

<210> SEQ ID NO 242
<211> LENGTH: 101
<212> TYPE: DNA
<213> ORGANISM: Artificial Sequence
<220> FEATURE:
<223> OTHER INFORMATION: partial polynucleotide specific to the variant
      of the present invention (D-OCBBF2010718.1 and D-OCBBF3004194.1),
      which is obtained by PCR using forward primer (SEQ ID NO:240) and
      reverse primer (SEQ ID NO:241)

<400> SEQUENCE: 242
gccttccttt gacgttttc taaacatggg atgcagtctg tgcagcctgc agaagcaaga      60
ggagcagtac aaattactct atgaagtttg tcaggtcaac g                        101

<210> SEQ ID NO 243
<211> LENGTH: 22
<212> TYPE: DNA
<213> ORGANISM: Artificial Sequence
<220> FEATURE:
<223> OTHER INFORMATION: forward primer used for specifically detecting
      the variant of the present invention (D-NT2RP8000826.1 and
      D-NT2RP7007268.1)

<400> SEQUENCE: 243
gcttagatcg caatgaaact gc                                              22

<210> SEQ ID NO 244
<211> LENGTH: 22
<212> TYPE: DNA
<213> ORGANISM: Artificial Sequence
<220> FEATURE:
<223> OTHER INFORMATION: reverse primer used for specifically detecting the variant of the present invention (D-NT2RP8000826.1 and
D-NT2RP7007268.1)

<400> SEQUENCE: 244
ccaaatacca tcttccacca tg    22

<210> SEQ ID NO 245
<211> LENGTH: 147
<212> TYPE: DNA
<213> ORGANISM: Artificial Sequence
<220> FEATURE:
<223> OTHER INFORMATION: partial polynucleotide specific to the variant
      of the present invention (D-NT2RP8000826.1 and D-NT2RP7007268.1),
      which is obtained by PCR using forward primer (SEQ ID NO:243) and
      reverse primer (SEQ ID NO:244)

<400> SEQUENCE: 245
gcttagatcg caatgaaact gcggacctgc aggctgcctt gcttcactga gtcaatttttt    60 aaatgaagat ggaacacaag aggatgatct tattgttcag taaatttact ctaatacata   120
aaccccatgg tggaagatgg tatttgg    147

<210> SEQ ID NO 246
<211> LENGTH: 25
<212> TYPE: DNA
<213> ORGANISM: Artificial Sequence
<220> FEATURE:
<223> OTHER INFORMATION: forward primer used for specifically detecting
      the variant of the present invention (D-BRAWH3008172.1)

<400> SEQUENCE: 246
ccaaatgttt aggatacacc tgaga    25

<210> SEQ ID NO 247
<211> LENGTH: 20
<212> TYPE: DNA
<213> ORGANISM: Artificial Sequence
<220> FEATURE:
<223> OTHER INFORMATION: reverse primer used for specifically detecting
      the variant of the present invention (D-BRAWH3008172.1)

<400> SEQUENCE: 247
ctgccgttga ccagggaaag    20

<210> SEQ ID NO 248
<211> LENGTH: 106
<212> TYPE: DNA
<213> ORGANISM: Artificial Sequence
<220> FEATURE:
<223> OTHER INFORMATION: partial polynucleotide specific to the variant
      of the present invention (D-BRAWH3008172.1), which is obtained by
      PCR using forward primer (SEQ ID NO:246) and reverse primer (SEQ
      ID NO:247)

<400> SEQUENCE: 248
ccaaatgttt aggatacacc tgagatgtct ctcttactga atagaaacaa catccctgga    60
agctctagac ttctgaggca ccccagcttt ccctggtcaa cggcag    106

<210> SEQ ID NO 249
<211> LENGTH: 27
<212> TYPE: DNA
<213> ORGANISM: Artificial Sequence
<220> FEATURE:
<223> OTHER INFORMATION: forward primer used for specifically detecting
      the variant of the present invention (D-BRAWH3011965.1)

<400> SEQUENCE: 249

```
cagtatctca gtcttcattt catacga                                         27

<210> SEQ ID NO 250
<211> LENGTH: 24
<212> TYPE: DNA
<213> ORGANISM: Artificial Sequence
<220> FEATURE:
<223> OTHER INFORMATION: reverse primer used for specifically detecting
      the variant of the present invention (D-BRAWH3011965.1)

<400> SEQUENCE: 250
ttgacctggt taatcatgtt tgat                                            24

<210> SEQ ID NO 251
<211> LENGTH: 150
<212> TYPE: DNA
<213> ORGANISM: Artificial Sequence
<220> FEATURE:
<223> OTHER INFORMATION: partial polynucleotide specific to the variant
      of the present invention (D-BRAWH3011965.1), which is obtained by
      PCR using forward primer (SEQ ID NO:249) and reverse primer (SEQ
      ID NO:250)

<400> SEQUENCE: 251
cagtatctca gtcttcattt catacgacat tcttcgggct cctcttgttc atctttgcag     60
actgaagtat ttatgaagga ccttcagaaa tctgattcct cctgatgaat caaagagtaa    120
agaagaatca aacatgatta accaggtcaa                                     150

<210> SEQ ID NO 252
<211> LENGTH: 19
<212> TYPE: DNA
<213> ORGANISM: Artificial Sequence
<220> FEATURE:
<223> OTHER INFORMATION: forward primer used for specifically detecting
      the known variant of the gene of the present invention
      (NM_015009.1)

<400> SEQUENCE: 252
gcaagggcga agaaaccaa                                                  19

<210> SEQ ID NO 253
<211> LENGTH: 22
<212> TYPE: DNA
<213> ORGANISM: Artificial Sequence
<220> FEATURE:
<223> OTHER INFORMATION: reverse primer used for specifically detecting
      the known variant of the gene of the present invention
      (NM_015009.1)

<400> SEQUENCE: 253
gatgatccat cgtggttatc ca                                              22

<210> SEQ ID NO 254
<211> LENGTH: 112
<212> TYPE: DNA
<213> ORGANISM: Artificial Sequence
<220> FEATURE:
<223> OTHER INFORMATION: partial polynucleotide specific to the known
      variant of the gene of the present invention (NM_015009.1), which
      is obtained by PCR using forward primer (SEQ ID NO:252) and
      reverse primer (SEQ ID NO:253)

<400> SEQUENCE: 254
gcaagggcga agaaaccaaa agtctgactc ttgtcctgca tcgggactcc ggctccctgg     60
gattcaatat tattggtggc cggccgagtg tggataacca cgatggatca tc            112
```

```
<210> SEQ ID NO 255
<211> LENGTH: 20
<212> TYPE: DNA
<213> ORGANISM: Artificial Sequence
<220> FEATURE:
<223> OTHER INFORMATION: forward primer used for detecting the variants
      of the gene of the present invention (D-OCBBF2010718.1,
      D-OCBBF3004194.1, D-NT2RP8000826.1, D-NT2RP7007268.1,
      D-BRAWH3008172.1, D-BRAWH3011965.1 and NM_015009.1)

<400> SEQUENCE: 255
caccactccc catacaagca                                              20

<210> SEQ ID NO 256
<211> LENGTH: 20
<212> TYPE: DNA
<213> ORGANISM: Artificial Sequence
<220> FEATURE:
<223> OTHER INFORMATION: reverse primer used for detecting the variants
      of the gene of the present invention (D-OCBBF2010718.1,
      D-OCBBF3004194.1, D-NT2RP8000826.1, D-NT2RP7007268.1,
      D-BRAWH3008172.1, D-BRAWH3011965.1 and NM_015009.1)

<400> SEQUENCE: 256
catctggctt tgcgcgtact                                              20

<210> SEQ ID NO 257
<211> LENGTH: 111
<212> TYPE: DNA
<213> ORGANISM: Artificial Sequence
<220> FEATURE:
<223> OTHER INFORMATION: partial polynucleotide common to the variants
      of the gene of the present invention (D-OCBBF2010718.1,
      D-OCBBF3004194.1, D-NT2RP8000826.1, D-NT2RP7007268.1,
      D-BRAWH3008172.1, D-BRAWH3011965.1 and NM_015009.1), which is
      obtained by PCR using forward primer (SEQ ID NO:255) and reverse
      primer (SEQ ID NO:256)

<400> SEQUENCE: 257
caccactccc catacaagca cgcgcacatc ccggcgcacg cccagcacta ccagagctac    60
atgcagctga tccagcagaa gtcggccgtg gagtacgcgc aaagccagat g           111

<210> SEQ ID NO 258
<211> LENGTH: 219
<212> TYPE: DNA
<213> ORGANISM: Homo sapiens

<400> SEQUENCE: 258
gagagcagcg ccaatgtgaa gcgttgcagt cgcttgactc acctgaggct ctccaaggat    60
accttcaatg cctgcactgt aagggagctg ctttttcccgg gtgctggcga gaacggaagc   120
cttcctttga cgtttttcta aacatgggat gcagtctgtg cagcctgcag aagcaagagg   180
agcagtacaa attactctat gaagtttgtc aggtcaacg                         219

<210> SEQ ID NO 259
<211> LENGTH: 204
<212> TYPE: DNA
<213> ORGANISM: Homo sapiens

<400> SEQUENCE: 259
gtgaagcgtt gcagtcgctt gactcacctg aggctctcca aggataccttcaatgcctgc    60 actgtaaggg agctgctttt cccgggtgct ggcgagaacg gaagccttcc tttgacgttt   120
ttctaaacat gggatgcagt ctgtgcagcc tgcagaagca agaggagcag tacaaattac   180
tctatgaagt ttgtcaggtc aacg                                         204
```

<210> SEQ ID NO 260
<211> LENGTH: 179
<212> TYPE: DNA
<213> ORGANISM: Homo sapiens

<400> SEQUENCE: 260

| | | |
|---|---|---|
| agcatttgct cagtactctc aacataaacc aagcttagat cgcaatgaaa ctgcggacct | 60 | |
| gcaggctgcc ttgcttcact gagtcaattt ttaaatgaag atggaacaca agaggatgat | 120 | |
| cttattgttc agtaaattta ctctaataca taaaccccat ggtggaagat ggtatttgg | 179 | |

<210> SEQ ID NO 261
<211> LENGTH: 179
<212> TYPE: DNA
<213> ORGANISM: Homo sapiens

<400> SEQUENCE: 261
agcatttgct cagtactctc aacataaacc aagcttagat cgcaatgaaa ctgcggacct     60
gcaggctgcc ttgcttcact gagtcaattt ttaaatgaag atggaacaca agaggatgat    120
cttattgttc agtaaattta ctctaataca taaaccccat ggtggaagat ggtatttgg    179

<210> SEQ ID NO 262
<211> LENGTH: 180
<212> TYPE: DNA
<213> ORGANISM: Homo sapiens

<400> SEQUENCE: 262
atatataata gccttgcaag tgaacggata agcaaagtca gttgctgaga ataacactt     60
ccgagctgac gcatccaaat gtttaggata cacctgagat gtctctctta ctgaatagaa    120
acaacatccc tggaagctct agacttctga ggcaccccag ctttccctgg tcaacggcag   180

<210> SEQ ID NO 263
<211> LENGTH: 316
<212> TYPE: DNA
<213> ORGANISM: Homo sapiens

<400> SEQUENCE: 263
gtagacgcct cggggcttaa gagaacgtga catggaagag acaggaaata tgtactcttg     60
tacaggtatg cggcacacat gtggccccct cccctcccagc ctcctcacta aagattatta   120
acctgcttat tctcctggtt cacctgaggc tgttttgaga gaatctcagt atctcagtct   180
tcatttcata cgacattctt cgggctcctc ttgttcatct ttgcagactg aagtatttat   240
gaaggacctt cagaaatctg attcctcctg atgaatcaaa gagtaaagaa gaatcaaaca   300
tgattaacca ggtcaa                                                    316

<210> SEQ ID NO 264
<211> LENGTH: 62
<212> TYPE: PRT
<213> ORGANISM: Homo sapiens

<400> SEQUENCE: 264

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu
    50                  55                  60

<210> SEQ ID NO 265
<211> LENGTH: 172
<212> TYPE: PRT
<213> ORGANISM: Homo sapiens

<400> SEQUENCE: 265

```
Met Pro Asn Pro Ser Ser Thr Ser Ser Pro Tyr Pro Leu Pro Glu Glu
1               5                   10                  15

Ile Arg Asn Leu Leu Ala Asp Val Glu Thr Phe Val Ala Asp Ile Leu
            20                  25                  30

Lys Gly Glu Asn Leu Ser Lys Lys Ala Lys Glu Lys Arg Glu Ser Leu
        35                  40                  45

Ile Lys Lys Ile Lys Asp Val Lys Ser Ile Tyr Leu Gln Glu Phe Gln
    50                  55                  60

Asp Lys Gly Asp Ala Glu Asp Gly Glu Tyr Asp Asp Pro Phe Ala
65                  70                  75                  80

Gly Pro Pro Asp Thr Ile Ser Leu Ala Ser Glu Arg Tyr Asp Lys Asp
                85                  90                  95

Asp Glu Ala Pro Ser Asp Gly Ala Gln Phe Pro Pro Ile Ala Ala Gln
            100                 105                 110

Asp Leu Pro Phe Val Leu Lys Ala Gly Tyr Leu Glu Lys Arg Arg Lys
            115                 120                 125

Asp His Ser Phe Leu Gly Phe Glu Trp Gln Lys Arg Trp Cys Ala Leu
    130                 135                 140

Ser Lys Thr Val Phe Tyr Tyr Tyr Gly Ser Asp Lys Asp Lys Gln Gln
145                 150                 155                 160

Lys Gly Glu Phe Ala Ile Asp Gly Tyr Ser Val Arg
                165                 170
```

<210> SEQ ID NO 266
<211> LENGTH: 16
<212> TYPE: PRT
<213> ORGANISM: Homo sapiens

<400> SEQUENCE: 266

```
Met Ser Asn Lys Cys Asp Val Val Val Gly Gly Gly Ile Ser Gly
1               5                   10                  15
```

The invention claimed is

1. An isolated polypeptide comprising the amino acid sequence of SEQ ID NO: 58.

2. The polypeptide of claim 1, wherein the polypeptide consists of the amino acid sequence of SEQ ID NO: 58.

3. The polypeptide of claim 2, which is fused with a polypeptide consisting of a heterologous amino acid sequence.

4. The polypeptide of claim 1, which is fused with a polypeptide consisting of a heterologous amino acid sequence.

5. An isolated polynucleotide that encodes a polypeptide comprising the amino acid sequence of SEQ ID NO: 58.

6. The polynucleotide of claim 5, wherein the polynucleotide encodes a polypeptide consisting of the amino acid sequence of SEQ ID NO: 58.

* * * * *